United States Patent
Sun et al.

(10) Patent No.: US 9,346,808 B2
(45) Date of Patent: May 24, 2016

(54) HSP90 INHIBITORS

(75) Inventors: Weilin Sun, New York, NY (US); Tony Taldone, New York, NY (US); Pallav Patel, Philadelphia, PA (US); Gabriela Chiosis, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 14/009,976

(22) PCT Filed: Apr. 5, 2012

(86) PCT No.: PCT/US2012/032371
§ 371 (c)(1),
(2), (4) Date: Oct. 4, 2013

(87) PCT Pub. No.: WO2012/138894
PCT Pub. Date: Oct. 11, 2012

(65) Prior Publication Data
US 2014/0088121 A1    Mar. 27, 2014

Related U.S. Application Data

(60) Provisional application No. 61/472,061, filed on Apr. 5, 2011.

(51) Int. Cl.
*A61K 31/52*     (2006.01)
*C07D 473/34*    (2006.01)
*C07D 473/40*    (2006.01)

(52) U.S. Cl.
CPC .............. *C07D 473/34* (2013.01); *A61K 31/52* (2013.01); *C07D 473/40* (2013.01)

(58) Field of Classification Search
USPC ............. 514/263.24, 263.37, 263.4; 544/276, 544/277
See application file for complete search history.

(56) References Cited

U.S. PATENT DOCUMENTS

| | | | |
|---|---|---|---|
| 7,067,507 | B2 | 6/2006 | Pulley et al. |
| 7,834,181 | B2 | 11/2010 | Chiosis et al. |
| 8,703,942 | B2 | 4/2014 | Chiosis et al. |
| 2005/0004026 | A1 | 1/2005 | Kasibhatla et al. |
| 2005/0049263 | A1 | 3/2005 | Kasibhatla et al. |
| 2005/0107343 | A1 | 5/2005 | Kasibhatla et al. |
| 2005/0113339 | A1 | 5/2005 | Kasibhatla et al. |
| 2005/0113340 | A1 | 5/2005 | Kasibhatla et al. |
| 2005/0119292 | A1 | 6/2005 | Gravestock et al. |
| 2005/0256183 | A1 | 11/2005 | Kasibhatla et al. |
| 2008/0096903 | A1 | 4/2008 | Chen et al. |
| 2008/0234297 | A1 | 9/2008 | Qian et al. |
| 2008/0234314 | A1 | 9/2008 | Cai et al. |
| 2009/0298857 | A1 | 12/2009 | Chiosis et al. |
| 2012/0208806 | A1 | 8/2012 | Chiosis et al. |
| 2014/0045867 | A1 | 2/2014 | Taldone et al. |
| 2014/0221343 | A1 | 8/2014 | Cai et al. |

(Continued)

FOREIGN PATENT DOCUMENTS

| | | | |
|---|---|---|---|
| JP | 2009-521446 | A | 6/2009 |
| JP | 2009-542716 | A | 12/2009 |
| JP | 2010-507582 | A | 3/2010 |

(Continued)

OTHER PUBLICATIONS

He et al., Identification of Potent Water Soluble Purine-Scaffold Inhibitors of the Heat Shock Protein 90, Journal of Medicinal Chemistry, 49(1): 381-390 (2006).
Dymock et al., Adenine derived inhibitors of the molecular chaperone HSP90-SAR explained Through Multiple X-Ray Structures, Bioorganic & Medicinal Chemistry Letters, 14(2): 325-328 (2004).
International Search Report of PCT/US2012/032371, 6 pages (mailed Aug. 20, 2012).
Written Opinion of PCT/US2012/032371, 10 pages (mailed Aug. 20, 2012).

(Continued)

*Primary Examiner* — Kristin Vajda
(74) *Attorney, Agent, or Firm* — Choate, Hall & Stewart LLP; John P. Rearick; Gang Wang

(57) ABSTRACT

The disclosure relates to Compounds of Formulae (IA) and (IB):

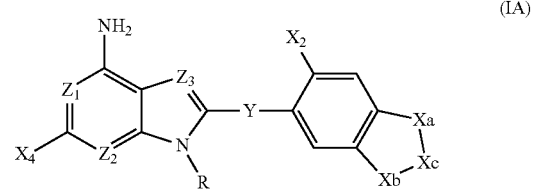

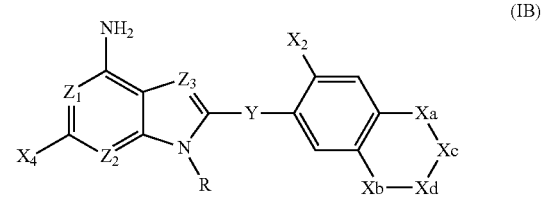

and pharmaceutically acceptable salts thereof wherein $Z_1$, $Z_2$, $Z_3$, Xa, Xb, Xc, Xd, Y, $X_2$, and $X_4$ are as defined herein, compositions comprising an effective amount of a Compound of Formula (IA) and/or (IB), and methods to treat or prevent a condition, such cancer which overexpresses Her-kinases, comprising administering to an patient in need thereof a therapeutically effective amount of a Compound of Formula (IA) or (IB). The disclosure further relates to compounds of Formulae (IA) and IB) in which $X_2$ is a leaving for introducing a radiolabeled atom, such as $^{124}$I or $^{131}$I and to methods of using such compounds in the preparation of radiolabeled compounds, particularly for use in imaging.

44 Claims, No Drawings

(56) References Cited

U.S. PATENT DOCUMENTS

| | | | |
|---|---|---|---|
| 2014/0227183 A1 | 8/2014 | Chiosis et al. | |
| 2014/0378452 A1 | 12/2014 | Chiosis | |

FOREIGN PATENT DOCUMENTS

| | | | |
|---|---|---|---|
| JP | 2010-522184 A | 7/2010 | |
| JP | 2013-507381 A | 3/2013 | |
| WO | WO-98/51702 A1 | 11/1998 | |
| WO | WO-00/61578 A1 | 10/2000 | |
| WO | WO-02/36075 A2 | 5/2002 | |
| WO | WO 2006/084030 A2 | 8/2006 | |
| WO | WO 2007/134298 A2 | 5/2007 | |
| WO | WO-2007/075572 A2 | 7/2007 | |
| WO | WO 2008/005937 A2 | 1/2008 | |
| WO | WO-2008/033747 A2 | 3/2008 | |
| WO | WO 2008/049105 A2 | 4/2008 | |
| WO | WO 2008/056120 A1 | 5/2008 | |
| WO | WO-2008/115262 A2 | 9/2008 | |
| WO | WO 2008/115719 A1 | 9/2008 | |
| WO | WO 2009/007399 A1 | 1/2009 | |
| WO | WO-2009/042646 A1 | 4/2009 | |
| WO | WO 2009/065035 A1 | 5/2009 | |
| WO | WO-2010/083403 A1 | 7/2010 | |
| WO | WO 2011/044394 A1 | 4/2011 | |
| WO | WO-2012/138894 A1 | 10/2012 | |
| WO | WO-2012/138896 A1 | 10/2012 | |

OTHER PUBLICATIONS

Written Opinion of PCT/US2012/032371, 5 pages (mailed Mar. 12, 2013).
American Chemical Societed (ACS), STN Chemical Abstract Service (CAS), CAS RN Database. (c) Oct. 2008).
Baade et al., One in Four Cancers Preventable—But First We Need the Willpower, (c) 2013, Available from: <http://theconversation.com/one-in-four-cancers-preventable0but-first-we-need-the-will-power-5820>.
Breinig et al., Targeting Heat Shock Protein 90 with Non-Quinone Inhibitors: A Novel Chemotherapeutic Approach in Human Hepatocellular Carcinoma, Hepatology, 50(1): 102-112 (2009).
Caldas-Lopes et al., Hsp90 Inhibitor PU-H71, a Multimodal Inhibitor of Malignancy, Induces Complete Responses in Triple-Negative Breast Cancer Models., PNAS Early Edition, 1-6 (2009).
Cerchietti et al., A Purine Scaffold Hsp90 Inhibitor Destabilize BCL-6 and has Specific Antitumor Activity in BCL-6-Dependent B Cell Lymphomas, Nature Medicine, 15(12): 1369-1377 (2009).
Chiosis, G. et al., Discovery and Development of Purine-Scaffold Hsp90 Inhibitors, Expert Opin. Drug Discov, 3(1): 99-114 (2008).
Chiosis, G., Targeting chaperones in transformed systems—a focus on Hsp90 and cancer, Expert Opin. Ther. Targets, 10(1): 37-50 (2006).
Du et al., High-throughput Screening Fluorescence Polarization Assay for Tumor-Specific hsp90, J. Biomol. Screen, 12: 915-924 (2007).
European Search Report for 12717520.6, 4 pages (Aug. 7, 2014).
International Preliminary Report on Patentability for PCT/US2012/032373, 5 pages (Jun. 19, 2013).
International Search Report of PCT/US2012/032373, 4 pages (Jun. 20, 2012).
List of Cancer Chemotherapy Drugs, (c) 2013. Available from: <https://www.navigatingcancer.com/library/all/chemotherapy_drugs>.
Marubayashi et al., HSP90 is a Therapeutic Target in JAK2-dependent Myeloproliferative Neoplasms in Mice and Humans, The Journal of Clinical Investigation, 120(10): 3587-3593 (2010).
Sgobba, M., et al., Structure-Based and in silico Design of Hsp90 Inhibitors, Chem. Med. Chem., 4(9): 1399-1409 (2009).
Written Opinion of PCT/US2012/032373, 5 pages (Jun. 20, 2012).
Written Opinion of PCT/US2012/032373, 5 pages (Mar. 14, 2013).
Young, A. B., Four Decades of Neurodegenerative Disease Research: How Far We Have Come!, The Journal of Neuroscience, 29(41), 12722-12728 (2009).
U.S. Appl. No. 13/176,903, filed Jul. 6, 2011, Chiosis.
Author Not Known, Degenerative Nerve Diseases, Medline Plus, 22 pages (2014), Page last updated on Oct. 9, 2014 <http://www.nlm.nih.gov/medlineplus/degenerativenervediseases.html>.
Hanson, D., Six highly treatable cancers, DailyRx.com, 3 pages (2014), retrieved on Mar. 10, 2015 <http://www.dailyrx.com/some-cancers-have-high-survival-rates-early-detection>.

HSP90 INHIBITORS

This application claims the benefit of and priority from U.S. provisional application No. 61/472,061, filed Apr. 5, 2011, the contents of which are incorporated herein by reference.

GOVERNMENT LICENSE RIGHTS

This invention was made with government support under grant number AG032969 awarded by The National Institute of Health. The government has certain rights in the invention.

1. BACKGROUND

This application relates to compounds that inhibit heat shock protein 90 (Hsp90).

The Hsp90 family of proteins has four recognized members in mammalian cells: Hsp90 α and β, Grp94 and Trap-1. Hsp90 α and β exist in the cytosol and the nucleus in association with a number of other proteins. Hsp90 in its various forms is the most abundant cellular chaperone, and has been shown in experimental systems to be required for ATP-dependent refolding of denatured or "unfolded" proteins. It has therefore been proposed to function as part of the cellular defense against stress. When cells are exposed to heat or other environmental stresses, the aggregation of unfolded proteins is prevented by pathways that catalyze their refolding or degradation. This process depends on the association of the unfolded protein in an ordered fashion with multiple chaperones (Hsp60, Hsp90, Hsp70 and p23), forming a "refoldosome" and ultimately the ATP-dependent release of the chaperones from the refolded protein.

Hsp90 can also play a role in maintaining the stability and function of mutated proteins. It seems to be required for expression of mutated p53 and v-src to a much greater extent than for their wild-type counterparts. It has been suggested that this occurs as a result of Hsp90-mediated suppression of the phenotypes of mutations that lead to protein unfolding.

Hsp90 is also necessary to the conformational maturation of several key proteins involved in the growth response of the cell to extracellular factors. These include the steroid receptors as well as certain kinases (i.e., Raf serine kinase, v-src and Her2). The mechanism whereby Hsp90 affects these proteins is not fully understood, but appears to be similar to its role in protein refolding. In the case of the progesterone receptor, it has been shown that binding and release of Hsp90 from the receptor occurs in a cyclic fashion in concert with release of other chaperones and immunophilins and is required for high affinity binding of the steroid to the receptor. Thus, Hsp90 could function as a physiologic regulator of signaling pathways, even in the absence of stress.

Hsp90 has been shown to be overexpressed in multiple tumor types and as a function of oncogenic transformation. Whether it plays a necessary role in maintaining transformation is unknown, but it could have at least three functions in this regard. Cancer cells grow in an environment of hypoxia, low pH and low nutrient concentration. They also rapidly adapt to or are selected to become resistant to radiation and cytotoxic chemotherapeutic agents. Thus, the general role of Hsp90 in maintaining the stability of proteins under stress may be necessary for cell viability under these conditions. Secondly, cancer cells harbor mutated oncogenic proteins. Some of these are gain-of-function mutations which are necessary for the transformed phenotype. Hsp90 may be required for maintaining the folded, functionally-active conformation of these proteins. Thirdly, activation of signaling pathways mediated by steroid receptors, Raf and other Hsp90 targets is necessary for the growth and survival of many tumors which thus probably also require functional Hsp90.

Hsp90 has been recognized as a viable target for therapeutic agents. Hsp90 family members possess a unique pocket in their N-terminal region that is specific to and conserved among all Hsp90s from bacteria to mammals, but which is not present in other molecular chaperones. The endogenous ligand for this pocket is not known, but it binds ATP and ADP with low affinity and has weak ATPase activity. The ansamycin antibiotics geldanamycin (GM) and herbimycin (HA) have been shown to bind to this conserved pocket, and this binding affinity has been shown for all members of the Hsp90 family. International Patent Publication No. WO98/51702 discloses the use of ansamycin antibiotics coupled to a targeting moiety to provide targeted delivery of the ansamycin leading to the degradation of proteins in and death of the targeted cells. International Patent Publication No. WO00/61578 relates to bifunctional molecules having two moieties which interact with the chaperone protein Hsp90, including in particular homo- and heterodimers of ansamycin antibiotics. These bifunctional molecules act to promote degradation and/or inhibition of HER-family tyrosine kinases and are effective for treatment of cancers which overexpress Her-kinases.

Exemplary small molecule therapeutics that bind to the same binding pocket of Hsp90 as ATP and the ansamycin antibiotics are disclosed in PCT Publication Nos. WO02/36075, WO2006/084030, WO2009/042646, WO2009/065035, and WO2011/044394; U.S. Pat. No. 7,834,181; and U.S. Patent Publication Nos. 2005/0113339, 2005/0004026, 2005/0049263, 2005/0256183, 2005/0119292, 2005/0113340, 2005/0107343, 2008/0096903, 2008/0234297, 2008/0234314, and 2009/0298857, all of which are incorporated herein by reference.

In particular, certain small molecule therapeutics that bind to the same binding pocket of Hsp90 can be described by the following general structural formula where $Z_1$, $Z_2$, and $Z_3$ are selected from CH and N and the variable substituents are selected from a number of options:

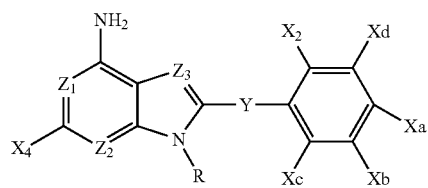

While these compounds can be active as inhibitors of Hsp90, their level of activity is extremely variable with measured values for $EC_{50}$ and $IC_{50}$ being reported in anywhere from the micromolar to nanomolar ranges.

2. SUMMARY

In one aspect of the disclosure, new compounds that inhibit Hsp90 are described.

Compounds of Formula (IA) or (IB) are herein disclosed:

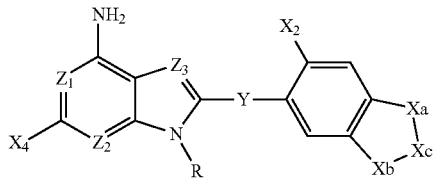
(IA)

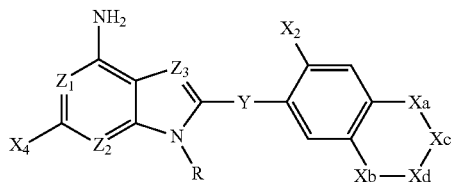
(IB)

or a pharmaceutically acceptable salt thereof, wherein:
(a) each of $Z_1$, $Z_2$ and $Z_3$ is independently CH or N;
(b) Y is $CH_2$, O, or S;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is halogen, aryl, alkynyl, or amino;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by 1, 2, or 3 groups selected from —S(O)N($R_A$)—, —$NR_A$S(O)—, —$SO_2$N($R_A$)—, —$NR_A SO_2$—, —C(O)N($R_A$)—, and —$NR_A$C(O)—, and/or terminated by —S(O)$NR_A R_B$, —$NR_A$S(O)$R_B$, —$SO_2 NR_A R_B$, —$NR_A SO_2 R_B$, —C(O)$NR_A R_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

3. DETAILED DESCRIPTION

The invention includes the following:
(1) A Compound of Formula (IA) or (IB):

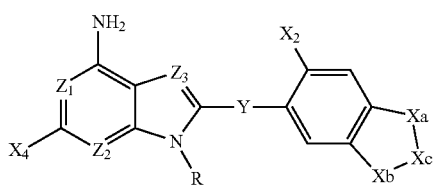
(IA)

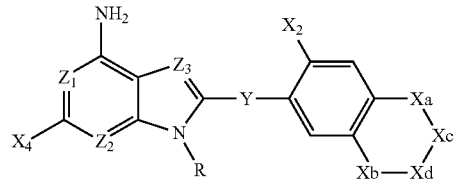
(IB)

or a pharmaceutically acceptable salt thereof, wherein:
(a) each of $Z_1$, $Z_2$ and $Z_3$ is independently CH or N;
(b) Y is $CH_2$, O, or S;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is halogen, aryl, alkynyl, or amino;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_A$S(O)—, —$SO_2$N($R_A$)—, —$NR_A SO_2$—, —C(O)N($R_A$)—, or —$NR_A$C(O)—, and/or terminated by —S(O)$NR_A R_B$, —$NR_A$S(O)$R_B$, —$SO_2 NR_A R_B$, —$NR_A SO_2 R_B$, —C(O)$NR_A R_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

(2) The compound as in the above (1) which is a Compound of Formula (1):

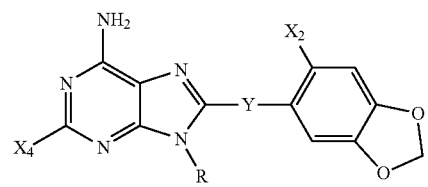
(1)

or a pharmaceutically acceptable salt thereof, wherein Y is $CH_2$ or S.

(3) The compound as in the above (1) which is a Compound of Formula (2):

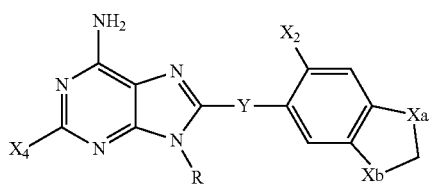
(2)

or a pharmaceutically acceptable salt thereof, wherein:
one of Xa and Xb is O and the other is $CH_2$; and
Y is $CH_2$ or S.

(4) The compound as in the above (1) which is a Compound of Formula (3):

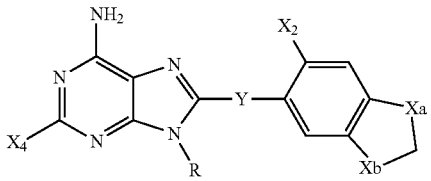

(3)

or a pharmaceutically acceptable salt thereof, wherein:
one of Xa and Xb is C(=O) and the other is $CH_2$; and
Y is $CH_2$ or S.

(5) The compound as in the above (1) which is a Compound of Formula (4):

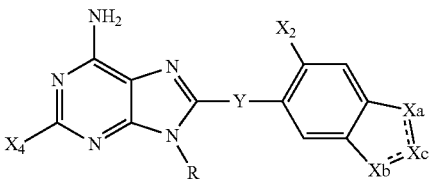

(4)

or a pharmaceutically acceptable salt thereof, wherein:
Xa-Xc-Xb is $CH_2$—$CH_2$—$CH_2$, CH=CH—$CH_2$, or $CH_2$—CH=CH; and
Y is $CH_2$ or S.

(6) The compound as the above (1) which is a Compound of Formula (5):

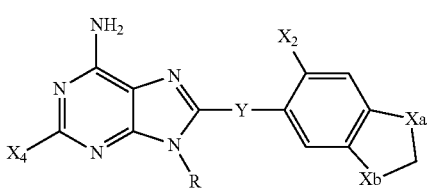

(5)

or a pharmaceutically acceptable salt thereof, wherein at least one of Xa and Xb is CHF or $CF_2$ and the other is CHF, $CF_2$, or $CH_2$.

(7) The compound as in the above (1) which is Compound of Formula (6):

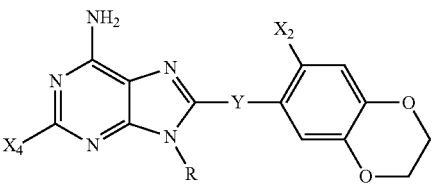

(6)

or a pharmaceutically acceptable salt thereof.

(8) The compound as in the above (1), wherein $Z_1$ is CH or $Z_2$ is CH or $Z_3$ is CH.

(9) The compound as in the above (1), wherein $Z_1$ and $Z_2$ are each CH or $Z_1$ and $Z_3$ are each CH or $Z_2$ and $Z_3$ are each CH.

(10) The compound as in the above (1), wherein $Z_1$, $Z_2$, and $Z_3$ are each CH.

(11) The compound as in the above (1) to (10), wherein R is interrupted by one or more —S(O)N($R_A$)—, —$NR_A$S(O)—, —$SO_2$N($R_A$)—, —$NR_A SO_2$—, —C(O)N($R_A$)—, or —$NR_A$C(O)— groups.

(12) The compound as in the above (1) to (11), wherein R is terminated by an —S(O)$NR_A R_B$, —$NR_A$S(O)$R_B$, —$SO_2 NR_A R_B$, —$NR_A SO_2 R_B$, —C(O)$NR_A R_B$, or —$NR_A$C(O)$R_B$ group.

(13) The compound as in one of the above (1) to (12), wherein R is 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesulfonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, or cyclopropane carboxylic acid 2-ethyl-amide.

(14) The compound as in one of the above (1) to (12), wherein R is cyclopropane carboxylic acid 3-propyl-amide, N-3-propyl 2,2-dimethyl-propionamide, N-propyl-2-methyl-propane-2-sulfinamide, t-butanesulfonic acid 3-propylamide, or cyclopropanesulfonic acid 3-propylamide.

(15) The compound as in one of the above (1) to (14), wherein $X_4$ is H or F.

(16) The compound as in one of the above (1) to (15), wherein Y is S.

(17) The compound as in one of the above (1) to (15), wherein Y is $CH_2$.

(18) The compound as in one of the above (1) to (17), wherein $X_2$ is optionally substituted heteroaryl.

(19) The compound as in one of the above (1) to (18), wherein $X_2$ is furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, or 5-methyloxazol-2-yl.

(20) The compound as in one of the above (1) to (17), wherein $X_2$ is alkynyl.

(21) The compound as in one of the above (1) to (17) or (20), wherein $X_2$ is ethynyl.

(22) The compound as in one of the above (1) to (17), wherein $X_2$ is halo.

(23) The compound as in one of the above (1) to (17) or (22), wherein $X_2$ is I.

(24) The compound as in one of the above (1) to (17), wherein $X_2$ is amino.

(25) The compound as in one of the above (1) to (17) or (24), wherein $X_2$ is dimethylamino.

(26) The compound as in one of the above (1) to (11) or (13) to (25), wherein $Z_1$ is N or $Z_2$ is N or $Z_3$ is N.

(27) The compound as in one of the above (1) to (10) or (13) to (25), wherein $Z_1$ and $Z_2$ are each N or $Z_1$ and $Z_3$ are each N or $Z_2$ and $Z_3$ are each N.

(28) A pharmaceutical composition comprising the compound as in one of the above (1) to (27) and a pharmaceutically acceptable carrier.

(29) A method for treating or preventing cancer or a neurodegenerative disorder, comprising administering to a patient in need thereof a therapeutically effective amount of a compound as in one of the above (1) to (27).

(30) Use of a compound as in one of the above (1) to (27) in formulating a pharmaceutical composition for the treatment or prevention of cancer or a neurodegenerative disorder.

(31) A method for the inhibition of Hsp90, comprising contacting Hsp90 with an Hsp90 function inhibiting amount of a compound as in one of the above (1) to (27).

(32) Use of a compound as in one of the above (1) to (27) in formulating a pharmaceutical composition for the inhibition of Hsp90.

(34) A Compound of Formula (IA) or (IB):

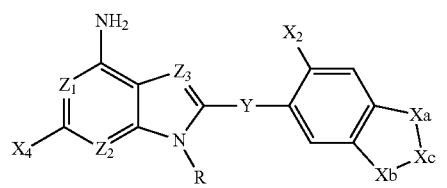

(IA)

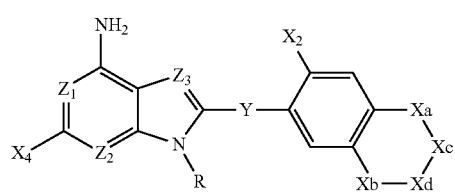

(IB)

or a salt thereof, wherein:

(a) each of $Z_1$, $Z_2$ and $Z_3$ is independently CH or N;
(b) Y is $CH_2$, O, or S;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is a leaving group for introduction of a radiolabeled atom to the structure;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more $—S(O)N(R_A)—$, $—NR_AS(O)—$, $—SO_2N(R_A)—$, $—NR_ASO_2—$, $—C(O)N(R_A)—$, or $—NR_AC(O)—$ groups, and/or terminated by an $—S(O)NR_AR_B$, $—NR_AS(O)R_B$, $—SO_BNR_AR_B$, $—NR_ASO_2R_B$, $—C(O)NR_AR_B$, or $—NR_AC(O)R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

(35) A compound as in (34) above, or a salt thereof, wherein $X_2$ is trialkyl tin or $—Sn(CH_2CH_2(CF_2)_5CF_3)_3$.

(36) Use of a compound as in (34) or (35) above, or a salt thereof, as a precursor for the formation of a radiolabeled compound.

A. COMPOUNDS OF FORMULAE (IA) AND (IB)

As stated above, the disclosure encompasses Compounds of Formulae (IA) and (IB):

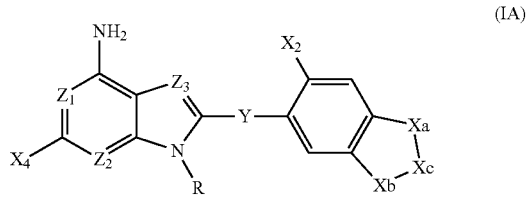

(IA)

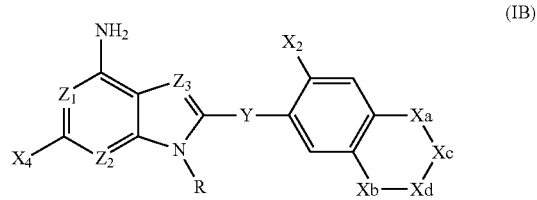

(IB)

or a pharmaceutically acceptable salt thereof, wherein:

(a) each of $Z_1$, $Z_2$ and $Z_3$ is independently CH or N;
(b) Y is $CH_2$, O, or S;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is halogen, aryl, alkynyl, or amino;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by $—S(O)N(R_A)—$, $—NR_AS(O)—$, $—SO_2N(R_A)—$, $—NR_ASO_2—$, $—C(O)N(R_A)—$, and $—NR_AC(O)—$, and/or terminated by $—S(O)NR_AR_B$, $—NR_AS(O)R_B$, $—SO_2NR_AR_B$, $—NR_ASO_2R_B$, $—C(O)NR_AR_B$, or $—NR_AC(O)R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

In certain embodiments, there may be 1, 2 or 3 interrupting and/or terminating groups, which may be the same or different. In general, the R groups of these compounds can be described as sulfonamido groups, sulfinamido groups, or amido groups.

In certain embodiments, specific R groups include without limitation: 2-ethanesulfonic acid isopropylamide, 2-ethanesulfonic acid ethylamide, 2-ethanesulfonic acid methylamide, 2-ethanesulfonic acid amide, 2-ethanesulfonic acid t-butylamide, 2-ethanesulfonic acid isobutylamide, 2-ethanesulfonic acid cyclopropylamide, isopropanesulfonic acid 2-ethylamide, ethanesulfonic acid 2-ethylamide, N-2 ethyl methanesulfonamide, 2-methyl-propane-2-sulfonic acid 2-ethylamide, 2-methyl-propane-2-sulfinic acid 2-ethylamide, 2-methyl-propane-1-sulfonic acid 2-ethylamide, cyclopropanesulfonic acid 2-ethylamide, 3-propane-1-sulfonic acid isopropylamide, 3-propane-1-sulfonic acid ethylamide, 3-propane-1-sulfonic acid methylamide, 3-propane-1-sulfonic acid amide, 3-propane-1-sulfonic acid t-butylamide, 3-propane-1-sulfonic acid isobutylamide, 3-propane-1-sulfonic acid cyclopropylamide, propane-2-sulfonic acid 3-propylamide, ethanesulfonic acid 3-propylamide, N-3-propyl methanesulfonamide, 2-methyl-propane-2-sulfonic acid 3-propylamide, 2-methyl-propane-2-sulfinic acid 3-propylamide, 2-methyl-propane-1-sulfonic acid 3-propylamide, cyclopropanesulfonic acid 3-propylamide, 3-N-isopropyl propionamide, 3-N-ethyl propionamide, 3-N-methyl propionamide, 3-propionamide, 3-N-t-butyl propionamide, 3-N-isobutyl propionamide, 3-N-cyclopropyl propionamide, N-2-ethyl isobutyramide, N-2-ethyl propionamide, N-2-ethyl acetamide, N-2-ethyl formamide, N-2-ethyl 2,2-dimethyl-propionamide, N-2-ethyl 3-methylbutyramide, and cyclopropane carboxylic acid 2-ethyl-amide.

In certain embodiments, specific R groups include without limitation: cyclopropane carboxylic acid 3-propyl-amide, N-3-propyl 2,2-dimethyl-propionamide, N-propyl-2-methyl-propane-2-sulfinamide, t-butanesulfonic acid 3-propylamide, and cyclopropanesulfonic acid 3-propylamide.

In another embodiment, $Z_1$ is CH. In another embodiment, $Z_2$ is CH. In another embodiment, $Z_3$ is CH. In another embodiment, $Z_1$ is N. In another embodiment, $Z_2$ is N. In another embodiment, $Z_3$ is N.

In another embodiment, $Z_1$ and $Z_2$ are each CH. In another embodiment, $Z_1$ and $Z_3$ are each CH. In another embodiment, $Z_2$ and $Z_3$ are each CH. In another embodiment, $Z_1$ and $Z_2$ are each N. In another embodiment, $Z_1$ and $Z_3$ are each N. In another embodiment, $Z_2$ and $Z_3$ are each N.

In another embodiment, $Z_1$ and $Z_2$ are each CH and $Z_3$ is N. In another embodiment, $Z_1$ and $Z_3$ are each CH and $Z_2$ is N. In another embodiment, $Z_2$ and $Z_3$ are each CH and $Z_1$ is N. In another embodiment, $Z_1$ and $Z_2$ are each N and $Z_3$ is CH. In another embodiment, $Z_1$ and $Z_3$ are each N and $Z_2$ is CH. In another embodiment, $Z_2$ and $Z_3$ are each N and $Z_1$ is CH. In another embodiment, $Z_1$, $Z_2$, and $Z_3$ are each CH. In another embodiment, $Z_1$, $Z_2$, and $Z_3$ are each N.

In the structures set forth in Formulae (1) through (6) below, embodiments are provided in which $Z_1$, $Z_2$, and $Z_3$ are each N. These embodiments are intended as exemplary, and are not intended to exclude the above embodiments in which one, two, or three of $Z_1$, $Z_2$, and $Z_3$ is CH with the same substituents or other substituent combinations within the scope of Formulae (IA) and (IB) as set forth above. In particular, embodiments in which $Z_2$ or $Z_3$ are each CH are considered to be within the scope of this disclosure.

B. DEFINITIONS

As used in connection with the present disclosure, the terms used herein have the following meaning:

The terms "alkyl" and "substituted alkyl" are interchangeable unless otherwise specifically noted and refer to substituted and unsubstituted $C_1$-$C_{10}$ straight-chain saturated aliphatic hydrocarbon groups, i.e., groups having 1, 2, 3, 4, 5, 6, 7, 8, 9, or 10 carbon atoms, and substituted and unsubstituted $C_3$-$C_{10}$ branched saturated aliphatic hydrocarbon groups, i.e., groups having 3, 4, 5, 6, 7, 8, 9, or 10 carbon atoms. For example, "alkyl" includes but is not limited to: methyl (Me), ethyl (Et), propyl (Pr), isopropyl, butyl (Bu), tert-butyl, pentyl, hexyl, heptyl, octyl, nonyl, decyl, and the like. In one embodiment, an alkyl is a $C_1$-$C_6$ alkyl, i.e., a group having 1, 2, 3, 4, 5, or 6 carbon atoms. An alkyl can be substituted with 1, 2, or 3 substituents or optionally substituted with 1, 2, or 3 substituents. Illustrative examples of substituted $C_1$-$C_6$ alkyl groups include —$CH_2OH$, —$CF_2OH$, —$CH_2C(CH_3)_2C(O)OCH_3$, —$CF_3$, —$C(O)CF_3$, —$C(O)CH_3$, —$(CH_2)_4SCH_3$, —$CH(C(O)OH)CH_2CH_2C(O)N(CH_3)_{23}$—$(CH_2)_3NHC(O)NH_2$, —$CH_2CH_2$-(4-fluorophenyl), —$CH(OCH_3)CH_2CH_3$, —$CH_2SO_2NH_2$, and —$CH(CH_3)CH_2CH_2OC(O)CH_3$.

The terms "alkenyl" and "substituted alkenyl" are interchangeable unless otherwise specifically noted and refer to substituted and unsubstituted $C_2$-$C_{10}$ straight-chain aliphatic hydrocarbon groups having 1, 2, or 3 carbon-carbon double bonds, i.e., groups having 1, 2, 3, 4, 5, 6, 7, 8, 9, or 10 carbon atoms, and substituted and unsubstituted $C_3$-$C_{10}$ branched aliphatic hydrocarbon groups having 1, 2, or 3 carbon-carbon double bonds, i.e., groups having 3, 4, 5, 6, 7, 8, 9, or 10 carbon atoms. For example, "alkenyl" includes but is not limited to: ethenyl, 1-prop-1-enyl, 1-prop-2-enyl, 2-prop-1-enyl, 1-but-3-enyl, 2-pent-2-enyl, 1-hex-6-enyl, 1-hept-7-enyl, 1-oct-8-enyl, and the like. In one embodiment, an alkenyl is a $C_2$-$C_6$ alkenyl, i.e., a group having 2, 3, 4, 5, or 6 carbon atoms and 1 or 2 carbon-carbon double bonds. An alkenyl can be substituted with 1, 2, or 3 substituents or optionally substituted with 1, 2, or 3 substituents. Illustrative examples of substituted $C_2$-$C_6$ alkenyl groups include —$C(H)=CHCH_2OH$, —$C(H)=CF_2$, —$CH_2C(H)=CH(CH_2)_2CF_2OH$, —$CH_2C(=CH_2)C(O)OCH_3$, —$C(H)=CHCF_3$, —$CH_2CH_2C(H)=CHC(O)CH_3$, —$C(H)=C(CH_3)SCH_3$, —$C(H)=CHC(H)=C(CH_3)C(O)OCH_3$, and —$C(H)=C=CHOC(O)CH_3$.

The terms "alkynyl" and "substituted alkynyl" are interchangeable unless otherwise specifically noted and refer to substituted and unsubstituted $C_2$-$C_{10}$ straight-chain aliphatic hydrocarbon groups having 1, 2, or 3 carbon-carbon triple bonds, i.e., groups having 1, 2, 3, 4, 5, 6, 7, 8, 9, or 10 carbon atoms, and substituted and unsubstituted $C_3$-$C_{10}$ branched aliphatic hydrocarbon groups having 1, 2, or 3 carbon-carbon triple bonds, i.e., groups having 3, 4, 5, 6, 7, 8, 9, or 10 carbon atoms. For example, "alkynyl" includes but is not limited to: ethynyl, 1-prop-1-ynyl, 1-prop-2-ynyl, 2-prop-1-ynyl, 3-prop-1-ynyl, 1-but-3-ynyl, 2-pent-2-ynyl, 1-hex-6-ynyl, 1-hept-7-ynyl, 1-oct-8ynyl, and the like. In one embodiment, an alkynyl is a $C_2$-$C_6$ alkynyl, i.e., a group having 2, 3, 4, 5, or 6 carbon atoms and 1 or 2 carbon-carbon triple bonds. An alkynyl can be substituted with 1, 2, or 3 substituents or optionally substituted with 1, 2, or 3 substituents. Illustrative examples of substituted $C_2$-$C_6$ alkynyl groups include —$C≡CCH_2OH$, —$C≡CF$, —$CH_2C≡C(CH_2)_2CF_2OH$, $C≡CCH_2C(O)OCH_3$, $CH_2C≡CCF_3$, —$CH_2CH_2C≡CC(O)CH_3$, $C≡CSCH_3$, and —$C≡CC(O)OC(O)CH_3$.

The terms "cycloalkyl" and "substituted cycloalkyl" are interchangeable unless otherwise specifically noted and refer to a mono- or multi-ringed carbocycle wherein each ring contains 3, 4, 5, 6, 7, 8, 9, or 10 carbon atoms, and wherein any ring can contain 1, 2, or 3 carbon-carbon double or triple bonds. For example, "cycloalkyl" includes but is not limited to: cyclopropyl, cyclobutyl, cyclopentyl, cyclohexyl, cycloalkenyl, cycloalkynyl, and cycloheptyl. A cycloalkyl can be substituted with 1, 2, or 3 substituents or optionally substituted with 1, 2, or 3 substituents.

The term "amino" refers to the group —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Optionally the amino group can be protonated to provide a compound in salt form. A protonated amino group, being positively charged, is usually associated with an anion known to those in the art, such as OH⁻, Cl⁻, Br⁻, $CH_3C(O)O^-$, $H_2PO_4^-$, or $HSO_4^-$.

The terms "aryl" and "substituted aryl" are interchangeable unless otherwise specifically noted and refer to a monocyclic, polycyclic, biaryl aromatic groups covalently attached at any ring position capable of forming a stable covalent bond, certain preferred points of attachment being apparent to those in the art (e.g., 3-phenyl, 4-naphthyl, and the like). An aryl can be substituted with 1, 2, or 3 substituents or optionally substituted with 1, 2, or 3 substituents. The definition of "aryl" includes but is not limited to heteroaryl. Illustrative examples of aryl groups include phenyl, biphenyl, naphthyl, dihydronaphthyl, tetrahydronaphthyl, indenyl, indanyl, azulenyl, anthryl, phenanthryl, fluorenyl, pyrenyl, anthracenyl, pyridyl, pyrimidyl, pyridizinyl, thiadiazolyl, and the like.

The term "heteroalkyl" refers to an alkyl group where one or more of the carbon atoms or hydrogen atoms present is replaced, independently, with a nitrogen, oxygen, sulfur, or halogen heteroatom. If the heteroatom does not have the same number of valence sites as the carbon atom it replaces, the number of hydrogens bonded to the replacement heteroatom may need to be increased or decreased to match the number of valence sites of the heteroatom. For example, if a carbon atom (with a valence of four) is replaced by a nitrogen atom (valence of three), one of the hydrogen atoms formerly attached to the replaced carbon is deleted. Likewise, if a carbon atom is replaced by a halogen atom (valence of one), three of the hydrogen atoms formerly attached to the replaced carbon is deleted. The term "heteroalkyl" also refers to (1) an alkyl group where at least one of the hydrogen atoms attached to a carbon or (2) to a heteroalkyl group where at least one of the hydrogen atoms attached to a heteroatom of the heteroalkyl can be substituted with at least one of the following: alkyl, aryl, and heteroalkyl.

The terms "heteroaryl" and "substituted heteroaryl" are interchangeable unless otherwise specifically noted and the terms "heterocyclo" and "substituted heterocyclo" are interchangeable unless otherwise specifically noted and these terms refer to a monovalent unsaturated group having a single ring or multiple condensed rings, from 1 to 8 carbon atoms, and from 1 to 4 heteroatoms within the ring, each heteroatom being independently selected from nitrogen, sulfur, or oxygen. In either heteroaryl or heterocyclo, the point of attachment to the molecule can be at a heteroatom or elsewhere within the ring. A heteroaryl or heterocyclo can be substituted with 1, 2, or 3 substituents or optionally substituted with 1, 2, or 3 substituents.

Illustrative examples of heteroaryl groups include thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrol-3-yl, pyrrol-1-yl, indolyl, isoindolyl, 3H-indolyl, indolinyl, indolizinyl, indazolyl, imidazolyl, imidazol-4-yl, 2H-imidazolinyl, benzimidazolyl, pyridyl, pyrazinyl, pyradazinyl, pyrimidinyl, pyrimidin-2-yl, triazinyl, quinolyl, isoquinolyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, pyrazol-3-yl, triazolyl, 1,2,4-triazol-1-yl, tetrazolyl, tetrazol-1-yl, thiazolyl, thiazol-4-yl, isothiazolyl, benzthiazolyl, oxazolyl, oxazol-2-yl, isoxazolyl, isoxazol-3-yl, benzoxazolyl, oxadiazolyl, 1,2,4-oxadiazol-3-yl, thiadiazolyl, pyridazin-4-yl, pyrazin-2-yl, thiophen-2-yl, furan-2-yl, pyridin-2-yl, pyridin-4-yl, pyrimidin-2-yl, and the like.

When any group is substituted with 1, 2, or 3 substituents or optionally substituted with 1, 2, or 3 substituents, each substituent is independently selected from the group comprising halo, —OH, —SH, —CN, —NO₂, —NH₂, trihalomethyl, pentahaloethyl, $arylC_0$-$C_{10}alkyl$, $C_0$-$C_{10}alkyloxyC_0$-$C_{10}alkyl$, $arylC_0$-$C_{10}alkyloxyC_0$-$C_{10}alkyl$, $C_0$-$C_{10}alkylthioC_0$-$C_{10}alkyl$, $arylC_0$-$C_{10}alkylthioC_0$-$C_{10}alkyl$, $C_0$-$C_{10}alkylaminoC_0$-$C_{10}alkyl$, $arylC_0$-$C_{10}alkylaminoC_0$-$C_{10}alkyl$, N-aryl-N—$C_0$-$C_{10}alkylaminoC_0$-$C_{10}alkyl$, $C_1$-$C_{10}alkylcarbonylC_0$-$C_{10}alkyl$, $arylC_1$-$C_{10}alkylcarbonylC_0$-$C_{10}$ alkyl, $C_1$-$C_{10}alkylcarboxyC_0$-$C_{10}alkyl$, $arylC_1$-$C_{10}alkylcarboxyC_0$-$C_{10}$ alkyl, $C_1$-$C_{10}alkylcarbonylaminoC_0$-$C_{10}alkyl$, $arylC_1$-$C_{10}alkylcarbonylaminoC_0$-$C_{10}alkyl$, —$C_0$-$C_{10}alkylC(O)OR_X$, and —$C_0$-$C_{10}alkylC(O)NR_YR_Z$ wherein $R_X$, $R_Y$ and $R_Z$ are independently selected from hydrogen, alkyl, and aryl or $R_Y$ and $R_Z$ are taken together with the nitrogen to which they are attached to form a saturated cyclic or unsaturated cyclic system having 3, 4, 5, 6, 7, or 8 carbon atoms with at least one substituent as defined above. A "$C_0$ alkyl," as in $C_0$-$C_{10}alkyl$, is a covalent bond.

The term "$C_0$-$C_{10}alkyloxy$" refers to an alkyl group having the indicated number of carbon atoms and attached to the molecule through an oxygen atom. In one embodiment, a $C_0$-$C_{10}$ alkyloxy is a $C_1$-$C_6alkyloxy$, i.e., a group having 1, 2, 3, 4, 5, or 6 carbon atoms. Illustrative examples of alkyloxy groups include methoxy, ethoxy, n-propyloxy, and isopropyloxy. Thus, the term "$C_0$-$C_{10}alkyloxyC_0$-$C_{10}alkyl$" refers to a $C_0$-$C_{10}alkyloxy$ attached through an oxygen atom to a $C_0$-$C_{10}alkyl$ which is attached to the molecule. Likewise, the term "$arylC_0$-$C_{10}alkyloxyC_0$-$C_{10}alkyl$" refers to a $C_0$-$C_{10}alkyloxy$, which is substituted by aryl, attached through an oxygen atom to a $C_0$-$C_{10}alkyl$ which is attached to the molecule. A "$C_0alkyloxy$" is —OH.

The term "$C_0$-$C_{10}alkylthio$" refers to an alkyl group having the indicated number of carbon atoms and attached to the molecule through a sulfur atom. In one embodiment, a $C_0$-$C_{10}alkylthio$ is a $C_1$-$C_6alkylthio$, i.e., a group having 1, 2, 3, 4, 5, or 6 carbon atoms. Illustrative examples of alkyloxy groups include methylthio, ethylthio, n-propylthio, and isopropylthio. Thus, the term "$C_0$-$C_{10}alkylthioC_0$-$C_{10}alkyl$" refers to a $C_0$-$C_{10}alkylthio$ attached through a sulfur atom to a $C_0$-$C_{10}alkyl$ which is attached to the molecule. Likewise, the term "$arylC_0$-$C_{10}alkylthioC_0$-$C_{10}alkyl$" refers to a $C_0$-$C_{10}alkylthio$, which is substituted by aryl, attached through a sulfur atom to a $C_0$-$C_{10}alkyl$ which is attached to the molecule. A "$C_0alkylthio$" is —SH.

The term "$C_1$-$C_{10}alkylcarbonyl$" refers to an alkyl group having the indicated number of carbon atoms and attached to the molecule through the carbon atom of a carbonyl group. In one embodiment, a $C_1$-$C_{10}alkylcarbonyl$ is a $C_1$-$C_6alkylcarbonyl$, i.e., a group having 1, 2, 3, 4, 5, or 6 carbon atoms, including the carbonyl carbon atom. Thus, the term "$C_1$-$C_{10}alkylcarbonylC_0$-$C_{10}alkyl$" refers to a $C_1$-$C_{10}alkylcarbonyl$ attached through the carbon atom of a carbonyl group to a $C_0$-$C_{10}alkyl$ which is attached to the molecule. Likewise, the term "$arylC_1$-$C_{10}alkylcarbonylC_0$-$C_{10}alkyl$" refers to a $C_1$-$C_{10}alkylcarbonyl$, which is substituted by aryl, attached through the carbon atom of a carbonyl group to a $C_0$-$C_{10}alkyl$ which is attached to the molecule.

The term "$C_1$-$C_{10}alkylcarboxy$" refers to an alkyl group having the indicated number of carbon atoms, including the carboxy's carbon atom, and attached to the molecule through the carboxy group, wherein the carboxy group has either a —C(=O)—O— or a —O—C(=O)— orientation. In one embodiment, a $C_1$-$C_{10}alkylcarboxy$ is a $C_1$-$C_6alkylcarboxy$, i.e., a group having 2, 3, 4, 5, or 6 carbon atoms, including the carboxy's carbon atom. Thus, the term "$C_1$-$C_{10}$ alkylcarboxy$C_0$-$C_{10}$alkyl" refers to a $C_1$-$C_{10}$alkylcarboxy attached through the carboxy group to a $C_0$-$C_{10}$alkyl which is attached to the molecule. Likewise, the term "aryl$C_1$-$C_{10}$alkylcarboxy$C_0$-$C_{10}$alkyl" refers to a $C_1$-$C_{10}$alkylcarboxy, which is substituted by aryl, attached through the carboxy group to a $C_0$-$C_{10}$ alkyl which is attached to the molecule.

The term "$C_0$-$C_{10}$alkylamino" refers to an alkyl group having the indicated number of carbon atoms and attached to the molecule through the nitrogen atom of the amino group —N($R_W$)—, wherein $R_W$ is H, $C_1$-$C_6$alkyl, or aryl. A "$C_0$alkylamino" is —NH$R_W$. In one embodiment, a $C_0$-$C_{10}$alkylamino is a $C_1$-$C_6$alkylamino, i.e., a group having 1, 2, 3, 4, 5, or 6 carbon atoms in the alkyl group and 0, 1, 2, 3, 4, 5, or 6 carbon atoms in the $R_W$ group. Thus, the term "$C_0$-$C_{10}$alkylamino$C_0$-$C_{10}$alkyl" refers to a $C_0$-$C_{10}$alkylamino attached through the nitrogen atom of an amino group to a $C_0$-$C_{10}$alkyl which is attached to the molecule. Likewise, the term "aryl$C_0$-$C_{10}$alkylamino$C_0$-$C_{10}$alkyl" refers to a $C_0$-$C_{10}$alkylamino, which is substituted by aryl, attached through the nitrogen atom of an amino group to a $C_0$-$C_{10}$alkyl which is attached to the molecule. The term "N-aryl-N—$C_0$-$C_{10}$alkylamino$C_0$-$C_{10}$alkyl" refers to an amine nitrogen atom substituted by aryl and $C_0$-$C_{10}$ alkyl, that nitrogen atom being further attached to a $C_0$-$C_{10}$alkyl which is attached to the molecule.

The term "$C_1$-$C_{10}$alkylcarbonylamino" refers to an alkyl group having the indicated number of carbon atoms, including the carbonylamino's (i.e., amide's) carbon atom, and attached to the molecule through the amide, group, wherein the amide group has either a —C(=O)N($R_V$)— or a —N($R_V$)C(=O)— orientation and wherein $R_V$ is H or $C_1$-$C_6$alkyl. In one embodiment, a $C_1$-$C_{10}$alkylcarbonylamino is a $C_1$-$C_6$alkylcarbonylamino, i.e., a group having 2, 3, 4, 5, or 6 carbon atoms, including the amide's carbon atom, in the alkyl group and 0, 1, 2, 3, 4, 5, or 6 carbon atoms in the $R_V$ group. Thus, the term "$C_1$-$C_{10}$alkylcarbonylamino$C_0$-$C_{10}$alkyl" refers to a $C_1$-$C_{10}$alkylcarbonylamino attached through the amide group to a $C_0$-$C_{10}$alkyl which is attached to the molecule. Likewise, the term "aryl$C_1$-$C_{10}$ alkylcarbonylamino$C_0$-$C_{10}$alkyl" refers to a $C_1$-$C_{10}$alkylcarbonylamino, which is substituted by aryl, attached through the amide group to a $C_0$-$C_{10}$alkyl which is attached to the molecule.

The term "alkylaryl" refers to an aryl group as defined above that is substituted with 1, 2, or 3 alkyl groups as defined above; a tolyl group is an exemplary alkylaryl. In one embodiment, an alkylaryl group is a "lower alkylaryl" group having 1, 2, or 3 alkyl groups attached to an aryl group, each alkyl group having, independently, 1, 2, 3, 4, 5, or 6 carbon atoms.

The term "arylalkyl" refers to an alkyl group as defined above that is substituted with 1, 2, or 3 aryl groups as defined above; a benzyl group is an exemplary arylalkyl. In one embodiment, an arylalkyl group is a "lower arylalkyl" group having 1, 2, or 3 aryl groups attached to an alkyl group having 1, 2, 3, 4, 5, or 6 carbon atoms.

The term "heterocycloalkyl" refers to an alkyl group as defined above that is substituted with 1, 2, or 3 heterocyclo groups as defined above. In one embodiment, a heterocycloalkyl group is a "lower heterocycloalkyl" group having 1, 2, or 3 heterocyclo groups attached to an alkyl group having 1, 2, 3, 4, 5, or 6 carbon atoms.

The term "alkylheteroaryl" refers to a heteroaryl group as defined above that is substituted with 1, 2, or 3 alkyl groups as defined above. In one embodiment, a alkylheteroaryl group is a "lower alkylheteroaryl" group having 1, 2, or 3 alkyl groups attached to a heteroaryl group, each alkyl group having, independently, 1, 2, 3, 4, 5, or 6 carbon atoms.

The term "heteroarylalkyl" refers to an alkyl group as defined above that is substituted with 1, 2, or 3 heteroaryl groups as defined above. In one embodiment, a heteroarylalkyl group is a "lower heteroarylalkyl" group having 1, 2, or 3 heteroaryl groups attached to an alkyl group having 1, 2, 3, 4, 5, or 6 carbon atoms.

The term "alkylheteroarylalkyl" refers to a heteroarylalkyl group as defined above that is substituted with 1, 2, or 3 alkyl groups as defined above. In one embodiment, an alkylheteroarylalkyl group is a "lower alkylheteroarylalkyl" group with each alkyl portion having, independently, 1, 2, 3, 4, 5, or 6 carbon atoms.

The terms "halogen" and "halo" refer to fluorine, chlorine, bromine, and iodine.

An R group disclosed to be "interrupted by —S(O)N($R_A$)—, —$NR_A$S(O)—, —$SO_2$N($R_A$)—, —$NR_A$$SO_2$—, —C(O)N($R_A$)—, and —$NR_A$C(O)—, and/or terminated by —S(O)$NR_A$$R_B$, —$NR_A$S(O)$R_B$, —$SO_2$$NR_A$$R_B$, —$NR_A$$SO_2$$R_B$, —C(O)$NR_A$$R_B$, or —$NR_A$C(O)$R_B$", means said R group is (1) interrupted by one or more (for example 1, 2, or 3) —S(O)N($R_A$)—, —$NR_A$S(O)—, —$SO_2$N($R_A$)—, —$NR_A$$SO_2$—, —C(O)N($R_A$)—, or —$NR_A$C(O)— groups, (2) terminated by —S(O)$NR_A$$R_B$, —$NR_A$S(O)$R_B$, —$SO_2$$NR_A$$R_B$, —$NR_A$$SO_2$$R_B$, —C(O)$NR_A$$R_B$, or —$NR_A$C(O)$R_B$ groups, or (3) interrupted by one or more (for example 1, 2, or 3) —S(O)N($R_A$)—, —$NR_A$S(O)—, —$SO_2$N($R_A$)—, —$NR_A$$SO_2$—, —C(O)N($R_A$)—, or —$NR_A$C(O)— groups and terminated by an —S(O)$NR_A$$R_B$, —$NR_A$S(O)$R_B$, —$SO_2$$NR_A$$R_B$, —$NR_A$$SO_2$$R_B$, —C(O)$NR_A$$R_B$, or —$NR_A$C(O)$R_B$ group. In one embodiment, there are two interruptions and no terminations of an alkyl R group as described above. In another embodiment, there is one interruption and no terminations of an alkyl R group as described above. In another embodiment, there is no interruption and a termination of an alkyl R group as described above. In another embodiment, there is one interruption and a termination of an alkyl R group as described above.

Should there be doubt as to the agreement of a depicted chemical structure and a chemical name, the depicted chemical structure governs.

The term "pharmaceutically acceptable salt" refers to those salts which retain the biological effectiveness and properties of the "free" compounds of Formulae (IA) and (IB). A pharmaceutically acceptable salt can be obtained from the reaction of the free base of a Compound of Formulae (IA) or (IB) with an inorganic acid, for example, hydrochloric acid, hydrobromic acid, sulfuric acid, nitric acid, phosphoric acid, and the like, or an organic acid, for example, sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g., (+)-tartaric acid or (−)-tartaric acid or mixtures thereof), and the like. Certain compounds of Formulae (IA) and (IB) have acidic substituents and can exist as pharmaceutically acceptable salts with pharmaceutically acceptable bases. The present disclosure includes such salts. Examples of such salts include metal counterion salts, such as sodium, potassium, lithium, magnesium, calcium, iron, copper, zinc, tin, silver, or aluminum salts, and organic amine salts, such as methylamine, dimethylamine, trimethylamine, diethylamine, triethylamine, n-propylamine, 2-propylamine, or dimethylisopropylamine salts, and the like. The term "pharmaceutically acceptable salt" includes mono-salts and compounds in which a plurality of salts is present, e.g., di-salts and/or tri-salts. Pharmaceutically acceptable salts can be prepared by methods known to those in the art.

Certain compounds of Formulae (IA) and (IB) and/or their pharmaceutically acceptable salts can exist in more than one crystal form and the present disclosure encompasses each crystal form and mixtures thereof. These crystal forms can be prepared by methods known to those in the art.

The term "solvate" refers to a complex or aggregate formed by one or more molecules of a solute, e.g., a Compound of Formulae (IA) or (IB) or its pharmaceutically acceptable salt, and one or more molecules of a solvent, which is present in stoichiometric or non-stoichiometric amount. Suitable solvents include but are not limited to water, acetic acid, ethanol, methanol, isopropanol, and n-propanol. Where the solvent is water, the solvate is a hydrate. Exemplary hydrates include but are not limited to a hemihydrate, a monohydrate, a dihydrate, a trihydrate, and a tetrahydrate. In one embodiment, the solvent is pharmaceutically acceptable. In another embodiment, the complex or aggregate is in a crystalline form. In another embodiment, the complex or aggregate is in a non-crystalline form. The present disclosure encompasses each solvate and mixtures thereof. These solvates can be prepared by methods known to those in the art.

Certain compounds of Formulae (IA) and (IB) may exist in different tautomeric forms or as different geometric isomers, and the present disclosure includes each tautomer and/or geometric isomer of compounds of Formulae (IA) and (IB) and mixtures thereof.

Certain compounds of Formulae (IA) and (IB) may contain one or more chiral centers and exist in different optically active forms, and the present disclosure includes each optically active form of compounds of Formulae (IA) and (IB) and mixtures thereof. When compounds of Formulae (IA) and (IB) contain one chiral center, the compounds exist in two enantiomeric forms and the present disclosure includes both enantiomers and mixtures of enantiomers, such as racemic mixtures. The enantiomers may be resolved by methods known to the art, for example, by formation of diastereoisomeric salts which may be separated, e.g., by crystallization or liquid chromatography. Alternatively, specific enantiomers may be synthesized by asymmetric synthesis using optically active reagents, substrates, catalysts or solvents, or by converting one enantiomer into the other by asymmetric transformation. When a Compound of Formulae (IA) or (IB) contains more than one chiral center, it may exist in diastereoisomeric forms. The diastereoisomeric compounds may be separated by methods known to the art, for example, by chromatography or crystallization, and the individual enantiomers may be separated as described above. The present disclosure includes each diastereoisomer of compounds of Formulae (IA) and (IB) and mixtures thereof.

The term "isotopically enriched" refers to a Compound of Formulae (IA) or (IB) that contains an unnatural proportion of an isotope at one or more of the atoms constituting the compound, and the present disclosure includes each isotopically enriched form of compounds of Formulae (IA) and (IB) and mixtures thereof. In certain embodiments, an isotopically enriched compound contains unnatural proportions of one or more isotopes, including but not limited to hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In another embodiment, an isotopically enriched compound contains unnatural proportions of one or more isotopes, including but not limited to $^1$H, $^2$H, $^{12}$C, $^{13}$C, $^{14}$N, $^{15}$N, $^{16}$O, $^{17}$O, $^{18}$O, $^{17}$F, $^{32}$S, $^{33}$S, $^{34}$S, $^{36}$S, $^{35}$Cl, $^{37}$Cl, $^{79}$Br, $^{81}$Br, and $^{127}$I. In another embodiment, an isotopically enriched compound is radioactive. In another embodiment, an isotopically enriched compound contains unnatural proportions of one or more isotopes, including but not limited to $^3$H, $^{11}$C, $^4$C, $^{13}$N, $^{14}$O, $^{15}$O, $^{11}$F, $^{35}$S, $^{36}$Cl, $^{123}$I, $^{125}$I, $^{129}$I, and $^{131}$I. In another embodiment, an isotopically enriched compound contains unnatural proportions of $^{123}$I, $^{124}$I, or $^{131}$I and another isotope selected from $^3$H, $^{11}$C, $^4$C, $_{13}$N, $^{14}$O, $^{15}$O, $^{18}$F, $^{35}$S, and $^{36}$Cl. In another embodiment, an isotopically enriched compound contains an unnatural proportion of $^{123}$I, $^{124}$I, and/or $^{131}$I. In another embodiment, an isotopically enriched compound contains an unnatural proportion of $^{123}$I. In another embodiment, an isotopically enriched compound contains an unnatural proportion of $^{124}$I. In another embodiment, an isotopically enriched compound contains an unnatural proportion of $^{131}$I.

The term "isotopically enriched" refers to the percentage of incorporation of a less prevalent isotope (e.g., deuterium for hydrogen) of an element at a given location in a molecule in place of a more prevalent isotope (e.g., $^1$H for hydrogen) of that element. When an atom at a particular location in a molecule is designated as a particular less prevalent isotope, it is understood that the abundance of that isotope at that location is substantially greater than its natural abundance.

The term "therapeutically effective amount" refers to an amount of a Compound of Formulae (IA) or (IB) or a combination of two or more such compounds that inhibits, totally or partially, the progression of the treated condition or alleviates, at least partially, one or more symptoms of the condition. A therapeutically effective amount can also be an amount which is prophylactically effective. The amount which is therapeutically effective depends on the patient's gender and size, the condition to be treated, the condition's severity, and the result sought. For a given patient, a therapeutically effective amount can be determined by methods known to those in the art.

The term "patient" refers to an animal, including but not limited to a mammal, a primate (e.g., a human), cow, pig, sheep, goat, horse, dog, cat, rabbit, rat, or mouse.

The term "cancer" or "neoplastic disorder" refers to a tumor resulting from abnormal or uncontrolled cellular growth. Examples of cancers include but are not limited to breast cancers, colon cancers, colorectal cancers, prostate cancers, ovarian cancers, pancreatic cancers, lung cancers, gastric cancers, esophageal cancers, glioma cancers, and hematologic malignancies. Examples of neoplastic disorders include but are not limited to hematopoietic disorders, such as the myeloproliferative disorders, essential thrombocytosis, thrombocythemia, angiogenic myeloid metaplasia, polycythemia vera, myelofibrosis, myelofibrosis with myeloid metaplasia, chronic idiopathic myelofibrosis, the cytopenias, and pre-malignant myelodysplastic syndromes.

The term "hematologic malignancy" refers to cancer of the bone marrow and lymphatic tissue—body's blood-forming and immune system. Examples of hematological malignancies include but are not limited to myelodysplasia, lymphomas, leukemias, lymphomas (non-Hodgkin's lymphoma), Hodgkin's disease (also known as Hodgkin's lymphoma), and myeloma, such as acute lymphocytic leukemia (ALL), adult T-cell ALL, acute myeloid leukemia (AML), AML with trilineage myelodysplasia, acute promyelocytic leukemia, acute undifferentiated leukemia, anaplastic large-cell lymphoma, chronic lymphocytic leukemia, chronic myeloid leukemia, chronic neutrophilic leukemia, juvenile myelomonocyctic leukemia, mixed lineage leukemia, myeloproliferative disorders, myelodysplastic syndromes, multiple myeloma, and prolymphocytic leukemia.

The term "leukemia" refers to malignant neoplasms of the blood-forming tissues including but not limited to acute lymphoblastic leukemia, acute myeloid leukemia, acute myeloblastic leukemia, chronic lymphocytic leukemia, and chronic myelocytic leukemia. The leukemia can be relapsed, refractory, or resistant to conventional therapy.

The term "neurodegenerative disorder" refers to a disorder in which progressive loss of neurons occurs either in the peripheral nervous system or in the central nervous system. Examples of neurodegenerative disorders include but are not limited to chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoffs related dementia (alcohol induced dementia), Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present disclosure include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including but not limited to epidural, subdural, subarachnoid, and intracerebral), and intracranial and intravertebral lesions (including but not limited to contusion, penetration, shear, compression, and laceration). Thus, the term "neurodegenerative disorder" also encompasses acute neurodegenerative disorders such as those involving stroke, traumatic brain injury, schizophrenia, peripheral nerve damage, hypoglycemia, spinal cord injury, epilepsy, anoxia, and hypoxia.

In certain embodiments, the neurodegenerative disorder is selected from Alzheimer's disease, Parkinson's disease, amyotrophic lateral sclerosis, age-related memory loss, senility, and age-related dementia. In another embodiment, the neurodegenerative disorder is Alzheimer's disease, also characterized as an amyloidosis. Thus, other embodiments of the disclosure relate to the treatment or prevention of other amyloidosis disorders which share features, including, but not limited to, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, Finnish amyloidosis, and Iowa amyloidosis.

The term "pharmaceutically acceptable carrier" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or an organ of a patient without excessive toxicity, irritation, allergic response, immunogenicity, or other problems or complications, commensurate with a reasonable benefit/risk ratio. Pharmaceutically acceptable carriers are known in the art; see, e.g., *Pharmaceutical Preformulation and Formulation* (Gibson, ed., Ed., CRC Press, Boca Raton, Fla., 2009); *Handbook of Pharmaceutical Additives* (Ash and Ash, eds., 3$^{rd}$ Ed., Gower Publishing Co., Aldershot, UK, 2007); *Remington's Pharmaceutical Sciences* (Gennaro, ed., 19$^{th}$ Ed., Mack Publishing, Easton, Pa., 1995); and *Handbook of Pharmaceutical Excipients* (Amer. Pharmaceutical Ass'n, Washington, D.C., 1986).

C. COMPOUNDS OF FORMULA (IA) IN WHICH XA AND XB ARE EACH O

In accordance with an embodiment of the disclosure, the compounds are of Formula (IA) in which Xa and Xb are each O and Xc is $CH_2$. In certain embodiments, the compounds of this embodiment can be represented by Formula (1):

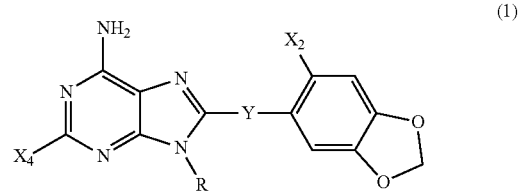

(1)

or a pharmaceutically acceptable salt thereof, wherein:

Y is $CH_2$ or S;

$X_4$ is hydrogen or halogen;

R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_AS(O)$—, —$SO_2N(R_A)$—, —$NR_ASO_2$—, —C(O)N($R_A$)—, or —$NR_AC(O)$—, and/or terminated by —S(O)$NR_AR_B$, —$NR_AS(O)R_B$, —$SO_2NR_AR_B$, —$NR_ASO_2R_B$, —C(O)$NR_AR_B$, or —$NR_AC(O)R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and $X_2$ is as disclosed below.

C-I. In some embodiments of the disclosure, $X_2$ is halogen. Table 1A lists specific examples of compounds within this embodiment. In each of the structures as drawn, $X_2$ is I and $X_4$ is H. However, corresponding structures in which $X_2$ is F, Cl, or Br are within the scope of the disclosure. In each of the structures in Table 1A, Y is S. However, corresponding structures in which Y is $CH_2$ and/or $X_4$ is F, Cl, Br, or I are also within the scope of the disclosure. Additionally, in connection with each of the structures in Table 1A, corresponding structures in which $X_2$ is F, Cl, or Br and Y is $CH_2$ are also within the scope of the disclosure.

TABLE 1A

| Compound No. | Structure | Name |
| --- | --- | --- |
| 1A-1 | 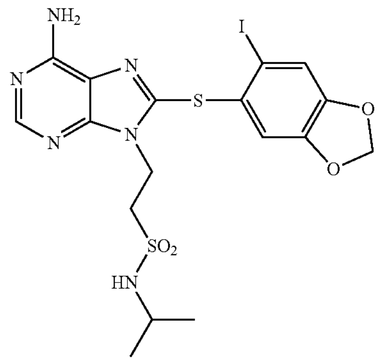 [SMILES: CC(C)NS(=O)(=O)CCn1c(Sc2cc3c(cc2I)OCO3)nc2c(N)ncnc21] | 2-[6-Amino-8-(6-iodo-benzo[1,3]dioxol-5-ylsulfanyl)-purin-9-yl]-ethanesulfonic acid isopropylamide |
| 1A-2 | 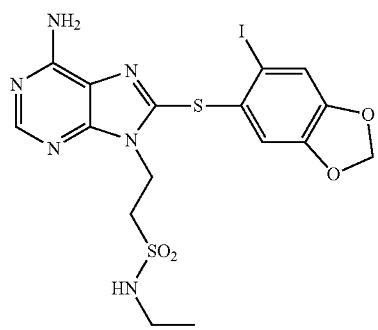 [SMILES: CCNS(=O)(=O)CCn1c(Sc2cc3c(cc2I)OCO3)nc2c(N)ncnc21] | 2-[6-Amino-8-(6-iodo-benzo[1,3]dioxol-5-ylsulfanyl)-purin-9-yl]-ethanesulfonic acid ethylamide |
| 1A-3 | 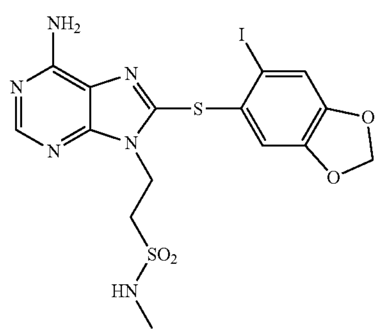 [SMILES: CNS(=O)(=O)CCn1c(Sc2cc3c(cc2I)OCO3)nc2c(N)ncnc21] | 2-[6-Amino-8-(6-iodo-benzo[1,3]dioxol-5-ylsulfanyl)-purin-9-yl]-ethanesulfonic acid methylamide |
| 1A-4 | 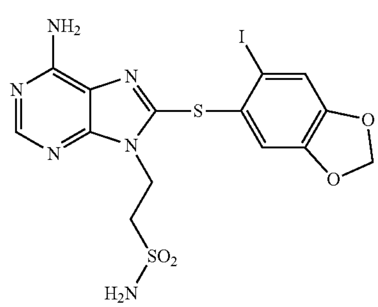 [SMILES: Nc1ncnc2c1nc(Sc1cc3c(cc1I)OCO3)n2CCS(N)(=O)=O] | 2-[6-Amino-8-(6-iodo-benzo[1,3]dioxol-5-ylsulfanyl)-purin-9-yl]-ethanesulfonic acid amide |

TABLE 1A-continued

| Compound No. | Structure | Name |
| --- | --- | --- |
| 1A-5 | 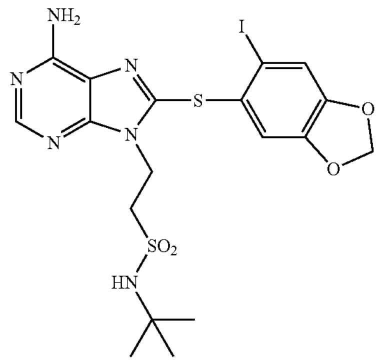 [SMILES: CC(C)(C)NS(=O)(=O)CCn1c(Sc2cc3c(cc2I)OCO3)nc2c(N)ncnc21] | 2-[6-Amino-8-(6-iodo-benzo[1,3]dioxol-5-ylsulfanyl)-purin-9-yl]-ethanesulfonic acid tert-butylamide |
| 1A-6 | 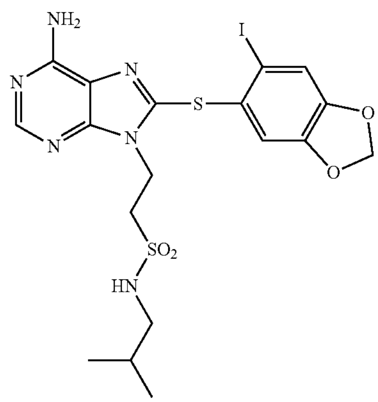 [SMILES: CC(C)CNS(=O)(=O)CCn1c(Sc2cc3c(cc2I)OCO3)nc2c(N)ncnc21] | 2-[6-Amino-8-(6-iodo-benzo[1,3]dioxol-5-ylsulfanyl)-purin-9-yl]-ethanesulfonic acid isobutyl-amide |
| 1A-7 | 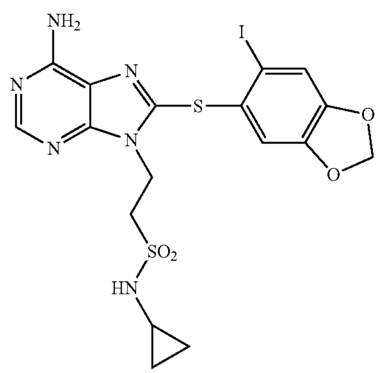 [SMILES: Nc1ncnc2c1nc(Sc1cc3c(cc1I)OCO3)n2CCS(=O)(=O)NC1CC1] | 2-[6-Amino-8-(6-iodo-benzo[1,3]dioxol-5-ylsulfanyl)-purin-9-yl]-ethanesulfonic acid cyclopropylamide |
| 1A-8 | 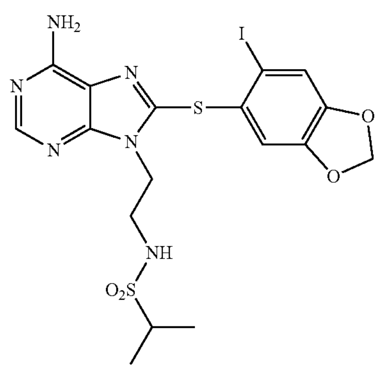 | Propane-2-sulfonic acid {2-[6-amino-8-(6-iodo-benzo[1,3]dioxol-5-ylsulfanyl)-purin-9-yl]-ethyl}-amide |

TABLE 1A-continued

| Compound No. | Structure | Name |
| --- | --- | --- |
| 1A-9 | 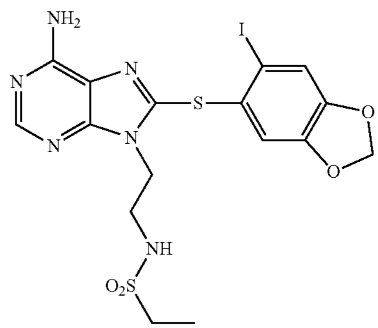 [SMILES: CCS(=O)(=O)NCCn1c(Sc2cc3c(cc2I)OCO3)nc2c(N)ncnc21] | Ethanesulfonic acid {2-[6-amino-8-(6-iodo-benzo[1,3]dioxol-5-ylsulfanyl)-purin-9-yl]-ethyl}-amide |
| 1A-10 | 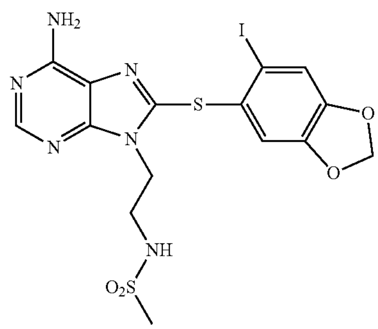 [SMILES: CS(=O)(=O)NCCn1c(Sc2cc3c(cc2I)OCO3)nc2c(N)ncnc21] | N-{2-[6-Amino-8-(6-iodo-benzo[1,3]dioxol-5-ylsulfanyl)-purin-9-yl]-ethyl}-methanesulfonamide |
| 1A-11 | 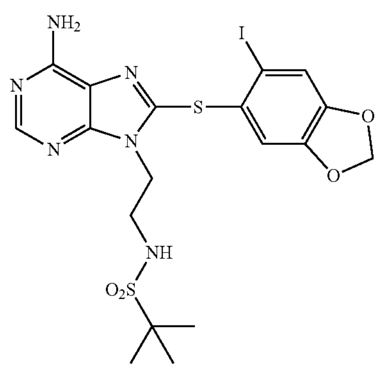 | 2-Methyl-propane-2-sulfonic acid {2-[6-amino-8-(6-iodo-benzo[1,3]dioxol-5-ylsulfanyl)-purin-9-yl]-ethyl}-amide |
| 1A-12 | 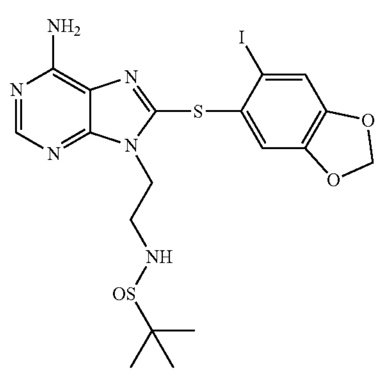 | 2-Methyl-propane-2-sulfonic acid {2-[6-amino-8-(6-iodo-benzo[1,3]dioxol-5-ylsulfanyl)-purin-9-yl]-ethyl}-amide |

TABLE 1A-continued

| Compound No. | Structure | Name |
|---|---|---|
| 1A-13 | 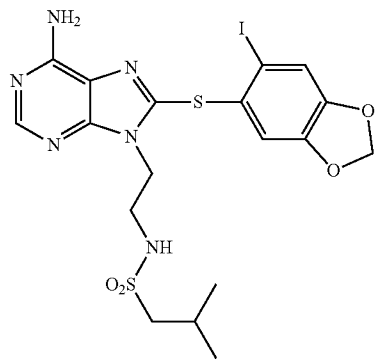 | 2-Methyl-propane-1-sulfonic acid {2-[6-amino-8-(6-iodo-benzo[1,3]dioxol-5-ylsulfanyl)-purin-9-yl]-ethyl}-amide |
| 1A-14 | 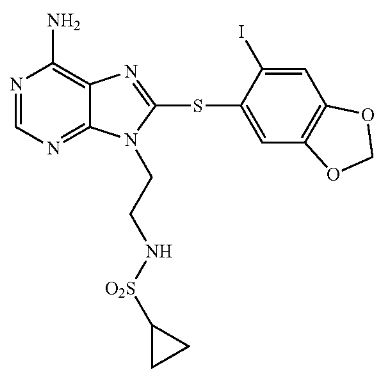 [SMILES: Nc1ncnc2c1nc(Sc1cc3c(cc1I)OCO3)n2CCNS(=O)(=O)C1CC1] | Cyclopropanesulfonic acid {2-[6-amino-8-(6-iodo-benzo[1,3]dioxol-5-ylsulfanyl)-purin-9-yl]-ethyl}-amide |
| 1A-15 | 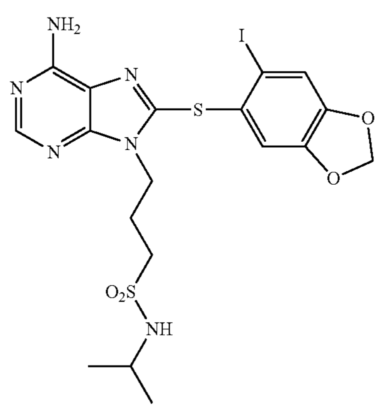 | 3-[6-Amino-8-(6-iodo-benzo[1,3]dioxol-5-ylsulfanyl)-purin-9-yl]-propane-1-sulfonic acid isopropylamide |
| 1A-16 | 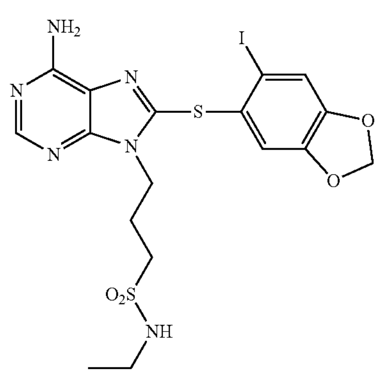 [SMILES: CCNS(=O)(=O)CCCn1c(Sc2cc3c(cc2I)OCO3)nc2c(N)ncnc21] | 3-[6-Amino-8-(6-iodo-benzo[1,3]dioxol-5-ylsulfanyl)-purin-9-yl]-propane-1-sulfonic acid ethylamide |

TABLE 1A-continued

| Compound No. | Structure | Name |
|---|---|---|
| 1A-17 | 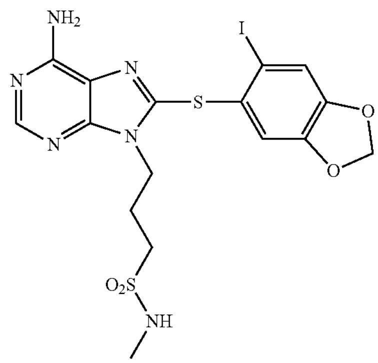 | 3-[6-Amino-8-(6-iodo-benzo[1,3]dioxol-5-ylsulfanyl)-purin-9-yl]-propane-1-sulfonic acid methylamide |
| 1A-18 | 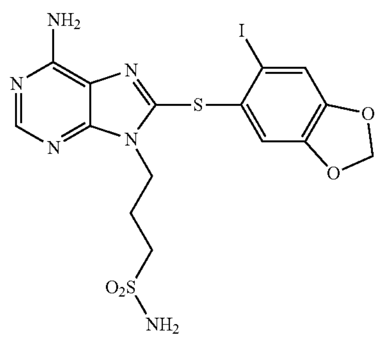 [SMILES: Nc1ncnc2c1nc(Sc1cc3c(cc1I)OCO3)n2CCCS(N)(=O)=O] | 3-[6-Amino-8-(6-iodo-benzo[1,3]dioxol-5-ylsulfanyl)-purin-9-yl]-propane-1-sulfonic acid amide |
| 1A-19 | 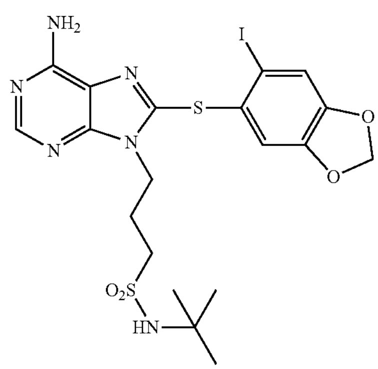 [SMILES: CC(C)(C)NS(=O)(=O)CCCn1c(Sc2cc3c(cc2I)OCO3)nc2c(N)ncnc21] | 3-[6-Amino-8-(6-iodo-benzo[1,3]dioxol-5-ylsulfanyl)-purin-9-yl]-propane-1-sulfonic acid tert-butylamide |
| 1A-20 | 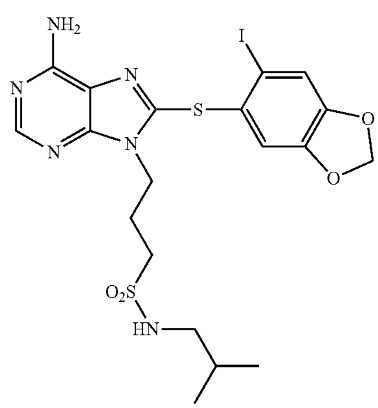 | 3-[6-Amino-8-(6-iodo-benzo[1,3]dioxol-5-ylsulfanyl)-purin-9-yl]-propane-1-sulfonic acid isobutylamide |

TABLE 1A-continued

| Compound No. | Structure | Name |
| --- | --- | --- |
| 1A-21 | 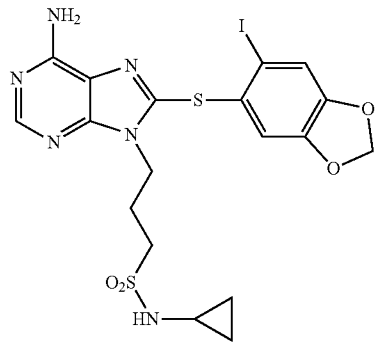 [SMILES: Nc1ncnc2c1nc(Sc1cc3c(cc1I)OCO3)n2CCCS(=O)(=O)NC1CC1] | 3-[6-Amino-8-(6-iodo-benzo[1,3]dioxol-5-ylsulfanyl)-purin-9-yl]-propane-1-sulfonic acid cyclopropylamide |
| 1A-22 | 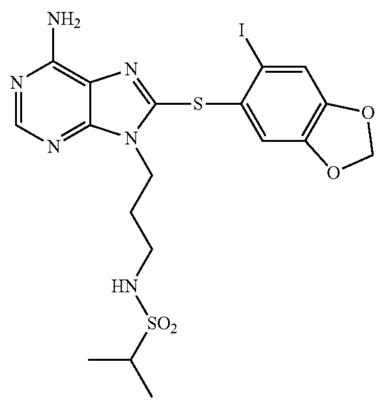 [SMILES: CC(C)S(=O)(=O)NCCCn1c(Sc2cc3c(cc2I)OCO3)nc2c(N)ncnc21] | Propane-2-sulfonic acid {3-[6-amino-8-(6-iodo-benzo[1,3]dioxol-5-ylsulfanyl)-purin-9-yl]-propyl}-amide |
| 1A-23 | 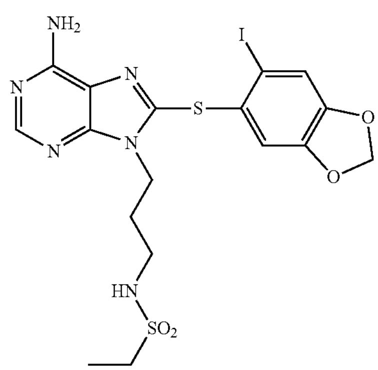 [SMILES: CCS(=O)(=O)NCCCn1c(Sc2cc3c(cc2I)OCO3)nc2c(N)ncnc21] | Ethanesulfonic acid {3-[6-amino-8-(6-iodo-benzo[1,3]dioxol-5-ylsulfanyl)-purin-9-yl]-propyl}-amide |
| 1A-24 | 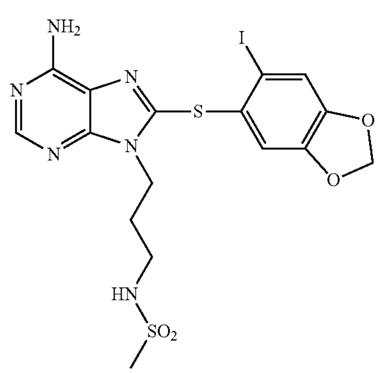 [SMILES: CS(=O)(=O)NCCCn1c(Sc2cc3c(cc2I)OCO3)nc2c(N)ncnc21] | N-{3-[6-Amino-8-(6-iodo-benzo[1,3]dioxol-5-ylsulfanyl)-purin-9-yl]-propyl}-methanesulfonamide |

TABLE 1A-continued

| Compound No. | Structure | Name |
|---|---|---|
| 1A-25 | 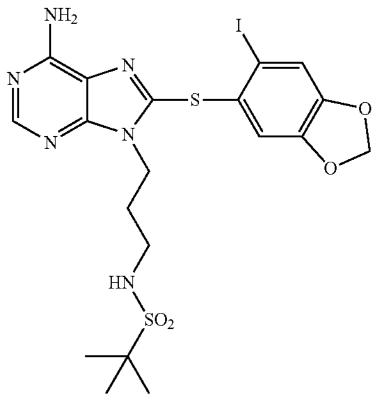 | 2-Methyl-propane-2-sulfonic acid {3-[6-amino-8-(6-iodo-benzo[1,3]dioxol-5-ylsulfanyl)-purin-9-yl]-propyl}-amide |
| 1A-26 | 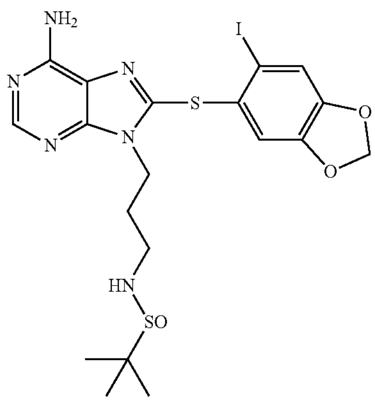 | 2-Methyl-propane-2-sulfinic acid {3-[6-amino-8-(6-iodo-benzo[1,3]dioxol-5-ylsulfanyl)-purin-9-yl]-propyl}-amide |
| 1A-27 | 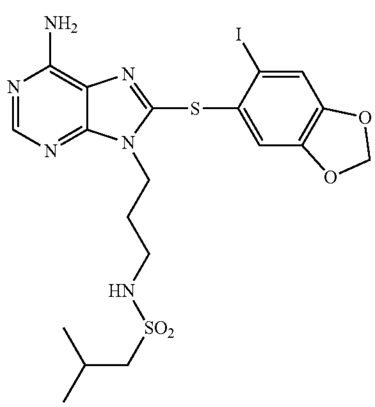 [SMILES: CC(C)CS(=O)(=O)NCCCn1c(Sc2cc3c(cc2I)OCO3)nc2c(N)ncnc21] | 2-Methyl-propane-1-sulfonic acid {3-[6-amino-8-(6-iodo-benzo[1,3]dioxol-5-ylsulfanyl)-purin-9-yl]-propyl}-amide |
| 1A-28 | 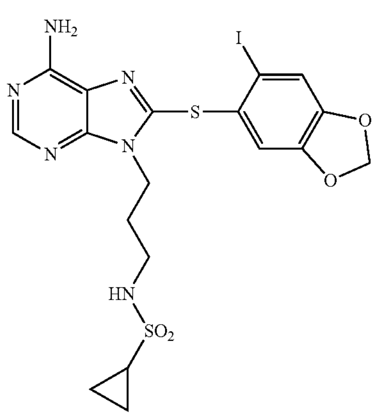 [SMILES: Nc1ncnc2c1nc(Sc1cc3c(cc1I)OCO3)n2CCCNS(=O)(=O)C1CC1] | Cyclopropanesulfonic acid {3-[6-amino-8-(6-iodo-benzo[1,3]dioxol-5-ylsulfanyl)-purin-9-yl]-propyl}-amide |

TABLE 1A-continued

| Compound No. | Structure | Name |
| --- | --- | --- |
| 1A-29 | 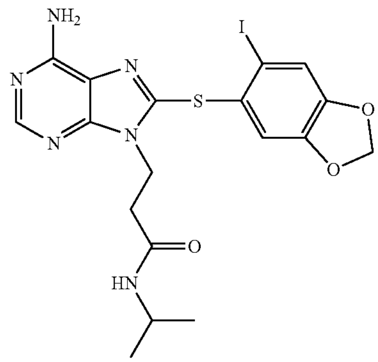 | 3-[6-Amino-8-(6-iodo-benzo[1,3]dioxol-5-ylsulfanyl)-purin-9-yl]-N-isopropyl-propionamide |
| 1A-30 | 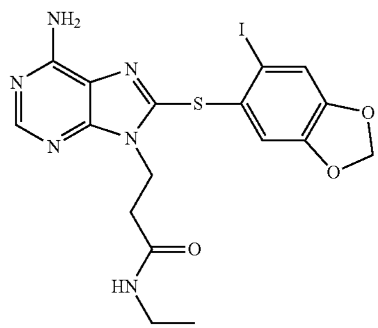 [SMILES: CCNC(=O)CCn1c(Sc2cc3c(cc2I)OCO3)nc2c(N)ncnc21] | 3-[6-Amino-8-(6-iodo-benzo[1,3]dioxol-5-ylsulfanyl)-purin-9-yl]-N-ethyl-propionamide |
| 1A-31 | 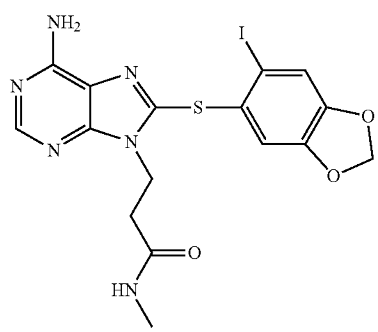 | 3-[6-Amino-8-(6-iodo-benzo[1,3]dioxol-5-ylsulfanyl)-purin-9-yl]-N-methyl-propionamide |
| 1A-32 | 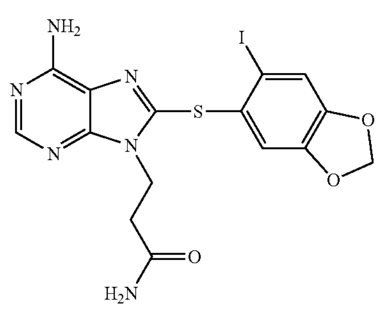 [SMILES: NC(=O)CCn1c(Sc2cc3c(cc2I)OCO3)nc2c(N)ncnc21] | 3-[6-Amino-8-(6-iodo-benzo[1,3]dioxol-5-ylsulfanyl)-purin-9-yl]-propionamide |

TABLE 1A-continued

| Compound No. | Structure | Name |
|---|---|---|
| 1A-33 | 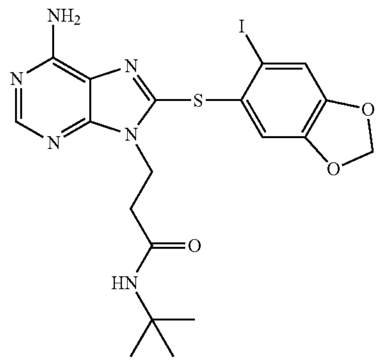 | 3-[6-Amino-8-(6-iodo-benzo[1,3]dioxol-5-ylsulfanyl)-purin-9-yl]-N-tert-butyl-propionamide |
| 1A-34 | 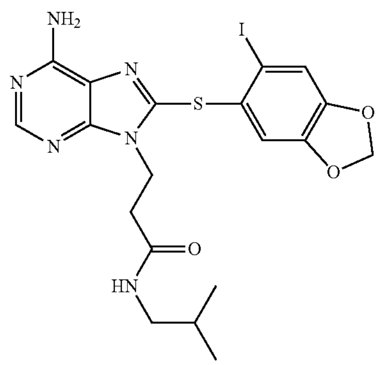 | 3-[6-Amino-8-(6-iodo-benzo[1,3]dioxol-5-ylsulfanyl)-purin-9-yl]-N-isobutyl-propionamide |
| 1A-35 | 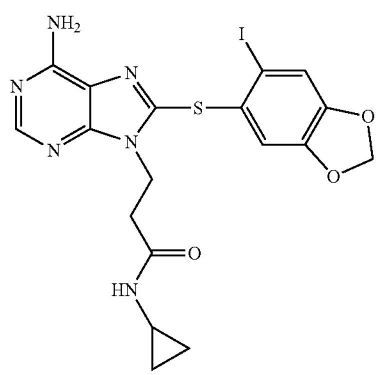 | 3-[6-Amino-8-(6-iodo-benzo[1,3]dioxol-5-ylsulfanyl)-purin-9-yl]-N-cyclopropyl-propionamide |
| 1A-36 | 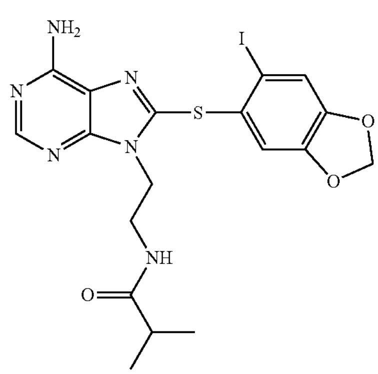 [SMILES: CC(C)C(=O)NCCn1c(Sc2cc3c(cc2I)OCO3)nc2c(N)ncnc21] | N-{2-[6-Amino-8-(6-iodo-benzo[1,3]dioxol-5-ylsulfanyl)-purin-9-yl]-ethyl}-isobutyramide |

TABLE 1A-continued

| Compound No. | Structure | Name |
|---|---|---|
| 1A-37 | 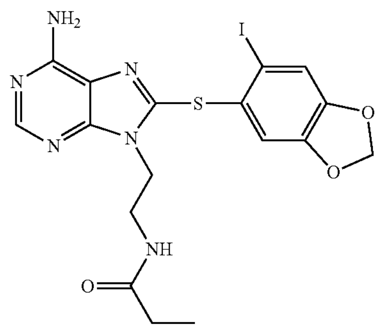 | N-{2-[6-Amino-8-(6-iodo-benzo[1,3]dioxol-5-ylsulfanyl)-purin-9-yl]-ethyl}-propionamide |
| 1A-38 | 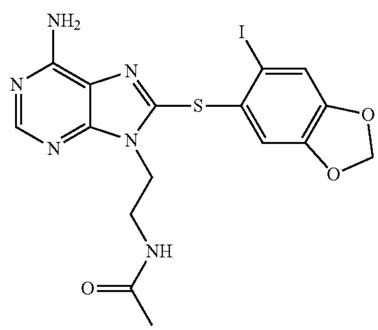 | N-{2-[6-Amino-8-(6-iodo-benzo[1,3]dioxol-5-ylsulfanyl)-purin-9-yl]-ethyl}-acetamide |
| 1A-39 | 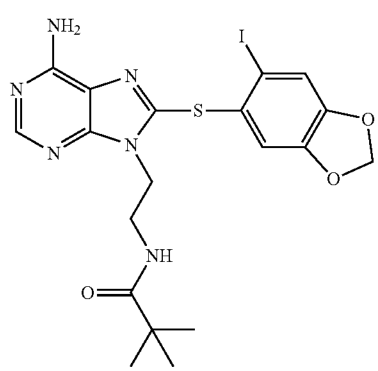 | N-{2-[6-Amino-8-(6-iodo-benzo[1,3]dioxol-5-ylsulfanyl)-purin-9-yl]-ethyl}-2,2-dimethyl-propionamide |
| 1A-40 | 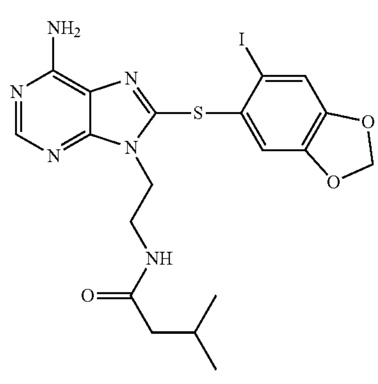 | N-{2-[6-Amino-8-(6-iodo-benzo[1,3]dioxol-5-ylsulfanyl)-purin-9-yl]-ethyl}-3-methyl-butyramide |

TABLE 1A-continued

| Compound No. | Structure | Name |
|---|---|---|
| 1A-41 | 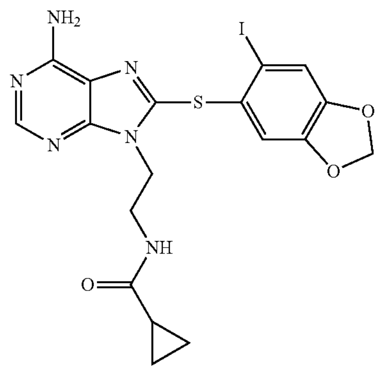 | Cyclopropanecarboxylic acid {2-[6-Amino-8-(6-iodo-benzo[1,3]dioxol-5-ylsulfanyl)-purin-9-yl]-ethyl}-amide |
| 1A-42 | 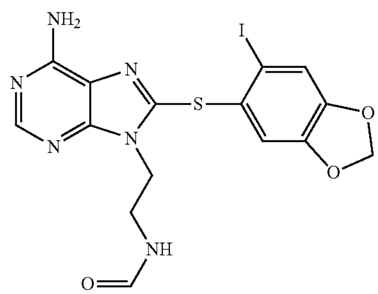 | N-{2-[6-Amino-8-(6-iodo-benzo[1,3]dioxol-5-ylsulfanyl)-purin-9-yl]-ethyl}-formamide |
| 1A-43 | 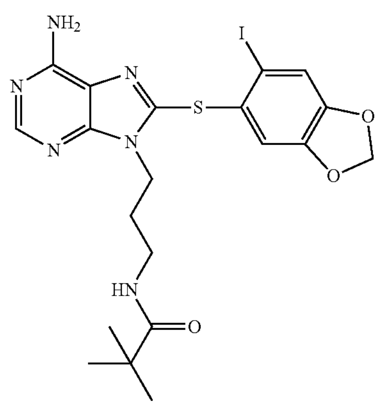 [SMILES: CC(C)(C)C(=O)NCCCn1c(Sc2cc3c(cc2I)OCO3)nc2c(N)ncnc21] | N-(3-(6-amino-8-((6-iodobenzo[d][1,3]dioxol-5-yl)thio)-9H-purin-9-yl)propyl)pivalamide |
| 1A-44 | 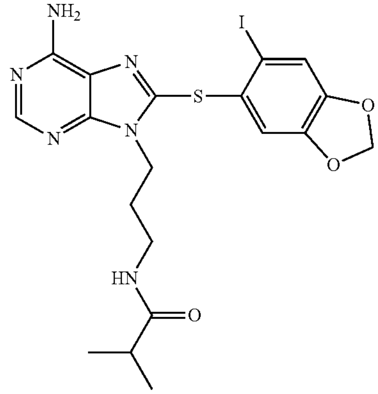 [SMILES: CC(C)C(=O)NCCCn1c(Sc2cc3c(cc2I)OCO3)nc2c(N)ncnc21] | N-(3-(6-Amino-8-((6-iodobenzo[d][1,3]dioxol-5-yl)thio)-9H-purin-9-yl)propyl)isobutyramide |

TABLE 1A-continued

| Compound No. | Structure | Name |
|---|---|---|
| 1A-45 | 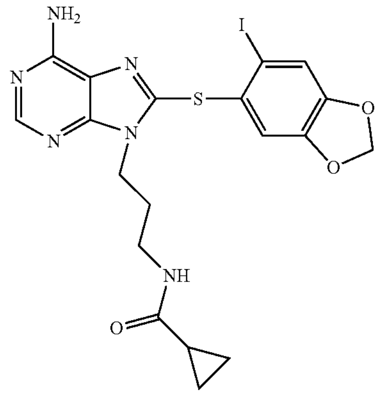 [SMILES: Nc1ncnc2c1nc(Sc1cc3c(cc1I)OCO3)n2CCCNC(=O)C1CC1] | N-(3-(6-amino-8-((6-iodobenzo[d][1,3]dioxol-5-yl)thio)-9H-purin-9-yl)propyl)cyclopropanecarboxamide |
| 1A-46 | 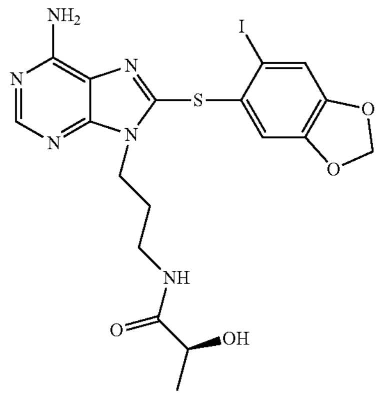 | N-(3-(6-Amino-8-((6-iodobenzo[d][1,3]dioxol-5-yl)thio)-9H-purin-9-yl)propyl)isobutyramide |
| 1A-47 | 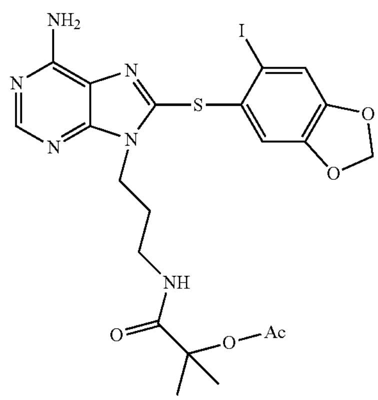 [SMILES: CC(=O)OC(C)(C)C(=O)NCCCn1c(Sc2cc3c(cc2I)OCO3)nc2c(N)ncnc21] | 1-((3-(6-Amino-8-((6-iodobenzo[d][1,3]dioxol-5-yl)thio)-9H-purin-9-yl)propyl)amino-2-methyl-1-oxopropan-2-yl acetate |
| 1A-48 | 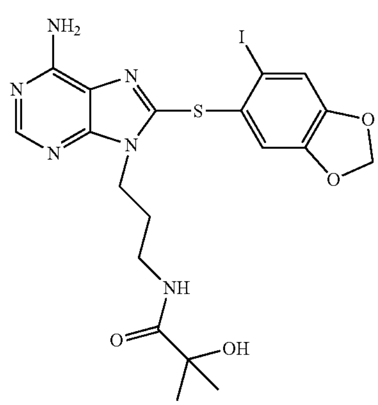 [SMILES: CC(C)(O)C(=O)NCCCn1c(Sc2cc3c(cc2I)OCO3)nc2c(N)ncnc21] | N-(3-(6-amino-8-((6-iodobenzo[d][1,3]dioxol-5-yl)thio)-9H-purin-9-yl)propyl)-2-hydroxy-2-methylpropanamide |

TABLE 1A-continued

| Compound No. | Structure | Name |
|---|---|---|
| 1A-49 | 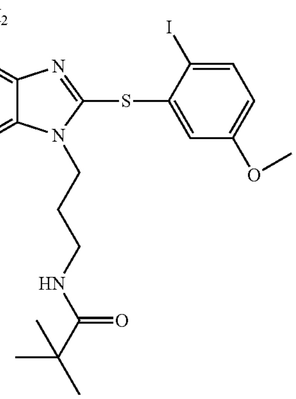 | N-(3-(6-amino-8-((2-iodo-5-methoxyphenyl)thio)-9H-purin-9-yl)propyl)pivalamide |
| 1A-50 | 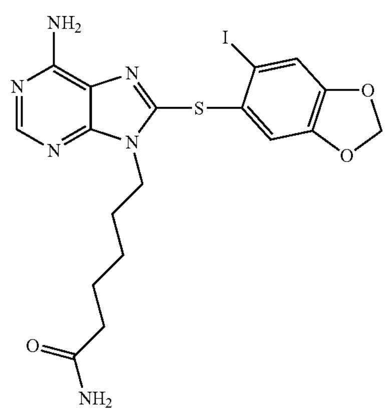 [SMILES: NC(=O)CCCCCn1c(Sc2cc3c(cc2I)OCO3)nc2c(N)ncnc21] | (6-(6-amino-8-((6-iodobenzo[d][1,3]dioxol-5-yl)thio)-9H-purin-9-yl)hexanamide |

Table 4A lists specific examples in which $X_2$ is halogen and $X_4$ is halogen. In each of the structures as drawn, $X_2$ is I and $X_4$ is F. However, corresponding structures in which $X_4$ is H, Cl, Br, or I are within the scope of the disclosure. In each of the structures in Table 4A, Y is $CH_2$. However, corresponding structures in which Y is S and/or $X_2$ is F, Cl, or Br are also within the scope of the disclosure. Additionally, in connection with each of the structures in Table 4A, corresponding structures in which $X_4$ is H, Cl, Br, or I and Y is S are also within the scope of the disclosure.

TABLE 4A

| Compound No. | Structure | Name |
|---|---|---|
| 4A-1 | 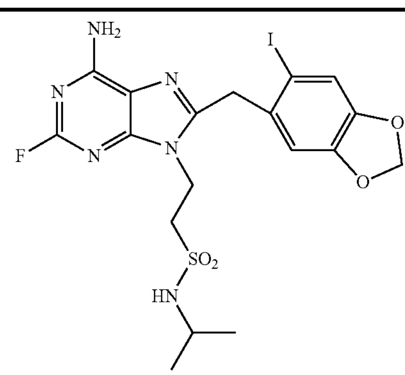 | 2-(6-amino-2-fluoro-8-((6-iodobenzo[d][1,3]dioxol-5-yl)methyl)-9H-purin-9-yl)-N-isopropyl-ethanesulfonamide |

TABLE 4A-continued

| Compound No. | Structure | Name |
| --- | --- | --- |
| 4A-2 | 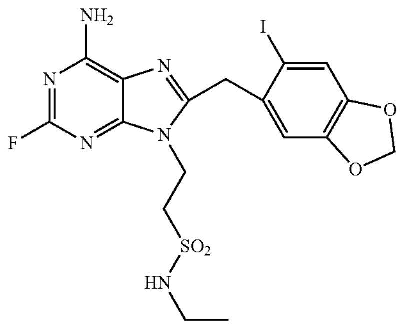 [SMILES: CCNS(=O)(=O)CCn1c(Cc2cc3c(cc2I)OCO3)nc2c(N)nc(F)nc21] | 2-(6-amino-2-fluoro-8-((6-iodobenzo[d][1,3]dioxol-5-yl)methyl)-9H-purin-9-yl)-N-ethylethanesulfonamide |
| 4A-3 | 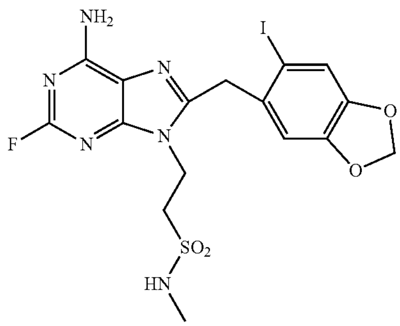 [SMILES: CNS(=O)(=O)CCn1c(Cc2cc3c(cc2I)OCO3)nc2c(N)nc(F)nc21] | 2-(6-amino-2-fluoro-8-((6-iodobenzo[d][1,3]dioxol-5-yl)methyl)-9H-purin-9-yl)-N-methylethanesulfonamide |
| 4A-4 | 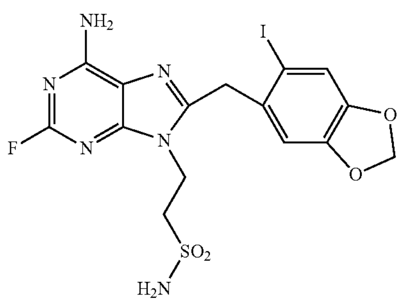 [SMILES: Nc1nc(F)nc2c1nc(Cc1cc3c(cc1I)OCO3)n2CCS(N)(=O)=O] | 2-(6-amino-2-fluoro-8-((6-iodobenzo[d][1,3]dioxol-5-yl)methyl)-9H-purin-9-yl)ethanesulfonamide |
| 4A-5 | 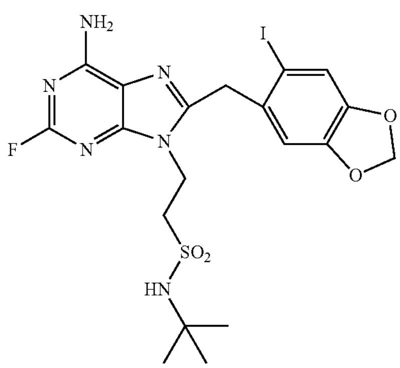 [SMILES: CC(C)(C)NS(=O)(=O)CCn1c(Cc2cc3c(cc2I)OCO3)nc2c(N)nc(F)nc21] | 2-(6-amino-2-fluoro-8-((6-iodobenzo[d][1,3]dioxol-5-yl)methyl)-9H-purin-9-yl)-N-(tert-butyl)ethanesulfonamide |

TABLE 4A-continued

| Compound No. | Structure | Name |
| --- | --- | --- |
| 4A-6 | 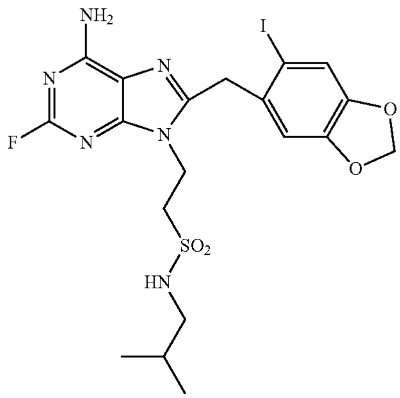 [SMILES: CC(C)CNS(=O)(=O)CCn1c(Cc2cc3c(cc2I)OCO3)nc2c(N)nc(F)nc21] | 2-(6-amino-2-fluoro-8-((6-iodobenzo[d][1,3]dioxol-5-yl)methyl)-9H-purin-9-yl)-N-isobutylethanesulfonamide |
| 4A-7 | 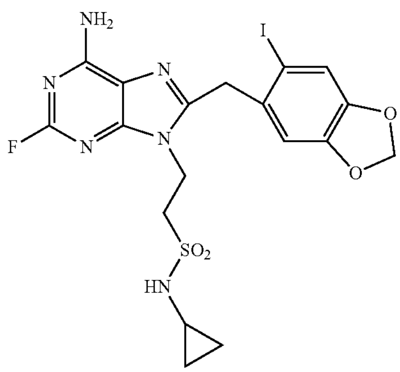 [SMILES: Nc1nc(F)nc2c1nc(Cc1cc3c(cc1I)OCO3)n2CCS(=O)(=O)NC1CC1] | 2-(6-amino-2-fluoro-8-((6-iodobenzo[d][1,3]dioxol-5-yl)methyl)-9H-purin-9-yl)-N-cyclopropyl-ethanesulfonamide |
| 4A-8 | 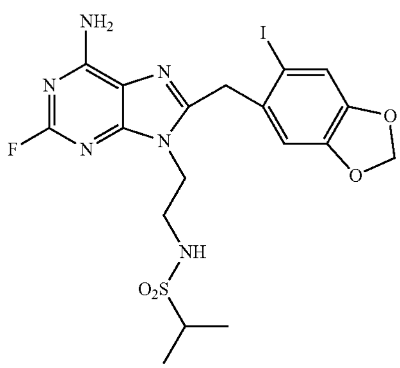 [SMILES: CC(C)S(=O)(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)propane-2-sulfonamide |
| 4A-9 | 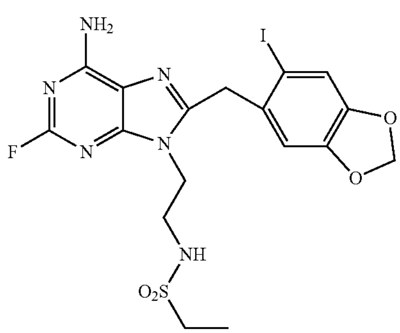 [SMILES: CCS(=O)(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)ethanesulfonamide |

TABLE 4A-continued

| Compound No. | Structure | Name |
| --- | --- | --- |
| 4A-10 | 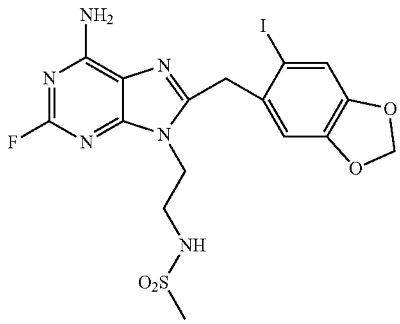 [SMILES: CS(=O)(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)methane-sulfonamide |
| 4A-11 | 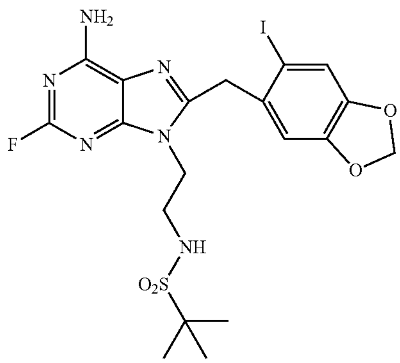 [SMILES: CC(C)(C)S(=O)(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)-2-methylpropane-2-sulfonamide |
| 4A-12 | 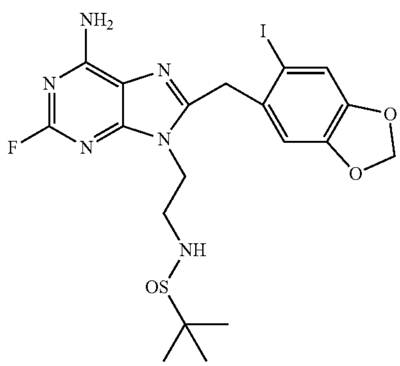 | N-(2-(6-amino-2-fluoro-8-((6-iodobenzo[d][1,3]dioxol-5-yl)methyl)-9H-purin-9-yl)ethyl)-2-methylpropane-2-sulfinamide |
| 4A-13 | 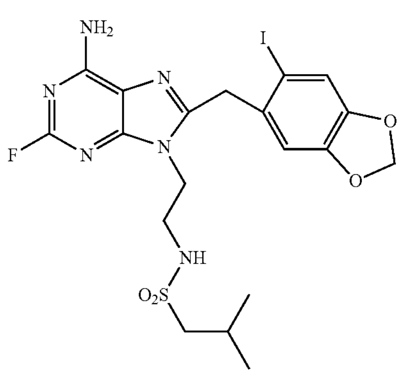 [SMILES: CC(C)CS(=O)(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)-2-methylpropane-1-sulfonamide |

TABLE 4A-continued

| Compound No. | Structure | Name |
| --- | --- | --- |
| 4A-14 | 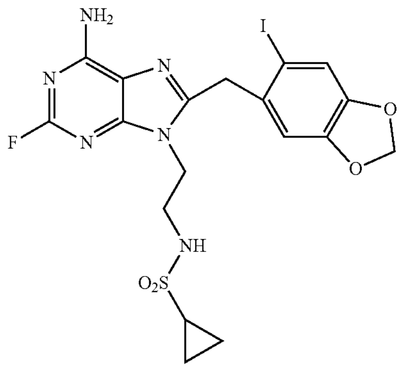 [SMILES: Nc1nc(F)nc2c1nc(Cc1cc3c(cc1I)OCO3)n2CCNS(=O)(=O)C1CC1] | N-(2-(6-amino-2-fluoro-8-((6-iodobenzo[d][1,3]dioxol-5-yl)methyl)-9H-purin-9-yl)ethyl)cyclopropane-sulfonamide |
| 4A-15 | 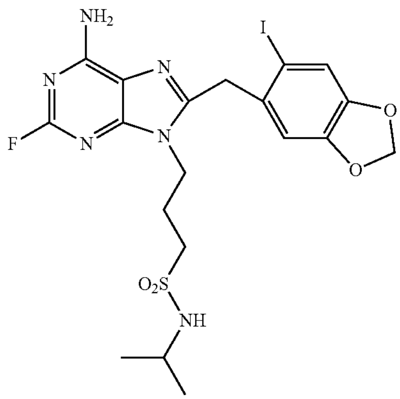 [SMILES: CC(C)NS(=O)(=O)CCCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-isopropylpropane-1-sulfonamide |
| 4A-16 | 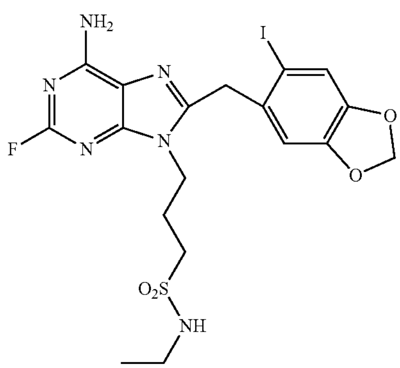 [SMILES: CCNS(=O)(=O)CCCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-ethylpropane-1-sulfonamide |
| 4A-17 | 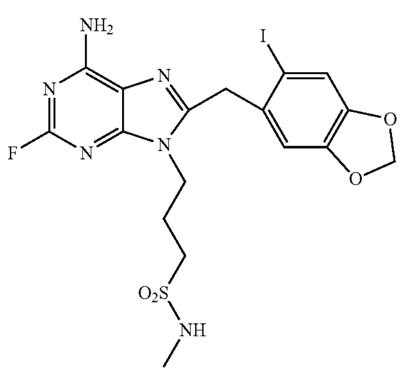 [SMILES: CNS(=O)(=O)CCCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-methylpropane-1-sulfonamide |

TABLE 4A-continued

| Compound No. | Structure | Name |
| --- | --- | --- |
| 4A-18 | 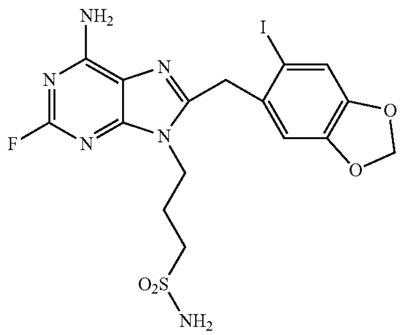 [SMILES: Nc1nc(F)nc2c1nc(Cc1cc3c(cc1I)OCO3)n2CCCS(N)(=O)=O] | 3-(6-amino-2-fluoro-8-((6-iodobenzo[d][1,3]dioxol-5-yl)methyl)-9H-purin-9-yl)propane-1-sulfonamide |
| 4A-19 | 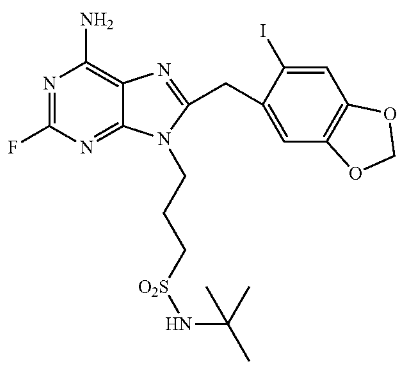 [SMILES: CC(C)(C)NS(=O)(=O)CCCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-(tert-butyl)propane-1-sulfonamide |
| 4A-20 | 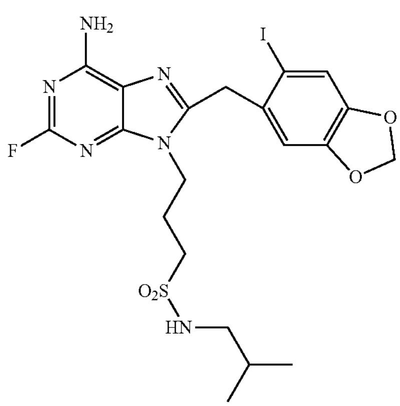 [SMILES: CC(C)CNS(=O)(=O)CCCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-isobutylpropane-1-sulfonamide |
| 4A-21 | 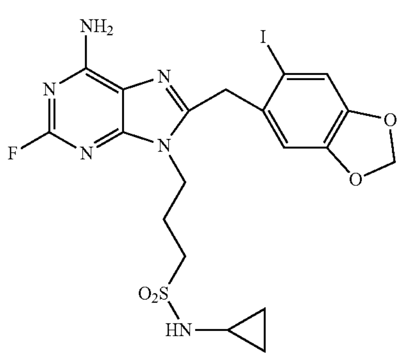 [SMILES: Nc1nc(F)nc2c1nc(Cc1cc3c(cc1I)OCO3)n2CCCS(=O)(=O)NC1CC1] | 3-(6-amino-2-fluoro-8-((6-iodobenzo[d][1,3]dioxol-5-yl)methyl)-9H-purin-9-yl)-N-cyclopropylpropane-1-sulfonamide |

TABLE 4A-continued

| Compound No. | Structure | Name |
|---|---|---|
| 4A-22 | 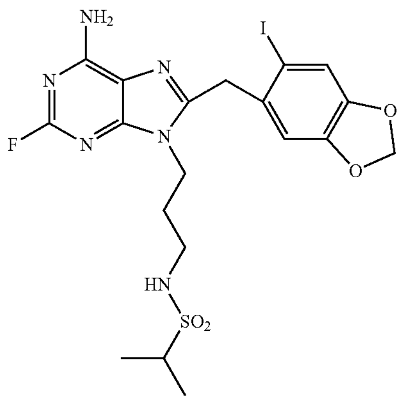 [SMILES: CC(C)S(=O)(=O)NCCCn1c(Cc2cc3c(cc2I)OCO3)nc2c(N)nc(F)nc21] | N-(3-(6-amino-2-fluoro-8-((6-iodobenzo[d][1,3]dioxol-5-yl)methyl)-9H-purin-9-yl)propyl)propane-2-sulfonamide |
| 4A-23 | 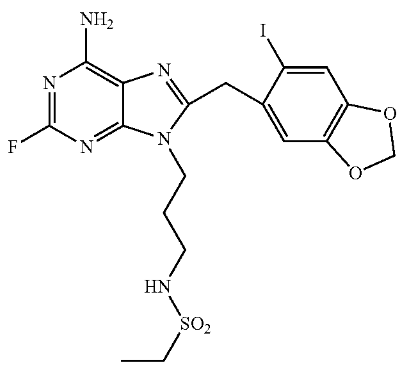 [SMILES: CCS(=O)(=O)NCCCn1c(Cc2cc3c(cc2I)OCO3)nc2c(N)nc(F)nc21] | N-(3-(6-amino-2-fluoro-8-((6-iodobenzo[d][1,3]dioxol-5-yl)methyl)-9H-purin-9-yl)propyl)ethane-sulfonamide |
| 4A-24 | 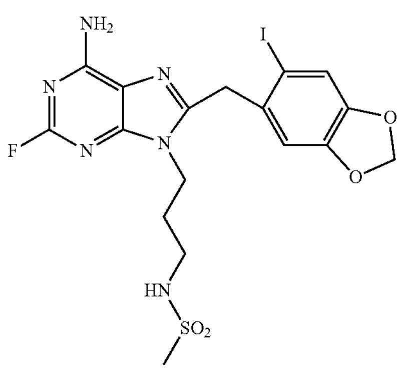 [SMILES: CS(=O)(=O)NCCCn1c(Cc2cc3c(cc2I)OCO3)nc2c(N)nc(F)nc21] | N-(3-(6-amino-2-fluoro-8-((6-iodobenzo[d][1,3]dioxol-5-yl)methyl)-9H-purin-9-yl)propyl)methane-sulfonamide |
| 4A-25 | 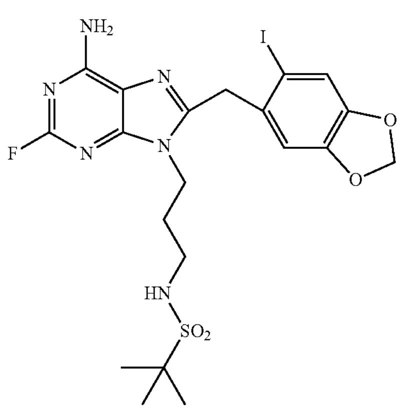 [SMILES: CC(C)(C)S(=O)(=O)NCCCn1c(Cc2cc3c(cc2I)OCO3)nc2c(N)nc(F)nc21] | N-(3-(6-amino-2-fluoro-8-((6-iodobenzo[d][1,3]dioxol-5-yl)methyl)-9H-purin-9-yl)propyl)-2-methylpropane-2-sulfonamide |

TABLE 4A-continued

| Compound No. | Structure | Name |
|---|---|---|
| 4A-26 | 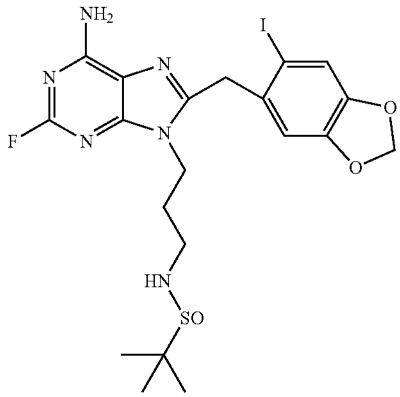 | N-(3-(6-amino-2-fluoro-8-((6-iodobenzo[d][1,3]dioxol-5-yl)methyl)-9H-purin-9-yl)propyl)-2-methylpropane-2-sulfinamide |
| 4A-27 | 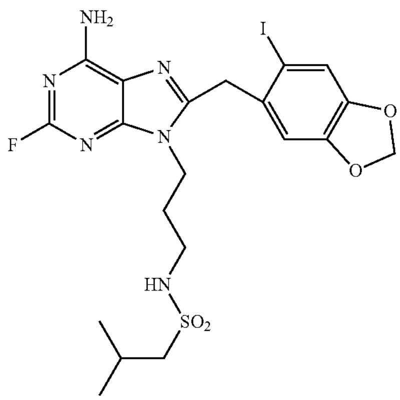 [SMILES: CC(C)CS(=O)(=O)NCCCn1c(Cc2cc3c(cc2I)OCO3)nc2c(N)nc(F)nc21] | N-(3-(6-amino-2-fluoro-8-((6-iodobenzo[d][1,3]dioxol-5-yl)methyl)-9H-purin-9-yl)propyl)-2-methylpropane-1-sulfonamide |
| 4A-28 | 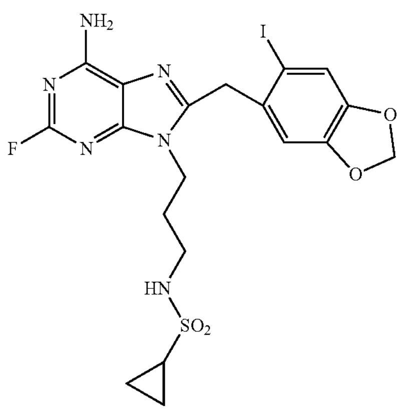 [SMILES: Nc1nc(F)nc2c1nc(Cc1cc3c(cc1I)OCO3)n2CCCNS(=O)(=O)C1CC1] | N-(3-(6-amino-2-fluoro-8-((6-iodobenzo[d][1,3]dioxol-5-yl)methyl)-9H-purin-9-yl)propyl)cyclopropanesulfonamide |
| 4A-29 | 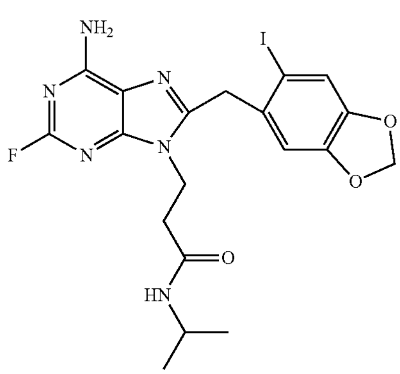 [SMILES: CC(C)NC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-isopropylpropanamide |

TABLE 4A-continued

| Compound No. | Structure | Name |
|---|---|---|
| 4A-30 | 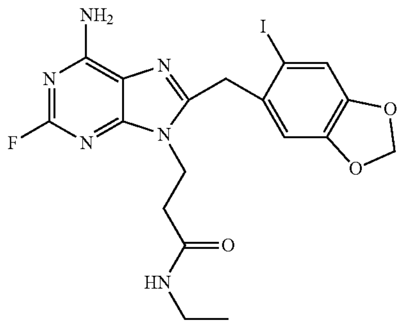 [SMILES: CCNC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-ethylpropanamide |
| 4A-31 | 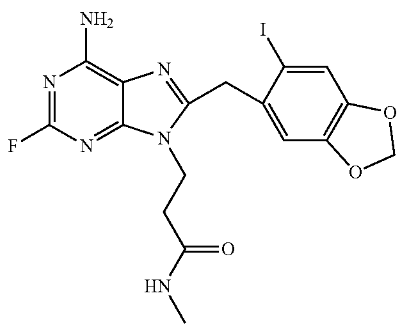 [SMILES: CNC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-methylpropanamide |
| 4A-32 | 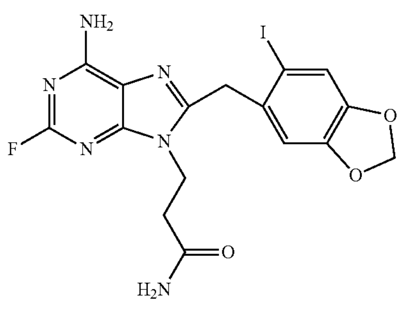 [SMILES: NC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)propanamide |
| 4A-33 | 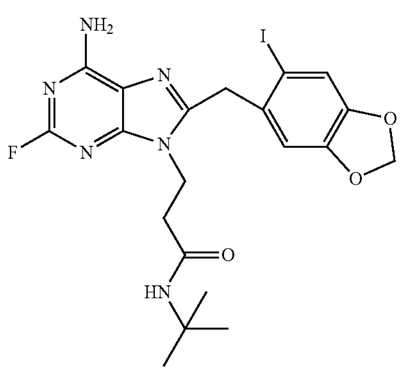 [SMILES: CC(C)(C)NC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-(tert-butyl)propanamide |

TABLE 4A-continued

| Compound No. | Structure | Name |
|---|---|---|
| 4A-34 | 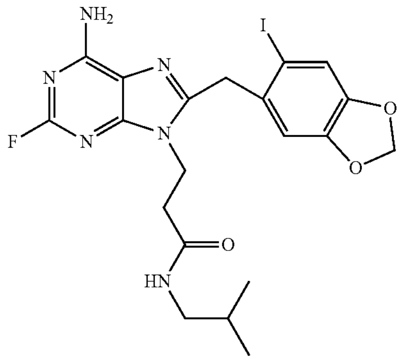 [SMILES: CC(C)CNC(=O)CCn1c(Cc2cc3c(cc2I)OCO3)nc2c(N)nc(F)nc21] | 3-(6-amino-2-fluoro-8-((6-iodobenzo[d][1,3]dioxol-5-yl)methyl)-9H-purin-9-yl)-N-isobutylpropanamide |
| 4A-35 | 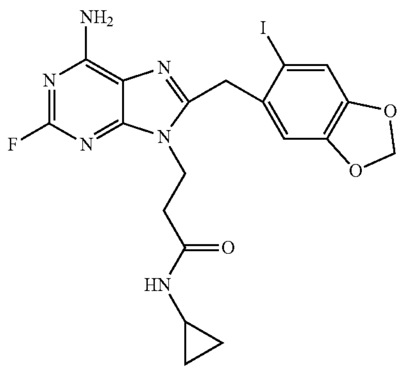 [SMILES: Nc1nc(F)nc2c1nc(Cc1cc3c(cc1I)OCO3)n2CCC(=O)NC1CC1] | 3-(6-amino-2-fluoro-8-((6-iodobenzo[d][1,3]dioxol-5-yl)methyl)-9H-purin-9-yl)-N-cyclopropylpropanamide |
| 4A-36 | 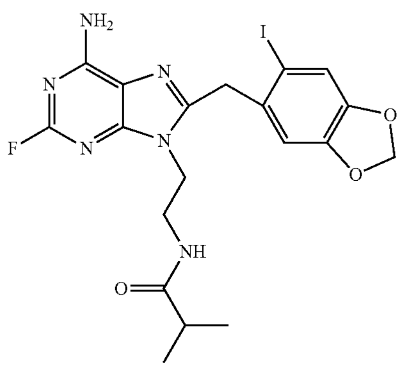 [SMILES: CC(C)C(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)isobutyramide |
| 4A-37 | 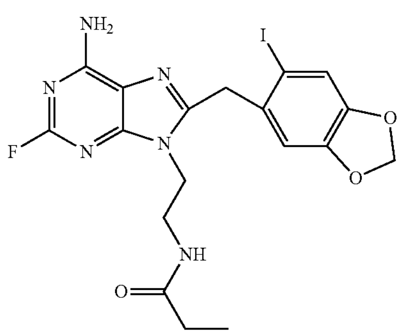 [SMILES: CCC(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)propionamide |

TABLE 4A-continued

| Compound No. | Structure | Name |
|---|---|---|
| 4A-38 | 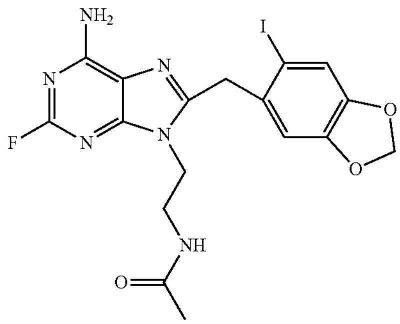 [SMILES: CC(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)acetamide |
| 4A-39 | 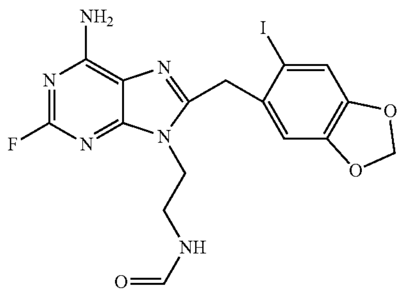 [SMILES: Nc1nc(F)nc2c1nc(Cc1cc3c(cc1I)OCO3)n2CCNC=O] | N-(2-(6-amino-2-fluoro-8-((6-iodobenzo[d][1,3]dioxol-5-yl)methyl)-9H-purin-9-yl)ethyl)formamide |
| 4A-40 | 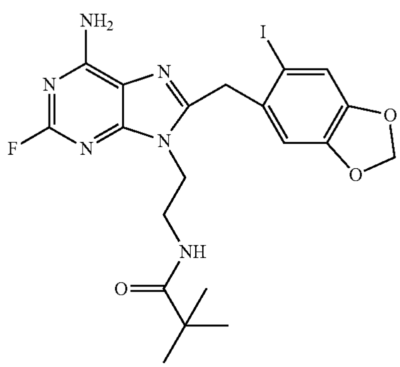 [SMILES: CC(C)(C)C(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)pivalamide |
| 4A-41 | 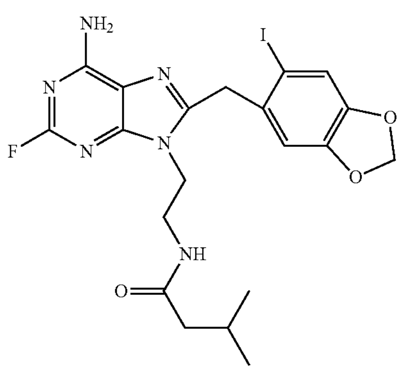 [SMILES: CC(C)CC(=O)NCCn1c(Cc2cc3c(cc2I)OCO3)nc2c(N)nc(F)nc21] | N-(2-(6-amino-2-fluoro-8-((6-iodobenzo[d][1,3]dioxol-5-yl)methyl)-9H-purin-9-yl)ethyl)-3-methylbutanamide |

TABLE 4A-continued

| Compound No. | Structure | Name |
| --- | --- | --- |
| 4A-42 | 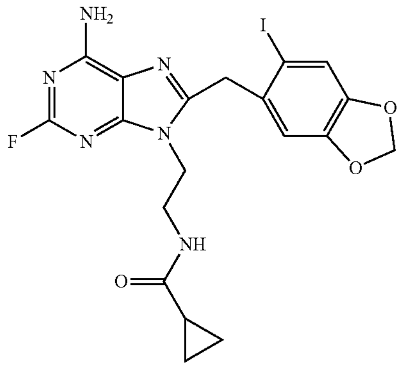 [SMILES: Nc1nc(F)nc2c1nc(Cc1cc3c(cc1I)OCO3)n2CCNC(=O)C1CC1] | N-(2-(6-amino-2-fluoro-8-((6-iodobenzo[d][1,3]dioxol-5-yl)methyl)-9H-purin-9-yl)ethyl)cyclopropane-carboxamide |
| 4A-43 | 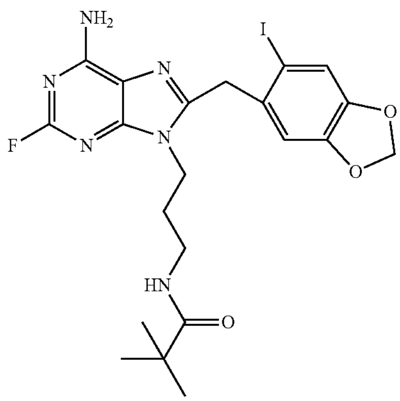 [SMILES: CC(C)(C)C(=O)NCCCn1c(Cc2cc3c(cc2I)OCO3)nc2c(N)nc(F)nc21] | N-{3-[6-Amino-2-fluoro-8-(6-iodo-benzo[1,3]dioxol-5-yl)methyl)-purin-9-yl]-propyl}-2,2-dimethyl-propionamide |
| 4A-44 | 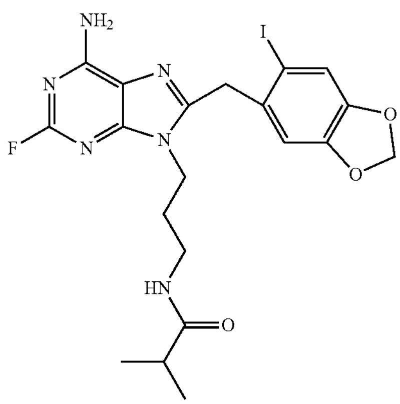 [SMILES: CC(C)C(=O)NCCCn1c(Cc2cc3c(cc2I)OCO3)nc2c(N)nc(F)nc21] | N-{3-[6-Amino-2-fluoro-8-(6-iodo-benzo[1,3]dioxol-5-ylmethyl)-purin-9-yl]-propyl}-isobutyramide |
| 4A-45 | 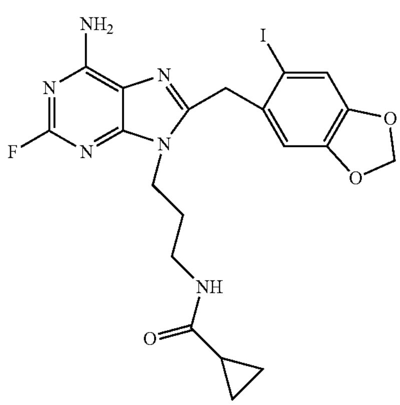 [SMILES: Nc1nc(F)nc2c1nc(Cc1cc3c(cc1I)OCO3)n2CCCNC(=O)C1CC1] | Cyclopropanecarboxylic acid {3-[6-amino-2-fluoro-8-(6-iodo-benzo[1,3]dioxol-5-ylmethyl)-purin-9-yl]-propyl}-amide |

TABLE 4A-continued

| Compound No. | Structure | Name |
|---|---|---|
| 4A-46 | 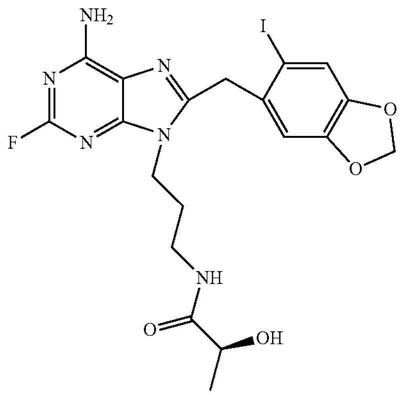 [SMILES: C[C@H](O)C(=O)NCCCn1c(Cc2cc3c(cc2I)OCO3)nc2c(N)nc(F)nc21] | N-{3-[6-Amino-2-fluoro-8-(6-iodo-benzo[1,3]dioxol-5-ylmethyl)-purin-9-yl]-propyl}-2-hydroxy-propionamide |
| 4A-47 | 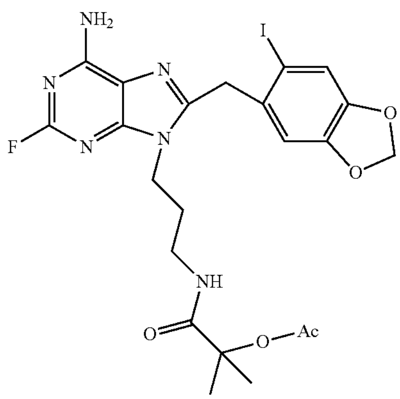 [SMILES: CC(=O)OC(C)(C)C(=O)NCCCn1c(Cc2cc3c(cc2I)OCO3)nc2c(N)nc(F)nc21] | Acetic acid 1-{3-[6-amino-2-fluoro-8-(6-iodo-benzo[1,3]dioxol-5-ylmethyl)-purin-9-yl]-propylcarbamoyl}-1-methyl-ethyl ester |
| 4A-48 | 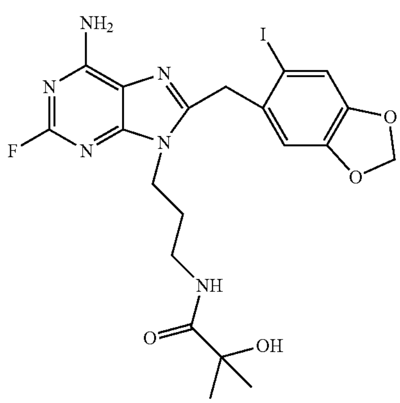 [SMILES: CC(C)(O)C(=O)NCCCn1c(Cc2cc3c(cc2I)OCO3)nc2c(N)nc(F)nc21] | N-{3-[6-Amino-2-fluoro-8-(6-iodo-benzo[1,3]dioxol-5-ylmethyl)-purin-9-yl]-propyl}-2-hydroxy-2-methyl-propionamide |

Hsp90 binding results are presented for Compounds 1A-5, 1A-10, 1A-11, 1A-12, 1A-15, 1A-19, 1A-22, 1A-24, 1A-25 to 1A-28, 1A-43 to 1A-50, 4A-26, 4A-28, 4A-43, and 4A-45 in Table 12 below. As can be noted therefrom, all compounds showed a high level of binding affinity.

C-II. In some embodiments of the disclosure, $X_2$ is an optionally substituted aryl. Table 1C lists specific examples of compounds within this embodiment. In each of the structures as drawn therein, $X_2$ is a nitrogen-containing heteroaryl group, specifically a pyrazolyl group, and $X_4$ is H. Corresponding structures in which $X_2$ is a different nitrogen-containing optionally substituted aryl group are within the scope of the disclosure. In each of the structures in Table 1C, Y is S and $X_4$ is H. However, corresponding structures in which Y is $CH_2$ and/or $X_4$ is F, Cl, Br, or I are also within the scope of the disclosure. Additionally, in connection with each of the structures in Table 1C, corresponding structures in which $X_2$ is a nitrogen-containing optionally substituted aryl group different from optionally substituted pyrazolyl, Y is $CH_2$, and/or $X_4$ is F, Cl, Br, or I are also within the scope of the disclosure.

TABLE 1C

| Compound No. | Structure | Name |
|---|---|---|
| 1C-1 | 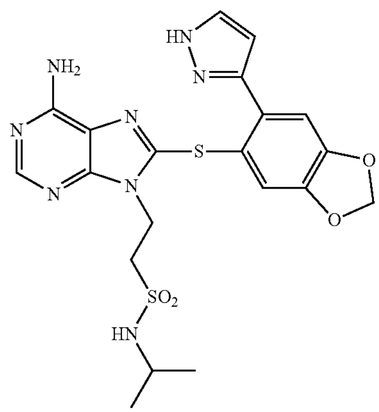 [SMILES: CC(C)NS(=O)(=O)CCn1c(Sc2cc3c(cc2-c2cc[nH]n2)OCO3)nc2c(N)ncnc21] | 2-{6-Amino-8-[6-(1H-pyrazol-3-yl)-benzo[1,3]dioxol-5-ylsulfanyl]-purin-9-yl}-ethanesulfonic acid isopropylamide |
| 1C-2 | 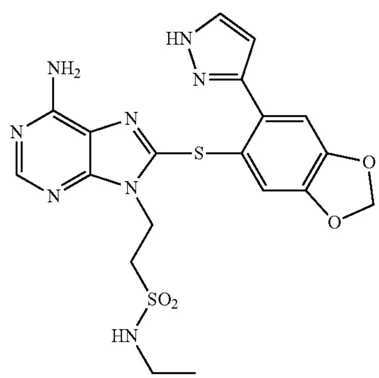 [SMILES: CCNS(=O)(=O)CCn1c(Sc2cc3c(cc2-c2cc[nH]n2)OCO3)nc2c(N)ncnc21] | 2-{6-Amino-8-[6-(1H-pyrazal-3-yl)-benzo[1,3]dioxol-5-ylsulfanyl]-purin-9-yl}-ethanesulfonic acid ethylamide |
| 1C-3 | 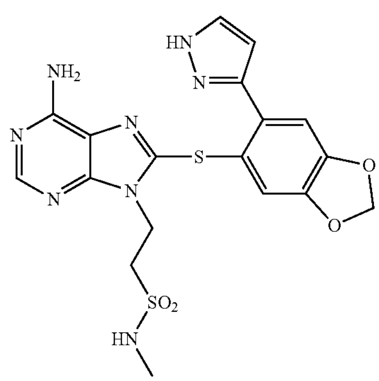 [SMILES: CNS(=O)(=O)CCn1c(Sc2cc3c(cc2-c2cc[nH]n2)OCO3)nc2c(N)ncnc21] | 2-{6-Amino-8-[6-(1H-pyrazol-3-yl)-benzo[1,3]dioxol-5-ylsulfanyl]-purin-9-yl}-ethanesulfonic acid methylamide |
| 1C-4 | 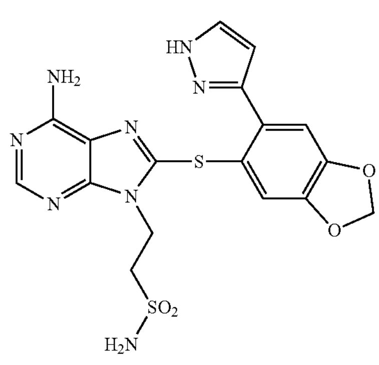 [SMILES: Nc1ncnc2c1nc(Sc1cc3c(cc1-c1cc[nH]n1)OCO3)n2CCS(N)(=O)=O] | 2-{6-Amino-8-[6-(1H-pyrazol-3-yl)-benzo[1,3]dioxol-5-ylsulfanyl]-purin-9-yl}-ethanesulfonic acid amide |

TABLE 1C-continued

| Compound No. | Structure | Name |
| --- | --- | --- |
| 1C-5 | 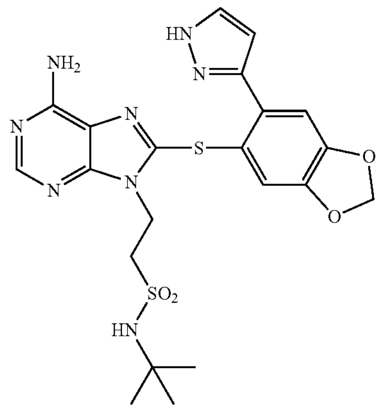 [SMILES: CC(C)(C)NS(=O)(=O)CCn1c(Sc2cc3c(cc2-c2cc[nH]n2)OCO3)nc2c(N)ncnc21] | 2-{6-Amino-8-[6-(1H-pyrazol-3-yl)-benzo[1,3]dioxol-5-ylsulfanyl]-purin-9-yl}-ethanesulfonic acid tert-butylamide |
| 1C-6 | 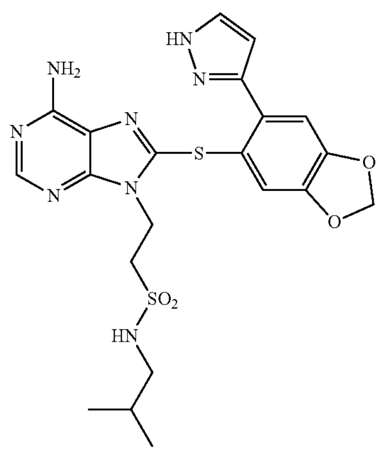 [SMILES: CC(C)CNS(=O)(=O)CCn1c(Sc2cc3c(cc2-c2cc[nH]n2)OCO3)nc2c(N)ncnc21] | 2-{6-Amino-8-[6-(1H-pyrazol-3-yl)-benzo[1,3]dioxol-5-ylsulfanyl]-purin-9-yl}-ethanesulfonic acid isobutyl-amide |
| 1C-7 | 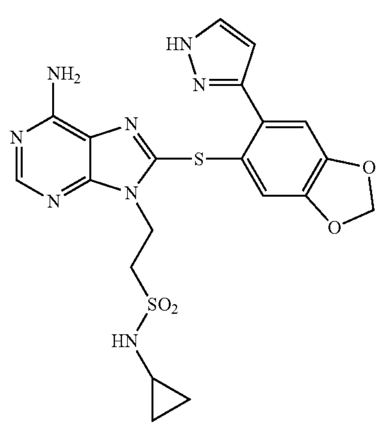 [SMILES: Nc1ncnc2c1nc(Sc1cc3c(cc1-c1cc[nH]n1)OCO3)n2CCS(=O)(=O)NC1CC1] | 2-{6-Amino-8-[6-(1H-pyrazol-3-yl)-benzo[1,3]dioxol-5-ylsulfanyl]-purin-9-yl}-ethanesulfonic acid cyclopropylamide |

TABLE 1C-continued

| Compound No. | Structure | Name |
|---|---|---|
| 1C-8 | 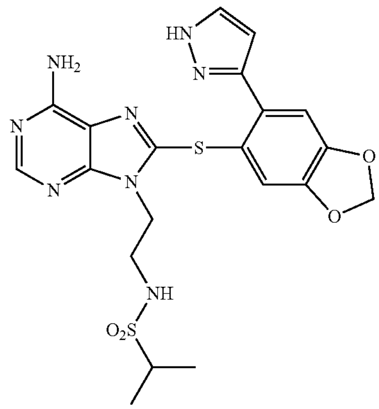 [SMILES: CC(C)S(=O)(=O)NCCn1c(Sc2cc3c(cc2-c2cc[nH]n2)OCO3)nc2c(N)ncnc21] | Propane-2-sulfonic acid (2-{6-amino-8-[6-(1H-pyrazol-3-yl)-benzo[1,3]dioxol-5-ylsulfanyl]-purin-9-yl}-ethyl)-amide |
| 1C-9 | 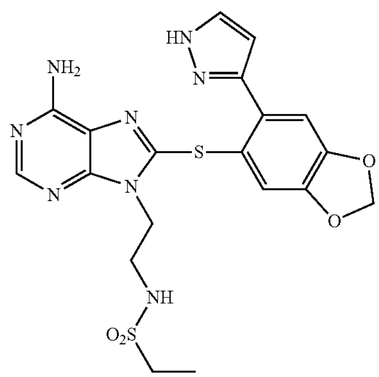 [SMILES: CCS(=O)(=O)NCCn1c(Sc2cc3c(cc2-c2cc[nH]n2)OCO3)nc2c(N)ncnc21] | Ethanesulfonic acid (2-{6-amino-8-[6-(1H-pyrazol-3-yl)-benzo[1,3]dioxol-5-ylsulfanyl]-purin-9-yl}-ethyl)-amide |
| 1C-10 | 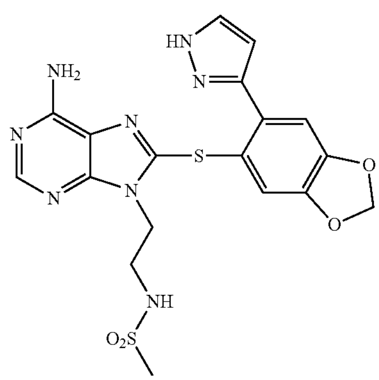 [SMILES: CS(=O)(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-methanesulfonamide |
| 1C-11 | 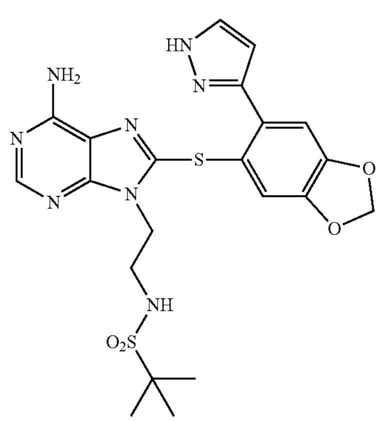 [SMILES: CC(C)(C)S(=O)(=O)NCCn1c(Sc2cc3c(cc2-c2cc[nH]n2)OCO3)nc2c(N)ncnc21] | 2-Methyl-propane-2-sulfonic acid (2-{6-amino-8-[6-(1H-pyrazol-3-yl)-benzo[1,3]dioxol-5-ylsulfanyl]-purin-9-yl}-ethyl)-amide |

TABLE 1C-continued

| Compound No. | Structure | Name |
| --- | --- | --- |
| 1C-12 | 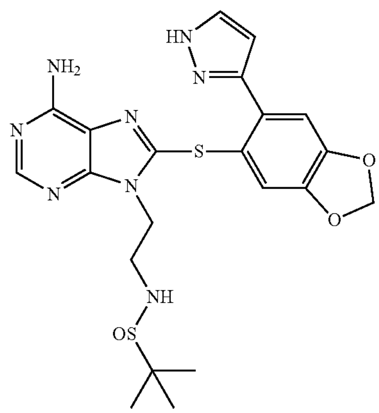 | 2-Methyl-propane-2-sulfinic acid (2-{6-amino-8-[6-(1H-pyrazol-3-yl)-benzo[1,3]dioxol-5-ylsulfanyl]-purin-9-yl}-ethyl)-amide |
| 1C-13 | 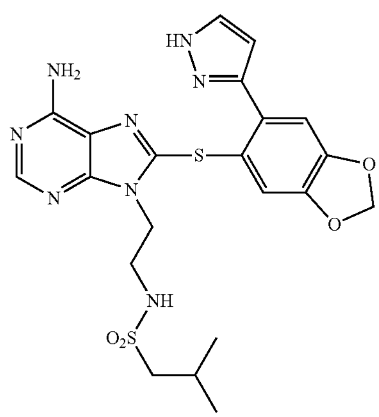 [SMILES: CC(C)CS(=O)(=O)NCCn1c(Sc2cc3c(cc2-c2cc[nH]n2)OCO3)nc2c(N)ncnc21] | 2-Methyl-propane-1-sulfonic acid (2-{6-amino-8-[6-(1H-pyrazol-3-yl)-benzo[1,3]dioxol-5-ylsulfanyl]-purin-9-yl}-ethyl)-amide |
| 1C-14 | 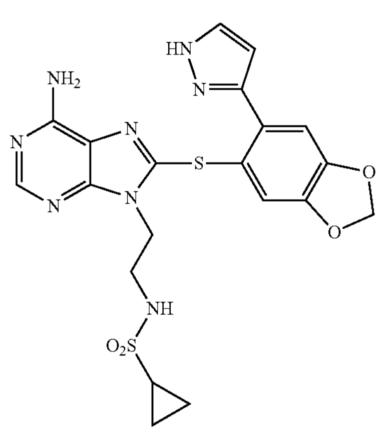 [SMILES: Nc1ncnc2c1nc(Sc1cc3c(cc1-c1cc[nH]n1)OCO3)n2CCNS(=O)(=O)C1CC1] | Cyclopropanesulfonic acid (2-{6-amino-8-[6-(1H-pyrazol-3-yl)-benzo[1,3]dioxol-5-ylsulfanyl]-purin-9-yl}-ethyl)-amide |

TABLE 1C-continued

| Compound No. | Structure | Name |
|---|---|---|
| 1C-15 | 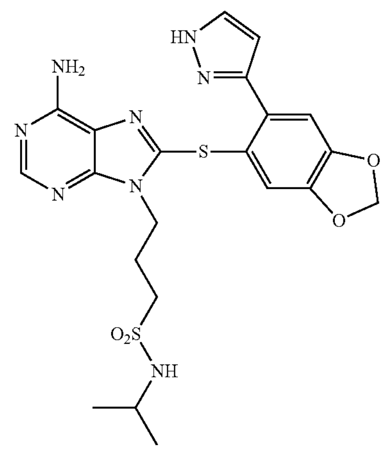 [SMILES: CC(C)NS(=O)(=O)CCCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propane-1-sulfonic acid isopropylamide |
| 1C-16 | 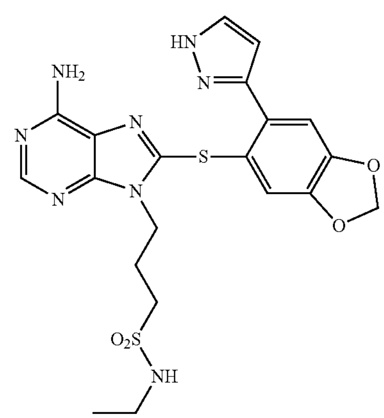 [SMILES: CCNS(=O)(=O)CCCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propane-1-sulfonic acid ethylamide |
| 1C-17 | 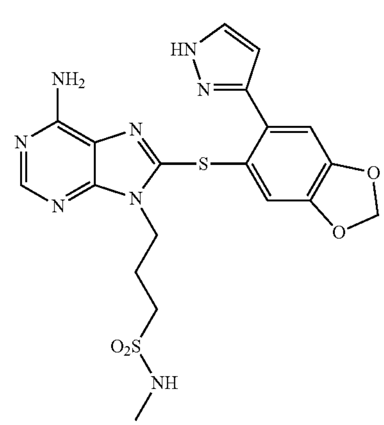 [SMILES: CNS(=O)(=O)CCCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propane-1-sulfonic acid methylamide |

TABLE 1C-continued

| Compound No. | Structure | Name |
| --- | --- | --- |
| 1C-18 | 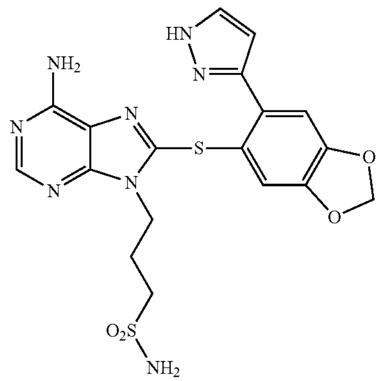 [SMILES: Nc1ncnc2c1nc(Sc1cc3c(cc1-c1cc[nH]n1)OCO3)n2CCCS(N)(=O)=O] | 3-{6-Amino-8-[6-(1H-pyrazol-3-yl)-benzo[1,3]dioxol-5-ylsulfanyl]-purin-9-yl}-propane-1-sulfonic acid amide |
| 1C-19 | 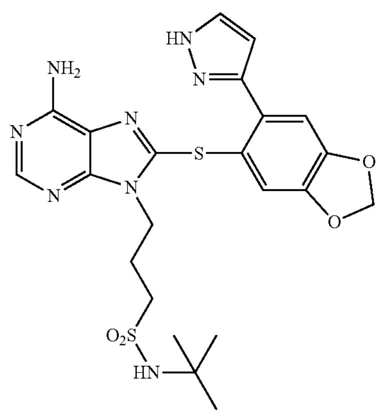 [SMILES: CC(C)(C)NS(=O)(=O)CCCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propane-1-sulfonic acid tert-butylamide |
| 1C-20 | 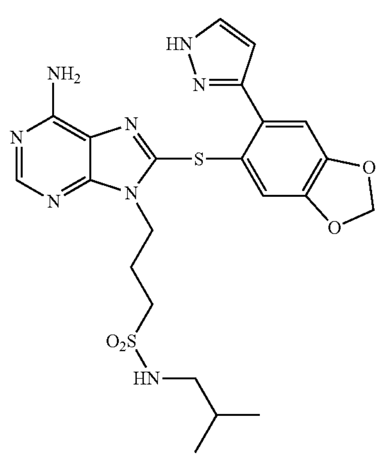 [SMILES: CC(C)CNS(=O)(=O)CCCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propane-1-sulfonic acid isobutyl-amide |

TABLE 1C-continued
| Compound No. | Structure | Name |
|---|---|---|
| 1C-21 | 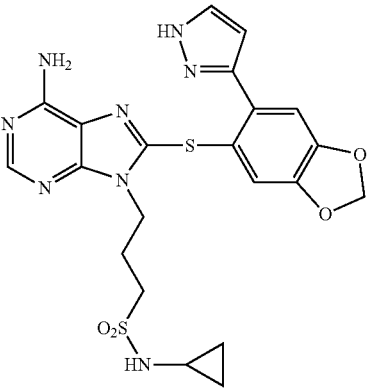 [SMILES: Nc1ncnc2c1nc(Sc1cc3c(cc1-c1cc[nH]n1)OCO3)n2CCCS(=O)(=O)NC1CC1] | 3-{6-Amino-8-[6-(1H-pyrazol-3-yl)-benzo[1,3]dioxol-5-ylsulfanyl]-purin-9-yl}-propane-1-sulfonic acid cyclopropylamide |
| 1C-22 | 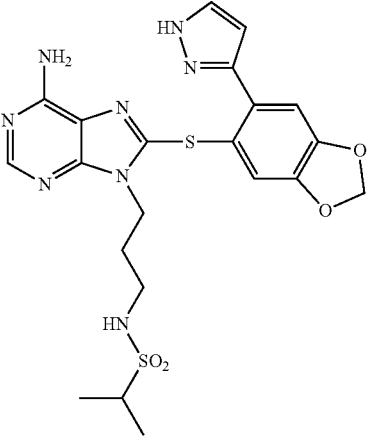 [SMILES: CC(C)S(=O)(=O)NCCCn1c(Sc2cc3c(cc2-c2cc[nH]n2)OCO3)nc2c(N)ncnc21] | Propane-2-sulfonic acid (3-{6-amino-8-[6-(1H-pyrazol-3-yl)-benzo[1,3]dioxol-5-ylsulfanyl]-purin-9-yl}-propyl)-amide |
| 1C-23 | 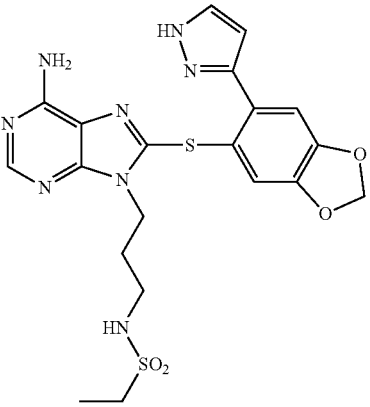 [SMILES: CCS(=O)(=O)NCCCn1c(Sc2cc3c(cc2-c2cc[nH]n2)OCO3)nc2c(N)ncnc21] | Ethanesulfonic acid (3-{6-amino-8-[6-(1H-pyrazol-3-yl)-benzo[1,3]dioxol-5-ylsulfanyl]-purin-9-yl}-propyl)-amide |

TABLE 1C-continued

| Compound No. | Structure | Name |
| --- | --- | --- |
| 1C-24 | 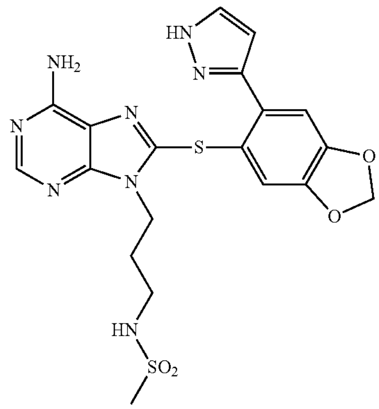 [SMILES: CS(=O)(=O)NCCCn1c(Sc2cc3c(cc2-c2cc[nH]n2)OCO3)nc2c(N)ncnc21] | N-(3-{6-Amino-8-[6-(1H-pyrazol-3-yl)-benzo[1,3]dioxol-5-ylsulfanyl]-purin-9-yl}-propyl)-methanesulfonamide |
| 1C-25 | 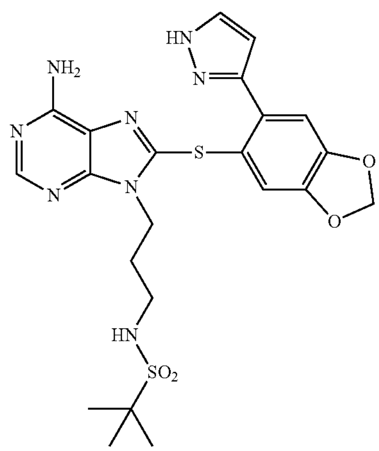 [SMILES: CC(C)(C)S(=O)(=O)NCCCn1c(Sc2cc3c(cc2-c2cc[nH]n2)OCO3)nc2c(N)ncnc21] | 2-Methyl-propane-2-sulfonic acid (3-{6-amino-8-[6-(1H-pyrazol-3-yl)-benzo[1,3]dioxol-5-ylsulfanyl]-purin-9-yl}-propyl)-amide |
| 1C-26 | 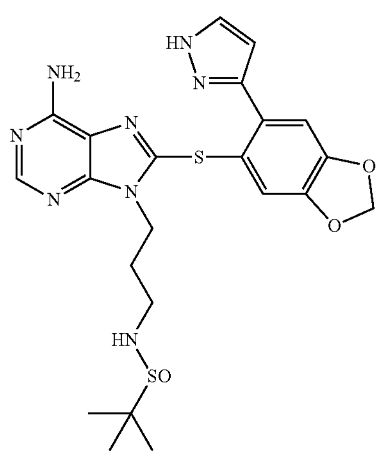 | 2-Methyl-propane-2-sulfinic acid (3-{6-amino-8-[6-(1H-pyrazol-3-yl)-benzo[1,3]dioxol-5-ylsulfanyl]-purin-9-yl}-propyl)-amide |

TABLE 1C-continued

| Compound No. | Structure | Name |
|---|---|---|
| 1C-27 | 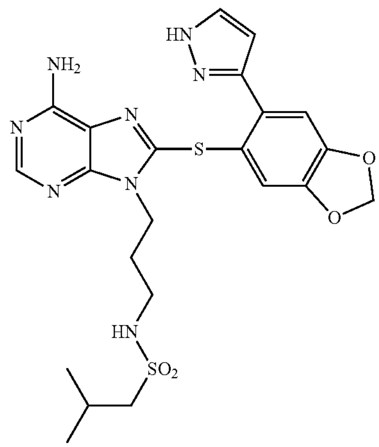 [SMILES: CC(C)CS(=O)(=O)NCCCn1c(Sc2cc3c(cc2-c2cc[nH]n2)OCO3)nc2c(N)ncnc21] | 2-Methyl-propane-1-sulfonic acid (3-{6-amino-8-[6-(1H-pyrazol-3-yl)-benzo[1,3]dioxol-5-ylsulfanyl]-purin-9-yl}-propyl)-amide |
| 1C-28 | 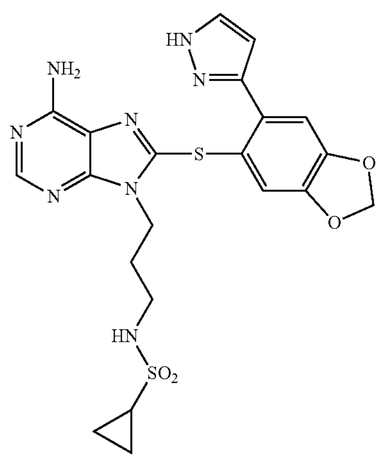 [SMILES: Nc1ncnc2c1nc(Sc1cc3c(cc1-c1cc[nH]n1)OCO3)n2CCCNS(=O)(=O)C1CC1] | Cyclopropanesulfonic acid (3-{6-amino-8-[6-(1H-pyrazol-3-yl)-benzo[1,3]dioxol-5-ylsulfanyl]-purin-9-yl}-propyl)-amide |
| 1C-29 | 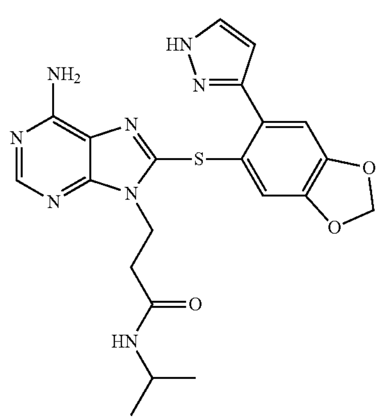 [SMILES: CC(C)NC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-N-isopropyl-propionamide |

TABLE 1C-continued

| Compound No. | Structure | Name |
|---|---|---|
| 1C-30 | 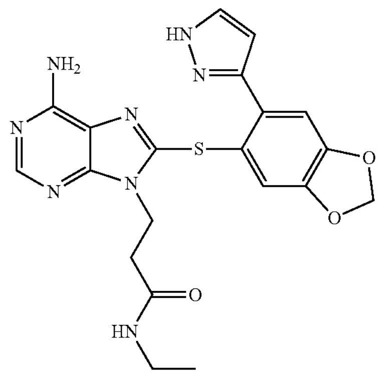 [SMILES: CCNC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-N-ethyl-propionamide |
| 1C-31 | 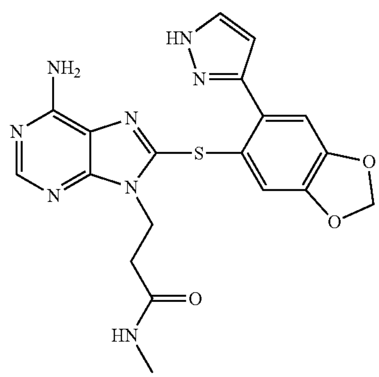 [SMILES: CNC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-N-methyl-propionamide |
| 1C-32 | 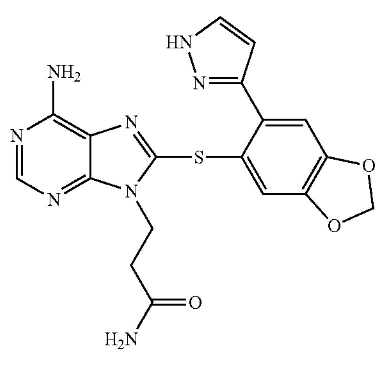 [SMILES: NC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-propionamide |
| 1C-33 | 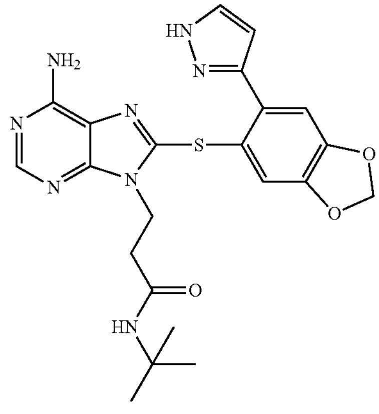 [SMILES: CC(C)(C)NC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-N-tert-butyl-propionamide |

TABLE 1C-continued

| Compound No. | Structure | Name |
|---|---|---|
| 1C-34 | 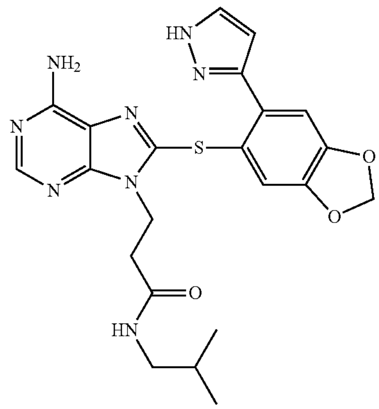 [SMILES: CC(C)CNC(=O)CCn1c(Sc2cc3c(cc2-c2cc[nH]n2)OCO3)nc2c(N)ncnc21] | 3-{6-Amino-8-[6-(1H-pyrazol-3-yl)-benzo[1,3]dioxol-5-ylsulfanyl]-purin-9-yl}-N-isobutyl-propionamide |
| 1C-35 | 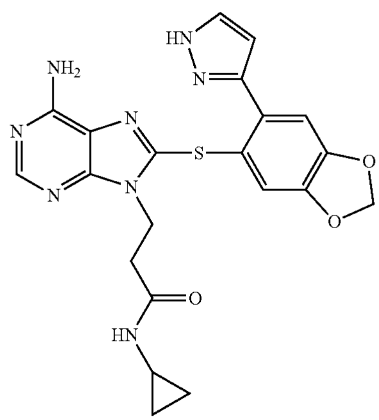 [SMILES: Nc1ncnc2c1nc(Sc1cc3c(cc1-c1cc[nH]n1)OCO3)n2CCC(=O)NC1CC1] | 3-{6-Amino-8-[6-(1H-pyrazol-3-yl)-benzo[1,3]dioxol-5-ylsulfanyl]-purin-9-yl}-N-cyclopropyl-propionamide |
| 1C-36 | 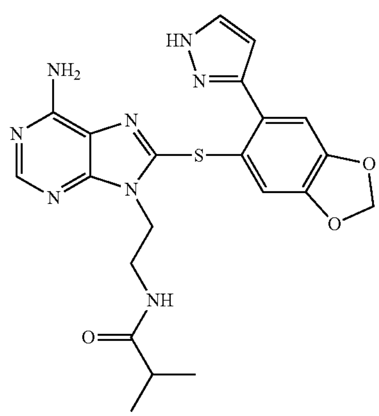 [SMILES: CC(C)C(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-isobutyramide |
| 1C-37 | 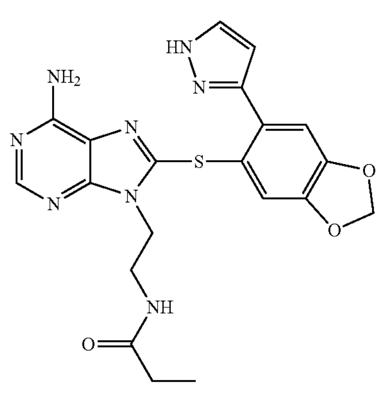 [SMILES: CCC(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-propionamide |

TABLE 1C-continued

| Compound No. | Structure | Name |
|---|---|---|
| 1C-38 | 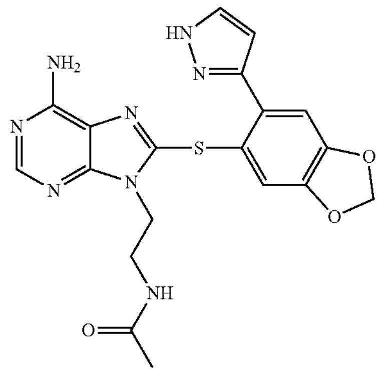 [SMILES: CC(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-acetamide |
| 1C-39 | 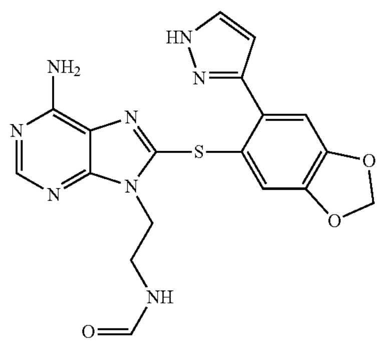 [SMILES: Nc1ncnc2c1nc(Sc1cc3c(cc1-c1cc[nH]n1)OCO3)n2CCNC=O] | N-(2-{6-Amino-8-[6-(1H-pyrazol-3-yl)-benzo[1,3]dioxol-5-ylsulfanyl]-purin-9-yl}-ethyl)-formamide |
| 1C-40 | 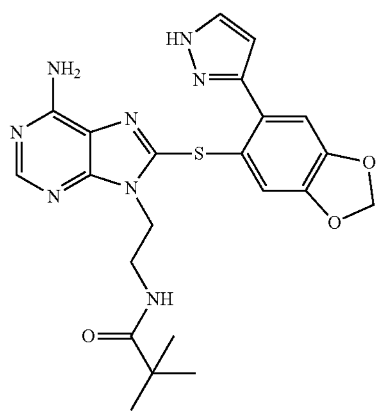 [SMILES: CC(C)(C)C(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-2,2-dimethyl-propionamide |
| 1C-41 | 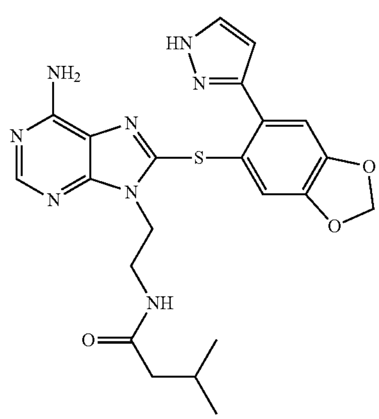 [SMILES: CC(C)CC(=O)NCCn1c(Sc2cc3c(cc2-c2cc[nH]n2)OCO3)nc2c(N)ncnc21] | N-(2-{6-Amino-8-[6-(1H-pyrazol-3-yl)-benzo[1,3]dioxol-5-ylsulfanyl]-purin-9-yl}-ethyl)-3-methyl-butyramide |

TABLE 1C-continued

| Compound No. | Structure | Name |
|---|---|---|
| 1C-42 | 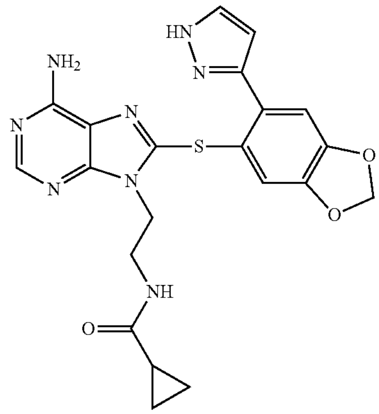 [SMILES: Nc1ncnc2c1nc(Sc1cc3c(cc1-c1cc[nH]n1)OCO3)n2CCNC(=O)C1CC1] | Cyclopropanecarboxylic acid (2-{6-amino-8-[6-(1H-pyrazol-3-yl)-benzo[1,3]dioxol-5-ylsulfanyl]-purin-9-yl}-ethyl)-amide |
| 1C-43 | 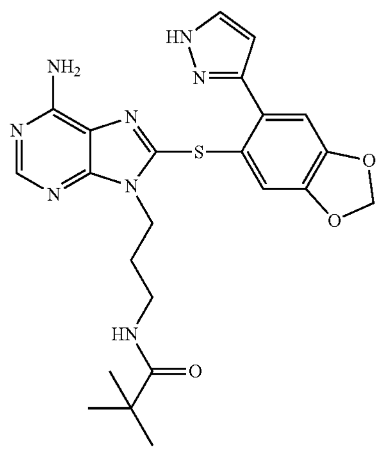 [SMILES: CC(C)(C)C(=O)NCCCn1c(Sc2cc3c(cc2-c2cc[nH]n2)OCO3)nc2c(N)ncnc21] | N-(3-{6-Amino-8-[6-(1H-pyrazol-3-yl)-benzo[1,3]dioxol-5-ylsulfanyl]-purin-9-yl}-propyl)-2,2-dimethyl-propionamide |
| 1C-44 | 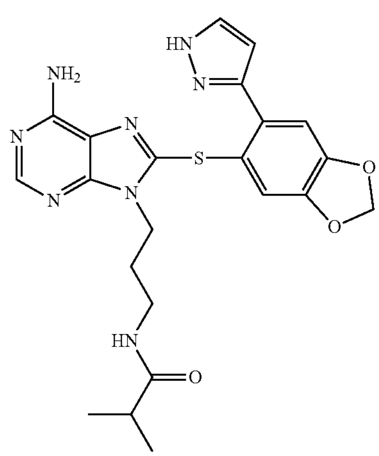 [SMILES: CC(C)C(=O)NCCCn1c(Sc2cc3c(cc2-c2cc[nH]n2)OCO3)nc2c(N)ncnc21] | N-(3-{6-Amino-8-[6-(1H-pyrazol-3-yl)-benzo[1,3]dioxol-5-ylsulfanyl]-purin-9-yl}-propyl)-isobutyramide |

TABLE 1C-continued

| Compound No. | Structure | Name |
|---|---|---|
| 1C-45 | 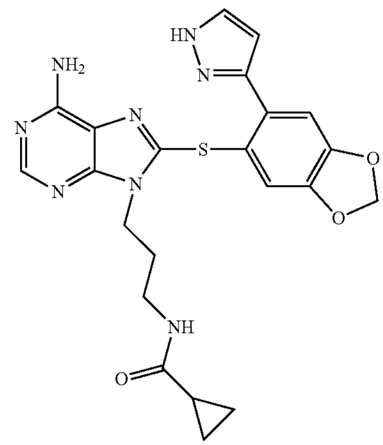 [SMILES: Nc1ncnc2c1nc(Sc1cc3c(cc1-c1cc[nH]n1)OCO3)n2CCCNC(=O)C1CC1] | Cyclopropanecarboxylic acid (3-{6-amino-8-[6-(1H-pyrazol-3-yl)-benzo[1,3]dioxol-5-ylsulfanyl]-purin-9-yl}-propyl)-amide |
| 1C-46 | 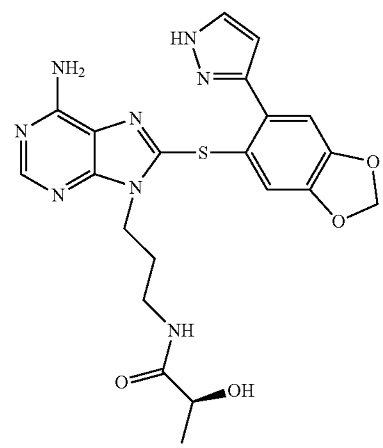 [SMILES: C[C@H](O)C(=O)NCCCn1c(Sc2cc3c(cc2-c2cc[nH]n2)OCO3)nc2c(N)ncnc21] | N-(3-{6-Amino-8-[6-(1H-pyrazol-3-yl)-benzo[1,3]dioxol-5-ylsulfanyl]-purin-9-yl}-propyl)-2-hydroxy-propionamide |
| 1C-47 | 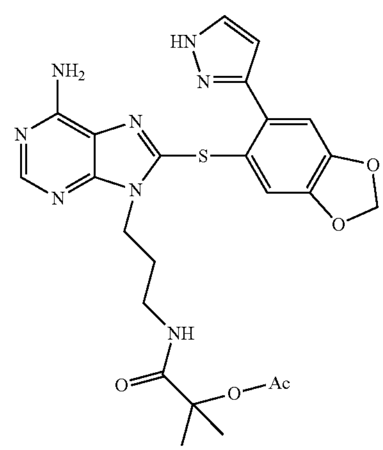 [SMILES: CC(=O)OC(C)(C)C(=O)NCCCn1c(Sc2cc3c(cc2-c2cc[nH]n2)OCO3)nc2c(N)ncnc21] | Acetic acid 1-(3-{6-amino-8-[6-(1H-pyrazol-3-yl)-benzo[1,3]dioxol-5-ylsulfanyl]-purin-9-yl}-propylcarbamoyl)-1-methyl-ethyl ester |

TABLE 1C-continued

| Compound No. | Structure | Name |
|---|---|---|
| 1C-48 | 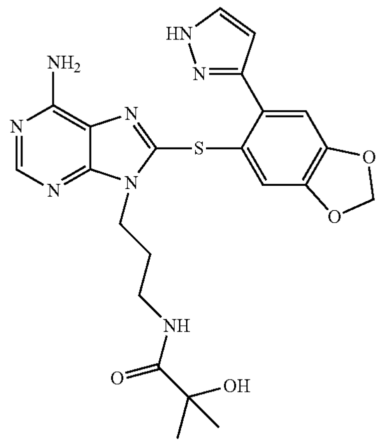 [SMILES: CC(C)(O)C(=O)NCCCn1c(Sc2cc3c(cc2-c2cc[nH]n2)OCO3)nc2c(N)ncnc21] | N-(3-{6-Amino-8-[6-(1H-pyrazol-3-yl)-benzo[1,3]dioxol-5-ylsulfanyl]-purin-9-yl}-propyl)-2-hydroxy-2-methyl-propionamide |
| 1C-49 | 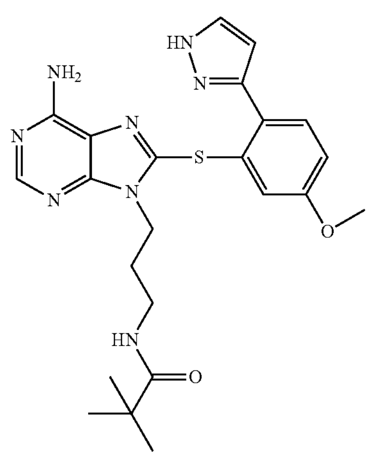 [SMILES: COc1ccc(-c2cc[nH]n2)c(Sc2nc3c(N)ncnc3n2CCCNC(=O)C(C)(C)C)c1] | N-(3-(6-amino-8-((5-methoxy-2-(1H-pyrazol-3-yl)phenyl)thio)-9H-purin-9-yl)propyl)pivalamide |

Table 1D lists specific examples of additional compounds within this embodiment. In each of the structures as drawn therein, $X_2$ is a nitrogen and oxygen-containing heteroaryl group, specifically an oxazolyl group, and $X_4$ is H. Corresponding structures in which $X_2$ is a different nitrogen and oxygen-containing optionally substituted aryl group are within the scope of the disclosure. In each of the structures in Table 1D, Y is S and $X_4$ is H. However, corresponding structures in which Y is $CH_2$ and/or $X_4$ is F, Cl, Br, or I are also within the scope of the disclosure. Additionally, in connection with each of the structures in Table 1D, corresponding structures in which $X_2$ is a nitrogen and oxygen-containing optionally substituted aryl group different from optionally substituted oxazolyl, Y is $CH_2$, and/or $X_4$ is F, Cl, Br, or I are also within the scope of the disclosure.

TABLE 1D

| Compound No. | Structure | Name |
|---|---|---|
| 1D-1 | 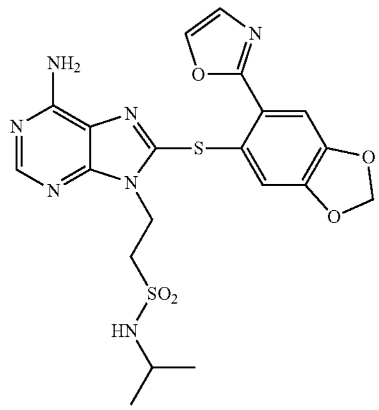 [SMILES: CC(C)NS(=O)(=O)CCn1c(Sc2cc3c(cc2-c2ncco2)OCO3)nc2c(N)ncnc21] | 2-(6-amino-8-((6-(oxazol-2-yl)benzo[d][1,3]dioxol-5-yl)thio)-9H-purin-9-yl)-N-isopropyl-ethanesulfonamide |
| 1D-2 | 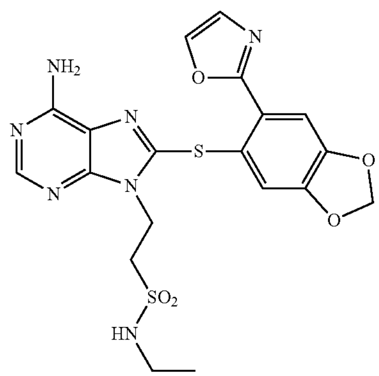 | 2-(6-amino-8-((6-(oxazol-2-yl)benzo[d][1,3]dioxol-5-yl)thio)-9H-purin-9-yl)-N-ethylethanesulfonamide |
| 1D-3 | 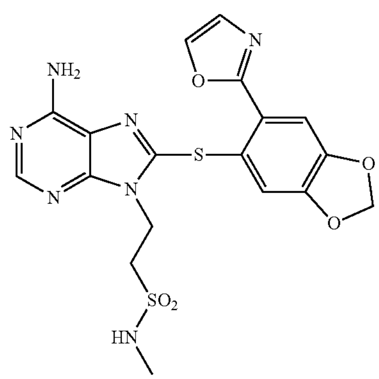 [SMILES: CNS(=O)(=O)CCn1c(Sc2cc3c(cc2-c2ncco2)OCO3)nc2c(N)ncnc21] | 2-(6-amino-8-((6-(oxazol-2-yl)benzo[d][1,3]dioxol-5-yl)thio)-9H-purin-9-yl)-N-methylethanesulfonamide |
| 1D-4 | 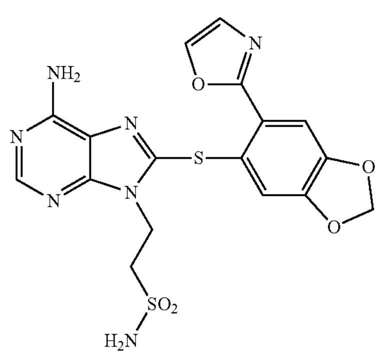 | 2-(6-amino-8-((6-(oxazol-2-yl)benzo[d][1,3]dioxol-5-yl)thio)-9H-purin-9-yl)ethanesulfonamide |

TABLE 1D-continued

| Compound No. | Structure | Name |
|---|---|---|
| 1D-5 | 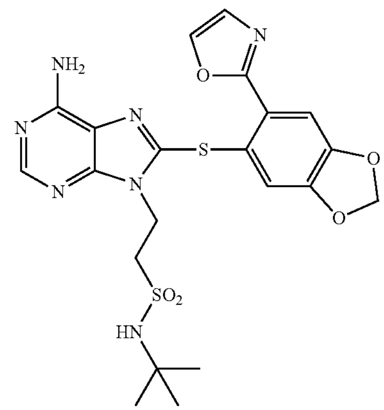 [SMILES: CC(C)(C)NS(=O)(=O)CCn1c(Sc2cc3c(cc2-c2ncco2)OCO3)nc2c(N)ncnc21] | 2-(6-amino-8-((6-(oxazol-2-yl)benzo[d][1,3]dioxol-5-yl)thio)-9H-purin-9-yl)-N-(tert-butyl)ethanesulfonamide |
| 1D-6 | 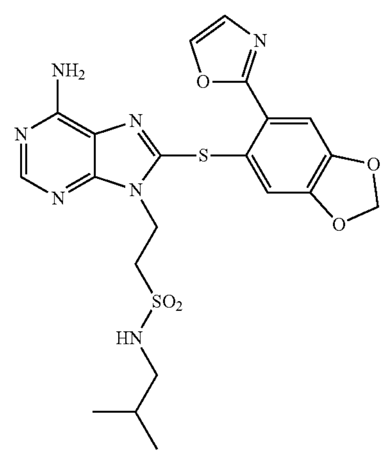 [SMILES: CC(C)CNS(=O)(=O)CCn1c(Sc2cc3c(cc2-c2ncco2)OCO3)nc2c(N)ncnc21] | 2-(6-amino-8-((6-(oxazol-2-yl)benzo[d][1,3]dioxol-5-yl)thio)-9H-purin-9-yl)-N-isobutylethanesulfonamide |
| 1D-7 | 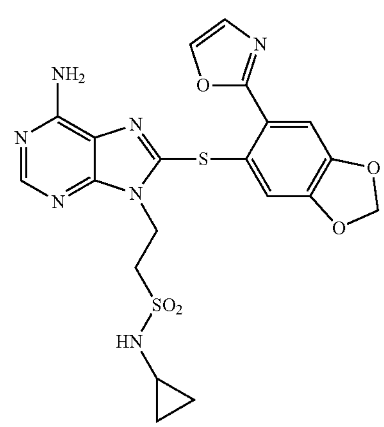 | 2-(6-amino-8-((6-(oxazol-2-yl)benzo[d][1,3]dioxol-5-yl)thio)-9H-purin-9-yl)-N-cyclopropyl-ethanesulfonamide |

TABLE 1D-continued

| Compound No. | Structure | Name |
|---|---|---|
| 1D-8 | 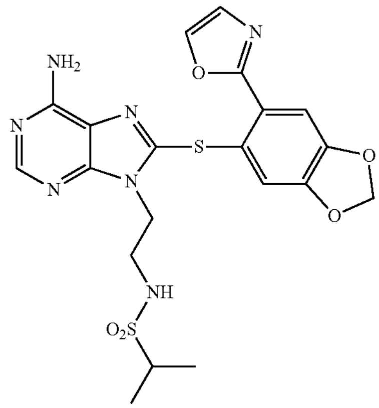 | N-(2-(6-amino-8-((6-(oxazol-2-yl)benzo[d][1,3]dioxol-5-yl)thio)-9H-purin-9-yl)ethyl)propane-2-sulfonamide |
| 1D-9 | 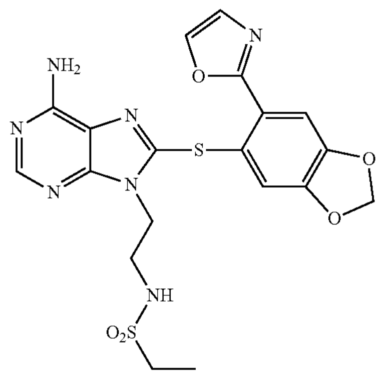 | N-(2-(6-amino-8-((6-(oxazol-2-yl)benzo[d][1,3]dioxol-5-yl)thio)-9H-purin-9-yl)ethyl)ethane-2-sulfonamide |
| 1D-10 | 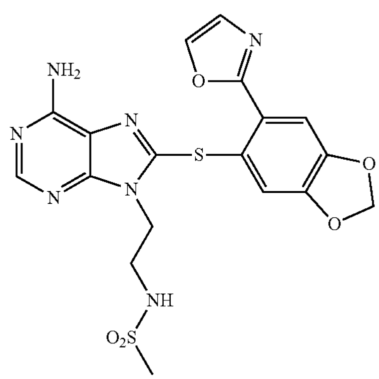 [SMILES: CS(=O)(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)methane-2-sulfonamide |
| 1D-11 | 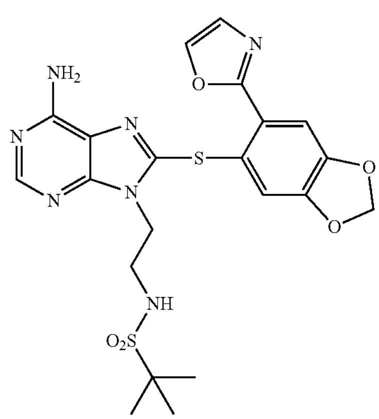 [SMILES: CC(C)(C)S(=O)(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)-2-methylpropane-2-sulfonamide |

TABLE 1D-continued
| Compound No. | Structure | Name |
|---|---|---|
| 1D-12 | 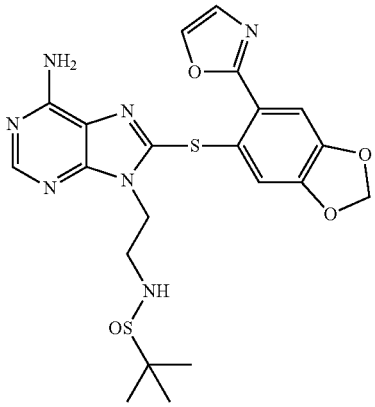 | N-(2-(6-amino-8-((6-(oxazol-2-yl)benzo[d][1,3]dioxol-5-yl)thio)-9H-purin-9-yl)ethyl)-2-methylpropane-2-sulfinamide |
| 1D-13 | 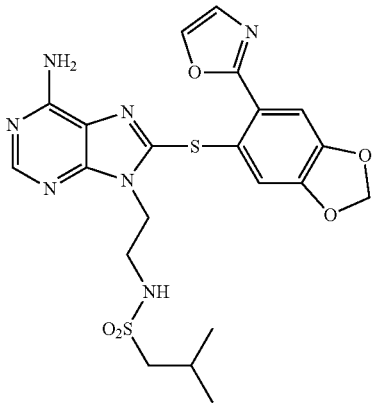 [SMILES: CC(C)CS(=O)(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)-2-methylpropane-1-sulfonamide |
| 1D-14 | 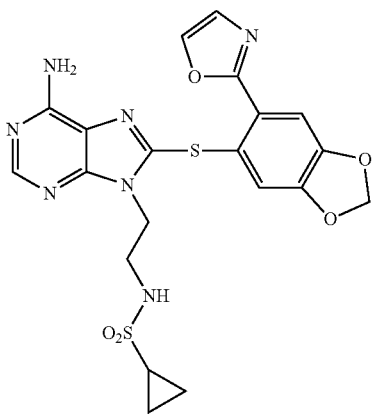 [SMILES: Nc1ncnc2c1nc(Sc1cc3c(cc1-c1ncco1)OCO3)n2CCNS(=O)(=O)C1CC1] | N-(2-(6-amino-8-((6-(oxazol-2-yl)benzo[d][1,3]dioxol-5-yl)thio)-9H-purin-9-yl)ethyl)cyclopropane-sulfonamide |

TABLE 1D-continued

| Compound No. | Structure | Name |
|---|---|---|
| 1D-15 | 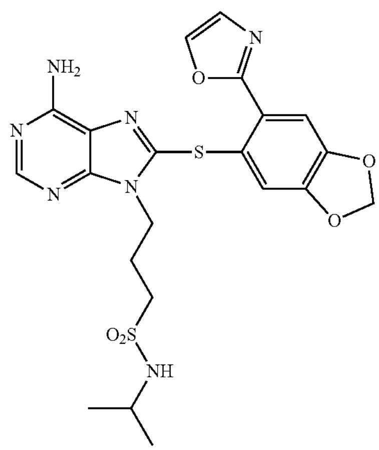 | 3-(6-amino-8-((6-(oxazol-2-yl)benzo[d][1,3]dioxol-5-yl)thio)-9H-purin-9-yl)-N-isopropylpropane-1-sulfonamide |
| 1D-16 | 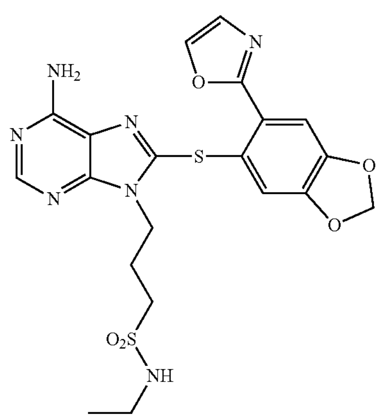 [SMILES: CCNS(=O)(=O)CCCn1c(Sc2cc3c(cc2-c2ncco2)OCO3)nc2c(N)ncnc21] | 3-(6-amino-8-((6-(oxazol-2-yl)benzo[d][1,3]dioxol-5-yl)thio)-9H-purin-9-yl)-N-ethylpropane-1-sulfonamide |
| 1D-17 | 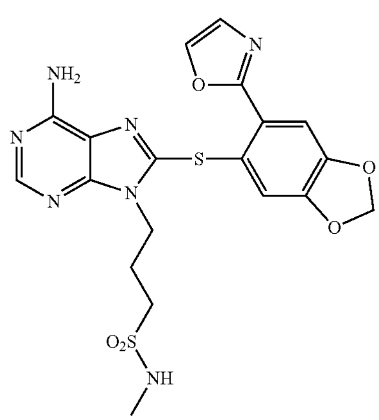 | 3-(6-amino-8-((6-(oxazol-2-yl)benzo[d][1,3]dioxol-5-yl)thio)-9H-purin-9-yl)-N-methylpropane-1-sulfonamide |

TABLE 1D-continued

| Compound No. | Structure | Name |
|---|---|---|
| 1D-18 | 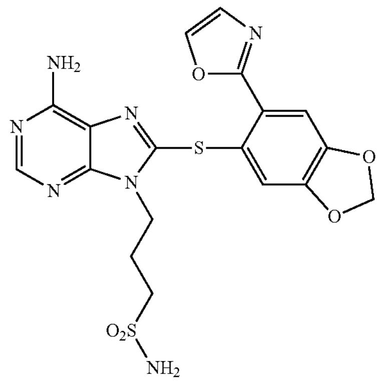 [SMILES: Nc1ncnc2c1nc(Sc1cc3c(cc1-c1ncco1)OCO3)n2CCCS(N)(=O)=O] | 3-(6-amino-8-((6-(oxazol-2-yl)benzo[d][1,3]dioxol-5-yl)thio)-9H-purin-9-yl)propane-1-sulfonamide |
| 1D-19 | 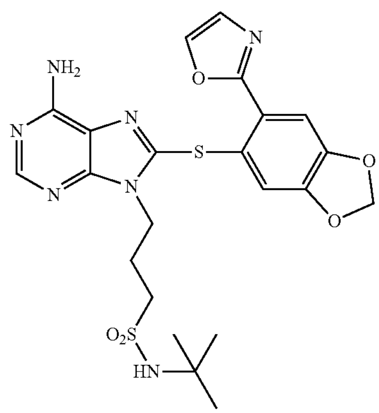 [SMILES: CC(C)(C)NS(=O)(=O)CCCn1c(Sc2cc3c(cc2-c2ncco2)OCO3)nc2c(N)ncnc21] | 3-(6-amino-8-((6-(oxazol-2-yl)benzo[d][1,3]dioxol-5-yl)thio)-9H-purin-9-yl)-N-(tert-butyl)propane-1-sulfonamide |
| 1D-20 | 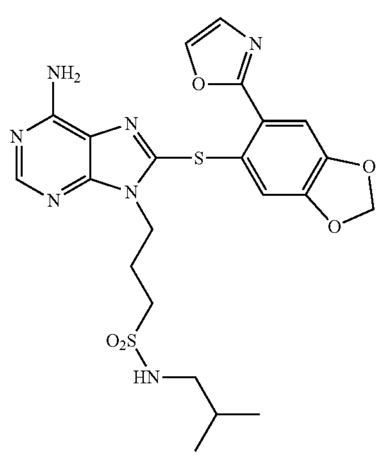 [SMILES: CC(C)CNS(=O)(=O)CCCn1c(Sc2cc3c(cc2-c2ncco2)OCO3)nc2c(N)ncnc21] | 3-(6-amino-8-((6-(oxazol-2-yl)benzo[d][1,3]dioxol-5-yl)thio)-9H-purin-9-yl)-N-isobutylpropane-1-sulfonamide |

TABLE 1D-continued

| Compound No. | Structure | Name |
| --- | --- | --- |
| 1D-21 | 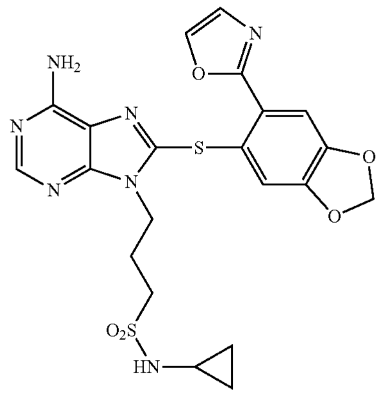 | 3-(6-amino-8-((6-(oxazol-2-yl)benzo[d][1,3]dioxol-5-yl)thio)-9H-purin-9-yl)-N-cyclopropylpropane-1-sulfonamide |
| 1D-22 | 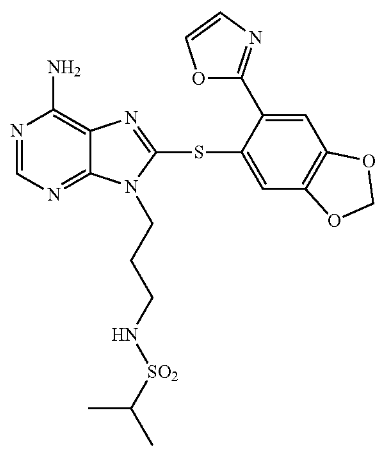 | N-(3-(6-amino-8-((6-(oxazol-2-yl)benzo[d][1,3]dioxol-5-yl)thio)-9H-purin-9-yl)propyl)propane-2-sulfonamide |
| 1D-23 | 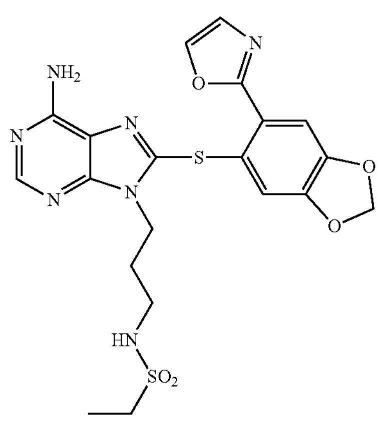 | N-(3-(6-amino-8-((6-(oxazol-2-yl)benzo[d][1,3]dioxol-5-yl)thio)-9H-purin-9-yl)propyl)ethane-sulfonamide |

TABLE 1D-continued

| Compound No. | Structure | Name |
|---|---|---|
| 1D-24 | 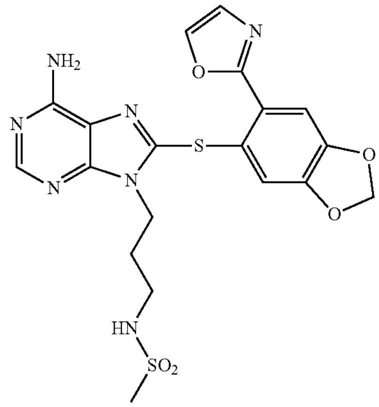 | N-(3-(6-amino-8-((6-(oxazol-2-yl)benzo[d][1,3]dioxol-5-yl)thio)-9H-purin-9-yl)propyl)methane-2-sulfonamide |
| 1D-25 | 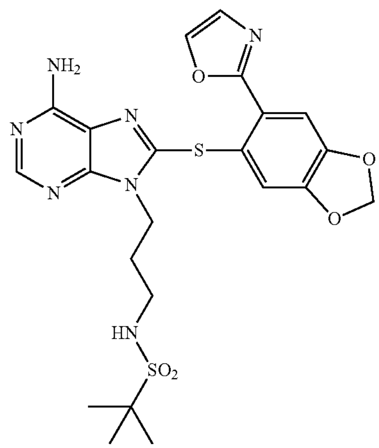 | N-(3-(6-amino-8-((6-(oxazol-2-yl)benzo[d][1,3]dioxol-5-yl)thio)-9H-purin-9-yl)propyl)-2-methylpropane-2-sulfonamide |
| 1D-26 | 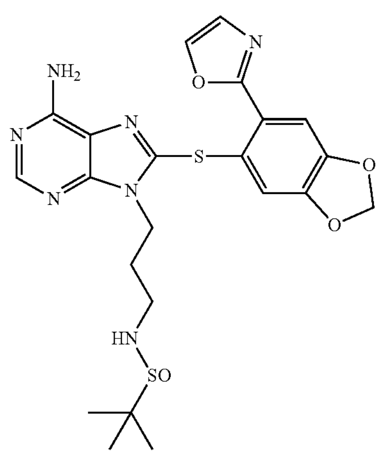 | N-(3-(6-amino-8-((6-(oxazol-2-yl)benzo[d][1,3]dioxol-5-yl)thio)-9H-purin-9-yl)propyl)-2-methylpropane-2-sulfinamide |

TABLE 1D-continued

| Compound No. | Structure | Name |
|---|---|---|
| 1D-27 | 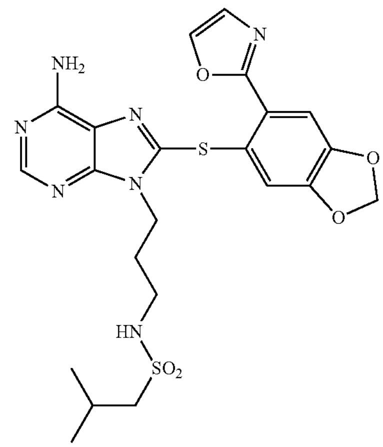 | N-(3-(6-amino-8-((6-(oxazol-2-yl)benzo[d][1,3]dioxol-5-yl)thio)-9H-purin-9-yl)propyl)-2-methylpropane-1-sulfonamide |
| 1D-28 | 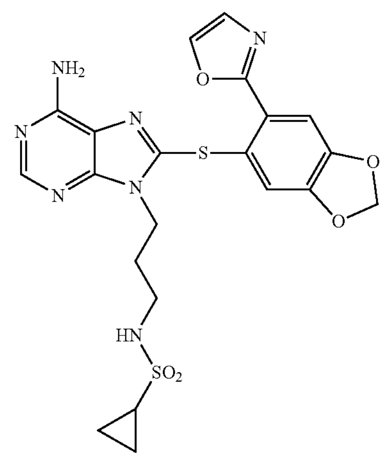 | N-(3-(6-amino-8-((6-(oxazol-2-yl)benzo[d][1,3]dioxol-5-yl)thio)-9H-purin-9-yl)propyl)cyclopropanesulfonamide |
| 1D-29 | 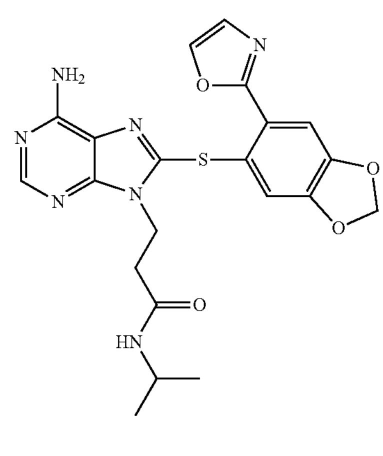 | 3-(6-amino-8-((6-(oxazol-2-yl)benzo[d][1,3]dioxol-5-yl)thio)-9H-purin-9-yl)-N-isopropylpropanamide |

TABLE 1D-continued

| Compound No. | Structure | Name |
|---|---|---|
| 1D-30 | 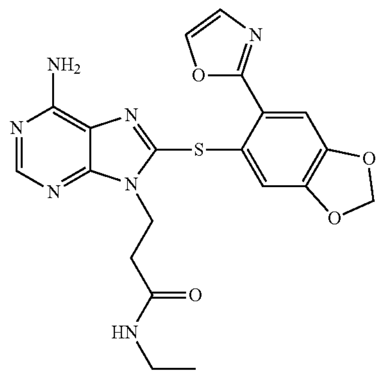 [SMILES: CCNC(=O)CCn1c(Sc2cc3c(cc2-c2ncco2)OCO3)nc2c(N)ncnc21] | 3-(6-amino-8-((6-(oxazol-2-yl)-benzo[d][1,3]dioxol-5-yl)thio)-9H-purin-9-yl)-N-ethylpropanamide |
| 1D-31 | 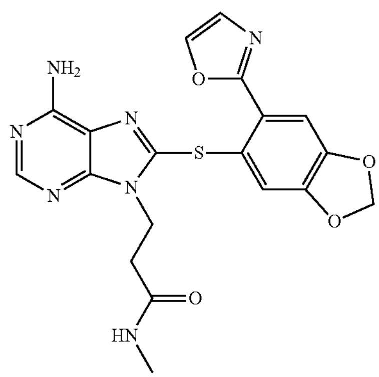 [SMILES: CNC(=O)CCn1c(Sc2cc3c(cc2-c2ncco2)OCO3)nc2c(N)ncnc21] | 3-(6-amino-8-((6-(oxazol-2-yl)benzo[d][1,3]-dioxol-5-yl)thio)-9H-purin-9-yl)-N-methylpropanamide |
| 1D-32 | 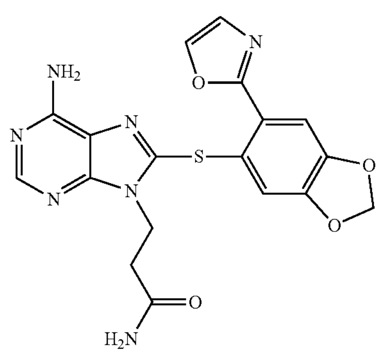 [SMILES: NC(=O)CCn1c(Sc2cc3c(cc2-c2ncco2)OCO3)nc2c(N)ncnc21] | 3-(6-amino-8-((6-(oxazol-2-yl)benzo[d][1,3]dioxol-5-yl)thio)-9H-purin-9-yl)propionamide |
| 1D-33 | 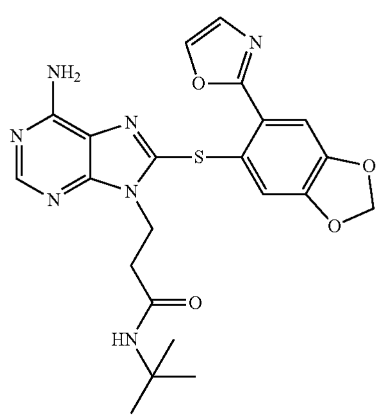 | 3-(6-amino-8-((6-(oxazol-2-yl)benzo[d][1,3]dioxol-5-yl)thio)-9H-purin-9-yl)-N-(tert-butyl)propanamide |

TABLE 1D-continued

| Compound No. | Structure | Name |
|---|---|---|
| 1D-34 | 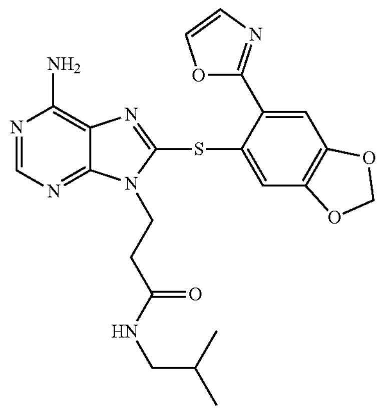 [SMILES: CC(C)CNC(=O)CCn1c(Sc2cc3c(cc2-c2ncco2)OCO3)nc2c(N)ncnc21] | 3-(6-amino-8-((6-(oxazol-2-yl)benzo[d][1,3]dioxol-5-yl)thio)-9H-purin-9-yl)-N-isobutylpropanamide |
| 1D-35 | 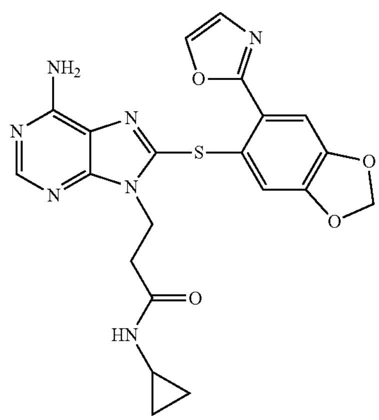 [SMILES: Nc1ncnc2c1nc(Sc1cc3c(cc1-c1ncco1)OCO3)n2CCC(=O)NC1CC1] | 3-(6-amino-8-((6-(oxazol-2-yl)benzo[d][1,3]dioxol-5-yl)thio)-9H-purin-9-yl)-N-cyclopropylpropanamide |
| 1D-36 | 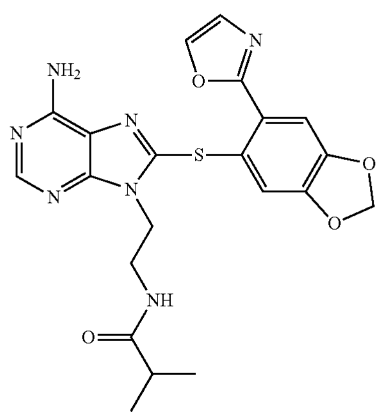 [SMILES: CC(C)C(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)isobutyramide |
| 1D-37 | 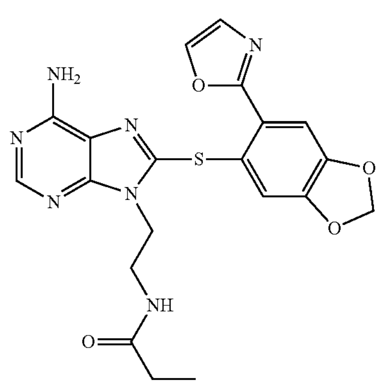 [SMILES: CCC(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)propionamide |

TABLE 1D-continued

| Compound No. | Structure | Name |
|---|---|---|
| 1D-38 | 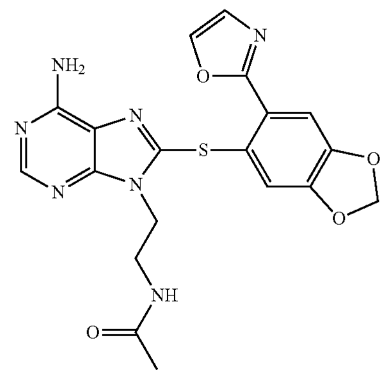 [SMILES: CC(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)acetamide |
| 1D-39 | 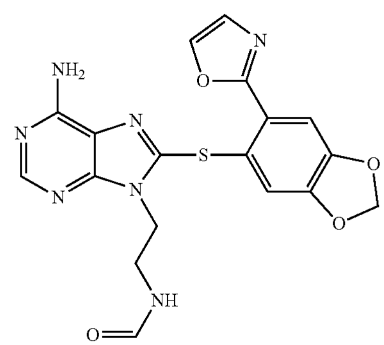 | N-(2-(6-amino-8-((6-(oxazol-2-yl)benzo[d][1,3]dioxol-5-yl)thio)-9H-purin-9-yl)ethyl)formamide |
| 1D-40 | 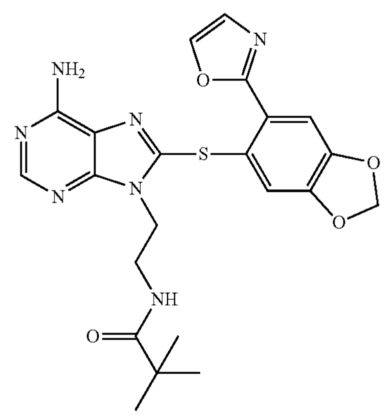 [SMILES: CC(C)(C)C(=O)NCCn1c(Sc2cc3c(cc2-c2ncco2)OCO3)nc2c(N)ncnc21] | N-(2-(6-amino-8-((6-(oxazol-2-yl)benzo[d][1,3]dioxol-5-yl)thio)-9H-purin-9-yl)ethyl)pivalamide |
| 1D-41 | 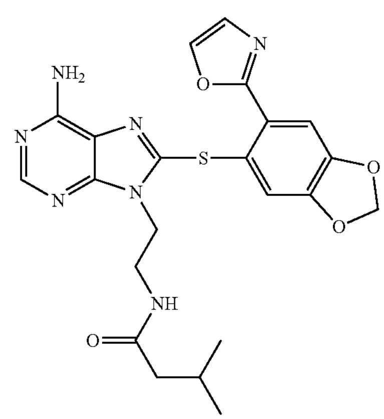 | N-(2-(6-amino-8-((6-(oxazol-2-yl)benzo[d][1,3]dioxol-5-yl)thio)-9H-purin-9-yl)ethyl)-3-methylbutanamide |

TABLE 1D-continued
| Compound No. | Structure | Name |
|---|---|---|
| 1D-42 | 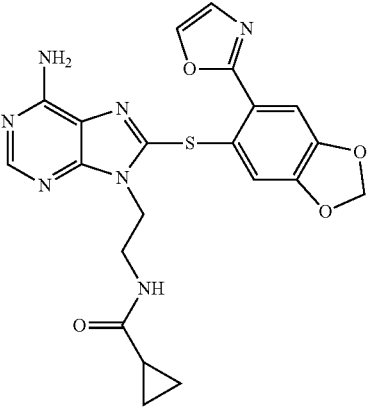 [SMILES: Nc1ncnc2c1nc(Sc1cc3c(cc1-c1ncco1)OCO3)n2CCNC(=O)C1CC1] | N-(2-(6-amino-8-((6-(oxazol-2-yl)benzo[d][1,3]dioxol-5-yl)thio)-9H-purin-9-yl)ethyl)cyclopropane-carboxamide |
| 1D-43 | 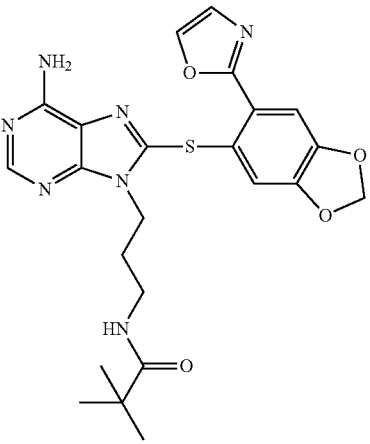 [SMILES: CC(C)(C)C(=O)NCCCn1c(Sc2cc3c(cc2-c2ncco2)OCO3)nc2c(N)ncnc21] | N-{3-[6-Amino-8-(6-oxazol-2-yl-benzo[1,3]dioxol-5-ylsulfanyl)-purin-9-yl]-propyl}-2,2-dimethyl-propionamide |
| 1D-44 | 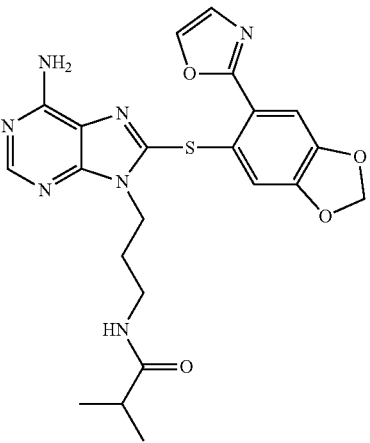 | N-{3-[6-Amino-8-(6-oxazol-2-yl-benzo[1,3]dioxol-5-ylsulfanyl)-purin-9-yl]-propyl}-isobutyramide |

TABLE 1D-continued

| Compound No. | Structure | Name |
|---|---|---|
| 1D-45 | 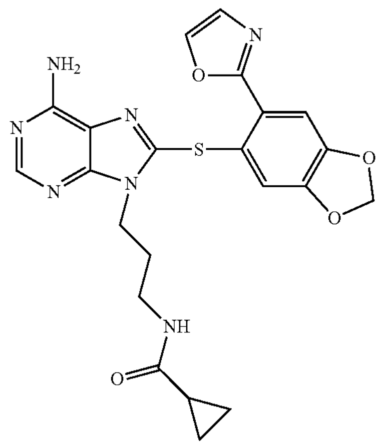 [SMILES: Nc1ncnc2c1nc(Sc1cc3c(cc1-c1ncco1)OCO3)n2CCCNC(=O)C1CC1] | Cyclopropanecarboxylic acid {3-[6-amino-8-(6-oxazol-2-yl-benzo[1,3]dioxol-5-ylsulfanyl)-purin-9-yl]-propyl}-amide |
| 1D-46 | 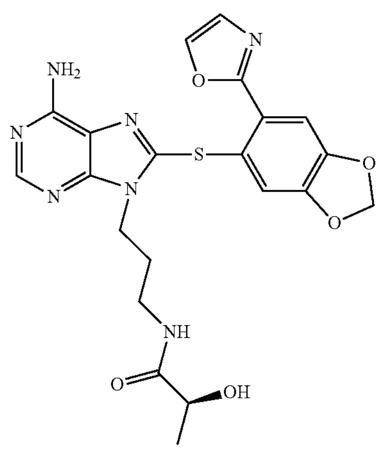 [SMILES: C[C@H](O)C(=O)NCCCn1c(Sc2cc3c(cc2-c2ncco2)OCO3)nc2c(N)ncnc21] | N-{3-[6-Amino-8-(6-oxazol-2-yl-benzo[1,3]dioxol-5-ylsulfanyl)-purin-9-yl]-propyl}-2-hydroxy-propionamide |
| 1D-47 | 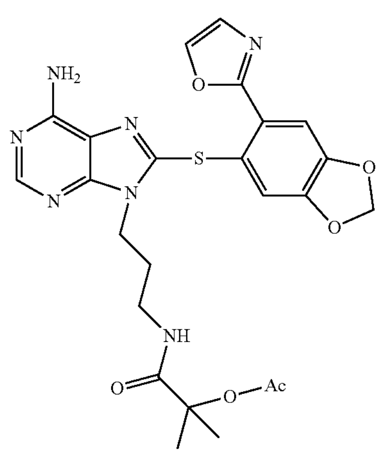 [SMILES: CC(=O)OC(C)(C)C(=O)NCCCn1c(Sc2cc3c(cc2-c2ncco2)OCO3)nc2c(N)ncnc21] | Acetic acid 1-{3-[6-amino-8-(6-oxazol-2-yl-benzo[1,3]dioxol-5-ylsulfanyl)-purin-9-yl]-propylcarbamoyl}-1-methyl-ethyl ester |

TABLE 1D-continued

| Compound No. | Structure | Name |
| --- | --- | --- |
| 1D-48 | 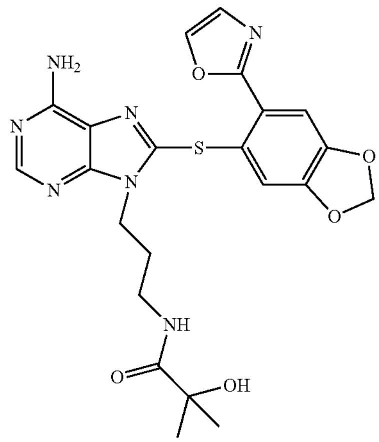 | N-{3-[6-Amino-8-(6-oxazol-2-yl-benzo[1,3]dioxol-5-ylsulfanyl)-purin-9-yl]-propyl}-2-hydroxy-2-methyl-propionamide |
| 1D-49 | 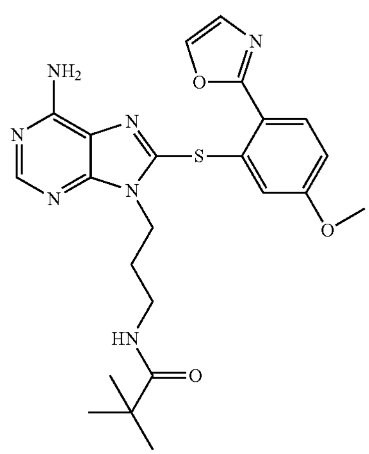 [SMILES: COc1ccc(-c2ncco2)c(Sc2nc3c(N)ncnc3n2CCCNC(=O)C(C)(C)C)c1] | N-(3-(6-amino-8-((5-methoxy-2-(oxazol-2-yl)phenyl)thio)-9H-purin-9-yl)propyl)pivalamide |

Table 1E lists specific examples of additional compounds within this embodiment. In each of the structures as drawn therein, $X_2$ is a nitrogen and sulfur-containing heteroaryl group, specifically a thiazolyl group, and $X_4$ is H. Corresponding structures in which $X_2$ is a different nitrogen and sulfur-containing optionally substituted aryl group are within the scope of the disclosure. In each of the structures in Table 1E, Y is S and $X_4$ is H. However, corresponding structures in which Y is $CH_2$ and/or $X_4$ is F, Cl, Br, or I are also within the scope of the disclosure. Additionally, in connection with each of the structures in Table 1E, corresponding structures in which $X_2$ is a nitrogen and sulfur-containing optionally substituted aryl group different from optionally substituted thiazolyl, Y is $CH_2$, and/or $X_4$ is F, Cl, Br, or I are also within the scope of the disclosure.

TABLE 1E
| Compound No. | Structure | Name |
|---|---|---|
| 1E-1 | 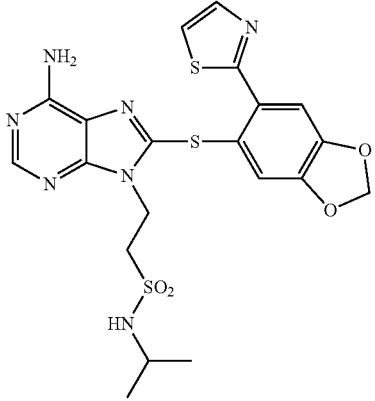 [SMILES: CC(C)NS(=O)(=O)CCn1c(Sc2cc3c(cc2-c2nccs2)OCO3)nc2c(N)ncnc21] | 2-(6-amino-8-((6-(thiazol-2-yl)benzo[d][1,3]dioxol-5-yl)thio)-9H-purin-9-yl)-N-isopropylethanesulfonamide |
| 1E-2 | 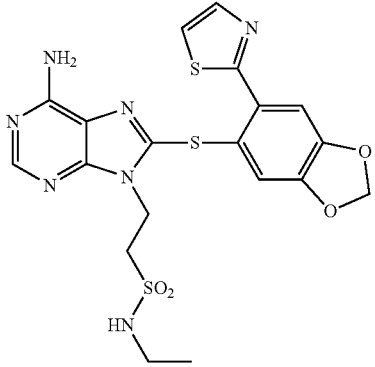 | 2-(6-amino-8-((6-(thiazol-2-yl)benzo[d][1,3]dioxol-5-yl)thio)-9H-purin-9-yl)-N-ethylethanesulfonamide |
| 1E-3 | 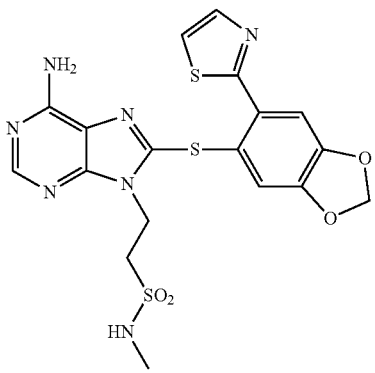 | 2-(6-amino-8-((6-(thiazol-2-yl)benzo[d][1,3]dioxol-5-yl)thio)-9H-purin-9-yl)-N-methylethanesulfonamide |
| 1E-4 | 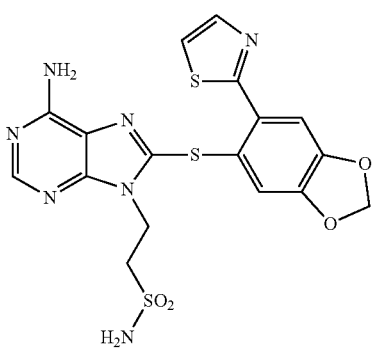 [SMILES: Nc1ncnc2c1nc(Sc1cc3c(cc1-c1nccs1)OCO3)n2CCS(N)(=O)=O] | 2-(6-amino-8-((6-(thiazol-2-yl)benzo[d][1,3]dioxol-5-yl)thio)-9H-purin-9-yl)ethanesulfonamide |

TABLE 1E-continued
| Compound No. | Structure | Name |
|---|---|---|
| 1E-5 | 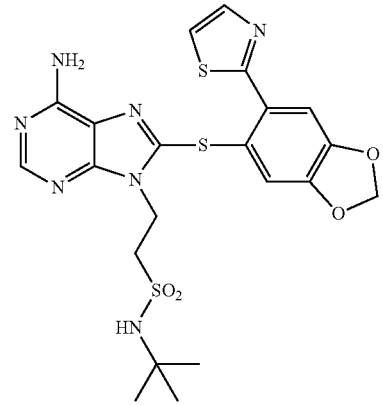 | 2-(6-amino-8-((6-(thiazol-2-yl)benzo[d][1,3]dioxol-5-yl)thio)-9H-purin-9-yl)-N-(tert-butyl)ethanesulfonamide |
| 1E-6 | 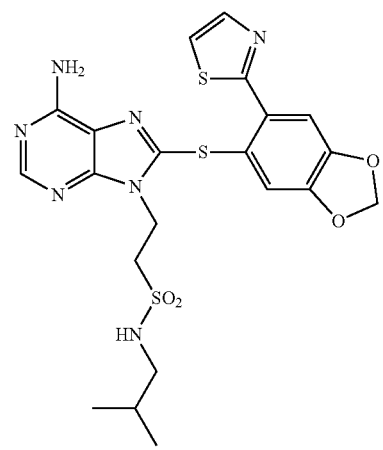 [SMILES: CC(C)CNS(=O)(=O)CCn1c(Sc2cc3c(cc2-c2nccs2)OCO3)nc2c(N)ncnc21] | 2-(6-amino-8-((6-(thiazol-2-yl)benzo[d][1,3]dioxol-5-yl)thio)-9H-purin-9-yl)-N-isobutylethanesulfonamide |
| 1E-7 | 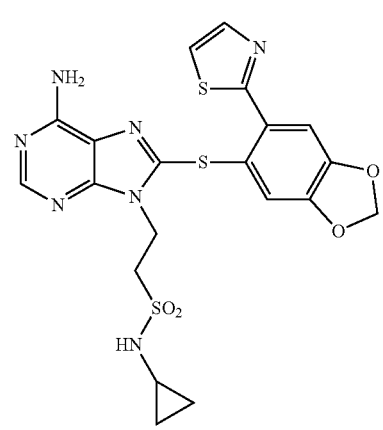 [SMILES: Nc1ncnc2c1nc(Sc1cc3c(cc1-c1nccs1)OCO3)n2CCS(=O)(=O)NC1CC1] | 2-(6-amino-8-((6-(thiazol-2-yl)benzo[d][1,3]dioxol-5-yl)thio)-9H-purin-9-yl)-N-cyclopropyl-ethanesulfonamide |

TABLE 1E-continued

| Compound No. | Structure | Name |
|---|---|---|
| 1E-8 | 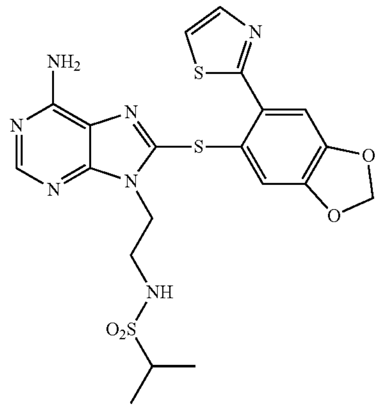 [SMILES: CC(C)S(=O)(=O)NCCn1c(Sc2cc3c(cc2-c2nccs2)OCO3)nc2c(N)ncnc21] | N-(2-(6-amino-8-((6-(thiazol-2-yl)benzo[d][1,3]dioxol-5-yl)thio)-9H-purin-9-yl)ethyl)propane-2-sulfonamide |
| 1E-9 | 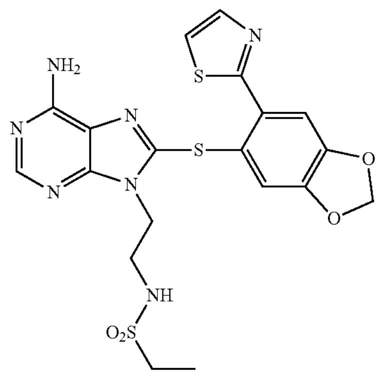 [SMILES: CCS(=O)(=O)NCCn1c(Sc2cc3c(cc2-c2nccs2)OCO3)nc2c(N)ncnc21] | N-(2-(6-amino-8-((6-(thiazol-2-yl)benzo[d][1,3]dioxol-5-yl)thio)-9H-purin-9-yl)ethyl)ethane-2-sulfonamide |
| 1E-10 | 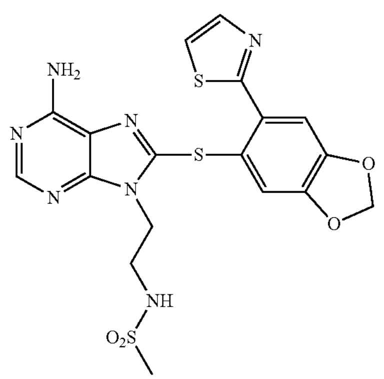 [SMILES: CS(=O)(=O)NCCn1c(Sc2cc3c(cc2-c2nccs2)OCO3)nc2c(N)ncnc21] | N-(2-(6-amino-8-((6-(thiazol-2-yl)benzo[d][1,3]dioxol-5-yl)thio)-9H-purin-9-yl)ethyl)methane-2-sulfonamide |
| 1E-11 | 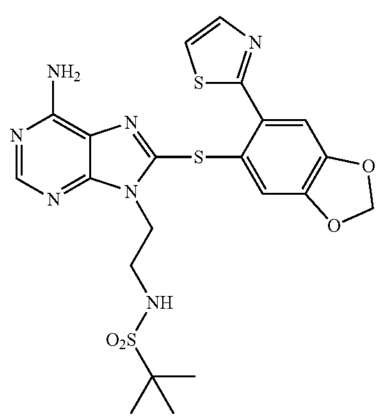 | N-(2-(6-amino-8-((6-(thiazol-2-yl)benzo[d][1,3]dioxol-5-yl)thio)-9H-purin-9-yl)ethyl)-2-methylpropane-2-sulfonamide |

TABLE 1E-continued
| Compound No. | Structure | Name |
| --- | --- | --- |
| 1E-12 | 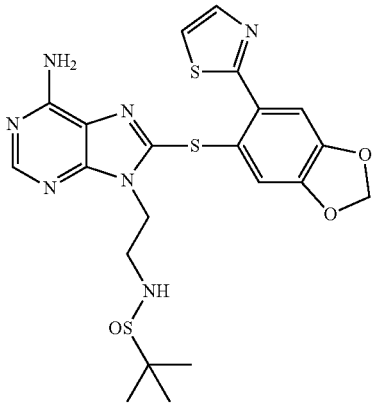 | N-(2-(6-amino-8-((6-(thiazol-2-yl)benzo[d][1,3]dioxol-5-yl)thio)-9H-purin-9-yl)ethyl)-2-methylpropane-2-sulfinamide |
| 1E-13 | 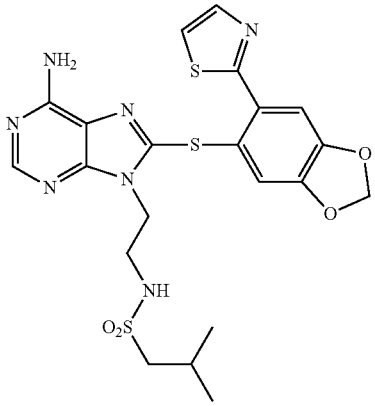 | N-(2-(6-amino-8-((6-(thiazol-2-yl)benzo[d][1,3]dioxol-5-yl)thio)-9H-purin-9-yl)ethyl)-2-methylpropane-1-sulfonamide |
| 1E-14 | 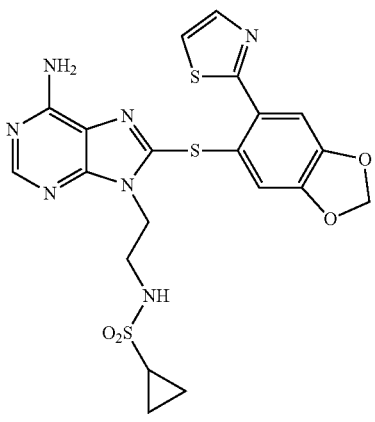 | N-(2-(6-amino-8-((6-(thiazol-2-yl)benzo[d][1,3]dioxol-5-yl)thio)-9H-purin-9-yl)ethyl)cyclopropane-sulfonamide |

TABLE 1E-continued
| Compound No. | Structure | Name |
|---|---|---|
| 1E-15 | 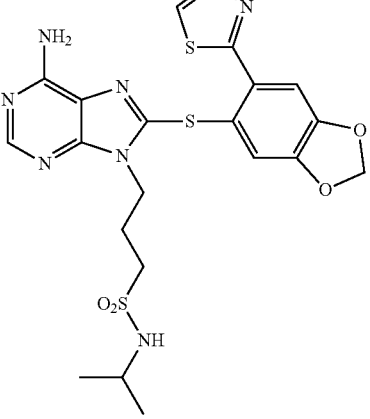 | 3-(6-amino-8-((6-(thiazol-2-yl)benzo[d][1,3]dioxol-5-yl)thio)-9H-purin-9-yl)-N-isopropylpropane-1-sulfonamide |
| 1E-16 | 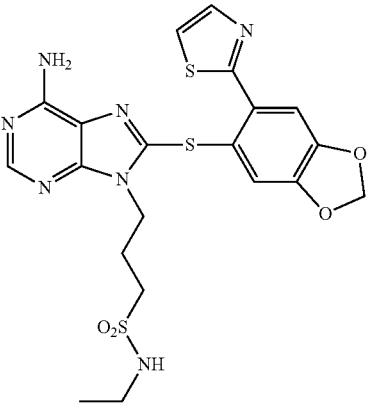 | 3-(6-amino-8-((6-(thiazol-2-yl)benzo[d][1,3]dioxol-5-yl)thio)-9H-purin-9-yl)-N-ethylpropane-1-sulfonamide |
| 1E-17 | 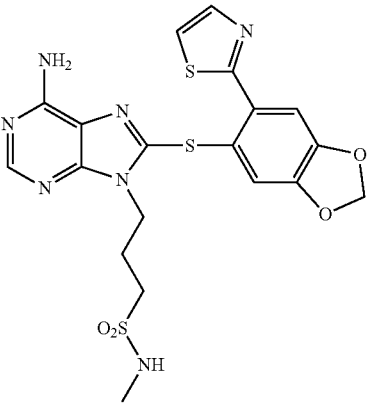 [SMILES: CNS(=O)(=O)CCCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-methylpropane-1-sulfonamide |

TABLE 1E-continued

| Compound No. | Structure | Name |
| --- | --- | --- |
| 1E-18 | 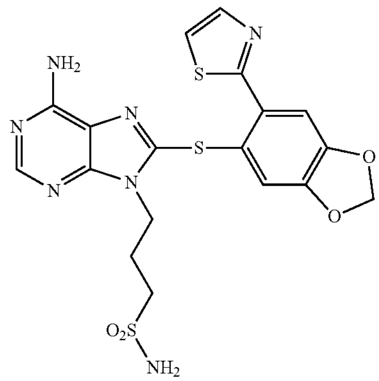 | 3-(6-amino-8-((6-(thiazol-2-yl)benzo[d][1,3]dioxol-5-yl)thio)-9H-purin-9-yl)propane-1-sulfonamide |
| 1E-19 | 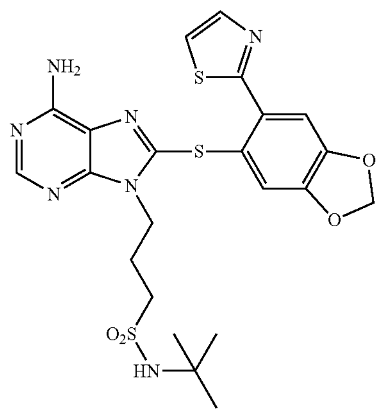 [SMILES: CC(C)(C)NS(=O)(=O)CCCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-(tert-butyl)propane-1-sulfonamide |
| 1E-20 | 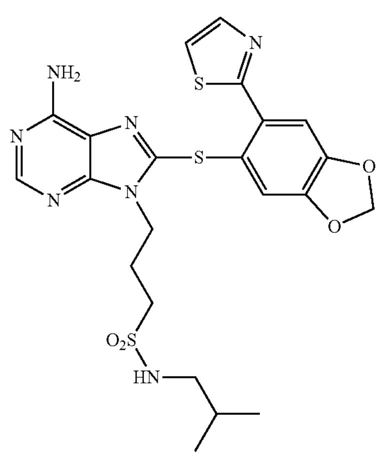 [SMILES: CC(C)CNS(=O)(=O)CCCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-isobutylpropane-1-sulfonamide |

TABLE 1E-continued
| Compound No. | Structure | Name |
|---|---|---|
| 1E-21 | 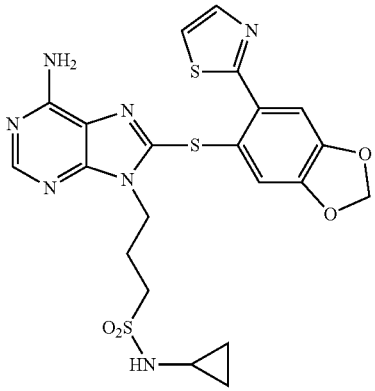 [SMILES: Nc1ncnc2c1nc(Sc1cc3c(cc1-c1nccs1)OCO3)n2CCCS(=O)(=O)NC1CC1] | 3-(6-amino-8-((6-(thiazol-2-yl)benzo[d][1,3]dioxol-5-yl)thio)-9H-purin-9-yl)-N-cyclopropylpropane-1-sulfonamide |
| 1E-22 | 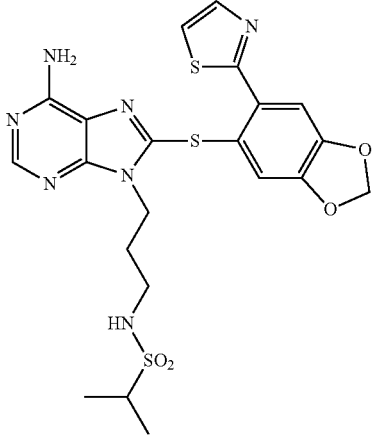 [SMILES: CC(C)S(=O)(=O)NCCCn1c(Sc2cc3c(cc2-c2nccs2)OCO3)nc2c(N)ncnc21] | N-(3-(6-amino-8-((6-(thiazol-2-yl)benzo[d][1,3]dioxol-5-yl)thio)-9H-purin-9-yl)propyl)propane-2-sulfonamide |
| 1E-23 | 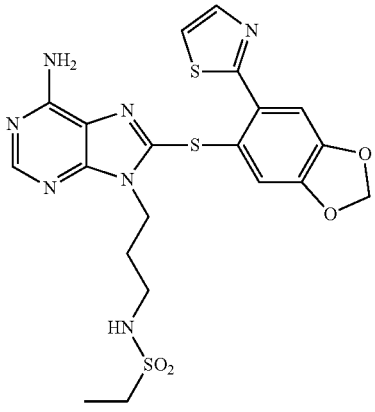 | N-(3-(6-amino-8-((6-(thiazol-2-yl)benzo[d][1,3]dioxol-5-yl)thio)-9H-purin-9-yl)propyl)ethane-2-sulfonamide |

TABLE 1E-continued

| Compound No. | Structure | Name |
| --- | --- | --- |
| 1E-24 | 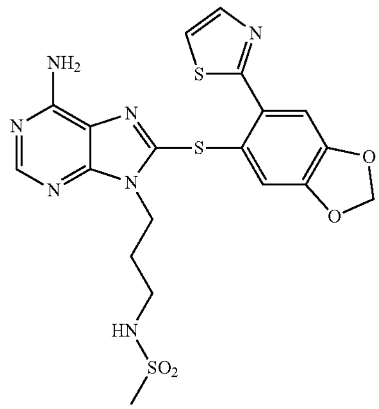 [SMILES: CS(=O)(=O)NCCCn1c(Sc2cc3c(cc2-c2nccs2)OCO3)nc2c(N)ncnc21] | N-(3-(6-amino-8-((6-(thiazol-2-yl)benzo[d][1,3]dioxol-5-yl)thio)-9H-purin-9-yl)propyl)methane-2-sulfonamide |
| 1E-25 | 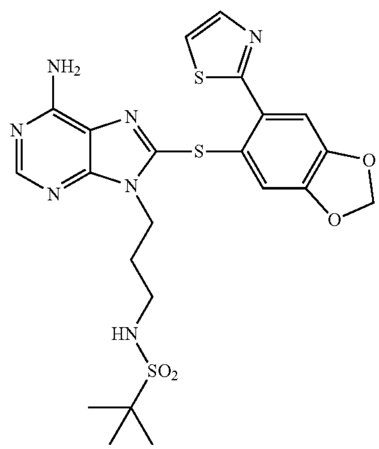 [SMILES: CC(C)(C)S(=O)(=O)NCCCn1c(Sc2cc3c(cc2-c2nccs2)OCO3)nc2c(N)ncnc21] | N-(3-(6-amino-8-((6-(thiazol-2-yl)benzo[d][1,3]dioxol-5-yl)thio)-9H-purin-9-yl)propyl)-2-methypropane-2-sulfonamide |
| 1E-26 | 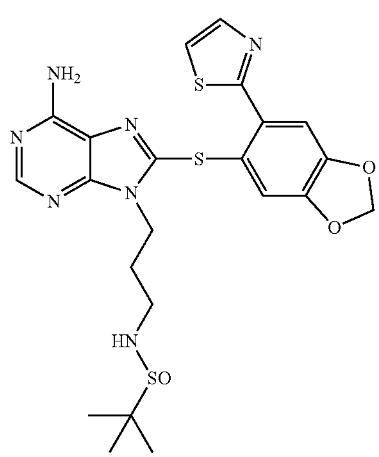 | N-(3-(6-amino-8-((6-(thiazol-2-yl)benzo[d][1,3]dioxol-5-yl)thio)-9H-purin-9-yl)propyl)-2-methypropane-2-sulfinamide |

TABLE 1E-continued

| Compound No. | Structure | Name |
|---|---|---|
| 1E-27 | 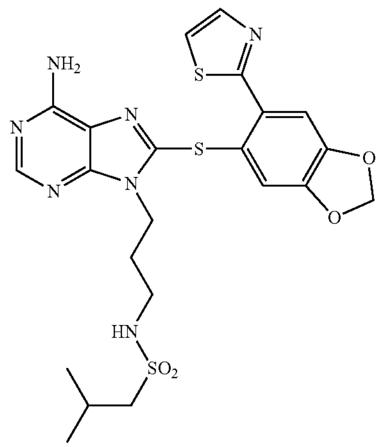 [SMILES: CC(C)CS(=O)(=O)NCCCn1c(Sc2cc3c(cc2-c2nccs2)OCO3)nc2c(N)ncnc21] | N-(3-(6-amino-8-((6-(thiazol-2-yl)benzo[d][1,3]dioxol-5-yl)thio)-9H-purin-9-yl)propyl)-2-methypropane-1-sulfonamide |
| 1E-28 | 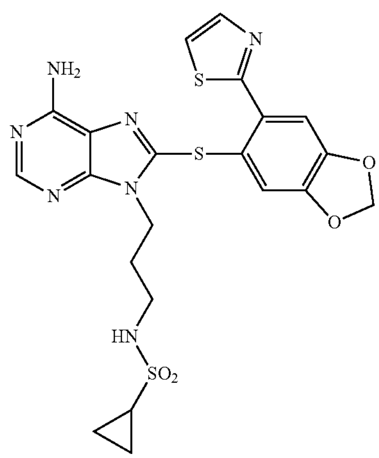 [SMILES: Nc1ncnc2c1nc(Sc1cc3c(cc1-c1nccs1)OCO3)n2CCCNS(=O)(=O)C1CC1] | N-(3-(6-amino-8-((6-(thiazol-2-yl)benzo[d][1,3]dioxol-5-yl)thio)-9H-purin-9-yl)propyl)cyclopropane-sulfonamide |
| 1E-29 | 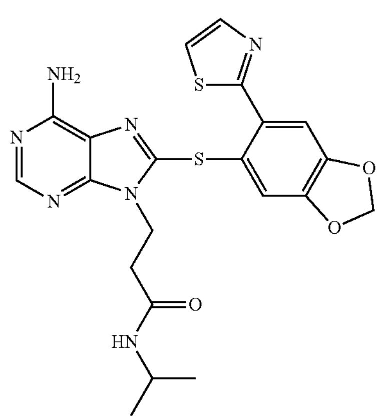 | 3-(6-amino-8-((6-(thiazol-2-yl)benzo[d][1,3]dioxol-5-yl)thio)-9H-purin-9-yl)-N-isopropylpropanamide |

TABLE 1E-continued

| Compound No. | Structure | Name |
| --- | --- | --- |
| 1E-30 | 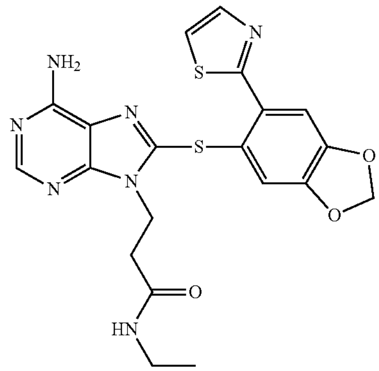 | 3-(6-amino-8-((6-(thiazol-2-yl)benzo[d][1,3]dioxol-5-yl)thio)-9H-purin-9-yl)-N-ethylpropanamide |
| 1E-31 | 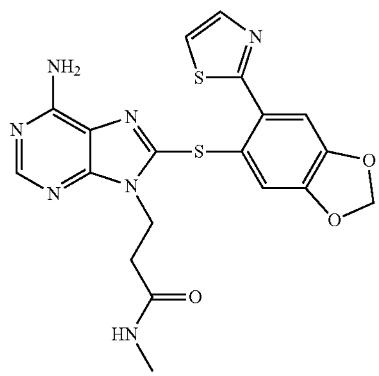 [SMILES: CNC(=O)CCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-methylpropanamide |
| 1E-32 | 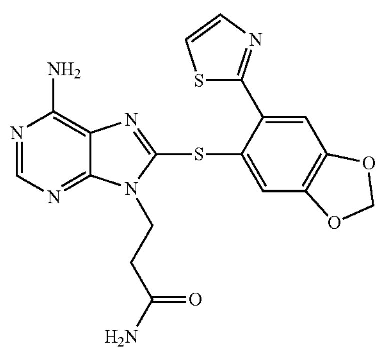 | 3-(6-amino-8-((6-(thiazol-2-yl)benzo[d][1,3]dioxol-5-yl)thio)-9H-purin-9-yl)propanamide |
| 1E-33 | 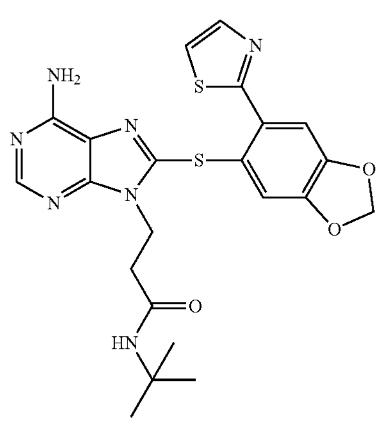 [SMILES: CC(C)(C)NC(=O)CCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-(tert-butyl)propanamide |

TABLE 1E-continued
| Compound No. | Structure | Name |
|---|---|---|
| 1E-34 | 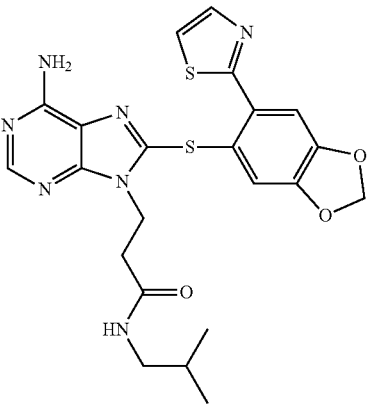 [SMILES: CC(C)CNC(=O)CCn1c(Sc2cc3c(cc2-c2nccs2)OCO3)nc2c(N)ncnc21] | 3-(6-amino-8-((6-(thiazol-2-yl)benzo[d][1,3]dioxol-5-yl)thio)-9H-purin-9-yl)-N-isobutylpropanamide |
| 1E-35 | 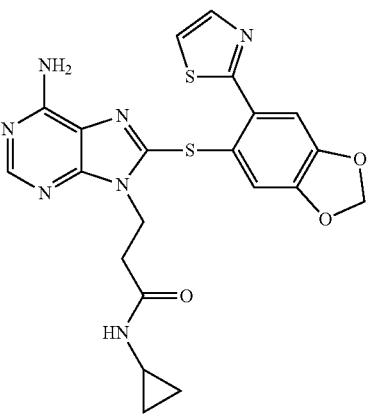 [SMILES: Nc1ncnc2c1nc(Sc1cc3c(cc1-c1nccs1)OCO3)n2CCC(=O)NC1CC1] | 3-(6-amino-8-((6-(thiazol-2-yl)benzo[d][1,3]dioxol-5-yl)thio)-9H-purin-9-yl)-N-cyclopropylpropanamide |
| 1E-36 | 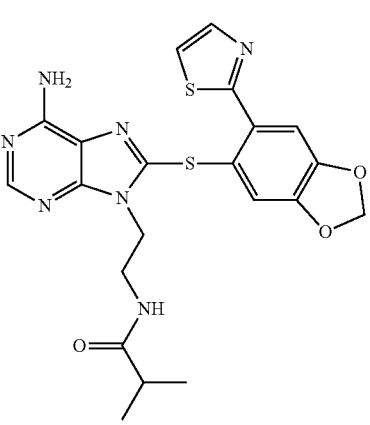 | N-(2-(6-amino-8-((6-(thiazol-2-yl)benzo[d][1,3]dioxol-5-yl)thio)-9H-purin-9-yl)ethyl)isobutyramide |
| 1E-37 | 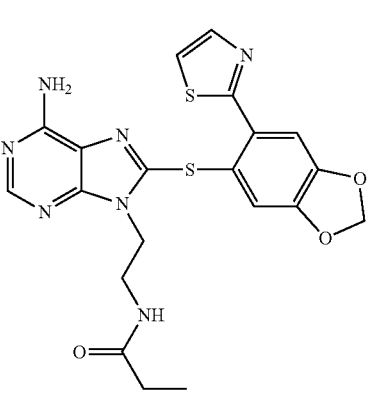 | N-(2-(6-amino-8-((6-(thiazol-2-yl)benzo[d][1,3]dioxol-5-yl)thio)-9H-purin-9-yl)ethyl)propionamide |

TABLE 1E-continued

| Compound No. | Structure | Name |
|---|---|---|
| 1E-38 | 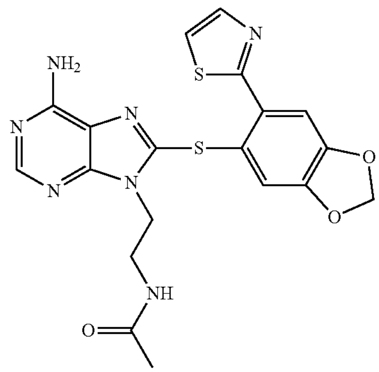 | N-(2-(6-amino-8-((6-(thiazol-2-yl)benzo[d][1,3]dioxol-5-yl)thio)-9H-purin-9-yl)ethyl)acetamide |
| 1E-39 | 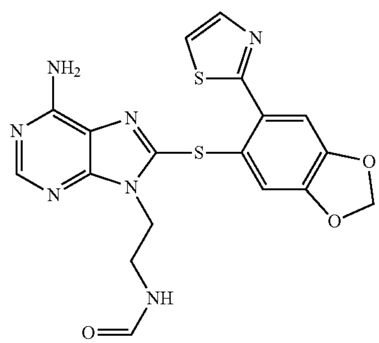 [SMILES: Nc1ncnc2c1nc(Sc1cc3c(cc1-c1nccs1)OCO3)n2CCNC=O] | N-(2-(6-amino-8-((6-(thiazol-2-yl)benzo[d][1,3]dioxol-5-yl)thio)-9H-purin-9-yl)ethyl)formamide |
| 1E-40 | 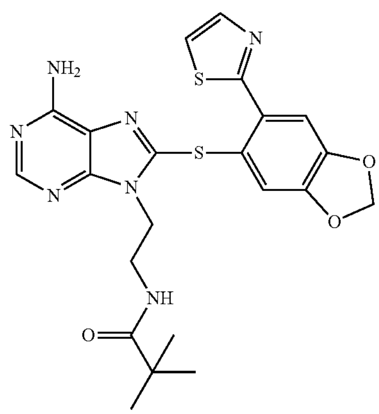 [SMILES: CC(C)(C)C(=O)NCCn1c(Sc2cc3c(cc2-c2nccs2)OCO3)nc2c(N)ncnc21] | N-(2-(6-amino-8-((6-(thiazol-2-yl)benzo[d][1,3]dioxol-5-yl)thio)-9H-purin-9-yl)ethyl)pivalamide |
| 1E-41 | 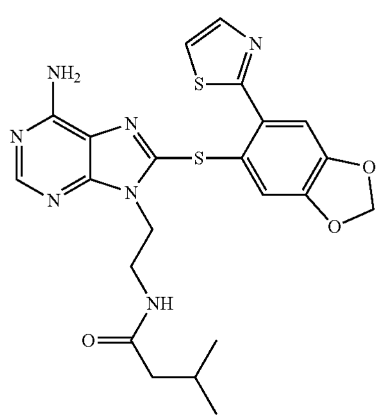 [SMILES: CC(C)CC(=O)NCCn1c(Sc2cc3c(cc2-c2nccs2)OCO3)nc2c(N)ncnc21] | N-(2-(6-amino-8-((6-(thiazol-2-yl)benzo[d][1,3]dioxol-5-yl)thio)-9H-purin-9-yl)ethyl)-3-methylbutanamide |

TABLE 1E-continued
| Compound No. | Structure | Name |
|---|---|---|
| 1E-42 | 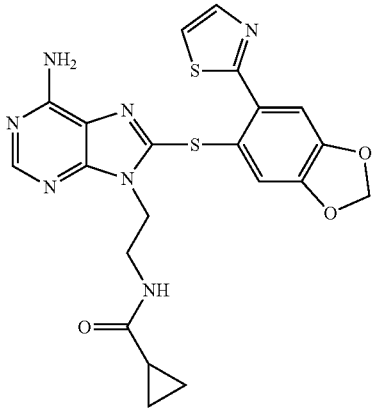 [SMILES: Nc1ncnc2c1nc(Sc1cc3c(cc1-c1nccs1)OCO3)n2CCNC(=O)C1CC1] | N-(2-(6-amino-8-((6-(thiazol-2-yl)benzo[d][1,3]dioxol-5-yl)thio)-9H-purin-9-yl)ethyl)cyclopropane-carboxamide |
| 1E-43 | 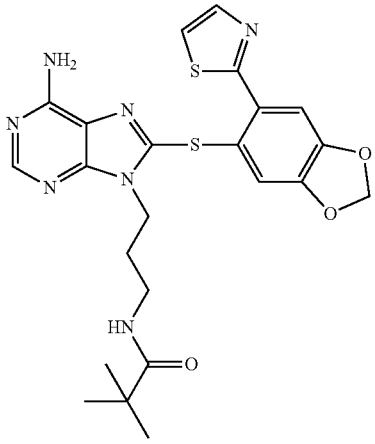 | N-{3-[6-Amino-8-(6-thiazol-2-yl-benzo[1,3]dioxol-5-ylsulfanyl)-purin-9-yl]-propyl}-2,2-dimethyl-propionamide |
| 1E-44 | 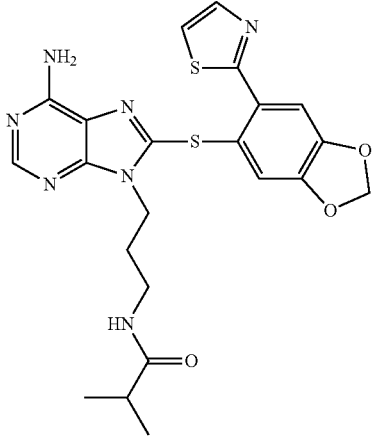 [SMILES: CC(C)C(=O)NCCCn1c(Sc2cc3c(cc2-c2nccs2)OCO3)nc2c(N)ncnc21] | N-{3-[6-Amino-8-(6-thiazol-2-yl-benzo[1,3]dioxol-5-ylsulfanyl)-purin-9-yl]-propyl}-isobutyramide |

TABLE 1E-continued
| Compound No. | Structure | Name |
|---|---|---|
| 1E-45 | 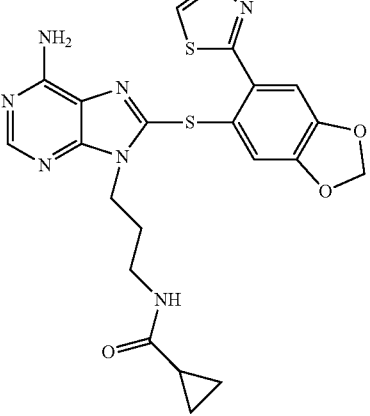 | Cyclopropanecarboxylic acid {3-[6-amino-8-(6-thiazol-2-yl-benzo[1,3]dioxol-5-ylsulfanyl)-purin-9-yl]-propyl}-amide |
| 1E-46 | 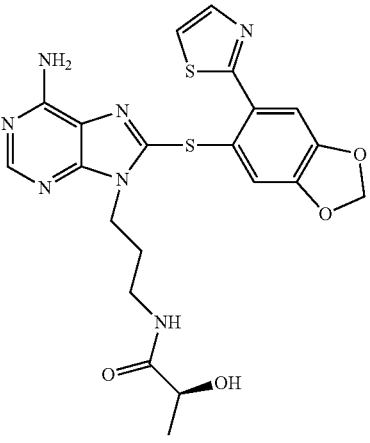 | N-{3-[6-Amino-8-(6-thiazol-2-yl-benzo[1,3]dioxol-5-ylsulfanyl)-purin-9-yl]-propyl}-2-hydroxy-propionamide |
| 1E-47 | 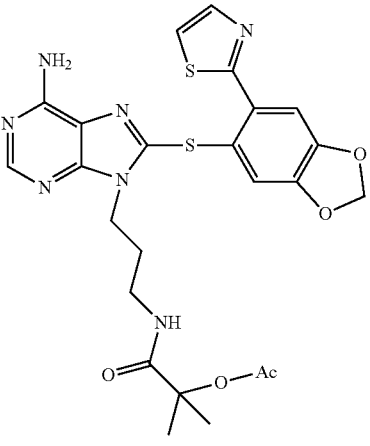 [SMILES: CC(=O)OC(C)(C)C(=O)NCCCn1c(Sc2cc3c(cc2-c2nccs2)OCO3)nc2c(N)ncnc21] | Acetic acid 1-{3-[6-amino-8-(6-thiazol-2-yl-benzo[1,3]dioxol-5-ylsulfanyl)-purin-9-yl]-propylcarbamoyl}-1-methyl-ethyl ester |

TABLE 1E-continued

| Compound No. | Structure | Name |
| --- | --- | --- |
| 1E-48 | 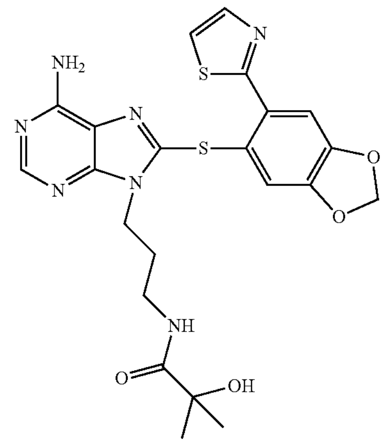 [SMILES: CC(C)(O)C(=O)NCCCn1c(Sc2cc3c(cc2-c2nccs2)OCO3)nc2c(N)ncnc21] | N-{3-[6-Amino-8-(6-thiazol-2-yl-benzo[1,3]dioxol-5-ylsulfanyl)-purin-9-yl]-propyl}-2-hydroxy-2-methyl-propionamide |
| 1E-49 | 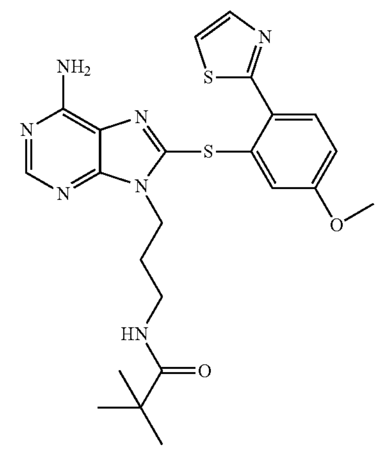 [SMILES: COc1ccc(-c2nccs2)c(Sc2nc3c(N)ncnc3n2CCCNC(=O)C(C)(C)C)c1] | N-(3-(6-amino-8-((5-methoxy-2-(thiazol-2-yl)phenyl)thio)-9H-purin-9-yl)propyl)pivalamide |

Table 1F lists specific examples of additional compounds within this embodiment. In each of the structures as drawn therein, $X_2$ is an oxygen-containing heteroaryl group, specifically a furanyl group, and $X_4$ is H. Corresponding structures in which $X_2$ is a different oxygen-containing optionally substituted aryl group are within the scope of the disclosure. In each of the structures in Table 1F, Y is S and $X_4$ is H. However, corresponding structures in which Y is $CH_2$ and/or $X_4$ is F, Cl, Br, or I are also within the scope of the disclosure. Additionally, in connection with each of the structures in Table 1F, corresponding structures in which $X_2$ is an oxygen-containing optionally substituted aryl group different from optionally substituted furanyl, Y is $CH_2$, and/or $X_4$ is F, Cl, Br, or I are also within the scope of the disclosure.

TABLE 1F

| Compound No. | Structure | Name |
| --- | --- | --- |
| 1F-1 | 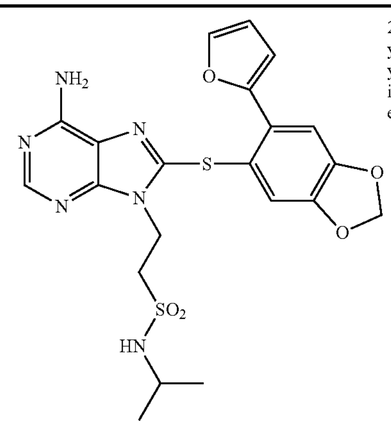 | 2-(6-amino-8-((6-(furan-2-yl)benzo[d][1,3]dioxol-5-yl)thio)-9H-purin-9-yl)-N-isopropyl-ethanesulfonamide |

TABLE 1F-continued

| Compound No. | Structure | Name |
|---|---|---|
| 1F-2 | 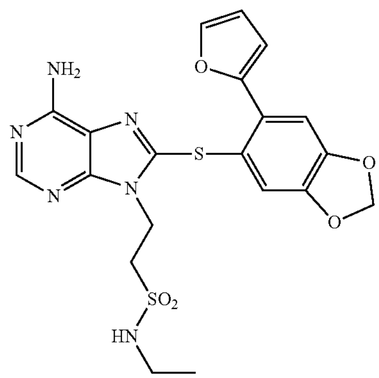 [SMILES: CCNS(=O)(=O)CCn1c(Sc2cc3c(cc2-c2ccco2)OCO3)nc2c(N)ncnc21] | 2-(6-amino-8-((6-(furan-2-yl)benzo[d][1,3]dioxol-5-yl)thio)-9H-purin-9-yl)-N-ethylethanesulfonamide |
| 1F-3 | 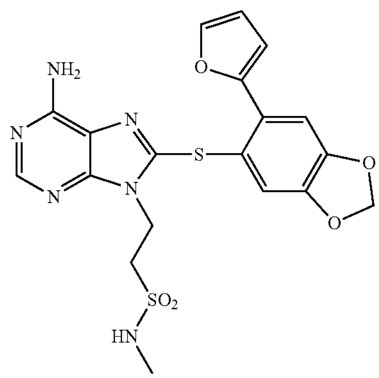 [SMILES: CNS(=O)(=O)CCn1c(Sc2cc3c(cc2-c2ccco2)OCO3)nc2c(N)ncnc21] | 2-(6-amino-8-((6-(furan-2-yl)benzo[d][1,3]dioxol-5-yl)thio)-9H-purin-9-yl)-N-methylethanesulfonamide |
| 1F-4 | 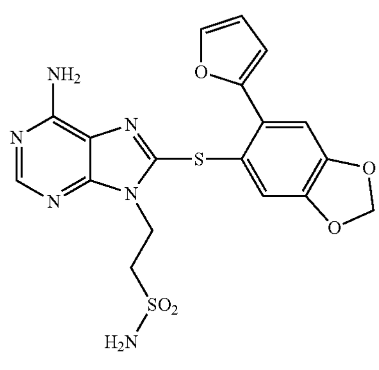 [SMILES: Nc1ncnc2c1nc(Sc1cc3c(cc1-c1ccco1)OCO3)n2CCS(N)(=O)=O] | 2-(6-amino-8-((6-(furan-2-yl)benzo[d][1,3]dioxol-5-yl)thio)-9H-purin-9-yl)ethanesulfonamide |
| 1F-5 | 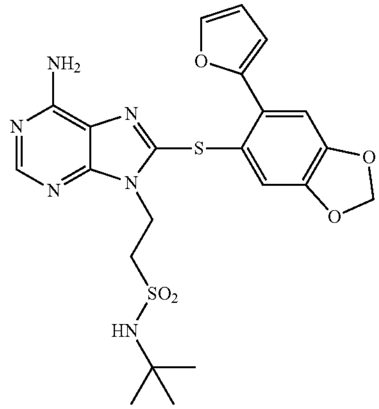 | 2-(6-amino-8-((6-(furan-2-yl)benzo[d][1,3]dioxol-5-yl)thio)-9H-purin-9-yl)-N-(tert-butyl)ethanesulfonamide |

TABLE 1F-continued
| Compound No. | Structure | Name |
|---|---|---|
| 1F-6 | 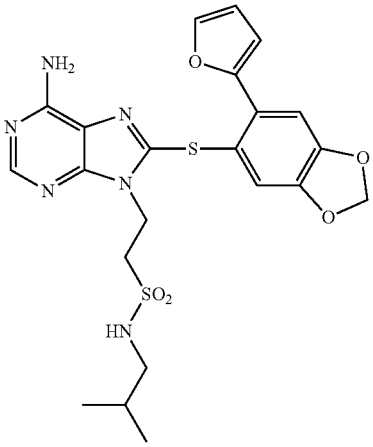 [SMILES: CC(C)CNS(=O)(=O)CCn1c(Sc2cc3c(cc2-c2ccco2)OCO3)nc2c(N)ncnc21] | 2-(6-amino-8-((6-(furan-2-yl)benzo[d][1,3]dioxol-5-yl)thio)-9H-purin-9-yl)-N-isobutylethanesulfonamide |
| 1F-7 | 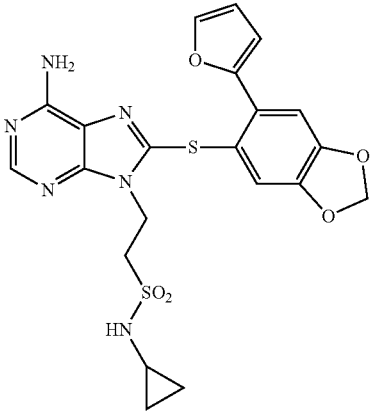 [SMILES: Nc1ncnc2c1nc(Sc1cc3c(cc1-c1ccco1)OCO3)n2CCS(=O)(=O)NC1CC1] | 2-(6-amino-8-((6-(furan-2-yl)benzo[d][1,3]dioxol-5-yl)thio)-9H-purin-9-yl)-N-cyclopropyl-ethanesulfonamide |
| 1F-8 | 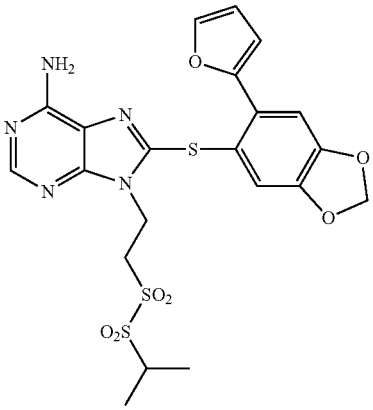 [SMILES: CC(C)S(=O)(=O)S(=O)(=O)CCn1c(Sc2cc3c(cc2-c2ccco2)OCO3)nc2c(N)ncnc21] | N-(2-(6-amino-8-((6-(furan-2-yl)benzo[d][1,3]dioxol-5-yl)thio)-9H-purin-9-yl)ethyl)propane-2-sulfonamide |

TABLE 1F-continued

| Compound No. | Structure | Name |
|---|---|---|
| 1F-9 | 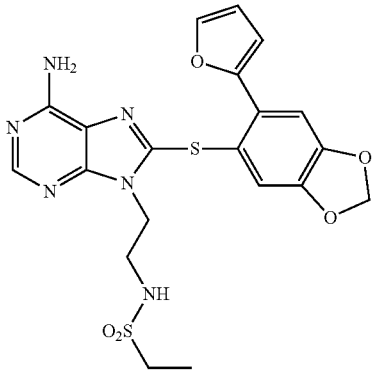 | N-(2-(6-amino-8-((6-(furan-2-yl)benzo[d][1,3]dioxol-5-yl)thio)-9H-purin-9-yl)ethyl)ethane-2-sulfonamide |
| 1F-10 | 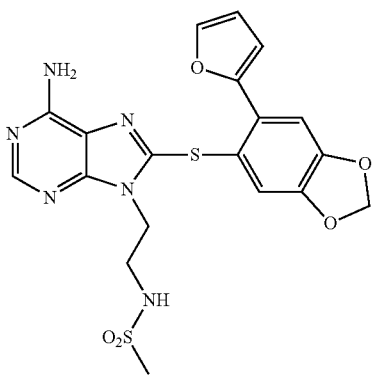 [SMILES: CS(=O)(=O)NCCn1c(Sc2cc3c(cc2-c2ccco2)OCO3)nc2c(N)ncnc21] | N-(2-(6-amino-8((6-(furan-2-yl)benzo[d][1,3]dioxol-5-yl)thio)-9H-purin-9-yl)ethyl)methane-2-sulfonamide |
| 1F-11 | 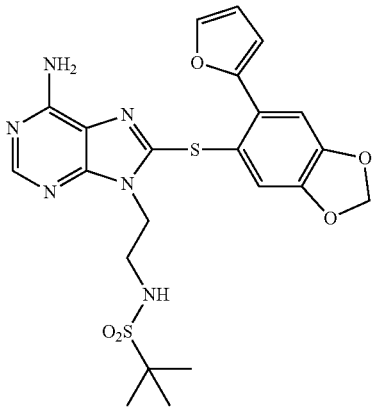 | N-(2-(6-amino-8-((6-((6-(furan-2-yl)benzo[d][1,3]dioxol-5-yl)thio)-9H-purin-9-yl)ethyl)-2-methylpropane-2-sulfonamide |
| 1F-12 | 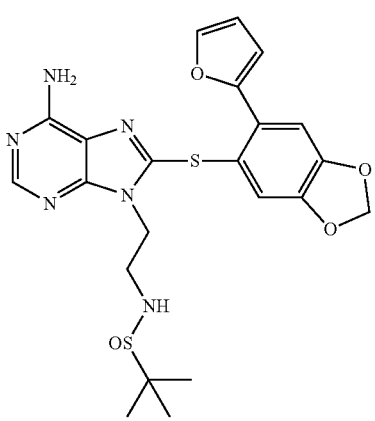 | N-(2-(6-amino-8-((6-(furan-2-yl)benzo[d][1,3]dioxol-5-yl)thio)-9H-purin-9-yl)ethyl)-2-methylpropane-2-sulfinamide |

TABLE 1F-continued

| Compound No. | Structure | Name |
| --- | --- | --- |
| 1F-13 | 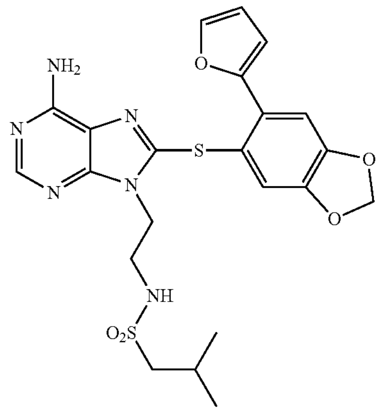 [SMILES: CC(C)CS(=O)(=O)NCCn1c(Sc2cc3c(cc2-c2ccco2)OCO3)nc2c(N)ncnc21] | N-(2-(6-amino-8-((6-(furan-2-yl)benzo[d][1,3]dioxol-5-yl)thio)-9H-purin-9-yl)ethyl)-2-methylpropane-1-sulfonamide |
| 1F-14 | 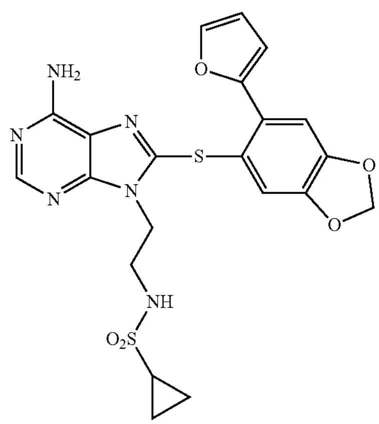 [SMILES: Nc1ncnc2c1nc(Sc1cc3c(cc1-c1ccco1)OCO3)n2CCNS(=O)(=O)C1CC1] | N-(2-(6-amino-8-((6-(furan-2-yl)benzo[d][1,3]dioxol-5-yl)thio)-9H-purin-9-yl)ethyl)cyclopropane-sulfonamide |
| 1F-15 | 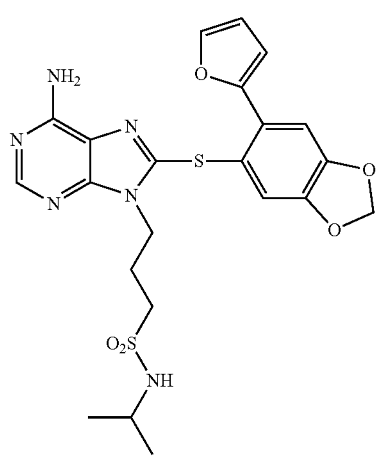 [SMILES: CC(C)NS(=O)(=O)CCCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-isopropylpropane-1-sulfonamide |

TABLE 1F-continued

| Compound No. | Structure | Name |
|---|---|---|
| 1F-16 | 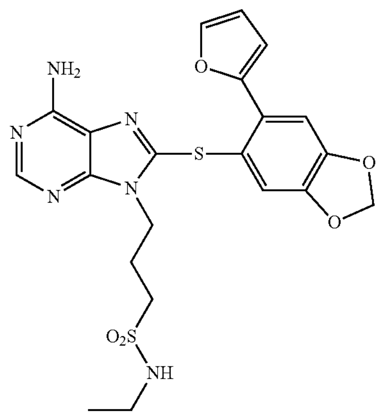 [SMILES: CCNS(=O)(=O)CCCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-ethylpropane-1-sulfonamide |
| 1F-17 | 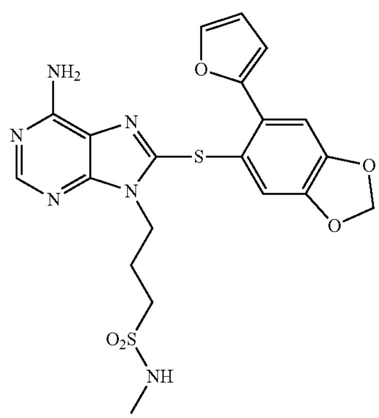 [SMILES: CNS(=O)(=O)CCCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9R-purin-9-yl)-N-methylpropane-1-sulfonamide |
| 1F-18 | 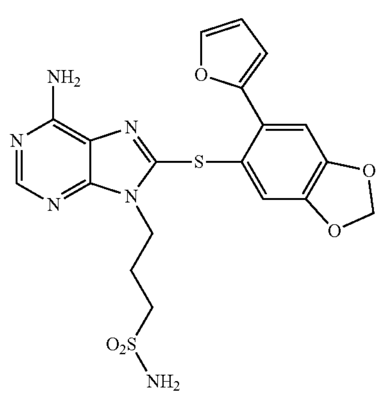 [SMILES: Nc1ncnc2c1nc(Sc1cc3c(cc1-c1ccco1)OCO3)n2CCCS(N)(=O)=O] | 3-(6-amino-8-((6-(furan-2-yl)benzo[d][1,3]dioxol-5-yl)thio)-9H-purin-9-yl)propane-1-sulfonamide |

TABLE 1F-continued

| Compound No. | Structure | Name |
| --- | --- | --- |
| 1F-19 | 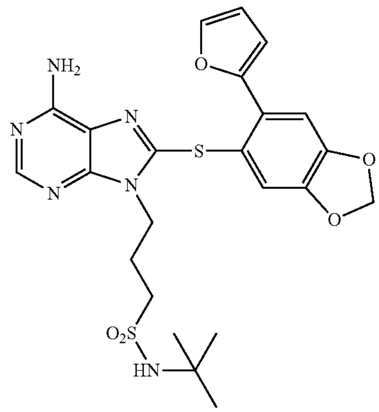 [SMILES: CC(C)(C)NS(=O)(=O)CCCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-(tert-butyl)propane-1-sulfonamide |
| 1F-20 | 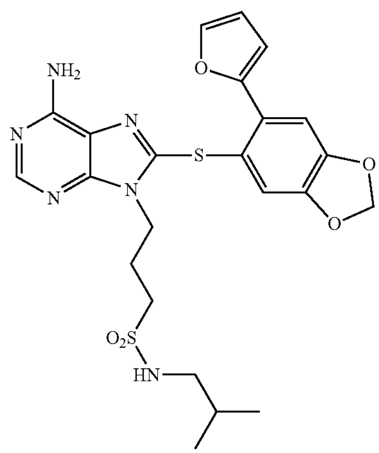 [SMILES: CC(C)CNS(=O)(=O)CCCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-isobutylpropane-1-sulfonamide |
| 1F-21 | 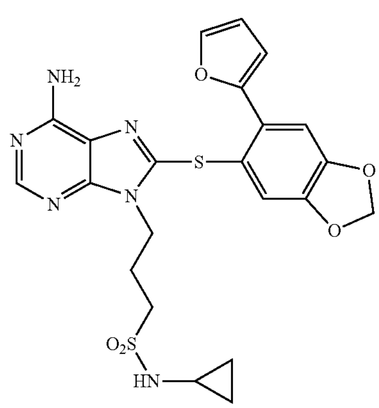 [SMILES: Nc1ncnc2c1nc(Sc1cc3c(cc1-c1ccco1)OCO3)n2CCCS(=O)(=O)NC1CC1] | 3-(6-amino-8-((6-(furan-2-yl)benzo[d][1,3]dioxol-5-yl)thio)-9H-purin-9-yl)-N-cyclopropylpropane-1-sulfonamide |

TABLE 1F-continued
| Compound No. | Structure | Name |
|---|---|---|
| 1F-22 | 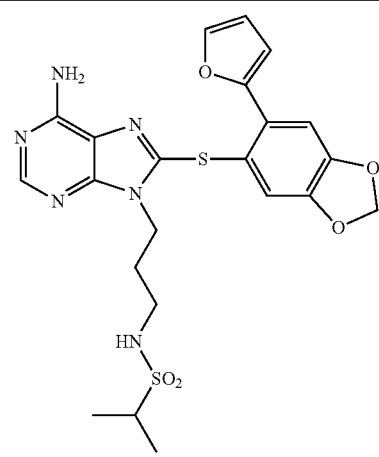 | N-(3-(6-amino-8-((6-(furan-2-yl)benzo[d][1,3]dioxol-5-yl)thio)-9H-purin-9-yl)propyl)propane-2-sulfonamide |
| 1F-23 | 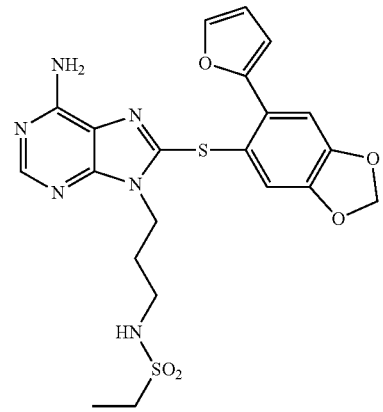 [SMILES: CCS(=O)(=O)NCCCn1c(Sc2cc3c(cc2-c2ccco2)OCO3)nc2c(N)ncnc21] | N-(3-(6-amino-8-((6-(furan-2-yl)benzo[d][1,3]dioxol-5-yl)thio)-9H-purin-9-yl)propyl)ethane-2-sulfonamide |
| 1F-24 | 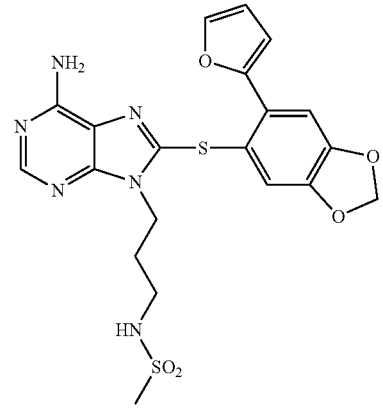 [SMILES: CS(=O)(=O)NCCCn1c(Sc2cc3c(cc2-c2ccco2)OCO3)nc2c(N)ncnc21] | N-(3-(6-amino-8-((6-(furan-2-yl)benzo[d][1,3]dioxol-5-yl)thio)-9H-purin-9-yl)propyl)methane-2-sulfonamide |

TABLE 1F-continued
| Compound No. | Structure | Name |
|---|---|---|
| 1F-25 | 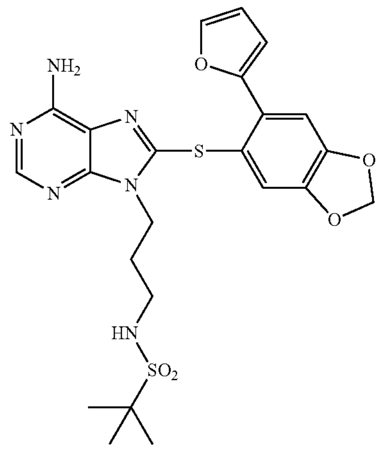 | N-(3-(6-amino-8-((6-(furan-2-yl)benzo[d][1,3]dioxol-5-yl)thio)-9H-purin-9-yl)propyl)-2-methylpropane-2-sulfonamide |
| 1F-26 | 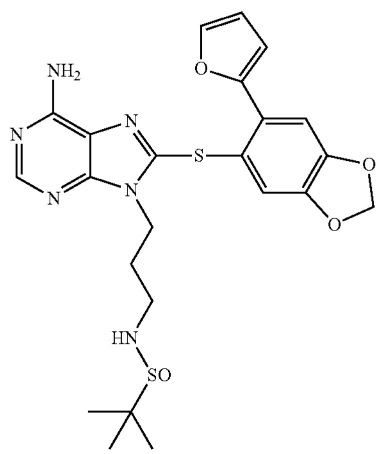 | N-(3-(6-amino-8-((6-(furan-2-yl)benzo[d][1,3]dioxol-5-yl)thio)-9H-purin-9-yl)propyl)propane-2-sulfinamide |
| 1F-27 | 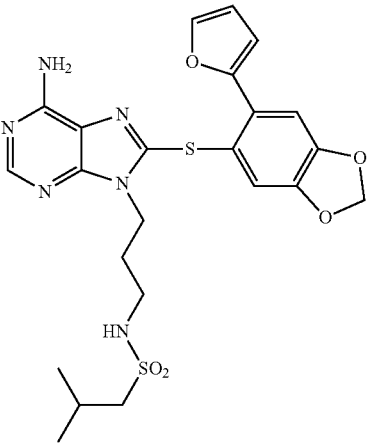 [SMILES: CC(C)CS(=O)(=O)NCCCn1c(Sc2cc3c(cc2-c2ccco2)OCO3)nc2c(N)ncnc21] | N-(3-(6-amino-8((6-(furan-2-yl)benzo[d][1,3]dioxol-5-yl)thio)-9H-purin-9-yl)propyl)2-methylpropane-1-sulfonamide |

TABLE 1F-continued
| Compound No. | Structure | Name |
|---|---|---|
| 1F-28 | 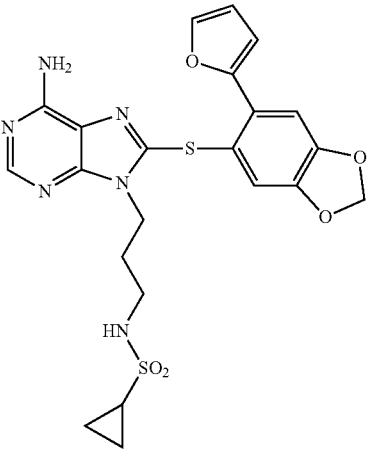 [SMILES: Nc1ncnc2c1nc(Sc1cc3c(cc1-c1ccco1)OCO3)n2CCCNS(=O)(=O)C1CC1] | N-(3-(6-amino-8-((6-(furan-2-yl)benzo[d][1,3]dioxol-5-yl)thio)-9H-purin-9-yl)propyl)cyclopropane-sulfonamide |
| 1F-29 | 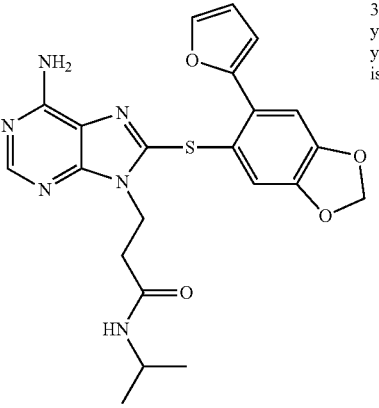 | 3-(6-amino-8-((6-(furan-2-yl)benzo[d][1,3]dioxol-5-yl)thio)-9H-purin-9-yl)-N-isopropylpropanamide |
| 1F-30 | 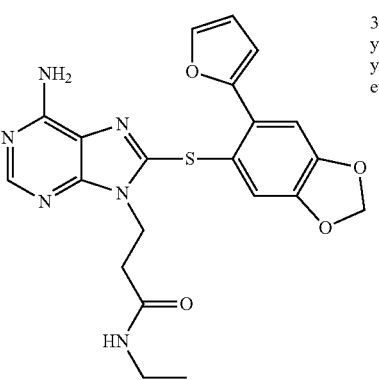 | 3-(6-amino-8-((6-(furan-2-yl)benzo[d][1,3]dioxol-5-yl)thio)-9H-purin-9-yl)-N-ethylpropanamide |

TABLE 1F-continued

| Compound No. | Structure | Name |
|---|---|---|
| 1F-31 | 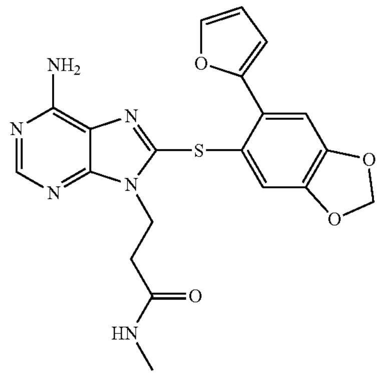 [SMILES: CNC(=O)CCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-methylpropanamide |
| 1F-32 | 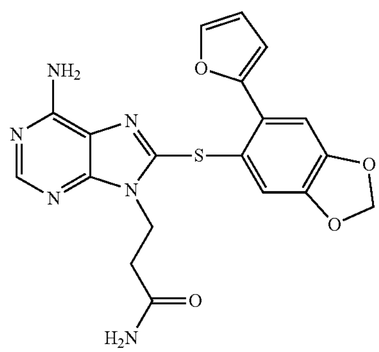 [SMILES: NC(=O)CCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)propanamide |
| 1F-33 | 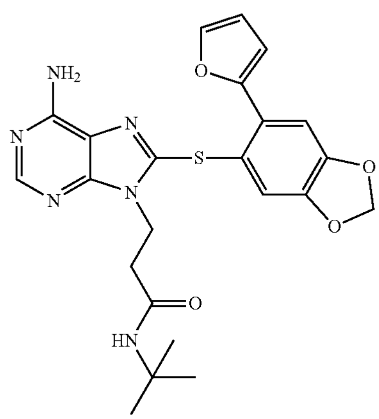 [SMILES: CC(C)(C)NC(=O)CCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-(tert-butyl)propanamide |
| 1F-34 | 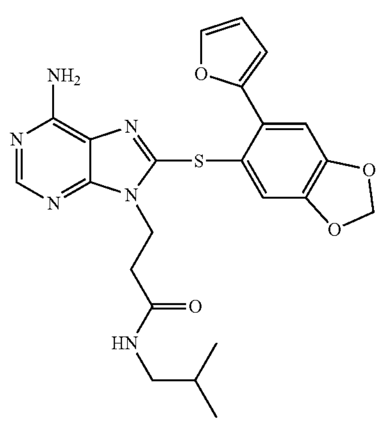 [SMILES: CC(C)CNC(=O)CCn1c(Sc2cc3c(cc2-c2ccco2)OCO3)nc2c(N)ncnc21] | 3-(6-amino-8-((6-(furan-2-yl)benzo[d][1,3]dioxol-5-yl)thio)-9H-purin-9-yl)-N-isobutylpropanamide |

TABLE 1F-continued

| Compound No. | Structure | Name |
| --- | --- | --- |
| 1F-35 | 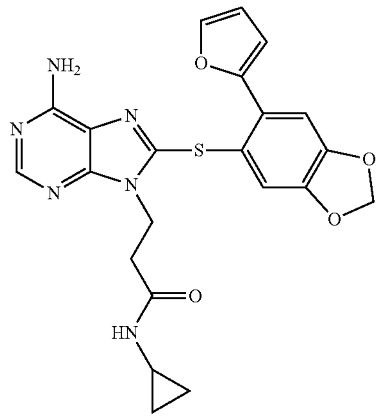 [SMILES: Nc1ncnc2c1nc(Sc1cc3c(cc1-c1ccco1)OCO3)n2CCC(=O)NC1CC1] | 3-(6-amino-8-((6-(furan-2-yl)benzo[d][1,3]dioxol-5-yl)thio)-9H-purin-9-yl)-N-cyclopropylpropanamide |
| 1F-36 | 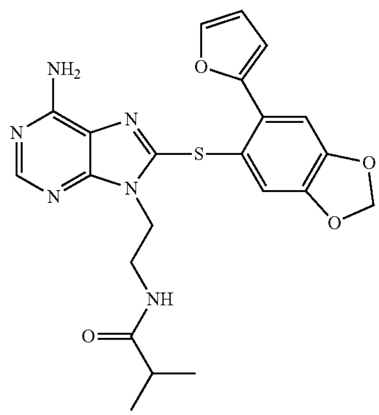 [SMILES: CC(C)C(=O)NCCn1c(Sc2cc3c(cc2-c2ccco2)OCO3)nc2c(N)ncnc21] | N-(2-(6-amino-8-((6-(furan-2-yl)benzo[d][1,3]dioxol-5-yl)thio)-9H-purin-9-yl)ethyl)isobutyramide |
| 1F-37 | 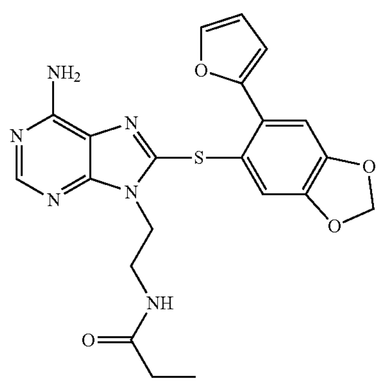 [SMILES: CCC(=O)NCCn1c(Sc2cc3c(cc2-c2ccco2)OCO3)nc2c(N)ncnc21] | N-(2-(6-amino-8-((6-(furan-2-yl)benzo[d][1,3]dioxol-5-yl)thio)-9H-purin-9-yl)ethyl)propanamide |
| 1F-38 | 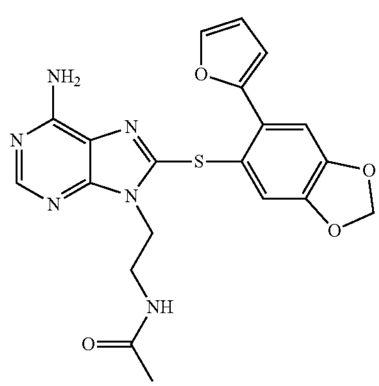 [SMILES: CC(=O)NCCn1c(Sc2cc3c(cc2-c2ccco2)OCO3)nc2c(N)ncnc21] | N-(2-(6-amino-8((6-(furan-2-yl)benzo[d][1,3]dioxol-5-yl)thio)-9H-purin-9-yl)ethyl)acetamide |

TABLE 1F-continued
| Compound No. | Structure | Name |
|---|---|---|
| 1F-39 | 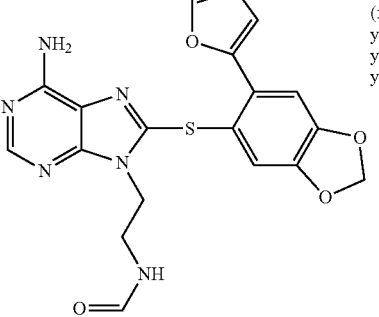 | N-(2-(6-amino-8((6-(furan-2-yl)benzo[d][1,3]dioxol-5-yl)thio)-9H-purin-9-yl)ethyl)formamide |
| 1F-40 | 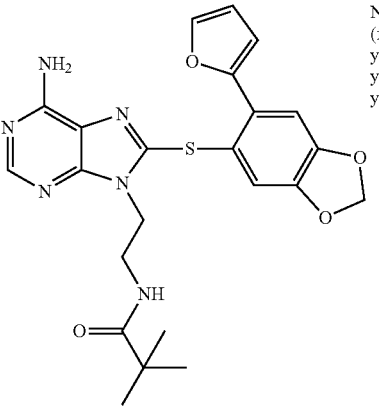 | N-(2-(6-amino-8((6-(furan-2-yl)benzo[d][1,3]dioxol-5-yl)thio)-9H-purin-9-yl)ethyl)pivalamide |
| 1F-41 | 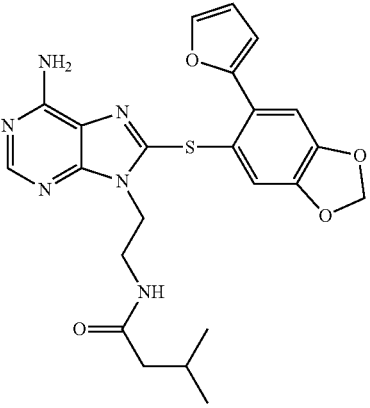 [SMILES: CC(C)CC(=O)NCCn1c(Sc2cc3c(cc2-c2ccco2)OCO3)nc2c(N)ncnc21] | N-(2-(6-amino-8-((6-(furan-2-yl)benzo[d][1,3]dioxol-5-yl)thio)-9H-purin-9-yl)ethyl)-3-methylbutanamide |
| 1F-42 | 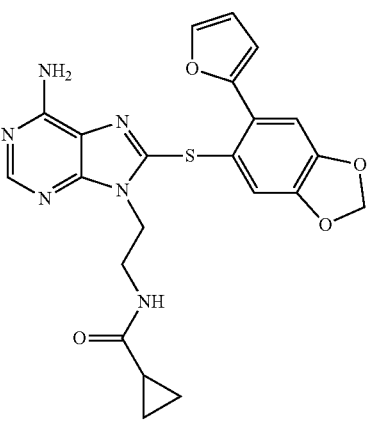 [SMILES: Nc1ncnc2c1nc(Sc1cc3c(cc1-c1ccco1)OCO3)n2CCNC(=O)C1CC1] | N-(2-(6-amino-8-((6-(furan-2-yl)benzo[d][1,3]dioxol-5-yl)thio)-9H-purin-9-yl)ethyl)cyclopropanecarboxamide |

TABLE 1F-continued

| Compound No. | Structure | Name |
|---|---|---|
| 1F-43 | 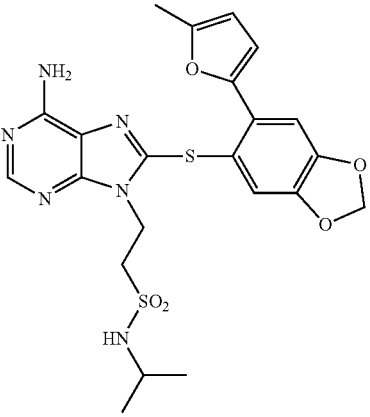 [SMILES: Cc1ccc(-c2cc3c(cc2Sc2nc4c(N)ncnc4n2CCS(=O)(=O)NC(C)C)OCO3)o1] | 2-(6-amino-8-((6-(5-methylfuran-2-yl)benzo[d][1,3]dioxol-5-yl)thio)-9H-purin-9-yl)-N-isopropyl-ethanesulfonamide |
| 1F-44 | 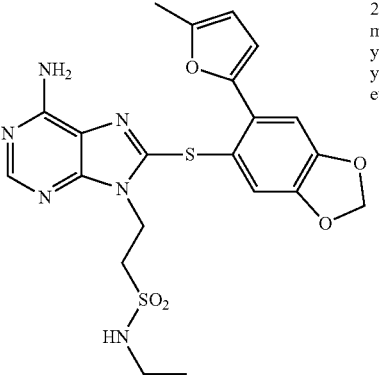 | 2-(6-amino-8-((6-(5-methylfuran-2-yl)benzo[d][1,3]dioxol-5-yl)thio)-9H-purin-9-yl)-N-ethylethanesulfonamide |
| 1F-45 | 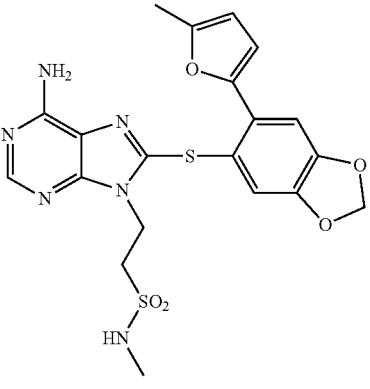 [SMILES: CNS(=O)(=O)CCn1c(Sc2cc3c(cc2-c2ccc(C)o2)OCO3)nc2c(N)ncnc21] | 2-(6-amino-8-(6-(5-methylfuran-2-yl)benzo[d][1,3]dioxol-5-yl)thio)-9H-purin-9-yl)-N-methylethanesulfonamide |
| 1F-46 | 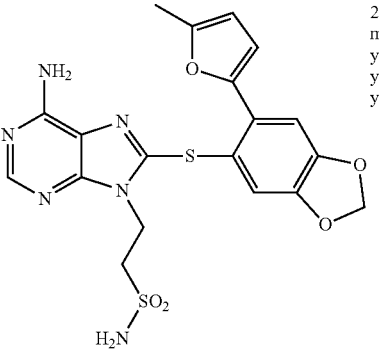 | 2-(6-amino-8-((6-(5-methylfuran-2-yl)benzo[d][1,3]dioxol-5-yl)thio)-9H-purin-9-yl)ethanesulfonamide |

TABLE 1F-continued

| Compound No. | Structure | Name |
|---|---|---|
| 1F-47 | 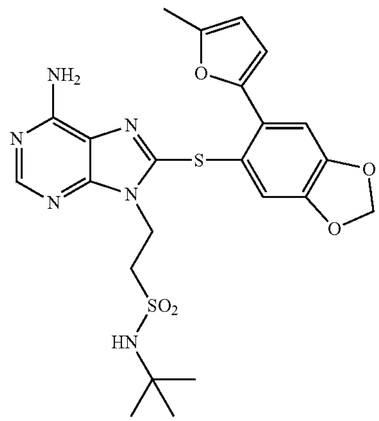 [SMILES: Cc1ccc(-c2cc3c(cc2Sc2nc4c(N)ncnc4n2CCS(=O)(=O)NC(C)(C)C)OCO3)o1] | 2-(6-amino-8((6-(5-methylfuran-2-yl)benzo[d][1,3]dioxol-5-yl)thio)-9H-purin-9-yl)-N-(tert-butyl)ethanesulfonamide |
| 1F-48 | 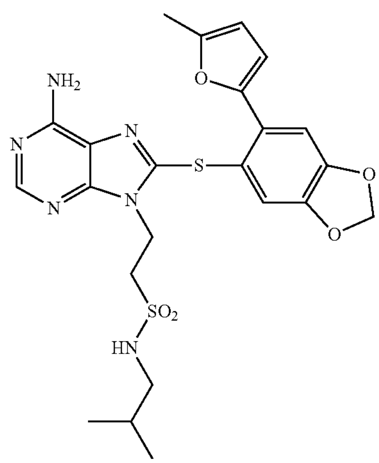 [SMILES: Cc1ccc(-c2cc3c(cc2Sc2nc4c(N)ncnc4n2CCS(=O)(=O)NCC(C)C)OCO3)o1] | 2-(6-amino-8-((6-(5-methylfuran-2-yl)benzo[1,3]dioxol-5-yl)thio)-9H-purin-9-yl)-N-isobutylethanesulfonamide |
| 1F-49 | 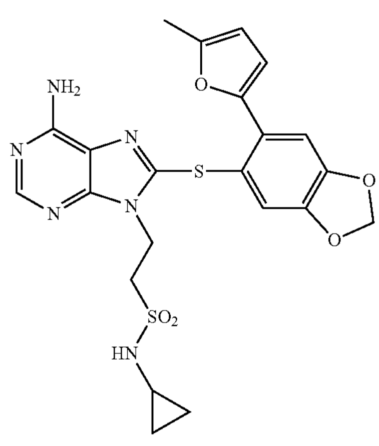 [SMILES: Cc1ccc(-c2cc3c(cc2Sc2nc4c(N)ncnc4n2CCS(=O)(=O)NC2CC2)OCO3)o1] | 2-(6-amino-8-((6-(5-methylfuran-2-yl)benzo[d][1,3]dioxol-5-yl)thio)-9H-purin-9-yl)-N-cyclopropyl-ethanesulfonamide |

TABLE 1F-continued

| Compound No. | Structure | Name |
|---|---|---|
| 1F-50 | 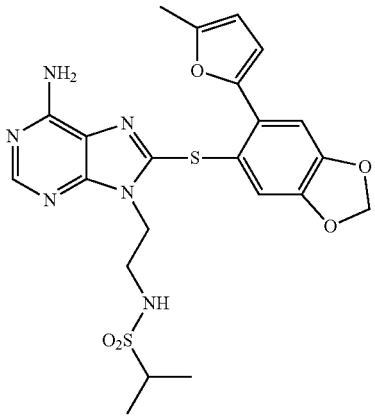 [SMILES: Cc1ccc(-c2cc3c(cc2Sc2nc4c(N)ncnc4n2CCNS(=O)(=O)C(C)C)OCO3)o1] | N-(2-(6-amino-8-((6-(5-methylfuran-2-yl)benzo[d][1,3]dioxol-5-yl)thio)-9H-purin-9-yl)ethyl)propane-2-sulfonamide |
| 1F-51 | 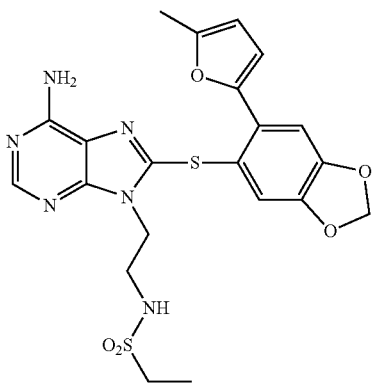 [SMILES: CCS(=O)(=O)NCCn1c(Sc2cc3c(cc2-c2ccc(C)o2)OCO3)nc2c(N)ncnc21] | N-(2-(6-amino-8-((6-(5-methylfuran-2-yl)benzo[d][1,3]dioxol-5-yl)thio)-9H-purin-9-yl)ethyl)ethane-2-sulfonamide |
| 1F-52 | 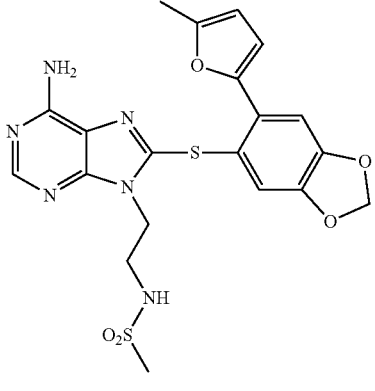 [SMILES: Cc1ccc(-c2cc3c(cc2Sc2nc4c(N)ncnc4n2CCNS(C)(=O)=O)OCO3)o1] | N-(2-(6-amino-8-(6-(5-methylfuran-2-yl)benzo[d][1,3]dioxol-5-yl)thio)-9H-purin-9-yl)ethyl)methane-2-sulfonamide |
| 1F-53 | 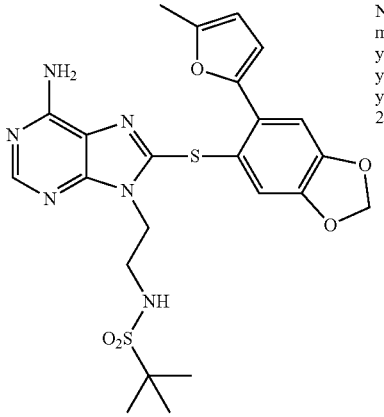 | N-(2-(6-amino-8-((6-(5-methylfuran-2-yl)benzo[d][1,3]dioxol-5-yl)thio)-9H-purin-9-yl)ethyl)-2-methylpropane-2-sulfonamide |

TABLE 1F-continued
| Compound No. | Structure | Name |
|---|---|---|
| 1F-54 | 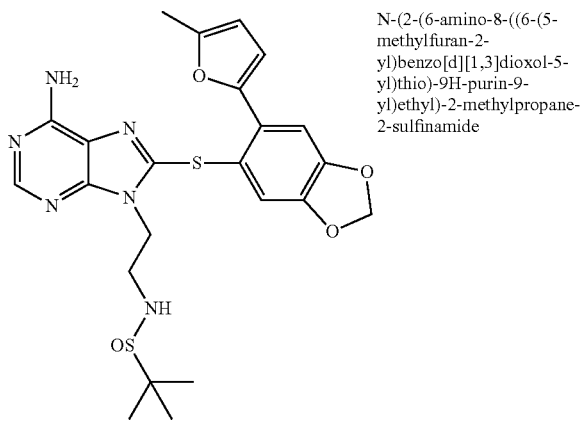 | N-(2-(6-amino-8-((6-(5-methylfuran-2-yl)benzo[d][1,3]dioxol-5-yl)thio)-9H-purin-9-yl)ethyl)-2-methylpropane-2-sulfinamide |
| 1F-55 | 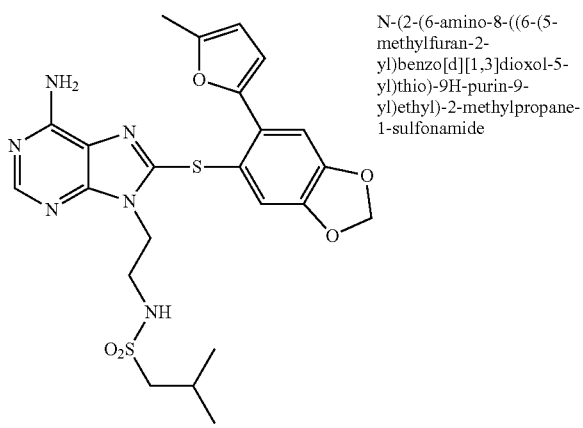 | N-(2-(6-amino-8-((6-(5-methylfuran-2-yl)benzo[d][1,3]dioxol-5-yl)thio)-9H-purin-9-yl)ethyl)-2-methylpropane-1-sulfonamide |
| 1F-56 | 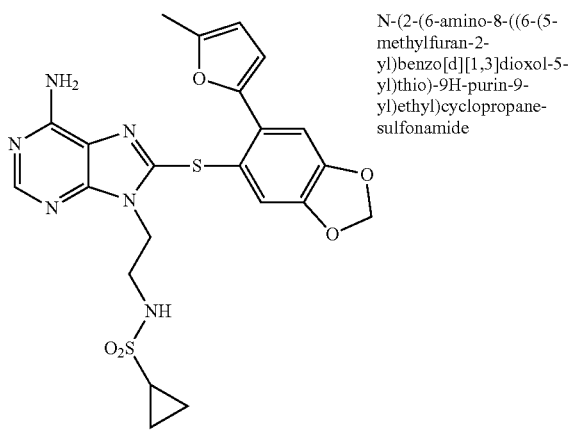 | N-(2-(6-amino-8-((6-(5-methylfuran-2-yl)benzo[d][1,3]dioxol-5-yl)thio)-9H-purin-9-yl)ethyl)cyclopropane-sulfonamide |

TABLE 1F-continued

| Compound No. | Structure | Name |
| --- | --- | --- |
| 1F-57 | 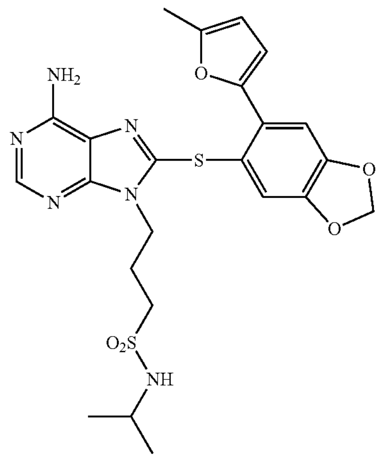 [SMILES: Cc1ccc(-c2cc3c(cc2Sc2nc4c(N)ncnc4n2CCCS(=O)(=O)NC(C)C)OCO3)o1] | 3-(6-amino-8-((6-(5-methylfuran-2-yl)benzo[d][1,3]dioxol-5-yl)thio)-9H-purin-9-yl)-N-isopropylpropane-1-sulfonamide |
| 1F-58 | 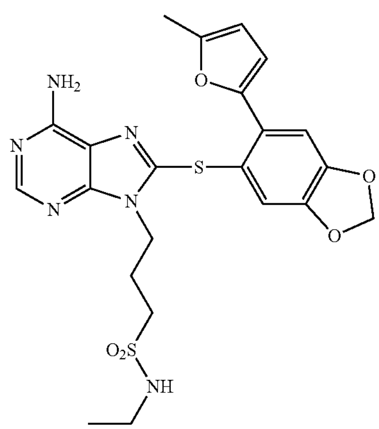 [SMILES: CCNS(=O)(=O)CCCn1c(Sc2cc3c(cc2-c2ccc(C)o2)OCO3)nc2c(N)ncnc21] | 3-(6-amino-8-((6-(5-methylfuran-2-yl)benzo[d][1,3]dioxol-5-yl)thio)-9H-purin-9-yl)-N-ethylpropane-1-sulfonamide |
| 1F-59 | 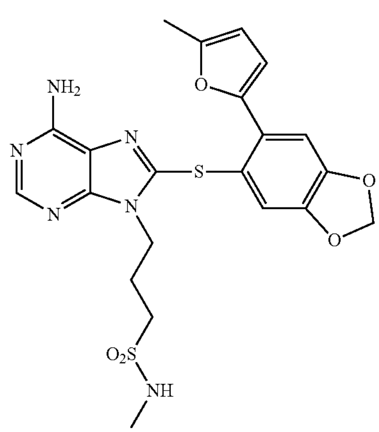 [SMILES: CNS(=O)(=O)CCCn1c(Sc2cc3c(cc2-c2ccc(C)o2)OCO3)nc2c(N)ncnc21] | 3-(6-amino-8-((6-(5-methylfuran-2-yl)benzo[d][1,3]dioxol-5-yl)thio)-9H-purin-9-yl)-N-methylpropane-1-sulfonamide |

TABLE 1F-continued

| Compound No. | Structure | Name |
| --- | --- | --- |
| 1F-60 | 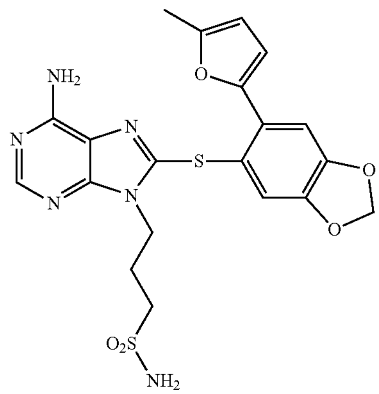 [SMILES: Cc1ccc(-c2cc3c(cc2Sc2nc4c(N)ncnc4n2CCCS(N)(=O)=O)OCO3)o1] | 3-(6-amino-8-((6-(5-methylfuran-2-yl)benzo[d][1,3]dioxol-5-yl)thio)-9H-purin-9-yl)propane-1-sulfonamide |
| 1F-61 | 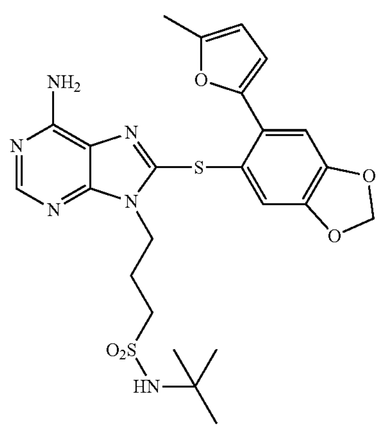 [SMILES: Cc1ccc(-c2cc3c(cc2Sc2nc4c(N)ncnc4n2CCCS(=O)(=O)NC(C)(C)C)OCO3)o1] | 3-(6-amino-8-((6-(5-methylfuran-2-yl)benzo[d][1,3]dioxol-5-yl)thio)-9H-purin-9-yl)-N-(tert-butyl)propane-1-sulfonamide |
| 1F-62 | 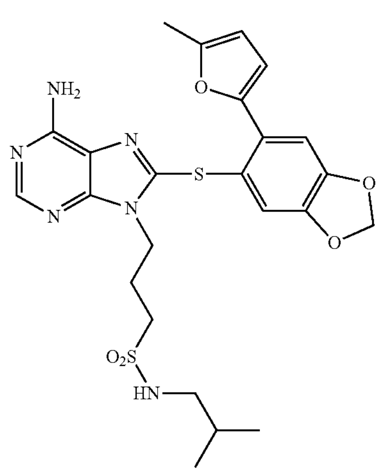 [SMILES: Cc1ccc(-c2cc3c(cc2Sc2nc4c(N)ncnc4n2CCCS(=O)(=O)NCC(C)C)OCO3)o1] | 3-(6-amino-8-((6-(5-methylfuran-2-yl)benzo[d][1,3]dioxol-5-yl)thio)-9H-purin-9-yl)-N-isobutylpropane-1-sulfonamide |

TABLE 1F-continued

| Compound No. | Structure | Name |
| --- | --- | --- |
| 1F-63 | 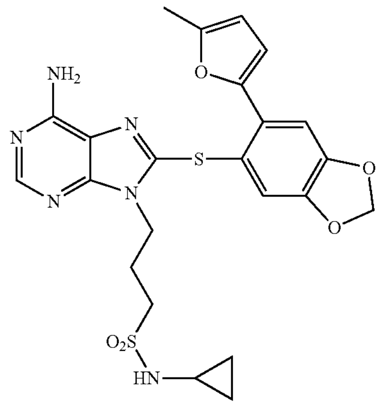 [SMILES: Cc1ccc(-c2cc3c(cc2Sc2nc4c(N)ncnc4n2CCCS(=O)(=O)NC2CC2)OCO3)o1] | 3-(6-amino-8-((6-(5-methylfuran-2-yl)benzo[d][1,3]dioxol-5-yl)thio)-9H-purin-9-yl)-N-cyclopropylpropane-1-sulfonamide |
| 1F-64 | 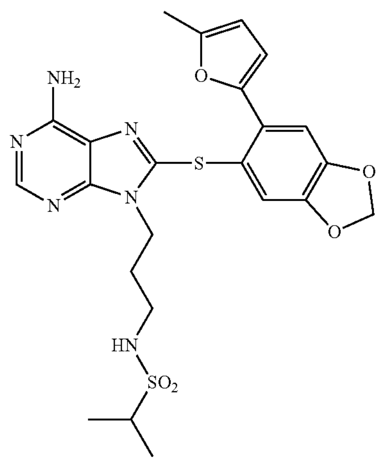 | N-(3-(6-amino-8-((6-(5-methylfuran-2-yl)benzo[d][1,3]dioxol-5-yl)thio)-9H-purin-9-yl)propyl)propane-2-sulfonamide |
| 1F-65 | 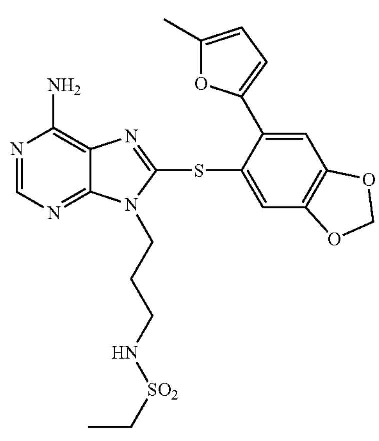 [SMILES: CCS(=O)(=O)NCCCn1c(Sc2cc3c(cc2-c2ccc(C)o2)OCO3)nc2c(N)ncnc21] | N-(3-(6-amino-8-((6-(5-methylfuran-2-yl)benzo[d][1,3]dioxol-5-yl)thio)-9H-purin-9-yl)propyl)ethane-2-sulfonamide |

TABLE 1F-continued

| Compound No. | Structure | Name |
|---|---|---|
| 1F-66 | 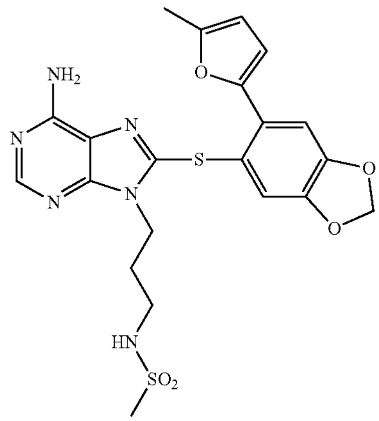 | N-(3-(6-amino-8-((6-(5-methylfuran-2-yl)benzo[d][1,3]dioxol-5-yl)thio)-9H-purin-9-yl)propyl)methane-2-sulfonamide |
| 1F-67 | 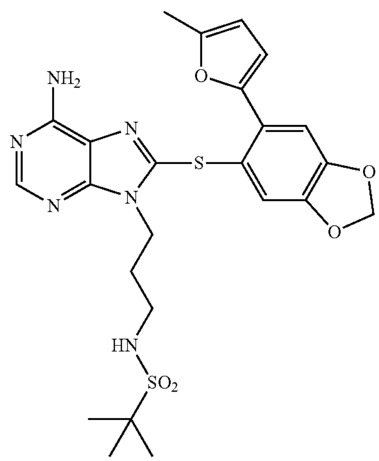 [SMILES: Cc1ccc(-c2cc3c(cc2Sc2nc4c(N)ncnc4n2CCCNS(=O)(=O)C(C)(C)C)OCO3)o1] | N-(3-(6-amino-8-((6-(5-methylfuran-2-yl)benzo[d][1,3]dioxol-5-yl)thio)-9H-purin-9-yl)propyl)-2-methylpropane-2-sulfonamide |
| 1F-68 | | N-(3-(6-amino-8-((6-(5-methylfuran-2-yl)benzo[d][1,3]dioxol-5-yl)thio)-9H-purin-9-yl)propyl)propane-2-sulfinamide |

TABLE 1F-continued

| Compound No. | Structure | Name |
|---|---|---|
| 1F-69 | 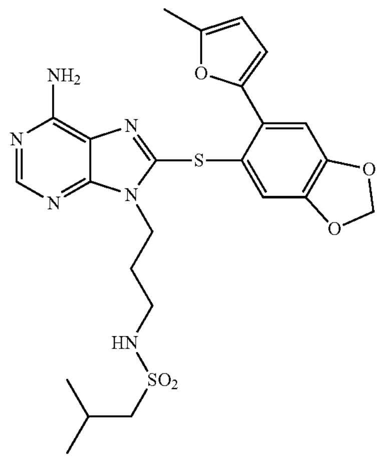 [SMILES: Cc1ccc(-c2cc3c(cc2Sc2nc4c(N)ncnc4n2CCCNS(=O)(=O)CC(C)C)OCO3)o1] | N-(3-(6-amino-8-((6-(5-methylfuran-2-yl)benzo[d][1,3]dioxol-5-yl)thio)-9H-purin-9-yl)propyl)2-methylpropane-1-sulfonamide |
| 1F-70 | 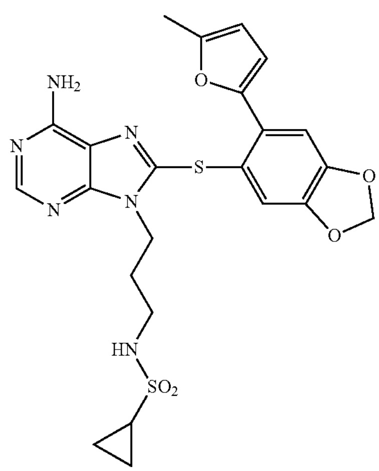 [SMILES: Cc1ccc(-c2cc3c(cc2Sc2nc4c(N)ncnc4n2CCCNS(=O)(=O)C2CC2)OCO3)o1] | N-(3-(6-amino-8-((6-(5-methylfuran-2-yl)benzo[d][1,3]dioxol-5-yl)thio)-9H-purin-9-yl)propyl)cyclopropane-sulfonamide |
| 1F-71 | 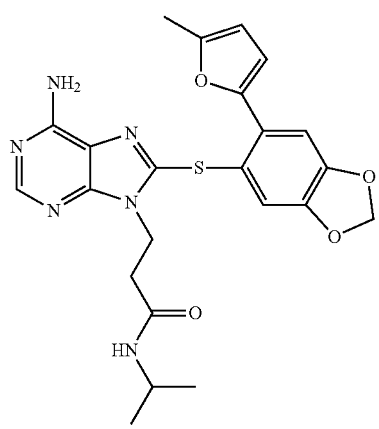 [SMILES: Cc1ccc(-c2cc3c(cc2Sc2nc4c(N)ncnc4n2CCC(=O)NC(C)C)OCO3)o1] | 3-(6-amino-8-((6-(5-methylfuran-2-yl)benzo[d][1,3]dioxol-5-yl)thio)-9H-purin-9-yl)-N-isopropylpropanamide |

TABLE 1F-continued

| Compound No. | Structure | Name |
| --- | --- | --- |
| 1F-72 | 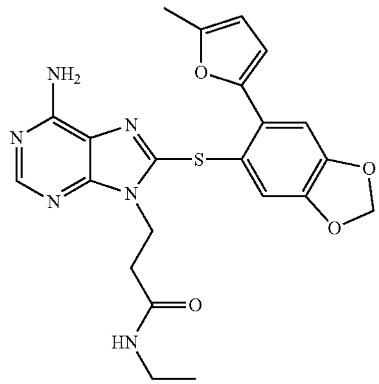 [SMILES: CCNC(=O)CCn1c(Sc2cc3c(cc2-c2ccc(C)o2)OCO3)nc2c(N)ncnc21] | 3-(6-amino-8-((6-(5-methylfuran-2-yl)benzo[d][1,3]dioxol-5-yl)thio)-9H-purin-9-yl)-N-ethylpropanamide |
| 1F-73 | 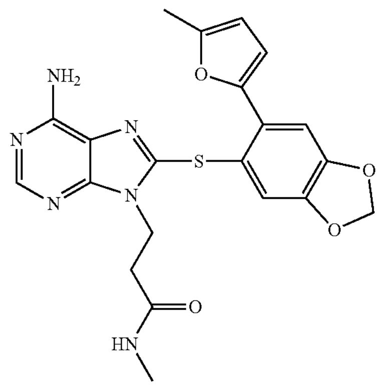 [SMILES: CNC(=O)CCn1c(Sc2cc3c(cc2-c2ccc(C)o2)OCO3)nc2c(N)ncnc21] | 3-(6-amino-8-((6-(5-methylfuran-2-yl)benzo[d][1,3]dioxol-5-yl)thio)-9H-purin-9-yl)-N-methylpropanamide |
| 1F-74 | 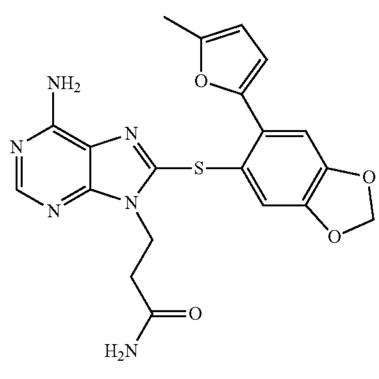 [SMILES: Cc1ccc(-c2cc3c(cc2Sc2nc4c(N)ncnc4n2CCC(N)=O)OCO3)o1] | 3-(6-amino-8-((6-(5-methylfuran-2-yl)benzo[d][1,3]dioxol-5-yl)thio)-9H-purin-9-yl)propanamide |
| 1F-75 | 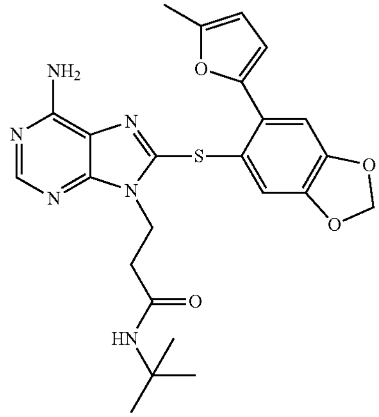 [SMILES: Cc1ccc(-c2cc3c(cc2Sc2nc4c(N)ncnc4n2CCC(=O)NC(C)(C)C)OCO3)o1] | 3-(6-amino-8-((6-(5-methylfuran-2-yl)benzo[d][1,3]dioxol-5-yl)thio)-9H-purin-9-yl)-N-(tert-butyl)propanamide |

TABLE 1F-continued
| Compound No. | Structure | Name |
|---|---|---|
| 1F-76 | 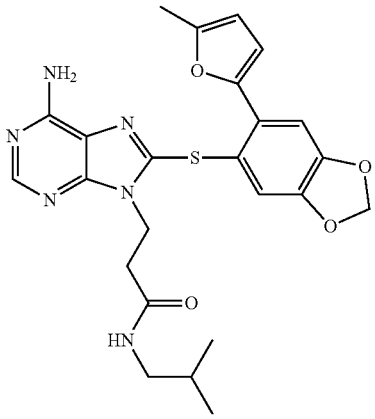 [SMILES: Cc1ccc(-c2cc3c(cc2Sc2nc4c(N)ncnc4n2CCC(=O)NCC(C)C)OCO3)o1] | 3-(6-amino-8-((6-(5-methylfuran-2-yl)benzo[d][1,3]dioxol-5-yl)thio)-9H-purin-9-yl)-N-isobutylpropanamide |
| 1F-77 | 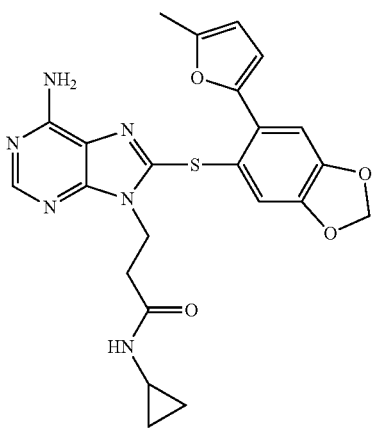 [SMILES: Cc1ccc(-c2cc3c(cc2Sc2nc4c(N)ncnc4n2CCC(=O)NC2CC2)OCO3)o1] | 3-(6-amino-8-((6-(5-methylfuran-2-yl)benzo[d][1,3]dioxol-5-yl)thio)-9H-purin-9-yl)-N-cyclopropylpropanamide |
| 1F-78 | 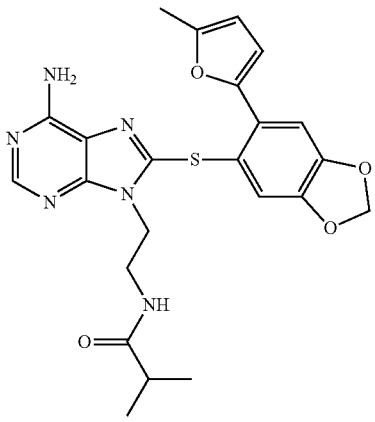 [SMILES: Cc1ccc(-c2cc3c(cc2Sc2nc4c(N)ncnc4n2CCNC(=O)C(C)C)OCO3)o1] | N-(2-(6-amino-8-((6-(5-methylfuran-2-yl)benzo[d][1,3]dioxol-5-yl)thio)-9H-purin-9-yl)ethyl)isobutyramide |

TABLE 1F-continued

| Compound No. | Structure | Name |
| --- | --- | --- |
| 1F-79 | 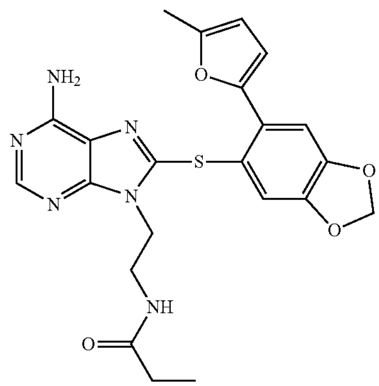 [SMILES: CCC(=O)NCCn1c(Sc2cc3c(cc2-c2ccc(C)o2)OCO3)nc2c(N)ncnc21] | N-(2-(6-amino-8-((6-(5-methylfuran-2-yl)benzo[d][1,3]dioxol-5-yl)thio)-9H-purin-9-yl)ethyl)propanamide |
| 1F-80 | 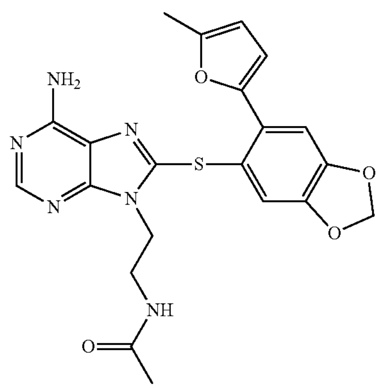 [SMILES: CC(=O)NCCn1c(Sc2cc3c(cc2-c2ccc(C)o2)OCO3)nc2c(N)ncnc21] | N-(2-(6-amino-8-((6-(5-methylfuran-2-yl)benzo[d][1,3]dioxol-5-yl)thio)-9H-purin-9-yl)ethyl)acetamide |
| 1F-81 | 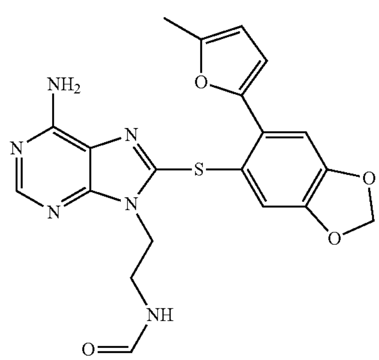 [SMILES: Cc1ccc(-c2cc3c(cc2Sc2nc4c(N)ncnc4n2CCNC=O)OCO3)o1] | N-(2-(6-amino-8-((6-(5-methylfuran-2-yl)benzo[d][1,3]dioxol-5-yl)thio)-9H-purin-9-yl)ethyl)formamide |
| 1F-82 | 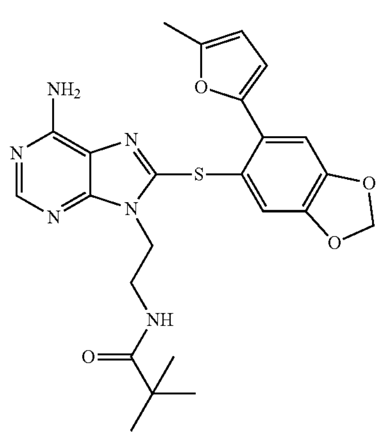 [SMILES: Cc1ccc(-c2cc3c(cc2Sc2nc4c(N)ncnc4n2CCNC(=O)C(C)(C)C)OCO3)o1] | N-(2-(6-amino-8-((6-(5-methylfuran-2-yl)benzo[1,3]dioxol-5-yl)thio)-9H-purin-9-yl)ethyl)pivalamide |

TABLE 1F-continued
| Compound No. | Structure | Name |
|---|---|---|
| 1F-83 | 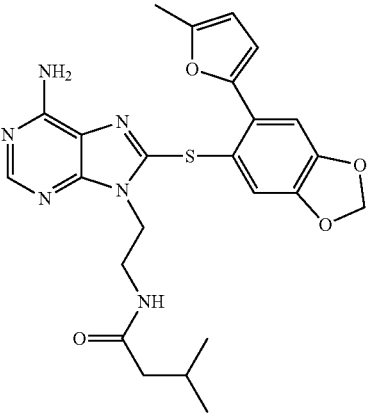 [SMILES: Cc1ccc(-c2cc3c(cc2Sc2nc4c(N)ncnc4n2CCNC(=O)CC(C)C)OCO3)o1] | N-(2-(6-amino-8-((6-(5-methylfuran-2-yl)benzo[d][1,3]dioxol-5-yl)thio)-9H-purin-9-yl)ethyl)-3-methylbutanamide |
| 1F-84 | 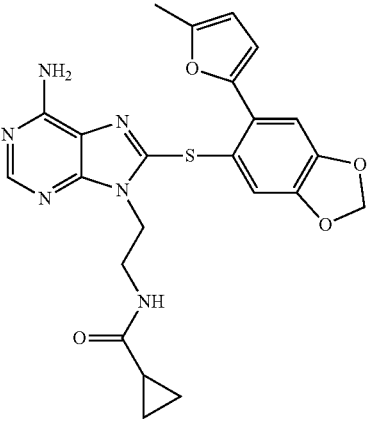 [SMILES: Cc1ccc(-c2cc3c(cc2Sc2nc4c(N)ncnc4n2CCNC(=O)C2CC2)OCO3)o1] | N-(2-(6-amino-8-((6-(5-methylfuran-2-yl)benzo[d][1,3]dioxol-5-yl)thio)-9H-purin-9-yl)ethyl)cyclopropane-carboxamide |
| 1F-85 | 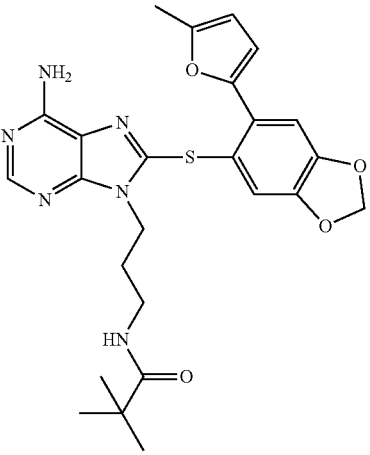 [SMILES: Cc1ccc(-c2cc3c(cc2Sc2nc4c(N)ncnc4n2CCCNC(=O)C(C)(C)C)OCO3)o1] | N-(3-{6-Amino-8-[6-(5-methyl-furan-2-yl)-benzo[1,3]dioxol-5-ylsulfanyl]-purin-9-yl}-propyl)-2,2-dimethyl-propionamide |

TABLE 1F-continued

| Compound No. | Structure | Name |
|---|---|---|
| 1F-86 | 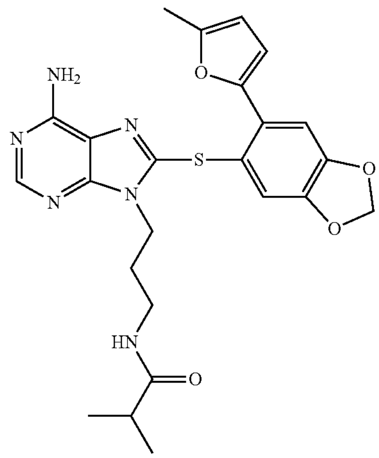 [SMILES: Cc1ccc(-c2cc3c(cc2Sc2nc4c(N)ncnc4n2CCCNC(=O)C(C)C)OCO3)o1] | N-(3-{6-Amino-8-[6-(5-methyl-furan-2-yl)-benzo[1,3]dioxol-5-ylsulfanyl]-purin-9-yl}-propyl)-isobutyramide |
| 1F-87 | 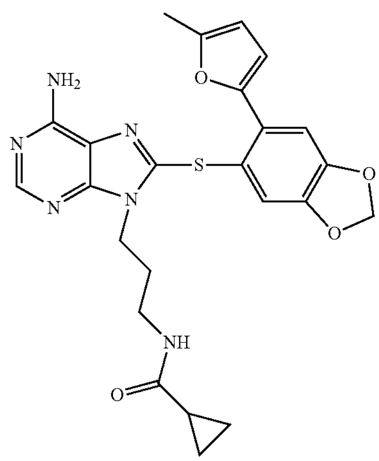 [SMILES: Cc1ccc(-c2cc3c(cc2Sc2nc4c(N)ncnc4n2CCCNC(=O)C2CC2)OCO3)o1] | Cyclopropanecarboxylic acid (3-{6-amino-8-[6-(5-methyl-furan-2-yl)-benzo[1,3]dioxol-5-ylsulfanyl]-purin-9-yl}-propyl)-amide |
| 1F-88 | 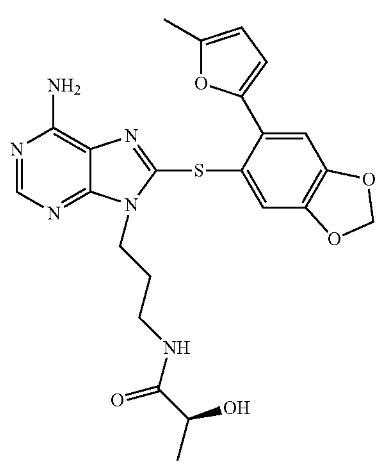 [SMILES: Cc1ccc(-c2cc3c(cc2Sc2nc4c(N)ncnc4n2CCCNC(=O)[C@H](C)O)OCO3)o1] | N-(3-{6-Amino-8-[6-(5-methyl-furan-2-yl)-benzo[1,3]dioxol-5-ylsulfanyl]-purin-9-yl}-propyl)-2-hydroxy-propionamide |

TABLE 1F-continued

| Compound No. | Structure | Name |
|---|---|---|
| 1F-89 | 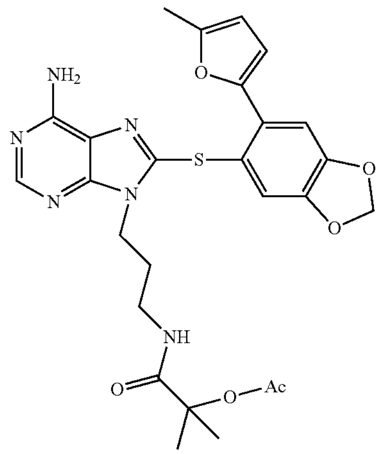 [SMILES: CC(=O)OC(C)(C)C(=O)NCCCn1c(Sc2cc3c(cc2-c2ccc(C)o2)OCO3)nc2c(N)ncnc21] | Acetic acid 1-(3-{6-amino-8-[6-(5-methyl-furan-2-yl)-benzo[1,3]dioxol-5-ylsulfanyl]-purin-9-yl}-propylcarbamoyl)-1-methyl-ethyl ester |
| 1F-90 | 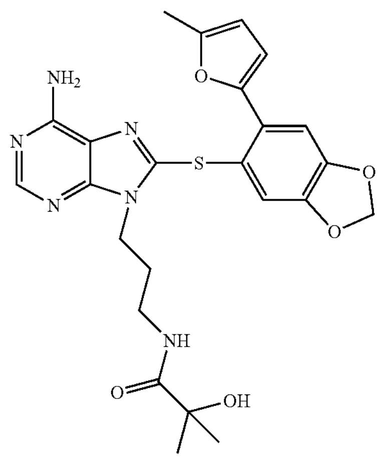 [SMILES: Cc1ccc(-c2cc3c(cc2Sc2nc4c(N)ncnc4n2CCCNC(=O)C(C)(C)O)OCO3)o1] | N-(3-{6-Amino-8-[6-(5-methyl-furan-2-yl)-benzo[1,3]dioxol-5-ylsulfanyl]-purin-9-yl}-propyl)-2-hydroxy-2-methyl-propionamide |
| 1F-91 | 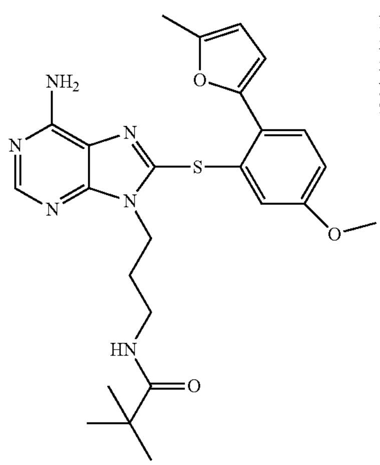 | N-(3-(6-amino-8-[(5-methoxy-2-(5-methylfuran-2-yl)phenyl)thio)-9H-purin-9-yl]propyl)pivalamide |

C-III. In some embodiments of the disclosure, $X_2$ is an alkynyl group, e.g., ethynyl, 1-prop-1-ynyl, and 3-prop-1-ynyl. Table 1B lists specific examples of compounds within this embodiment. In each of the structures as drawn, $X_2$ is ethynyl and $X_4$ is H. However, corresponding structures in which $X_2$ is another alkynyl group, including specifically for example propynyl or butynyl, are within the scope of the disclosure. In each of the structures in Table 1B, Y is S. However, corresponding structures in which Y is $CH_2$ and/or $X_4$ is F, Cl, Br, or I are also within the scope of the disclosure. Additionally, in connection with each of the structures in Table 1B, corresponding structures in which $X_2$ is another alkynyl group, including specifically for example propynyl or butynyl, and Y is $CH_2$ are also within the scope of the disclosure.

TABLE 1B

| Compound No. | Structure | Name |
| --- | --- | --- |
| 1B-1 | 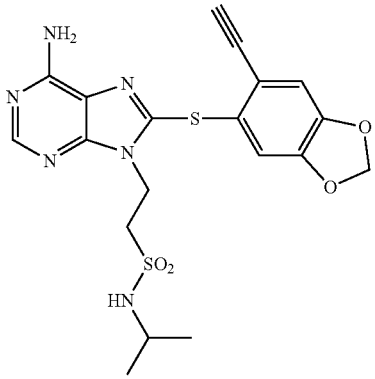 [SMILES: C#Cc1cc2c(cc1Sc1nc3c(N)ncnc3n1CCS(=O)(=O)NC(C)C)OCO2] | 2-[6-Amino-8-(6-ethynyl-benzo[1,3]dioxol-5-ylsulfanyl)-purin-9-yl]-ethanesulfonic acid isopropylamide |
| 1B-2 | 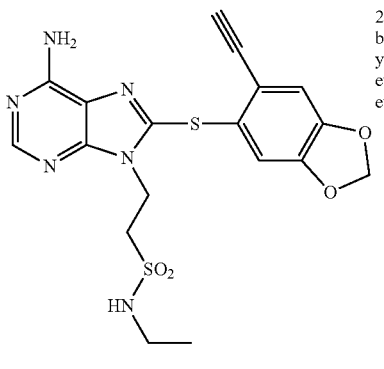 | 2-[6-Amino-8-(6-ethynyl-benzo[1,3]dioxol-5-ylsulfanyl)-purin-9-yl]-ethanesulfonic acid ethylamide |
| 1B-3 | 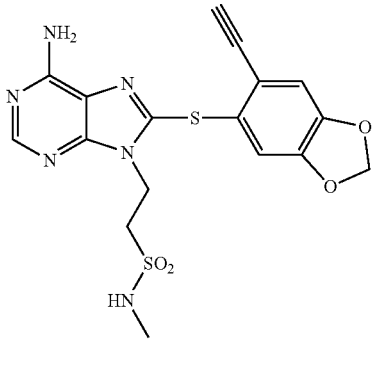 [SMILES: C#Cc1cc2c(cc1Sc1nc3c(N)ncnc3n1CCS(=O)(=O)NC)OCO2] | 2-[6-Amino-8-(6-ethynyl-benzo[1,3]dioxol-5-ylsulfanyl)-purin-9-yl]-ethanesulfonic acid methylamide |
| 1B-4 | 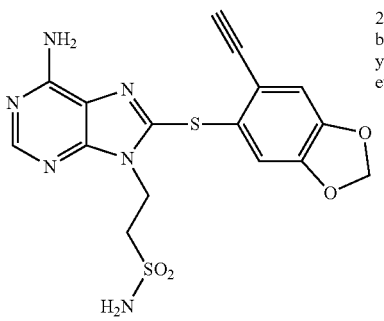 | 2-[6-Amino-8-(6-ethynyl-benzo[1,3]dioxol-5-ylsulfanyl)-purin-9-yl]-ethanesulfonic acid amide |

TABLE 1B-continued

| Compound No. | Structure | Name |
|---|---|---|
| 1B-5 | 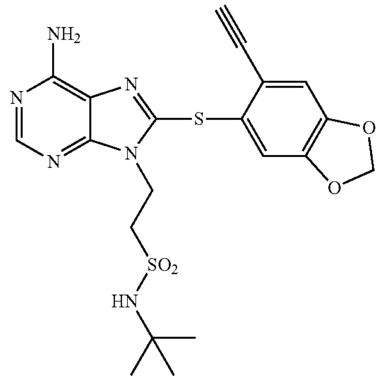 [SMILES: C#Cc1cc2c(cc1Sc1nc3c(N)ncnc3n1CCS(=O)(=O)NC(C)(C)C)OCO2] | 2-[6-Amino-8-(6-ethynyl-benzo[1,3]dioxol-5-ylsulfanyl)-purin-9-yl]-ethanesulfonic acid tert-butylamide |
| 1B-6 | 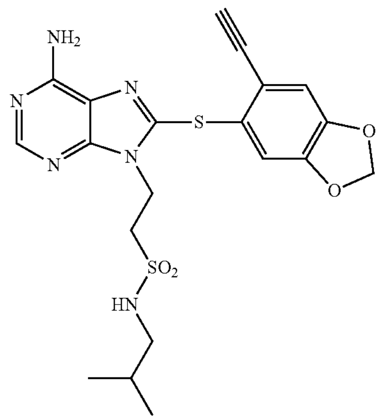 [SMILES: C#Cc1cc2c(cc1Sc1nc3c(N)ncnc3n1CCS(=O)(=O)NCC(C)C)OCO2] | 2-[6-Amino-8-(6-ethynyl-benzo[1,3]dioxol-5-ylsulfanyl)-purin-9-yl]-ethanesulfonic acid isobutyl-amide |
| 1B-7 | 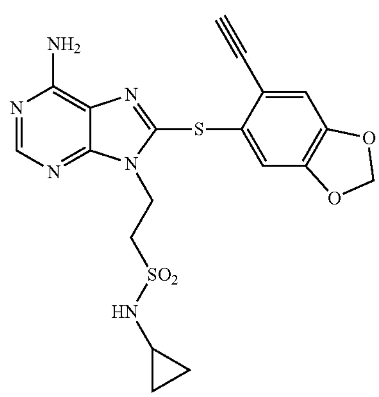 [SMILES: C#Cc1cc2c(cc1Sc1nc3c(N)ncnc3n1CCS(=O)(=O)NC1CC1)OCO2] | 2-[6-Amino-8-(6-ethynyl-benzo[1,3]dioxol-5-ylsulfanyl)-purin-9-yl]-ethanesulfonic acid cyclopropylamide |
| 1B-8 | 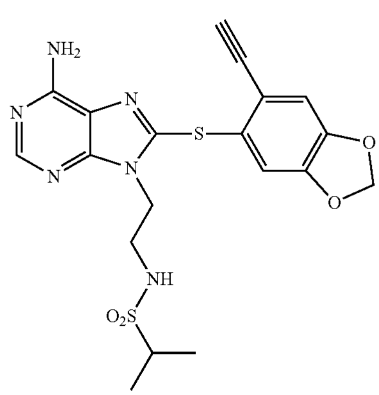 [SMILES: C#Cc1cc2c(cc1Sc1nc3c(N)ncnc3n1CCNS(=O)(=O)C(C)C)OCO2] | Propane-2-sulfonic acid {2-[6-amino-8-(6-ethynyl-benzo[1,3]dioxol-5-ylsulfanyl)-purin-9-yl]-ethyl}-amide |

TABLE 1B-continued

| Compound No. | Structure | Name |
|---|---|---|
| 1B-9 | 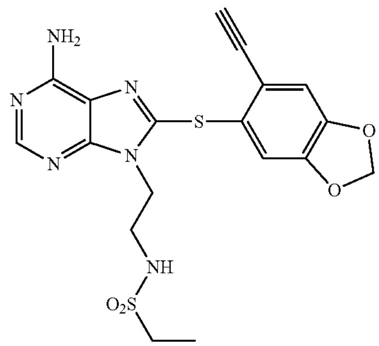 [SMILES: C#Cc1cc2c(cc1Sc1nc3c(N)ncnc3n1CCNS(=O)(=O)CC)OCO2] | Ethanesulfonic acid {2-[6-amino-8-(6-ethynyl-benzo[1,3]dioxol-5-ylsulfanyl)-purin-9-yl]-ethyl}-amide |
| 1B-10 | 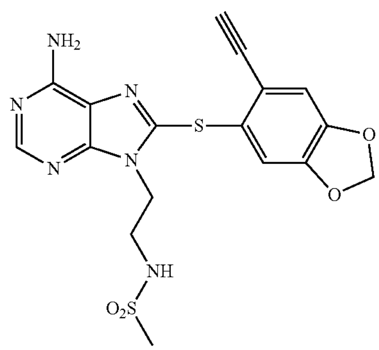 [SMILES: C#Cc1cc2c(cc1Sc1nc3c(N)ncnc3n1CCNS(C)(=O)=O)OCO2] | N-{2-[6-Amino-8-(6-ethynyl-benzo[1,3]dioxol-5-ylsulfanyl)-purin-9-yl]-ethyl}-methanesulfonamide |
| 1B-11 | 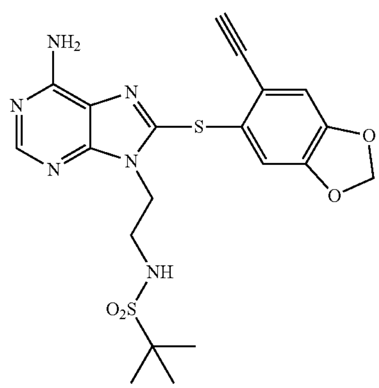 [SMILES: C#Cc1cc2c(cc1Sc1nc3c(N)ncnc3n1CCNS(=O)(=O)C(C)(C)C)OCO2] | 2-Methyl-propane-2-sulfonic acid {2-[6-amino-8-(6-ethynyl-benzo[1,3]dioxol-5-ylsulfanyl)-purin-9-yl]-ethyl}-amide |
| 1B-12 | 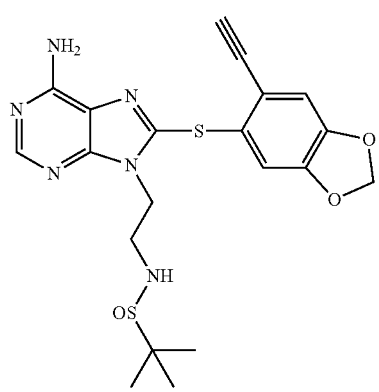 | 2-Methyl-propane-2-sulfinic acid {2-[6-amino-8-(6-ethynyl-benzo[1,3]dioxol-5-ylsulfanyl)-purin-9-yl]-ethyl}-amide |

TABLE 1B-continued

| Compound No. | Structure | Name |
| --- | --- | --- |
| 1B-13 | 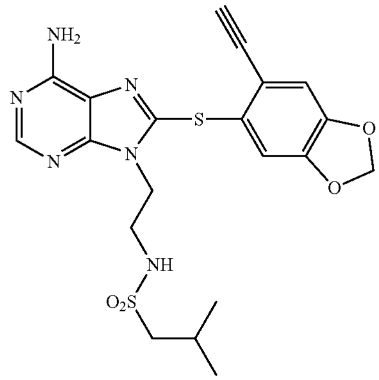 [SMILES: C#Cc1cc2c(cc1Sc1nc3c(N)ncnc3n1CCNS(=O)(=O)CC(C)C)OCO2] | 2-Methyl-propane-1-sulfonic acid {2-[6-amino-8-(6-ethynyl-benzo[1,3]dioxol-5-ylsulfanyl)-purin-9-yl]-ethyl}-amide |
| 1B-14 | 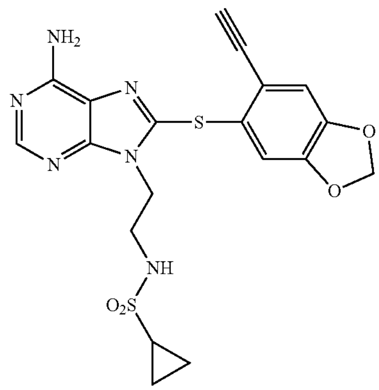 [SMILES: C#Cc1cc2c(cc1Sc1nc3c(N)ncnc3n1CCNS(=O)(=O)C1CC1)OCO2] | Cyclopropanesulfonic acid {2-[6-amino-8-(6-ethynyl-benzo[1,3]dioxol-5-ylsulfanyl)-purin-9-yl]-ethyl}-amide |
| 1B-15 | 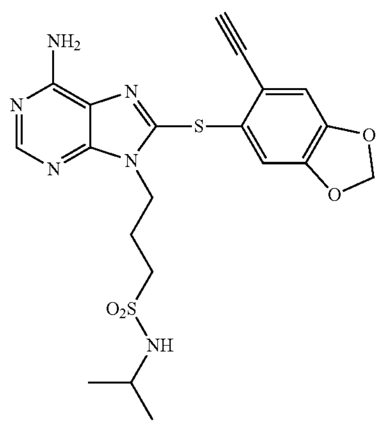 [SMILES: C#Cc1cc2c(cc1Sc1nc3c(N)ncnc3n1CCCS(=O)(=O)NC(C)C)OCO2] | 3-[6-Amino-8-(6-ethynyl-benzo[1,3]dioxol-5-ylsulfanyl)-purin-9-yl]-propane-1-sulfonic acid isopropylamide |
| 1B-16 | 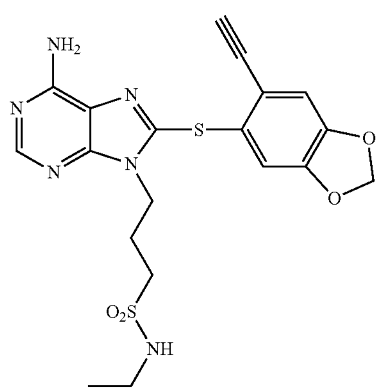 [SMILES: C#Cc1cc2c(cc1Sc1nc3c(N)ncnc3n1CCCS(=O)(=O)NCC)OCO2] | 3-[6-Amino-8-(6-ethynyl-benzo[1,3]dioxol-5-ylsulfanyl)-purin-9-yl]-propane-1-sulfonic acid ethylamide |

TABLE 1B-continued

| Compound No. | Structure | Name |
|---|---|---|
| 1B-17 | 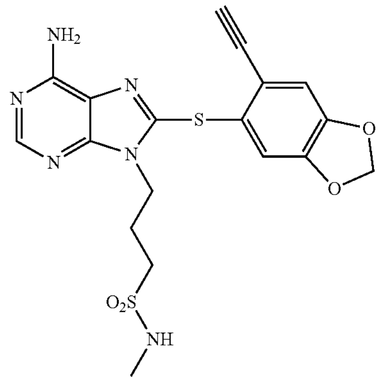 [SMILES: C#Cc1cc2c(cc1Sc1nc3c(N)ncnc3n1CCCS(=O)(=O)NC)OCO2] | 3-[6-Amino-8-(6-ethynyl-benzo[1,3]dioxol-5-ylsulfanyl)-purin-9-yl]-propane-1-sulfonic acid methylamide |
| 1B-18 | 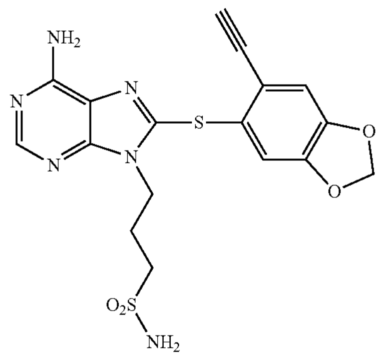 [SMILES: C#Cc1cc2c(cc1Sc1nc3c(N)ncnc3n1CCCS(N)(=O)=O)OCO2] | 3-[6-Amino-8-(6-ethynyl-benzo[1,3]dioxol-5-ylsulfanyl)-purin-9-yl]-propane-1-sulfonic acid amide |
| 1B-19 | 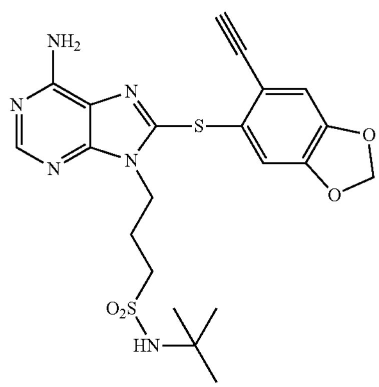 [SMILES: C#Cc1cc2c(cc1Sc1nc3c(N)ncnc3n1CCCS(=O)(=O)NC(C)(C)C)OCO2] | 3-[6-Amino-8-(6-ethynyl-benzo[1,3]dioxol-5-ylsulfanyl)-purin-9-yl]-propane-1-sulfonic acid tert-butylamide |
| 1B-20 | 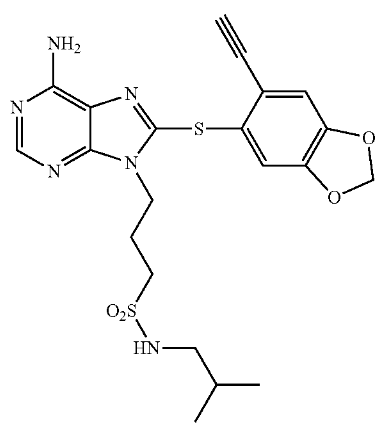 [SMILES: C#Cc1cc2c(cc1Sc1nc3c(N)ncnc3n1CCCS(=O)(=O)NCC(C)C)OCO2] | 3-[6-Amino-8-(6-ethynyl-benzo[1,3]dioxol-5-ylsulfanyl)-purin-9-yl]-propane-1-sulfonic acid isobutyl-amide |

TABLE 1B-continued

| Compound No. | Structure | Name |
|---|---|---|
| 1B-21 | 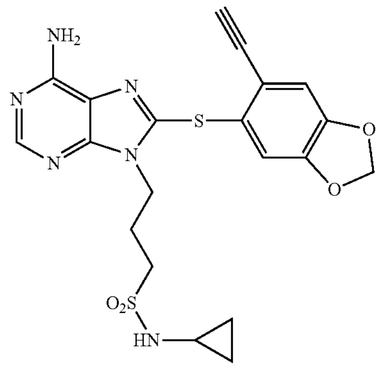 [SMILES: C#Cc1cc2c(cc1Sc1nc3c(N)ncnc3n1CCCS(=O)(=O)NC1CC1)OCO2] | 3-[6-Amino-8-(6-ethynyl-benzo[1,3]dioxol-5-ylsulfanyl)-purin-9-yl]-propane-1-sulfonic acid cyclopropylamide |
| 1B-22 | 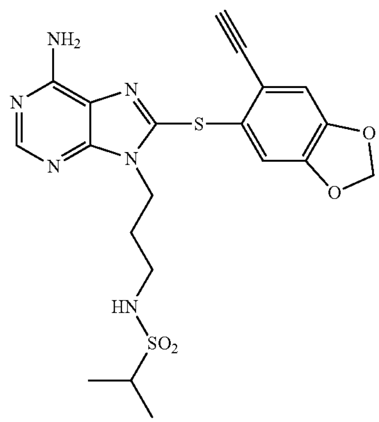 [SMILES: C#Cc1cc2c(cc1Sc1nc3c(N)ncnc3n1CCCNS(=O)(=O)C(C)C)OCO2] | Propane-2-sulfonic acid {3-[6-amino-8-(6-ethynyl-benzo[1,3]dioxol-5-ylsulfanyl)-purin-9-yl]-propyl}-amide |
| 1B-23 | 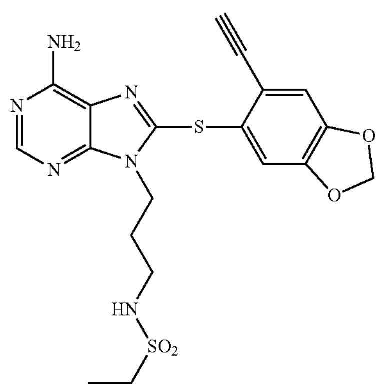 [SMILES: C#Cc1cc2c(cc1Sc1nc3c(N)ncnc3n1CCCNS(=O)(=O)CC)OCO2] | Ethanesulfonic acid {3-[6-amino-8-(6-ethynyl-benzo[1,3]dioxol-5-ylsulfanyl)-purin-9-yl]-propyl}-amide |
| 1B-24 | 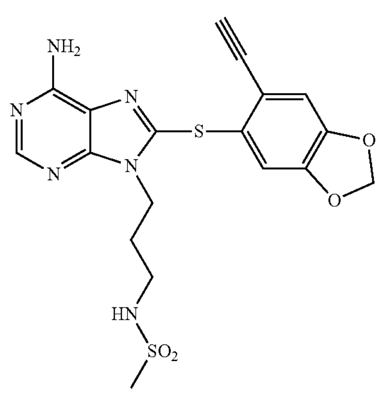 [SMILES: C#Cc1cc2c(cc1Sc1nc3c(N)ncnc3n1CCCNS(C)(=O)=O)OCO2] | N-{3-[6-Amino-8-(6-ethynyl-benzo[1,3]dioxol-5-ylsulfanyl)-purin-9-yl]-propyl}-methanesulfonamide |

TABLE 1B-continued

| Compound No. | Structure | Name |
| --- | --- | --- |
| 1B-25 | 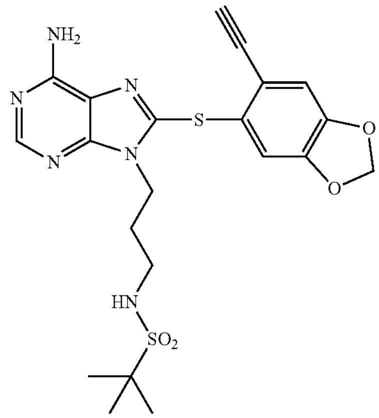 [SMILES: C#Cc1cc2c(cc1Sc1nc3c(N)ncnc3n1CCCNS(=O)(=O)C(C)(C)C)OCO2] | 2-Methyl-propane-2-sulfonic acid {3-[6-amino-8-(6-ethynyl-benzo[1,3]dioxol-5-ylsulfanyl)-purin-9-yl]-propyl}-amide |
| 1B-26 | 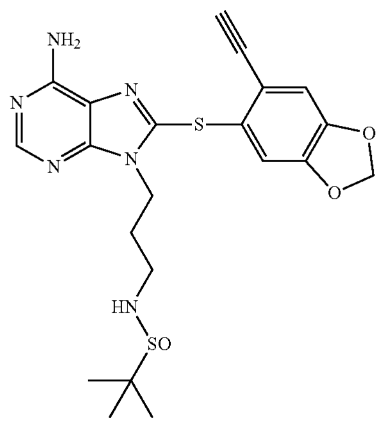 | 2-Methyl-propane-2-sulfinic acid {3-[6-amino-8-(6-ethynyl-benzo[1,3]dioxol-5-ylsulfanyl)-purin-9-yl]-propyl}-amide |
| 1B-27 | 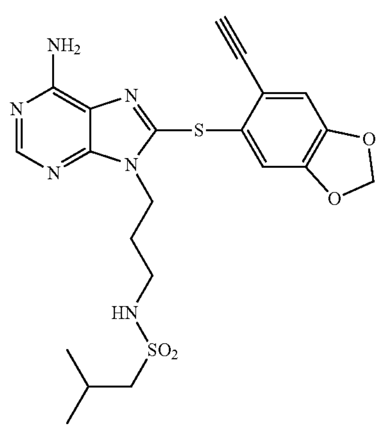 [SMILES: C#Cc1cc2c(cc1Sc1nc3c(N)ncnc3n1CCCNS(=O)(=O)CC(C)C)OCO2] | 2-Methyl-propane-1-sulfonic acid {3-[6-amino-8-(6-ethynyl-benzo[1,3]dioxol-5-ylsulfanyl)-purin-9-yl]-propyl}-amide |

TABLE 1B-continued

| Compound No. | Structure | Name |
|---|---|---|
| 1B-28 | 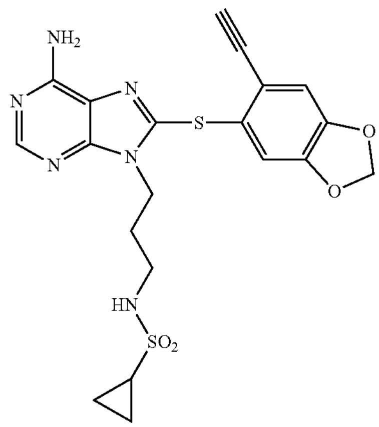 [SMILES: C#Cc1cc2c(cc1Sc1nc3c(N)ncnc3n1CCCNS(=O)(=O)C1CC1)OCO2] | Cyclopropanesulfonic acid {3-[6-amino-8-(6-ethynyl-benzo[1,3]dioxol-5-ylsulfanyl)-purin-9-yl]-propyl}-amide |
| 1B-29 | 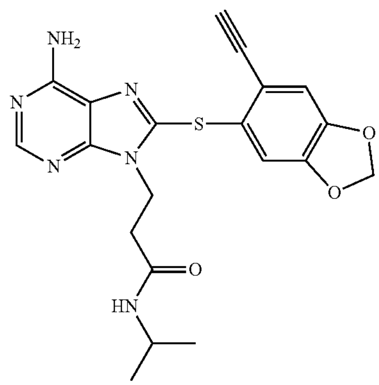 [SMILES: C#Cc1cc2c(cc1Sc1nc3c(N)ncnc3n1CCC(=O)NC(C)C)OCO2] | 3-[6-Amino-8-(6-ethynyl-benzo[1,3]dioxol-5-ylsulfanyl)-purin-9-yl]-N-isopropyl-propionamide |
| 1B-30 | 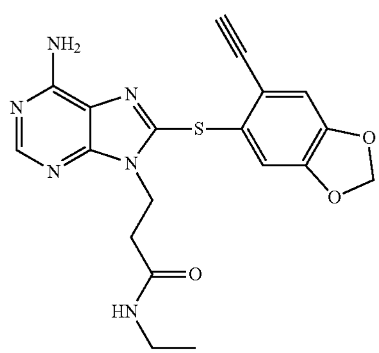 [SMILES: C#Cc1cc2c(cc1Sc1nc3c(N)ncnc3n1CCC(=O)NCC)OCO2] | 3-[6-Amino-8-(6-ethynyl-benzo[1,3]dioxol-5-ylsulfanyl)-purin-9-yl]-N-ethyl-propionamide |
| 1B-31 | 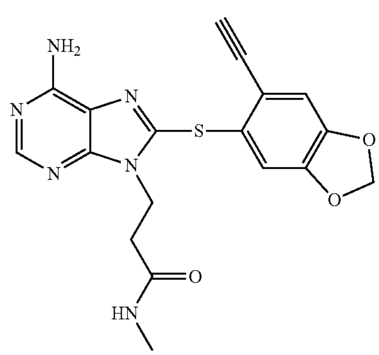 [SMILES: C#Cc1cc2c(cc1Sc1nc3c(N)ncnc3n1CCC(=O)NC)OCO2] | 3-[6-Amino-8-(6-ethynyl-benzo[1,3]dioxol-5-ylsulfanyl)-purin-9-yl]-N-methyl-propionamide |

TABLE 1B-continued

| Compound No. | Structure | Name |
| --- | --- | --- |
| 1B-32 | 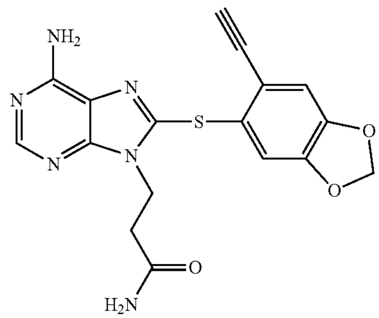 [SMILES: C#Cc1cc2c(cc1Sc1nc3c(N)ncnc3n1CCC(N)=O)OCO2] | 3-[6-Amino-8-(6-ethynyl-benzo[1,3]dioxol-5-ylsulfanyl)-purin-9-yl]-propionamide |
| 1B-33 | 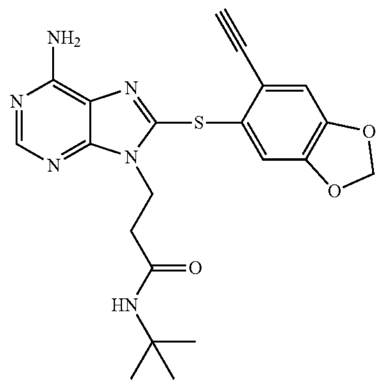 [SMILES: C#Cc1cc2c(cc1Sc1nc3c(N)ncnc3n1CCC(=O)NC(C)(C)C)OCO2] | 3-[6-Amino-8-(6-ethynyl-benzo[1,3]dioxol-5-ylsulfanyl)-purin-9-yl]-N-tert-butyl-propionamide |
| 1B-34 | 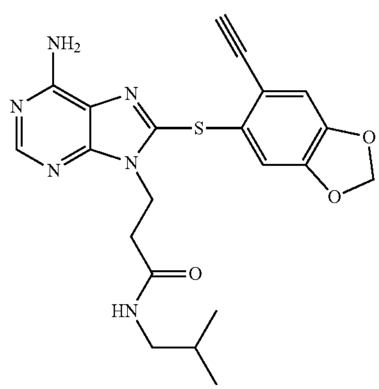 [SMILES: C#Cc1cc2c(cc1Sc1nc3c(N)ncnc3n1CCC(=O)NCC(C)C)OCO2] | 3-[6-Amino-8-(6-ethynyl-benzo[1,3]dioxol-5-ylsulfanyl)-purin-9-yl]-N-isobutyl-propionamide |
| 1B-35 | 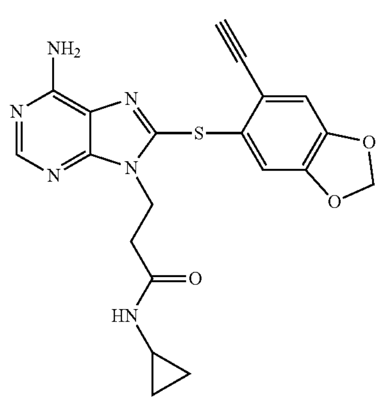 [SMILES: C#Cc1cc2c(cc1Sc1nc3c(N)ncnc3n1CCC(=O)NC1CC1)OCO2] | 3-[6-Amino-8-(6-ethynyl-benzo[1,3]dioxol-5-ylsulfanyl)-purin-9-yl]-N-cyclopropyl-propionamide |

TABLE 1B-continued

| Compound No. | Structure | Name |
| --- | --- | --- |
| 1B-36 | 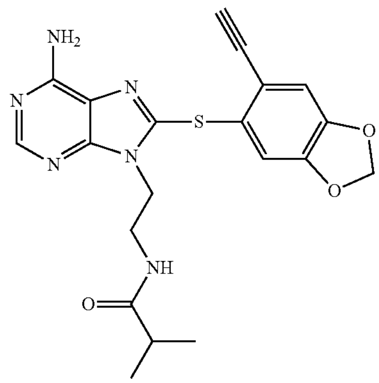 [SMILES: C#Cc1cc2c(cc1Sc1nc3c(N)ncnc3n1CCNC(=O)C(C)C)OCO2] | N-{2-[6-Amino-8-(6-ethynyl-benzo[1,3]dioxol-5-ylsulfanyl)-purin-9-yl]-ethyl}-isobutyramide |
| 1B-37 | 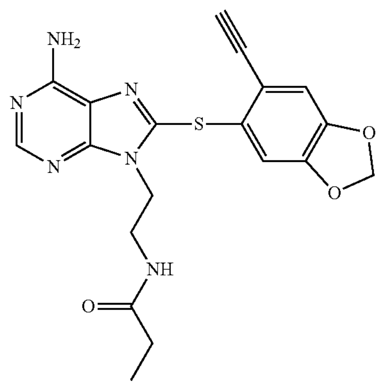 [SMILES: C#Cc1cc2c(cc1Sc1nc3c(N)ncnc3n1CCNC(=O)CC)OCO2] | N-{2-[6-Amino-8-(6-ethynyl-benzo[1,3]dioxol-5-ylsulfanyl)-purin-9-yl]-ethyl}-propionamide |
| 1B-38 | 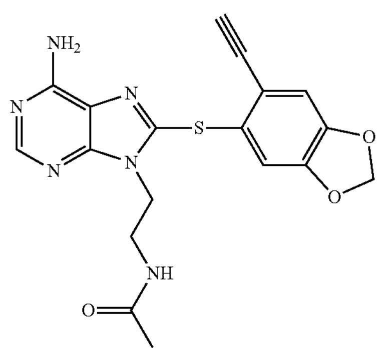 [SMILES: C#Cc1cc2c(cc1Sc1nc3c(N)ncnc3n1CCNC(C)=O)OCO2] | N-{2-[6-Amino-8-(6-ethynyl-benzo[1,3]dioxol-5-ylsulfanyl)-purin-9-yl]-ethyl}-acetamide |
| 1B-39 | 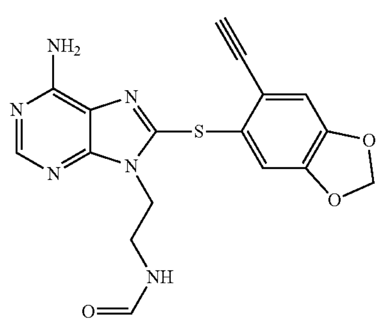 [SMILES: C#Cc1cc2c(cc1Sc1nc3c(N)ncnc3n1CCNC=O)OCO2] | N-{2-[6-Amino-8-(6-ethynyl-benzo[1,3]dioxol-5-ylsulfanyl)-purin-9-yl]-ethyl}-formamide |

TABLE 1B-continued

| Compound No. | Structure | Name |
|---|---|---|
| 1B-40 | 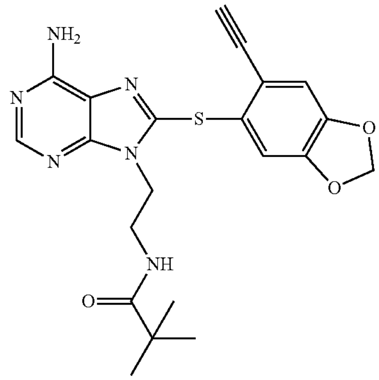 [SMILES: C#Cc1cc2c(cc1Sc1nc3c(N)ncnc3n1CCNC(=O)C(C)(C)C)OCO2] | N-{2-[6-Amino-8-(6-ethynyl-benzo[1,3]dioxol-5-ylsulfanyl)-purin-9-yl]-ethyl}-2,2-dimethyl-propionamide |
| 1B-41 | 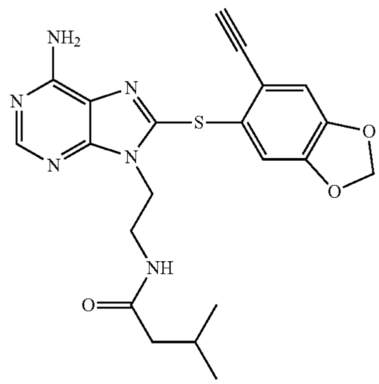 [SMILES: C#Cc1cc2c(cc1Sc1nc3c(N)ncnc3n1CCNC(=O)CC(C)C)OCO2] | N-{2-[6-Amino-8-(6-ethynyl-benzo[1,3]dioxol-5-ylsulfanyl)-purin-9-yl]-ethyl}-3-methyl-butyramide |
| 1B-42 | 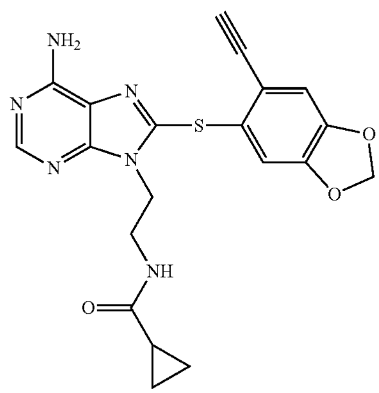 [SMILES: C#Cc1cc2c(cc1Sc1nc3c(N)ncnc3n1CCNC(=O)C1CC1)OCO2] | Cyclopropanecarboxylic acid {2-[6-amino-8-(6-ethynyl-benzo[1,3]dioxol-5-ylsulfanyl)-purin-9-yl]-ethyl}-amide |
| 1B-43 | 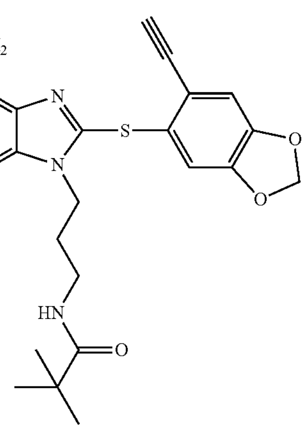 | N-{3-[6-Amino-8-(6-ethynyl-benzo[1,3]dioxol-5-ylsulfanyl)-purin-9-yl]-propyl}-2,2-dimethyl-propionamide |

TABLE 1B-continued

| Compound No. | Structure | Name |
| --- | --- | --- |
| 1B-44 | 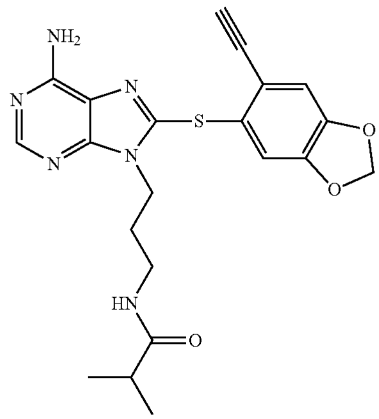 [SMILES: C#Cc1cc2c(cc1Sc1nc3c(N)ncnc3n1CCCNC(=O)C(C)C)OCO2] | N-{3-[6-Amino-8-(6-ethynyl-benzo[1,3]dioxol-5-ylsulfanyl)-purin-9-yl]-propyl}-isobutyramide |
| 1B-45 | 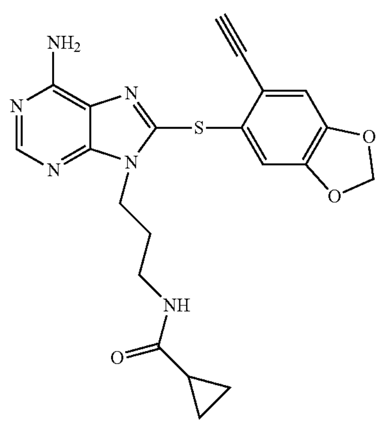 [SMILES: C#Cc1cc2c(cc1Sc1nc3c(N)ncnc3n1CCCNC(=O)C1CC1)OCO2] | Cyclopropanecarboxylic acid {3-[6-amino-8-(6-ethynyl-benzo[1,3]dioxol-5-ylsulfanyl)-purin-9-yl]-propyl}-amide |
| 1B-46 | 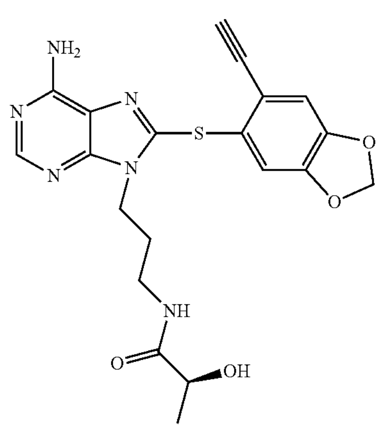 [SMILES: C#Cc1cc2c(cc1Sc1nc3c(N)ncnc3n1CCCNC(=O)[C@H](C)O)OCO2] | N-{3-[6-Amino-8-(6-ethynyl-benzo[1,3]dioxol-5-ylsulfanyl)-purin-9-yl]-propyl}-2-hydroxy-propionamide |

TABLE 1B-continued

| Compound No. | Structure | Name |
|---|---|---|
| 1B-47 | 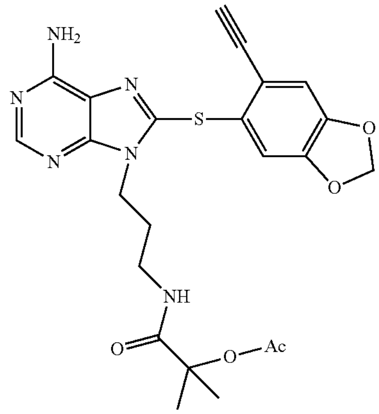 [SMILES: C#Cc1cc2c(cc1Sc1nc3c(N)ncnc3n1CCCNC(=O)C(C)(C)OC(C)=O)OCO2] | Acetic acid 1-{3-[6-amino-8-(6-ethynyl-benzo[1,3]dioxol-5-ylsulfanyl)-purin-9-yl]-propylcarbamoyl}-1-methyl-ethyl ester |
| 1B-48 | 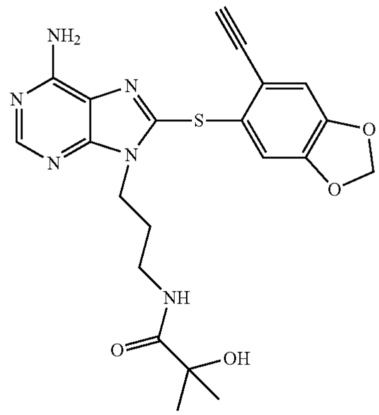 [SMILES: C#Cc1cc2c(cc1Sc1nc3c(N)ncnc3n1CCCNC(=O)C(C)(C)O)OCO2] | N-{3-[6-Amino-8-(6-ethynyl-benzo[1,3]dioxol-5-ylsulfanyl)-purin-9-yl]-propyl}-2-hydroxy-2-methyl-propionamide |
| 1B-49 | 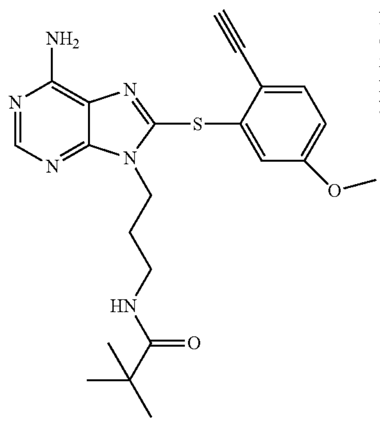 | N-(3-(6-amino-8-((2-ethynyl-5-methoxyphenyl)thio)-9H-purin-9-yl)propyl)pivalamide |

Hsp90 binding results are presented for Compounds 1B-28, 1B-43, and 1B-45 in Table 12 below. As can be noted therefrom, all compounds showed a high level of binding affinity.

C-IV. In some embodiments of the disclosure, $X_2$ is an amino group, i.e., —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Table 1G lists specific examples of compounds within this embodiment. In each of the structures as drawn, $X_2$ is dimethylamino and $X_4$ is H. However, corresponding structures in which $X_2$ is another amino group, including specifically for example diethylamino, methylethylamino or cyclopropylamino, are within the scope of the disclosure. In each of the structures in Table 1G, Y is S. However, corresponding structures in which Y is $CH_2$ and/or $X_4$ is F, Cl, Br, or I are also within the scope of the disclosure. Additionally, in connection with each of the structures in Table 1G, corresponding structures in which $X_2$ is another amino group, including specifically for example diethylamino, methylethylamino or cyclopropylamino, and Y is $CH_2$ are also within the scope of the disclosure.

TABLE 1G

| Compound No. | Structure | Name |
|---|---|---|
| 1G-1 | 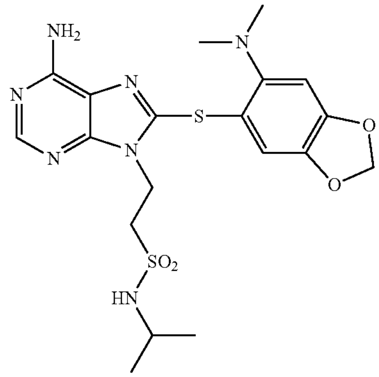 [SMILES: CC(C)NS(=O)(=O)CCn1c(Sc2cc3c(cc2N(C)C)OCO3)nc2c(N)ncnc21] | 2-(6-amino-8-((6-(dimethylamino)benzo[d][1,3]dioxol-5-yl)thio)-9H-purin-9-yl)-N-isopropyl-ethanesulfonamide |
| 1G-2 | 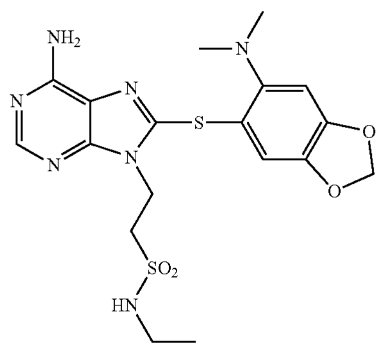 [SMILES: CCNS(=O)(=O)CCn1c(Sc2cc3c(cc2N(C)C)OCO3)nc2c(N)ncnc21] | 2-(6-amino-8-((6-(dimethylamino)benzo[d][1,3]dioxol-5-yl)thio)-9H-purin-9-yl)-N-ethyethanesulfonamide |
| 1G-3 | 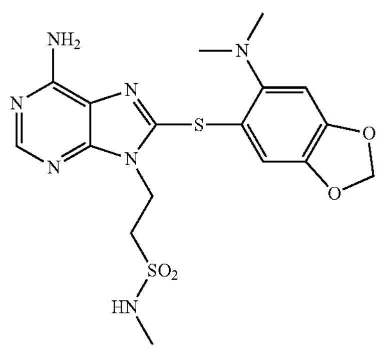 [SMILES: CNS(=O)(=O)CCn1c(Sc2cc3c(cc2N(C)C)OCO3)nc2c(N)ncnc21] | 2-(6-amino-8-((6-(dimethylamino)benzo[d][1,3]dioxol-5-yl)thio)-9H-purin-9-yl)-N-methylethanesulfonamide |
| 1G-4 | 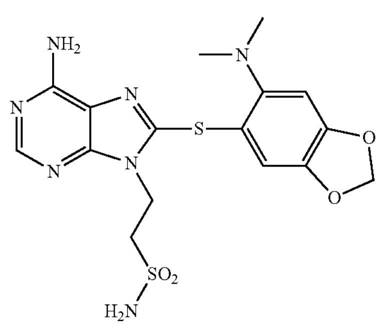 [SMILES: CN(C)c1cc2c(cc1Sc1nc3c(N)ncnc3n1CCS(N)(=O)=O)OCO2] | 2-(6-amino-8-((6-(dimethylamino)benzo[d][1,3]dioxol-5-yl)thio)-9H-purin-9-yl)ethanesulfonamide |

TABLE 1G-continued

| Compound No. | Structure | Name |
|---|---|---|
| 1G-5 | 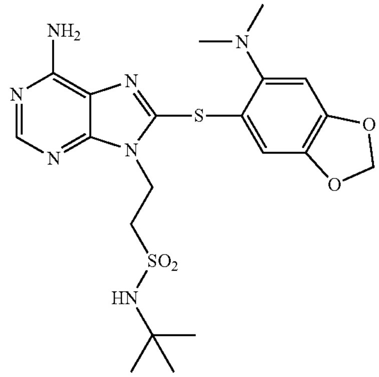 [SMILES: CN(C)c1cc2c(cc1Sc1nc3c(N)ncnc3n1CCS(=O)(=O)NC(C)(C)C)OCO2] | 2-(6-amino-8-((6-(dimethylamino)benzo[d][1,3]dioxol-5-yl)thio)-9H-purin-9-yl)-N-(tert-butyl)ethanesulfonamide |
| 1G-6 | 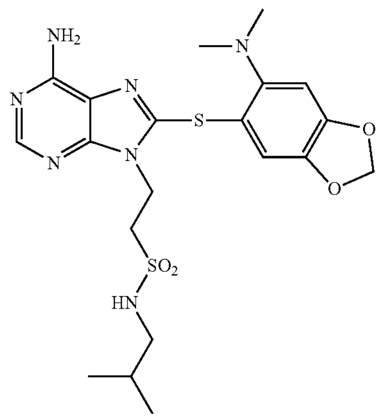 [SMILES: CC(C)CNS(=O)(=O)CCn1c(Sc2cc3c(cc2N(C)C)OCO3)nc2c(N)ncnc21] | 2-(6-amino-8-((6-(dimethylamino)benzo[d][1,3]dioxol-5-yl)thio)-9H-purin-9-yl)-N-isobutylethanesulfonamide |
| 1G-7 | 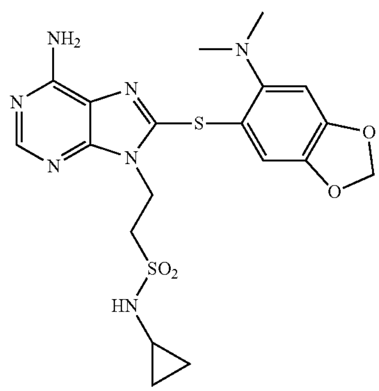 [SMILES: CN(C)c1cc2c(cc1Sc1nc3c(N)ncnc3n1CCS(=O)(=O)NC1CC1)OCO2] | 2-(6-amino-8-((6-(dimethylamino)benzo[d][1,3]dioxol-5-yl)thio)-9H-purin-9-yl)-N-cyclopropyl-ethanesulfonamide |
| 1G-8 | 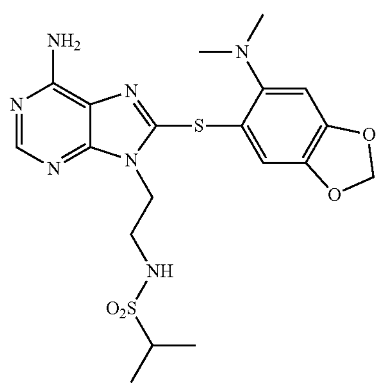 [SMILES: CC(C)S(=O)(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)propane-2-sulfonamide |

TABLE 1G-continued

| Compound No. | Structure | Name |
|---|---|---|
| 1G-9 | 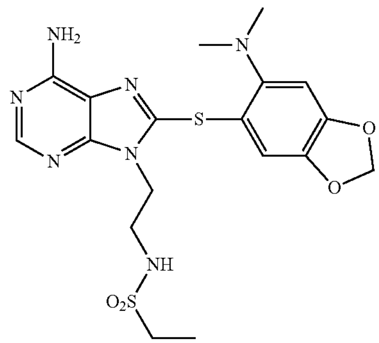 [SMILES: CCS(=O)(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)ethane-2-sulfonamide |
| 1G-10 | 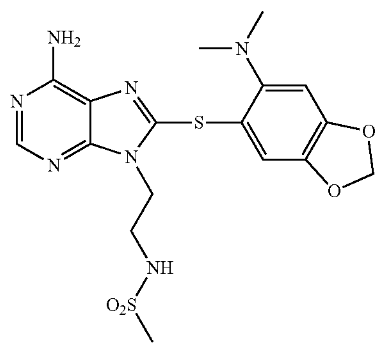 [SMILES: CN(C)c1cc2c(cc1Sc1nc3c(N)ncnc3n1CCNS(C)(=O)=O)OCO2] | N-(2-(6-amino-8-((6-(dimethylamino)benzo[d][1,3]dioxol-5-yl)thio)-9H-purin-9-yl)ethyl)methane-2-sulfonamide |
| 1G-11 | 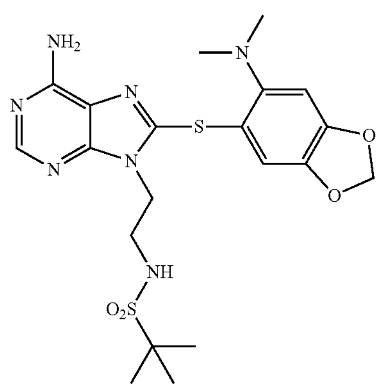 [SMILES: CN(C)c1cc2c(cc1Sc1nc3c(N)ncnc3n1CCNS(=O)(=O)C(C)(C)C)OCO2] | N-(2-(6-amino-8-((6-(dimethylamino)benzo[d][1,3]dioxol-5-yl)thio)-9H-purin-9-yl)ethyl)-2-methylpropane-2-sulfonamide |
| 1G-12 | 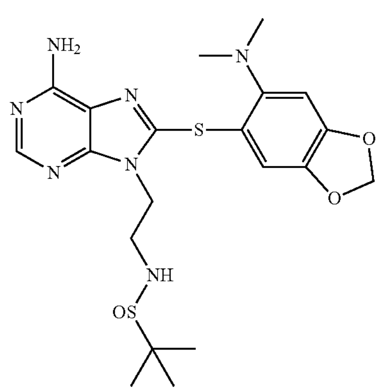 | N-(2-(6-amino-8-((6-(dimethylamino)benzo[d][1,3]dioxol-5-yl)thio)-9H-purin-9-yl)ethyl)-2-methylpropane-2-sulfinamide |

TABLE 1G-continued

| Compound No. | Structure | Name |
|---|---|---|
| 1G-13 | 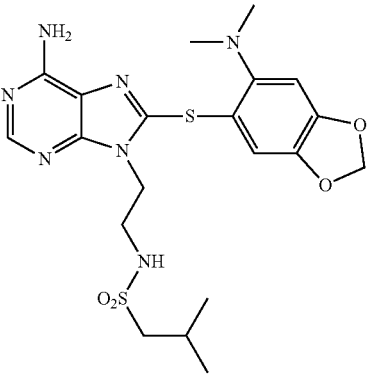 [SMILES: CC(C)CS(=O)(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)-2methylpropane-1-sulfonamide |
| 1G-14 | 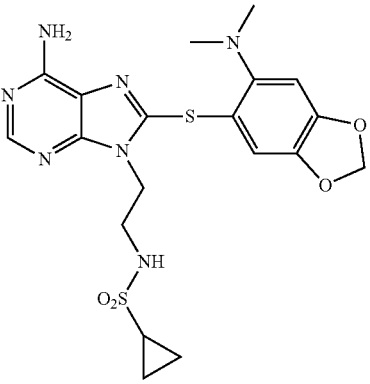 [SMILES: CN(C)c1cc2c(cc1Sc1nc3c(N)ncnc3n1CCNS(=O)(=O)C1CC1)OCO2] | N-(2-(6-amino-8-((6-(dimethylamino)benzo[d][1,3]dioxol-5-yl)thio)-9H-purin-9-yl)ethyl)cyclopropane-sulfonamide |
| 1G-15 | 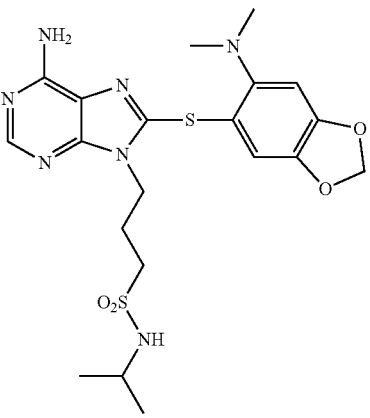 [SMILES: CC(C)NS(=O)(=O)CCCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-isopropylpropane-1-sulfonamide |
| 1G-16 | 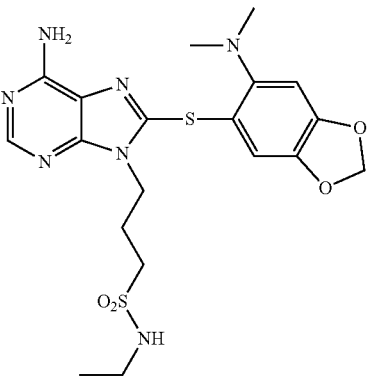 [SMILES: CCNS(=O)(=O)CCCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-ethylpropane-1-sulfonamide |

TABLE 1G-continued

| Compound No. | Structure | Name |
|---|---|---|
| 1G-17 | 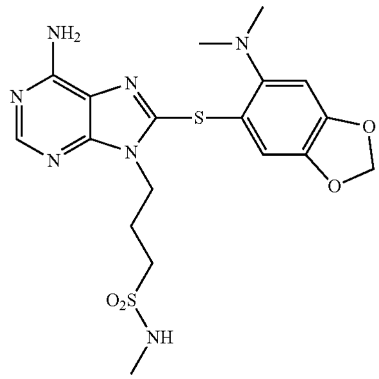 [SMILES: CNS(=O)(=O)CCCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-methylpropane-1-sulfonamide |
| 1G-18 | 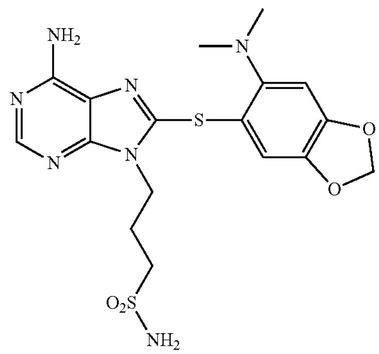 [SMILES: CN(C)c1cc2c(cc1Sc1nc3c(N)ncnc3n1CCCS(N)(=O)=O)OCO2] | 3-(6-amino-8-((6-(dimethylamino)benzo[d][1,3]dioxol-5-yl)thio)-9H-purin-9-yl)-propane-1-sulfonamide |
| 1G-19 | 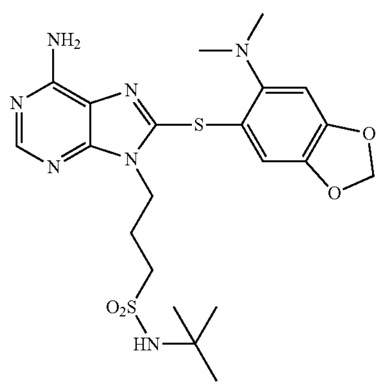 [SMILES: CN(C)c1cc2c(cc1Sc1nc3c(N)ncnc3n1CCCS(=O)(=O)NC(C)(C)C)OCO2] | 3-(6-amino-8-((6-(dimethylamino)benzo[d][1,3]dioxol-5-yl)thio)-9H-purin-9-yl)-N-(tert-butyl)propane-1-sulfonamide |
| 1G-20 | 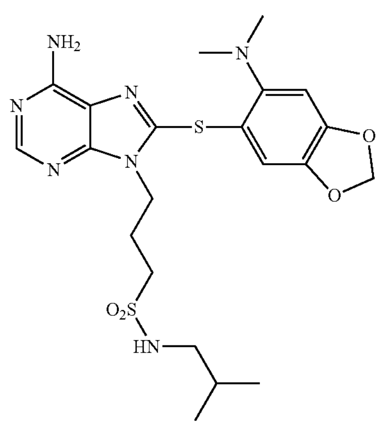 [SMILES: CC(C)CNS(=O)(=O)CCCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-isobutylpropane-1-sulfonamide |

TABLE 1G-continued

| Compound No. | Structure | Name |
|---|---|---|
| 1G-21 | 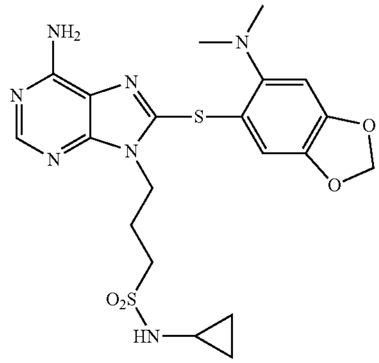 [SMILES: CN(C)c1cc2c(cc1Sc1nc3c(N)ncnc3n1CCCS(=O)(=O)NC1CC1)OCO2] | 3-(6-amino-8-((6-(dimethylamino)benzo[d][1,3]dioxol-5-yl)thio)-9H-purin-9-yl)-N-cyclopropylpropane-1-sulfonamide |
| 1G-22 | 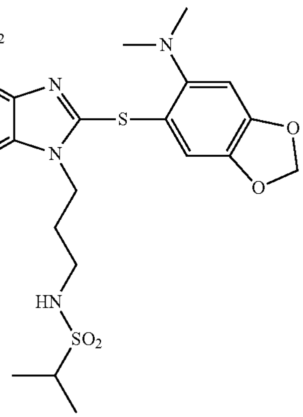 | N-(3-(6-amino-8-((6-(dimethylamino)benzo[d][1,3]dioxol-5-yl)thio)-9H-purin-9-yl)propyl)propane-2-sulfonamide |
| 1G-23 | 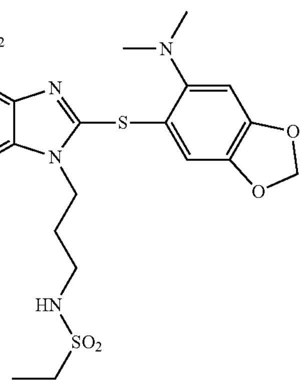 | N-(3-(6-amino-8-((6-(dimethylamino)benzo[d][1,3]dioxol-5-yl)thio)-9H-purin-9-yl)propyl)ethane-2-sulfonamide |
| 1G-24 | 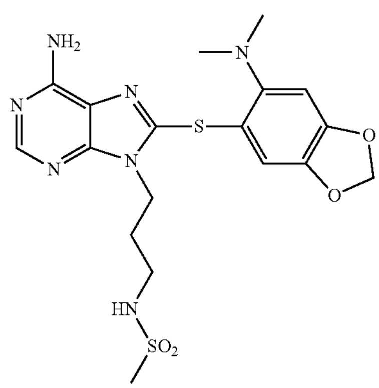 [SMILES: CN(C)c1cc2c(cc1Sc1nc3c(N)ncnc3n1CCCNS(C)(=O)=O)OCO2] | N-(3-(6-amino-8-((6-(dimethylamino)benzo[d][1,3]dioxol-5-yl)thio)-9H-purin-9-yl)propyl)methane-2-sulfonamide |

TABLE 1G-continued

| Compound No. | Structure | Name |
|---|---|---|
| 1G-25 | 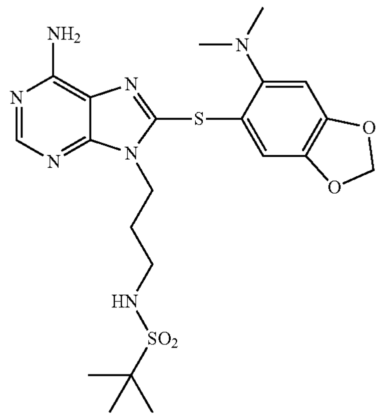 [SMILES: CN(C)c1cc2c(cc1Sc1nc3c(N)ncnc3n1CCCNS(=O)(=O)C(C)(C)C)OCO2] | N-(3-(6-amino-8-((6-(dimethylamino)benzo[d][1,3]dioxol-5-yl)thio)-9H-purin-9-yl)propyl)-2-methylpropane-2-sulfonamide |
| 1G-26 | 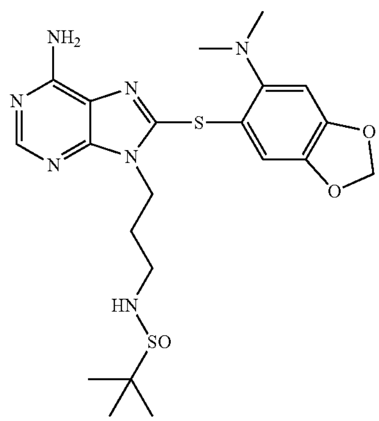 | N-(3-(6-amino-8-((6-(dimethylamino)benzo[d][1,3]dioxol-5-yl)thio)-9H-purin-9-yl)propyl)-2-methylpropane-2-sulfinamide |
| 1G-27 | 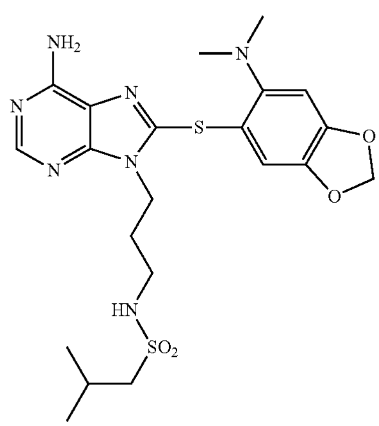 [SMILES: CC(C)CS(=O)(=O)NCCCn1c(Sc2cc3c(cc2N(C)C)OCO3)nc2c(N)ncnc21] | N-(3-(6-amino-8-((6-(dimethylamino)benzo[d][1,3]dioxol-5-yl)thio)-9H-purin-9-yl)propyl)-2-methylpropane-1-sulfonamide |

TABLE 1G-continued

| Compound No. | Structure | Name |
|---|---|---|
| 1G-28 | 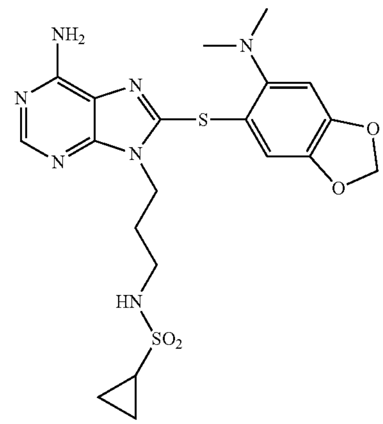 [SMILES: CN(C)c1cc2c(cc1Sc1nc3c(N)ncnc3n1CCCNS(=O)(=O)C1CC1)OCO2] | N-(3-(6-amino-8-((6-(dimethylamino)benzo[d][1,3]dioxol-5-yl)thio)-9H-purin-9-yl)propyl)cyclopropane-sulfonamide |
| 1G-29 | 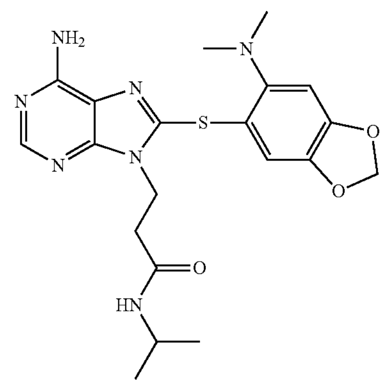 [SMILES: CC(C)NC(=O)CCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-isopropylpropanamide |
| 1G-30 | 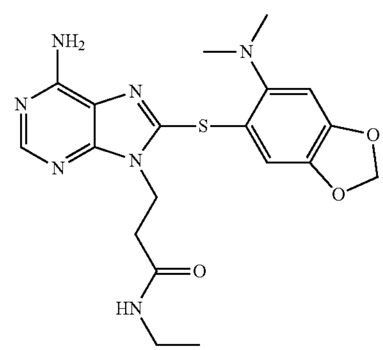 [SMILES: CCNC(=O)CCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-ethylpropanamide |
| 1G-31 | 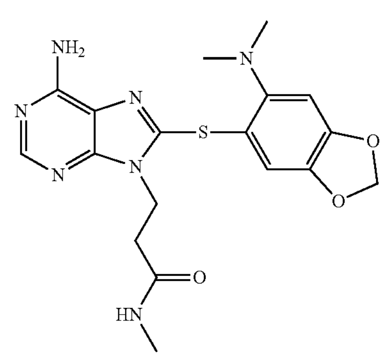 [SMILES: CNC(=O)CCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-methylpropanamide |

TABLE 1G-continued

| Compound No. | Structure | Name |
| --- | --- | --- |
| 1G-32 | 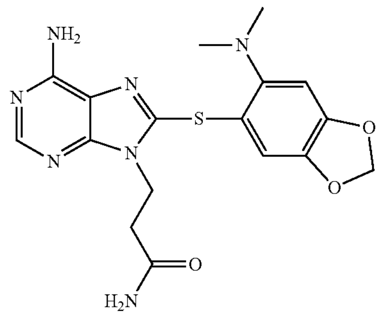 [SMILES: CN(C)c1cc2c(cc1Sc1nc3c(N)ncnc3n1CCC(N)=O)OCO2] | 3-(6-amino-8-((6-(dimethylamino)benzo[d][1,3]dioxol-5-yl)thio)-9H-purin-9-yl)propanamide |
| 1G-33 | 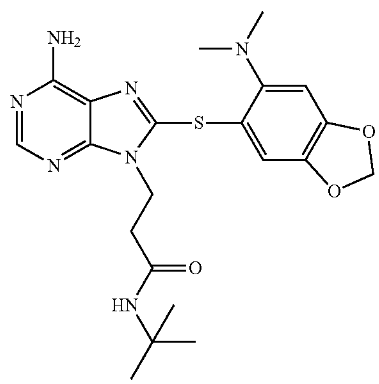 [SMILES: CN(C)c1cc2c(cc1Sc1nc3c(N)ncnc3n1CCC(=O)NC(C)(C)C)OCO2] | 3-(6-amino-8-((6-(dimethylamino)benzo[d][1,3]dioxol-5-yl)thio)-9H-purin-9-yl)-N-(tert-butyl)propanamide |
| 1G-34 | 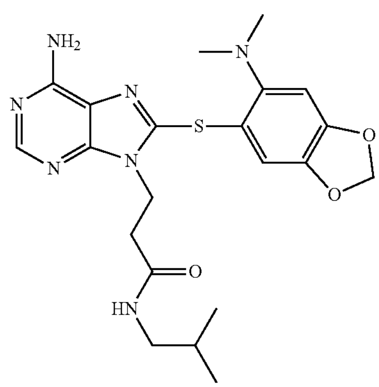 [SMILES: CC(C)CNC(=O)CCn1c(Sc2cc3c(cc2N(C)C)OCO3)nc2c(N)ncnc21] | 3-(6-amino-8-((6-(dimethylamino)benzo[d][1,3]dioxol-5-yl)thio)-9H-purin-9-yl)-N-isobutylpropanamide |
| 1G-35 | 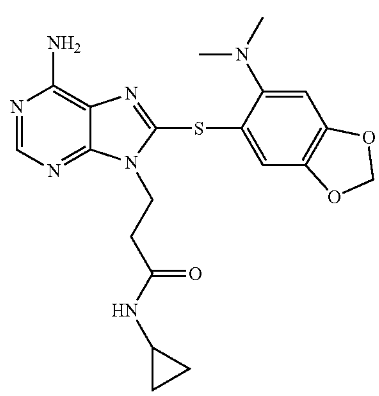 [SMILES: CN(C)c1cc2c(cc1Sc1nc3c(N)ncnc3n1CCC(=O)NC1CC1)OCO2] | 3-(6-amino-8-((6-(dimethylamino)benzo[d][1,3]dioxol-5-yl)thio)-9H-purin-9-yl)-N-cyclopropylpropanamide |

TABLE 1G-continued

| Compound No. | Structure | Name |
|---|---|---|
| 1G-36 | 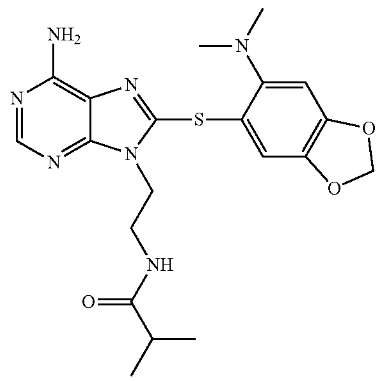 [SMILES: CC(C)C(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)isobutyramide |
| 1G-37 | 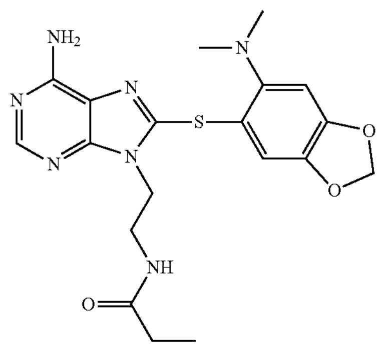 [SMILES: CCC(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)propanamide |
| 1G-38 | 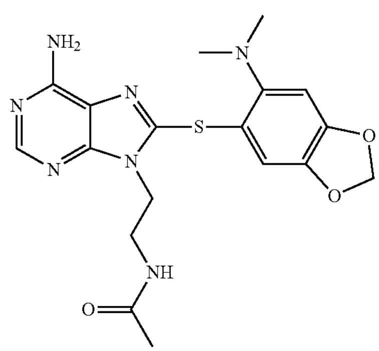 [SMILES: CC(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)acetamide |
| 1G-39 | 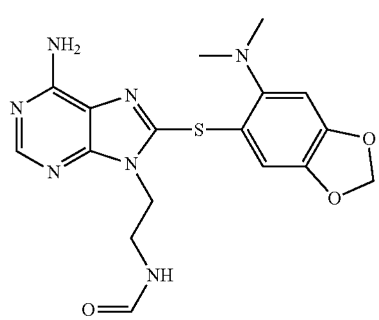 [SMILES: CN(C)c1cc2c(cc1Sc1nc3c(N)ncnc3n1CCNC=O)OCO2] | N-(2-(6-amino-8-((6-(dimethylamino)benzo[d][1,3]dioxol-5-yl)thio)-9H-purin-9-yl)ethyl)formamide |

TABLE 1G-continued

| Compound No. | Structure | Name |
|---|---|---|
| 1G-40 | 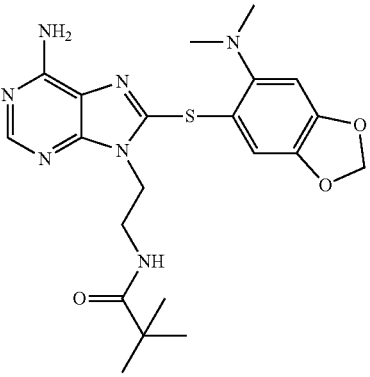 [SMILES: CN(C)c1cc2c(cc1Sc1nc3c(N)ncnc3n1CCNC(=O)C(C)(C)C)OCO2] | N-(2-(6-amino-8-((6-(dimethylamino)benzo[d][1,3]dioxol-5-yl)thio)-9H-purin-9-yl)ethyl)pivalamide |
| 1G-41 | 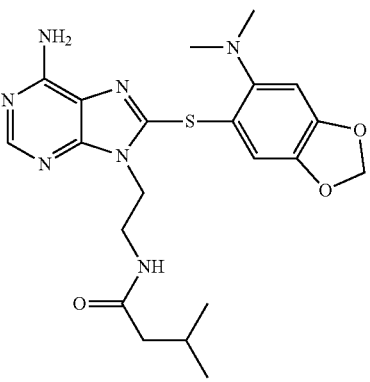 [SMILES: CC(C)CC(=O)NCCn1c(Sc2cc3c(cc2N(C)C)OCO3)nc2c(N)ncnc21] | N-(2-(6-amino-8-((6-(dimethylamino)benzo[d][1,3]dioxol-5-yl)thio)-9H-purin-9-yl)ethyl)-3-methylbutanamide |
| 1G-42 | 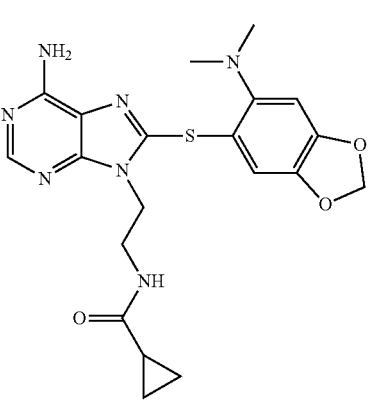 [SMILES: CN(C)c1cc2c(cc1Sc1nc3c(N)ncnc3n1CCNC(=O)C1CC1)OCO2] | N-(2-(6-amino-8-((6-(dimethylamino)benzo[d][1,3]dioxol-5-yl)thio)-9H-purin-9-yl)ethyl)cyclopropane-carboxamide |
| 1G-43 | 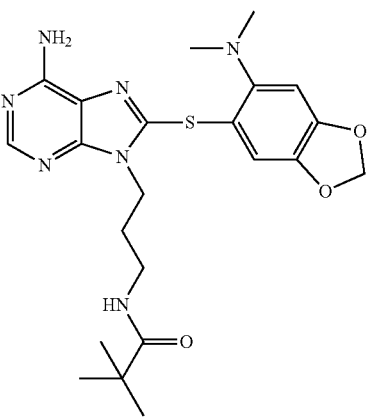 [SMILES: CN(C)c1cc2c(cc1Sc1nc3c(N)ncnc3n1CCCNC(=O)C(C)(C)C)OCO2] | N-{3-[6-Amino-8-(6-dimethylamino-benzo[1,3]dioxol-5-ylsulfanyl)-purin-9-yl]-propyl}-2,2-dimethyl-propionamide |

TABLE 1G-continued
| Compound No. | Structure | Name |
|---|---|---|
| 1G-44 | 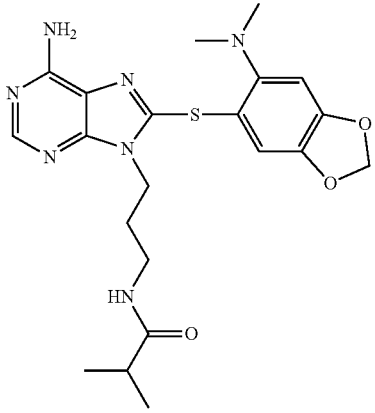 [SMILES: CC(C)C(=O)NCCCn1c(Sc2cc3c(cc2N(C)C)OCO3)nc2c(N)ncnc21] | N-{3-[6-Amino-8-(6-dimethylamino-benzo[1,3]dioxol-5-ylsulfanyl)-purin-9-yl]-propyl}-isobutyramide |
| 1G-45 | 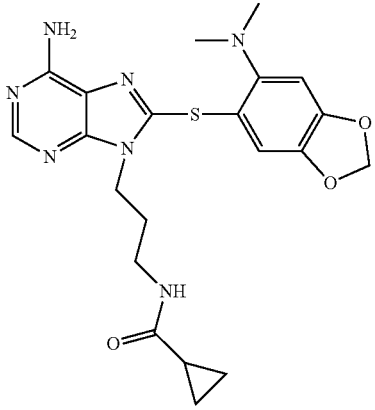 [SMILES: CN(C)c1cc2c(cc1Sc1nc3c(N)ncnc3n1CCCNC(=O)C1CC1)OCO2] | Cyclopropanecarboxylic acid {3-[6-amino-8-(6-dimethylamino-benzo[1,3]dioxol-5-ylsulfanyl)-purin-9-yl]-propyl}-amide |
| 1G-46 | 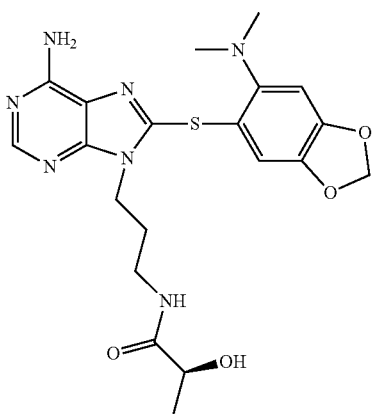 [SMILES: C[C@H](O)C(=O)NCCCn1c(Sc2cc3c(cc2N(C)C)OCO3)nc2c(N)ncnc21] | N-{3-[6-Amino-8-(6-dimethylamino-benzo[1,3]dioxol-5-ylsulfanyl)-purin-9-yl]-propyl}-2-hydroxy-propionamide |

TABLE 1G-continued

| Compound No. | Structure | Name |
|---|---|---|
| 1G-47 | 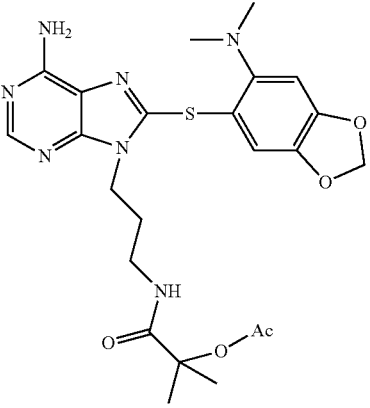 [SMILES: CC(=O)OC(C)(C)C(=O)NCCCn1c(Sc2cc3c(cc2N(C)C)OCO3)nc2c(N)ncnc21] | Acetic acid 1-{3-[6-amino-8-(6-dimethylamino-benzo[1,3]dioxol-5-ylsulfanyl)-purin-9-yl]-propylcarbamoyl}-1-methyl-ethyl ester |
| 1G-48 | 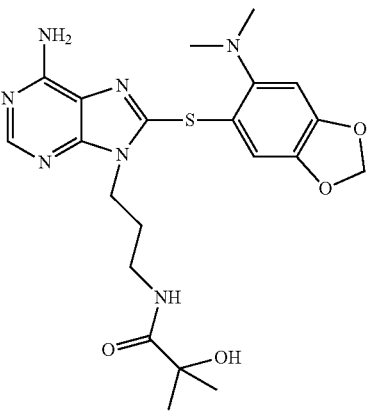 [SMILES: CN(C)c1cc2c(cc1Sc1nc3c(N)ncnc3n1CCCNC(=O)C(C)(C)O)OCO2] | N-{3-[6-Amino-8-(6-dimethylamino-benzo[1,3]dioxol-5-ylsulfanyl)-purin-9-yl]-propyl}-2-hydroxy-2-methyl-propionamide |
| 1G-49 | 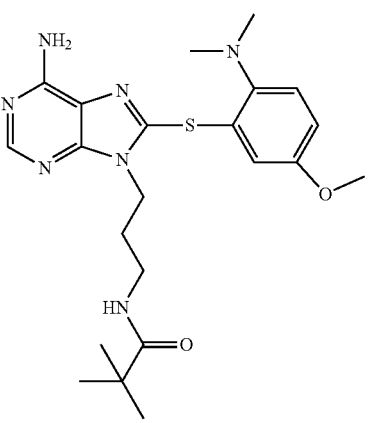 [SMILES: COc1ccc(N(C)C)c(Sc2nc3c(N)ncnc3n2CCCNC(=O)C(C)(C)C)c1] | N-(3-(6-Amino-8-((2-(dimethylamino)-5-methoxyphnyl)thio)-9H-purin-9-yl)propyl)pivalamide |

Hsp90 binding results are presented for Compounds 1G-28, 1G-43, and 1G-45 in Table 12 below. As can be noted therefrom, all compounds showed a high level of binding affinity.

D. COMPOUNDS OF FORMULA (IA) IN WHICH XA OR XB IS O

In accordance with another embodiment of the disclosure, the compounds are of Formula (IA) in which one of Xa and Xb is O and Xc and the other of Xa and Xb is CH$_2$. Thus, the compounds of this embodiment can be represented by Formula (2):

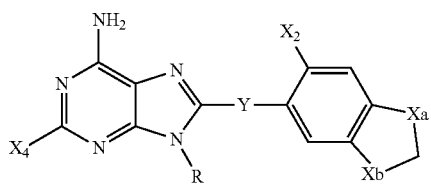

(2)

or a pharmaceutically acceptable salt thereof, wherein:
one of Xa and Xb is O and the other is CH$_2$;
Y is CH$_2$ or S;
X$_4$ is hydrogen or halogen;

R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_A$S(O)—, —$SO_2$N($R_A$)—, —$NR_A SO_2$—, —C(O)N($R_A$)—, or —$NR_A$C(O)—, and/or terminated by —S(O)$NR_A R_B$, —$NR_A$S(O)$R_B$, —$SO_2 NR_A R_B$, —$NR_A SO_2 R_B$, —C(O)$NR_A R_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and $X_2$ is as disclosed below.

D-I. In some embodiments of the disclosure, $X_2$ is halogen. Table 2A lists specific examples of compounds within this embodiment. In each of the structures as drawn, $X_2$ is I and $X_4$ is H. However, corresponding structures in which $X_2$ is F, Cl, or Br are within the scope of the disclosure. In each of the structures in Table 2A, Y is S. However, corresponding structures in which Y is $CH_2$ and/or $X_4$ is F, Cl, Br, or I are also within the scope of the disclosure. Additionally, in connection with each of the structures in Table 2A, corresponding structures in which $X_2$ is F, Cl, or Br and Y is $CH_2$ are also within the scope of the disclosure,

TABLE 2A

| Compound No. | Structure | Name |
|---|---|---|
| 2A-1 | 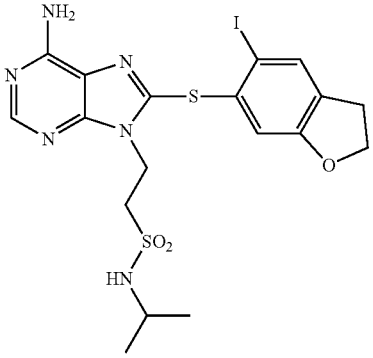 [SMILES: CC(C)NS(=O)(=O)CCn1c(Sc2cc3c(cc2I)CCO3)nc2c(N)ncnc21] | 2-[6-Amino-8-(5-iodo-2,3-dihydro-benzofuran-6-ylsulfanyl)-purin-9-yl]-ethanesulfonic acid isopropylamide |
| 2A-2 | 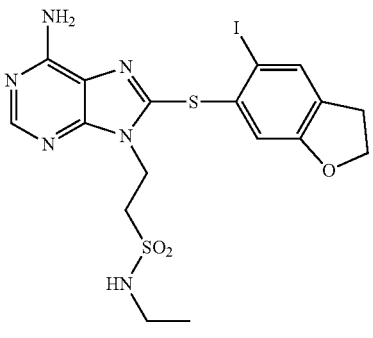 [SMILES: CCNS(=O)(=O)CCn1c(Sc2cc3c(cc2I)CCO3)nc2c(N)ncnc21] | 2-[6-Amino-8-(5-iodo-2,3-dihydro-benzofuran-6-ylsulfanyl)-purin-9-yl]-ethanesulfonic acid ethylamide |
| 2A-3 | 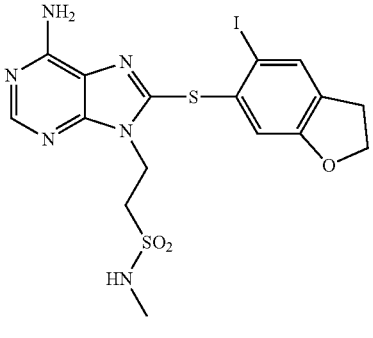 [SMILES: CNS(=O)(=O)CCn1c(Sc2cc3c(cc2I)CCO3)nc2c(N)ncnc21] | 2-[6-Amino-8-(5-iodo-2,3-dihydro-benzofuran-6-ylsulfanyl)-purin-9-yl]-ethanesulfonic acid methylamide |

TABLE 2A-continued

| Compound No. | Structure | Name |
|---|---|---|
| 2A-4 | 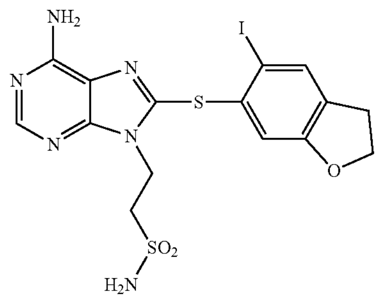 [SMILES: Nc1ncnc2c1nc(Sc1cc3c(cc1I)CCO3)n2CCS(N)(=O)=O] | 2-[6-Amino-8-(5-iodo-2,3-dihydro-benzofuran-6-ylsulfanyl)-purin-9-yl]-ethanesulfonic acid amide |
| 2A-5 | 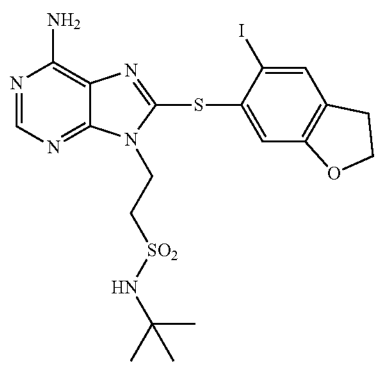 [SMILES: CC(C)(C)NS(=O)(=O)CCn1c(Sc2cc3c(cc2I)CCO3)nc2c(N)ncnc21] | 2-[6-Amino-8-(5-iodo-2,3-dihydro-benzofuran-6-ylsulfanyl)-purin-9-yl]-ethanesulfonic acid tert-butylamide |
| 2A-6 | 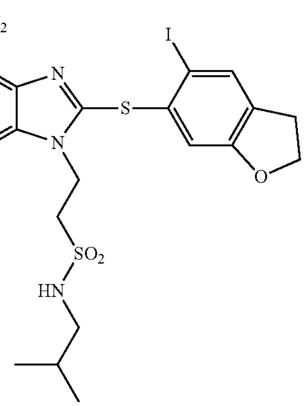 | 2-[6-Amino-8-(5-iodo-2,3-dihydro-benzofuran-6-ylsulfanyl)-purin-9-yl]-ethanesulfonic acid isobutyl-amide |
| 2A-7 | 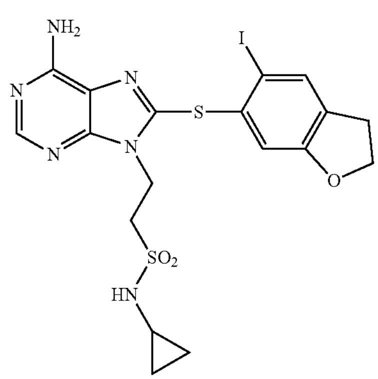 [SMILES: Nc1ncnc2c1nc(Sc1cc3c(cc1I)CCO3)n2CCS(=O)(=O)NC1CC1] | 2-[6-Amino-8-(5-iodo-2,3-dihydro-benzofuran-6-ylsulfanyl)-purin-9-yl]-ethanesulfonic acid cyclopropylamide |

TABLE 2A-continued

| Compound No. | Structure | Name |
|---|---|---|
| 2A-8 | 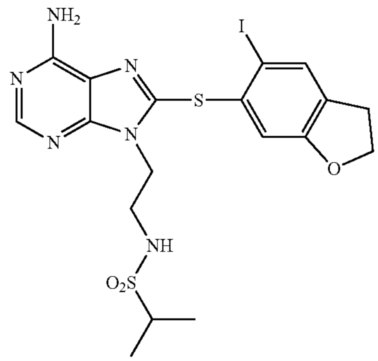 [SMILES: CC(C)S(=O)(=O)NCCn1c(Sc2cc3c(cc2I)CCO3)nc2c(N)ncnc21] | Propane-2-sulfonic acid {2-[6-amino-8-(5-iodo-2,3-dihydro-benzofuran-6-ylsulfanyl)-purin-9-yl]-ethyl}-amide |
| 2A-9 | 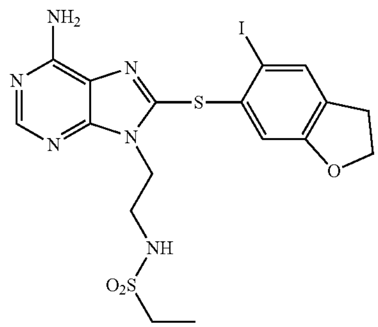 [SMILES: CCS(=O)(=O)NCCn1c(Sc2cc3c(cc2I)CCO3)nc2c(N)ncnc21] | Ethanesulfonic acid {2-[6-amino-8-(5-iodo-2,3-dihydro-benzofuran-6-ylsulfanyl)-purin-9-yl]-ethyl}-amide |
| 2A-10 | 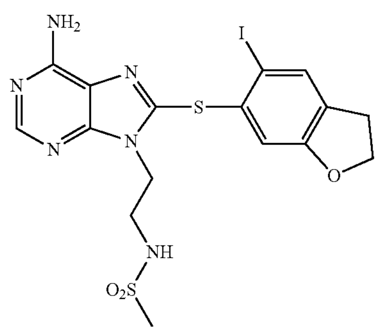 [SMILES: CS(=O)(=O)NCCn1c(Sc2cc3c(cc2I)CCO3)nc2c(N)ncnc21] | N-(2-(6-Amino-8-(5-iodo-2,3-dihydro-benzofuran-6-ylsulfanyl)-purin-9-yl)-ethyl)-methanesulfonamide |
| 2A-11 | 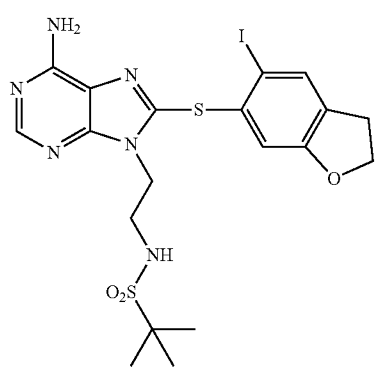 [SMILES: CC(C)(C)S(=O)(=O)NCCn1c(Sc2cc3c(cc2I)CCO3)nc2c(N)ncnc21] | 2-Methyl-propane-2-sulfonic acid {2-[6-amino-8-(5-iodo-2,3-dihydro-benzofuran-6-ylsulfanyl)-purin-9-yl]-ethyl}-amide |

TABLE 2A-continued

| Compound No. | Structure | Name |
|---|---|---|
| 2A-12 | 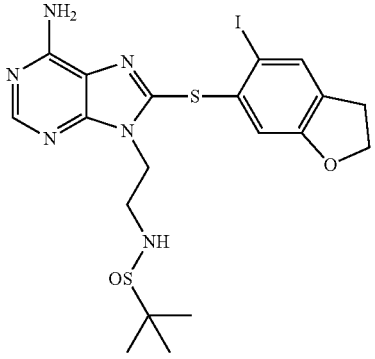 | 2-Methyl-propane-2-sulfinic acid {2-[6-amino-8-(5-iodo-2,3-dihydro-benzofuran-6-ylsulfanyl)-purin-9-yl]-ethyl}-amide |
| 2A-13 | 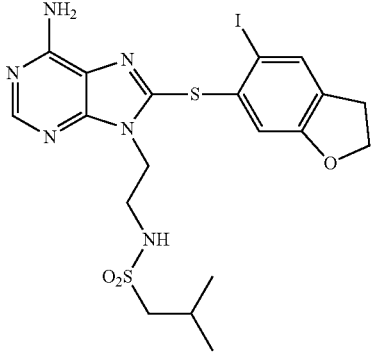 [SMILES: CC(C)CS(=O)(=O)NCCn1c(Sc2cc3c(cc2I)CCO3)nc2c(N)ncnc21] | 2-Methyl-propane-1-sulfonic acid {2-[6-amino-8-(5-iodo-2,3-dihydro-benzofuran-6-ylsulfanyl)-purin-9-yl]-ethyl}-amide |
| 2A-14 | 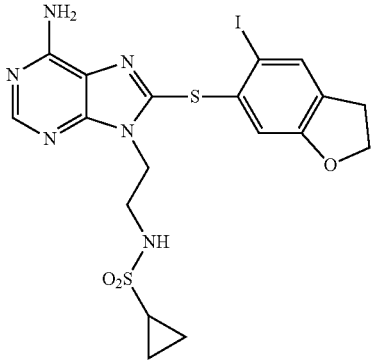 [SMILES: Nc1ncnc2c1nc(Sc1cc3c(cc1I)CCO3)n2CCNS(=O)(=O)C1CC1] | Cyclopropanesulfonic acid {2-[6-amino-8-(5-iodo-2,3-dihydro-benzofuran-6-ylsulfanyl)-purin-9-yl]-ethyl}-amide |
| 2A-15 | 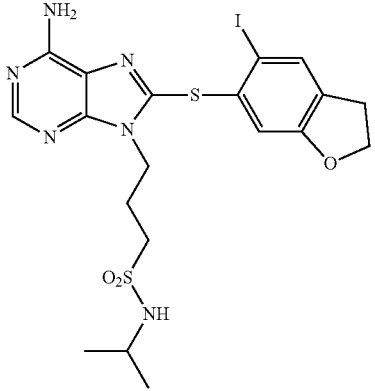 | 3-[6-Amino-8-(5-iodo-2,3-dihydro-benzofuran-6-ylsulfanyl)-purin-9-yl]-propane-1-sulfonic acid isopropylamide |

TABLE 2A-continued

| Compound No. | Structure | Name |
| --- | --- | --- |
| 2A-16 | 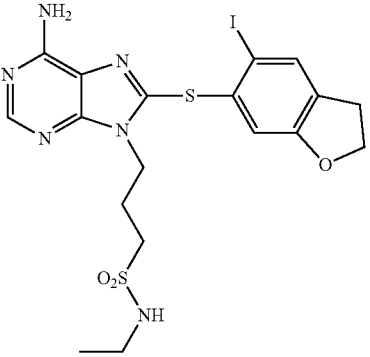 [SMILES: CCNS(=O)(=O)CCCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-propane-1-sulfonic acid ethylamide |
| 2A-17 | 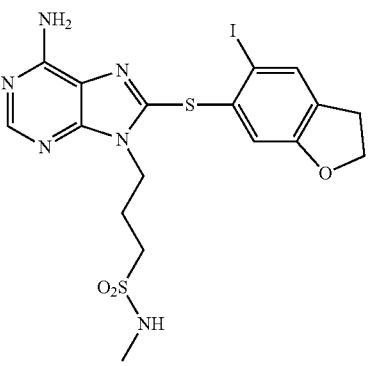 | 3-[6-Amino-8-(5-iodo-2,3-dihydro-benzofuran-6-ylsulfanyl)-purin-9-yl]-propane-1-sulfonic acid methylamide |
| 2A-18 | 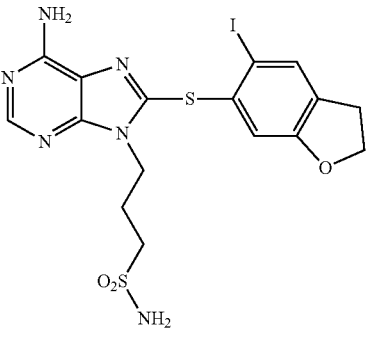 | 3-[6-Amino-8-(5-iodo-2,3-dihydro-benzofuran-6-ylsulfanyl)-purin-9-yl]-propane-1-sulfonic acid amide |
| 2A-19 | 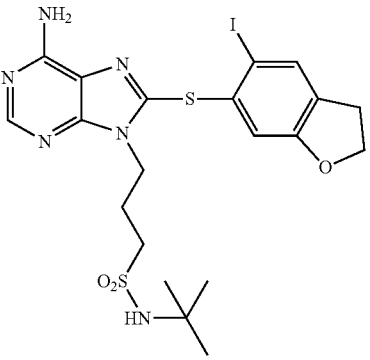 [SMILES: CC(C)(C)NS(=O)(=O)CCCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-propane-1-sulfonic acid tert-butylamide |

TABLE 2A-continued

| Compound No. | Structure | Name |
| --- | --- | --- |
| 2A-20 | 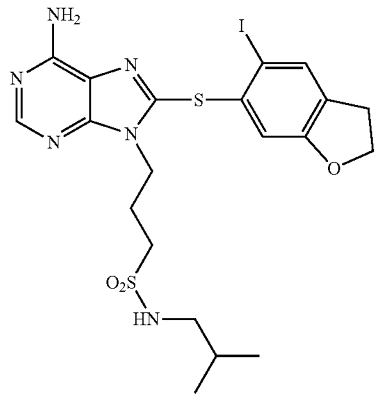 [SMILES: CC(C)CNS(=O)(=O)CCCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-propane-1-sulfonic acid isobutyl-amide |
| 2A-21 | 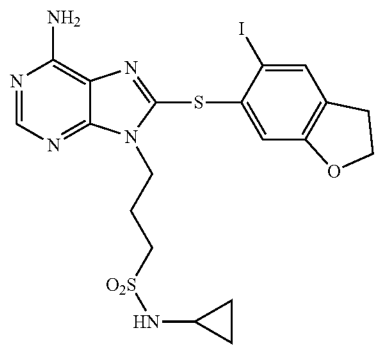 [SMILES: Nc1ncnc2c1nc(Sc1cc3c(cc1I)CCO3)n2CCCS(=O)(=O)NC1CC1] | 3-[6-Amino-8-(5-iodo-2,3-dihydro-benzofuran-6-ylsulfanyl)-purin-9-yl]-propane-1-sulfonic acid cyclopropylamide |
| 2A-22 | 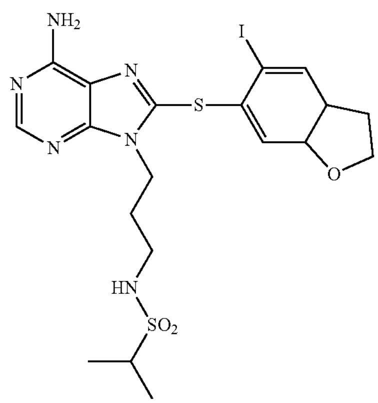 | Propane-2-sulfonic acid {3-[6-amino-8-(5-iodo-2,3,3a,7a-tetrahydro-benzofuran-6-ylsulfanyl)-purin-9-yl]-propyl}-amide |
| 2A-23 | 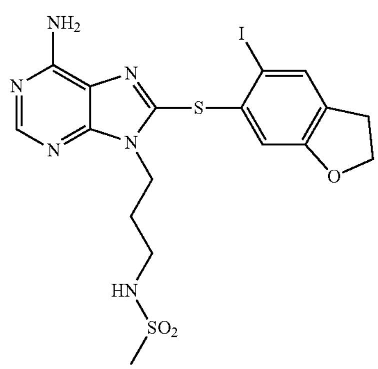 [SMILES: CS(=O)(=O)NCCCn1c(Sc2cc3c(cc2I)CCO3)nc2c(N)ncnc21] | Ethanesulfonic acid {3-[6-amino-8-(5-iodo-2,3-dihydro-benzofuran-6-ylsulfanyl)-purin-9-yl]-propyl}-amide |

TABLE 2A-continued

| Compound No. | Structure | Name |
|---|---|---|
| 2A-24 | 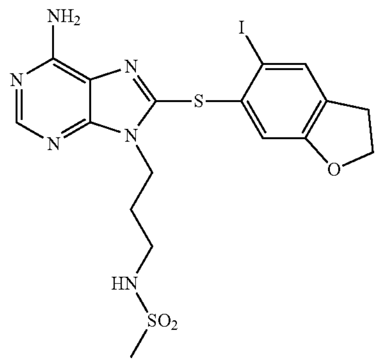 [SMILES: CS(=O)(=O)NCCCn1c(Sc2cc3c(cc2I)CCO3)nc2c(N)ncnc21] | N-{3-[6-Amino-8-(5-iodo-2,3-dihydro-benzofuran-6-ylsulfanyl)-purin-9-yl]-propyl}-methanesulfonamide |
| 2A-25 | 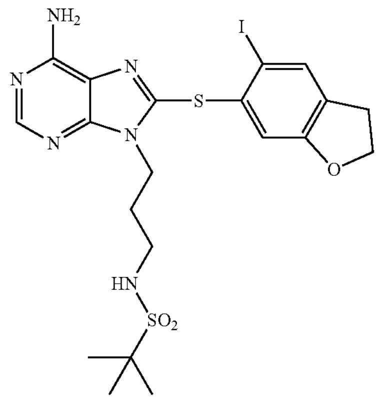 | 2-Methyl-propane-2-sulfonic acid {3-[6-amino-8-(5-iodo-2,3-dihydro-benzofuran-6-ylsulfanyl)-purin-9-yl]-propyl}-amide |
| 2A-26 | 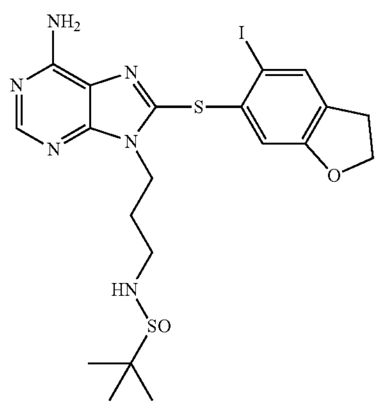 | 2-Methyl-propane-2-sulfinic acid {3-[6-amino-8-(5-iodo-2,3-dihydro-benzofuran-6-ylsulfanyl)-purin-9-yl]-propyl}-amide |
| 2A-27 | 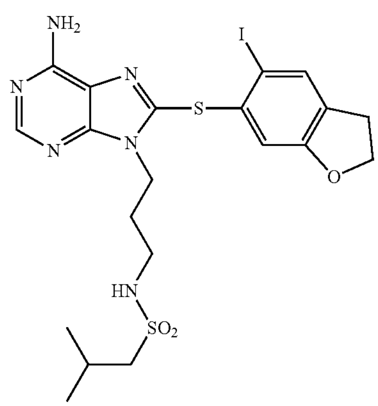 | 2-Methyl-propane-1-sulfonic acid {3-[6-amino-8-(5-iodo-2,3-dihydro-benzofuran-6-ylsulfanyl)-purin-9-yl]-propyl}-amide |

TABLE 2A-continued

| Compound No. | Structure | Name |
| --- | --- | --- |
| 2A-28 | 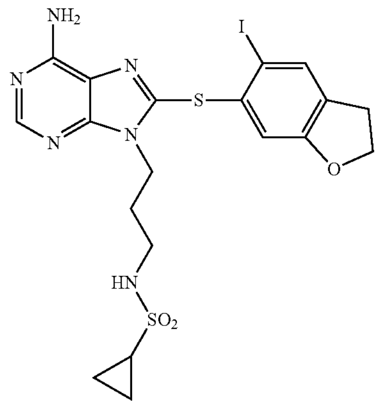 | Cyclopropanesulfonic acid {3-[6-amino-8-(5-iodo-2,3-dihydro-benzofuran-6-ylsulfanyl)-purin-9-yl]-propyl}-amide |
| 2A-29 | 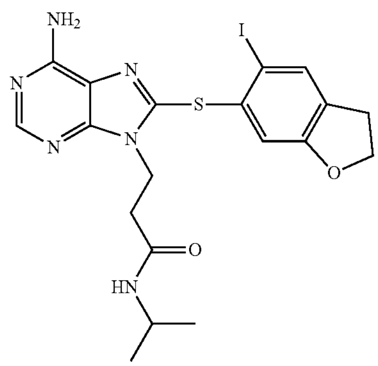 [SMILES: CC(C)NC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-N-isopropyl-propionamide |
| 2A-30 | 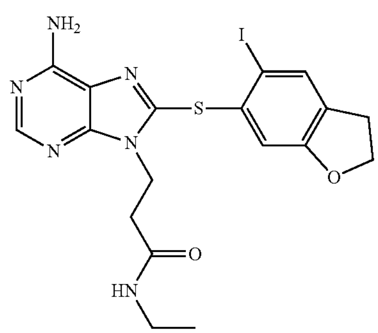 [SMILES: CCNC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-N-ethyl-propionamide |
| 2A-31 | 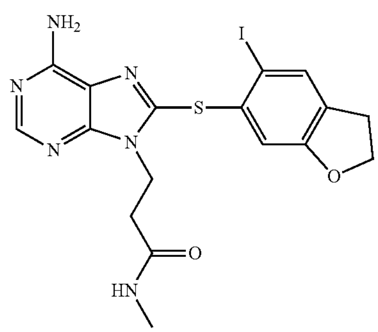 [SMILES: CNC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-N-methyl-propionamide |

TABLE 2A-continued

| Compound No. | Structure | Name |
|---|---|---|
| 2A-32 | 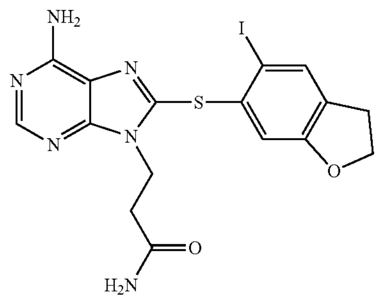 [SMILES: NC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-propionamide |
| 2A-33 | 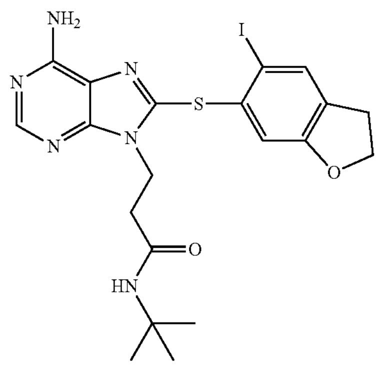 [SMILES: CC(C)(C)NC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-N-tert-butyl-propionamide |
| 2A-34 | 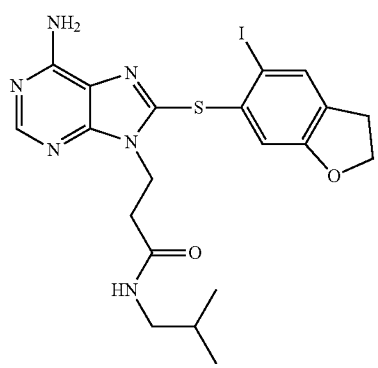 [SMILES: CC(C)CNC(=O)CCn1c(Sc2cc3c(cc2I)CCO3)nc2c(N)ncnc21] | 3-[6-Amino-8-(5-iodo-2,3-dihydro-benzofuran-6-ylsulfanyl)-purin-9-yl]-N-isobutyl-propionamide |
| 2A-35 | 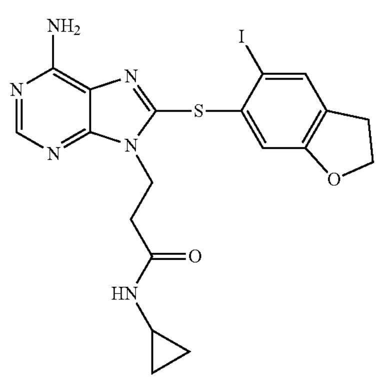 [SMILES: Nc1ncnc2c1nc(Sc1cc3c(cc1I)CCO3)n2CCC(=O)NC1CC1] | 3-[6-Amino-8-(5-iodo-2,3-dihydro-benzofuran-6-ylsulfanyl)-purin-9-yl]-N-cyclopropyl-propionamide |

TABLE 2A-continued

| Compound No. | Structure | Name |
| --- | --- | --- |
| 2A-36 | 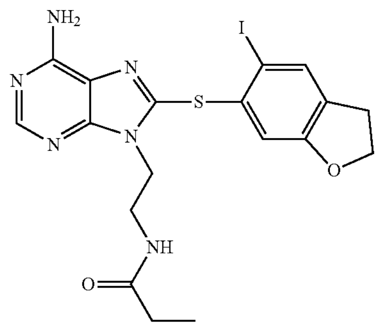 [SMILES: CCC(=O)NCCn1c(Sc2cc3c(cc2I)CCO3)nc2c(N)ncnc21] | N-{2-[6-Amino-8-(5-iodo-2,3-dihydro-benzofuran-6-ylsulfanyl)-purin-9-yl]-ethyl}-propionamide |
| 2A-37 | 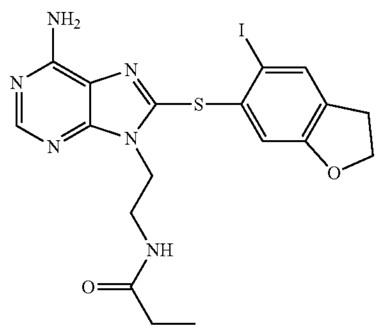 [SMILES: CCC(=O)NCCn1c(Sc2cc3c(cc2I)CCO3)nc2c(N)ncnc21] | N-{2-[6-Amino-8-(5-iodo-2,3-dihydro-benzofuran-6-ylsulfanyl)-purin-9-yl]-ethyl}-propionamide |
| 2A-38 | 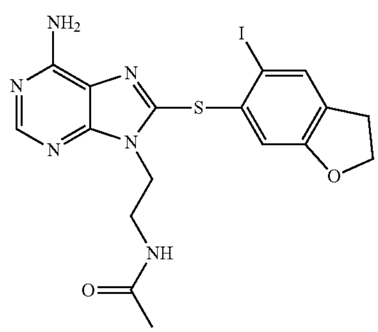 [SMILES: CC(=O)NCCn1c(Sc2cc3c(cc2I)CCO3)nc2c(N)ncnc21] | N-{2-[6-Amino-8-(5-iodo-2,3-dihydro-benzofuran-6-ylsulfanyl)-purin-9-yl]-ethyl}-acetamide |
| 2A-39 | 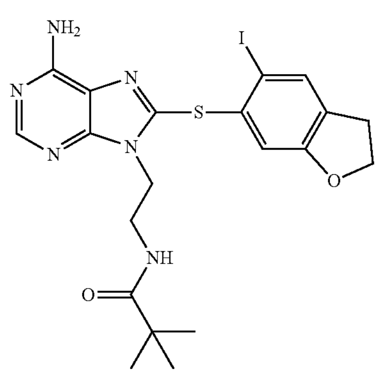 [SMILES: CC(C)(C)C(=O)NCCn1c(Sc2cc3c(cc2I)CCO3)nc2c(N)ncnc21] | N-{2-[6-Amino-8-(5-iodo-2,3-dihydro-benzofuran-6-ylsulfanyl)-purin-9-yl]-ethyl}-2,2-dimethyl-propionamide |

TABLE 2A-continued

| Compound No. | Structure | Name |
|---|---|---|
| 2A-40 | 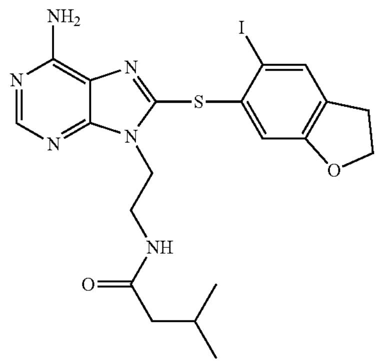 [SMILES: CC(C)CC(=O)NCCn1c(Sc2cc3c(cc2I)CCO3)nc2c(N)ncnc21] | N-{2-[6-Amino-8-(5-iodo-2,3-dihydro-benzofuran-6-ylsulfanyl)-purin-9-yl]-ethyl}-3-methyl-butyramide |
| 2A-41 | 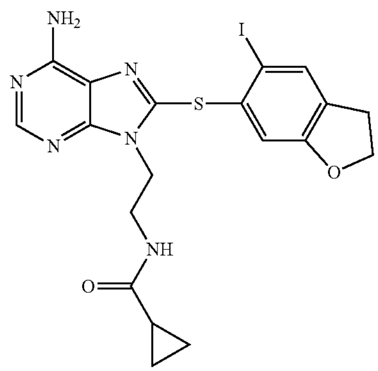 [SMILES: Nc1ncnc2c1nc(Sc1cc3c(cc1I)CCO3)n2CCNC(=O)C1CC1] | Cyclopropanecarboxylic acid {2-[6-amino-8-(5-iodo-2,3-dihydro-benzofuran-6-ylsulfanyl)-purin-9-yl]-ethyl}-amide |
| 2A-42 | 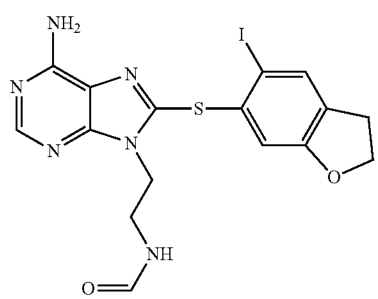 [SMILES: Nc1ncnc2c1nc(Sc1cc3c(cc1I)CCO3)n2CCNC=O] | N-{2-[6-Amino-8-(5-iodo-2,3-dihydro-benzofuran-6-ylsulfanyl)-purin-9-yl]-ethyl}-formamide |
| 2A-43 | 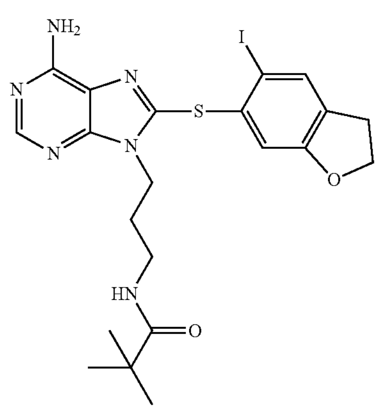 [SMILES: CC(C)(C)C(=O)NCCCn1c(Sc2cc3c(cc2I)CCO3)nc2c(N)ncnc21] | N-{3-[6-Amino-8-(5-iodo-2,3-dihydro-benzofuran-6-ylsulfanyl)-purin-9-yl]-propyl}-2,2-dimethyl-propionamide |

TABLE 2A-continued

| Compound No. | Structure | Name |
| --- | --- | --- |
| 2A-44 | 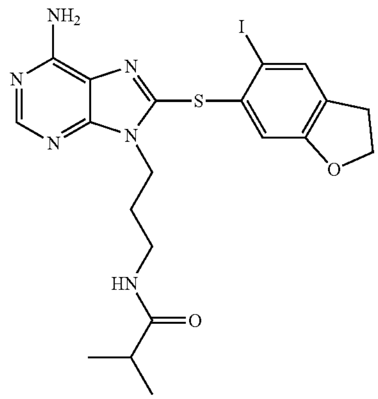 [SMILES: CC(C)C(=O)NCCCn1c(Sc2cc3c(cc2I)CCO3)nc2c(N)ncnc21] | N-{3-[6-Amino-8-(5-iodo-2,3-dihydro-benzofuran-6-ylsulfanyl)-purin-9-yl]-propyl}-isobutyramide |
| 2A-45 | 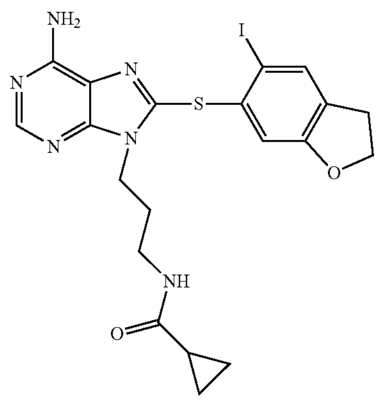 [SMILES: Nc1ncnc2c1nc(Sc1cc3c(cc1I)CCO3)n2CCCNC(=O)C1CC1] | Cyclopropanecarboxylic acid {3-[6-amino-8-(5-iodo-2,3-dihydro-benzofuran-6-ylsulfanyl)-purin-9-yl]-propyl}-amide |
| 2A-46 | 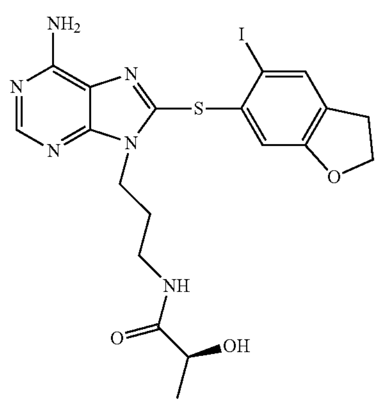 [SMILES: C[C@H](O)C(=O)NCCCn1c(Sc2cc3c(cc2I)CCO3)nc2c(N)ncnc21] | N-{3-[6-Amino-8-(5-iodo-2,3-dihydro-benzofuran-6-ylsulfanyl)-purin-9-yl]-propyl}-2-hydroxy-propionamide |
| 2A-47 | 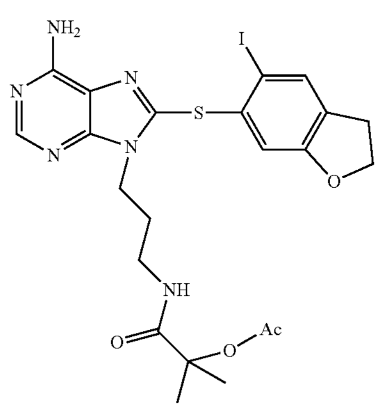 [SMILES: CC(=O)OC(C)(C)C(=O)NCCCn1c(Sc2cc3c(cc2I)CCO3)nc2c(N)ncnc21] | Acetic acid 1-{3-[6-amino-8-(5-iodo-2,3-dihydro-benzofuran-6-ylsulfanyl)-purin-9-yl]-propylcarbamoyl}-1-methyl-ethyl ester |

TABLE 2A-continued

| Compound No. | Structure | Name |
|---|---|---|
| 2A-48 | 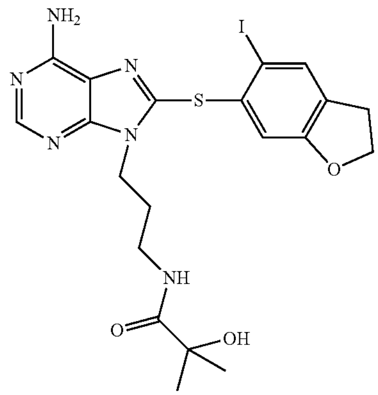 [SMILES: CC(C)(O)C(=O)NCCCn1c(Sc2cc3c(cc2I)CCO3)nc2c(N)ncnc21] | N-{3-[6-Amino-8-(5-iodo-2,3-dihydro-benzofuran-6-ylsulfanyl)-purin-9-yl]-propyl}-2-hydroxy-2-methyl-propionamide |

Table 5A lists specific examples in which $X_2$ is halogen and $X_4$ is halogen. In each of the structures as drawn, $X_2$ is I and $X_4$ is F. However, corresponding structures in which $X_4$ is H, Cl, Br, or I are within the scope of the disclosure. In each of the structures in Table 5A, Y is $CH_2$. However, corresponding structures in which Y is S and/or $X_2$ is F, Cl, or Br are also within the scope of the disclosure. Additionally, in connection with each of the structures in Table 5A, corresponding structures in which $X_4$ is H, Cl, Br, or I and Y is S are also within the scope of the disclosure.

TABLE 5A

| Compound No. | Structure | Name |
|---|---|---|
| 5A-1 | 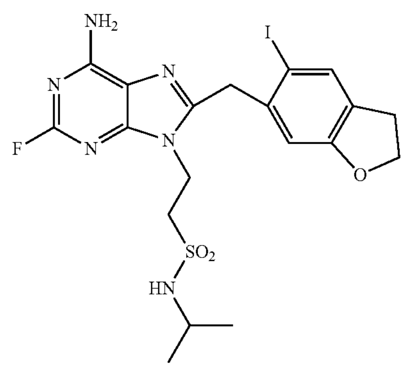 | 2-(6-amino-2-fluoro-8-((5-iodo-2,3-dihydrobenzofuran-6-yl)methyl)-9H-purin-9-yl)-N-isopropyl-ethanesulfonamide |
| 5A-2 | 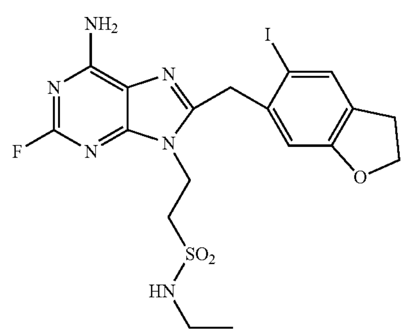 [SMILES: CCNS(=O)(=O)CCn1c(Cc2cc3c(cc2I)CCO3)nc2c(N)nc(F)nc21] | 2-(6-amino-2-fluoro-8-((5-iodo-2,3-dihydrobenzofuran-6-yl)methyl)-9H-purin-9-yl)-N-ethylethanesulfonamide |

TABLE 5A-continued

| Compound No. | Structure | Name |
| --- | --- | --- |
| 5A-3 | 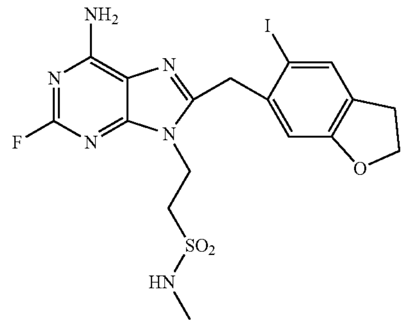 [SMILES: CNS(=O)(=O)CCn1c(Cc2cc3c(cc2I)CCO3)nc2c(N)nc(F)nc21] | 2-(6-amino-2-fluoro-8-((5-iodo-2,3-dihydrobenzofuran-6-yl)methyl)-9H-purin-9-yl)-N-methylethanesulfonamide |
| 5A-4 | 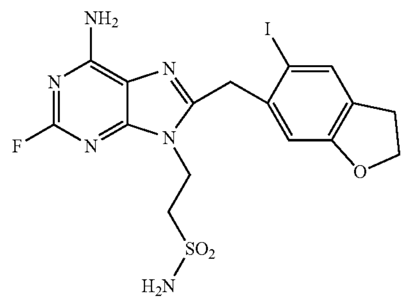 | 2-(6-amino-2-fluoro-8-((5-iodo-2,3-dihydrobenzofuran-6-yl)methyl)-9H-purin-9-yl)sulfonamide |
| 5A-5 | 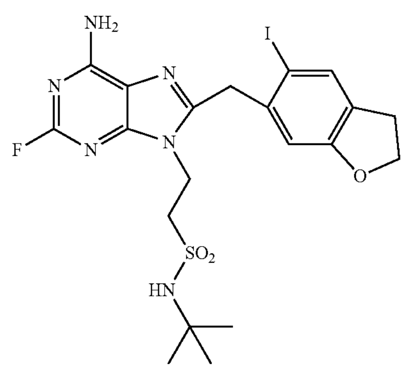 | 2-(6-amino-2-fluoro-8-((5-iodo-2,3-dihydrobenzofuran-6-yl)methyl)-9H-purin-9-yl)-N-(tert-butyl)ethanesulfonamide |
| 5A-6 | 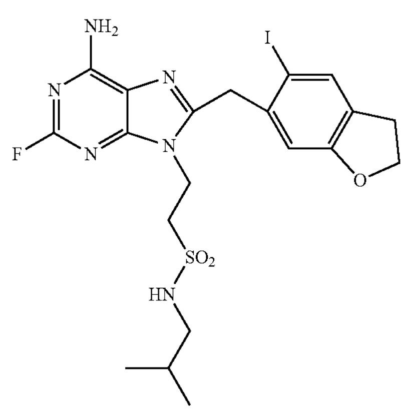 [SMILES: CC(C)CNS(=O)(=O)CCn1c(Cc2cc3c(cc2I)CCO3)nc2c(N)nc(F)nc21] | 2-(6-amino-2-fluoro-8-((5-iodo-2,3-dihydrobenzofuran-6-yl)methyl)-9H-purin-9-yl)-N-isobutylethanesulfonamide |

TABLE 5A-continued

| Compound No. | Structure | Name |
|---|---|---|
| 5A-7 | 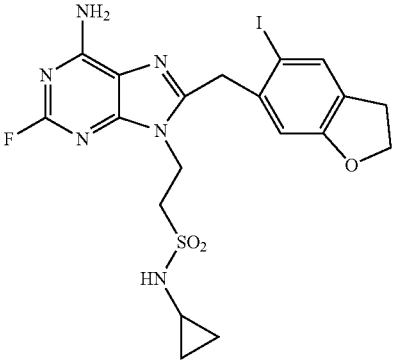 | 2-(6-amino-2-fluoro-8-((5-iodo-2,3-dihydrobenzofuran-6-yl)methyl)-9H-purin-9-yl)-N-cyclopropyl-ethanesulfonamide |
| 5A-8 | 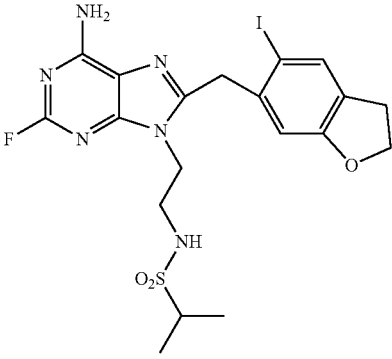 | N-(2-(6-amino-2-fluoro-8-((5-iodo-2,3-dihydrobenzofuran-6-yl)methyl)-9H-purin-9-yl)ethyl)propane-2-sulfonamide |
| 5A-9 | 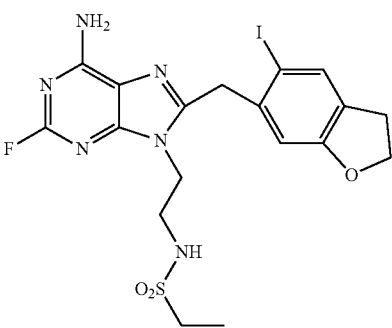 [SMILES: CCS(=O)(=O)NCCn1c(Cc2cc3c(cc2I)CCO3)nc2c(N)nc(F)nc21] | N-(2-(6-amino-2-fluoro-8-((5-iodo-2,3-dihydrobenzofuran-6-yl)methyl)-9H-purin-9-yl)ethyl)ethanesulfonamide |
| 5A-10 | 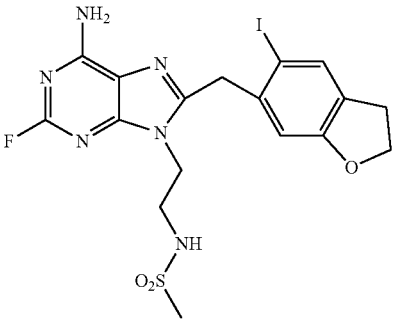 [SMILES: CS(=O)(=O)NCCn1c(Cc2cc3c(cc2I)CCO3)nc2c(N)nc(F)nc21] | N-(2-(6-amino-2-fluoro-8-((5-iodo-2,3-dihydrobenzofuran-6-yl)methyl)-9H-purin-9-yl)ethyl)methane-sulfonamide |

TABLE 5A-continued

| Compound No. | Structure | Name |
|---|---|---|
| 5A-11 | 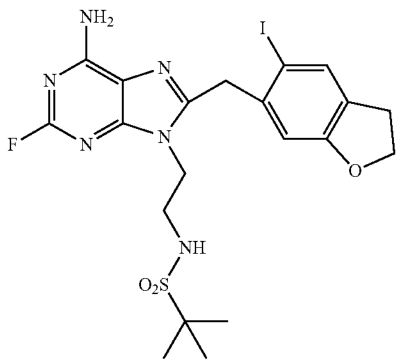 | N-(2-(6-amino-2-fluoro-8-((5-iodo-2,3-dihydrobenzofuran-6-yl)methyl)-9H-purin-9-yl)ethyl)-2-methylpropane-2-sulfonamide |
| 5A-12 | 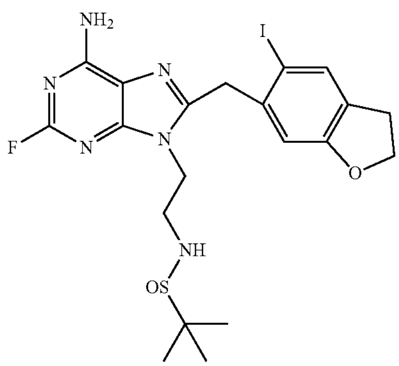 | N-(2-(6-amino-2-fluoro-8-((5-iodo-2,3-dihydrobenzofuran-6-yl)methyl)-9H-purin-9-yl)ethyl)-2-methylpropane-2-sulfonamide |
| 5A-13 | 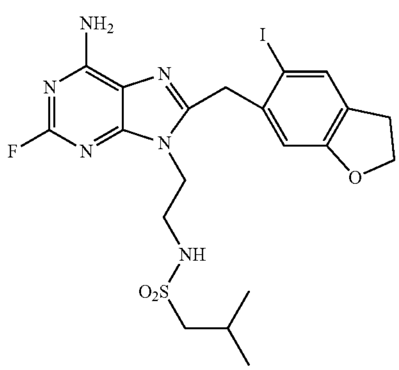 [SMILES: CC(C)CS(=O)(=O)NCCn1c(Cc2cc3c(cc2I)CCO3)nc2c(N)nc(F)nc21] | N-(2-(6-amino-2-fluoro-8-((5-iodo-2,3-dihydrobenzofuran-6-yl)methyl)-9H-purin-9-yl)ethyl)-2-methylpropane-1-sulfonamide |
| 5A-14 | 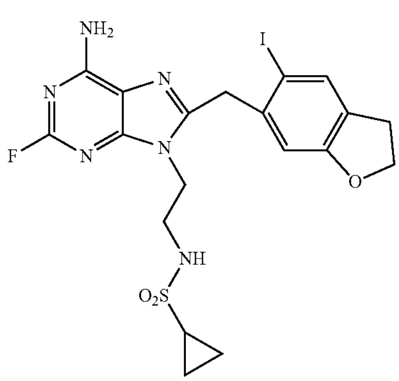 [SMILES: Nc1nc(F)nc2c1nc(Cc1cc3c(cc1I)CCO3)n2CCNS(=O)(=O)C1CC1] | N-(2-(6-amino-2-fluoro-8-((5-iodo-2,3-dihydrobenzofuran-6-yl)methyl)-9H-purin-9-yl)ethyl)cyclopropane-sulfonamide |

TABLE 5A-continued

| Compound No. | Structure | Name |
|---|---|---|
| 5A-15 | 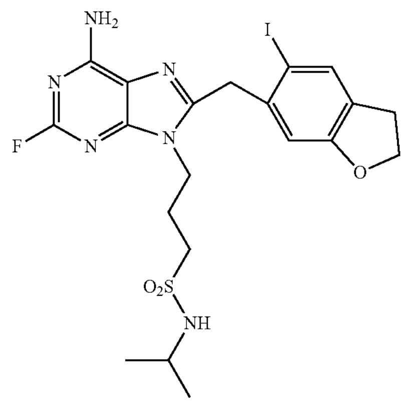 [SMILES: CC(C)NS(=O)(=O)CCCn1c(Cc2cc3c(cc2I)CCO3)nc2c(N)nc(F)nc21] | 3-(6-amino-2-fluoro-8-((5-iodo-2,3-dihydrobenzofuran-6-yl)methyl)-9H-purin-9-yl)-N-isopropylpropane-1-sulfonamide |
| 5A-16 | 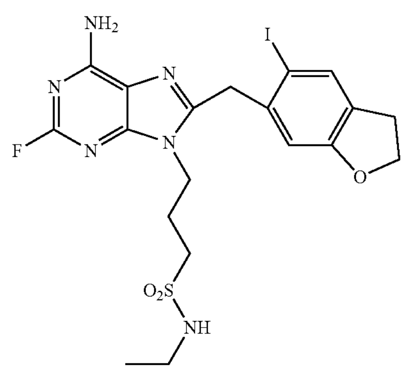 | 3-(6-amino-2-fluoro-8-((5-iodo-2,3-dihydrobenzofuran-6-yl)methyl)-9H-purin-9-yl)-N-ethylpropane-1-sulfonamide |
| 5A-17 | 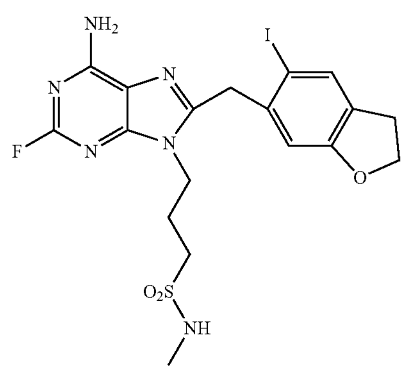 | 3-(6-amino-2-fluoro-8-((5-iodo-2,3-dihydrobenzofuran-6-yl)methyl)-9H-purin-9-yl)-N-methylpropane-1-sulfonamide |
| 5A-18 | 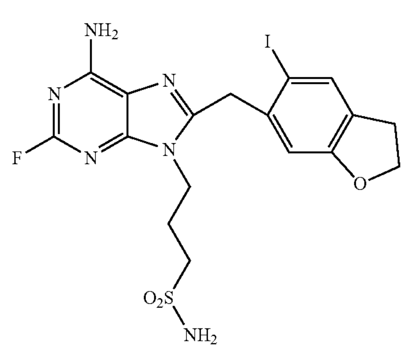 | 3-(6-amino-2-fluoro-8-((5-iodo-2,3-dihydrobenzofuran-6-yl)methyl)-9H-purin-9-yl)propane-1-sulfonamide |

TABLE 5A-continued

| Compound No. | Structure | Name |
|---|---|---|
| 5A-19 | 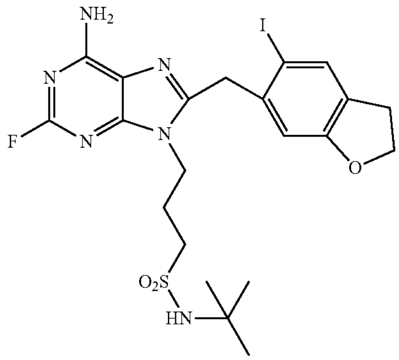 | 3-(6-amino-2-fluoro-8-((5-iodo-2,3-dihydrobenzofuran-6-yl)methyl)-9H-purin-9-yl)-N-(tert-butyl)propane-1-sulfonamide |
| 5A-20 | 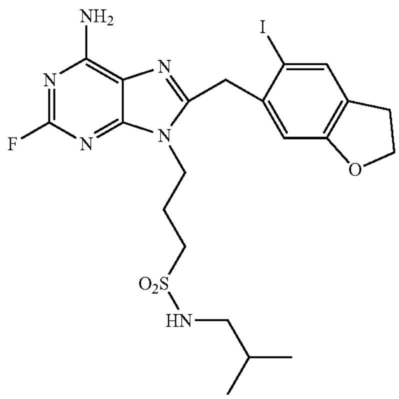 | 3-(6-amino-2-fluoro-8-((5-iodo-2,3-dihydrobenzofuran-6-yl)methyl)-9H-purin-9-yl)-N-cyclopropylpropane-1-sulfonamide |
| 5A-21 | 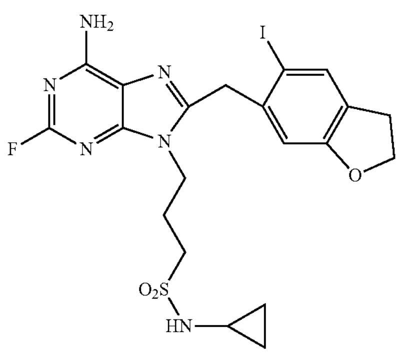 [SMILES: Nc1nc(F)nc2c1nc(Cc1cc3c(cc1I)CCO3)n2CCCS(=O)(=O)NC1CC1] | 3-(6-amino-2-fluoro-8-((5-iodo-2,3-dihydrobenzofuran-6-yl)methyl)-9H-purin-9-yl)-N-cyclopropylpropane-1-sulfonamide |
| 5A-22 | 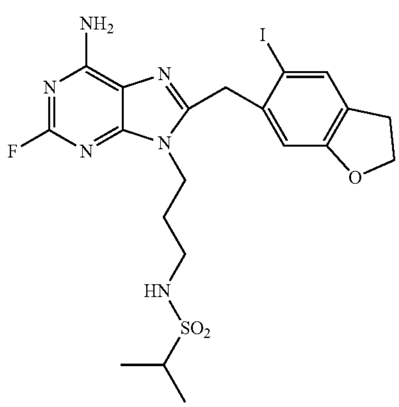 | N-(3-(6-amino-2-fluoro-8-((5-iodo-2,3-dihydrobenzofuran-6-yl)methyl)-9H-purin-9-yl)propyl)propane-2-sulfonamide |

TABLE 5A-continued

| Compound No. | Structure | Name |
|---|---|---|
| 5A-23 | 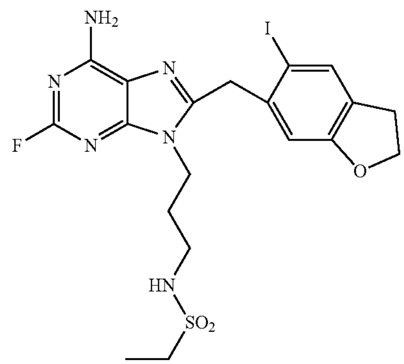 [SMILES: CCS(=O)(=O)NCCCn1c(Cc2cc3c(cc2I)CCO3)nc2c(N)nc(F)nc21] | N-(3-(6-amino-2-fluoro-8-((5-iodo-2,3-dihydrobenzofuran-6-yl)methyl)-9H-purin-9-yl)propyl)ethane-sulfonamide |
| 5A-24 | 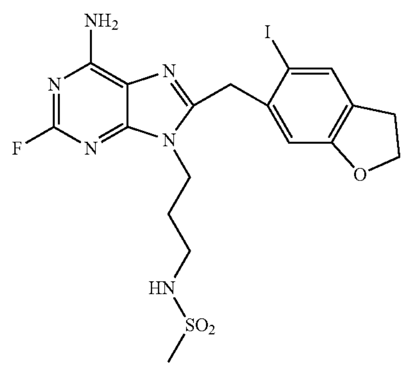 | N-(3-(6-amino-2-fluoro-8-((5-iodo-2,3-dihydrobenzofuran-6-yl)methyl)-9H-purin-9-yl)propyl)methane-sulfonamide |
| 5A-25 | 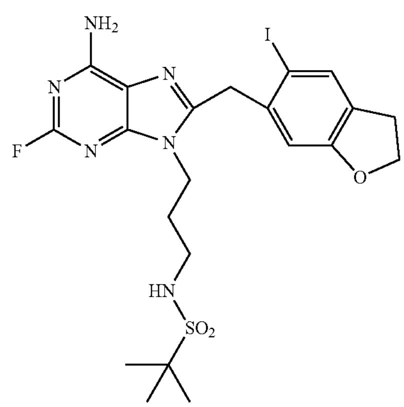 | N-(3-(6-amino-2-fluoro-8-((5-iodo-2,3-dihydrobenzofuran-6-yl)methyl)-9H-purin-9-yl)propyl)-2-methylpropane-2-sulfonamide |
| 5A-26 | 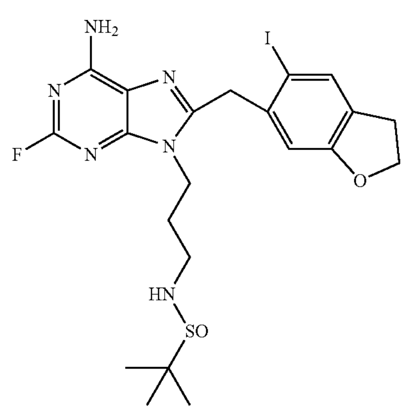 | N-(3-(6-amino-2-fluoro-8-((5-iodo-2,3-dihydrobenzofuran-6-yl)methyl)-9H-purin-9-yl)propyl)-2-methylpropane-2-sulfinamide |

TABLE 5A-continued

| Compound No. | Structure | Name |
|---|---|---|
| 5A-27 | 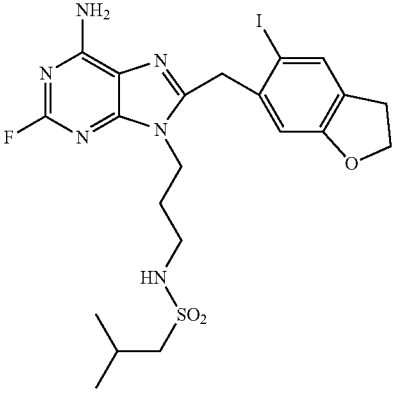 | N-(3-(6-amino-2-fluoro-8-((5-iodo-2,3-dihydrobenzofuran-6-yl)methyl)-9H-purin-9-yl)propyl)-2-methylpropane-1-sulfonamide |
| 5A-28 | 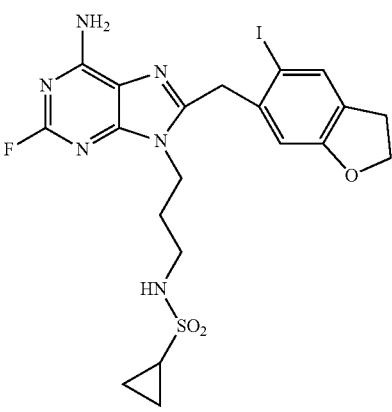 | N-(3-(6-amino-2-fluoro-8-((5-iodo-2,3-dihydrobenzofuran-6-yl)methyl)-9H-purin-9-yl)propyl)cyclopropanesulfonamide |
| 5A-29 | 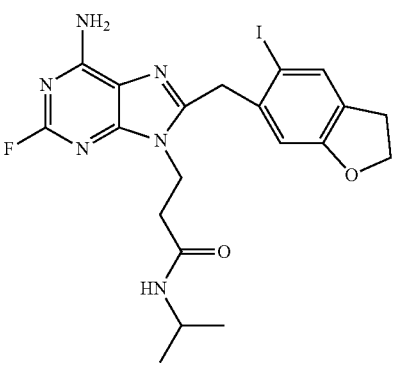 [SMILES: CC(C)NC(=O)CCn1c(Cc2cc3c(cc2I)CCO3)nc2c(N)nc(F)nc21] | 3-(6-amino-2-fluoro-8-((5-iodo-2,3-dihydrobenzofuran-6-yl)methyl)-9H-purin-9-yl)-N-isopropylpropanamide |
| 5A-30 | 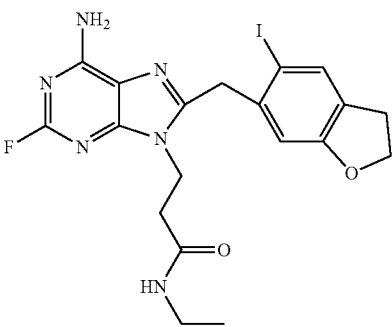 | 3-(6-amino-2-fluoro-8-((5-iodo-2,3-dihydrobenzofuran-6-yl)methyl)-9H-purin-9-yl)-N-ethylpropanamide |

TABLE 5A-continued

| Compound No. | Structure | Name |
|---|---|---|
| 5A-31 | 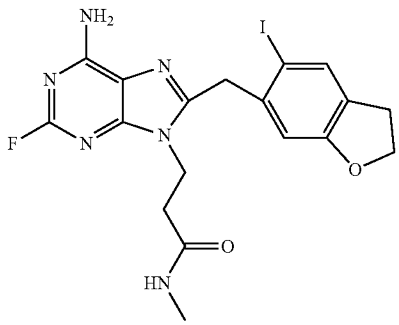 [SMILES: CNC(=O)CCn1c(Cc2cc3c(cc2I)CCO3)nc2c(N)nc(F)nc21] | 3-(6-amino-2-fluoro-8-((5-iodo-2,3-dihydrobenzofuran-6-yl)methyl)-9H-purin-9-yl)-N-methylpropanamide |
| 5A-32 | 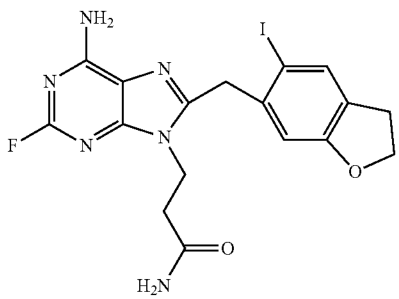 [SMILES: NC(=O)CCn1c(Cc2cc3c(cc2I)CCO3)nc2c(N)nc(F)nc21] | 3-(6-amino-2-fluoro-8-((5-iodo-2,3-dihydrobenzofuran-6-yl)methyl)-9H-purin-9-yl)propanamide |
| 5A-33 | 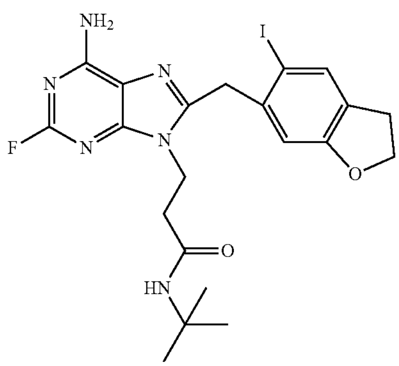 | 3-(6-amino-2-fluoro-8-((5-iodo-2,3-dihydrobenzofuran-6-yl)methyl)-9H-purin-9-yl)-N-(tert-butyl)propanamide |
| 5A-34 | 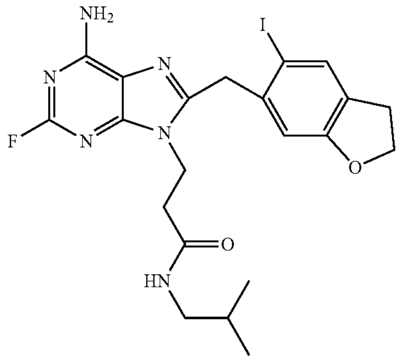 [SMILES: CC(C)CNC(=O)CCn1c(Cc2cc3c(cc2I)CCO3)nc2c(N)nc(F)nc21] | 3-(6-amino-2-fluoro-8-((5-iodo-2,3-dihydrobenzofuran-6-yl)methyl)-9H-purin-9-yl)-N-isobutylpropanamide |

TABLE 5A-continued

| Compound No. | Structure | Name |
|---|---|---|
| 5A-35 | 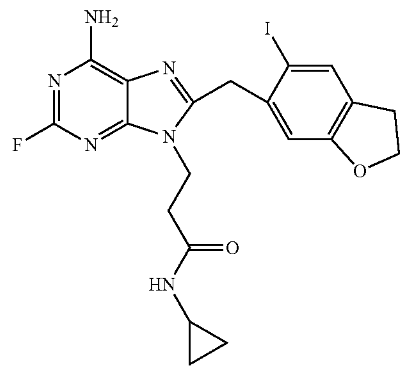 [SMILES: Nc1nc(F)nc2c1nc(Cc1cc3c(cc1I)CCO3)n2CCC(=O)NC1CC1] | 3-(6-amino-2-fluoro-8-((5-iodo-2,3-dihydrobenzofuran-6-yl)methyl)-9H-purin-9-yl)-N-cyclopropylpropanamide |
| 5A-36 | 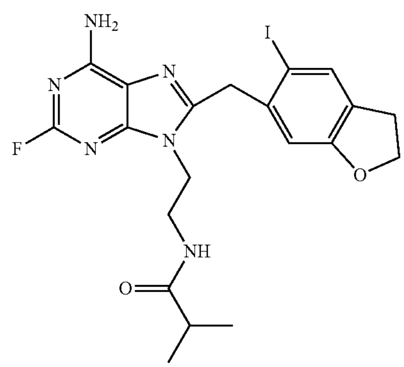 | N-(2-(6-amino-2-fluoro-8-((5-iodo-2,3-dihydrobenzofuran-6-yl)methyl)-9H-purin-9-yl)ethyl)isobutyramide |
| 5A-37 | 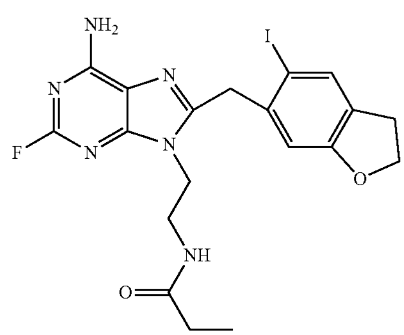 | N-(2-(6-amino-2-fluoro-8-((5-iodo-2,3-dihydrobenzofuran-6-yl)methyl)-9H-purin-9-yl)ethyl)propionamide |
| 5A-38 | 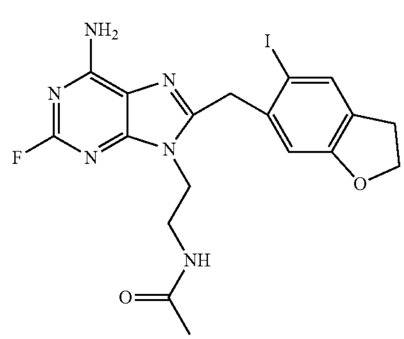 | N-(2-(6-amino-2-fluoro-8-((5-iodo-2,3-dihydrobenzofuran-6-yl)methyl)-9H-purin-9-yl)ethyl)acetamide |

TABLE 5A-continued

| Compound No. | Structure | Name |
| --- | --- | --- |
| 5A-39 | 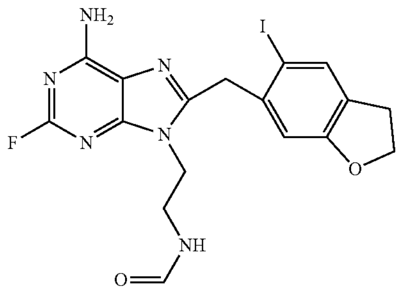 | N-(2-(6-amino-2-fluoro-8-((5-iodo-2,3-dihydrobenzofuran-6-yl)methyl)-9H-purin-9-yl)ethyl)formamide |
| 5A-40 | 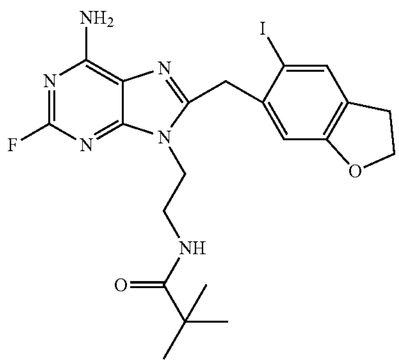 | N-(2-(6-amino-2-fluoro-8-((5-iodo-2,3-dihydrobenzofuran-6-yl)methyl)-9H-purin-9-yl)ethyl)pivalamide |
| 5A-41 | 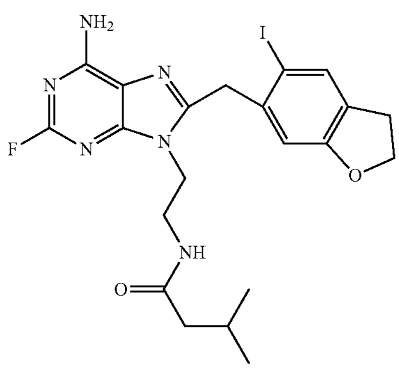 | N-(2-(6-amino-2-fluoro-8-((5-iodo-2,3-dihydrobenzofuran-6-yl)methyl)-9H-purin-9-yl)ethyl)-3-methylbutanamide |
| 5A-42 | 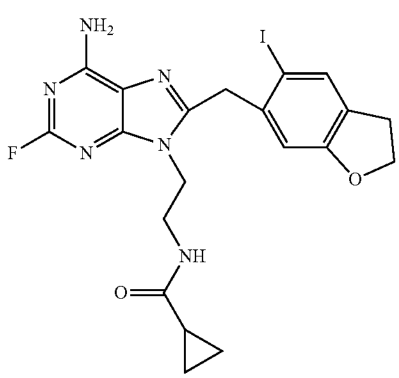 | N-(2-(6-amino-2-fluoro-8-((5-iodo-2,3-dihydrobenzofuran-6-yl)methyl)-9H-purin-9-yl)ethyl)cyclopropanecarboxamide |

TABLE 5A-continued

| Compound No. | Structure | Name |
|---|---|---|
| 5A-43 | 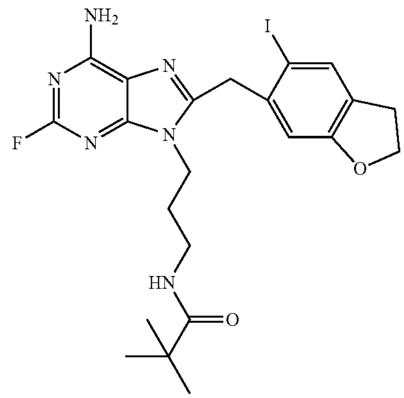 | N-{3-[6-Amino-2-fluoro-8-(5-iodo-2,3-dihydro-benzofuran-6-ylmethyl)-purin-9-yl]-propyl}-2,2-dimethyl-propionamide |
| 5A-44 | 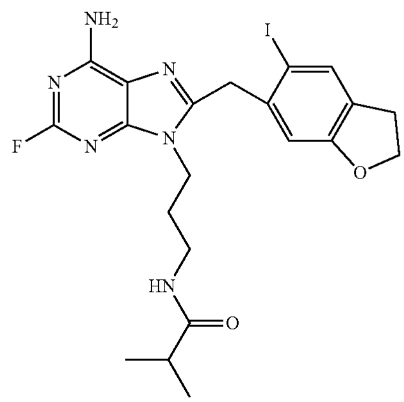 [SMILES: CC(C)C(=O)NCCCn1c(Cc2cc3c(cc2I)CCO3)nc2c(N)nc(F)nc21] | N-{3-[6-Amino-2-fluoro-8-(5-iodo-2,3-dihydro-benzofuran-6-ylmethyl)-purin-9-yl]-propyl}-isobutyramide |
| 5A-45 | 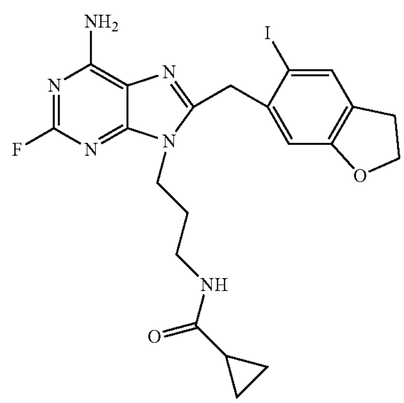 | Cyclopropanecarboxylic acid {3-[6-amino-2-fluoro-8-(5-iodo-2,3-dihydro-benzofuran-6-ylmethyl)-purin-9-yl]-propyl}-amide |
| 5A-46 | 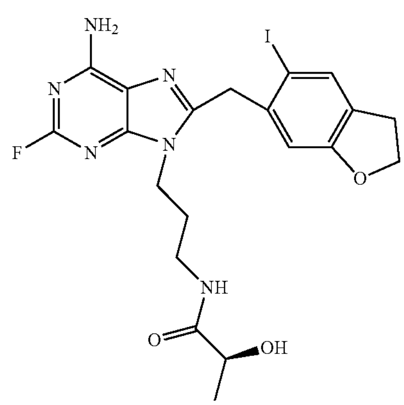 | N-{3-[6-Amino-2-fluoro-8-(5-iodo-2,3-dihydro-benzofuran-6-ylmethyl)-purin-9-yl]-propyl}-2-hydroxy-propionamide |

TABLE 5A-continued

| Compound No. | Structure | Name |
|---|---|---|
| 5A-47 | 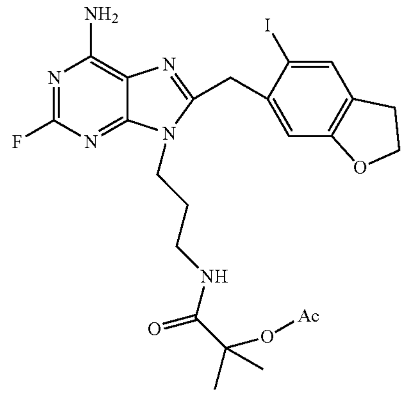 [SMILES: CC(=O)OC(C)(C)C(=O)NCCCn1c(Cc2cc3c(cc2I)CCO3)nc2c(N)nc(F)nc21] | Acetic acid 1-{3-[6-amino-2-fluoro-8-(5-iodo-2,3-dihydro-benzofuran-6-ylmethyl)-purin-9-yl]-propylcarbamoyl}-1-methyl-ethyl ester |
| 5A-48 | 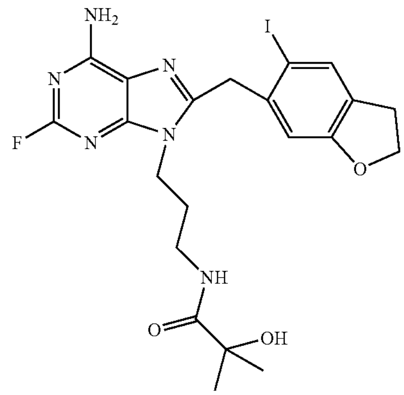 [SMILES: CC(C)(O)C(=O)NCCCn1c(Cc2cc3c(cc2I)CCO3)nc2c(N)nc(F)nc21] | N-{3-[6-Amino-2-fluoro-8-(5-iodo-2,3-dihydro-benzofuran-6-ylmethyl)-purin-9-yl]-propyl}-2-hydroxy-2-methyl-propionamide |

In each of the structures Xb is O and Xa is $CH_2$. However, corresponding structures in which Xb is $CH_2$ and Xa is O are also within the scope of the disclosure.

Hsp90 binding results are presented for Compounds 2A-11, 2A-12, 2A-26 and 2A-45 in Table 12 below. As can be noted therefrom, the compounds showed a high level of binding affinity.

D-II. In some embodiments of the disclosure, $X_2$ is an optionally substituted aryl. Specific examples of compounds within the scope of this aspect of the disclosure correspond to the compounds disclosed in Tables 2A and 5A, or variations thereof as described in A. and D-I. above, in which $X_2$ is an optionally substituted aryl, including but not limited to pyrazolyl, 1H-pyrazol-3-yl, oxazolyl, oxazol-2-yl, thiazolyl, thiazol-2-yl, furanyl, furan-2-yl, and 5-methylfuran-2-yl.

D-III. In some embodiments of the disclosure, $X_2$ is an alkynyl group, e.g., ethynyl, 1-prop-1-ynyl, and 3-prop-1-ynyl. Specific examples of compounds within the scope of this aspect of the disclosure correspond to the compounds disclosed in Tables 2A and 5A, or variations thereof as described in A. and D-I. above, in which $X_2$ is an alkynyl group.

D-IV. In some embodiments of the disclosure, $X_2$ is an amino group, i.e., $-NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Specific examples of compounds within the scope of this aspect of the disclosure correspond to the compounds disclosed in Tables 2A and 5A, or variations thereof as described in A. and D-I. above, in which $X_2$ is an amino group.

E. COMPOUNDS OF FORMULA (IA) IN WHICH XA OR XB IS C(=O)

In accordance with another embodiment of the disclosure, the compounds are of Formula (IA) in which one of Xa and Xb is C(=O) and Xc and the other of Xa and Xb is $CH_2$. Thus, the compounds of this embodiment can be represented by Formula (3):

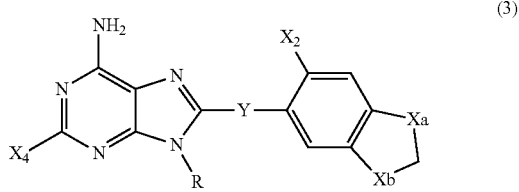

(3)

or a pharmaceutically acceptable salt thereof, wherein:
one of Xa and Xb is a carbonyl group, i.e., C(=O), and the other is $CH_2$;
Y is $CH_2$ or S;
$X_4$ is hydrogen or halogen;
R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N(R$_A$)—, —NR$_A$S(O)—, —SO$_2$N(R$_A$)—, —NR$_A$SO$_2$—, —C(O)N(R$_A$)—, or —NR$_A$C(O)—, and/or terminated by —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and X$_2$ is as disclosed below.

E-I. In some embodiments of the disclosure, X$_2$ is halogen. Table 7A lists specific examples of compounds within this embodiment. In each of the structures as drawn, X$_2$ is I and X$_4$ is H. However, corresponding structures in which X$_2$ is F, Cl, or Br are within the scope of the disclosure. In each of the structures in Table 7A, Y is S. However, corresponding structures in which Y is CH$_2$ and/or X$_4$ is F, Cl, Br, or I are also within the scope of the disclosure. In each of the structures in Table 7A, Xb is C(=O) and Xa is CH$_2$. However, corresponding structures where Xa is C(=O) and Xb is CH$_2$ are also within the scope of the disclosure. Additionally, in connection with each of the structures in Table 7A, corresponding structures in which X$_2$ is F, Cl, or Br, Y is CH$_2$, Xa is C(=O), and Xb is CH$_2$ are also within the scope of the disclosure.

TABLE 7A

| Compound No. | Structure | Name |
| --- | --- | --- |
| 7A-1 | 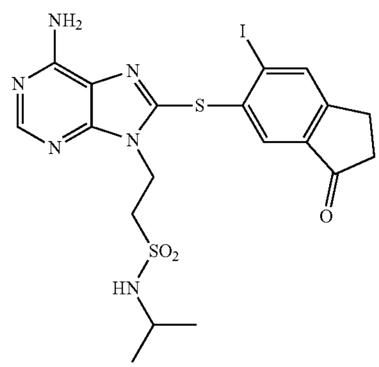 [SMILES: CC(C)NS(=O)(=O)CCn1c(Sc2cc3c(cc2I)CCC3=O)nc2c(N)ncnc21] | 2-(6-amino-8-((6-iodo-3-oxo-2,3-dihydro-1H-inden-5-yl)thio)-9H-purin-9-yl)-N-isopropylethanesulfonamide |
| 7A-2 | 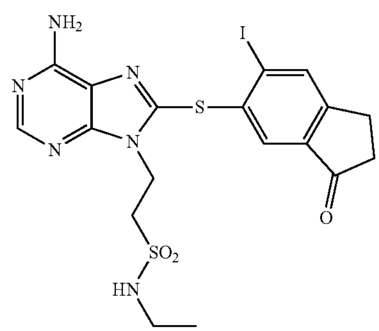 [SMILES: CCNS(=O)(=O)CCn1c(Sc2cc3c(cc2I)CCC3=O)nc2c(N)ncnc21] | 2-(6-amino-8-((6-iodo-3-oxo-2,3-dihydro-1H-inden-5-yl)thio)-9H-purin-9-yl)-N-ethylethanesulfonamide |
| 7A-3 | 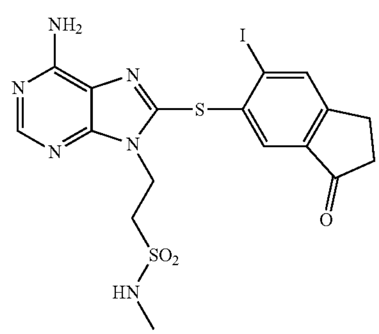 [SMILES: CNS(=O)(=O)CCn1c(Sc2cc3c(cc2I)CCC3=O)nc2c(N)ncnc21] | 2-(6-amino-8-((6-iodo-3-oxo-2,3-dihydro-1H-inden-5-yl)thio)-9H-purin-9-yl)-N-methylethanesulfonamide |

TABLE 7A-continued

| Compound No. | Structure | Name |
|---|---|---|
| 7A-4 | 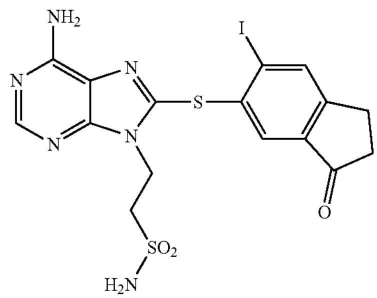 [SMILES: Nc1ncnc2c1nc(Sc1cc3c(cc1I)CCC3=O)n2CCS(N)(=O)=O] | 2-(6-amino-8-((6-iodo-3-oxo-2,3-dihydro-1H-inden-5-yl)thio)-9H-purin-9-yl)ethanesulfonamide |
| 7A-5 | 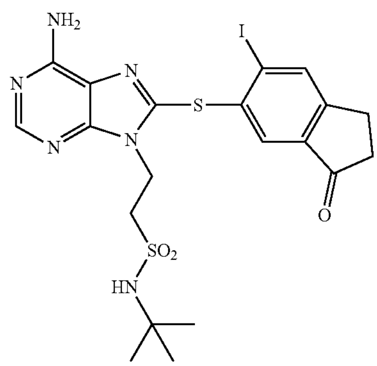 [SMILES: CC(C)(C)NS(=O)(=O)CCn1c(Sc2cc3c(cc2I)CCC3=O)nc2c(N)ncnc21] | 2-(6-amino-8-((6-iodo-3-oxo-2,3-dihydro-1H-inden-5-yl)thio)-9H-purin-9-yl)-N-(tert-butyl)ethanesulfonamide |
| 7A-6 | 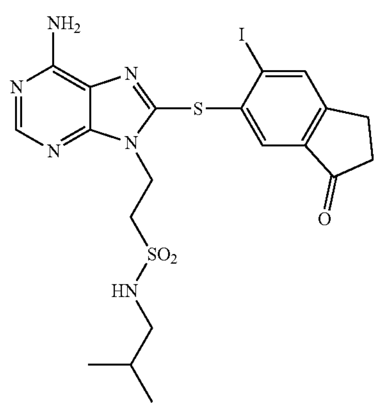 [SMILES: CC(C)CNS(=O)(=O)CCn1c(Sc2cc3c(cc2I)CCC3=O)nc2c(N)ncnc21] | 2-(6-amino-8-((6-iodo-3-oxo-2,3-dihydro-1H-inden-5-yl)thio)-9H-purin-9-yl)-N-isobutylethanesulfonamide |
| 7A-7 | 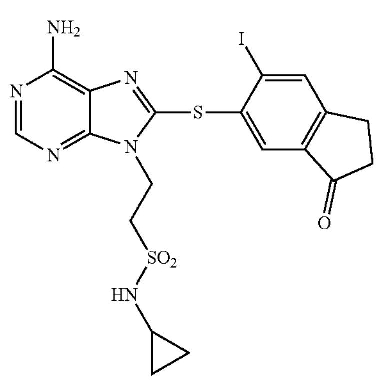 [SMILES: Nc1ncnc2c1nc(Sc1cc3c(cc1I)CCC3=O)n2CCS(=O)(=O)NC1CC1] | 2-(6-amino-8-((6-iodo-3-oxo-2,3-dihydro-1H-inden-5-yl)thio)-9H-purin-9-yl)-N-cyclopropyl-ethanesulfonamide |

TABLE 7A-continued

| Compound No. | Structure | Name |
|---|---|---|
| 7A-8 | 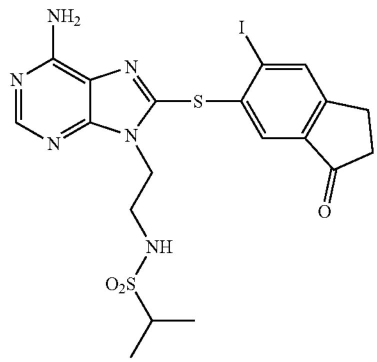 [SMILES: CC(C)S(=O)(=O)NCCn1c(Sc2cc3c(cc2I)CCC3=O)nc2c(N)ncnc21] | N-(2-(6-amino-8-((6-iodo-3-oxo-2,3-dihydro-1H-inden-5-yl)thio)-9H-purin-9-yl)ethyl)propane-2-sulfonamide |
| 7A-9 | 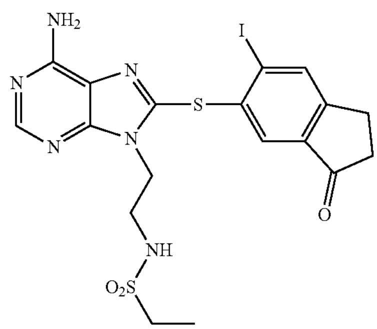 [SMILES: CCS(=O)(=O)NCCn1c(Sc2cc3c(cc2I)CCC3=O)nc2c(N)ncnc21] | N-(2-(6-amino-8-((6-iodo-3-oxo-2,3-dihydro-1H-inden-5-yl)thio)-9H-purin-9-yl)ethyl)ethanesulfonamide |
| 7A-10 | 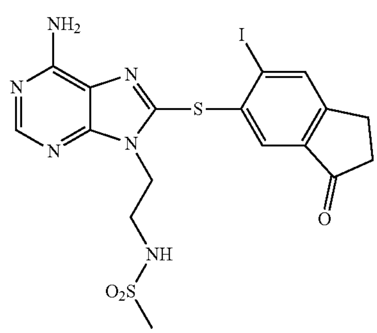 [SMILES: CS(=O)(=O)NCCn1c(Sc2cc3c(cc2I)CCC3=O)nc2c(N)ncnc21] | N-(2-(6-amino-8-((6-iodo-3-oxo-2,3-dihydro-1H-inden-5-yl)thio)-9H-purin-9-yl)ethyl)methanesulfonamide |
| 7A-11 | 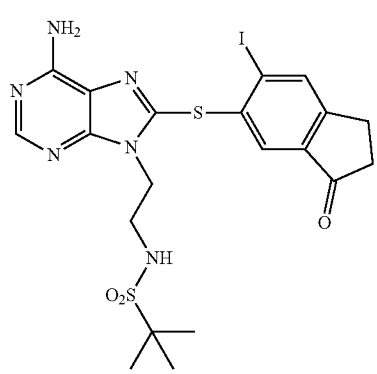 | N-(2-(6-amino-8-((6-iodo-3-oxo-2,3-dihydro-1H-inden-5-yl)thio)-9H-purin-9-yl)ethyl)-2-methylpropane-2-sulfonamide |

TABLE 7A-continued

| Compound No. | Structure | Name |
|---|---|---|
| 7A-12 | 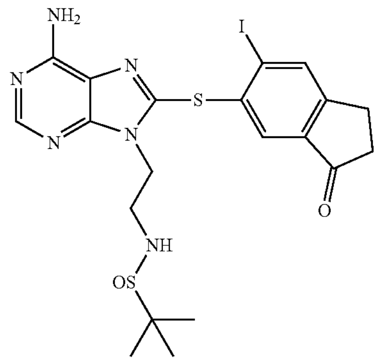 | N-(2-(6-amino-8-((6-iodo-3-oxo-2,3-dihydro-1H-inden-5-yl)thio)-9H-purin-9-yl)ethyl)-2-methylpropane-2-sulfinamide |
| 7A-13 | 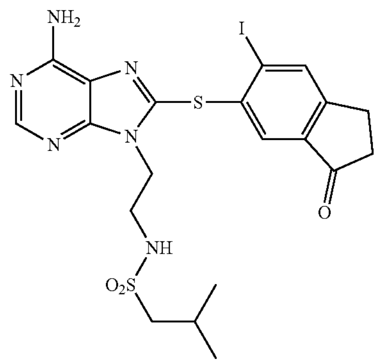 [SMILES: CC(C)CS(=O)(=O)NCCn1c(Sc2cc3c(cc2I)CCC3=O)nc2c(N)ncnc21] | N-(2-(6-amino-8-((6-iodo-3-oxo-2,3-dihydro-1H-inden-5-yl)thio)-9H-purin-9-yl)ethyl)-2-methylpropane-1-sulfonamide |
| 7A-14 | 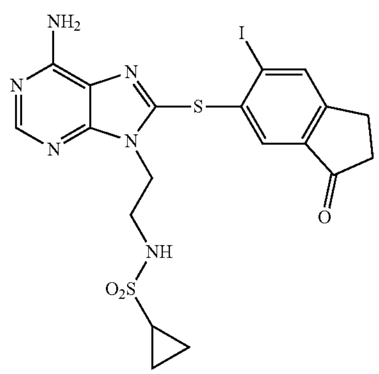 [SMILES: Nc1ncnc2c1nc(Sc1cc3c(cc1I)CCC3=O)n2CCNS(=O)(=O)C1CC1] | N-(2-(6-amino-8-((6-iodo-3-oxo-2,3-dihydro-1H-inden-5-yl)thio)-9H-purin-9-yl)ethyl)cyclopropane-sulfonamide |
| 7A-15 | 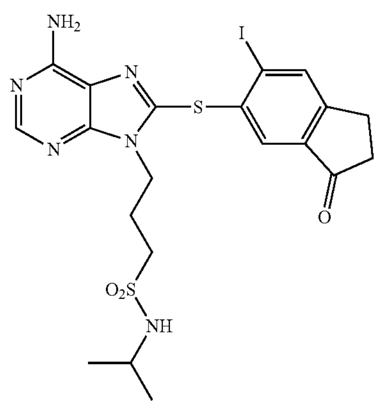 [SMILES: CC(C)NS(=O)(=O)CCCn1c(Sc2cc3c(cc2I)CCC3=O)nc2c(N)ncnc21] | 3-(6-amino-8-((6-iodo-3-oxo-2,3-dihydro-1H-inden-5-yl)thio)-9H-purin-9-yl)-N-isopropylpropane-1-sulfonamide |

TABLE 7A-continued

| Compound No. | Structure | Name |
| --- | --- | --- |
| 7A-16 | 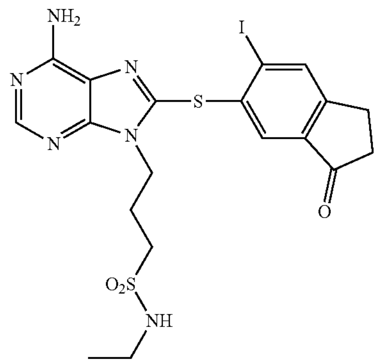 [SMILES: CCNS(=O)(=O)CCCn1c(Sc2cc3c(cc2I)CCC3=O)nc2c(N)ncnc21] | 3-(6-amino-8-((6-iodo-3-oxo-2,3-dihydro-1H-inden-5-yl)thio)-9H-purin-9-yl)-N-ethylpropane-1-sulfonamide |
| 7A-17 | 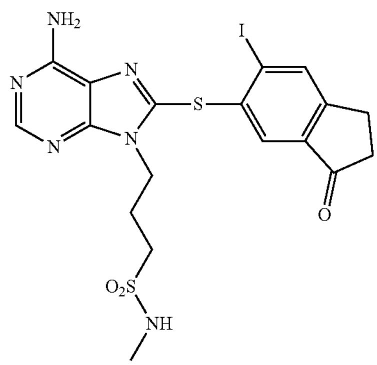 [SMILES: CNS(=O)(=O)CCCn1c(Sc2cc3c(cc2I)CCC3=O)nc2c(N)ncnc21] | 3-(6-amino-8-((6-iodo-3-oxo-2,3-dihydro-1H-inden-5-yl)thio)-9H-purin-9-yl)-N-methylpropane-1-sulfonamide |
| 7A-18 | 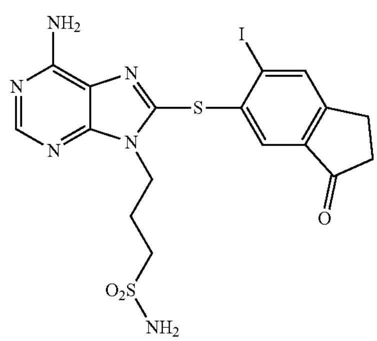 [SMILES: Nc1ncnc2c1nc(Sc1cc3c(cc1I)CCC3=O)n2CCCS(N)(=O)=O] | 3-(6-amino-8-((6-iodo-3-oxo-2,3-dihydro-1H-inden-5-yl)thio)-9H-purin-9-yl)propane-1-sulfonamide |
| 7A-19 | 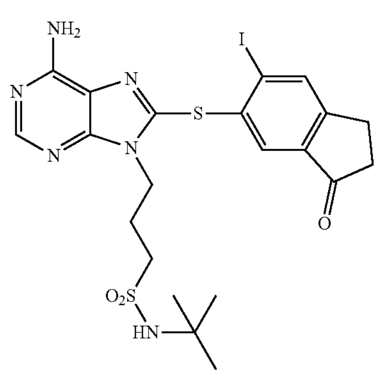 [SMILES: CC(C)(C)NS(=O)(=O)CCCn1c(Sc2cc3c(cc2I)CCC3=O)nc2c(N)ncnc21] | 3-[6-Amino-8-(6-iodo-3-oxo-indan-5-ylsulfanyl)-purin-9-yl]-propane-1-sulfonic acid tert-butylamide |

TABLE 7A-continued

| Compound No. | Structure | Name |
|---|---|---|
| 7A-20 | 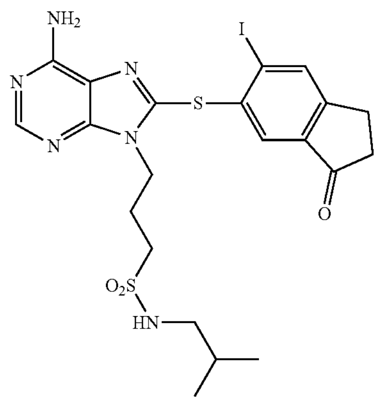 [SMILES: CC(C)CNS(=O)(=O)CCCn1c(Sc2cc3c(cc2I)CCC3=O)nc2c(N)ncnc21] | 3-[6-Amino-8-(6-iodo-3-oxo-indan-5-ylsulfanyl)-purin-9-yl]-propane-1-sulfonic acid isobutyl-amide |
| 7A-21 | 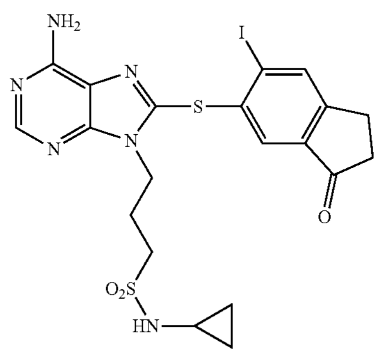 [SMILES: Nc1ncnc2c1nc(Sc1cc3c(cc1I)CCC3=O)n2CCCS(=O)(=O)NC1CC1] | 3-[6-Amino-8-(6-iodo-3-oxo-indan-5-ylsulfanyl)-purin-9-yl]-propane-1-sulfonic acid cyclopropylamide |
| 7A-22 | 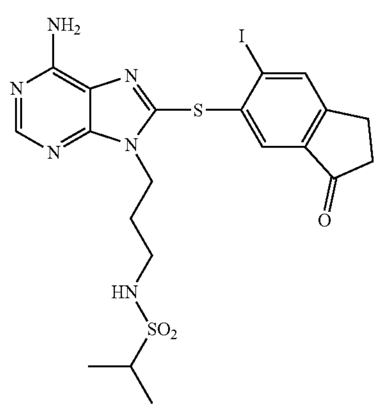 [SMILES: CC(C)S(=O)(=O)NCCCn1c(Sc2cc3c(cc2I)CCC3=O)nc2c(N)ncnc21] | Propane-2-sulfonic acid {3-[6-amino-8-(6-iodo-3-oxo-indan-5-ylsulfanyl)-purin-9-yl]-propyl}-amide |
| 7A-23 | 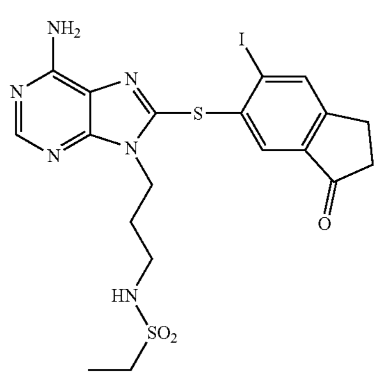 [SMILES: CCS(=O)(=O)NCCCn1c(Sc2cc3c(cc2I)CCC3=O)nc2c(N)ncnc21] | Ethanesulfonic acid {3-[6-amino-8-(6-iodo-3-oxo-indan-5-ylsulfanyl)-purin-9-yl]-propyl}-amide |

TABLE 7A-continued

| Compound No. | Structure | Name |
|---|---|---|
| 7A-24 | 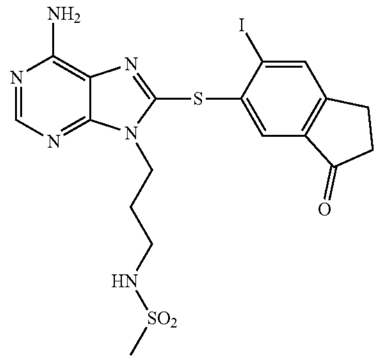 [SMILES: CS(=O)(=O)NCCCn1c(Sc2cc3c(cc2I)CCC3=O)nc2c(N)ncnc21] | N-{3-[6-Amino-8-(6-iodo-3-oxo-indan-5-ylsulfanyl)-purin-9-yl]-propyl}-methanesulfonamide |
| 7A-25 | 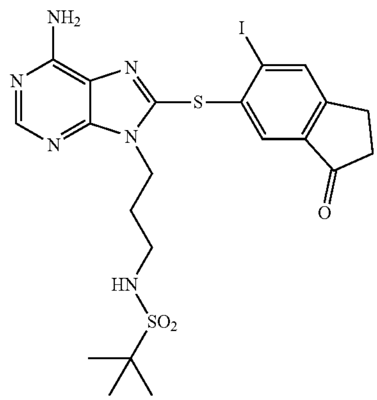 [SMILES: CC(C)(C)S(=O)(=O)NCCCn1c(Sc2cc3c(cc2I)CCC3=O)nc2c(N)ncnc21] | 2-Methyl-propane-2-sulfonic acid {3-[6-amino-8-(6-iodo-3-oxo-indan-5-ylsulfanyl)-purin-9-yl]-propyl}-amide |
| 7A-26 | 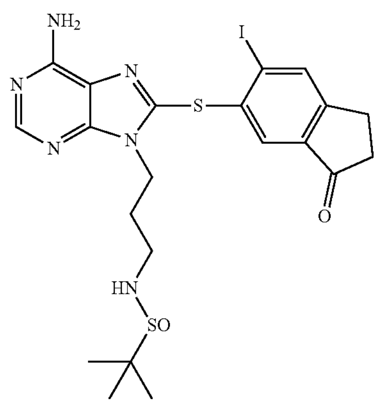 | 2-Methyl-propane-2-sulfinic acid {3-[6-amino-8-(6-iodo-3-oxo-indan-5-ylsulfanyl)-purin-9-yl]-propyl}-amide |
| 7A-27 | 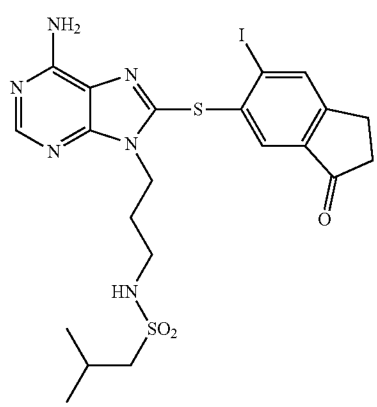 [SMILES: CC(C)CS(=O)(=O)NCCCn1c(Sc2cc3c(cc2I)CCC3=O)nc2c(N)ncnc21] | 2-Methyl-propane-1-sulfonic acid {3-[6-amino-8-(6-iodo-3-oxo-indan-5-ylsulfanyl)-purin-9-yl]-propyl}-amide |

TABLE 7A-continued

| Compound No. | Structure | Name |
| --- | --- | --- |
| 7A-28 | 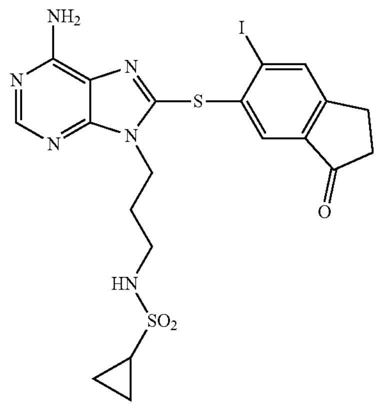 [SMILES: Nc1ncnc2c1nc(Sc1cc3c(cc1I)CCC3=O)n2CCCNS(=O)(=O)C1CC1] | Cyclopropanesulfonic acid {3-[6-amino-8-(6-iodo-3-oxo-indan-5-ylsulfanyl)-purin-9-yl]-propyl}-amide |
| 7A-29 | 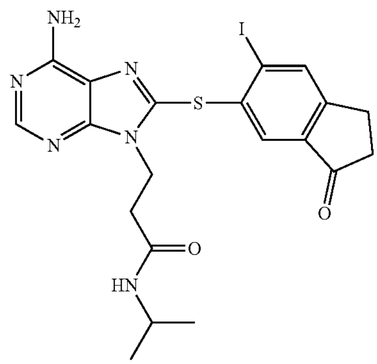 [SMILES: CC(C)NC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-N-isopropyl-propionamide |
| 7A-30 | 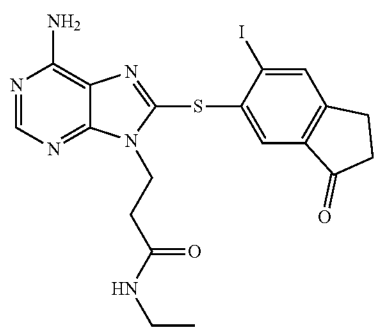 [SMILES: CCNC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-N-ethyl-propionamide |
| 7A-31 | 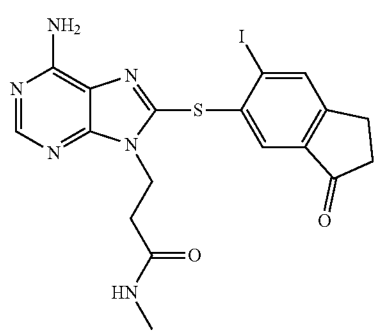 [SMILES: CNC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-N-methyl-propionamide |

TABLE 7A-continued

| Compound No. | Structure | Name |
|---|---|---|
| 7A-32 | 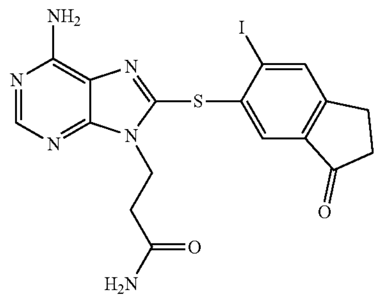 [SMILES: NC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-propionamide |
| 7A-33 | 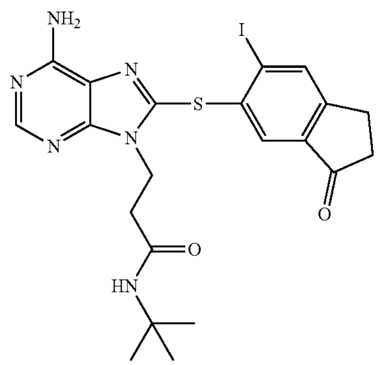 [SMILES: CC(C)(C)NC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-N-tert-butyl-propionamide |
| 7A-34 | 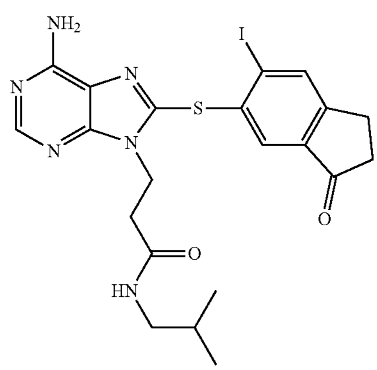 [SMILES: CC(C)CNC(=O)CCn1c(Sc2cc3c(cc2I)CCC3=O)nc2c(N)ncnc21] | 3-[6-Amino-8-(6-iodo-3-oxo-indan-5-ylsulfanyl)-purin-9-yl]-N-isobutyl-propionamide |
| 7A-35 | 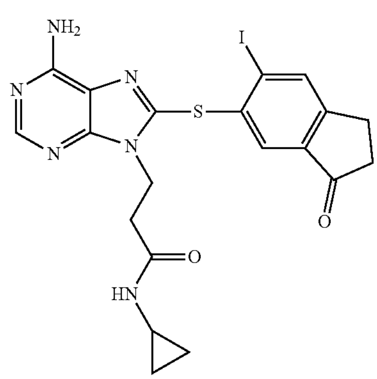 [SMILES: Nc1ncnc2c1nc(Sc1cc3c(cc1I)CCC3=O)n2CCC(=O)NC1CC1] | 3-[6-Amino-8-(6-iodo-3-oxo-indan-5-ylsulfanyl)-purin-9-yl]-N-cyclopropyl-propionamide |

TABLE 7A-continued

| Compound No. | Structure | Name |
|---|---|---|
| 7A-36 | 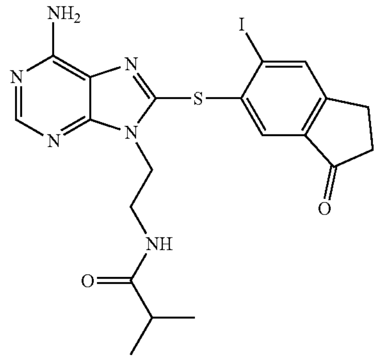 [SMILES: CC(C)C(=O)NCCn1c(Sc2cc3c(cc2I)CCC3=O)nc2c(N)ncnc21] | N-{2-[6-Amino-8-(6-iodo-3-oxo-indan-5-ylsulfanyl)-purin-9-yl]-ethyl}-isobutyramide |
| 7A-37 | 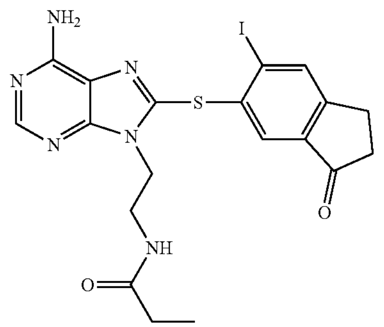 [SMILES: CCC(=O)NCCn1c(Sc2cc3c(cc2I)CCC3=O)nc2c(N)ncnc21] | N-{2-[6-Amino-8-(6-iodo-3-oxo-indan-5-ylsulfanyl)-purin-9-yl]-ethyl}-propionamide |
| 7A-38 | 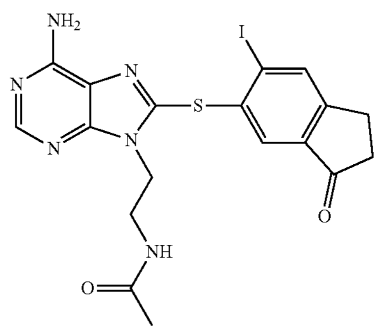 [SMILES: CC(=O)NCCn1c(Sc2cc3c(cc2I)CCC3=O)nc2c(N)ncnc21] | N-{2-[6-Amino-8-(6-iodo-3-oxo-indan-5-ylsulfanyl)-purin-9-yl]-ethyl}-acetamide |
| 7A-39 | 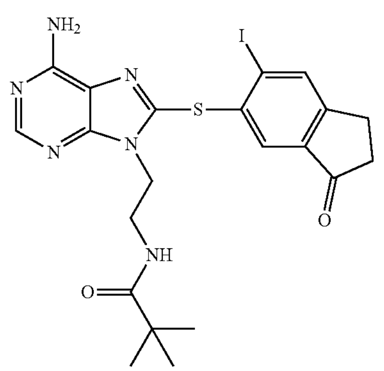 [SMILES: CC(C)(C)C(=O)NCCn1c(Sc2cc3c(cc2I)CCC3=O)nc2c(N)ncnc21] | N-{2-[6-Amino-8-(6-iodo-3-oxo-indan-5-ylsulfanyl)-purin-9-yl]-ethyl}-2,2-dimethyl-propionamide |

TABLE 7A-continued

| Compound No. | Structure | Name |
|---|---|---|
| 7A-40 | 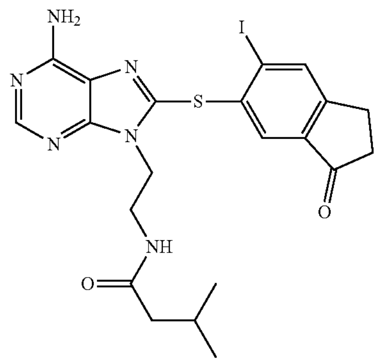 [SMILES: CC(C)CC(=O)NCCn1c(Sc2cc3c(cc2I)CCC3=O)nc2c(N)ncnc21] | N-{2-[6-Amino-8-(6-iodo-3-oxo-indan-5-ylsulfanyl)-purin-9-yl]-ethyl}-3-methyl-butyramide |
| 7A-41 | 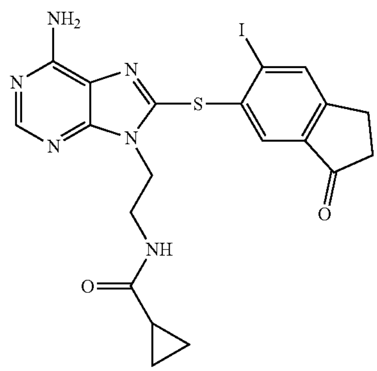 [SMILES: Nc1ncnc2c1nc(Sc1cc3c(cc1I)CCC3=O)n2CCNC(=O)C1CC1] | Cyclopropanecarboxylic acid {2-[6-amino-8-(6-iodo-3-oxo-indan-5-ylsulfanyl)-purin-9-yl]-ethyl}-amide |
| 7A-42 | 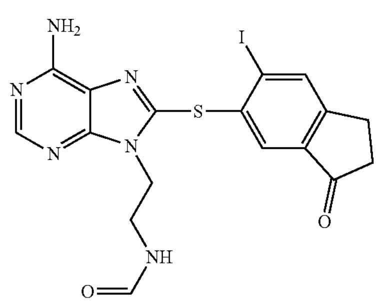 [SMILES: Nc1ncnc2c1nc(Sc1cc3c(cc1I)CCC3=O)n2CCNC=O] | N-{2-[6-Amino-8-(6-iodo-3-oxo-indan-5-ylsulfanyl)-purin-9-yl]-ethyl}-formamide |

Table 9A lists specific examples in which $X_2$ is halogen and $X_4$ is halogen. In each of the structures as drawn, $X_2$ is I and $X_4$ is F. However, corresponding structures in which $X_4$ is H, Cl, Br, or I are within the scope of the disclosure. In each of the structures in Table 9A, Y is $CH_2$. However, corresponding structures in which Y is S and/or $X_2$ is F, Cl, or Br are also within the scope of the disclosure. In each of the structures in Table 9A, Xb is C(=O) and Xa is $CH_2$. However, corresponding structures where Xa is C(=O) and Xb is $CH_2$ are also within the scope of the disclosure. However, corresponding structures in which Y is S are also within the scope of the disclosure. Additionally, in connection with each of the structures in Table 9A, corresponding structures in which $X_4$ is H, Cl, Br, or I, Y is S, Xa is C(=O), and Xb is $CH_2$ are also within the scope of the disclosure.

TABLE 9A

| Compound No. | Structure | Name |
| --- | --- | --- |
| 9A-1 | 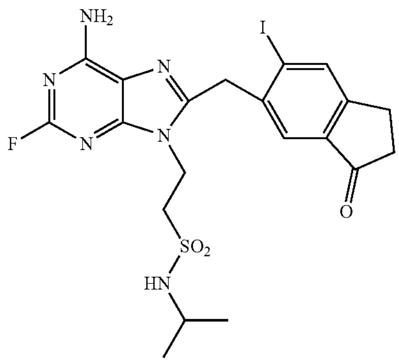 [SMILES: CC(C)NS(=O)(=O)CCn1c(Cc2cc3c(cc2I)CCC3=O)nc2c(N)nc(F)nc21] | 2-(6-amino-2-fluoro-8-((6-iodo-3-oxo-2,3-dihydro-1H-inden-5-yl)methyl)-9H-purin-9-yl)-N-isopropylethanesulfonamide |
| 9A-2 | 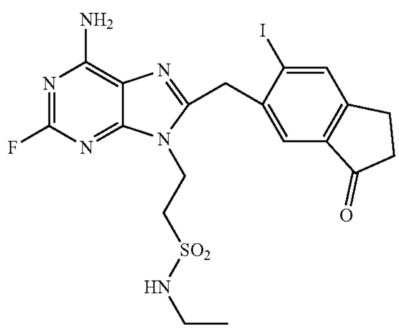 [SMILES: CCNS(=O)(=O)CCn1c(Cc2cc3c(cc2I)CCC3=O)nc2c(N)nc(F)nc21] | 2-(6-amino-2-fluoro-8-((6-iodo-3-oxo-2,3-dihydro-1H-inden-5-yl)methyl)-9H-purin-9-yl)-N-ethylethanesulfonamide |
| 9A-3 | 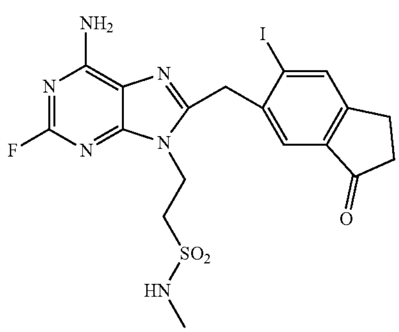 [SMILES: CNS(=O)(=O)CCn1c(Cc2cc3c(cc2I)CCC3=O)nc2c(N)nc(F)nc21] | 2-(6-amino-2-fluoro-8-((6-iodo-3-oxo-2,3-dihydro-1H-inden-5-yl)methyl)-9H-purin-9-yl)-N-methylethanesulfonamide |
| 9A-4 | 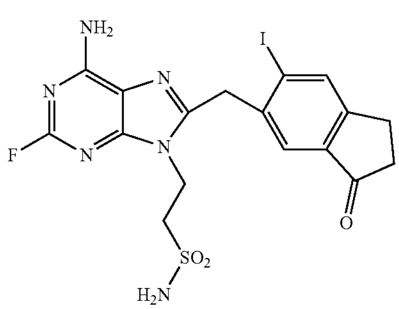 [SMILES: Nc1nc(F)nc2c1nc(Cc1cc3c(cc1I)CCC3=O)n2CCS(N)(=O)=O] | 2-(6-amino-2-fluoro-8-((6-iodo-3-oxo-2,3-dihydro-1H-inden-5-yl)methyl)-9H-purin-9-yl)ethanesulfonamide |

TABLE 9A-continued

| Compound No. | Structure | Name |
|---|---|---|
| 9A-5 | 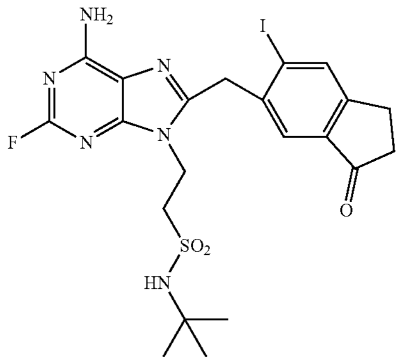 | 2-(6-amino-2-fluoro-8-((6-iodo-3-oxo-2,3-dihydro-1H-inden-5-yl)methyl)-9H-purin-9-yl)-N-(tert-butyl)ethanesulfonamide |
| 9A-6 | 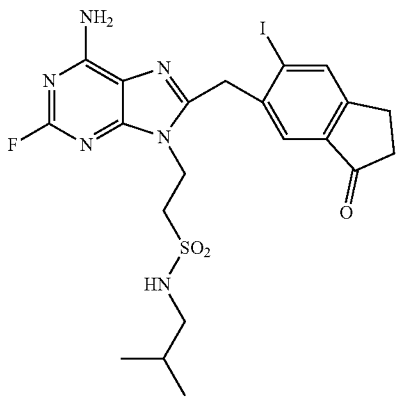 [SMILES: CC(C)CNS(=O)(=O)CCn1c(Cc2cc3c(cc2I)CCC3=O)nc2c(N)nc(F)nc21] | 2-(6-amino-2-fluoro-8-((6-iodo-3-oxo-2,3-dihydro-1H-inden-5-yl)methyl)-9H-purin-9-yl)-N-isobutylethanesulfonamide |
| 9A-7 | 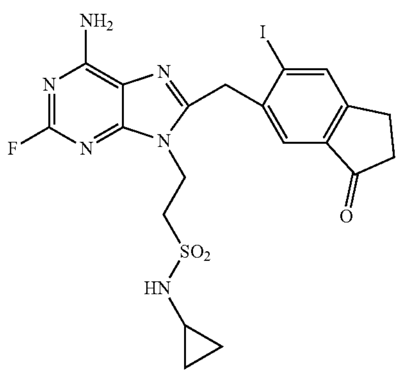 [SMILES: Nc1nc(F)nc2c1nc(Cc1cc3c(cc1I)CCC3=O)n2CCS(=O)(=O)NC1CC1] | 2-(6-amino-2-fluoro-8-((6-iodo-3-oxo-2,3-dihydro-1H-inden-5-yl)methyl)-9H-purin-9-yl)-N-cyclopropyl-ethanesulfonamide |
| 9A-8 | 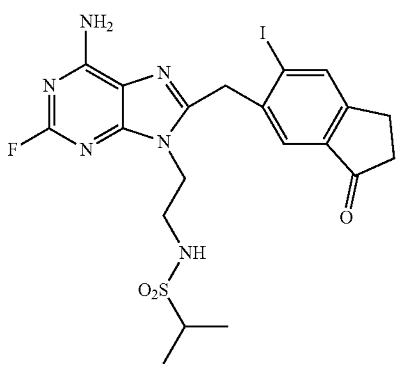 [SMILES: CC(C)S(=O)(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)propane-2-sulfonamide |

TABLE 9A-continued

| Compound No. | Structure | Name |
|---|---|---|
| 9A-9 | 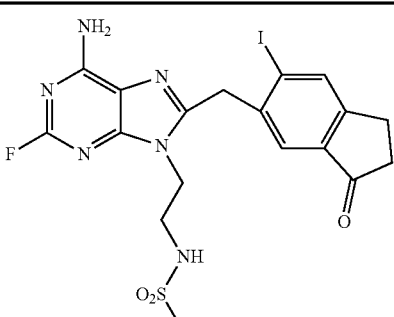 | N-(2-(6-amino-2-fluoro-8-((6-iodo-3-oxo-2,3-dihydro-1H-inden-5-yl)methyl)-9H-purin-9-yl)ethyl)ethanesulfonamide |
| 9A-10 | 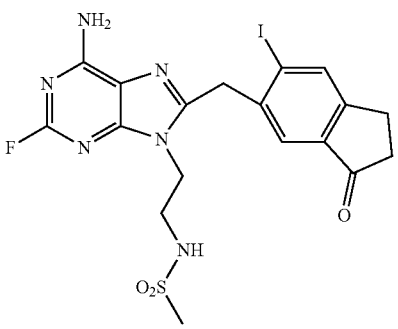 [SMILES: CS(=O)(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)methane-sulfonamide |
| 9A-11 | 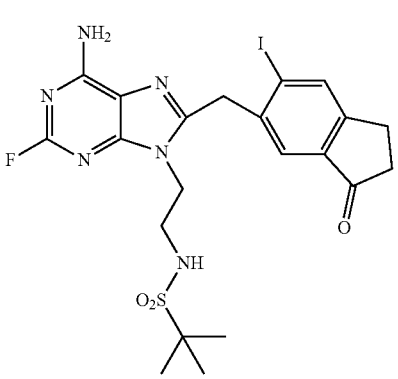 | N-(2-(6-amino-2-fluoro-8-((6-iodo-3-oxo-2,3-dihydro-1H-inden-5-yl)methyl)-9H-purin-9-yl)ethyl)-2-methylpropane-2-sulfonamide |
| 9A-12 | 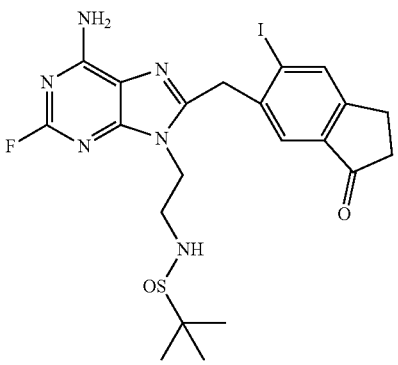 | N-(2-(6-amino-2-fluoro-8-((6-iodo-3-oxo-2,3-dihydro-1H-inden-5-yl)methyl)-9H-purin-9-yl)ethyl)-2-methylpropane-2-sulfinamide |

TABLE 9A-continued

| Compound No. | Structure | Name |
|---|---|---|
| 9A-13 | 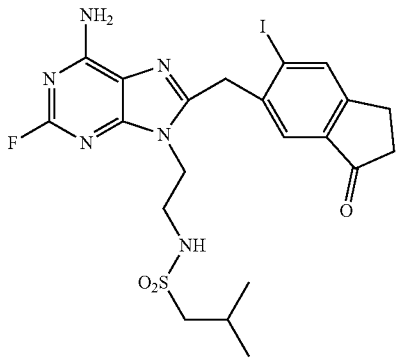 [SMILES: CC(C)CS(=O)(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)-2-methylpropane-1-sulfonamide |
| 9A-14 | 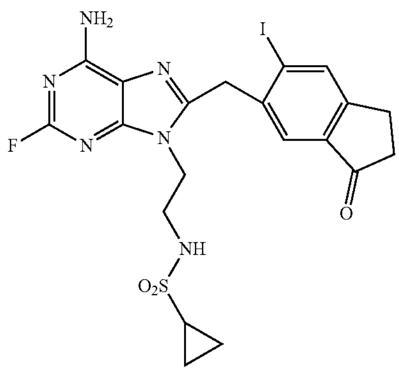 [SMILES: Nc1nc(F)nc2c1nc(Cc1cc3c(cc1I)CCC3=O)n2CCNS(=O)(=O)C1CC1] | N-(2-(6-amino-2-fluoro-8-((6-iodo-3-oxo-2,3-dihydro-1H-inden-5-yl)methyl)-9H-purin-9-yl)ethyl)cyclopropane-sulfonamide |
| 9A-15 | 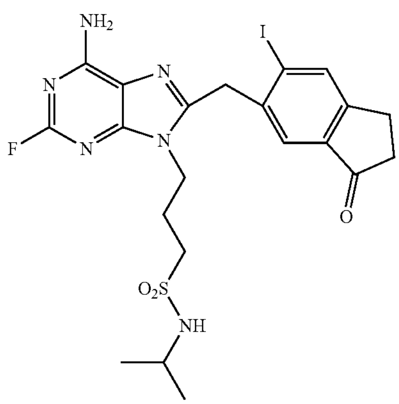 [SMILES: CC(C)NS(=O)(=O)CCCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-isopropylpropane-1-sulfonamide |
| 9A-16 | 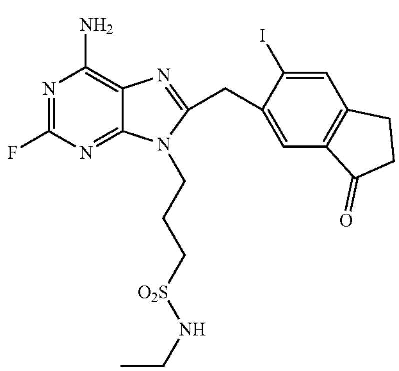 [SMILES: CCNS(=O)(=O)CCCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-ethylpropane-1-sulfonamide |

TABLE 9A-continued

| Compound No. | Structure | Name |
|---|---|---|
| 9A-17 | 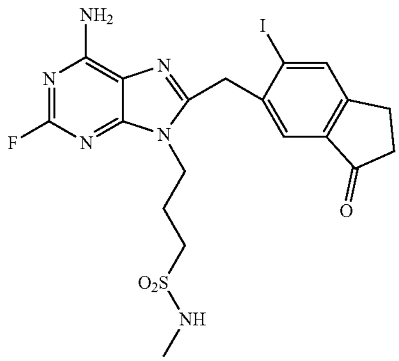 [SMILES: CNS(=O)(=O)CCCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-methylpropane-1-sulfonamide |
| 9A-18 | 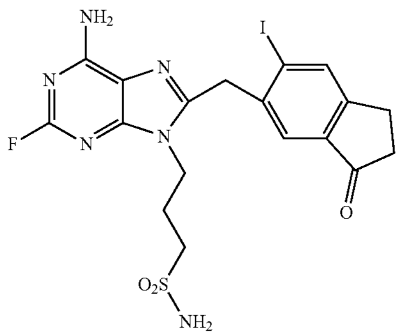 [SMILES: Nc1nc(F)nc2c1nc(Cc1cc3c(cc1I)CCC3=O)n2CCCS(N)(=O)=O] | 3-(6-amino-2-fluoro-8-((6-iodo-3-oxo-2,3-dihydro-1H-inden-5-yl)methyl)-9H-purin-9-yl)propane-1-sulfonamide |
| 9A-19 | 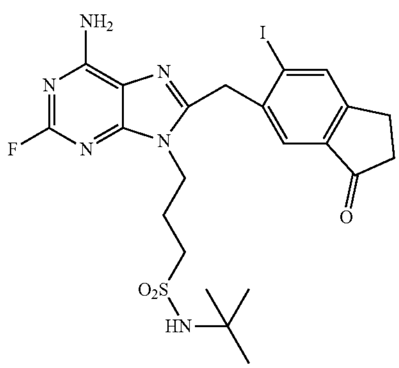 [SMILES: CC(C)(C)NS(=O)(=O)CCCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-(tert-butyl)propane-1-sulfonamide |
| 9A-20 | 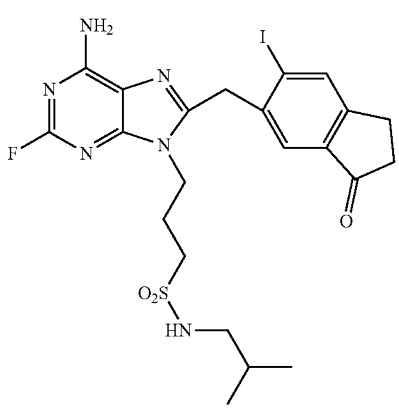 [SMILES: CC(C)CNS(=O)(=O)CCCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-isobutylpropane-1-sulfonamide |

TABLE 9A-continued

| Compound No. | Structure | Name |
|---|---|---|
| 9A-21 | 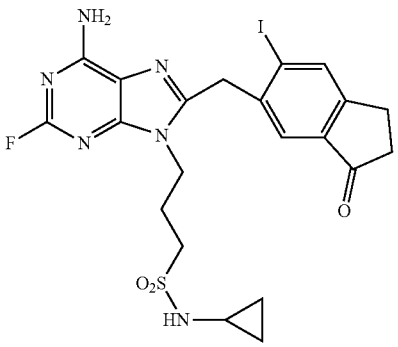 [SMILES: Nc1nc(F)nc2c1nc(Cc1cc3c(cc1I)CCC3=O)n2CCCS(=O)(=O)NC1CC1] | 3-(6-amino-2-fluoro-8-((6-iodo-3-oxo-2,3-dihydro-1H-inden-5-yl)methyl)-9H-purin-9-yl)-N-cyclopropylpropane-1-sulfonamide |
| 9A-22 | 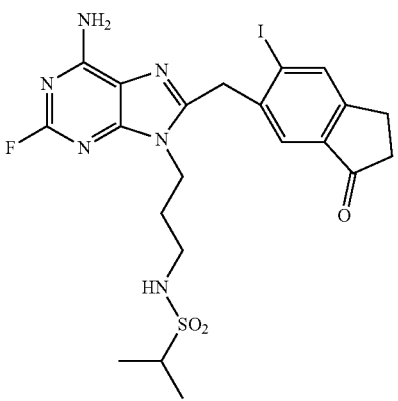 | N-(3-(6-amino-2-fluoro-8-((6-iodo-3-oxo-2,3-dihydro-1H-inden-5-yl)methyl)-9H-purin-9-yl)propyl)propane-2-sulfonamide |
| 9A-23 | 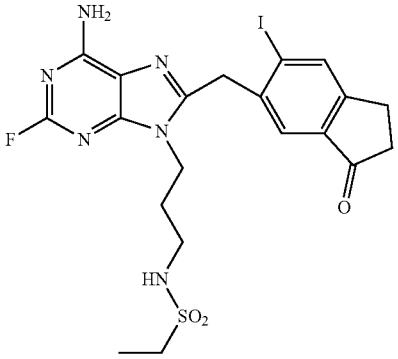 [SMILES: CCS(=O)(=O)NCCCn1c(Cc2cc3c(cc2I)CCC3=O)nc2c(N)nc(F)nc21] | N-(3-(6-amino-2-fluoro-8-((6-iodo-3-oxo-2,3-dihydro-1H-inden-5-yl)methyl)-9H-purin-9-yl)propyl)ethanesulfonamide |
| 9A-24 | 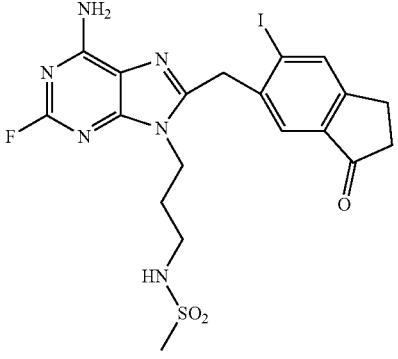 | N-(3-(6-amino-2-fluoro-8-((6-iodo-3-oxo-2,3-dihydro-1H-inden-5-yl)methyl)-9H-purin-9-yl)propyl)methanesulfonamide |

TABLE 9A-continued

| Compound No. | Structure | Name |
|---|---|---|
| 9A-25 | 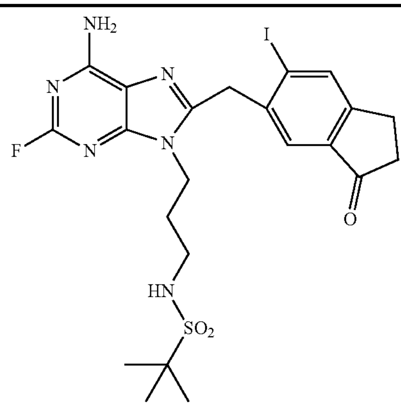 | N-(3-(6-amino-2-fluoro-8-((6-iodo-3-oxo-2,3-dihydro-1H-inden-5-yl)methyl)-9H-purin-9-yl)propyl)-2-methylpropane-2-sulfonamide |
| 9A-26 | 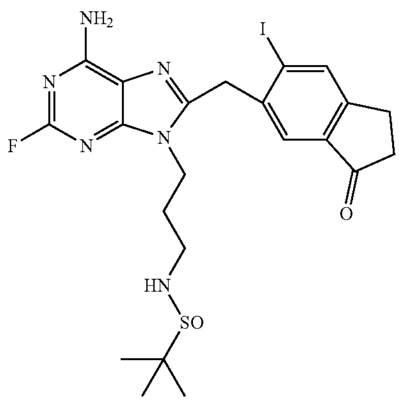 | N-(3-(6-amino-2-fluoro-8-((6-iodo-3-oxo-2,3-dihydro-1H-inden-5-yl)methyl)-9H-purin-9-yl)propyl)-2-methylpropane-2-sulfinamide |
| 9A-27 | 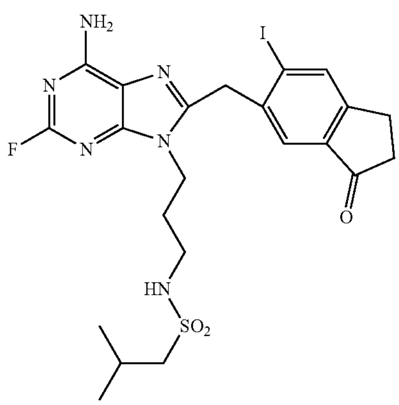 [SMILES: CC(C)CS(=O)(=O)NCCCn1c(Cc2cc3c(cc2I)CCC3=O)nc2c(N)nc(F)nc21] | N-(3-(6-amino-2-fluoro-8-((6-iodo-3-oxo-2,3-dihydro-1H-inden-5-yl)methyl)-9H-purin-9-yl)propyl)-2-methylpropane-1-sulfonamide |
| 9A-28 | 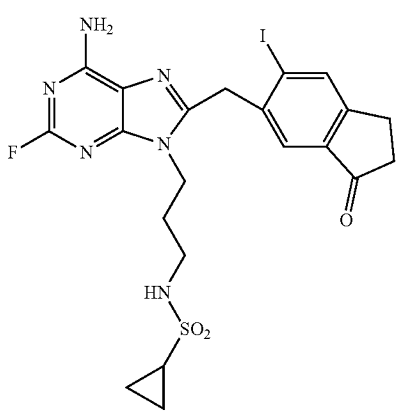 [SMILES: Nc1nc(F)nc2c1nc(Cc1cc3c(cc1I)CCC3=O)n2CCCNS(=O)(=O)C1CC1] | N-(3-(6-amino-2-fluoro-8-((6-iodo-3-oxo-2,3-dihydro-1H-inden-5-yl)methyl)-9H-purin-9-yl)propyl)cyclopropane-sulfonamide |

TABLE 9A-continued

| Compound No. | Structure | Name |
|---|---|---|
| 9A-29 | 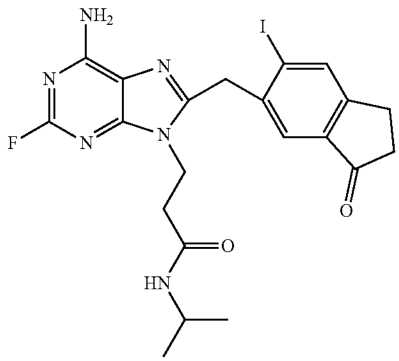 [SMILES: CC(C)NC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-isopropylpropanamide |
| 9A-30 | 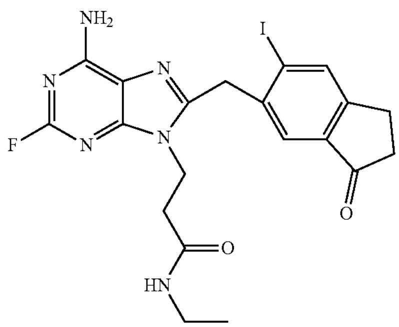 [SMILES: CCNC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-ethylpropanamide |
| 9A-31 | 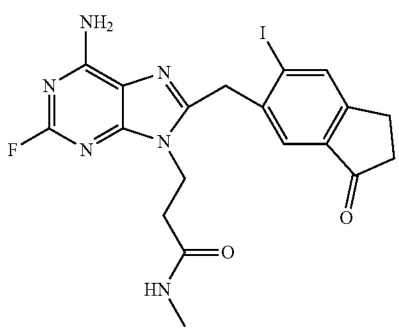 [SMILES: CNC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-methylpropan-amide |
| 9A-32 | 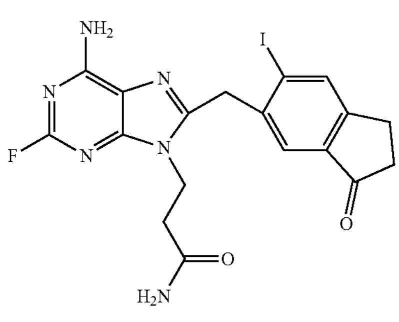 [SMILES: NC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)propanamide |

TABLE 9A-continued

| Compound No. | Structure | Name |
|---|---|---|
| 9A-33 | 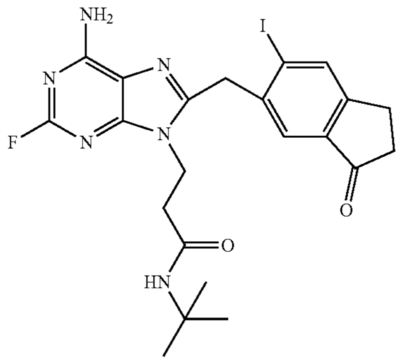 [SMILES: CC(C)(C)NC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-(tert-butyl)propanamide |
| 9A-34 | 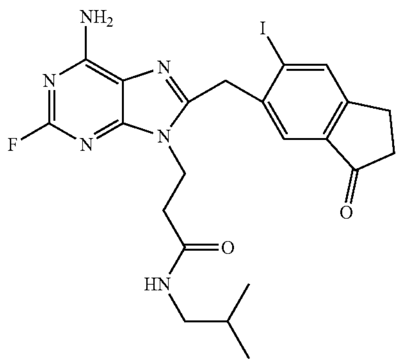 [SMILES: CC(C)CNC(=O)CCn1c(Cc2cc3c(cc2I)CCC3=O)nc2c(N)nc(F)nc21] | 3-(6-amino-2-fluoro-8-((6-iodo-3-oxo-2,3-dihydro-1H-inden-5-yl)methyl)-9H-purin-9-yl)-N-isobutylpropanamide |
| 9A-35 | 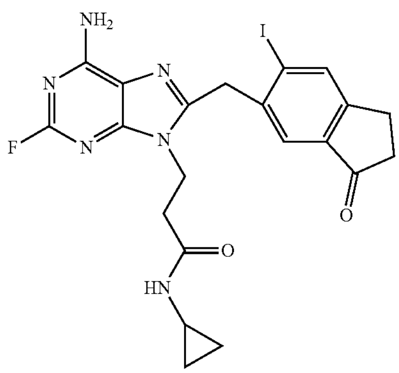 [SMILES: Nc1nc(F)nc2c1nc(Cc1cc3c(cc1I)CCC3=O)n2CCC(=O)NC1CC1] | 3-(6-amino-2-fluoro-8-((6-iodo-3-oxo-2,3-dihydro-1H-inden-5-yl)methyl)-9H-purin-9-yl)-N-cyclopropylpropanamide |
| 9A-36 | 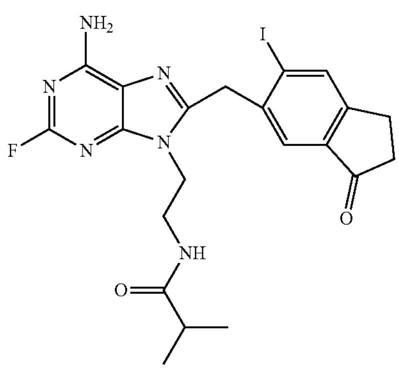 [SMILES: CC(C)C(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)isobutyramide |

TABLE 9A-continued

| Compound No. | Structure | Name |
| --- | --- | --- |
| 9A-37 | 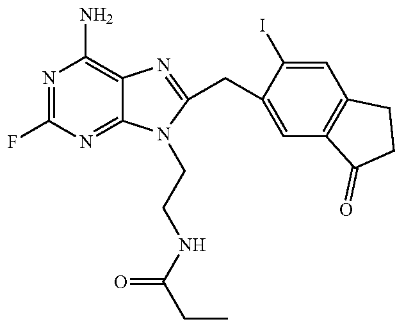 [SMILES: CCC(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)propionamide |
| 9A-38 | 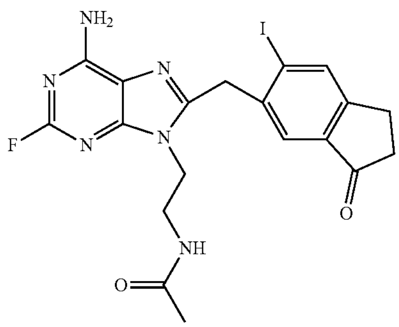 [SMILES: CC(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)acetamide |
| 9A-39 | 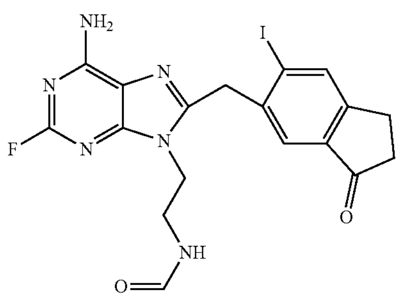 [SMILES: Nc1nc(F)nc2c1nc(Cc1cc3c(cc1I)CCC3=O)n2CCNC=O] | N-(2-(6-amino-2-fluoro-8-((6-iodo-3-oxo-2,3-dihydro-1H-inden-5-yl)methyl)-9H-purin-9-yl)ethyl)formamide |
| 9A-40 | 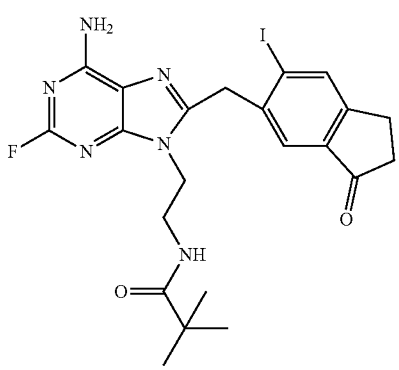 [SMILES: CC(C)(C)C(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)pivalamide |

TABLE 9A-continued

| Compound No. | Structure | Name |
|---|---|---|
| 9A-41 | 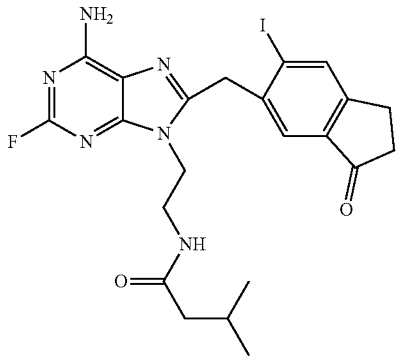 [SMILES: CC(C)CC(=O)NCCn1c(Cc2cc3c(cc2I)CCC3=O)nc2c(N)nc(F)nc21] | N-(2-(6-amino-2-fluoro-8-((6-iodo-3-oxo-2,3-dihydro-1H-inden-5-yl)methyl)-9H-purin-9-yl)ethyl)-3-methylbutanamide |
| 9A-42 | 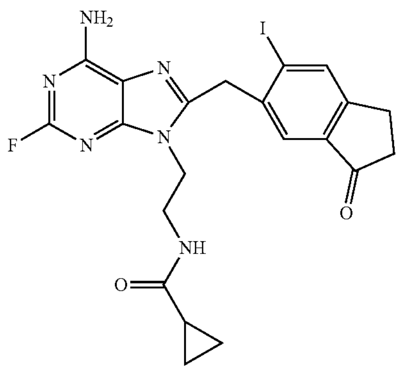 [SMILES: Nc1nc(F)nc2c1nc(Cc1cc3c(cc1I)CCC3=O)n2CCNC(=O)C1CC1] | N-(2-(6-amino-2-fluoro-8-((6-iodo-3-oxo-2,3-dihydro-1H-inden-5-yl)methyl)-9H-purin-9-yl)ethyl)cyclopropanecarboxamide |

E-II. In some embodiments of the disclosure, $X_2$ is an optionally substituted aryl. Specific examples of compounds within the scope of this aspect of the disclosure correspond to the compounds disclosed in Tables 7A and 9A, or variations thereof as described in A. and E-I. above, in which $X_2$ is an optionally substituted aryl, including but not limited to pyrazolyl, 1H-pyrazol-3-yl, oxazolyl, oxazol-2-yl, thiazolyl, thiazol-2-yl, furanyl, furan-2-yl, and 5-methylfuran-2-yl.

E-III. In some embodiments of the disclosure, $X_2$ is an alkynyl group, e.g., ethynyl, 1-prop-1-ynyl, and 3-prop-1-ynyl. Specific examples of compounds within the scope of this aspect of the disclosure correspond to the compounds disclosed in Tables 7A and 9A, or variations thereof as described in A. and E-I. above, in which $X_2$ is an alkynyl group.

E-IV. In some embodiments of the disclosure, $X_2$ is an amino group, i.e., wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Specific examples of compounds within the scope of this aspect of the disclosure correspond to the compounds disclosed in Tables 7A and 9A, or variations thereof as described in A. and E-I. above, in which $X_2$ is an amino group.

F. COMPOUNDS OF FORMULA (IA) IN WHICH XA AND XB EACH COMPRISE HYDROCARBON

In accordance with another embodiment of the disclosure, the compounds are of Formula (IA) in which Xa, Xb and Xc all comprise hydrocarbon and are connected by two single bonds or one single bond and one double bond. Thus, the compounds of this embodiment can be represented by Formula (4):

$$(4)$$

or a pharmaceutically acceptable salt thereof, wherein:

Xa-Xc-Xb is $CH_2$—$CH_2$—$CH_2$, $CH$=$CH$—$CH_2$, or $CH_2$—$CH$=$CH$;

Y is $CH_2$ or S;

$X_4$ is hydrogen or halogen;

R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_A$S(O)—, —$SO_2$N($R_A$)—, —$NR_A$$SO_2$—, —C(O)N($R_A$)—, or —$NR_A$C(O)—, and/or terminated by —S(O)$NR_A$$R_B$, —$NR_A$S(O)$R_B$, —$SO_2$$NR_A$$R_B$, —$NR_A$$SO_2$$R_B$, —C(O)$NR_A$$R_B$, or —$NR_A$C(O)$R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and $X_2$ is as disclosed below.

F-I. In some embodiments of the disclosure, $X_2$ is halogen. Table 3A lists specific examples of compounds within this embodiment. In each of the structures as drawn, $X_2$ is I and $X_4$ is H. However, corresponding structures in which $X_2$ is F, Cl, or Br are within the scope of the disclosure. In each of the structures in Table 3A, Y is S. However, corresponding structures in which Y is $CH_2$ and/or $X_4$ is F, Cl, Br, or I are also within the scope of the disclosure. Additionally, in connection with each of the structures in Table 3A, corresponding structures in which $X_2$ is F, Cl, or Br and Y is $CH_2$ are also within the scope of the disclosure.

TABLE 3A

| Compound No. | Structure | Name |
|---|---|---|
| 3A-1 | 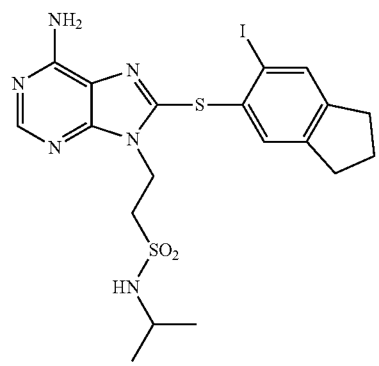 | 2-[6-Amino-8-(6-iodo-indan-5-ylsulfanyl)-purin-9-yl]-ethanesulfonic acid isopropylamide |
| 3A-2 | 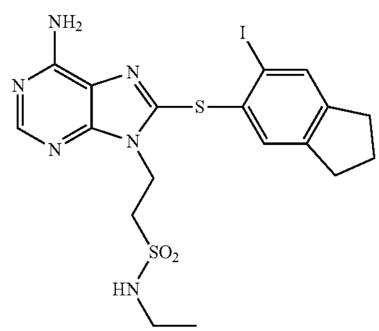 | 2-[6-Amino-8-(6-iodo-indan-5-ylsulfanyl)-purin-9-yl]-ethanesulfonic acid ethylamide |
| 3A-3 | 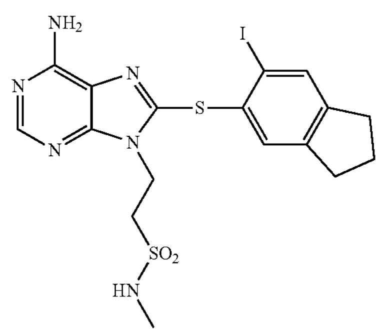 | 2-[6-Amino-8-(6-iodo-indan-5-ylsulfanyl)-purin-9-yl]-ethanesulfonic acid methylamide |
| 3A-4 | 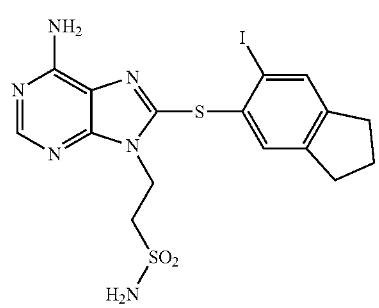 | 2-[6-Amino-8-(6-iodo-indan-5-ylsulfanyl)-purin-9-yl]-ethanesulfonic acid amide |

TABLE 3A-continued

| Compound No. | Structure | Name |
|---|---|---|
| 3A-5 | 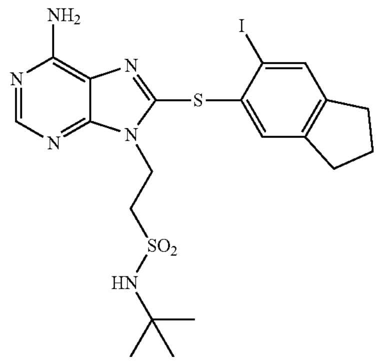 | 2-[6-Amino-8-(6-iodo-indan-5-ylsulfanyl)-purin-9-yl]-ethanesulfonic acid tert-butylamide |
| 3A-6 | 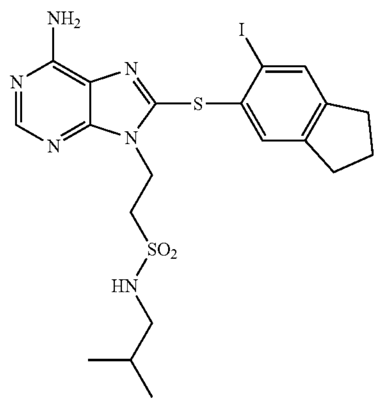 | 2-[6-Amino-8-(6-iodo-indan-5-ylsulfanyl)-purin-9-yl]-ethanesulfonic acid isobutyl-amide |
| 3A-7 | 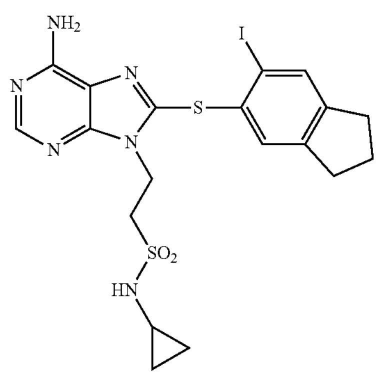 | 2-[6-Amino-8-(6-iodo-indan-5-ylsulfanyl)-purin-9-yl]-ethanesulfonic acid cyclopropylamide |
| 3A-8 | 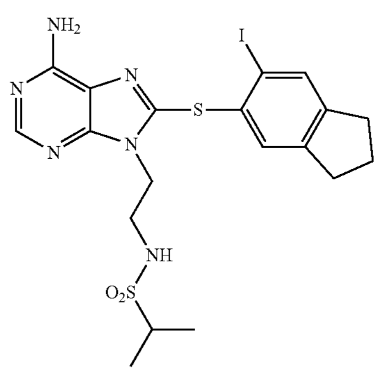 | Propane-2-sulfonic acid {2-[6-amino-8-(6-iodo-indan-5-ylsulfanyl)-purin-9-yl]-ethyl}-amide |

TABLE 3A-continued

| Compound No. | Structure | Name |
| --- | --- | --- |
| 3A-9 | 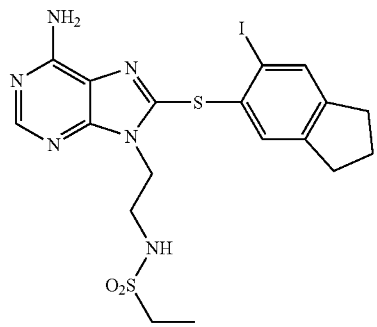 | Ethanesulfonic acid {2-[6-amino-8-(6-iodo-indan-5-ylsulfanyl)-purin-9-yl]-ethyl}-amide |
| 3A-10 | 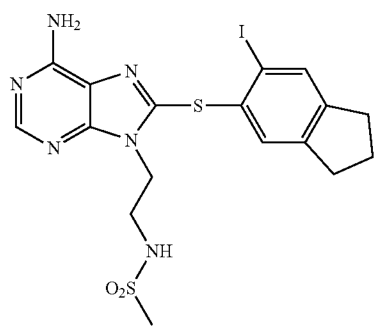 | N-{2-[6-Amino-8-(6-iodo-indan-5-ylsulfanyl)-purin-9-yl]-ethyl}-methanesulfonamide |
| 3A-11 | 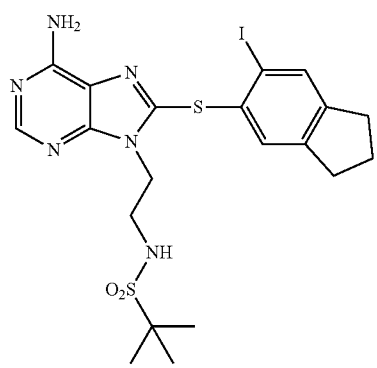 | 2-Methyl-propane-2-sulfonic acid {2-[6-amino-8-(6-iodo-indan-5-ylsulfanyl)-purin-9-yl]-ethyl}-amide |
| 3A-12 | 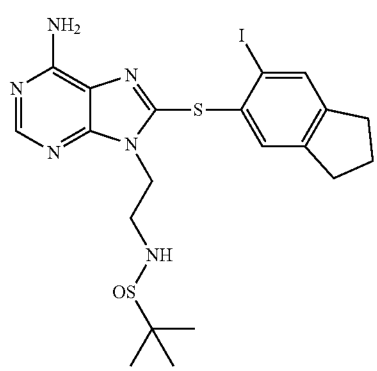 | 2-Methyl-propane-2-sulfinic acid {2-[6-amino-8-(6-iodo-indan-5-ylsulfanyl)-purin-9-yl]-ethyl}-amide |

TABLE 3A-continued

| Compound No. | Structure | Name |
|---|---|---|
| 3A-13 | 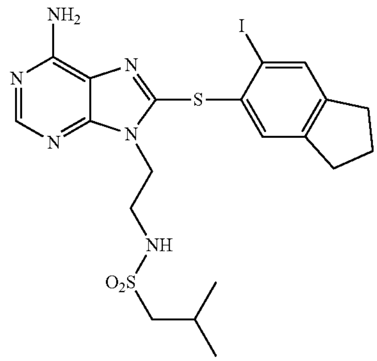 | 2-Methyl-propane-1-sulfonic acid {2-[6-amino-8-(6-iodo-indan-5-ylsulfanyl)-purin-9-yl]-ethyl}-amide |
| 3A-14 | 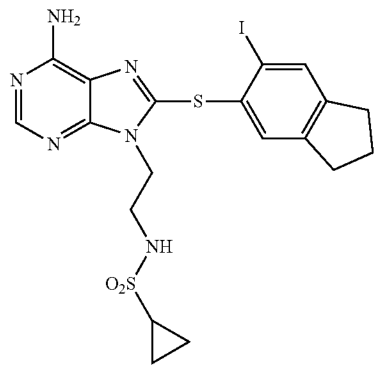 | Cyclopropanesulfonic acid {2-[6-amino-8-(6-iodo-indan-5-ylsulfanyl)-purin-9-yl]-ethyl}-amide |
| 3A-15 | 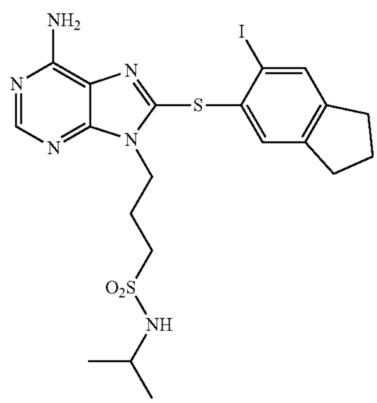 | 3-[6-Amino-8-(6-iodo-indan-5-ylsulfanyl)-purin-9-yl]-propane-1-sulfonic acid isopropylamide |
| 3A-16 | 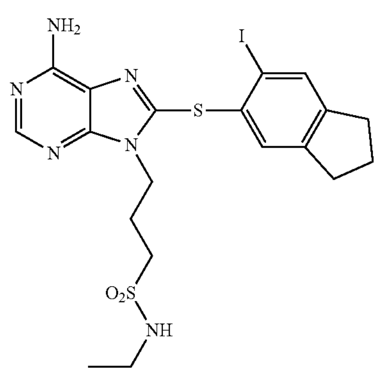 | 3-[6-Amino-8-(6-iodo-indan-5-ylsulfanyl)-purin-9-yl]-propane-1-sulfonic acid ethylamide |

TABLE 3A-continued

| Compound No. | Structure | Name |
|---|---|---|
| 3A-17 | 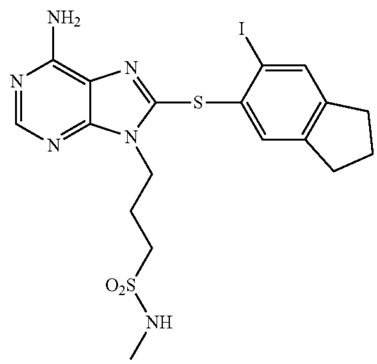 | 3-[6-Amino-8-(6-iodo-indan-5-ylsulfanyl)-purin-9-yl]-propane-1-sulfonic acid methylamide |
| 3A-18 | 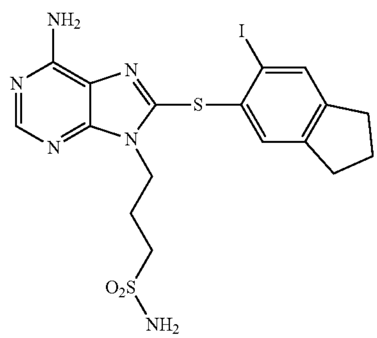 [SMILES: Nc1ncnc2c1nc(Sc1cc3c(cc1I)CCC3)n2CCCS(N)(=O)=O] | 3-[6-Amino-8-(6-iodo-indan-5-ylsulfanyl)-purin-9-yl]-propane-1-sulfonic acid amide |
| 3A-19 | 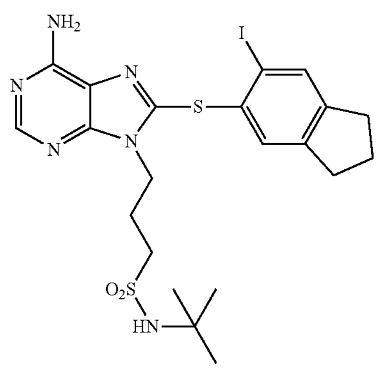 | 3-[6-Amino-8-(6-iodo-indan-5-ylsulfanyl)-purin-9-yl]-propane-1-sulfonic acid tert-butylamide |
| 3A-20 | 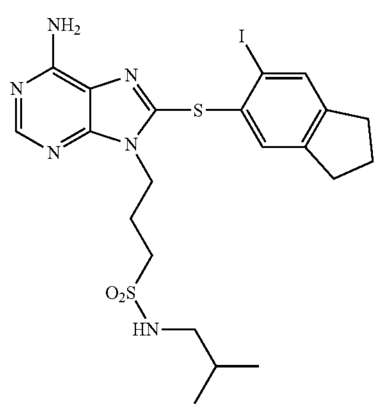 | 3-[6-Amino-8-(6-iodo-indan-5-ylsulfanyl)-purin-9-yl]-propane-1-sulfonic acid isobutyl-amide |

TABLE 3A-continued

| Compound No. | Structure | Name |
|---|---|---|
| 3A-21 | 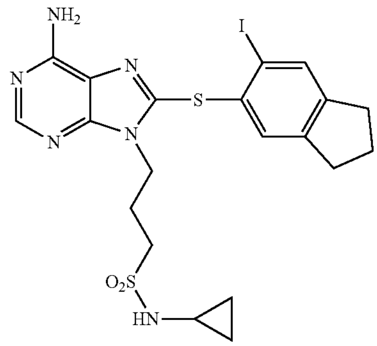 | 3-[6-Amino-8-(6-iodo-indan-5-ylsulfanyl)-purin-9-yl]-propane-1-sulfonic acid cyclopropylamide |
| 3A-22 | 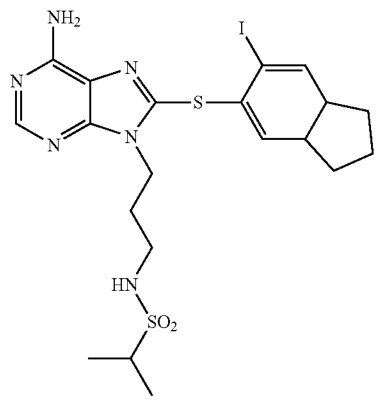 [SMILES: CC(C)S(=O)(=O)NCCCn1c(SC2=CC3CCCC3C=C2I)nc2c(N)ncnc21] | Propane-2-sulfonic acid {3-[6-amino-8-(6-iodo-2,3,3a,7a-tetrahydro-1H-inden-5-ylsulfanyl)-purin-9-yl]-propyl}-amide |
| 3A-23 | 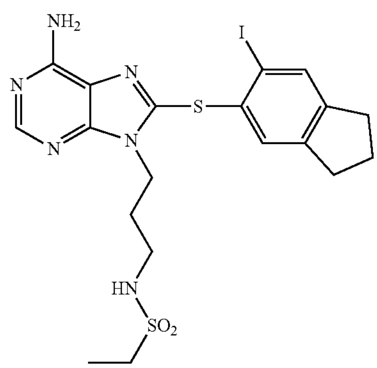 [SMILES: CCS(=O)(=O)NCCCn1c(Sc2cc3c(cc2I)CCC3)nc2c(N)ncnc21] | Ethanesulfonic acid {3-[6-amino-8-(6-iodo-indan-5-ylsulfanyl)-purin-9-yl]-propyl}-amide |
| 3A-24 | 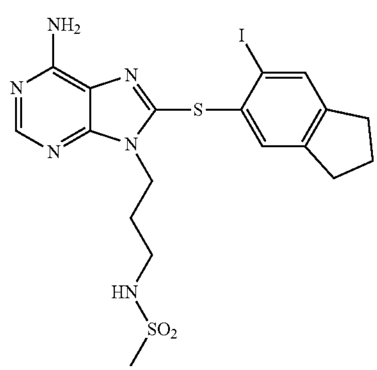 | N-{3-[6-Amino-8-(6-iodo-indan-5-ylsulfanyl)-purin-9-yl]-propyl}-methanesulfonamide |

| Compound No. | Structure | Name |
|---|---|---|
| 3A-25 | 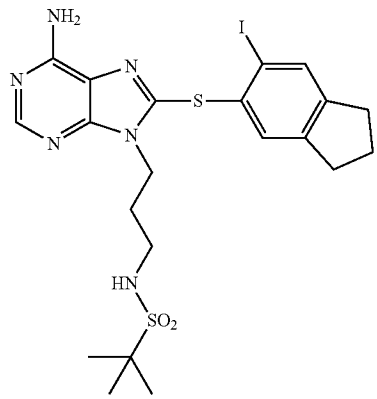 | 2-Methyl-propane-2-sulfonic acid {3-[6-amino-8-(6-iodo-indan-5-ylsulfanyl)-purin-9-yl]-propyl}-amide |
| 3A-26 | 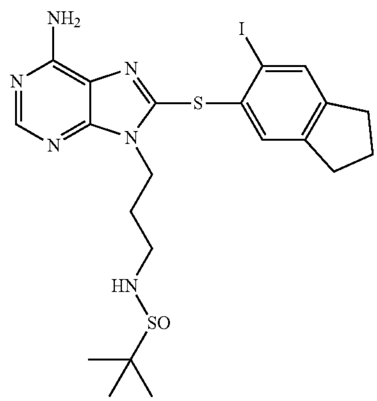 | 2-Methyl-propane-2-sulfinic acid {3-[6-amino-8-(6-iodo-indan-5-ylsulfanyl)-purin-9-yl]-propyl}-amide |
| 3A-27 | 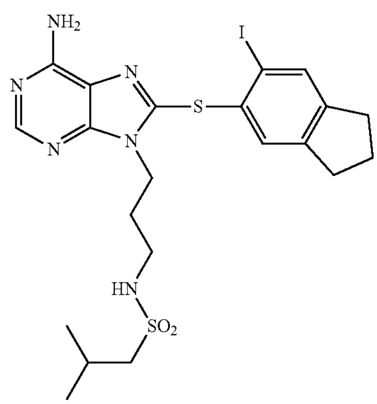 [SMILES: CC(C)CS(=O)(=O)NCCCn1c(Sc2cc3c(cc2I)CCC3)nc2c(N)ncnc21] | 2-Methyl-propane-1-sulfonic acid {3-[6-amino-8-(6-iodo-indan-5-ylsulfanyl)-purin-9-yl]-propyl}-amide |
| 3A-28 | 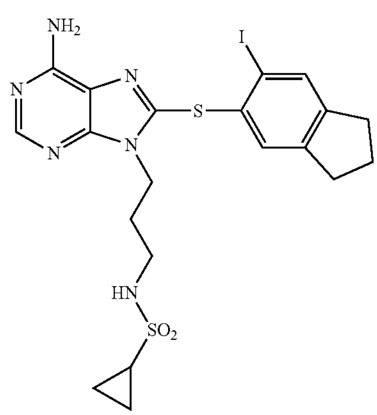 [SMILES: Nc1ncnc2c1nc(Sc1cc3c(cc1I)CCC3)n2CCCNS(=O)(=O)C1CC1] | Cyclopropanesulfonic acid {3-[6-amino-8-(6-iodo-indan-5-ylsulfanyl)-purin-9-yl]-propyl}-amide |

TABLE 3A-continued
| Compound No. | Structure | Name |
|---|---|---|
| 3A-29 | 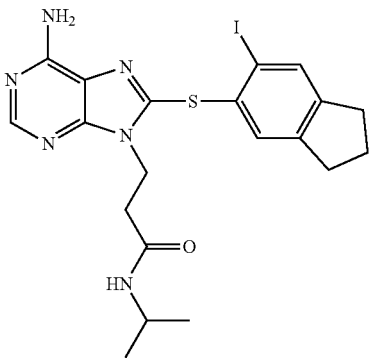 | 3-[6-Amino-8-(6-iodo-indan-5-ylsulfanyl)-purin-9-yl]-N-isopropyl-propionamide |
| 3A-30 | 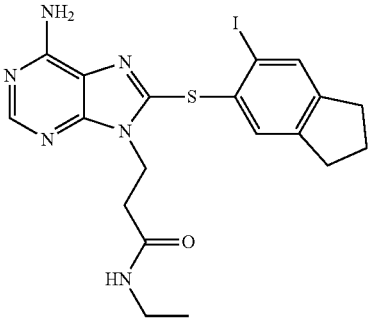 | 3-[6-Amino-8-(6-iodo-indan-5-ylsulfanyl)-purin-9-yl]-N-ethyl-propionamide |
| 3A-31 | 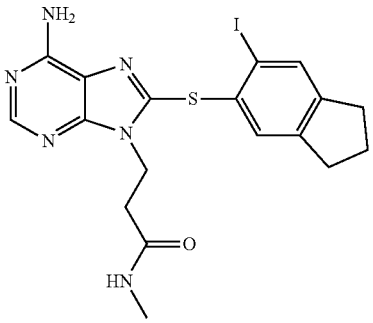 | 3-[6-Amino-8-(6-iodo-indan-5-ylsulfanyl)-purin-9-yl]-N-methyl-propionamide |
| 3A-32 | 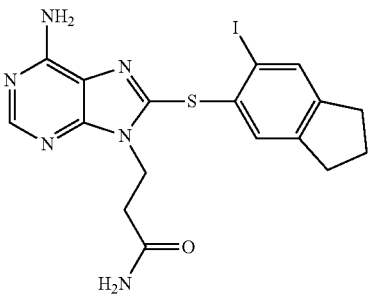 | 3-[6-Amino-8-(6-iodo-indan-5-ylsulfanyl)-purin-9-yl]-propionamide |

TABLE 3A-continued

| Compound No. | Structure | Name |
|---|---|---|
| 3A-33 | 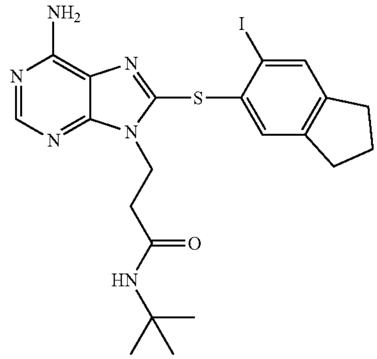 | 3-[6-Amino-8-(6-iodo-indan-5-ylsulfanyl)-purin-9-yl]-N-tert-butyl-propionamide |
| 3A-34 | 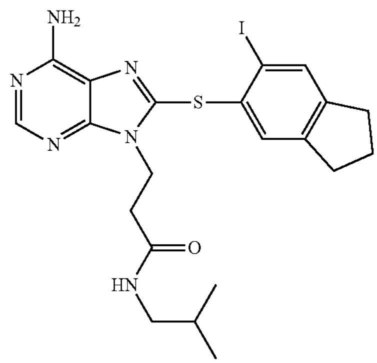 | 3-[6-Amino-8-(6-iodo-indan-5-ylsulfanyl)-purin-9-yl]-N-isobutyl-propionamide |
| 3A-35 | 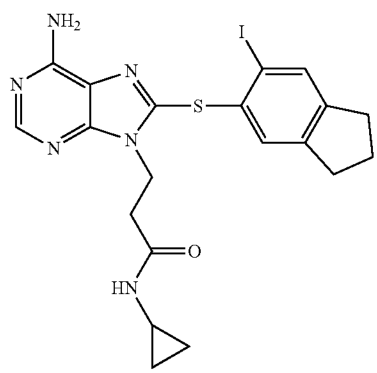 | 3-[6-Amino-8-(6-iodo-indan-5-ylsulfanyl)-purin-9-yl]-N-cyclopropyl-propionamide |
| 3A-36 | 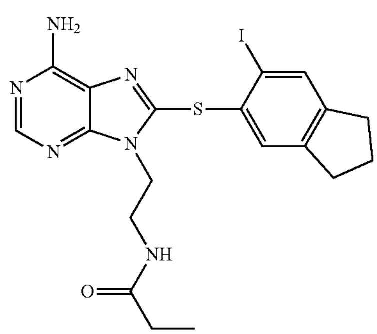 | N-{2-[6-Amino-8-(6-iodo-indan-5-ylsulfanyl)-purin-9-yl]-ethyl}-propionamide |

TABLE 3A-continued
| Compound No. | Structure | Name |
|---|---|---|
| 3A-37 | 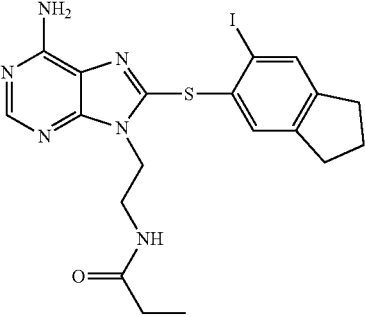 | N-{2-[6-Amino-8-(6-iodo-indan-5-ylsulfanyl)-purin-9-yl]-ethyl}-propionamide |
| 3A-38 | 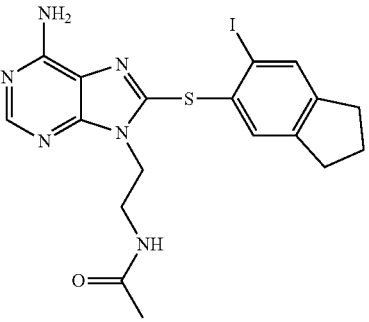 [SMILES: CC(=O)NCCn1c(Sc2cc3c(cc2I)CCC3)nc2c(N)ncnc21] | N-{2-[6-Amino-8-(6-iodo-indan-5-ylsulfanyl)-purin-9-yl]-ethyl}-acetamide |
| 3A-39 | 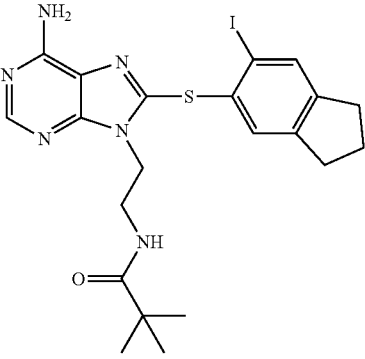 | N-{2-[6-Amino-8-(6-iodo-indan-5-ylsulfanyl)-purin-9-yl]-ethyl}-2,2-dimethyl-propionamide |
| 3A-40 | 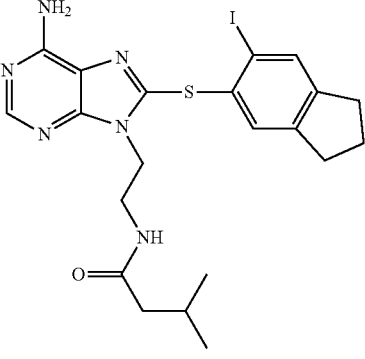 | N-{2-[6-Amino-8-(6-iodo-indan-5-ylsulfanyl)-purin-9-yl]-ethyl}-3-methyl-butyramide |

TABLE 3A-continued

| Compound No. | Structure | Name |
|---|---|---|
| 3A-41 | 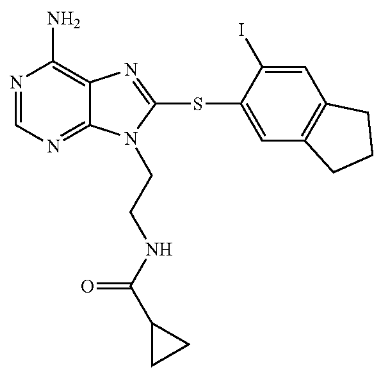 | Cyclopropanecarboxylic acid {2-[6-amino-8-(6-iodo-indan-5-ylsulfanyl)-purin-9-yl]-ethyl}-amide |
| 3A-42 | 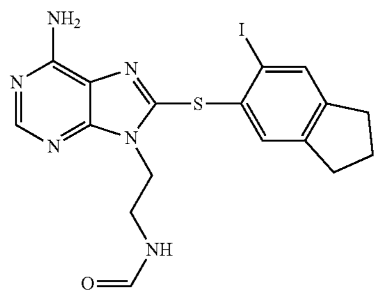 | N-{2-[6-Amino-8-(6-iodo-indan-5-ylsulfanyl)-purin-9-yl]-ethyl}-formamide |
| 3A-43 | 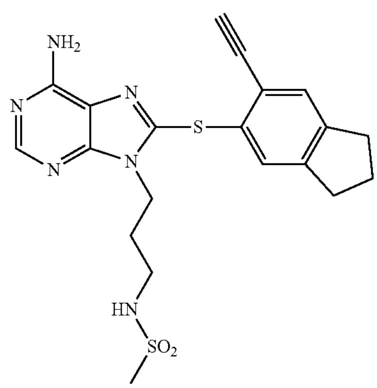 | N-{3-[6-Amino-8-(6-ethynyl-indan-5-ylsulfanyl)-purin-9-yl]-propyl}-methanesulfonamide |
| 3A-44 | 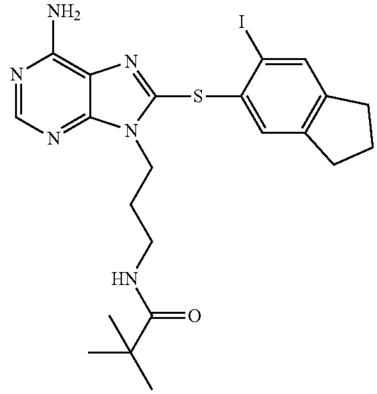 | N-{3-[6-Amino-8-(6-iodo-indan-5-ylsulfanyl)-purin-9-yl]-propyl}-2,2-dimethyl-propionamide |

| Compound No. | Structure | Name |
|---|---|---|
| 3A-45 | 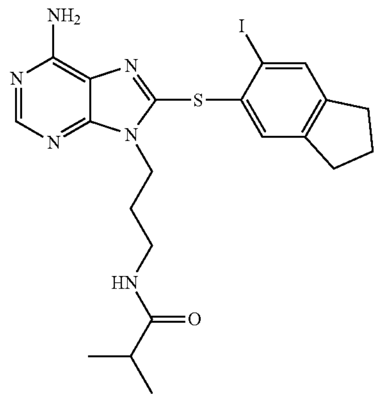 | N-{3-[6-Amino-8-(6-iodo-indan-5-ylsulfanyl)-purin-9-yl]-propyl}-isobutyramide |
| 3A-46 | 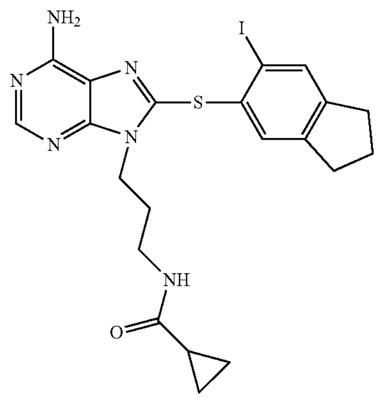 | Cyclopropanecarboxylic acid {3-[6-amino-8-(6-iodo-indan-5-ylsulfanyl)-purin-9-yl]-propyl}-amide |
| 3A-47 | 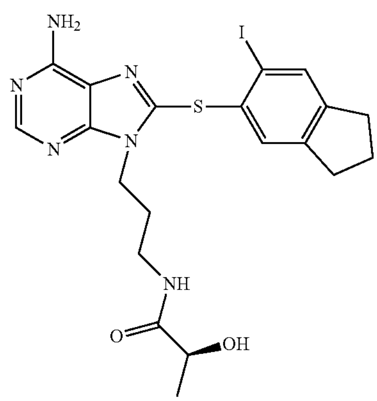 | N-{3-[6-Amino-8-(6-iodo-indan-5-ylsulfanyl)-purin-9-yl]-propyl}-2-hydroxy-propionamide |
| 3A-48 | 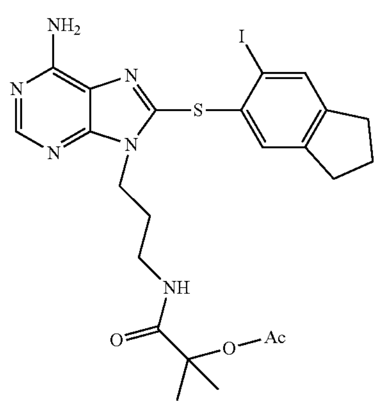 | Acetic acid 1-{3-[6-amino-8-(6-iodo-indan-5-ylsulfanyl)-purin-9-yl]-propylcarbamoyl}-1-methyl-ethyl ester |

TABLE 3A-continued

| Compound No. | Structure | Name |
| --- | --- | --- |
| 3A-49 | 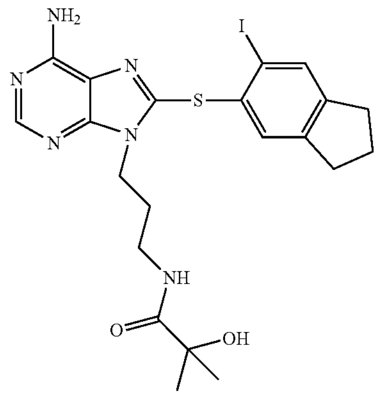 [SMILES: CC(C)(O)C(=O)NCCCn1c(Sc2cc3c(cc2I)CCC3)nc2c(N)ncnc21] | N-{3-[6-Amino-8-(6-iodo-indan-5-ylsulfanyl)-purin-9-yl]-propyl}-2-hydroxy-2-methyl-propionamide |

Table 6A lists specific examples in which $X_2$ is halogen and $X_4$ is halogen. In each of the structures as drawn, $X_2$ is I and $X_4$ is F. However, corresponding structures in which $X_4$ is H, Cl, Br, or I are within the scope of the disclosure. In each of the structures in Table 6A, Y is $CH_2$. However, corresponding structures in which Y is S and/or $X_2$ is F, Cl, or Br are also within the scope of the disclosure. Additionally, in connection with each of the structures in Table 6A, corresponding structures in which $X_4$ is H, Cl, Br, or I and Y is S are also within the scope of the disclosure.

TABLE 6A

| Compound No. | Structure | Name |
| --- | --- | --- |
| 6A-1 | 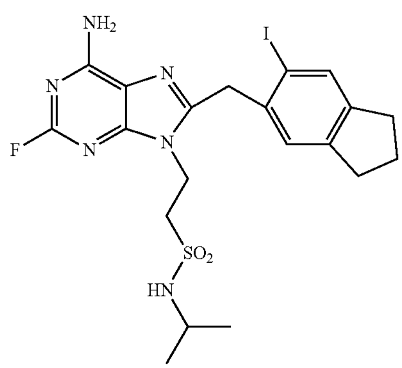 [SMILES: CC(C)NS(=O)(=O)CCn1c(Cc2cc3c(cc2I)CCC3)nc2c(N)nc(F)nc21] | 2-(6-amino-2-fluoro-8-((6-iodo-2,3-dihydro-1H-inden-5-yl)methyl)-9H-purin-9-yl)-N-isopropylethanesulfonamide |
| 6A-2 | 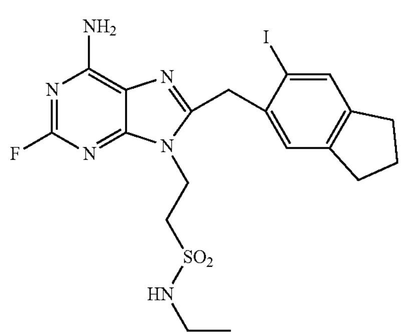 | 2-(6-amino-2-fluoro-8-((6-iodo-2,3-dihydro-1H-inden-5-yl)methyl)-9H-purin-9-yl)-N-ehtylethanesulfonamide |

TABLE 6A-continued

| Compound No. | Structure | Name |
| --- | --- | --- |
| 6A-3 | 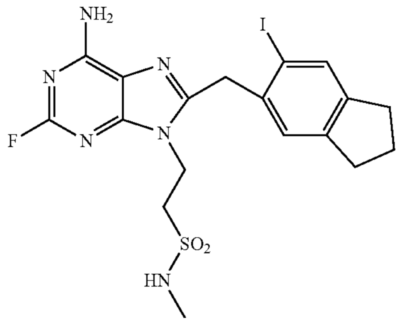 | 2-(6-amino-2-fluoro-8-((6-iodo-2,3-dihydro-1H-inden-5-yl)methyl)-9H-purin-9-yl)-N-methylethanesulfonamide |
| 6A-4 | 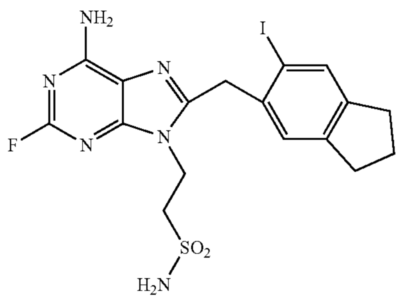 | 2-(6-amino-2-fluoro-8-((6-iodo-2,3-dihydro-1H-inden-5-yl)methyl)-9H-purin-9-yl)ethanesulfonamide |
| 6A-5 | 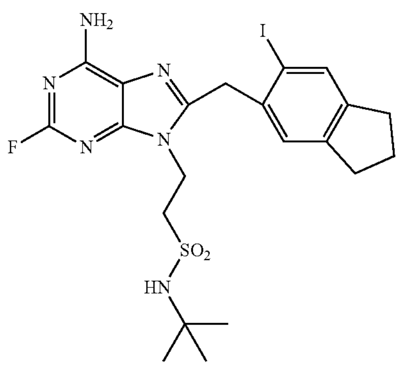 | 2-(6-amino-2-fluoro-8-((6-iodo-2,3-dihydro-1H-inden-5-yl)methyl)-9H-purin-9-yl)-N-(tert-butyl)ethanesulfonamide |
| 6A-6 | 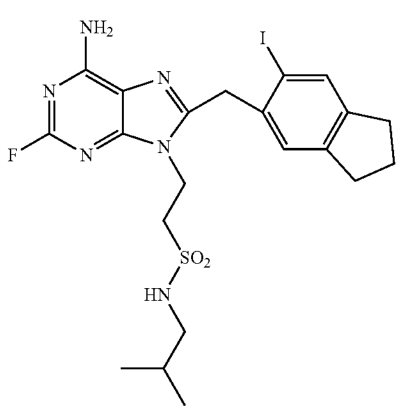 | 2-(6-amino-2-fluoro-8-((6-iodo-2,3-dihydro-1H-inden-5-yl)methyl)-9H-purin-9-yl)-N-isobutylethanesulfonamide |

TABLE 6A-continued

| Compound No. | Structure | Name |
|---|---|---|
| 6A-7 | 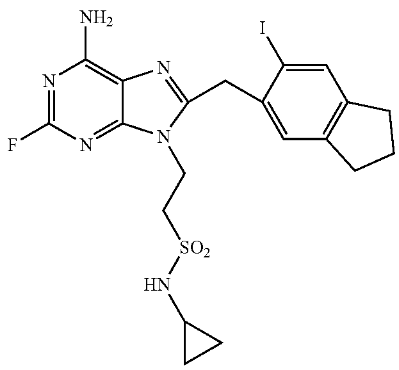 | 2-(6-amino-2-fluoro-8-((6-iodo-2,3-dihydro-1H-inden-5-yl)methyl)-9H-purin-9-yl)-N-cyclopropyl-ethanesulfonamide |
| 6A-8 | 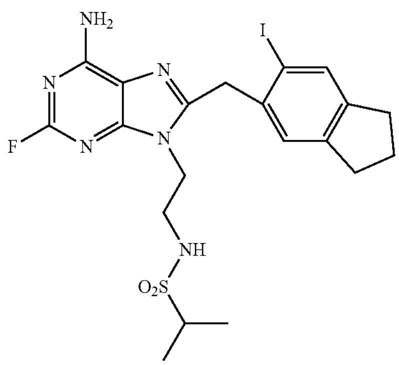 | N-(2-(6-amino-2-fluoro-8-((6-iodo-2,3-dihydro-1H-inden-5-yl)methyl)-9H-purin-9-yl)ethyl)propane-2-sulfonamide |
| 6A-9 | 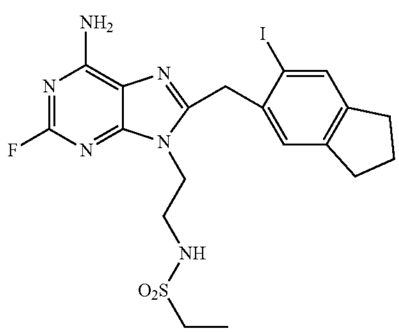 | N-(2-(6-amino-2-fluoro-8-((6-iodo-2,3-dihydro-1H-inden-5-yl)methyl)-9H-purin-9-yl)ethyl)ethanesulfonamide |
| 6A-10 | 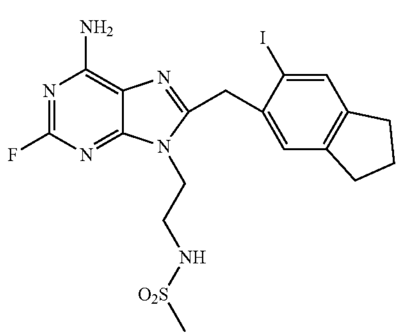 | N-(2-(6-amino-2-fluoro-8-((6-iodo-2,3-dihydro-1H-inden-5-yl)methyl)-9H-purin-9-yl)ethyl)methanesulfonamide |

TABLE 6A-continued

| Compound No. | Structure | Name |
|---|---|---|
| 6A-11 | 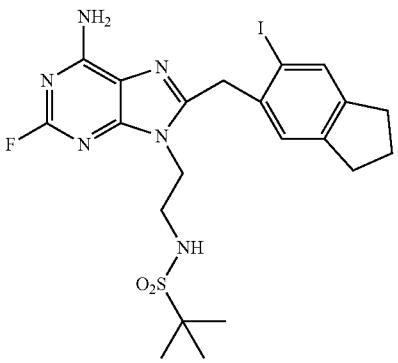 | N-(2-(6-amino-2-fluoro-8-((6-iodo-2,3-dihydro-1H-inden-5-yl)methyl)-9H-purin-9-yl)ethyl)-2-methylpropane-2-sulfonamide |
| 6A-12 | 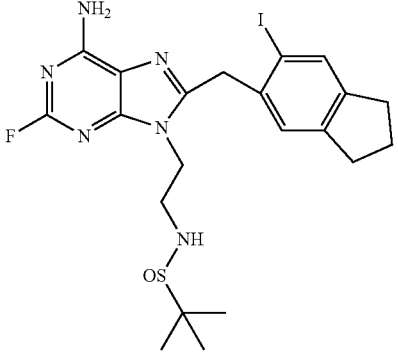 | N-(2-(6-amino-2-fluoro-8-((6-iodo-2,3-dihydro-1H-inden-5-yl)methyl)-9H-purin-9-yl)ethyl)-2-methylpropane-2-sulfinamide |
| 6A-13 | 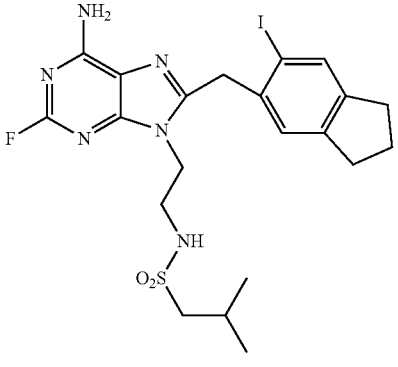 [SMILES: CC(C)CS(=O)(=O)NCCn1c(Cc2cc3c(cc2I)CCC3)nc2c(N)nc(F)nc21] | N-(2-(6-amino-2-fluoro-8-((6-iodo-2,3-dihydro-1H-inden-5-yl)methyl)-9H-purin-9-yl)ethyl)-2-methylpropane-1-sulfonamide |
| 6A-14 | 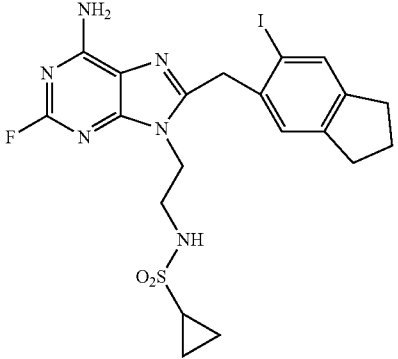 | N-(2-(6-amino-2-fluoro-8-((6-iodo-2,3-dihydro-1H-inden-5-yl)methyl)-9H-purin-9-yl)ethyl)cyclopropane-sulfonamide |

TABLE 6A-continued

| Compound No. | Structure | Name |
|---|---|---|
| 6A-15 | 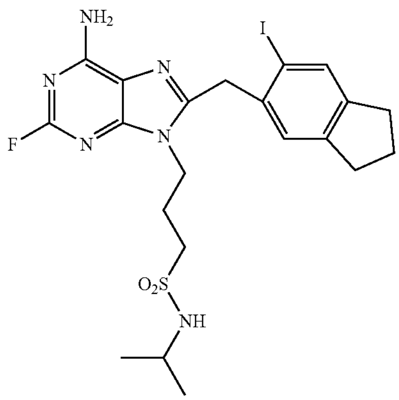 | 3-(6-amino-2-fluoro-8-((6-iodo-2,3-dihydro-1H-inden-5-yl)methyl)-9H-purin-9-yl)-N-isopropylpropane-1-sulfonamide |
| 6A-16 | 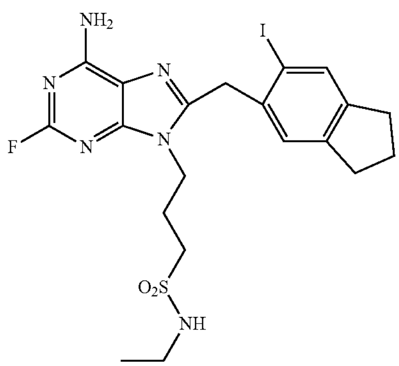 | 3-(6-amino-2-fluoro-8-((6-iodo-2,3-dihydro-1H-inden-5-yl)methyl)-9H-purin-9-yl)-N-ethylpropane-1-sulfonamide |
| 6A-17 | 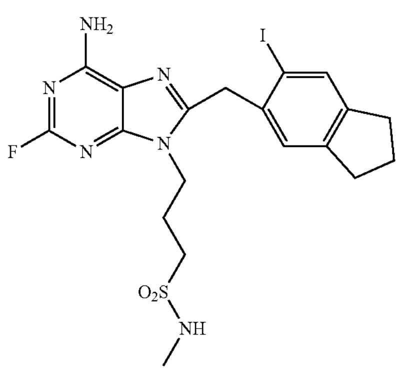 | 3-(6-amino-2-fluoro-8-((6-iodo-2,3-dihydro-1H-inden-5-yl)methyl)-9H-purin-9-yl)-N-methylpropane-1-sulfonamide |
| 6A-18 | 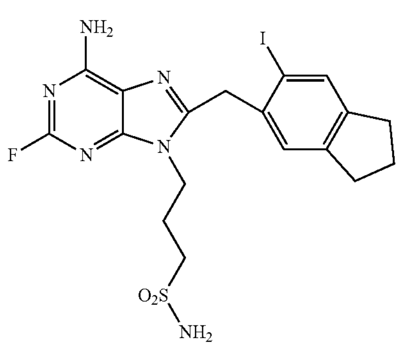 | 3-(6-amino-2-fluoro-8-((6-iodo-2,3-dihydro-1H-inden-5-yl)methyl)-9H-purin-9-yl)-N-propanesulfonamide |

TABLE 6A-continued

| Compound No. | Structure | Name |
| --- | --- | --- |
| 6A-19 | 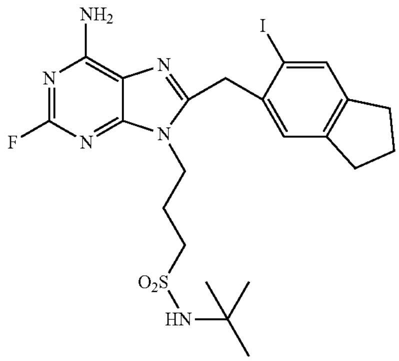 | 3-(6-amino-2-fluoro-8-((6-iodo-2,3-dihydro-1H-inden-5-yl)methyl)-9H-purin-9-yl)-N-(tert-butyl)propane-1-sulfonamide |
| 6A-20 | 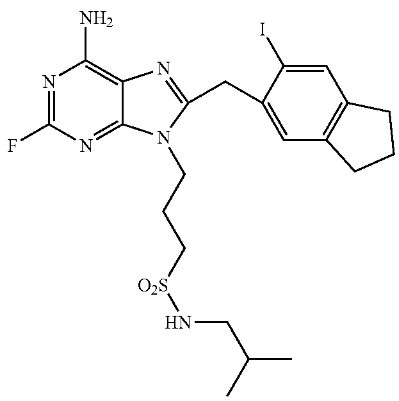 | 3-(6-amino-2-fluoro-8-((6-iodo-2,3-dihydro-1H-inden-5-yl)methyl)-9H-purin-9-yl)-N-isobutylpropane-1-sulfonamide |
| 6A-21 | 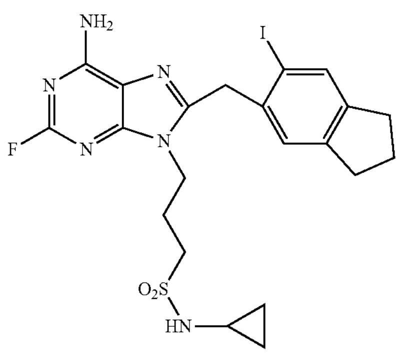 | 3-(6-amino-2-fluoro-8-((6-iodo-2,3-dihydro-1H-inden-5-yl)methyl)-9H-purin-9-yl)-N-cyclopropylpropane-1-sulfonamide |
| 6A-22 | 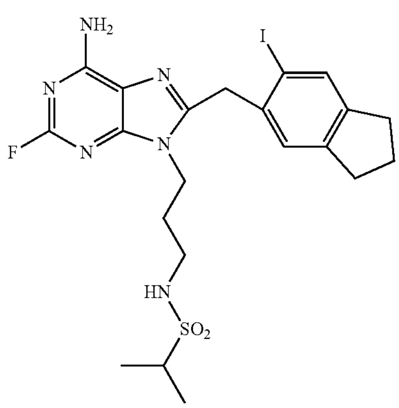 | N-(3-(6-amino-2-fluoro-8-((6-iodo-2,3-dihydro-1H-inden-5-yl)methyl)-9H-purin-9-yl)propyl)propane-2-sulfonamide |

TABLE 6A-continued

| Compound No. | Structure | Name |
|---|---|---|
| 6A-23 | 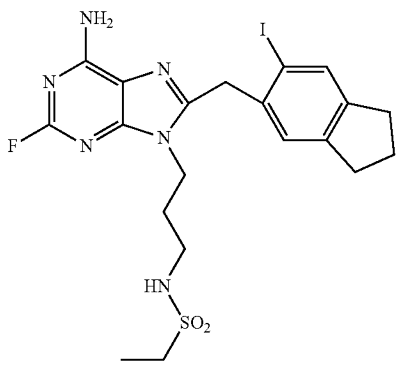 | N-(3-(6-amino-2-fluoro-8-((6-iodo-2,3-dihydro-1H-inden-5-yl)methyl)-9H-purin-9-yl)propyl)ethanesulfonamide |
| 6A-24 | 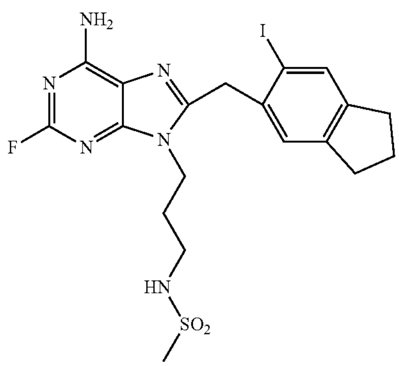 | N-(3-(6-amino-2-fluoro-8-((6-iodo-2,3-dihydro-1H-inden-5-yl)methyl)-9H-purin-9-yl)propyl)methanesulfonamide |
| 6A-25 | 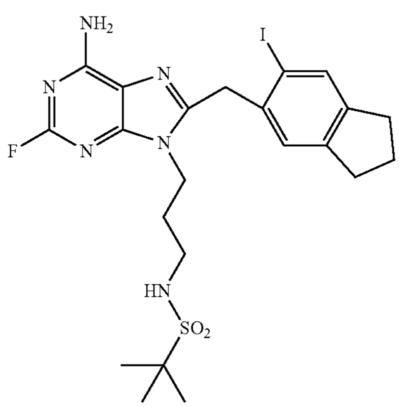 | N-(3-(6-amino-2-fluoro-8-((6-iodo-2,3-dihydro-1H-inden-5-yl)methyl)-9H-purin-9-yl)propyl)-2-methylpropane-2-sulfonamide |
| 6A-26 | 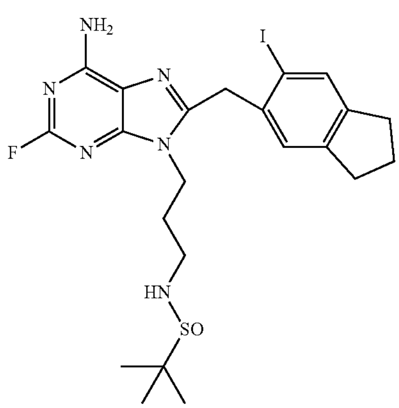 | N-(3-(6-amino-2-fluoro-8-((6-iodo-2,3-dihydro-1H-inden-5-yl)methyl)-9H-purin-9-yl)propyl)-2-methylpropane-2-sulfinamide |

TABLE 6A-continued

| Compound No. | Structure | Name |
|---|---|---|
| 6A-27 | 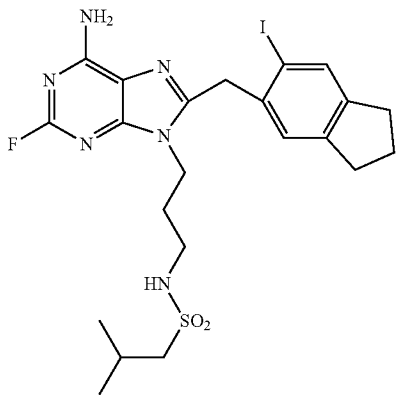 | N-(3-(6-amino-2-fluoro-8-((6-iodo-2,3-dihydro-1H-inden-5-yl)methyl)-9H-purin-9-yl)propyl)-2-methylpropane-1-sulfonamide |
| 6A-28 | 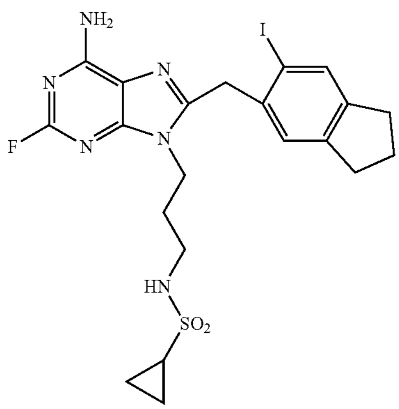 | N-(3-(6-amino-2-fluoro-8-((6-iodo-2,3-dihydro-1H-inden-5-yl)methyl)-9H-purin-9-yl)propyl)cyclopropane-sulfonamide |
| 6A-29 | 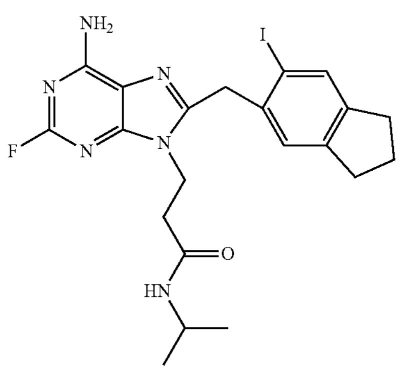 | 3-(6-amino-2-fluoro-8-((6-iodo-2,3-dihydro-1H-inden-5-yl)methyl)-9H-purin-9-yl)-N-isopropylpropanamide |
| 6A-30 | 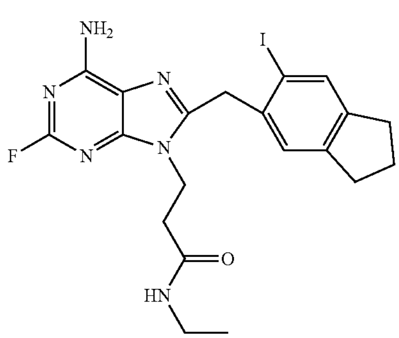 | 3-(6-amino-2-fluoro-8-((6-iodo-2,3-dihydro-1H-inden-5-yl)methyl)-9H-purin-9-yl)-N-ethylpropanamide |

TABLE 6A-continued

| Compound No. | Structure | Name |
|---|---|---|
| 6A-31 | 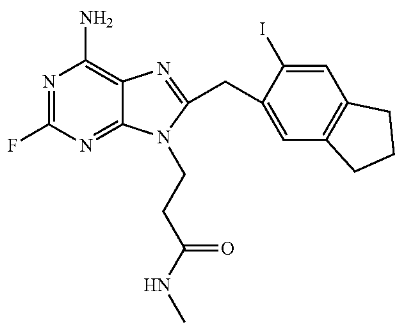 | 3-(6-amino-2-fluoro-8-((6-iodo-2,3-dihydro-1H-inden-5-yl)methyl)-9H-purin-9-yl)-N-methylpropanamide |
| 6A-32 | 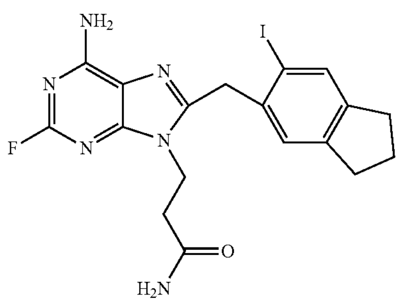 | 3-(6-amino-2-fluoro-8-((6-iodo-2,3-dihydro-1H-inden-5-yl)methyl)-9H-purin-9-yl)-N-propanamide |
| 6A-33 | 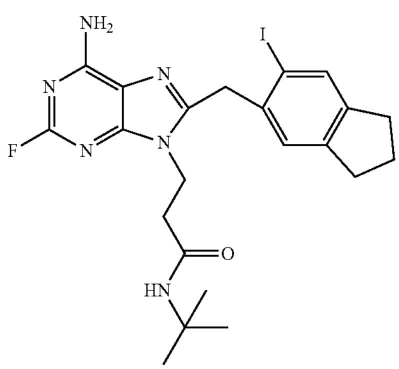 | 3-(6-amino-2-fluoro-8-((6-iodo-2,3-dihydro-1H-inden-5-yl)methyl)-9H-purin-9-yl)-N-(tert-butyl)propanamide |
| 6A-34 | 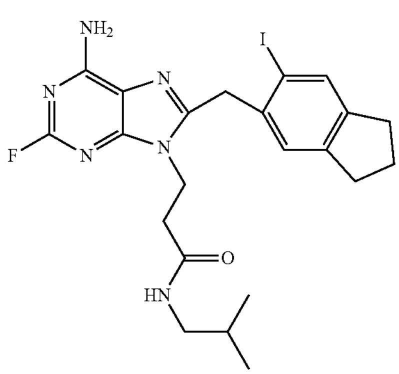 | 3-(6-amino-2-fluoro-8-((6-iodo-2,3-dihydro-1H-inden-5-yl)methyl)-9H-purin-9-yl)-N-isobutylpropanamide |

TABLE 6A-continued
| Compound No. | Structure | Name |
|---|---|---|
| 6A-35 | 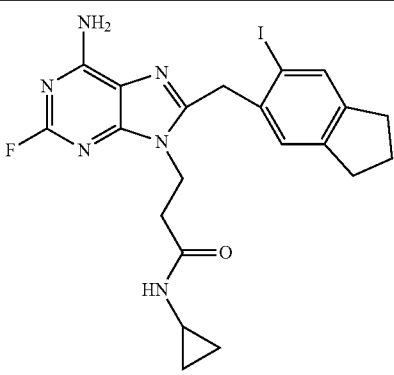 | 3-(6-amino-2-fluoro-8-((6-iodo-2,3-dihydro-1H-inden-5-yl)methyl)-9H-purin-9-yl)-N-cyclopropylpropanamide |
| 6A-36 | 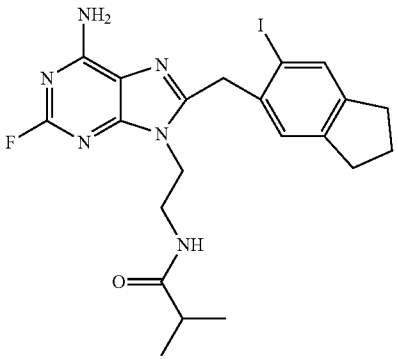 [SMILES: CC(C)C(=O)NCCn1c(Cc2cc3c(cc2I)CCC3)nc2c(N)nc(F)nc21] | N-(2-(6-amino-2-fluoro-8-((6-odo-2,3-dihydro-1H-inden-5-yl)methyl)-9H-purin-9-yl)ethyl)isobutyramide |
| 6A-37 | 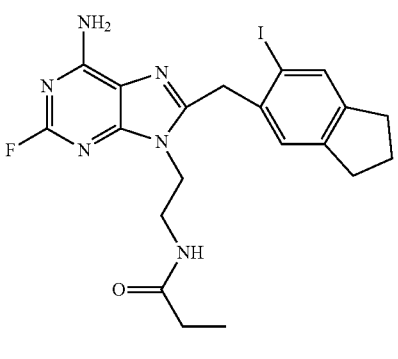 | N-(2-(6-amino-2-fluoro-8-((6-iodo-2,3-dihydro-1H-inden-5-yl)methyl)-9H-purin-9-yl)ethyl)propionamide |
| 6A-38 | 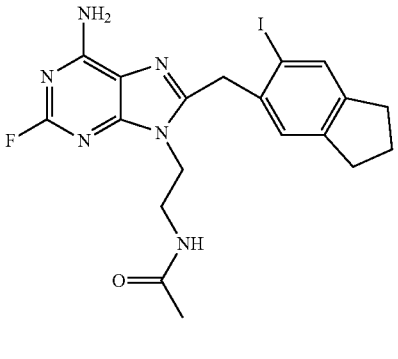 [SMILES: CC(=O)NCCn1c(Cc2cc3c(cc2I)CCC3)nc2c(N)nc(F)nc21] | N-(2-(6-amino-2-fluoro-8-((6-iodo-2,3-dihydro-1H-inden-5-yl)methyl)-9H-purin-9-yl)ethyl)acetamide |

TABLE 6A-continued

| Compound No. | Structure | Name |
|---|---|---|
| 6A-39 | 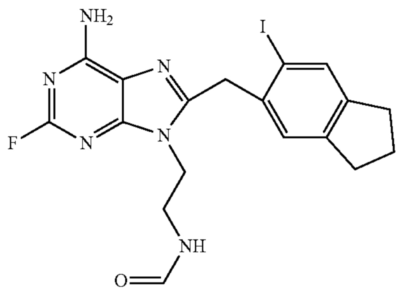 [SMILES: Nc1nc(F)nc2c1nc(Cc1cc3c(cc1I)CCC3)n2CCNC=O] | N-(2-(6-amino-2-fluoro-8-((6-iodo-2,3-dihydro-1H-inden-5-yl)methyl)-9H-purin-9-yl)ethyl)formamide |
| 6A-40 | 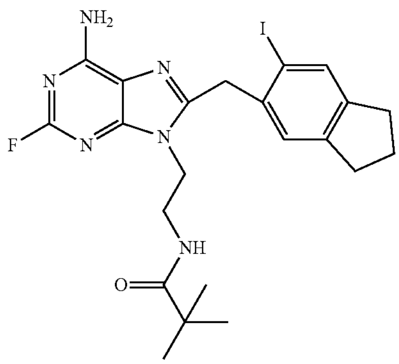 | N-(2-(6-amino-2-fluoro-8-((6-iodo-2,3-dihydro-1H-inden-5-yl)methyl)-9H-purin-9-yl)ethyl)pivalamide |
| 6A-41 | 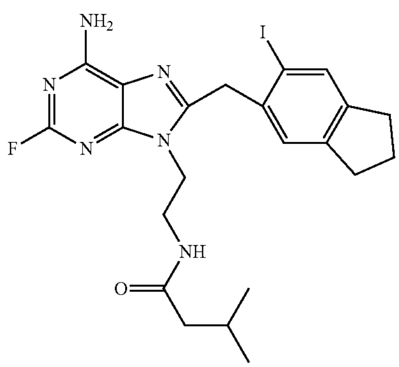 | N-(2-(6-amino-2-fluoro-8-((6-iodo-2,3-dihydro-1H-inden-5-yl)methyl)-9H-purin-9-yl)ethyl)-3-methylbutanamide |
| 6A-42 | 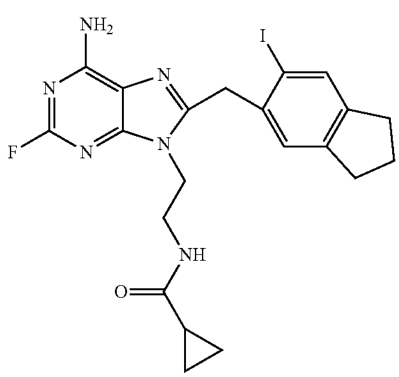 | N-(2-(6-amino-2-fluoro-8-((6-iodo-2,3-dihydro-1H-inden-5-yl)methyl)-9H-purin-9-yl)ethyl)cyclopropane-carboxamide |

Hsp90 binding results are presented for Compounds 3A-10, 3A-11, 3A-12, 3A-24 and 3A-26 in Table 12 below. As can be noted therefrom, all compounds showed a high level of binding affinity.

F-II. In some embodiments of the disclosure, $X_2$ is an optionally substituted aryl. Specific examples of compounds within the scope of this aspect of the disclosure correspond to the compounds disclosed in Tables 3A and 6A, or variations thereof as described in A. and F-I. above, in which $X_2$ is an optionally substituted aryl, including but not limited to pyrazolyl, 1H-pyrazol-3-yl, oxazolyl, oxazol-2-yl, thiazolyl, thiazol-2-yl, furanyl, furan-2-yl, and 5-methylfuran-2-yl.

F-III. In some embodiments of the disclosure, $X_2$ is an alkynyl group, e.g., ethynyl, 1-prop-1-ynyl, and 3-prop-1-ynyl. Specific examples of compounds within the scope of this aspect of the disclosure correspond to the compounds disclosed in Tables 3A and 6A, or variations thereof as described in A. and F-I. above, in which $X_2$ is an alkynyl group. Hsp90 binding results are presented for Compound 3A-43 in Table 12 below. As can be noted therefrom, the compound showed a high level of binding affinity.

F-IV. In some embodiments of the disclosure, $X_2$ is an amino group, i.e., —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Specific examples of compounds within the scope of this aspect of the disclosure correspond to the compounds disclosed in Tables 3A and 6A, or variations thereof as described in A. and F-I. above, in which $X_2$ is an amino group.

G. COMPOUNDS OF FORMULA (IA) IN WHICH AT LEAST ONE OF XA AND XB IS CHF OR $CF_2$

In accordance with another embodiment of the disclosure, the compounds are of Formula (IA) in which at least one of Xa and Xb is CHF or $CF_2$, the other of Xa and Xb is CHF, $CF_2$, or $CH_2$, and Xc is $CH_2$. Thus, the compounds of this embodiment can be represented by Formula (5):

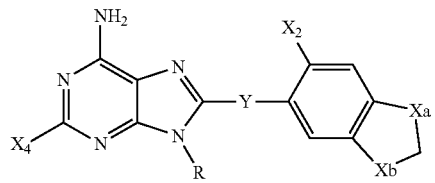

(5)

or a pharmaceutically acceptable salt thereof, wherein:
at least one of Xa and Xb is CHF or $CF_2$ and the other is CHF, $CF_2$, or $CH_2$;
Y is $CH_2$, O, or S;
$X_4$ is hydrogen or halogen;
R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_AS(O)$—, —$SO_2N(R_A)$—, —$NR_ASO_2$—, —C(O)N($R_A$)—, or —$NR_AC(O)$—, and/or terminated by —S(O)$NR_AR_B$, —$NR_AS(O)R_B$, —$SO_2NR_AR_B$, —$NR_ASO_2R_B$, —C(O)$NR_AR_B$, or —$NR_AC(O)R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and $X_2$ is as disclosed below.

In one embodiment, Y is O.

In another embodiment, Y is $CH_2$ or O.

In another embodiment, Y is $CH_2$ or S.

In another embodiment, Y is O or S.

G-I. In some embodiments of the disclosure, $X_2$ is halogen. Table 8A lists specific examples of compounds within this embodiment. In each of the structures as drawn, $X_2$ is I and $X_4$ is H. However, corresponding structures in which $X_2$ is F, Cl, or Br are within the scope of the disclosure. In each of the structures in Table 8A, Y is S. However, corresponding structures in which Y is $C_{1-2}$ or O and/or $X_4$ is F, Cl, Br, or I are also within the scope of the disclosure. In each of the structures in Table 8A, Xb is CHF and Xa is $CH_2$. However, corresponding structures in which Xa is CHF and Xb is $CH_2$, Xa is $CF_2$ and Xb is $CH_2$, Xb is $CF_2$ and Xa is $CH_2$, Xa is CHF and Xb is $CF_2$, Xb is CHF and Xa is $CF_2$, Xa is CHF and Xb is CHF, or Xa is $CF_2$ and Xb is $CF_2$ are also within the scope of the disclosure. Additionally, in connection with each of the structures in Table 8A, corresponding structures in which $X_2$ is F, Cl, or Br, Y is $CH_2$ or O, and Xa is CHF and Xb is $CH_2$, Xa is $CF_2$ and Xb is $CH_2$, Xb is $CF_2$ and Xa is $CH_2$, Xa is CHF and Xb is $CF_2$, Xb is CHF and Xa is $CF_2$, Xa is CHF and Xb is CHF, or Xa is $CF_2$ and Xb is $CF_2$ are also within the scope of the disclosure.

TABLE 8

| Compound No. | Structure | Name |
| --- | --- | --- |
| 8A-1 | ![structure] | 2-[6-Amino-8-(3-fluoro-6-iodo-indan-5-ylsulfanyl)-purin-9-yl]-ethanesulfonic acid isopropylamide |

TABLE 8-continued

| Compound No. | Structure | Name |
|---|---|---|
| 8A-2 | 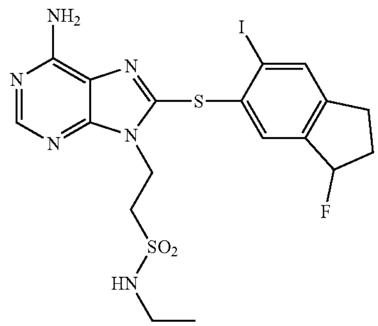 [SMILES: CCNS(=O)(=O)CCn1c(Sc2cc3c(cc2I)CCC3F)nc2c(N)ncnc21] | 2-[6-Amino-8-(3-fluoro-6-iodo-indan-5-ylsulfanyl)-purin-9-yl]-ethanesulfonic acid ethylamide |
| 8A-3 | 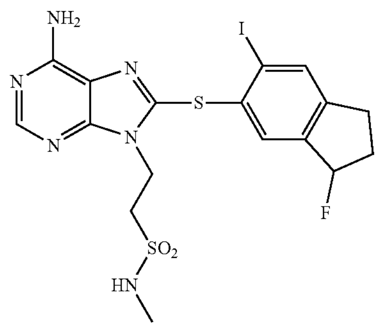 [SMILES: CNS(=O)(=O)CCn1c(Sc2cc3c(cc2I)CCC3F)nc2c(N)ncnc21] | 2-[6-Amino-8-(3-fluoro-6-iodo-indan-5-ylsulfanyl)-purin-9-yl]-ethanesulfonic acid methylamide |
| 8A-4 | 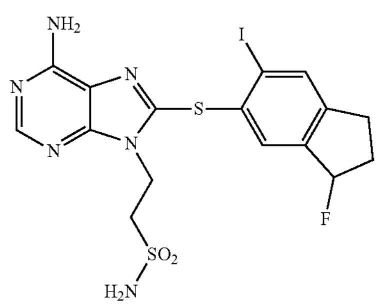 [SMILES: Nc1ncnc2c1nc(Sc1cc3c(cc1I)CCC3F)n2CCS(N)(=O)=O] | 2-[6-Amino-8-(3-fluoro-6-iodo-indan-5-ylsulfanyl)-pur-9-yl]-ethanesulfonic acid amide |
| 8A-5 | 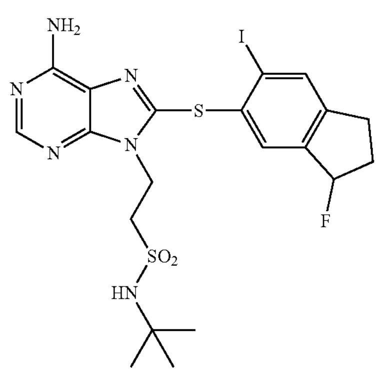 [SMILES: CC(C)(C)NS(=O)(=O)CCn1c(Sc2cc3c(cc2I)CCC3F)nc2c(N)ncnc21] | 2-[6-Amino-8-(3-fluoro-6-iodo-indan-5-ylsulfanyl)-purin-9-yl]-ethanesulfonic acid tert-butylamide |

TABLE 8-continued

| Compound No. | Structure | Name |
|---|---|---|
| 8A-6 | 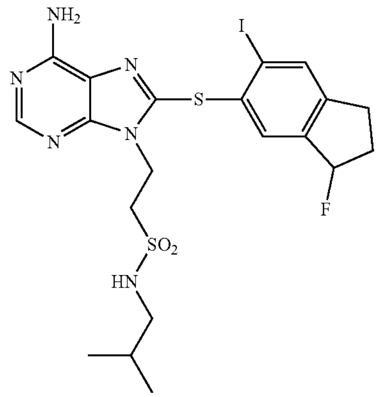 [SMILES: CC(C)CNS(=O)(=O)CCn1c(Sc2cc3c(cc2I)CCC3F)nc2c(N)ncnc21] | 2-[6-Amino-8-(3-fluoro-6-iodo-indan-5-ylsulfanyl)-purin-9-yl]-ethanesulfonic acid isobutyl-amide |
| 8A-7 | 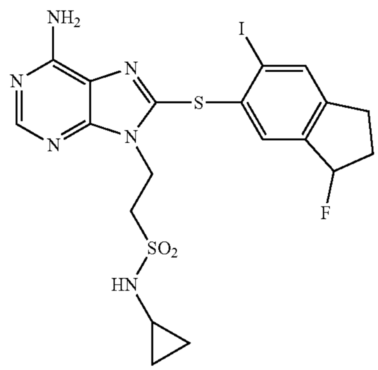 [SMILES: Nc1ncnc2c1nc(Sc1cc3c(cc1I)CCC3F)n2CCS(=O)(=O)NC1CC1] | 2-[6-Amino-8-(3-fluoro-6-iodo-indan-5-ylsulfanyl)-purin-9-yl]-ethanesulfonic acid cyclopropylamide |
| 8A-8 | 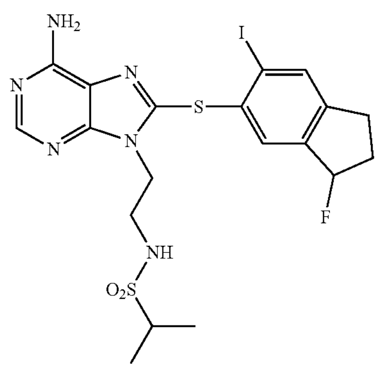 [SMILES: CC(C)S(=O)(=O)NCCn1c(Sc2cc3c(cc2I)CCC3F)nc2c(N)ncnc21] | Propane-2-sulfonic acid {2-[6-amino-8-(3-fluoro-6-iodo-indan-5-ylsulfanyl)-purin-9-yl]-ethyl}-amide |
| 8A-9 | 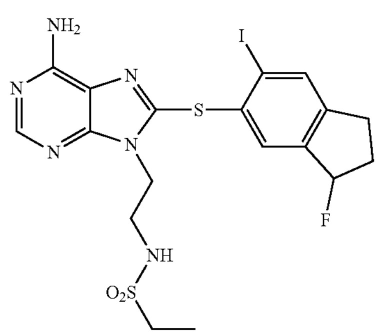 [SMILES: CCS(=O)(=O)NCCn1c(Sc2cc3c(cc2I)CCC3F)nc2c(N)ncnc21] | Ethanesulfonic acid {2-[6-amino-8-(3-fluoro-6-iodo-indan-5-ylsulfanyl)-purin-9-yl]-ethyl}-amide |

TABLE 8-continued

| Compound No. | Structure | Name |
|---|---|---|
| 8A-10 | 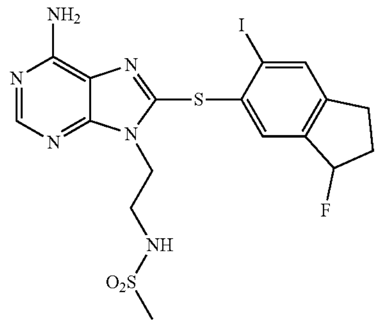 [SMILES: CS(=O)(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-methanesulfonamide |
| 8A-11 | 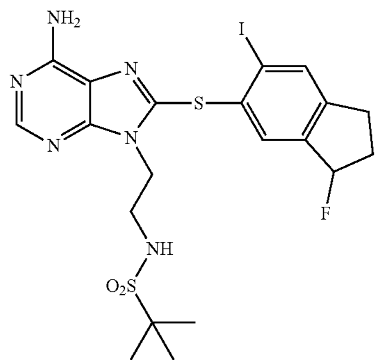 [SMILES: CC(C)(C)S(=O)(=O)NCCn1c(Sc2cc3c(cc2I)CCC3F)nc2c(N)ncnc21] | 2-Methyl-propane-2-sulfonic acid {2-[6-amino-8-(3-fluoro-6-iodo-indan-5-ylsulfanyl)-purin-9-yl]-ethyl}-amide |
| 8A-12 | 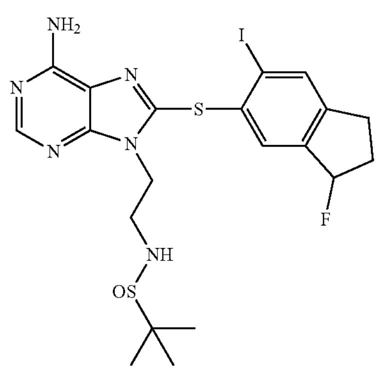 | 2-Methyl-propane-2-sulfinic acid {2-[6-amino-8-(3-fluoro-6-iodo-indan-5-ylsulfanyl)-purin-9-yl]-ethyl}-amide |
| 8A-13 | 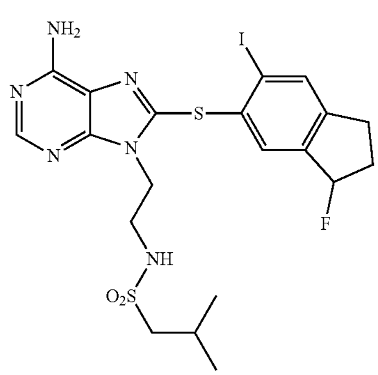 | 2-Methyl-propane-1-sulfonic acid {2-[6-amino-8-(3-fluoro-6-iodo-indan-5-ylsulfanyl)-purin-9-yl]-ethyl}-amide |

TABLE 8-continued

| Compound No. | Structure | Name |
|---|---|---|
| 8A-14 | 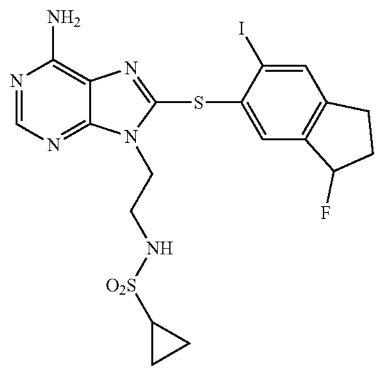 [SMILES: Nc1ncnc2c1nc(Sc1cc3c(cc1I)CCC3F)n2CCNS(=O)(=O)C1CC1] | Cyclopropanesulfonic acid {2-[6-amino-8-(3-fluoro-6-iodo-indan-5-ylsulfanyl)-purin-9-yl]-ethyl}-amide |
| 8A-15 | 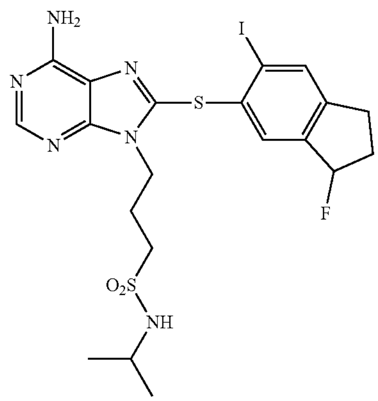 [SMILES: CC(C)NS(=O)(=O)CCCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propane-1-sulfonic acid isopropylamide |
| 8A-16 | 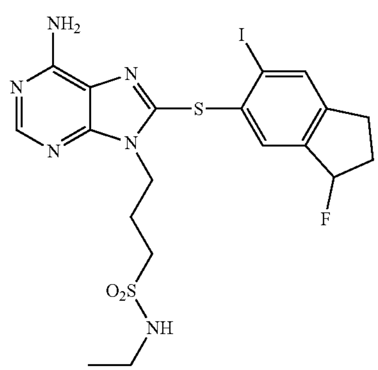 [SMILES: CCNS(=O)(=O)CCCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propane-1-sulfonic acid ethylamide |
| 8A-17 | 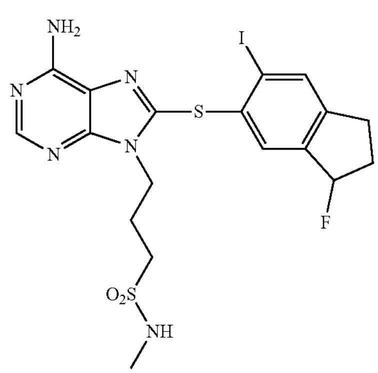 [SMILES: CNS(=O)(=O)CCCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propane-1-sulfonic acid methylamide |

TABLE 8-continued

| Compound No. | Structure | Name |
|---|---|---|
| 8A-18 | 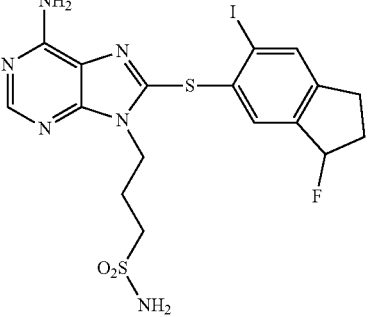 | 3-[6-Amino-8-(3-fluoro-6-iodo-indan-5-ylsulfanyl)-purin-9-yl]-propane-1-sulfonic acid amide |
| 8A-19 | 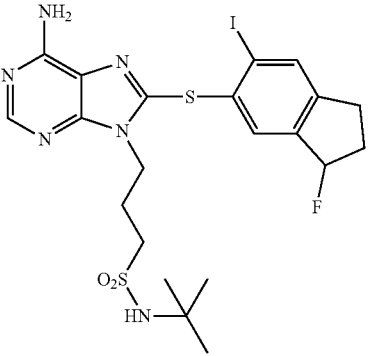 [SMILES: CC(C)(C)NS(=O)(=O)CCCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propane-1-sulfonic acid tert-butylamide |
| 8A-20 | 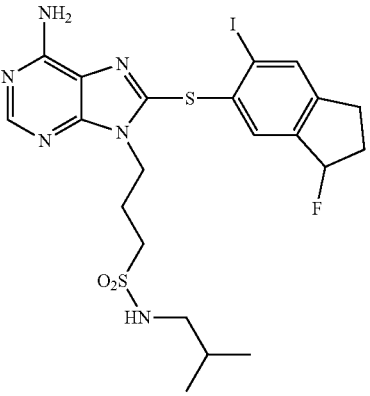 [SMILES: CC(C)CNS(=O)(=O)CCCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propane-1-sulfonic acid isobutyl-amide |
| 8A-21 | 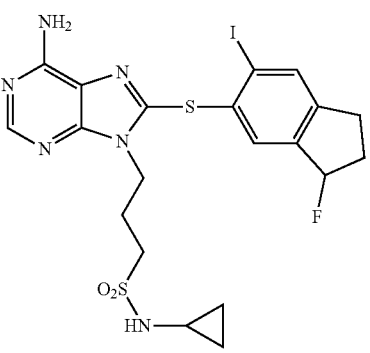 [SMILES: Nc1ncnc2c1nc(Sc1cc3c(cc1I)CCC3F)n2CCCS(=O)(=O)NC1CC1] | 3-[6-Amino-8-(3-fluoro-6-iodo-indan-5-ylsulfanyl)-purin-9-yl]-propane-1-sulfonic acid cyclopropylamide |

TABLE 8-continued

| Compound No. | Structure | Name |
| --- | --- | --- |
| 8A-22 | 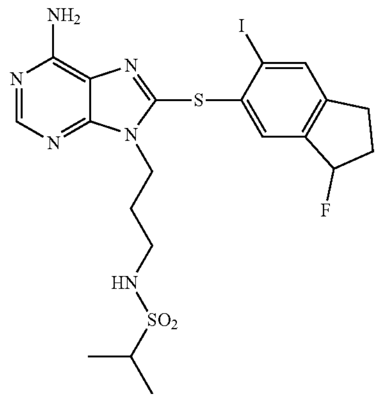 [SMILES: CC(C)S(=O)(=O)NCCCn1c(Sc2cc3c(cc2I)CCC3F)nc2c(N)ncnc21] | Propane-2-sulfonic acid {3-[6-amino-8-(3-fluoro-6-iodo-indan-5-ylsulfanyl)-purin-9-yl]-propyl}-amide |
| 8A-23 | 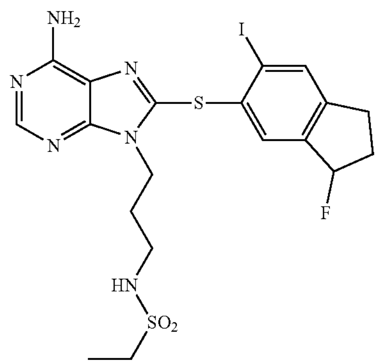 [SMILES: CCS(=O)(=O)NCCCn1c(Sc2cc3c(cc2I)CCC3F)nc2c(N)ncnc21] | Ethanesulfonic acid {3-[6-amino-8-(3-fluoro-6-iodo-indan-5-ylsulfanyl)-purin-9-yl]-propyl}-amide |
| 8A-24 | 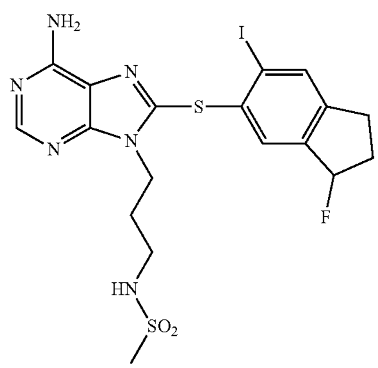 [SMILES: CS(=O)(=O)NCCCn1c(Sc2cc3c(cc2I)CCC3F)nc2c(N)ncnc21] | N-{3-[6-Amino-8-(3-fluoro-6-iodo-indan-5-ylsulfanyl)-purin-9-yl]-propyl}-methanesulfonamide |
| 8A-25 | 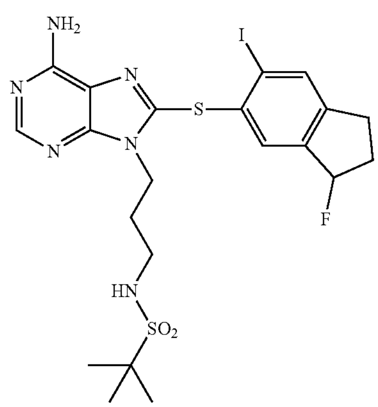 [SMILES: CC(C)(C)S(=O)(=O)NCCCn1c(Sc2cc3c(cc2I)CCC3F)nc2c(N)ncnc21] | 2-Methyl-propane-2-sulfonic acid {3-[6-amino-8-(3-fluoro-6-iodo-indan-5-ylsulfanyl)-purin-9-yl]-propyl}-amide |

TABLE 8-continued

| Compound No. | Structure | Name |
|---|---|---|
| 8A-26 | 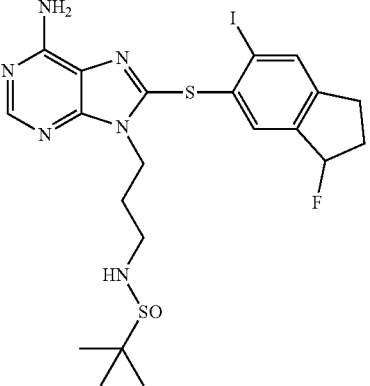 | 2-Methyl-propane-2-sulfinic acid {3-[6-amino-8-(3-fluoro-6-iodo-indan-5-ylsulfanyl)-purin-9-yl]-propyl}-amide |
| 8A-27 | 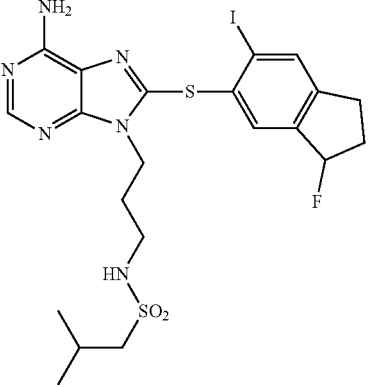 [SMILES: CC(C)CS(=O)(=O)NCCCn1c(Sc2cc3c(cc2I)CCC3F)nc2c(N)ncnc21] | 2-Methyl-propane-1-sulfonic acid {3-[6-amino-8-(3-fluoro-6-iodo-indan-5-ylsulfanyl)-purin-9-yl]-propyl}-amide |
| 8A-28 | 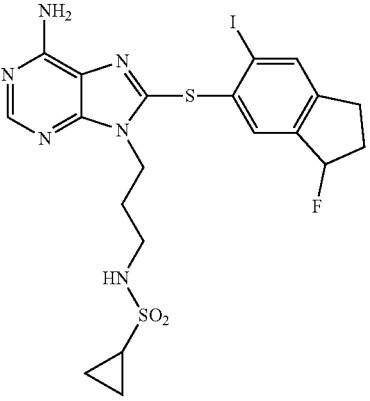 [SMILES: Nc1ncnc2c1nc(Sc1cc3c(cc1I)CCC3F)n2CCCNS(=O)(=O)C1CC1] | Cyclopropanesulfonic acid {3-[6-amino-8-(3-fluoro-6-iodo-indan-5-ylsulfanyl)-purin-9-yl]-propyl}-amide |
| 8A-29 | 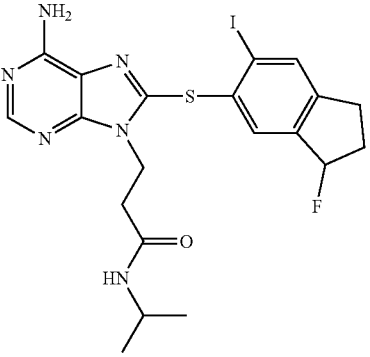 [SMILES: CC(C)NC(=O)CCn1c(Sc2cc3c(cc2I)CCC3F)nc2c(N)ncnc21] | 3-[6-Amino-8-(3-fluoro-6-iodo-indan-5-ylsulfanyl)-purin-9-yl]-N-isopropyl-propionamide |

TABLE 8-continued

| Compound No. | Structure | Name |
|---|---|---|
| 8A-30 | 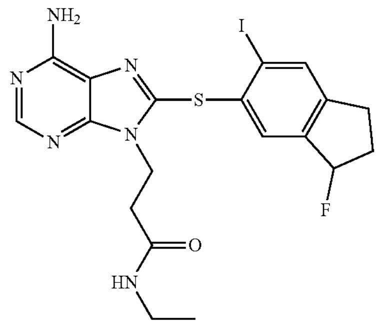 [SMILES: CCNC(=O)CCn1c(Sc2cc3c(cc2I)CCC3F)nc2c(N)ncnc21] | 3-[6-Amino-8-(3-fluoro-6-iodo-indan-5-ylsulfanyl)-purin-9-yl]-N-ethyl-propionamide |
| 8A-31 | 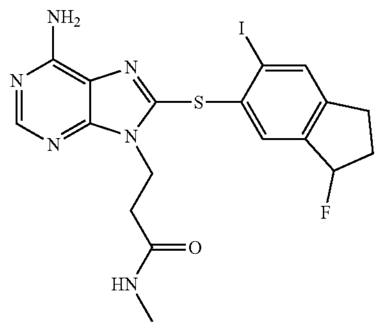 [SMILES: CNC(=O)CCn1c(Sc2cc3c(cc2I)CCC3F)nc2c(N)ncnc21] | 3-[6-Amino-8-(3-fluoro-6-iodo-indan-5-ylsulfanyl)-purin-9-yl]-N-methyl-propionamide |
| 8A-32 | 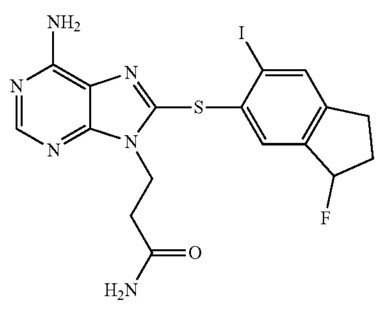 [SMILES: NC(=O)CCn1c(Sc2cc3c(cc2I)CCC3F)nc2c(N)ncnc21] | 3-[6-Amino-8-(3-fluoro-6-iodo-indan-5-ylsulfanyl)-purin-9-yl]-propionamide |
| 8A-33 | 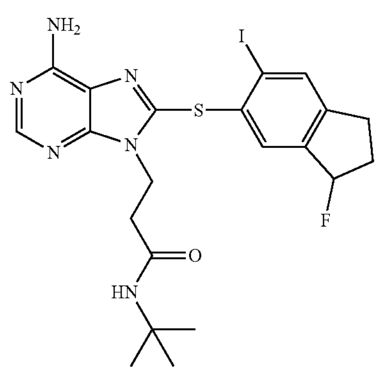 [SMILES: CC(C)(C)NC(=O)CCn1c(Sc2cc3c(cc2I)CCC3F)nc2c(N)ncnc21] | 3-[6-Amino-8-(3-fluoro-6-iodo-indan-5-ylsulfanyl)-purin-9-yl]-N-tert-butyl-propionamide |

TABLE 8-continued
| Compound No. | Structure | Name |
|---|---|---|
| 8A-34 | 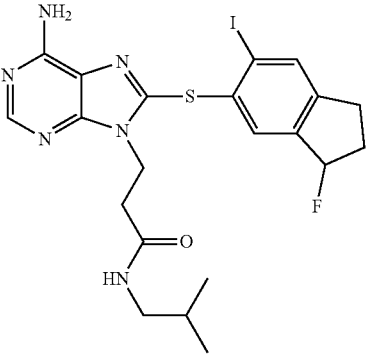 | 3-[6-Amino-8-(3-fluoro-6-iodo-indan-5-ylsulfanyl)-purin-9-yl]-N-isobutyl-propionamide |
| 8A-35 | 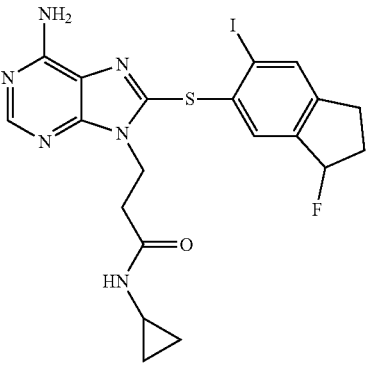 [SMILES: Nc1ncnc2c1nc(Sc1cc3c(cc1I)CCC3F)n2CCC(=O)NC1CC1] | 3-[6-Amino-8-(3-fluoro-6-iodo-indan-5-ylsulfanyl)-purin-9-yl]-N-cyclopropyl-propionamide |
| 8A-36 | 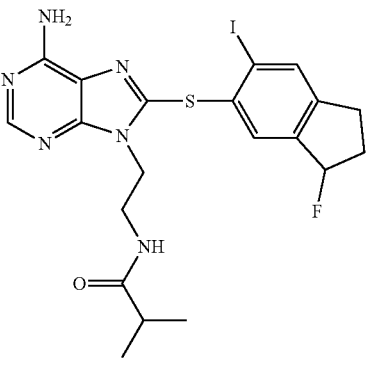 [SMILES: CC(C)C(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-isobutyramide |
| 8A-37 | 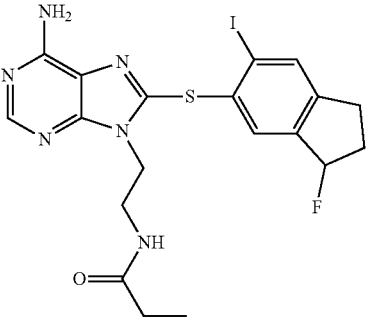 [SMILES: CCC(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-propionamide |

TABLE 8-continued

| Compound No. | Structure | Name |
| --- | --- | --- |
| 8A-38 | 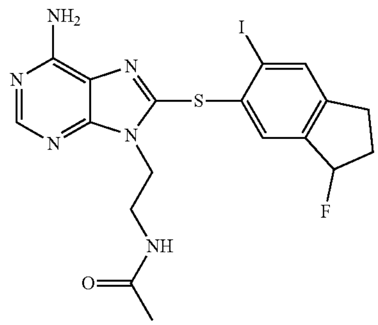 [SMILES: CC(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-acetamide |
| 8A-39 | 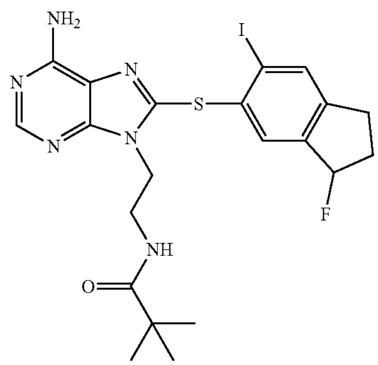 [SMILES: CC(C)(C)C(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-2,2-dimethyl-propionamide |
| 8A-40 | 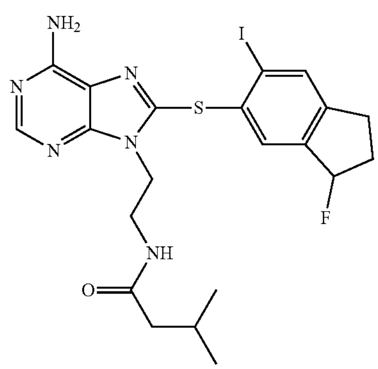 [SMILES: CC(C)CC(=O)NCCn1c(Sc2cc3c(cc2I)CCC3F)nc2c(N)ncnc21] | N-{2-[6-Amino-8-(3-fluoro-6-iodo-indan-5-ylsulfanyl)-purin-9-yl]-ethyl}-3-methyl-butyramide |
| 8A-41 | 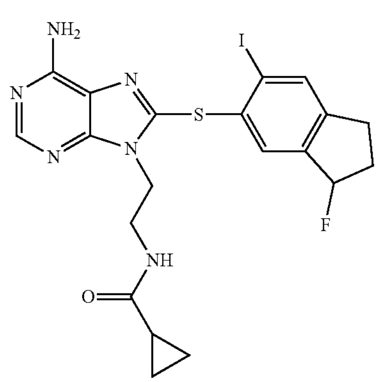 [SMILES: Nc1ncnc2c1nc(Sc1cc3c(cc1I)CCC3F)n2CCNC(=O)C1CC1] | Cyclopropanecarboxylic acid {2-[6-amino-8-(3-fluoro-6-iodo-indan-5-ylsulfanyl)-purin-9-yl]-ethyl}-amide |

TABLE 8-continued

| Compound No. | Structure | Name |
|---|---|---|
| 8A-42 | 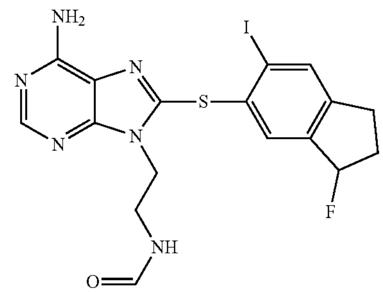 [SMILES: Nc1ncnc2c1nc(Sc1cc3c(cc1I)CCC3F)n2CCNC=O] | N-{2-[6-Amino-8-(3-fluoro-6-iodo-indan-5-ylsulfanyl)-purin-9-yl]-ethyl}-formamide |

Table 10A lists specific examples in which $X_2$ is halogen and $X_4$ is halogen. In each of the structures as drawn, $X_2$ is I and $X_4$ is F. However, corresponding structures in which $X_4$ is H, Cl, Br, or I are within the scope of the disclosure. In each of the structures in Table 10A, Y is $CH_2$. However, corresponding structures in which Y is S or O and/or $X_2$ is F, Cl, or Br are also within the scope of the disclosure. In each of the structure in Table 10A, Xb is CHF and Xa is $CH_2$. However, corresponding structures in which Xa is CHF and Xb is $CH_2$, Xa is $CF_2$ and Xb is $CH_2$, Xb is $CF_2$ and Xa is $CH_2$, Xa is CHF and Xb is $CF_2$, Xb is CHF and Xa is $CF_2$, Xa is CHF and Xb is CHF, or Xa is $CF_2$ and Xb is $CF_2$ are also within the scope of the disclosure. Additionally, in connection with each of the structures in Table 10A, corresponding structures in which $X_4$ is H, Cl, Br, or I, Y is S or O, and Xa is CHF and Xb is $CH_2$, Xa is $CF_2$ and Xb is $CH_2$, Xb is $CF_2$ and Xa is $CH_2$, Xa is CHF and Xb is $CF_2$, Xb is CHF and Xa is $CF_2$, Xa is CHF and Xb is CHF, or Xa is $CF_2$ and Xb is $CF_2$ are also within the scope of the disclosure.

TABLE 10A

| Compound No. | Structure | Name |
|---|---|---|
| 10A-1 | 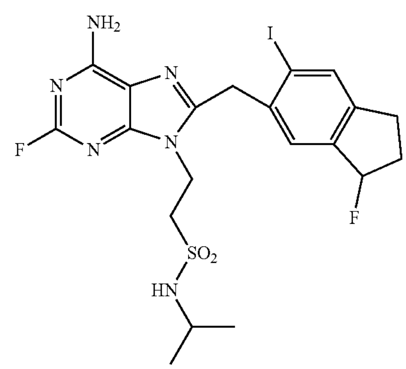 [SMILES: CC(C)NS(=O)(=O)CCn1c(Cc2cc3c(cc2I)CCC3F)nc2c(N)nc(F)nc21] | 2-(6-amino-2-fluoro-8-((3-fluoro-6-iodo-2,3-dihydro-1H-inden-5-yl)methyl)-9H-purin-9-yl)-N-isopropylethanesulfonamide |
| 10A-2 | 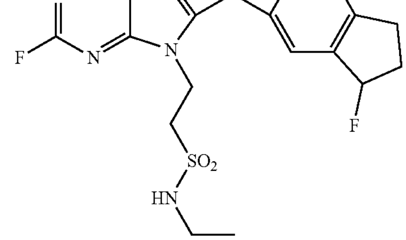 | 2-(6-amino-2-fluoro-8-((3-fluoro-6-iodo-2,3-dihydro-1H-inden-5-yl)methyl)-9H-purin-9-yl)-N-ethylethanesulfonamide |

TABLE 10A-continued

| Compound No. | Structure | Name |
|---|---|---|
| 10A-3 | 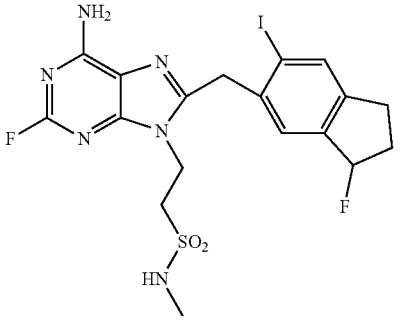 [SMILES: CNS(=O)(=O)CCn1c(Cc2cc3c(cc2I)CCC3F)nc2c(N)nc(F)nc21] | 2-(6-amino-2-fluoro-8-((3-fluoro-6-iodo-2,3-dihydro-1H-inden-5-yl)methyl)-9H-purin-9-yl)-N-methylethanesulfonamide |
| 10A-4 | 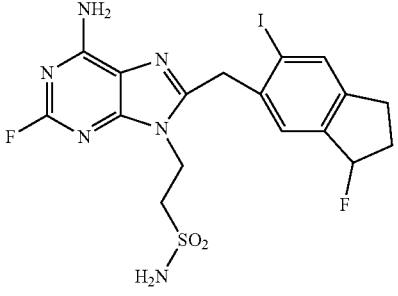 [SMILES: Nc1nc(F)nc2c1nc(Cc1cc3c(cc1I)CCC3F)n2CCS(N)(=O)=O] | 2-(6-amino-2-fluoro-8-((3-fluoro-6-iodo-2,3-dihydro-1H-inden-5-yl)methyl)-9H-purin-9-yl)ethanesulfonamide |
| 10A-5 | 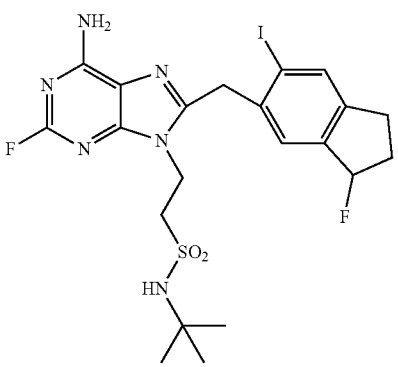 [SMILES: CC(C)(C)NS(=O)(=O)CCn1c(Cc2cc3c(cc2I)CCC3F)nc2c(N)nc(F)nc21] | 2-(6-amino-2-fluoro-8-((3-fluoro-6-iodo-2,3-dihydro-1H-inden-5-yl)methyl)-9H-purin-9-yl)-N-(tert-butyl)ethanesulfonamide |
| 10A-6 | 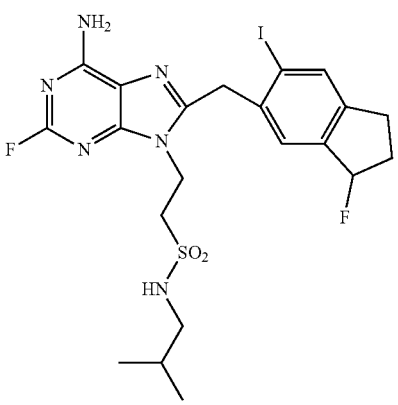 [SMILES: CC(C)CNS(=O)(=O)CCn1c(Cc2cc3c(cc2I)CCC3F)nc2c(N)nc(F)nc21] | 2-(6-amino-2-fluoro-8-((3-fluoro-6-iodo-2,3-dihydro-1H-inden-5-yl)methyl)-9H-purin-9-yl)-N-isobutylethanesulfonamide |

TABLE 10A-continued

| Compound No. | Structure | Name |
|---|---|---|
| 10A-7 | 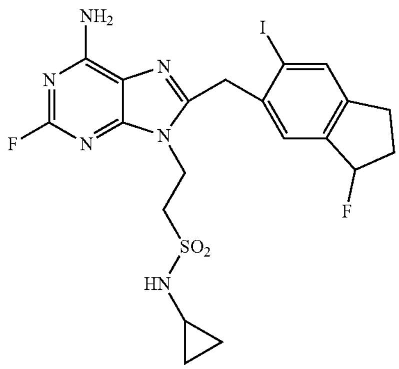 [SMILES: Nc1nc(F)nc2c1nc(Cc1cc3c(cc1I)CCC3F)n2CCS(=O)(=O)NC1CC1] | 2-(6-amino-2-fluoro-8-((3-fluoro-6-iodo-2,3-dihydro-1H-inden-5-yl)methyl)-9H-purin-9-yl)-N-cyclopropyl-ethanesulfonamide |
| 10A-8 | 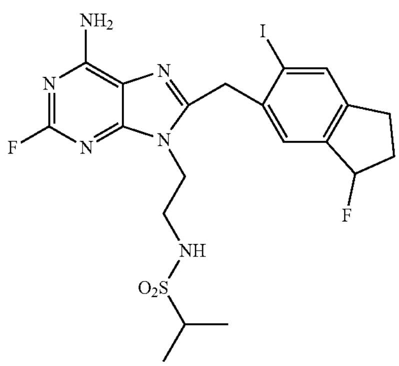 [SMILES: CC(C)S(=O)(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)propane-2-sulfonamide |
| 10A-9 | 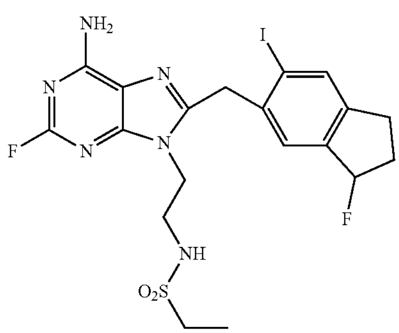 [SMILES: CCS(=O)(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)ethanesulfonamide |
| 10A-10 | 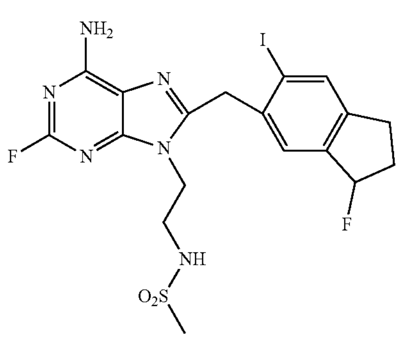 [SMILES: CS(=O)(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)methanesulfonamide |

TABLE 10A-continued

| Compound No. | Structure | Name |
|---|---|---|
| 10A-11 | 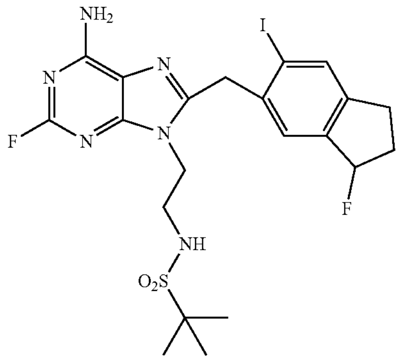 [SMILES: CC(C)(C)S(=O)(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)-2-methylpropane-2-sulfonamide |
| 10A-12 | 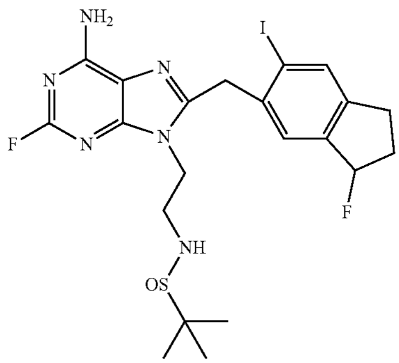 | NN-(2-(6-amino-2-fluoro-8-((3-fluoro-6-iodo-2,3-dihydro-1H-inden-5-yl)methyl)-9H-purin-9-yl)ethyl)-2-methylpropane-2-sulfinamide |
| 10A-13 | 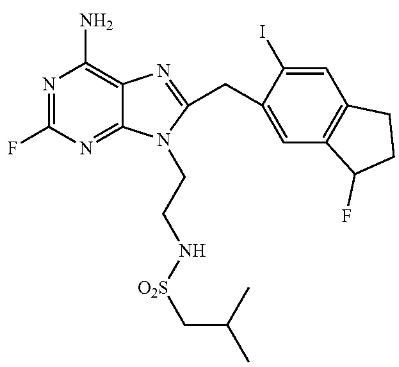 [SMILES: CC(C)CS(=O)(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)-2-methylpropane-1-sulfonamide |
| 10A-14 | 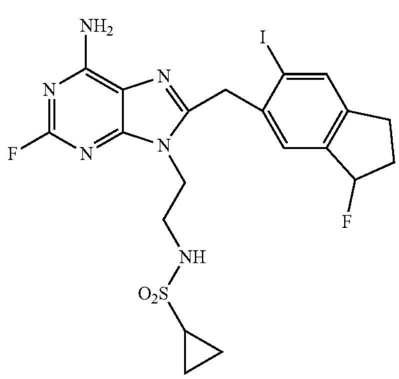 [SMILES: Nc1nc(F)nc2c1nc(Cc1cc3c(cc1I)CCC3F)n2CCNS(=O)(=O)C1CC1] | N-(2-(6-amino-2-fluoro-8-((3-fluoro-6-iodo-2,3-dihydro-1H-inden-5-yl)methyl)-9H-purin-9-yl)ethyl)cyclopropane-sulfonamide |

TABLE 10A-continued

| Compound No. | Structure | Name |
|---|---|---|
| 10A-15 | 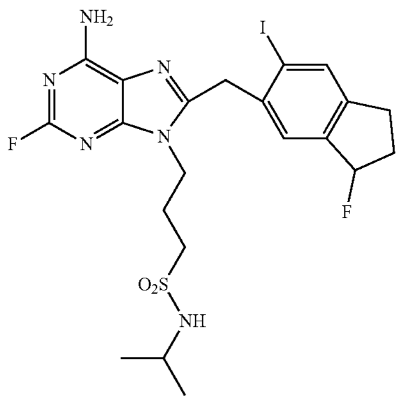 [SMILES: CC(C)NS(=O)(=O)CCCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-isopropylpropane-1-sulfonamide |
| 10A-16 | 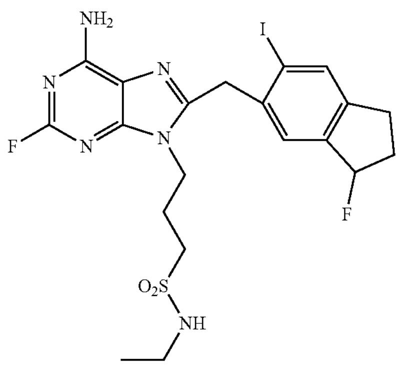 [SMILES: CCNS(=O)(=O)CCCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-ethylpropane-1-sulfonamide |
| 10A-17 | 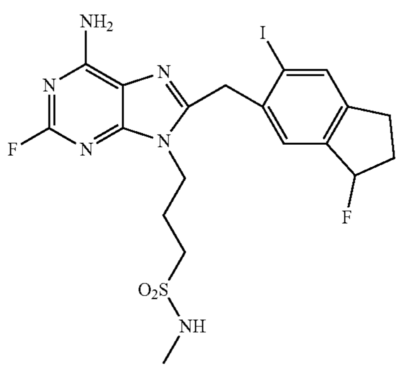 [SMILES: CNS(=O)(=O)CCCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-methylpropane-1-sulfonamide |
| 10A-18 | 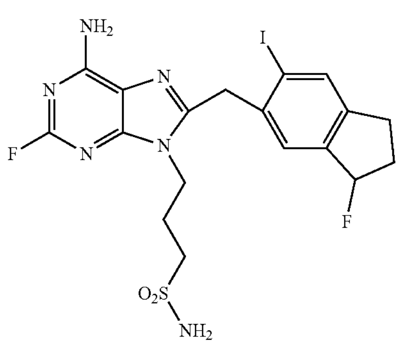 [SMILES: Nc1nc(F)nc2c1nc(Cc1cc3c(cc1I)CCC3F)n2CCCS(N)(=O)=O] | 3-(6-amino-2-fluoro-8-((3-fluoro-6-iodo-2,3-dihydro-1H-inden-5-yl)methyl)-9H-purin-9-yl)propane-1-sulfonamide |

TABLE 10A-continued

| Compound No. | Structure | Name |
|---|---|---|
| 10A-19 | 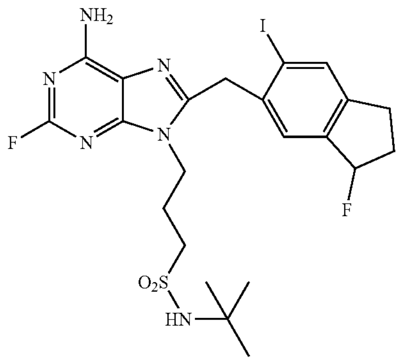 [SMILES: CC(C)(C)NS(=O)(=O)CCCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-(tert-butyl)propane-1-sulfonamide |
| 10A-20 | 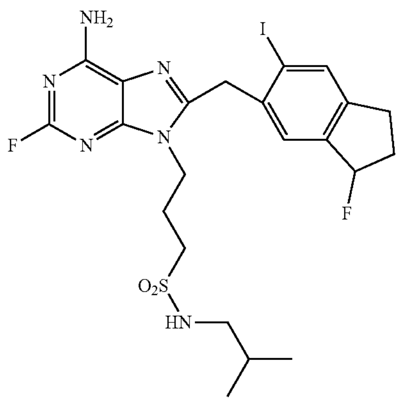 [SMILES: CC(C)CNS(=O)(=O)CCCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-isobutylpropane-1-sulfonamide |
| 10A-21 | 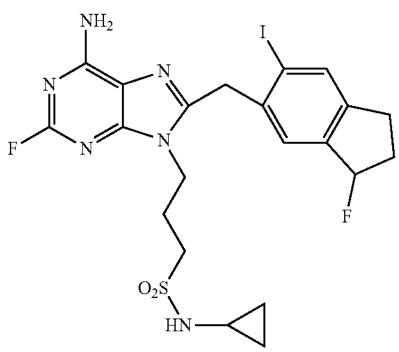 [SMILES: Nc1nc(F)nc2c1nc(Cc1cc3c(cc1I)CCC3F)n2CCCS(=O)(=O)NC1CC1] | 3-(6-amino-2-fluoro-8-((3-fluoro-6-iodo-2,3-dihydro-1H-inden-5-yl)methyl)-9H-purin-9-yl)-N-cyclopropylpropane-1-sulfonamide |
| 10A-22 | 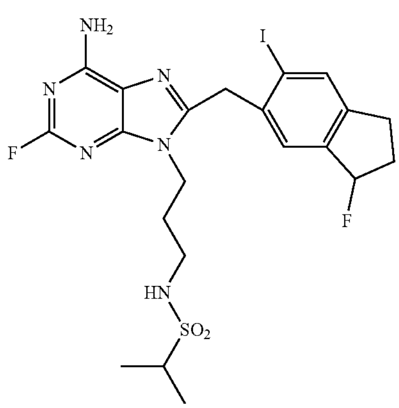 [SMILES: CC(C)S(=O)(=O)NCCCn1c(Cc2cc3c(cc2I)CCC3F)nc2c(N)nc(F)nc21] | N-(3-(6-amino-2-fluoro-8-((3-fluoro-6-iodo-2,3-dihydro-1H-inden-5-yl)methyl)-9H-purin-9-yl)propyl)propane-2-sulfonamide |

TABLE 10A-continued

| Compound No. | Structure | Name |
|---|---|---|
| 10A-23 | 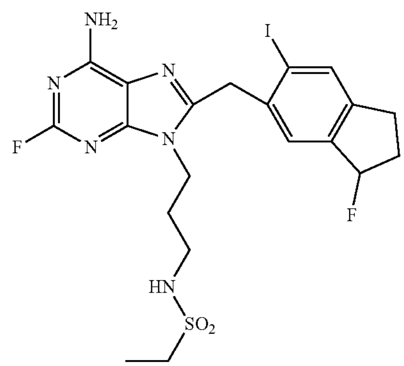 [SMILES: CCS(=O)(=O)NCCCn1c(Cc2cc3c(cc2I)CCC3F)nc2c(N)nc(F)nc21] | N-(3-(6-amino-2-fluoro-8-((3-fluoro-6-iodo-2,3-dihydro-1H-inden-5-yl)methyl)-9H-purin-9-yl)propyl)ethanesulfonamide |
| 10A-24 | 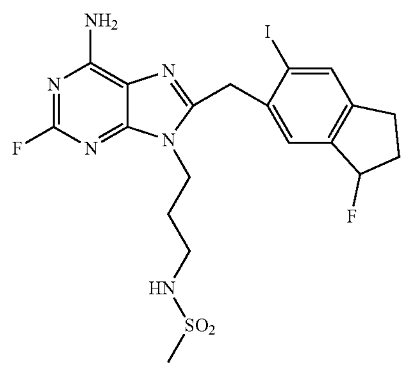 [SMILES: CS(=O)(=O)NCCCn1c(Cc2cc3c(cc2I)CCC3F)nc2c(N)nc(F)nc21] | N-(3-(6-amino-2-fluoro-8-((3-fluoro-6-iodo-2,3-dihydro-1H-inden-5-yl)methyl)-9H-purin-9-yl)propyl)methanesulfonamide |
| 10A-25 | 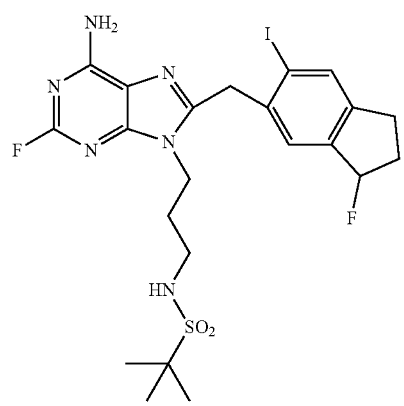 | N-(3-(6-amino-2-fluoro-8-((3-fluoro-6-iodo-2,3-dihydro-1H-inden-5-yl)methyl)-9H-purin-9-yl)propyl)-2-methylpropane-2-sulfonamide |
| 10A-26 | 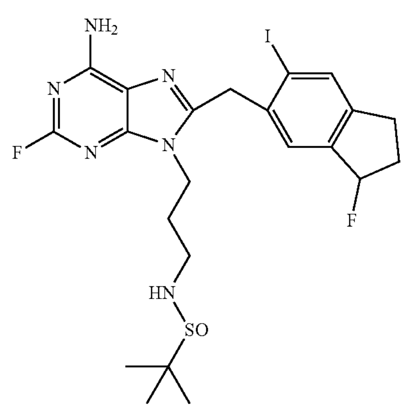 | N-(3-(6-amino-2-fluoro-8-((3-fluoro-6-iodo-2,3-dihydro-1H-inden-5-yl)methyl)-9H-purin-9-yl)propyl)-2-methylpropane-2-sulfinamide |

TABLE 10A-continued

| Compound No. | Structure | Name |
|---|---|---|
| 10A-27 | 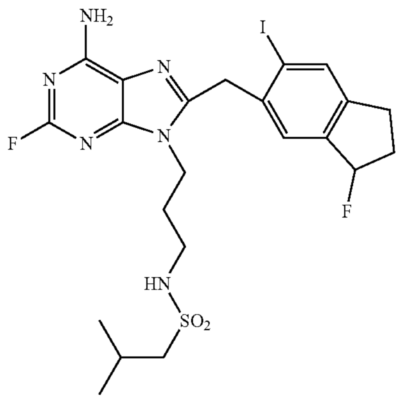 [SMILES: CC(C)CS(=O)(=O)NCCCn1c(Cc2cc3c(cc2I)CCC3F)nc2c(N)nc(F)nc21] | N-(3-(6-amino-2-fluoro-8-((3-fluoro-6-iodo-2,3-dihydro-1H-inden-5-yl)methyl)-9H-purin-9-yl)propyl)-2-methylpropane-1-sulfonamide |
| 10A-28 | 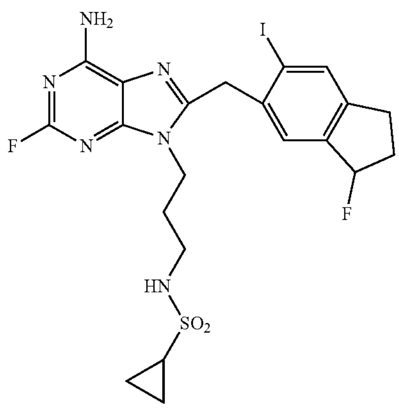 [SMILES: Nc1nc(F)nc2c1nc(Cc1cc3c(cc1I)CCC3F)n2CCCNS(=O)(=O)C1CC1] | N-(3-(6-amino-2-fluoro-8-((3-fluoro-6-iodo-2,3-dihydro-1H-inden-5-yl)methyl)-9H-purin-9-yl)propyl)cyclopropanesulfonamide |
| 10A-29 | 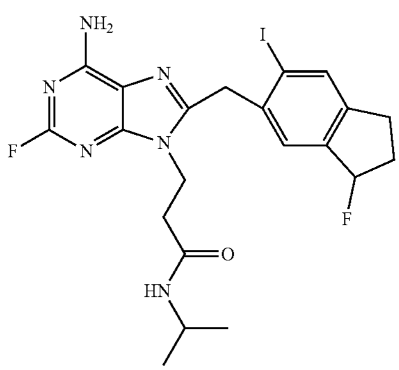 [SMILES: CC(C)NC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-isopropylpropanamide |
| 10A-30 | 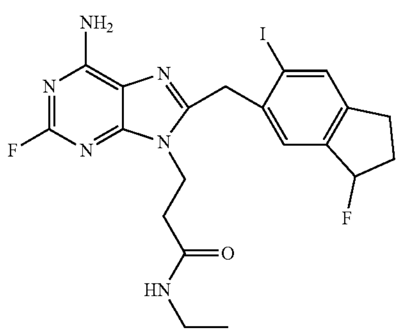 [SMILES: CCNC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-ethylpropanamide |

TABLE 10A-continued

| Compound No. | Structure | Name |
|---|---|---|
| 10A-31 | 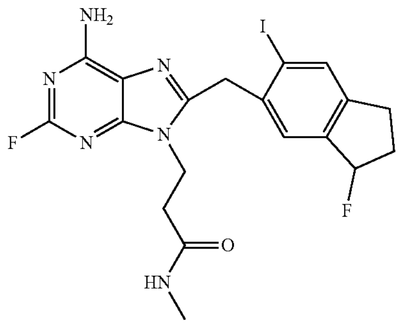 [SMILES: CNC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-methylpropanamide |
| 10A-32 | 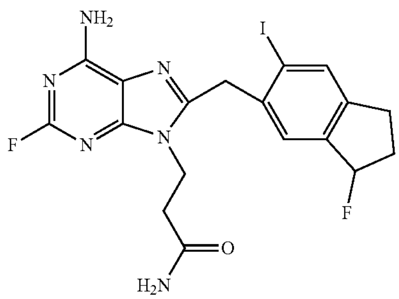 [SMILES: NC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)propanamide |
| 10A-33 | 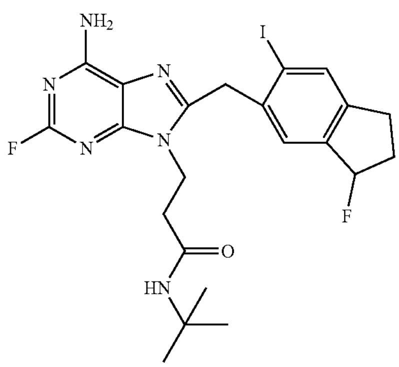 [SMILES: CC(C)(C)NC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-(tert-butyl)propanamide |
| 10A-34 | 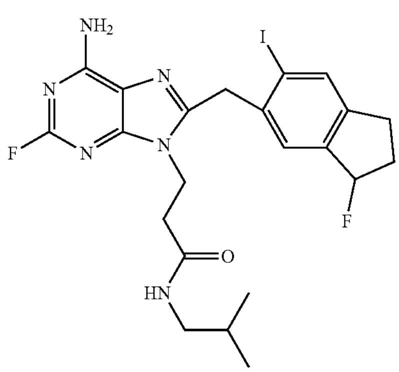 [SMILES: CC(C)CNC(=O)CCn1c(Cc2cc3c(cc2I)CCC3F)nc2c(N)nc(F)nc21] | 3-(6-amino-2-fluoro-8-((3-fluoro-6-iodo-2,3-dihydro-1H-inden-5-yl)methyl)-9H-purin-9-yl)-N-isobutylpropanamide |

TABLE 10A-continued

| Compound No. | Structure | Name |
|---|---|---|
| 10A-35 | 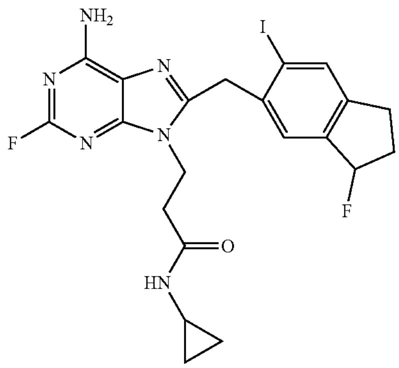 [SMILES: Nc1nc(F)nc2c1nc(Cc1cc3c(cc1I)CCC3F)n2CCC(=O)NC1CC1] | 3-(6-amino-2-fluoro-8-((3-fluoro-6-iodo-2,3-dihydro-1H-inden-5-yl)methyl)-9H-purin-9-yl)-N-cyclopropylpropanamide |
| 10A-36 | 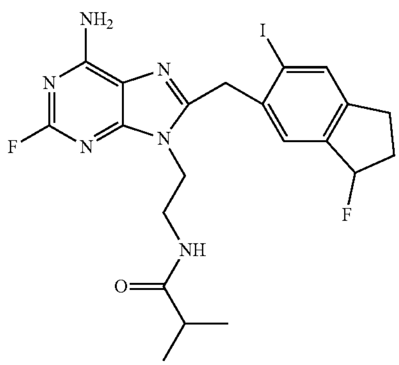 [SMILES: CC(C)C(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)isobutyramide |
| 10A-37 | 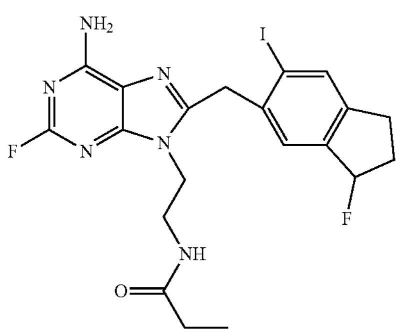 [SMILES: CCC(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)propionamide |
| 10A-38 | 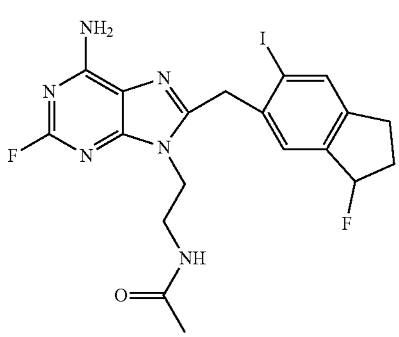 [SMILES: CC(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)acetamide |

TABLE 10A-continued

| Compound No. | Structure | Name |
|---|---|---|
| 10A-39 | 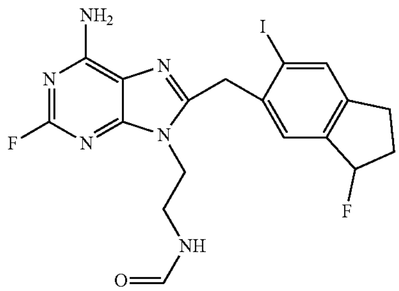 [SMILES: Nc1nc(F)nc2c1nc(Cc1cc3c(cc1I)CCC3F)n2CCNC=O] | N-(2-(6-amino-2-fluoro-8-((3-fluoro-6-iodo-2,3-dihydro-1H-inden-5-yl)methyl)-9H-purin-9-yl)ethyl)formamide |
| 10A-40 | 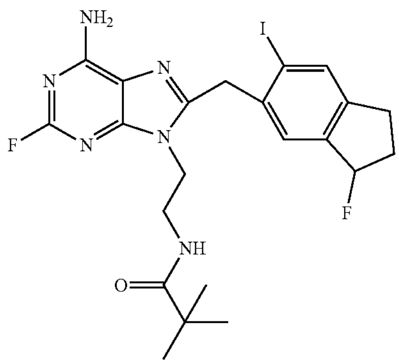 [SMILES: CC(C)(C)C(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)pivalamide |
| 10A-41 | 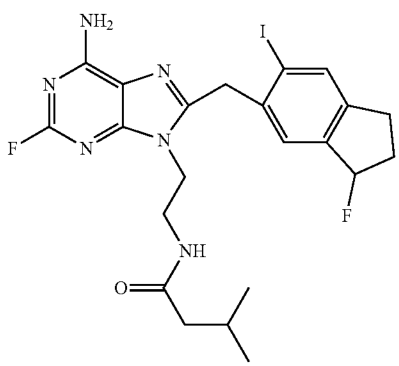 [SMILES: CC(C)CC(=O)NCCn1c(Cc2cc3c(cc2I)CCC3F)nc2c(N)nc(F)nc21] | N-(2-(6-amino-2-fluoro-8-((3-fluoro-6-iodo-2,3-dihydro-1H-inden-5-yl)methyl)-9H-purin-9-yl)ethyl)-3-methylbutanamide |
| 10A-42 | 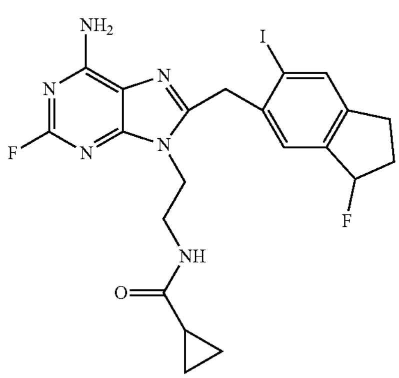 [SMILES: Nc1nc(F)nc2c1nc(Cc1cc3c(cc1I)CCC3F)n2CCNC(=O)C1CC1] | N-(2-(6-amino-2-fluoro-8-((3-fluoro-6-iodo-2,3-dihydro-1H-inden-5-yl)methyl)-9H-purin-9-yl)ethyl)cyclopropanecarboxamide |

G-II. In some embodiments of the disclosure, $X_2$ is an optionally substituted aryl. Specific examples of compounds within the scope of this aspect of the disclosure correspond to the compounds disclosed in Tables 8A and 10A, or variations thereof as described in A., G. and G-I. above, in which $X_2$ is an optionally substituted aryl, including but not limited to pyrazolyl, 1H-pyrazol-3-yl, oxazolyl, oxazol-2-yl, thiazolyl, thiazol-2-yl, furanyl, furan-2-yl, and 5-methylfuran-2-yl.

G-III. In some embodiments of the disclosure, $X_2$ is an alkynyl group, e.g., ethynyl, 1-prop-1-ynyl, and 3-prop-1-ynyl. Specific examples of compounds within the scope of this aspect of the disclosure correspond to the compounds disclosed in Tables 8A and 10A, or variations thereof as described in A., G. and G-I. above, in which $X_2$ is an alkynyl group.

G-IV. In some embodiments of the disclosure, $X_2$ is an amino group, i.e., —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Specific examples of compounds within the scope of this aspect of the disclosure correspond to the compounds disclosed in Tables 8A and 10A, or variations thereof as described in A., G. and G-I. above, in which $X_2$ is an amino group.

H. COMPOUNDS OF FORMULA (IB) IN WHICH XA AND XB ARE EACH O

In accordance with another embodiment of the disclosure, the compounds are of Formula (IB) in which each of Xa and Xb are O and each of Xc and Xd are $CH_2$. Thus, the compounds of this embodiment can be represented by Formula (6):

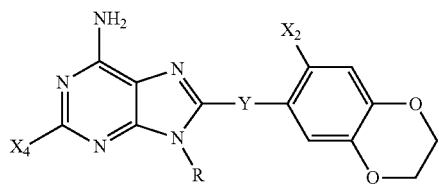

(6)

or a pharmaceutically acceptable salt thereof, wherein:
Y is $CH_2$, O, or S;
$X_4$ is hydrogen or halogen;

R is a is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by —S(O)N($R_A$)—, —$NR_AS(O)$—, —$SO_2N(R_A)$—, —$NR_ASO_2$—, —C(O)N($R_A$)—, or —$NR_AC(O)$—, and/or terminated by —S(O)$NR_AR_B$, —$NR_AS(O)R_B$, —$SO_2NR_AR_B$, —$NR_ASO_2R_B$, —C(O)$NR_AR_B$, or —$NR_AC(O)R_B$, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and $X_2$ is as disclosed below.

In one embodiment, Y is O.

In another embodiment, Y is $CH_2$ or O

In another embodiment, Y is $CH_2$ or S.

In another embodiment, Y is O or S.

H-I. In some embodiments of the disclosure, $X_2$ is halogen. Table 11A lists specific examples of compounds within this embodiment. In each of the structures as drawn, $X_2$ is I and $X_4$ is H. However, corresponding structures in which $X_2$ is F, Cl, or Br are within the scope of the disclosure. In each of the structures in Table 11A, Y is S. However, corresponding structures in which Y is $CH_2$ or O and/or $X_4$ is F, Cl, Br, or I are also within the scope of the disclosure. Additionally, in connection with each of the structures in Table 11A, corresponding structures in which $X_2$ is F, Cl, or Br and Y is CH, or O are also within the scone of the disclosure.

TABLE 11A

| Compound No. | Structure | Name |
|---|---|---|
| 11A-1 | 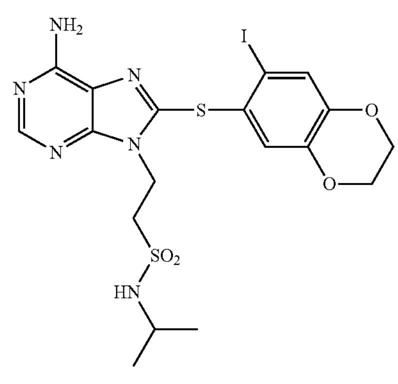 [SMILES: CC(C)NS(=O)(=O)CCn1c(Sc2cc3c(cc2I)OCCO3)nc2c(N)ncnc21] | 2-(6-amino-8-((7-iodo-2,3-dihydrobenzo[b][1,4]dioxin-6-yl)thio)-9H-purin-9-yl)-N-isopropylethanesulfonamide |
| 11A-2 | 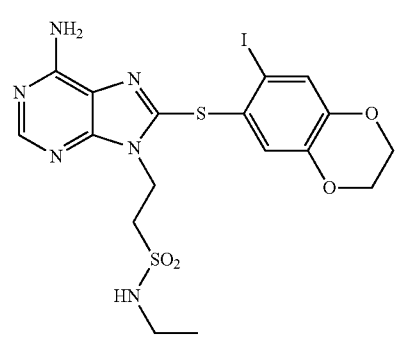 [SMILES: CCNS(=O)(=O)CCn1c(Sc2cc3c(cc2I)OCCO3)nc2c(N)ncnc21] | 2-(6-amino-8-((7-iodo-2,3-dihydrobenzo[b][1,4]dioxin-6-yl)thio)-9H-purin-9-yl)-N-ethylethanesulfonamide |

TABLE 11A-continued

| Compound No. | Structure | Name |
|---|---|---|
| 11A-3 | 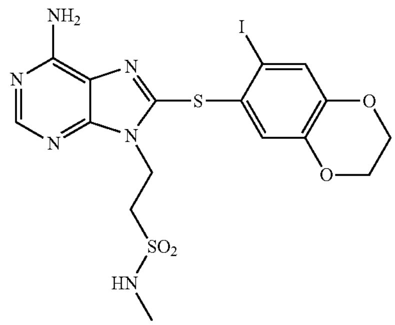 [SMILES: CNS(=O)(=O)CCn1c(Sc2cc3c(cc2I)OCCO3)nc2c(N)ncnc21] | 2-(6-amino-8-((7-iodo-2,3-dihydrobenzo[b][1,4]dioxin-6-yl)thio)-9H-purin-9-yl)-N-methylethanesulfonamide |
| 11A-4 | 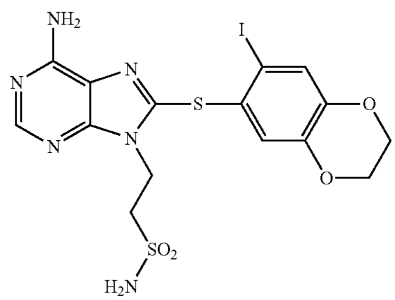 [SMILES: Nc1ncnc2c1nc(Sc1cc3c(cc1I)OCCO3)n2CCS(N)(=O)=O] | 2-(6-amino-8-((7-iodo-2,3-dihydrobenzo[b][1,4]dioxin-6-yl)thio)-9H-purin-9-yl)ethanesulfonamide |
| 11A-5 | 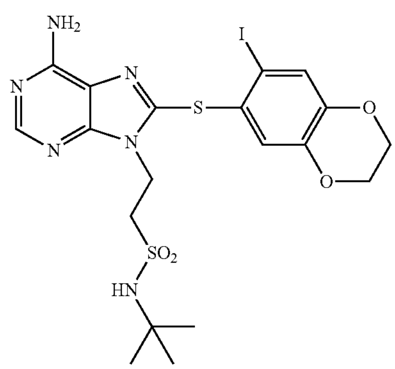 [SMILES: CC(C)(C)NS(=O)(=O)CCn1c(Sc2cc3c(cc2I)OCCO3)nc2c(N)ncnc21] | 2-(6-amino-8-((7-iodo-2,3-dihydrobenzo[b][1,4]dioxin-6-yl)thio)-9H-purin-9-yl)-N-(tert-butyl)ethanesulfonamide |
| 11A-6 | 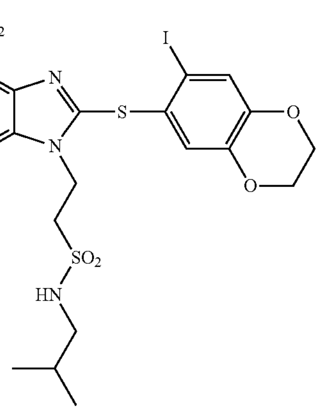 | 2-(6-amino-8-((7-iodo-2,3-dihydrobenzo[b][1,4]dioxin-6-yl)thio)-9H-purin-9-yl)-N-isobutylethanesulfonamide |

TABLE 11A-continued

| Compound No. | Structure | Name |
|---|---|---|
| 11A-7 | 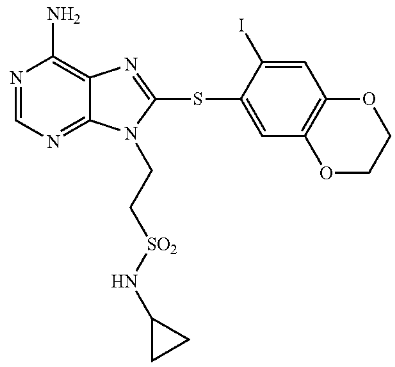 [SMILES: Nc1ncnc2c1nc(Sc1cc3c(cc1I)OCCO3)n2CCS(=O)(=O)NC1CC1] | 2-(6-amino-8-((7-iodo-2,3-dihydrobenzo[b][1,4]dioxin-6-yl)thio)-9H-purin-9-yl)-N-cyclopropyl-ethanesulfonamide |
| 11A-8 | 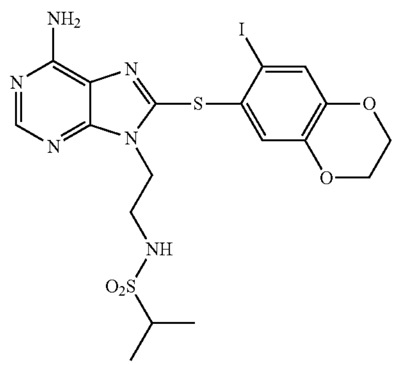 [SMILES: CC(C)S(=O)(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)propane-2-sulfonamide |
| 11A-9 | 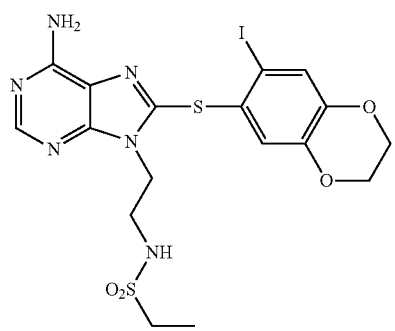 [SMILES: CCS(=O)(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)ethanesulfonamide |
| 11A-10 | 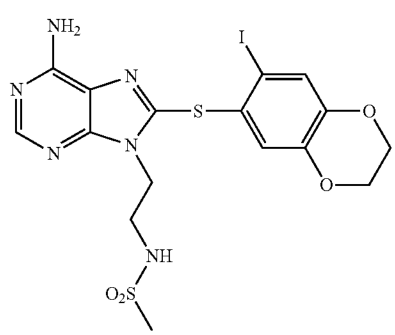 [SMILES: CS(=O)(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)methanesulfonamide |

TABLE 11A-continued

| Compound No. | Structure | Name |
|---|---|---|
| 11A-11 | 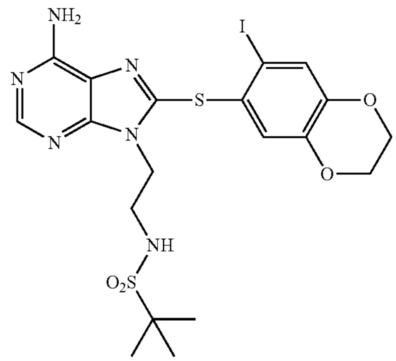 [SMILES: CC(C)(C)S(=O)(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)-2-methylpropane-2-sulfonamide |
| 11A-12 | 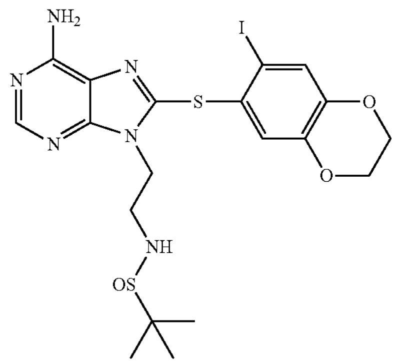 | N-(2-(6-amino-8-((7-iodo-2,3-dihydrobenzo[b][1,4]dioxin-6-yl)thio)-9H-purin-9-yl)ethyl)-2-methylpropane-2-sulfinamide |
| 11A-13 | 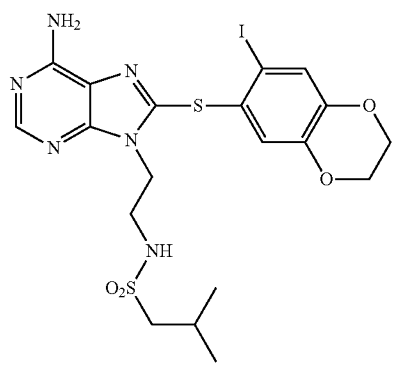 [SMILES: CC(C)CS(=O)(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)-2-methylpropane-1-sulfonamide |
| 11A-14 | 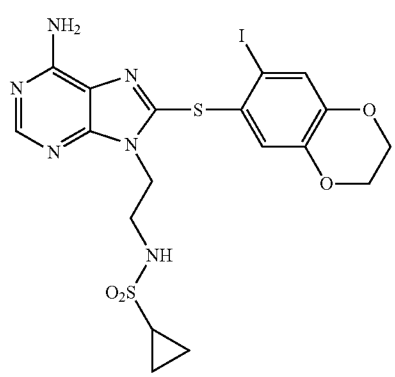 [SMILES: Nc1ncnc2c1nc(Sc1cc3c(cc1I)OCCO3)n2CCNS(=O)(=O)C1CC1] | N-(2-(6-amino-8-((7-iodo-2,3-dihydrobenzo[b][1,4]dioxin-6-yl)thio)-9H-purin-9-yl)ethyl)cyclopropanesulfonamide |

TABLE 11A-continued

| Compound No. | Structure | Name |
|---|---|---|
| 11A-15 | 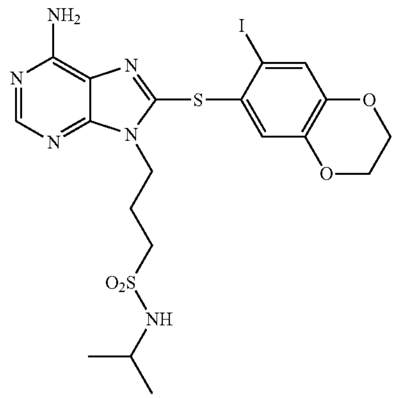 | 3-(6-amino-8-((7-iodo-2,3-dihydrobenzo[b][1,4]dioxin-6-yl)thio)-9H-purin-9-yl)-N-isopropylpropane-1-sulfonamide |
| 11A-16 | 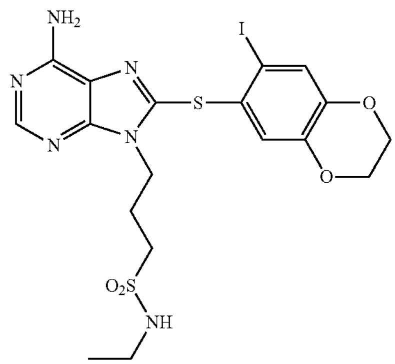 [SMILES: CCNS(=O)(=O)CCCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-ethylpropane-1-sulfonamide |
| 11A-17 | 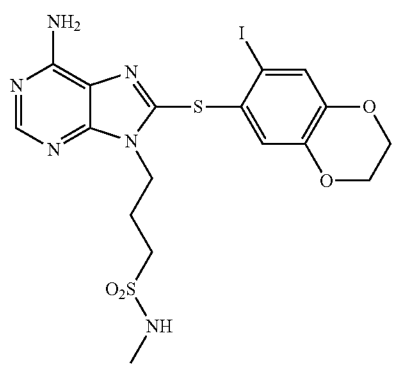 [SMILES: CNS(=O)(=O)CCCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-methylpropane-1-sulfonamide |
| 11A-18 | 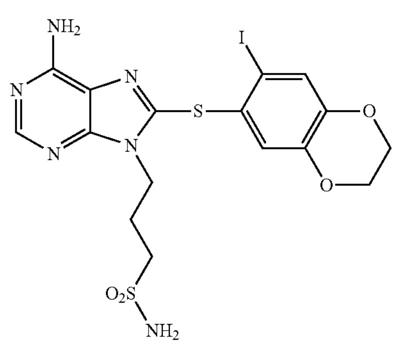 [SMILES: Nc1ncnc2c1nc(Sc1cc3c(cc1I)OCCO3)n2CCCS(N)(=O)=O] | 3-(6-amino-8-((7-iodo-2,3-dihydrobenzo[b][1,4]dioxin-6-yl)thio)-9H-purin-9-yl)propane-1-sulfonamide |

TABLE 11A-continued

| Compound No. | Structure | Name |
|---|---|---|
| 11A-19 | 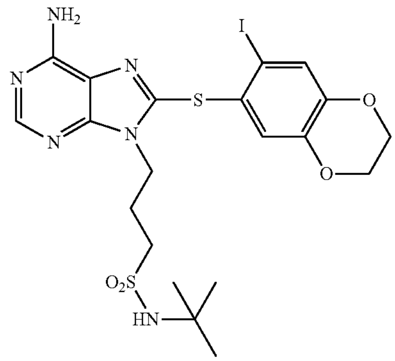 [SMILES: CC(C)(C)NS(=O)(=O)CCCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-(tert-butyl)propane-1-sulfonamide |
| 11A-20 | 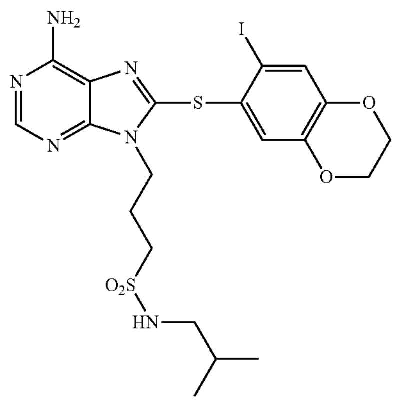 [SMILES: CC(C)CNS(=O)(=O)CCCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-isobutylpropane-1-sulfonamide |
| 11A-21 | 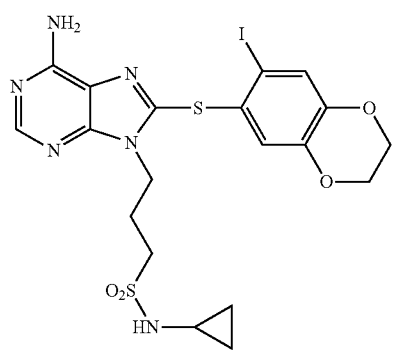 [SMILES: Nc1ncnc2c1nc(Sc1cc3c(cc1I)OCCO3)n2CCCS(=O)(=O)NC1CC1] | 3-(6-amino-8-((7-iodo-2,3-dihydrobenzo[b][1,4]dioxin-6-yl)thio)-9H-purin-9-yl)-N-cyclopropylpropane-1-sulfonamide |
| 11A-22 | 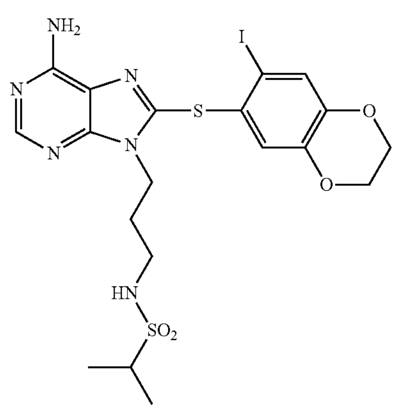 [SMILES: CC(C)S(=O)(=O)NCCCn1c(Sc2cc3c(cc2I)OCCO3)nc2c(N)ncnc21] | N-(3-(6-amino-8-((7-iodo-2,3-dihydrobenzo[b][1,4]dioxin-6-yl)thio)-9H-purin-9-yl)propyl)propane-2-sulfonamide |

TABLE 11A-continued

| Compound No. | Structure | Name |
| --- | --- | --- |
| 11A-23 | 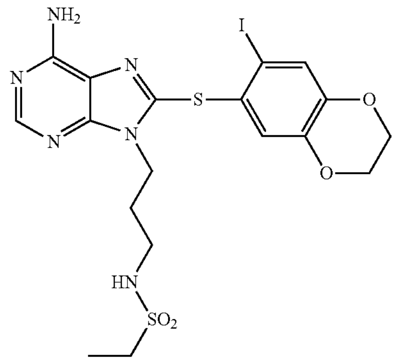 [SMILES: CCS(=O)(=O)NCCCn1c(Sc2cc3c(cc2I)OCCO3)nc2c(N)ncnc21] | N-(3-(6-amino-8-((7-iodo-2,3-dihydrobenzo[b][1,4]dioxin-6-yl)thio)-9H-purin-9-yl)propyl)ethanesulfonamide |
| 11A-24 | 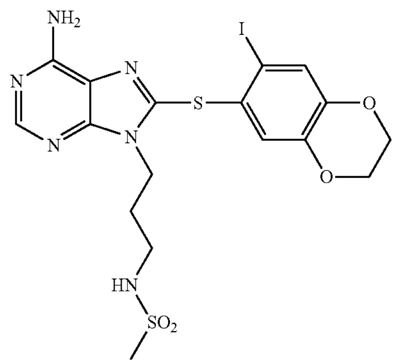 [SMILES: CS(=O)(=O)NCCCn1c(Sc2cc3c(cc2I)OCCO3)nc2c(N)ncnc21] | N-(3-(6-amino-8-((7-iodo-2,3-dihydrobenzo[b][1,4]dioxin-6-yl)thio)-9H-purin-9-yl)propyl)methane-sulfonamide |
| 11A-25 | 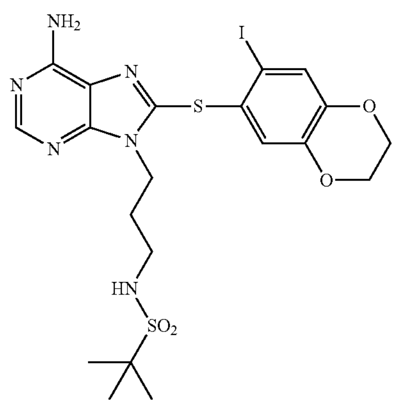 [SMILES: CC(C)(C)S(=O)(=O)NCCCn1c(Sc2cc3c(cc2I)OCCO3)nc2c(N)ncnc21] | N-(3-(6-amino-8-((7-iodo-2,3-dihydrobenzo[b][1,4]dioxin-6-yl)thio)-9H-purin-9-yl)propyl)-2-methylpropane-2-sulfonamide |
| 11A-26 | 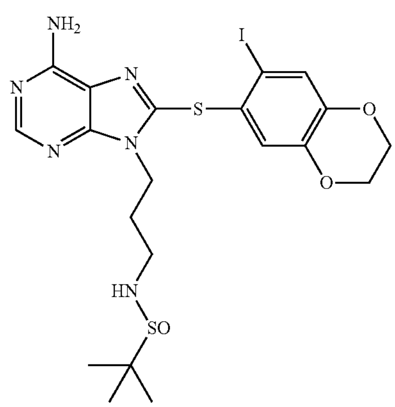 | N-(3-(6-amino-8-((7-iodo-2,3-dihydrobenzo[b][1,4]dioxin-6-yl)thio)-9H-purin-9-yl)propyl)-2-methylpropane-2-sulfinamide |

TABLE 11A-continued

| Compound No. | Structure | Name |
| --- | --- | --- |
| 11A-27 | 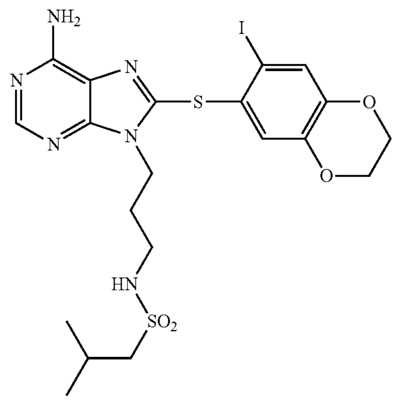 [SMILES: CC(C)CS(=O)(=O)NCCCn1c(Sc2cc3c(cc2I)OCCO3)nc2c(N)ncnc21] | N-(3-(6-amino-8-((7-iodo-2,3-dihydrobenzo[b][1,4]dioxin-6-yl)thio)-9H-purin-9-yl)propyl)-2-methylpropane-1-sulfonamide |
| 11A-28 | 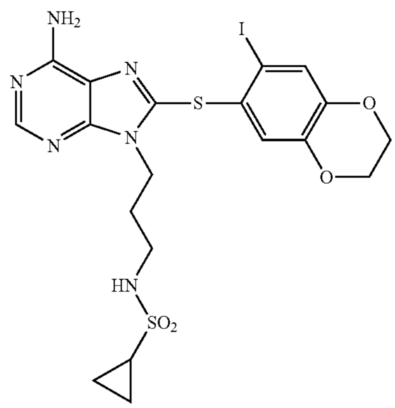 [SMILES: Nc1ncnc2c1nc(Sc1cc3c(cc1I)OCCO3)n2CCCNS(=O)(=O)C1CC1] | N-(3-(6-amino-8-((7-iodo-2,3-dihydrobenzo[b][1,4]dioxin-6-yl)thio)-9H-purin-9-yl)propyl)cyclopropane-sulfonamide |
| 11A-29 | 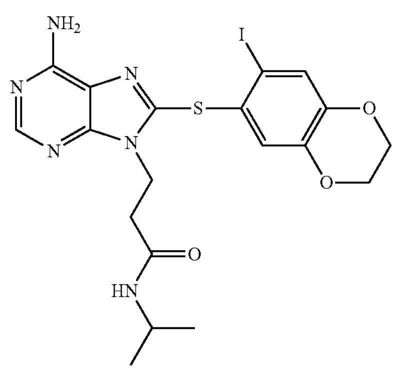 [SMILES: CC(C)NC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-isopropylpropanamide |
| 11A-30 | 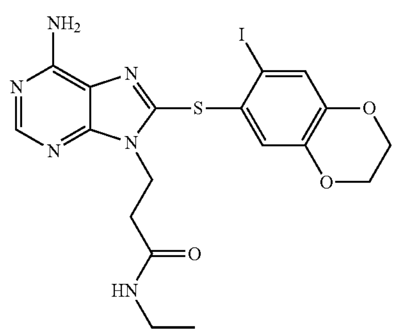 [SMILES: CCNC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-ethylpropanamide |

TABLE 11A-continued

| Compound No. | Structure | Name |
| --- | --- | --- |
| 11A-31 | 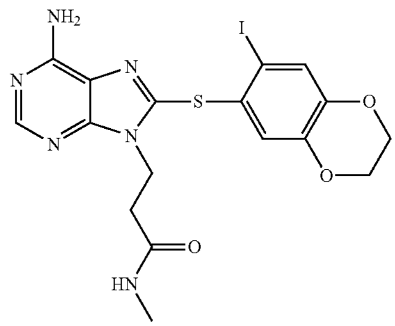 [SMILES: CNC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-methylpropanamide |
| 11A-32 | 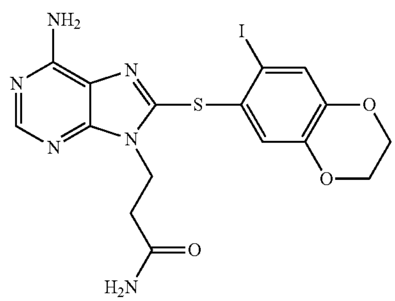 [SMILES: NC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)propanamide |
| 11A-33 | 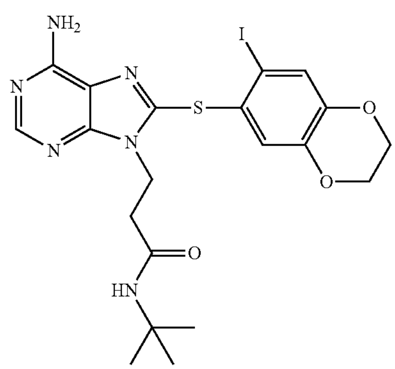 [SMILES: CC(C)(C)NC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-(tert-butyl)propanamide |
| 11A-34 | 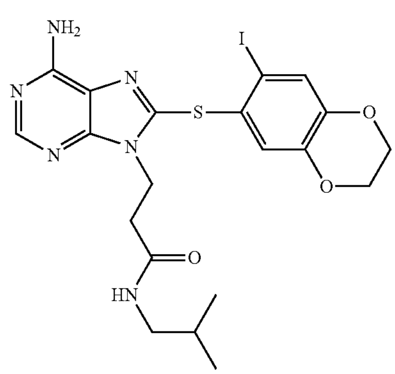 [SMILES: CC(C)CNC(=O)CCn1c(Sc2cc3c(cc2I)OCCO3)nc2c(N)ncnc21] | 3-(6-amino-8-((7-iodo-2,3-dihydrobenzo[b][1,4]dioxin-6-yl)thio)-9H-purin-9-yl)-N-isobutylpropanamide |

TABLE 11A-continued

| Compound No. | Structure | Name |
|---|---|---|
| 11A-35 | 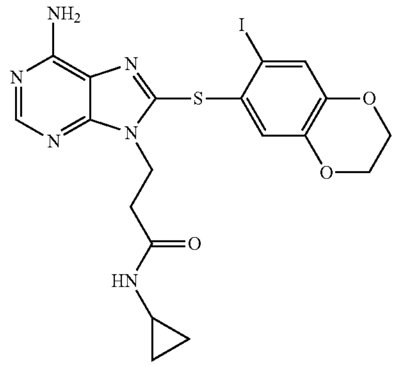 [SMILES: Nc1ncnc2c1nc(Sc1cc3c(cc1I)OCCO3)n2CCC(=O)NC1CC1] | 3-(6-amino-8-((7-iodo-2,3-dihydrobenzo[b][1,4]dioxin-6-yl)thio)-9H-purin-9-yl)-N-cyclopropylpropanamide |
| 11A-36 | 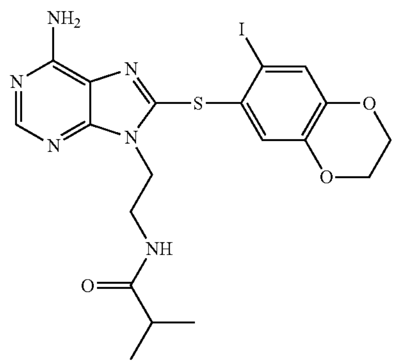 [SMILES: CC(C)C(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)isobutyramide |
| 11A-37 | 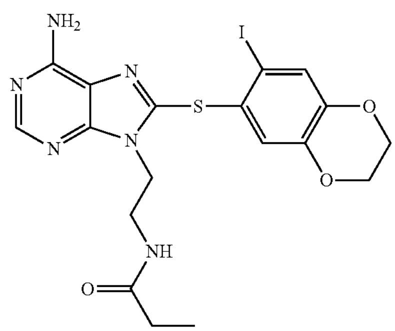 [SMILES: CCC(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)propionamide |
| 11A-38 | 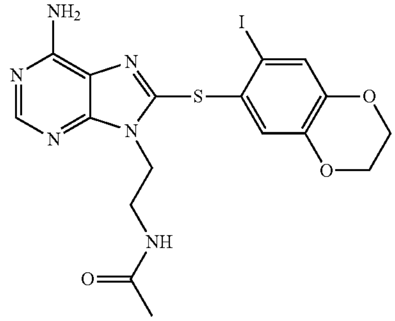 [SMILES: CC(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)acetamide |

TABLE 11A-continued

| Compound No. | Structure | Name |
|---|---|---|
| 11A-39 | 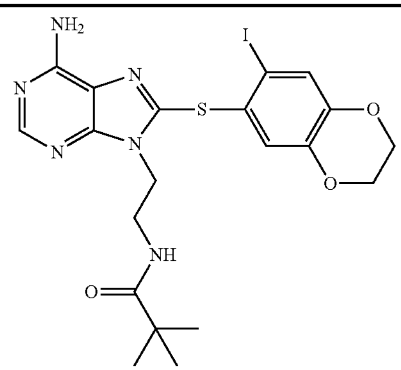 | N-(2-(6-amino-8-((7-iodo-2,3-dihydrobenzo[b][1,4]dioxin-6-yl)thio)-9H-purin-9-yl)ethyl)pivalamide |
| 11A-40 | 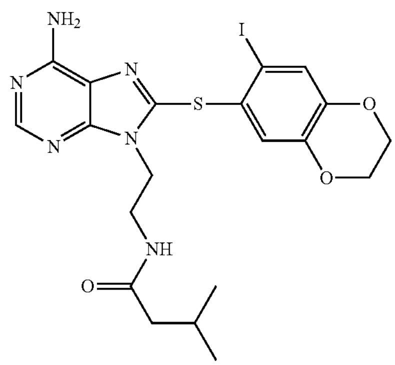 [SMILES: CC(C)CC(=O)NCCn1c(Sc2cc3c(cc2I)OCCO3)nc2c(N)ncnc21] | N-(2-(6-amino-8-((7-iodo-2,3-dihydrobenzo[b][1,4]dioxin-6-yl)thio)-9H-purin-9-yl)ethyl)-3-methylbutanamide |
| 11A-41 | 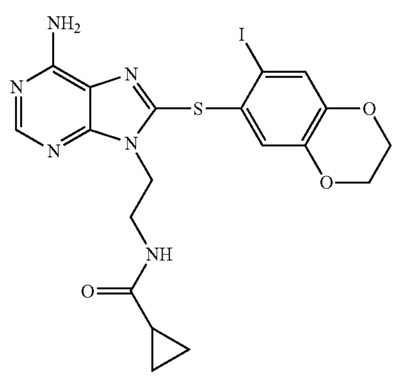 [SMILES: Nc1ncnc2c1nc(Sc1cc3c(cc1I)OCCO3)n2CCNC(=O)C1CC1] | N-(2-(6-amino-8-((7-iodo-2,3-dihydrobenzo[b][1,4]dioxin-6-yl)thio)-9H-purin-9-yl)ethyl)cyclopropane-carboxamide |
| 11A-42 | 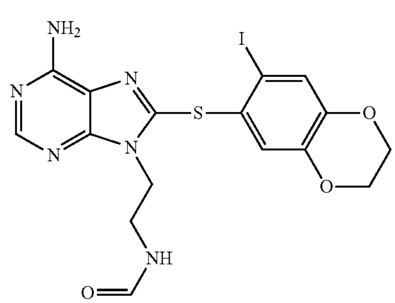 [SMILES: Nc1ncnc2c1nc(Sc1cc3c(cc1I)OCCO3)n2CCNC=O] | N-(2-(6-amino-8-((7-iodo-2,3-dihydrobenzo[b][1,4]dioxin-6-yl)thio)-9H-purin-9-yl)ethyl)formamide |

H-II. In some embodiments of the disclosure, $X_2$ is an optionally substituted aryl. Specific examples of compounds within the scope of this aspect of the disclosure correspond to the compounds disclosed in Table 11A, or variations thereof as described in A., H. and H-I. above, in which $X_2$ is an optionally substituted aryl, including but not limited to pyrazolyl, 1H-pyrazol-3-yl, oxazolyl, oxazol-2-yl, thiazolyl, thiazol-2-yl, furanyl, furan-2-yl, and 5-methylfuran-2-yl.

H-III. In some embodiments of the disclosure, $X_2$ is an alkynyl group, e.g., ethynyl, 1-prop-1-ynyl, and 3-prop-1-ynyl. Specific examples of compounds within the scope of this aspect of the disclosure correspond to the compounds disclosed in Table 11A, or variations thereof as described in A., H. and H-I. above, in which $X_2$ is an alkynyl group.

H-IV. In some embodiments of the disclosure, $X_2$ is an amino group, i.e., —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl. Specific examples of compounds within the scope of this aspect of the disclosure correspond to the compounds disclosed in Table 11A, or variations thereof as described in A., H. and H-I. above, in which $X_2$ is an amino group.

J. ADDITIONAL EMBODIMENTS

Each of the following embodiments relates to the compounds of Formulae (IA) and (IB) and, particularly, to each of the appropriate embodiments C-1 through H-IV of the compounds of Formulae (1) through (6).

In one embodiment, Y is $CH_2$. In another embodiment, Y is S.

In another embodiment, $X_4$ is H. In another embodiment, $X_4$ is halogen. In another embodiment, $X_4$ is F, Cl, or Br. In another embodiment, $X_4$ is F, Cl, or I. In another embodiment, $X_4$ is F, Br, or I. In another embodiment, $X_4$ is Cl, Br, or I. In another embodiment, $X_4$ is F or I. In another embodiment, $X_4$ is F or Br. In another embodiment, $X_4$ is F or Cl. In another embodiment, $X_4$ is Cl or I. In another embodiment, $X_4$ is Cl or Br. In another embodiment, $X_4$ is Br or I. In another embodiment, $X_4$ is F. In another embodiment, $X_4$ is Cl. In another embodiment, $X_4$ is Br. In another embodiment, $X_4$ is I. In another embodiment, $X_4$ is H, F, Cl, or Br. In another embodiment, $X_4$ is H, F, Cl, or I. In another embodiment, $X_4$ is H, F, Br, or I. In another embodiment, $X_4$ is H, Cl, Br, or I. In another embodiment, $X_4$ is H, F, or I. In another embodiment, $X_4$ is H, F, or Br. In another embodiment, $X_4$ is H, F, or Cl. In another embodiment, $X_4$ is H, Cl, or I. In another embodiment, $X_4$ is H, Cl, or Br. In another embodiment, $X_4$ is H, Br, or I. In another embodiment, $X_4$ is H or F. In another embodiment, $X_4$ is H or Cl. In another embodiment, $X_4$ is H or Br. In another embodiment, $X_4$ is H or I.

In another embodiment, $X_2$ is halogen, aryl, or alkynyl. In another embodiment, $X_2$ is halogen, aryl, or amino. In another embodiment, $X_2$ is halogen, alkynyl, or amino. In another embodiment, $X_2$ is aryl, alkynyl, or amino. In another embodiment, $X_2$ is halogen or amino. In another embodiment, $X_2$ is halogen or alkynyl. In another embodiment, $X_2$ is halogen or aryl. In another embodiment, $X_2$ is halogen. In another embodiment, $X_2$ is aryl. In another embodiment, $X_2$ is alkynyl. In another embodiment, $X_2$ is amino. In another embodiment, $X_2$ is halogen, heteroaryl, alkynyl, or amino. In another embodiment, $X_2$ is halogen, heteroaryl, or alkynyl. In another embodiment, $X_2$ is halogen, heteroaryl, or amino. In another embodiment, $X_2$ is heteroaryl, alkynyl, or amino. In another embodiment, $X_2$ is halogen or heteroaryl. In another embodiment, $X_2$ is heteroaryl. In another embodiment, $X_2$ is alkyl-substituted heteroaryl. In another embodiment, $X_2$ is $C_1$-$C_6$ alkyl-substituted heteroaryl. In another embodiment, $X_2$ is methyl-, ethyl-, n-propyl-, or isopropyl-substituted heteroaryl. In another embodiment, $X_2$ is methyl- or ethyl-substituted heteroaryl. In another embodiment, $X_2$ is methyl-substituted heteroaryl. In another embodiment, $X_2$ is ethyl-substituted heteroaryl.

In another embodiment, $X_2$ is F, Cl, or Br. In another embodiment, $X_2$ is F, Cl, or I. In another embodiment, $X_2$ is F, Br, or I. In another embodiment, $X_2$ is Cl, Br, or I. In another embodiment, $X_2$ is F or I. In another embodiment, $X_2$ is F or Br. In another embodiment, $X_2$ is F or Cl. In another embodiment, $X_2$ is Cl or I. In another embodiment, $X_2$ is Cl or Br. In another embodiment, $X_2$ is Br or I. In another embodiment, $X_2$ is F. In another embodiment, $X_2$ is Cl. In another embodiment, $X_2$ is Br. In another embodiment, $X_2$ is I.

In another embodiment, $X_2$ is optionally substituted heteroaryl. In another embodiment, $X_2$ is unsubstituted heteroaryl. In another embodiment, $X_2$ is furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, 5-methyloxazol-2-yl, thiophene-2-yl, thiophene-3-yl, 1H-imidazo-2-yl, 1H-imidazo-4-yl, or 1H-imidazo-5-yl. In another embodiment, $X_2$ is furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, or 5-methyloxazol-2-yl. In another embodiment, $X_2$ is furan-2-yl, furan-3-yl, or 5-methylfuran-2-yl. In another embodiment, $X_2$ is 1H-pyrazol-2-yl or 1H-pyrazol-3-yl. In another embodiment, $X_2$ is thiazol-2-yl or 5-methylthiazol-2-yl. In another embodiment, $X_2$ is oxazol-2-yl or 5-methyloxazol-2-yl. In another embodiment, $X_2$ is thiophene-2-yl, thiophene-3-yl, 1H-imidazo-2-yl, 1H-imidazo-4-yl, or 1H-imidazo-5-yl. In another embodiment, $X_2$ is thiophene-2-yl or thiophene-3-yl. In another embodiment, $X_2$ is 1H-imidazo-2-yl, 1H-imidazo-4-yl, or 1H-imidazo-5-yl.

In another embodiment, $X_2$ is ethynyl, propynyl, or butynyl. In another embodiment, $X_2$ is ethynyl or propynyl. In another embodiment, $X_2$ is ethynyl or butynyl. In another embodiment, $X_2$ is propynyl or butynyl. In another embodiment, $X_2$ is ethynyl. In another embodiment, $X_2$ is propynyl. In another embodiment, $X_2$ is butynyl.

In another embodiment, $X_2$ is dimethylamino, diethylamino, methylethylamino, or cyclopropylamino. In another embodiment, $X_2$ is dimethylamino, diethylamino, or methylethylamino. In another embodiment, $X_2$ is dimethylamino, diethylamino, or cyclopropylamino. In another embodiment, $X_2$ is dimethylamino, methylethylamino, or cyclopropylamino. In another embodiment, $X_2$ is diethylamino, methylethylamino, or cyclopropylamino. In another embodiment, $X_2$ is dimethylamino or diethylamino. In another embodiment, $X_2$ is dimethylamino or methylethylamino. In another embodiment, $X_2$ is dimethylamino or cyclopropylamino. In another embodiment, $X_2$ is diethylamino or methylethylamino. In another embodiment, $X_2$ is diethylamino or cyclopropylamino. In another embodiment, $X_2$ is methylethylamino or cyclopropylamino. In another embodiment, $X_2$ is dimethylamino. In another embodiment, $X_2$ is diethylamino. In another embodiment, $X_2$ is methylethylamino. In another embodiment, $X_2$ is cyclopropylamino.

In another embodiment, $X_2$ is Br, I, furan-2-yl, furan-3-yl, 5-methylfuran-2-yl, 1H-pyrazol-2-yl, 1H-pyrazol-3-yl, thiazol-2-yl, 5-methylthiazol-2-yl, 5-methyloxazol-2-yl, ethynyl, propynyl, dimethylamino, diethylamino, or methylethylamino. In another embodiment, $X_2$ is I, furan-2-yl, furan-3-yl, 5-methylfuran-2-yl, ethynyl, dimethylamino, diethylamino, or methylethylamino. In another embodiment, $X_2$ is Br, furan-2-yl, furan-3-yl, 5-methylfuran-2-yl, ethynyl, dimethylamino, diethylamino, or methylethylamino. In another embodiment, $X_2$ is I, furan-2-yl, furan-3-yl, 5-methylfuran-2-yl, ethynyl, or dimethylamino. In another embodiment, $X_2$ is Br, furan-2-yl, furan-3-yl, 5-methylfuran-2-yl, ethynyl, or dimethylamino. In another embodiment, $X_2$ is I, 1H-pyrazol-2-yl, 1H-pyrazol-3-yl, ethynyl, dimethylamino, diethylamino, or methylethylamino. In another embodiment, $X_2$ is Br, 1H-pyrazol-2-yl, 1H-pyrazol-3-yl, ethynyl, dimethylamino, diethylamino, or methylethylamino. In another embodiment, $X_2$ is I, 1H-pyrazol-2-yl, 1H-pyrazol-3-yl, ethynyl, or dimethylamino. In another embodiment, $X_2$ is Br, 1H-pyrazol-2-yl, 1H-pyrazol-3-yl, ethynyl, or dimethylamino. In another embodiment, $X_2$ is I, thiazol-2-yl, 5-methylthiazol-2-yl, ethynyl, dimethylamino, diethylamino, or methylethylamino. In another embodiment, $X_2$ is Br, thiazol-2-yl, 5-methylthiazol-2-yl, ethynyl, dimethylamino, diethylamino, or methylethylamino. In another embodiment, $X_2$ is I, thiazol-2-yl, 5-methylthiazol-2-yl, ethynyl, or dimethylamino. In another embodiment, $X_2$ is Br, thiazol-2-yl, 5-methylthiazol-2-yl, ethynyl, or dimethylamino. In another embodiment, $X_2$ is I, oxazol-2-yl, 5-methyloxazol-2-yl, ethynyl, dimethylamino, diethylamino, or methylethylamino. In another embodiment, $X_2$ is Br, oxazol-2-yl, 5-methyloxazol-2-yl, ethynyl, dimethylamino, diethylamino, or methylethylamino. In another embodiment, $X_2$ is I, oxazol-2-yl, 5-methyloxazol-2-yl, ethynyl, or dimethylamino. In another embodiment, $X_2$ is Br, oxazol-2-yl, 5-methyloxazol-2-yl, ethynyl, or dimethylamino.

In another embodiment, $X_2$ is halogen, aryl, or alkynyl and Y is S. In another embodiment, $X_2$ is halogen, aryl, or amino and Y is S. In another embodiment, $X_2$ is halogen, alkynyl, or amino and Y is S. In another embodiment, $X_2$ is aryl, alkynyl, or amino and Y is S. In another embodiment, $X_2$ is halogen or amino and Y is S. In another embodiment, $X_2$ is halogen or alkynyl and Y is S. In another embodiment, $X_2$ is halogen or aryl and Y is S. In another embodiment, $X_2$ is halogen and Y is S. In another embodiment, $X_2$ is aryl and Y is S. In another embodiment, $X_2$ is alkynyl and Y is S. In another embodiment, $X_2$ is amino and Y is S. In another embodiment, $X_2$ is halogen, heteroaryl, alkynyl, or amino and Y is S. In another embodiment, $X_2$ is halogen, heteroaryl, or alkynyl and Y is S. In another embodiment, $X_2$ is halogen, heteroaryl, or amino and Y is S. In another embodiment, $X_2$ is heteroaryl, alkynyl, or amino and Y is S. In another embodiment, $X_2$ is halogen or heteroaryl and Y is S. In another embodiment, $X_2$ is heteroaryl and Y is S. In another embodiment, $X_2$ is alkyl-substituted heteroaryl and Y is S. In another embodiment, $X_2$ is $C_1$-$C_6$ alkyl-substituted heteroaryl and Y is S. In another embodiment, $X_2$ is methyl-, ethyl-, n-propyl-, or isopropyl-substituted heteroaryl and Y is S. In another embodiment, $X_2$ is methyl- or ethyl-substituted heteroaryl and Y is S. In another embodiment, $X_2$ is methyl-substituted heteroaryl and Y is S. In another embodiment, $X_2$ is ethyl-substituted heteroaryl and Y is S. In another embodiment, $X_2$ is Br, I, furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, 5-methyloxazol-2-yl, ethynyl, propynyl, dimethylamino, diethylamino, or methylethylamino and Y is S. In another embodiment, $X_2$ is I, furan-2-yl, furan-3-yl, 5-methylfuran-2-yl, ethynyl, dimethylamino, diethylamino, or methylethylamino and Y is S. In another embodiment, $X_2$ is Br, furan-2-yl, furan-3-yl, 5-methylfuran-2-yl, ethynyl, dimethylamino, diethylamino, or methylethylamino and Y is S. In another embodiment, $X_2$ is I, furan-2-yl, furan-3-yl, 5-methylfuran-2-yl, ethynyl, or dimethylamino and Y is S. In another embodiment, $X_2$ is Br, furan-2-yl, furan-3-yl, 5-methylfuran-2-yl, ethynyl, or dimethylamino and Y is S. In another embodiment, $X_2$ is I, 1H-pyrazol-2-yl, 1H-pyrazol-3-yl, ethynyl, dimethylamino, diethylamino, or methylethylamino and Y is S. In another embodiment, $X_2$ is Br, 1H-pyrazol-2-yl, 1H-pyrazol-3-yl, ethynyl, dimethylamino, diethylamino, or methylethylamino and Y is S. In another embodiment, $X_2$ is I, 1H-pyrazol-2-yl, 1H-pyrazol-3-yl, ethynyl, or dimethylamino and Y is S. In another embodiment, $X_2$ is Br, 1H-pyrazol-2-yl, 1H-pyrazol-3-yl, ethynyl, or dimethylamino and Y is S. In another embodiment, $X_2$ is I, thiazol-2-yl, 5-methylthiazol-2-yl, ethynyl, dimethylamino, diethylamino, or methylethylamino and Y is S. In another embodiment, $X_2$ is Br, thiazol-2-yl, 5-methylthiazol-2-yl, ethynyl, dimethylamino, diethylamino, or methylethylamino and Y is S. In another embodiment, $X_2$ is I, thiazol-2-yl, 5-methylthiazol-2-yl, ethynyl, or dimethylamino and Y is S. In another embodiment, $X_2$ is Br, thiazol-2-yl, 5-methylthiazol-2-yl, ethynyl, or dimethylamino and Y is S. In another embodiment, $X_2$ is I, oxazol-2-yl, 5-methyloxazol-2-yl, ethynyl, dimethylamino, diethylamino, or methylethylamino and Y is S. In another embodiment, $X_2$ is Br, oxazol-2-yl, 5-methyloxazol-2-yl, ethynyl, dimethylamino, diethylamino, or methylethylamino and Y is S. In another embodiment, $X_2$ is I, oxazol-2-yl, 5-methyloxazol-2-yl, ethynyl, or dimethylamino and Y is S. In another embodiment, $X_2$ is Br, oxazol-2-yl, 5-methyloxazol-2-yl, ethynyl, or dimethylamino and Y is S.

In another embodiment, $X_2$ is halogen, aryl, or alkynyl and Y is $CH_2$. In another embodiment, $X_2$ is halogen, aryl, or amino and Y is $CH_2$. In another embodiment, $X_2$ is halogen, alkynyl, or amino and Y is $CH_2$. In another embodiment, $X_2$ is aryl, alkynyl, or amino and Y is $CH_2$. In another embodiment, $X_2$ is halogen or amino and Y is $CH_2$. In another embodiment, $X_2$ is halogen or alkynyl and Y is $CH_2$. In another embodiment, $X_2$ is halogen or aryl and Y is $CH_2$. In another embodiment, $X_2$ is halogen and Y is $CH_2$. In another embodiment, $X_2$ is aryl and Y is $CH_2$. In another embodiment, $X_2$ is alkynyl and Y is $CH_2$. In another embodiment, $X_2$ is amino and Y is $CH_2$. In another embodiment, $X_2$ is halogen, heteroaryl, alkynyl, or amino and Y is $CH_2$. In another embodiment, $X_2$ is halogen, heteroaryl, or alkynyl and Y is $CH_2$. In another embodiment, $X_2$ is halogen, heteroaryl, or amino and Y is $CH_2$. In another embodiment, $X_2$ is heteroaryl, alkynyl, or amino and Y is $CH_2$. In another embodiment, $X_2$ is halogen or heteroaryl and Y is $CH_2$. In another embodiment, $X_2$ is heteroaryl and Y is $CH_2$. In another embodiment, $X_2$ is alkyl-substituted heteroaryl and Y is $CH_2$. In another embodiment, $X_2$ is $C_1$-$C_6$ alkyl-substituted heteroaryl and Y is $CH_2$. In another embodiment, $X_2$ is methyl-, ethyl-, n-propyl-, or isopropyl-substituted heteroaryl and Y is $CH_2$. In another embodiment, $X_2$ is methyl- or ethyl-substituted heteroaryl and Y is $CH_2$. In another embodiment, $X_2$ is methyl-substituted heteroaryl and Y is $CH_2$. In another embodiment, $X_2$ is ethyl-substituted heteroaryl and Y is $CH_2$. In another embodiment, $X_2$ is Br, I, furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, 5-methyloxazol-2-yl, ethynyl, propynyl, dimethylamino, diethylamino, or methylethylamino and Y is $CH_2$. In another embodiment, $X_2$ is I, furan-2-yl, furan-3-yl, 5-methylfuran-2-yl, ethynyl, dimethylamino, diethylamino, or methylethylamino and Y is $CH_2$. In another embodiment, $X_2$ is Br, furan-2-yl, furan-3-yl, 5-methylfuran-2-yl, ethynyl, dimethylamino, diethylamino, or methylethylamino and Y is $CH_2$. In another embodiment, $X_2$ is I, furan-2-yl, furan-3-yl, 5-methylfuran-2-yl, ethynyl, or dimethylamino and Y is $CH_2$. In another embodiment, $X_2$ is Br, furan-2-yl, furan-3-yl, 5-methylfuran-2-yl, ethynyl, or dimethylamino and Y is $CH_2$. In another embodiment, $X_2$ is I, 1H-pyrazol-2-yl, 1H-pyrazol-3-yl, ethynyl, dimethylamino, diethylamino, or methylethylamino and Y is $CH_2$. In another embodiment, $X_2$ is Br, 1H-pyrazol-2-yl, 1H-pyrazol-3-yl, ethynyl, dimethylamino, diethylamino, or methylethylamino and Y is $CH_2$. In another embodiment, $X_2$ is I, 1H-pyrazol-2-yl, 1H-pyrazol-3-yl, ethynyl, or dimethylamino and Y is $CH_2$. In another embodiment, $X_2$ is Br, 1H-pyrazol-2-yl, 1H-pyrazol-3-yl, ethynyl, or dimethylamino and Y is $CH_2$. In another embodiment, $X_2$ is I, thiazol-2-yl, 5-methylthiazol-2-yl, ethynyl, dimethylamino, diethylamino, or methylethylamino and Y is $CH_2$. In another embodiment, $X_2$ is Br, thiazol-2-yl, 5-methylthiazol-2-yl, ethynyl, dimethylamino, diethylamino, or methylethylamino and Y is $CH_2$. In another embodiment, $X_2$ is I, thiazol-2-yl, 5-methylthiazol-2-yl, ethynyl, or dimethylamino and Y is $CH_2$. In another embodiment, $X_2$ is Br, thiazol-2-yl, 5-methylthiazol-2-yl, ethynyl, or dimethylamino and Y is $CH_2$. In another embodiment, $X_2$ is I, oxazol-2-yl, 5-methyloxazol-2-yl, ethynyl, dimethylamino, diethylamino, or methylethylamino and Y is $CH_2$. In another embodiment, $X_2$ is Br, oxazol-2-yl, 5-methyloxazol-2-yl, ethynyl, dimethylamino, diethylamino, or methylethylamino and Y is $CH_2$. In another embodiment, $X_2$ is I, oxazol-2-yl, 5-methyloxazol-2-yl, ethynyl, or dimethylamino and Y is $CH_2$. In another embodiment, $X_2$ is Br, oxazol-2-yl, 5-methyloxazol-2-yl, ethynyl, or dimethylamino and Y is $CH_2$.

In another embodiment, $X_4$ is H and Y is S. In another embodiment, $X_4$ is halogen and Y is S. In another embodiment, $X_4$ is F, Cl, or Br and Y is S. In another embodiment, $X_4$ is F, Cl, or I and Y is S. In another embodiment, $X_4$ is F, Br, or I and Y is S. In another embodiment, $X_4$ is Cl, Br, or I and Y is S. In another embodiment, $X_4$ is F or I and Y is S. In another embodiment, $X_4$ is F or Br and Y is S. In another embodiment, $X_4$ is F or Cl and Y is S. In another embodiment, $X_4$ is Cl or I and Y is S. In another embodiment, $X_4$ is Cl or Br and Y is S. In another embodiment, $X_4$ is Br or I and Y is S. In another embodiment, $X_4$ is F and Y is S. In another embodiment, $X_4$ is Cl and Y is S. In another embodiment, $X_4$ is Br and Y is S. In another embodiment, $X_4$ is I and Y is S.

In another embodiment, $X_4$ is H, F, Cl, or Br and Y is S. In another embodiment, $X_4$ is H, F, Cl, or I and Y is S. In another embodiment, $X_4$ is H, F, Br, or I and Y is S. In another embodiment, $X_4$ is H, Cl, Br, or I and Y is S. In another embodiment, $X_4$ is H, F, or I and Y is S. In another embodiment, $X_4$ is H, F, or Br and Y is S. In another embodiment, $X_4$ is H, F, or Cl and Y is S. In another embodiment, $X_4$ is H, Cl, or I and Y is S. In another embodiment, $X_4$ is H, Cl, or Br and Y is S. In another embodiment, $X_4$ is H, Br, or I and Y is S. In another embodiment, $X_4$ is H or F and Y is S. In another embodiment, $X_4$ is H or Cl and Y is S. In another embodiment, $X_4$ is H or Br and Y is S. In another embodiment, $X_4$ is H or I and Y is S.

In another embodiment, $X_4$ is H and Y is $CH_2$. In another embodiment, $X_4$ is halogen and Y is $CH_2$. In another embodiment, $X_4$ is F, Cl, or Br and Y is $CH_2$. In another embodiment, $X_4$ is F, Cl, or I and Y is $CH_2$. In another embodiment, $X_4$ is F, Br, or I and Y is $CH_2$. In another embodiment, $X_4$ is Cl, Br, or I and Y is $CH_2$. In another embodiment, $X_4$ is F or I and Y is $CH_2$. In another embodiment, $X_4$ is F or Br and Y is $CH_2$. In another embodiment, $X_4$ is F or Cl and Y is $CH_2$. In another embodiment, $X_4$ is Cl or I and Y is $CH_2$. In another embodiment, $X_4$ is Cl or Br and Y is $CH_2$. In another embodiment, $X_4$ is Br or I and Y is $CH_2$. In another embodiment, $X_4$ is F and Y is $CH_2$. In another embodiment, $X_4$ is Cl and Y is $CH_2$. In another embodiment, $X_4$ is Br and Y is $CH_2$. In another embodiment, $X_4$ is I and Y is $CH_2$.

In another embodiment, $X_4$ is H, F, Cl, or Br and Y is $CH_2$. In another embodiment, $X_4$ is H, F, Cl, or I and Y is $CH_2$. In another embodiment, $X_4$ is H, F, Br, or I and Y is $CH_2$. In another embodiment, $X_4$ is H, Cl, Br, or I and Y is $CH_2$. In another embodiment, $X_4$ is H, F, or I and Y is $CH_2$. In another embodiment, $X_4$ is H, F, or Br and Y is $CH_2$. In another embodiment, $X_4$ is H, F, or Cl and Y is $CH_2$. In another embodiment, $X_4$ is H, Cl, or I and Y is $CH_2$. In another embodiment, $X_4$ is H, Cl, or Br and Y is $CH_2$. In another embodiment, $X_4$ is H, Br, or I and Y is $CH_2$. In another embodiment, $X_4$ is H or F and Y is $CH_2$. In another embodiment, $X_4$ is H or Cl and Y is $CH_2$. In another embodiment, $X_4$ is H or Br and Y is $CH_2$. In another embodiment, $X_4$ is H or I and Y is $CH_2$.

In another embodiment, $X_2$ is halogen, aryl, or alkynyl, $X_4$ is H or F, and Y is S. In another embodiment, $X_2$ is halogen, aryl, or amino, $X_4$ is H or F, and Y is S. In another embodiment, $X_2$ is halogen, alkynyl, or amino, $X_4$ is H or F, and Y is S. In another embodiment, $X_2$ is aryl, alkynyl, or amino, $X_4$ is H or F, and Y is S. In another embodiment, $X_2$ is halogen or amino, $X_4$ is H or F, and Y is S. In another embodiment, $X_2$ is halogen or alkynyl, $X_4$ is H or F, and Y is S. In another embodiment, $X_2$ is halogen or aryl, $X_4$ is H or F, and Y is S. In another embodiment, $X_2$ is halogen, $X_4$ is H or F, and Y is S. In another embodiment, $X_2$ is aryl, $X_4$ is H or F, and Y is S. In another embodiment, $X_2$ is alkynyl, $X_4$ is H or F, and Y is S. In another embodiment, $X_2$ is amino, $X_4$ is H or F, and Y is S. In another embodiment, $X_2$ is halogen, heteroaryl, alkynyl, or amino, $X_4$ is H or F, and Y is S. In another embodiment, $X_2$ is halogen, heteroaryl, or alkynyl, $X_4$ is H or F, and Y is S. In another embodiment, $X_2$ is halogen, heteroaryl, or amino, $X_4$ is H or F, and Y is S. In another embodiment, $X_2$ is heteroaryl, alkynyl, or amino, $X_4$ is H or F, and Y is S. In another embodiment, $X_2$ is halogen or heteroaryl, $X_4$ is H or F, and Y is S. In another embodiment, $X_2$ is heteroaryl, $X_4$ is H or F, and Y is S. In another embodiment, $X_2$ is alkyl-substituted heteroaryl, $X_4$ is H or F, and Y is S. In another embodiment, $X_2$ is $C_1$-$C_6$ alkyl-substituted heteroaryl, $X_4$ is H or F, and Y is S. In another embodiment, $X_2$ is methyl-, ethyl-, n-propyl-, or isopropyl-substituted heteroaryl, $X_4$ is H or F, and Y is S. In another embodiment, $X_2$ is methyl- or ethyl-substituted heteroaryl, $X_4$ is H or F, and Y is S. In another embodiment, $X_2$ is methyl-substituted heteroaryl, $X_4$ is H or F, and Y is S. In another embodiment, $X_2$ is ethyl-substituted heteroaryl, $X_4$ is H or F, and Y is S. In another embodiment, $X_2$ is Br, I, furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, 5-methyloxazol-2-yl, ethynyl, propynyl, dimethylamino, diethylamino, or methylethylamino, $X_4$ is H or F, and Y is S. In another embodiment, $X_2$ is I, furan-2-yl, furan-3-yl, 5-methylfuran-2-yl, ethynyl, dimethylamino, diethylamino, or methylethylamino, $X_4$ is H or F, and Y is S. In another embodiment, $X_2$ is Br, furan-2-yl, furan-3-yl, 5-methylfuran-2-yl, ethynyl, dimethylamino, diethylamino, or methylethylamino, $X_4$ is H or F, and Y is S. In another embodiment, $X_2$ is I, furan-2-yl, furan-3-yl, 5-methylfuran-2-yl, ethynyl, or dimethylamino, $X_4$ is H or F, and Y is S. In another embodiment, $X_2$ is Br, furan-2-yl, furan-3-yl, 5-methylfuran-2-yl, ethynyl, or dimethylamino, $X_4$ is H or F, and Y is S. In another embodiment, $X_2$ is I, 1H-pyrazol-2-yl, 1H-pyrazol-3-yl, ethynyl, dimethylamino, diethylamino, or methylethylamino, $X_4$ is H or F, and Y is S. In another embodiment, $X_2$ is Br, 1H-pyrazol-2-yl, 1H-pyrazol-3-yl, ethynyl, dimethylamino, diethylamino, or methylethylamino, $X_4$ is H or F, and Y is S. In another embodiment, $X_2$ is I, 1H-pyrazol-2-yl, 1H-pyrazol-3-yl, ethynyl, or dimethylamino, $X_4$ is H or F, and Y is S. In another embodiment, $X_2$ is Br, 1H-pyrazol-2-yl, 1H-pyrazol-3-yl, ethynyl, or dimethylamino, $X_4$ is H or F, and Y is S. In another embodiment, $X_2$ is I, thiazol-2-yl, 5-methylthiazol-2-yl, ethynyl, dimethylamino, diethylamino, or methylethylamino, $X_4$ is H or F, and Y is S. In another embodiment, $X_2$ is Br, thiazol-2-yl, 5-methylthiazol-2-yl, ethynyl, dimethylamino, diethylamino, or methylethylamino, $X_4$ is H or F, and Y is S. In another embodiment, $X_2$ is I, thiazol-2-yl, 5-methylthiazol-2-yl, ethynyl, or dimethylamino, $X_4$ is H or F, and Y is S. In another embodiment, $X_2$ is Br, thiazol-2-yl, 5-methylthiazol-2-yl, ethynyl, or dimethylamino, $X_4$ is H or F, and Y is S. In another embodiment, $X_2$ is I, oxazol-2-yl, 5-methyloxazol-2-yl, ethynyl, dimethylamino, diethylamino, or methylethylamino, $X_4$ is H or F, and Y is S. In another embodiment, $X_2$ is Br, oxazol-2-yl, 5-methyloxazol-2-yl, ethynyl, dimethylamino, diethylamino, or methylethylamino, $X_4$ is H or F, and Y is S. In another embodiment, $X_2$ is I, oxazol-2-yl, 5-methyloxazol-2-yl, ethynyl, or dimethylamino, $X_4$ is H or F, and Y is S. In another embodiment, $X_2$ is Br, oxazol-2-yl, 5-methyloxazol-2-yl, ethynyl, or dimethylamino, $X_4$ is H or F, and Y is S.

In another embodiment, $X_2$ is halogen, aryl, or alkynyl, $X_4$ is H or F, and Y is $CH_2$. In another embodiment, $X_2$ is halogen, aryl, or amino, $X_4$ is H or F, and Y is $CH_2$. In another embodiment, $X_2$ is halogen, alkynyl, or amino, $X_4$ is H or F, and Y is $CH_2$. In another embodiment, $X_2$ is aryl, alkynyl, or amino, $X_4$ is H or F, and Y is $CH_2$. In another embodiment, $X_2$ is halogen or amino, $X_4$ is H or F, and Y is $CH_2$. In another embodiment, $X_2$ is halogen or alkynyl, $X_4$ is H or F, and Y is $CH_2$. In another embodiment, $X_2$ is halogen or aryl, $X_4$ is H or F, and Y is $CH_2$. In another embodiment, $X_2$ is halogen, $X_4$ is H or F, and Y is $CH_2$. In another embodiment, $X_2$ is aryl, $X_4$ is H or F, and Y is $CH_2$. In another embodiment, $X_2$ is alkynyl, $X_4$ is H or F, and Y is $CH_2$. In another embodiment, $X_2$ is amino, $X_4$ is H or F, and Y is $CH_2$. In another embodiment, $X_2$ is halogen, heteroaryl, alkynyl, or amino, $X_4$ is H or F, and Y is $CH_2$. In another embodiment, $X_2$ is halogen, heteroaryl, or alkynyl, $X_4$ is H or F, and Y is $CH_2$. In another embodiment, $X_2$ is halogen, heteroaryl, or amino, $X_4$ is H or F, and Y is $CH_2$. In another embodiment, $X_2$ is heteroaryl, alkynyl, or amino, $X_4$ is H or F, and Y is $CH_2$. In another embodiment, $X_2$ is halogen or heteroaryl, $X_4$ is H or F, and Y is $CH_2$. In another embodiment, $X_2$ is heteroaryl, $X_4$ is H or F, and Y is $CH_2$. In another embodiment, $X_2$ is alkyl-substituted heteroaryl, $X_4$ is H or F, and Y is $CH_2$. In another embodiment, $X_2$ is $C_1$-$C_6$ alkyl-substituted heteroaryl, $X_4$ is H or F, and Y is $CH_2$. In another embodiment, $X_2$ is methyl-, ethyl-, n-propyl-, or isopropyl-substituted heteroaryl, $X_4$ is H or F, and Y is $CH_2$. In another embodiment, $X_2$ is methyl- or ethyl-substituted heteroaryl, $X_4$ is H or F, and Y is $CH_2$. In another embodiment, $X_2$ is methyl-substituted heteroaryl, $X_4$ is H or F, and Y is $CH_2$. In another embodiment, $X_2$ is ethyl-substituted heteroaryl, $X_4$ is H or F, and Y is $CH_2$. In another embodiment, $X_2$ is Br, I, furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, 5-methyloxazol-2-yl, ethynyl, propynyl, dimethylamino, diethylamino, or methylethylamino, $X_4$ is H or F, and Y is $CH_2$. In another embodiment, $X_2$ is I, furan-2-yl, furan-3-yl, 5-methylfuran-2-yl, ethynyl, dimethylamino, diethylamino, or methylethylamino, $X_4$ is H or F, and Y is $CH_2$. In another embodiment, $X_2$ is Br, furan-2-yl, furan-3-yl, 5-methylfuran-2-yl, ethynyl, dimethylamino, diethylamino, or methylethylamino, $X_4$ is H or F, and Y is $CH_2$. In another embodiment, $X_2$ is I, furan-2-yl, furan-3-yl, 5-methylfuran-2-yl, ethynyl, or dimethylamino, $X_4$ is H or F, and Y is $CH_2$. In another embodiment, $X_2$ is Br, furan-2-yl, furan-3-yl, 5-methylfuran-2-yl, ethynyl, or dimethylamino, $X_4$ is H or F, and Y is $CH_2$. In another embodiment, $X_2$ is I, 1H-pyrazol-2-yl, 1H-pyrazol-3-yl, ethynyl, dimethylamino, diethylamino, or methylethylamino, $X_4$ is H or F, and Y is $CH_2$. In another embodiment, $X_2$ is Br, 1H-pyrazol-2-yl, 1H-pyrazol-3-yl, ethynyl, dimethylamino, diethylamino, or methylethylamino, $X_4$ is H or F, and Y is $CH_2$. In another embodiment, $X_2$ is I, 1H-pyrazol-2-yl, 1H-pyrazol-3-yl, ethynyl, or dimethylamino, $X_4$ is H or F, and Y is $CH_2$. In another embodiment, $X_2$ is Br, 1H-pyrazol-2-yl, 1H-pyrazol-3-yl, ethynyl, or dimethylamino, $X_4$ is H or F, and Y is $CH_2$. In another embodiment, $X_2$ is I, thiazol-2-yl, 5-methylthiazol-2-yl, ethynyl, dimethylamino, diethylamino, or methylethylamino, $X_4$ is H or F, and Y is $CH_2$. In another embodiment, $X_2$ is Br, thiazol-2-yl, 5-methylthiazol-2-yl, ethynyl, dimethylamino, diethylamino, or methylethylamino, is H or F, and Y is $CH_2$. In another embodiment, $X_2$ is I, thiazol-2-yl, 5-methylthiazol-2-yl, ethynyl, or dimethylamino, $X_4$ is H or F, and Y is $CH_2$. In another embodiment, $X_2$ is Br, thiazol-2-yl, 5-methylthiazol-2-yl, ethynyl, or dimethylamino, $X_1$ is H or F, and Y is $CH_2$. In another embodiment, $X_2$ is I, oxazol-2-yl, 5-methyloxazol-2-yl, ethynyl, dimethylamino, diethylamino, or methylethylamino, $X_4$ is H or F, and Y is $CH_2$. In another embodiment, $X_2$ is Br, oxazol-2-yl, 5-methyloxazol-2-yl, ethynyl, dimethylamino, diethylamino, or methylethylamino, $X_4$ is H or F, and Y is $CH_2$. In another embodiment, $X_2$ is I, oxazol-2-yl, 5-methyloxazol-2-yl, ethynyl, or dimethylamino, $X_4$ is H or F, and Y is $CH_2$. In another embodiment, $X_2$ is Br, oxazol-2-yl, 5-methyloxazol-2-yl, ethynyl, or dimethylamino, $X_4$ is H or F, and Y is $CH_2$.

In connection with each of the R groups containing a sulfonamide structure, the corresponding structure in which the sulfonamide has the reverse orientation or in which R contains a sulfinamide or an amide (each of either orientation) is within the scope of the disclosure as if each was specifically disclosed herein. In connection with each of the R groups containing a sulfinamide structure, the corresponding structure in which the sulfinamide has the reverse orientation or in which R contains a sulfonamide or an amide (each of either orientation) is within the scope of the disclosure as if each was specifically disclosed herein. In connection with each of the R groups containing an amide structure, the corresponding structure in which the amide has the reverse orientation or in which R contains a sulfonamide or a sulfinamide (each of either orientation) is within the scope of the disclosure as if each was specifically disclosed herein. Thus, by way of example, in each instance the disclosure of a compound in which the R group contains an —$SO_2N(R_A)$— structure should also be considered as a disclosure of a compound in which the R group contains an —$NR_ASO_2$—, —$S(O)N(R_A)$—, —$NR_AS(O)$—, —$C(O)N(R_A)$—, or —$NR_AC(O)$— structure in place of the —$SO_2N(R_A)$— structure.

Specific R groups include without limitation: 2-ethanesulfonic acid isopropylamide, i.e.,

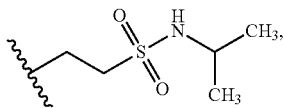 [SMILES: *CCS(=O)(=O)NC(C)C]

2-ethanesulfonic acid ethylamide, i.e.,

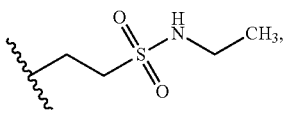 [SMILES: *CCS(=O)(=O)NCC]

2-ethanesulfonic acid methylamide, i.e.,

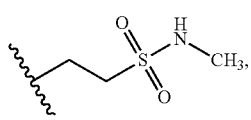 [SMILES: *CCS(=O)(=O)NC]

2-ethanesulfonic acid amide, i.e.,

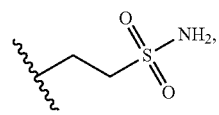 [SMILES: *CCS(N)(=O)=O]

2-ethanesulfonic acid t-butylamide, i.e.,

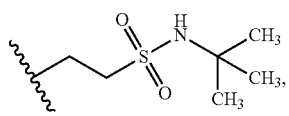 [SMILES: *CCS(=O)(=O)NC(C)(C)C]

2-ethanesulfonic acid isobutylamide, i.e.,

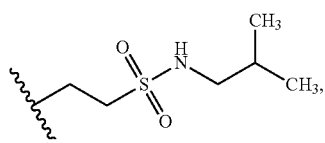 [SMILES: *CCS(=O)(=O)NCC(C)C]

2-ethanesulfonic acid cyclopropylamide, i.e.,

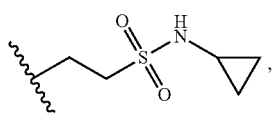 [SMILES: *CCS(=O)(=O)NC1CC1]

isopropanesulfonic acid 2-ethylamide, i.e.,

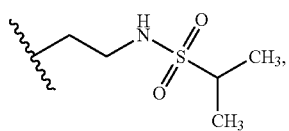

ethanesulfonic acid 2-ethylamide, i.e.,

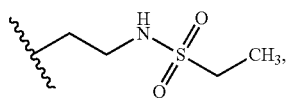 [SMILES: *CCNS(=O)(=O)CC]

N-2 ethyl methanesulfonamide, i.e.,

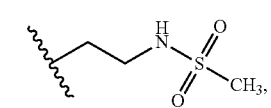 [SMILES: *CCNS(C)(=O)=O]

2-methyl-propane-2-sulfonic acid 2-ethylamide, i.e.,

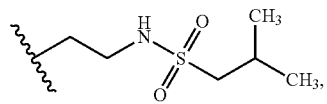 [SMILES: *CCNS(=O)(=O)CC(C)C]

2-methyl-propane-2-sulfinic acid 2-ethylamide, i.e.,

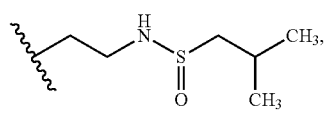

2-methyl-propane-1-sulfonic acid 2-ethylamide, i.e.,

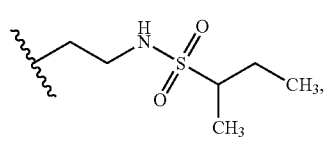 [SMILES: *CCNS(=O)(=O)C(C)CC]

cyclopropanesulfonic acid 2-ethylamide, i.e.,

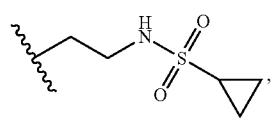 [SMILES: *CCNS(=O)(=O)C1CC1]

3-propane-1-sulfonic acid isopropylamide, i.e.,

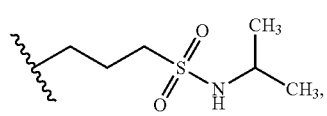 [SMILES: *CCCS(=O)(=O)NC(C)C]

3-propane-1-sulfonic acid ethylamide, i.e.,

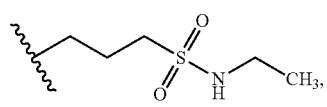 [SMILES: *CCCS(=O)(=O)NCC]

3-propane-1-sulfonic acid methylamide, i.e.,

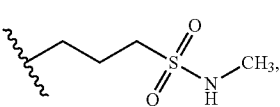 [SMILES: *CCCS(=O)(=O)NC]

3-propane-1-sulfonic acid amide, i.e.,

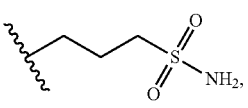 [SMILES: *CCCS(N)(=O)=O]

481

3-propane-1-sulfonic acid t-butylamide, i.e.,

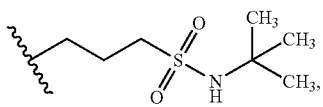 [SMILES: *CCCS(=O)(=O)NC(C)(C)C]

3-propane-1-sulfonic acid isobutylamide, i.e.,

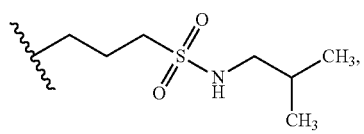 [SMILES: *CCCS(=O)(=O)NCC(C)C]

3-propane-1-sulfon c acid cyclopropylamide, i.e.,

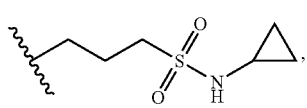 [SMILES: *CCCS(=O)(=O)NC1CC1]

propane-2-sulfonic acid 3-propylamide, i.e.,

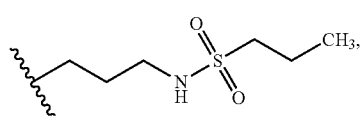 [SMILES: *CCCNS(=O)(=O)CCC]

ethanesulfonic acid 3-propylamide, i.e.,

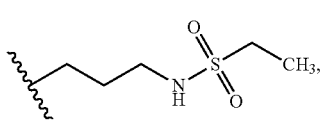 [SMILES: *CCCNS(=O)(=O)CC]

N-3-propyl methanesulfonamide, i.e.,

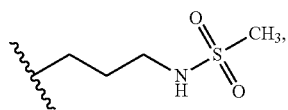 [SMILES: *CCCNS(C)(=O)=O]

2-methyl-propane-2-sulfonic acid 3-propylamide, i.e.,

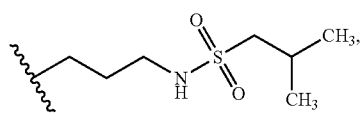 [SMILES: *CCCNS(=O)(=O)CC(C)C]

482

2-methyl-propane-2-sulfinic acid 3-propylamide, i.e.,

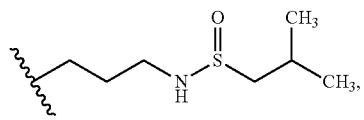 [SMILES: *CCCNS(=O)CC(C)C]

2-methyl-propane-1-sulfonic acid 3-propylamide, i.e.,

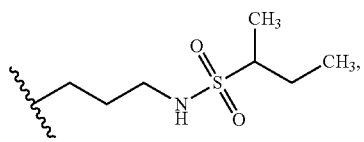 [SMILES: *CCCNS(=O)(=O)C(C)CC]

cyclopropanesulfonic acid 3-propylamide, i.e.,

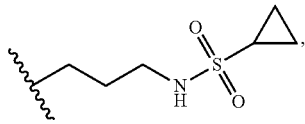 [SMILES: *CCCNS(=O)(=O)C1CC1]

3-N-isopropyl propionamide, i.e.,

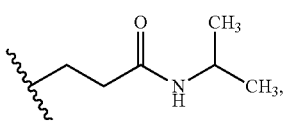 [SMILES: *CCC(=O)NC(C)C]

3-N-ethyl propionamide, i.e.,

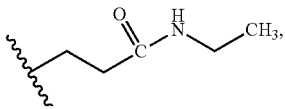 [SMILES: *CCC(=O)NCC]

3-N-methyl propionamide, i.e.,

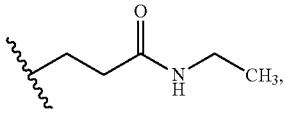 [SMILES: *CCC(=O)NCC]

3-propionamide, i.e.,

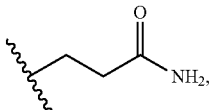 [SMILES: *CCC(N)=O]

483

3-N-t-butyl propionamide, i.e.,

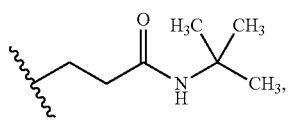 [SMILES: *CCC(=O)NC(C)(C)C]

3-N-isobutyl propionamide, i.e.,

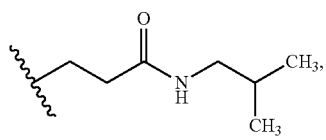 [SMILES: *CCC(=O)NCC(C)C]

3-N-cyclopropyl propionamide, i.e.,

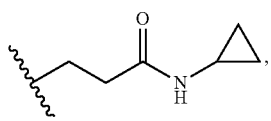 [SMILES: *CCC(=O)NC1CC1]

N-2-ethyl isobutyramide, i.e.,

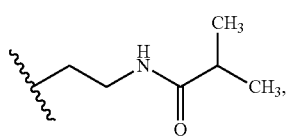 [SMILES: *CCNC(=O)C(C)C]

N-2-ethyl propionamide, i.e.,

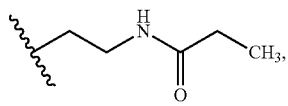 [SMILES: *CCNC(=O)CC]

N-2-ethyl acetamide, i.e.,

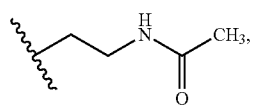 [SMILES: *CCNC(C)=O]

N-2-ethyl formamide, i.e.,

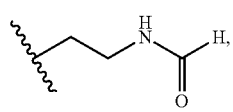

484

N-2-ethyl 2,2-dimethyl-propionamide, i.e.,

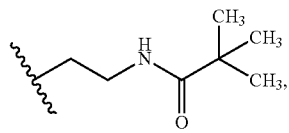 [SMILES: *CCNC(=O)C(C)(C)C]

N-2-ethyl 3-methylbutyramide, i.e.,

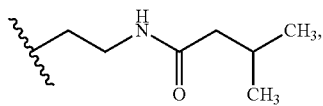 [SMILES: *CCNC(=O)CC(C)C]

cyclopropane carboxylic acid 2-ethyl-amide, i.e.,

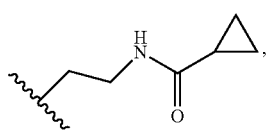 [SMILES: *CCNC(=O)C1CC1]

cyclopropane carboxylic acid 3-propyl-amide, i.e.,

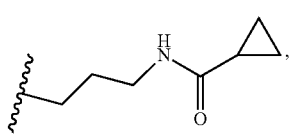 [SMILES: *CCCNC(=O)C1CC1]

N-3-propyl 2,2-dimethyl-propionamide, i.e.,

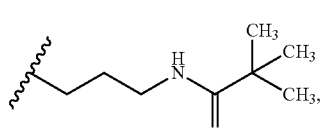

N-propyl-2-methyl-propane-2-sulfinamide, i.e.,

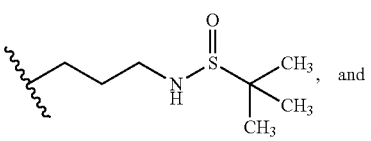 [SMILES: *CCCNS(=O)C(C)(C)C], and t-butanesulfonic acid 3-propylamide, i.e.,

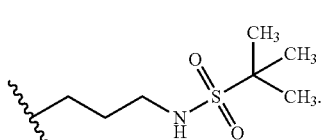

In connection with each of the $X_4$ groups of the structures disclosed herein, a corresponding structure in which $X_4$ is hydrogen, a fluoro group, or other halogen is within the scope of the disclosure as if each was specifically disclosed herein.

In a further aspect of the invention, each of the compounds described above can be made as a precursor compound in which $X_2$ is a leaving group which can be replaced by iodine for use as a radiolabel, for example $^{124}$I or $^{131}$I, useful as imaging tools. Exemplary leaving groups include without limitation trialkyl tin, for example trimethyl, or tributyl tin, trialkyl silicon, trialkyl geranium, or fluorus analogs of trialkyl tin such as —Sn(CH$_2$CH$_2$(CF$_2$)$_5$CF$_3$)$_3$, aryl boronic acids, thalium trifluoroacetates, triazines, and metallated arenes. Techniques for radioiodination are well known in the art, for example from Seevers, et al. *Chem. Rev.*, 1982, 82 (6), pp 575-590 and McIntee et al., *J. Org. Chem.* 2008, 73, 8236-8243 which are incorporated herein by reference.

The precursor compound in which $X_2$ is a leaving group are provided as reagents or in kits for addition of a radiolabeled $X_2$ substituent, for example $^{124}$I or $^{131}$I in the time immediately prior to use as an imaging marker. The precursor is readily shipped and stored prior to use since it is not itself radioactive, but it is readily converted to the labeled imaging marker.

In another embodiment, a pharmaceutical composition is formed from a Compound of Formulae (IA) or (IB) and a pharmaceutically acceptable carrier by a method known in the art. Thus, another embodiment relates to a pharmaceutical composition comprising a Compound of Formulae (IA) or (IB) and a pharmaceutically acceptable carrier. Such a composition is useful for treating or preventing cancer or a neurodegenerative disorder, e.g., in a patient in need thereof.

Another embodiment relates to a method for treating or preventing cancer or a neurodegenerative disorder, comprising administering to a patient in need thereof a therapeutically effective amount of a Compound of Formulae (IA) and/or (IB). Another embodiment relates to a method for treating or preventing cancer or a neurodegenerative disorder, comprising administering to a patient in need thereof a therapeutically effective amount of a pharmaceutical composition comprising a Compound of Formulae (IA) and/or (IB). Another embodiment relates to a method for treating cancer or a neurodegenerative disorder, comprising administering to a patient in need thereof a therapeutically effective amount of a Compound of Formulae (IA) and/or (IB). Another embodiment relates to a method for treating cancer or a neurodegenerative disorder, comprising administering to a patient in need thereof a therapeutically effective amount of a pharmaceutical composition of Formulae (IA) and/or (IB). Another embodiment relates to a method for preventing cancer or a neurodegenerative disorder, comprising administering to a patient in need thereof a therapeutically effective amount of a Compound of Formulae (IA) and/or (IB). Another embodiment relates to a method for preventing cancer or a neurodegenerative disorder, comprising administering to a patient in need thereof a therapeutically effective amount of a pharmaceutical composition comprising a Compound of Formulae (IA) and/or (IB). Another embodiment relates to the use of a Compound of Formulae (IA) or (IB) in the manufacture of a medicament useful for treating cancer or a neurodegenerative disorder or for preventing cancer or a neurodegenerative disorder.

Another embodiment relates to a method for the inhibition of Hsp90, comprising contacting Hsp90 with an Hsp90 function inhibiting amount of a Compound of Formulae (IA) or (M). An exemplary determination of an Hsp90 function inhibiting amount is provided in the example below entitled "Hsp90 Binding Assay." In one embodiment, the IC$_{50}$ determined by the "Hsp90 Binding Assay" provided herein is less than 10 µM. In another embodiment, the IC$_{50}$ determined by the "Hsp90 Binding Assay" provided herein is less than 1 µM. In another embodiment, the IC$_{50}$ determined by the "Hsp90 Binding Assay" provided herein is ≤0.1 µM. Another embodiment relates to the use of a Compound of Formulae (IA) or (IB) in formulating a pharmaceutical composition for the inhibition of Hsp90.

The following examples are set forth to assist in understanding the invention and should not be construed as specifically limiting the invention as described and claimed herein. Variations of the invention, including the substitution of all equivalents now known or later developed, that would be within the purview of those in the art, and changes in formulation or changes in experimental design, are to be considered to fall within the scope of the invention incorporated herein.

4. EXAMPLES

Certain examples below relate to the synthesis of illustrative compounds of the disclosure.

Synthetic Methods:

-M$_1$-M$_2$-R is —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$, wherein each R$_A$ and R$_D$ is independently selected from H, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

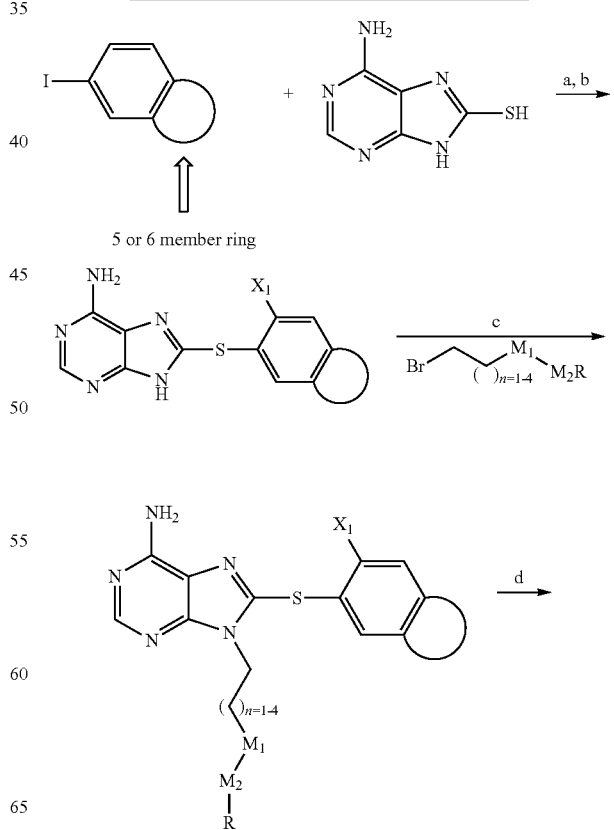

Scheme 1. Synthesis of S-linker Adenine Derivatives

487
-continued

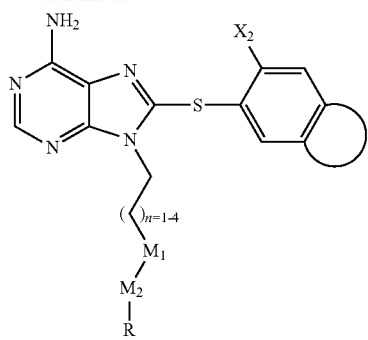

(a) CuI, neocuproine, NaOt-Bu, DMF, 110° C.; (b) NIS, acetonitrile, RT; (c) $Cs_2CO_3$; (d) $X_2M$, Pd (cat.), DMF, 50-100° C.

Scheme 2. Synthesis of Methylene-linker Adenine Derivatives

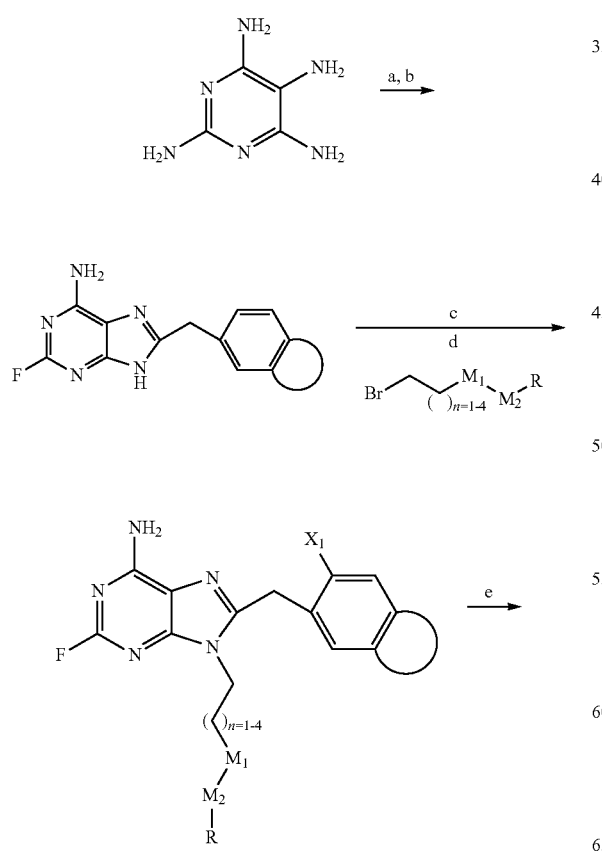

488
-continued

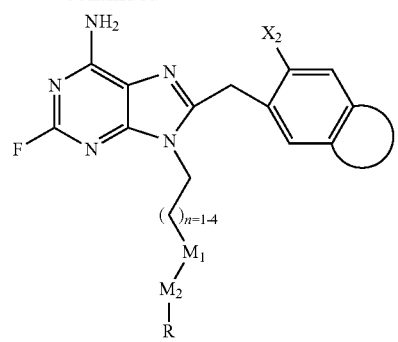

(a) triphenyl phosphite, pyridine, microwave; (b) HF-pyridine, $NaNO_2$; (c) NIS, acetonitrile, rt; (d) $Cs_2CO_3$; (e) $X_2M$, Pd (cat.), DMF, 50-100° C.

Scheme 3. Synthesis of Pyridine Derivatives (The definitions of R and $X_2$ as an amino group in this scheme are described above.)

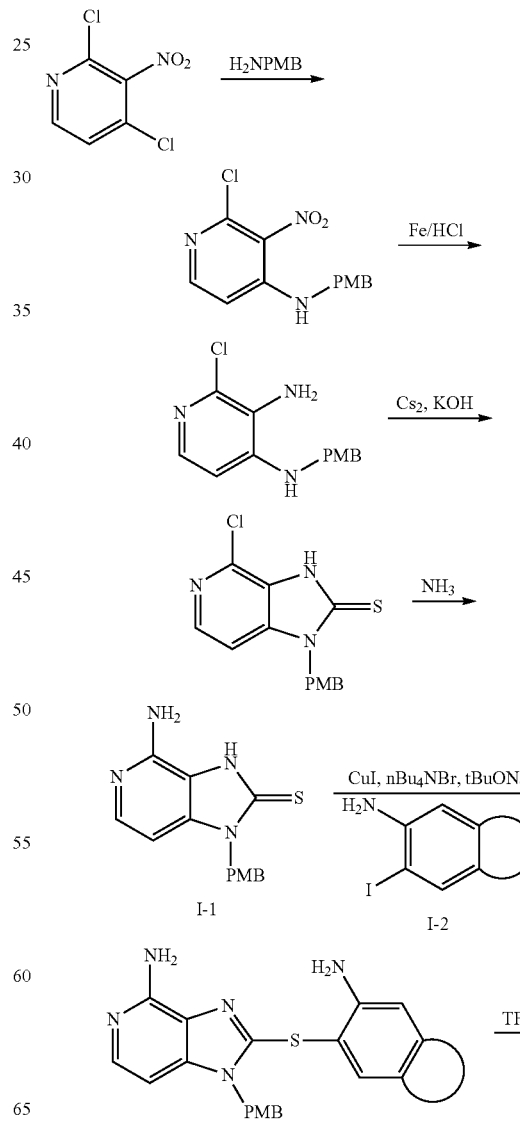

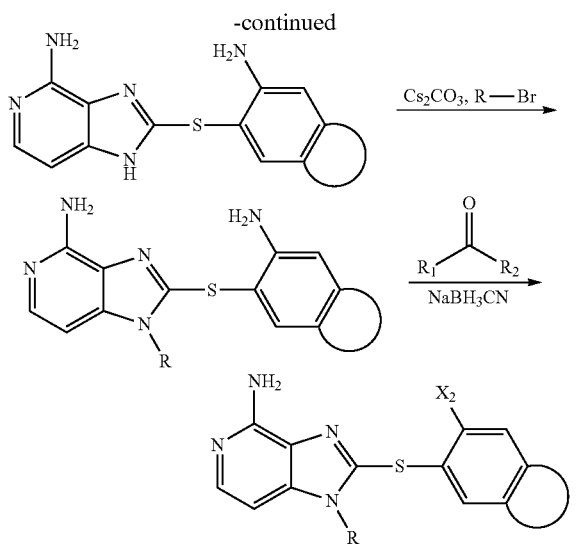

General Methods:

$^1$H and $^{13}$C NMR spectra were recorded on a Bruker 500 MHz instrument. Chemical shifts are reported in δ values in ppm downfield from TMS as the internal standard. $^1$H data are reported as follows: chemical shift, multiplicity (s=singlet, d=doublet, t=triplet, q=quartet, br=broad, m=multiplet), coupling constant (Hz), integration. $^{13}$C chemical shifts are reported in δ values in ppm downfield from TMS as the internal standard. High resolution mass spectra were recorded on a Waters LCT Premier system. Low resolution mass spectra were obtained on a Waters Acquity Ultra Performance LC with electrospray ionization and SQ detector. High-performance liquid chromatography analyses were performed on a Waters Autopurification system with PDA, MicroMass ZQ, and ELSD detector, and a reversed phase column (Waters X-Bridge C18, 4.6×150 mm, 5 μm).

N-(3-(6-amino-8-(6-iodo-benzo[1,3]dioxol-5-ylsulfanyl)-purin-9-yl)-propyl)-methanesulfonamide (WS34)

To a solution of 2-bromoethaneamomium bromide (2 g, 9.8 mmol) in 60 mL of CH$_2$Cl$_2$ was added triethylamine (3.4 mL, 24.4 mmol). The resulting mixture was stirred at a temperature of about 25° C. for 30 min, then cooled down at 0° C., methanesulfonic chloride (0.83 mL, 10.7 mmol) was added dropwise, kept stirring for 1 hr and allowed to warm up to a temperature of about 25° C. and stirred for about 16 hours. The resulting mixture was condensed and dried under reduced pressure to provide N-(2-bromoethyl)methanesulfonamide without further purification. N-(3-bromopropyl)methanesulfonamide was prepared in a similar manner.

To a solution of 8-((6-iodobenzo[d][1,3]dioxol-5-yl)thio)-9H-purin-6-amine (150 mg, 0.36 mmol) in 10 mL of dry DMF was added N-(3-bromopropyl)methanesulfonamide (300 mg, 1.4 mmol) and Cs$_2$CO$_3$ (190 mg, 0.58 mmol). The resulting mixture was stirred at a temperature of about 25° C. for 3 hrs, condensed under reduced pressure and purified by flash chromatography to provide compound WS34 as white solid (49 mg, 25% yield).

$^1$H NMR (500 MHz, MeOH-d$_4$/CDCl$_3$, δ): 8.21 (s, 1H), 7.41 (s, 1H), 7.10 (s, 1H), 6.08 (s, 2H), 4.34 (t, J=7.2 Hz, 2H), 3.16 (t, J=6.5 Hz, 2H), 2.96 (s, 3H), 2.09 (m, 2H).

HRMS (ESI) m/z [M+H]$^+$ calc'd. for C$_{14}$H$_{18}$IN$_6$O$_4$S$_2$=548.9876. found 548.9858.

Scheme 4. Synthesis of WS34 and WS35

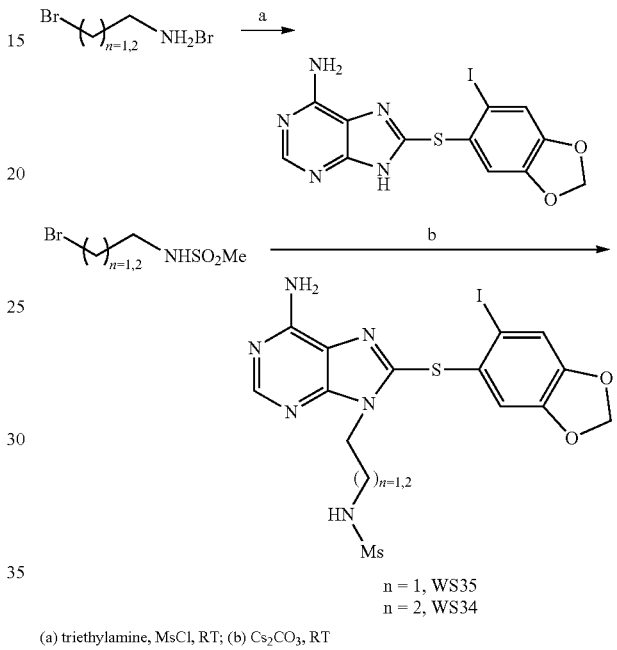

(a) triethylamine, MsCl, RT; (b) Cs$_2$CO$_3$, RT

N-(2-(6-amino-8-(6-iodo-benzo[1,3]dioxol-5-ylsulfanyl)-purin-9-yl)-ethyl)-methanesulfonamide (WS35)

To a solution of 8-((6-iodobenzo[d][1,3]dioxol-5-yl)thio)-9H-purin-6-amine (100 mg, 0.24 mmol) in 5 mL of dry DMF was added N-(2-bromoethyl)methanesulfonamide (150 mg, 0.7 mmol) and Cs$_2$CO$_3$ (150 mg, 0.46 mmol). The resulting mixture was stirred at a temperature of about 25° C. for 3 hrs, condensed under reduced pressure and purified by flash chromatography to provide compound WS35 as white solid (35 mg, 27% yield).

$^1$H NMR (500 MHz, MeOH-d$_4$/CDCl$_3$, δ): 8.19 (s, 1H), 7.41 (s, 1H), 7.18 (s, 1H), 6.07 (s, 2H), 4.23 (m, 2H), 3.65 (m, 2H), 2.97 (s, 3H).

HRMS (ESI) m/z [M+H]$^+$ calc'd. for C$_{15}$H$_{16}$IN$_6$O$_4$S$_2$=534.9719. found 534.9709.

Scheme 5. Synthesis of WS36, WS37, and WS38

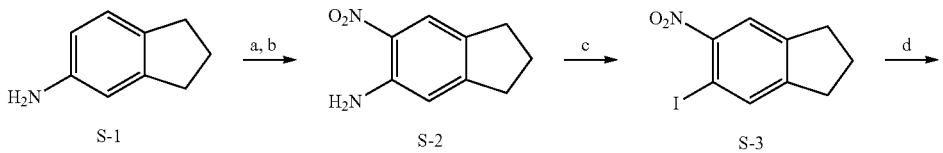

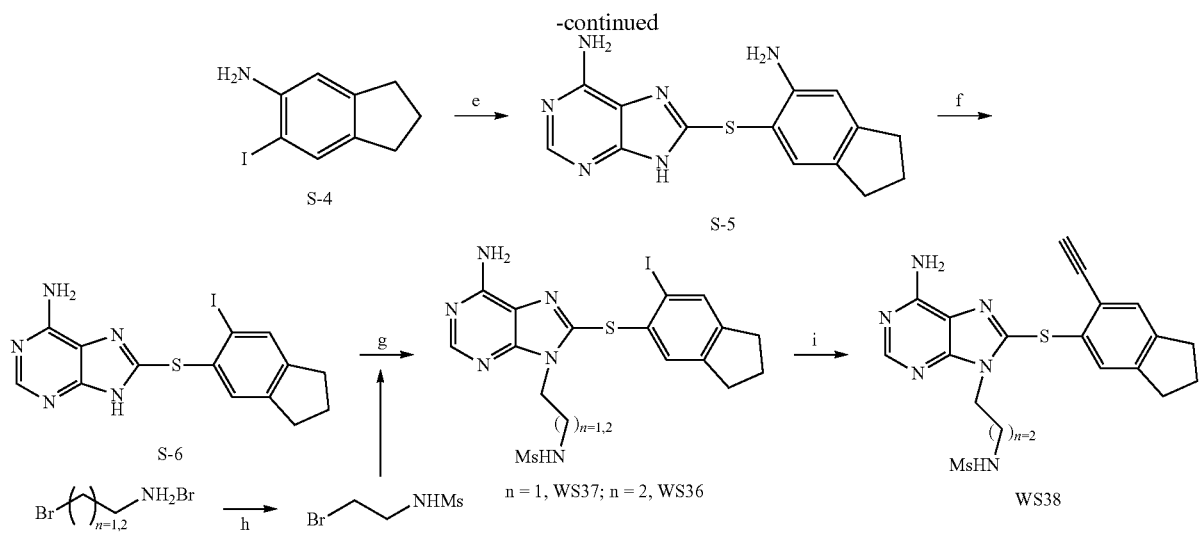

Reagents and conditions: (a) Ac₂O, dioxane, 0° C. to rt; (b) KNO₃, H₂SO₄, 0° C. to rt; (c) NaNO₂, KI, AcOH, 0° C. to rt; (d) Fe, NH₄Cl, isopropanol, reflux; (e) 8-mercaptoadenine, CuI, nBu₄NBr, NaOt-Bu, mv; (f) NaNO₂, KI, AcOH, 0° C.; (g) 1,3-dibromopropane or 1,2-dibromoethane, Cs₂CO₃, DMF, rt; (h) triethylamine, MsCl, 0° - rt; (i) CuI, PdCl₂(PPh₃)₂, trimethylsilanylacetylene, Et₃N, DMF, 90° C.

5-Amino-6-nitro-indane (S-2)

A solution of 5-aminoindane (S-1; 10 g, 75 mmol) in 100 mL of dioxane cooled in ice bath was added acetic anhydride (15 mL) dropwise and kept stirring at a temperature of about 25° C. for 2 days. The resulting mixture was condensed and dried under reduced pressure. The residue was dissolved in 100 mL of concentrated H₂SO₄, cooled in ice bath. KNO₃ in 15 mL of concentrated H₂SO₄ was added dropwise. The resulting solution was stirred at 0° C. for 2 h and then at a temperature of about 25° C. for 2 h. The reaction mixture was poured into 150 g of ice and the resulting yellow precipitate was filtered and washed with cold water to provide S-2 (7.1 g, 43% yield).

$^1$H NMR (500 MHz, CDCl₃, δ): 7.94 (s, 1H), 6.65 (s, 1H), 6.02 (br, 2H), 2.83 (m, 4H), 2.06 (m, 2H).
$^{13}$C NMR (125 MHz, CDCl₃, δ): 154.4, 144.2, 134.1, 131.2, 120.8, 113.5, 33.1, 31.4, 25.7.

5-Iodo-6-nitro-indane (S-3)

To a solution of S-2 (0.14 g, 0.78 mmol) in acetic acid cooled in ice bath was added NaNO₂ (65 mg, 0.94 mmol). The reaction mixture was stirred for 2 minutes. KI (0.39 g, 2.45 mmol) was added and the mixture was stirred at a temperature of about 25° C. for 20 minutes. The resulting suspension was quenched with water (15 mL) and extracted with ethyl acetate (2×20 mL). The organic layer was washed with saturated aqueous Na₂S₂O₃ solution, washed with brine and dried over MgSO₄ and evaporated to dryness to provide a residue that was purified by flash chromatography (ethyl acetate/hexane, gradient 0% to 50%) to provide S-3 (0.12 g, 65% yield) as a yellow solid.

$^1$H NMR (500 MHz, CDCl₃, δ): 7.83 (s, 1H), 7.71 (s, 1H), 2.95 (m, 4H), 2.11 (m, 2H).

5-Amino-6-iodo-indane (S-4)

To a solution of S-3 (1.65 g, 5.7 mmol) in isopropanol (100 mL) and saturated aqueous NH₄Cl solution (20 mL) was added iron powder (1.1 g). The resulting suspension was refluxed for 1 h. The reaction mixture was filtered and the filtrate was condensed and purified by flash chromatography (ethyl acetate/hexane, gradient 0% to 50%) to provide S-4 (1.36 g, 92% yield) as a pale yellow solid.

$^1$H NMR (500 MHz, CDCl₃, δ): 7.44 (s, 1H), 6.59 (s, 1H), 3.88 (s, 2H), 2.74 (m, 4H), 1.98 (m, 2H).
$^{13}$C NMR (125 MHz, CDCl₃, δ): 146.2, 144.9, 136.5, 134.1, 111.0, 32.8, 31.8, 26.1.
MS (ESI): m/z=259.99 [M+H]⁺

8-((6-Amino-2,3-dihydro-1H-inden-5-yl)thio)-9-H-purin-6-amine (S-5)

The mixture of 8-mercaptoadenine (64 mg, 0.38 mmol), S-4 (100 mg, 0.38 mmol), CuI (14.7 mg, 0.07 mmol), sodium t-butoxide (111 mg, 1.15 mmol) and tetrabutylammonium bromide (24.9 mg, 0.07 mmol) in anhydrous DMF (4 mL) was vortexed and heated at 190° C. under microwave for 1 h. The resulting mixture was condensed and purified by flash chromatography (methylene chloride/methanol, gradient 0% to 10%) to provide S-5 (54 mg, 47% yield) as a while solid.

$^1$H NMR (500 MHz, MeOH-d₄/CDCl₃, δ): 8.11 (s, 1H), 7.36 (s, 1H), 6.81 (s, 1H), 2.85 (m, 4H), 2.06 (m, 2H).
MS (ESI): m/z=299.02 [M+H]⁺.

8-((6-Iodo-2,3-dihydro-1H-inden-5-yl)thio)-9-H-purin-6-amine (S-6)

To a solution of S-5 (54 mg, 0.18 mmol) in acetic acid (5 mL) cooled in ice bath was added NaNO₂ (15 mg, 0.22 mmol) followed by KI (90 mg, 0.54 mmol). The reaction mixture was stirred at 0° C. for 15 min and quenched with water (10 mL). The resulting mixture was extracted with methylene chloride (2×20 mL). The organic layer was washed with saturated aqueous Na₂S₂O₃, washed with brine, dried over MgSO₄ and evaporated to dryness. The residue was purified by flash chromatography (methylene chloride/methanol, gradient 0% to 10%) to provide S-6 (42 mg, 56% yield) as a white solid.

$^1$H NMR (500 MHz, CDCl₃, δ): 8.12 (s, 1H), 7.84 (s, 1H), 7.39 (s, 1H), 2.91 (m, 4H), 2.11 (m, 2H).
MS (ESI): m/z=410.10 [M+H]⁺.

N-(3-(6-amino-8-(6-iodo-indan-5-ylsulfanyl)-purin-9-yl)-propyl)-methanesulfonamide (WS36)

To a solution of S-6 (50 mg, 0.12 mmol) in 3 mL of dry DMF was added N-(3-bromopropyl)methanesulfonamide (200 mg, 0.9 mmol) and Cs$_2$CO$_3$ (100 mg, 0.31 mmol). The resulting mixture was stirred at a temperature of about 25° C. for about 16 hours, condensed under reduced pressure and purified by flash chromatography to provide compound WS36 as a white solid (30 mg, 30% yield).

$^1$H NMR (500 MHz, CDCl$_3$, δ): 8.33 (s, 1H), 7.78 (s, 1H), 7.17 (s, 1H), 5.89 (br, 2H), 4.37 (t, J=6.2 Hz, 2H), 2.99 (q, 2H), 2.90 (t, J=7.5 Hz, 2H), 2.81 (t, J=7.5 Hz, 2H), 2.08 (m, 2H), 1.94 (m, 2H).

$^{13}$C NMR (125 MHz, CDCl$_3$, δ): 154.7, 153.0, 151.9, 147.6, 146.6, 136.1, 132.6, 127.9, 119.9, 98.4, 40.7, 40.2, 39.1, 32.5, 32.3, 30.3, 25.5.

HRMS (ESI) m/z [M+H]$^+$ calc'd. for C$_{18}$H$_{22}$IN$_6$O$_4$S$_2$=545.0290. found 545.0284.

N-(2-(6-amino-8-(6-iodo-indan-5-ylsulfanyl)-purin-9-yl)-ethyl)-methanesulfonamide (WS37)

To a solution of S-6 (50 mg, 0.12 mmol) in 3 mL of dry DMF was added N-(3-bromopropyl)methanesulfonamide (200 mg, 0.99 mmol) and Cs$_2$CO$_3$ (100 mg, 0.31 mmol). The resulting mixture was stirred at a temperature of about 25° C. for about 16 hours, condensed under reduced pressure and purified by flash chromatography to provide compound WS37 as a white solid (18 mg, 28% yield).

$^1$H NMR (500 MHz, CDCl$_3$, δ): 8.29 (s, 1H), 7.74 (s, 1H), 7.01 (s, 1H), 6.91 (br, 1H), 5.96 (br, 2H), 4.41 (t, J=5.4 Hz, 2H), 3.60 (m, 2H), 2.88 (m, 2H), 2.76 (t, J=10.2 Hz, 2H), 2.05 (m, 2H).

$^{13}$C NMR (125 MHz, CDCl$_3$, δ): 154.6, 153.5, 151.8, 147.5, 146.8, 146.0, 135.9, 133.2, 127.1, 119.8, 97.3, 44.7, 42.5, 40.7, 32.5, 32.2, 25.4.

HRMS (ESI) m/z [M+H]$^+$ calc'd. for C$_{17}$H$_{20}$IN$_6$O$_2$S$_2$=531.0134. found 531.0121.

N-(3-(6-amino-8-(6-ethynyl-indan-5-ylsulfanyl)-purin-9-yl)propyl)-methanesulfonamide (WS38)

To a solution of WS36 (10 mg, 0.02 mmol) in 2 mL of DMF was added CuI (0.7 mg, 0.004 mmol), PhCl$_2$(Ph$_3$)$_2$ (2.6 mg, 0.004 mmol), ethynyltrimethylsilane (8.6 µL, 0.06 mmol) and triethylamine (25 µL). The resulting mixture was stirred at 60° C. for 15 min, condensed and purified by chromatography. The intermediate was treated with KOH (5 mg) in methanol (1 mL) for 30 min at a temperature of about 25° C. The reaction mixture was condensed and purified by flash chromatography to provide compound WS38 as white solid (1.8 mg, 22% yield).

$^1$H NMR (500 MHz, CDCl$_2$, δ): 8.25 (s, 1H), 7.36 (s, 1H), 7.11 (s, 1H), 6.33 (br, 1H), 5.54 (br, 2H), 4.30 (t, J=6.1 Hz, 2H), 3.25 (s, 1H), 2.89 (q, 2H), 2.80 (m, 4H), 2.00 (m, 2H), 1.88 (m, 2H).

HRMS (ESI) m/z [M+H]$^+$ calc'd. for C$_{20}$H$_{23}$N$_6$O$_2$S$_2$=443.1324. found 443.1328.

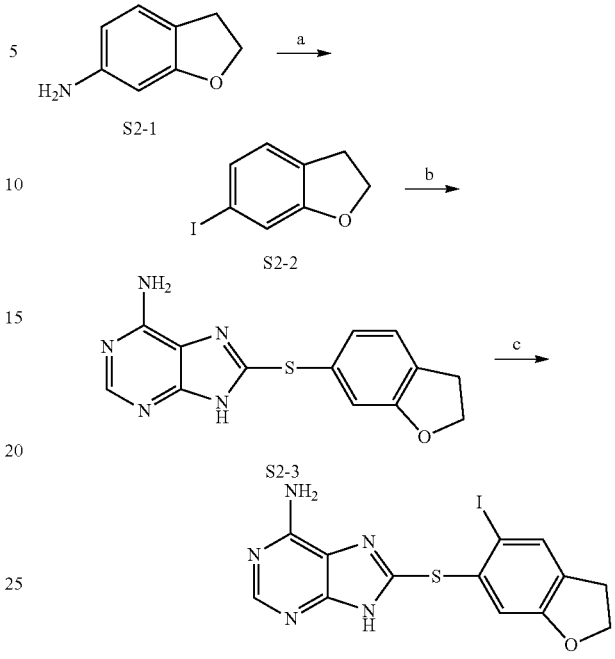

Scheme 6. Synthesis of Dihydrobenzofuran Intermediate

Reagents and conditions: (a) NaNO$_2$, KI, AcOH/TFA, 0° C.; (b) 8-mercaptoadenine, Cs$_2$CO$_3$, PdCl$_2$(dppf), DMF, 80° C., 48 h; (c) NIS, TFA, CH$_3$CN, rt, 2 h

6-Iodo-2,3-dihydrobenzofuran (S2-2)

A solution of 2,3-dihydrobenzofuran-6-amine (S2-1; 0.74 g, 5.5 mmol) in acetic acid (25 mL) and TFA (2 mL) was cooled in an ice bath for 5 minutes. NaNO$_2$ (0.454 g, 6.6 mmol) was added in 3 portions followed by KI (2.73 g, 16.4 mmol). The resulting mixture was stirred at 0° C. for 15 minutes and quenched with H$_2$O (20 mL). The mixture was extracted with EtOAc (3×150 mL) and the organic layer was washed with Na$_2$S$_2$O$_3$, washed with brine, dried over MgSO$_4$ and filtered. The filtrate was condensed under reduced pressure and the residue was purified by flash chromatography (hexane:EtOAc, 90:10 to 40:60) to provide S2-2 (0.82 g, 61% yield) as a pale-yellow solid.

$^1$H NMR (500 MHz, CDCl$_3$, δ): 7.14 (d, J=7.6 Hz, 1H), 7.11 (s, 1H), 6.89 (d, J=7.6 Hz, 1H), 4.54 (t, J=8.7 Hz, 2H), 3.14 (t, J=8.7 Hz, 2H).

$^{13}$C NMR (125 MHz, CDCl$_3$, δ): 161.1, 129.4, 127.1, 126.4, 118.7, 91.7, 71.6, 29.4.

8-(2,3-Dihydrobenzofuran-6-ylthio)-9H-purin-6-amine (S2-3)

To a solution of S2-2 (50 mg, 0.2 mmol) in DMF (2 mL) was added 8-mercaptoadenine (34 mg, 0.2 mmol), Cs$_2$CO$_3$ (99.4 mg, 0.3 mmol) and PdCl$_2$(dppf) (33 mg, 0.02 mmol). The mixture was degassed for 5 minutes with argon and stirred at 80° C. under argon protection for 48 h. The resulting mixture was concentrated under reduced pressure and the residue was purified by flash chromatography (CH$_2$Cl$_2$:MeOH, 100:0 to 90:10) to provide S2-3 (25 mg, 44% yield) as a yellow solid.

¹H NMR (500 MHz, CD₃OD, δ): 8.14 (s, 1H), 7.24 (d, J=7.6 Hz, 1H), 7.07 (d, J=7.3 Hz, 1H), 6.97 (s, 1H), 4.62 (t, J=8.7 Hz, 2H), 3.25 (t, J=8.7 Hz, 2H).
MS (ESI): m/z=285.8 [M+H]⁺.
HRMS (ESI) m/z [M+H]⁺ calc'd. for C₁₃H₁₂N₅OS=286.0763. found 286.0768.

8-(5-iodo-2,3-dihydrobenzofuran-6-ylthio)-9H-purin-6-amine (S2-4)

To a solution of S2-3 (40 mg, 0.14 mmol) in 6 mL of acetonitrile was added TFA (40 μL) and NIS (63 mg, 0.28 mmol). The resulting mixture was stirred at a temperature of about 25° C. for 2 h. The reaction mixture was concentrated under reduced pressure and the residue was purified by flash chromatography (CH₂Cl₂:MeOH, 100:0 to 90:10) to provide S2-4 (48 mg, 53% yield) as a yellow gum.
¹H NMR (500 MHz, CDCl₃, δ): 8.26 (s, 1H), 7.79 (s, 1H), 7.12 (s, 1H), 4.65 (t, J=8.8 Hz, 2H), 3.28 (t, J=8.7 Hz, 2H).
MS (ESI): m/z=412.0 [M+H]⁺.

temperature of about 25° C. for 30 min, then cooled down at 0° C. 2-methylpropane-2-sulfinic chloride (0.73 mL, 2.2 mmol) was added dropwise, kept stirring for 1 hr and allowed to warm up to a temperature of about 25° C. and stirred for about 16 hours. The resulting mixture was condensed and purified by flash chromatography to provide 2-methyl-propane-2-sulfinic acid (2-bromo-ethyl)-amide as a white solid (0.42 g, 86% yield).
¹H NMR (500 MHz, CDCl₃, δ): 3.80 (br, 1H), 3.45-3.56 (m, 4H), 1.20 (s, 9H).
¹³C NMR (125 MHz, CDCl₃, δ): 56.1, 47.3, 33.4, 22.6.

2-Methyl-propane-2-sulfonic acid (2-bromo-ethyl)-amide

To a solution of 2-methyl-propane-2-sulfinic acid (2-bromo-ethyl)-amide (0.8 g, 3.5 mmol) was added mCPBA (77%, 0.95 g, 4.2 mmol) and stirred at a temperature of about 25° C. for 2 hrs. The reaction mixture was condensed and

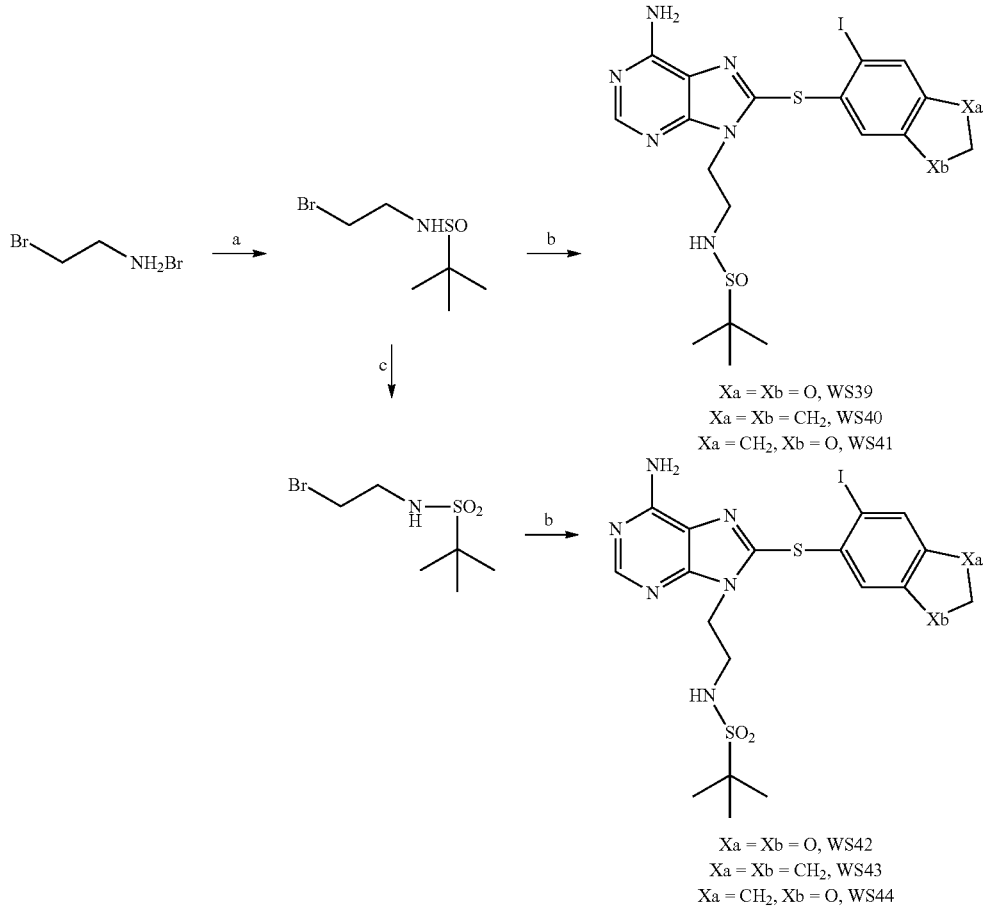

(a): triethylamine, tbutylsulfinic chloride; (b) adenine intermediates, Cs₂CO₃; (c) MCPBA 2-Methyl-propane-2-sulfinic acid (2-bromo-ethyl)-amide To a solution of 2-bromoethaneamomium bromide (410 mg, 2 mmol) in 20 mL of CH₂Cl₂ was added triethylamine (3697 μL, 5 mmol). The resulting mixture was stirred at a purified to provide 2-methyl-propane-2-sulfonic acid (2-bromo-ethyl)-amide as a white solid (0.4 g, 46% yield).

¹H NMR (500 MHz, MeOH-d₄/CDCl₃, δ): 3.87-3.97 (m, 2H), 3.36-3.47 (m, 2H), 1.32 (s, 9H).
¹³C NMR (125 MHz, CDCl₃, δ): 42.8, 29.6, 25.6, 23.2.

2-Methyl-propane-2-sulfuric acid (2-(6-amino-8-(6-iodo-benzo[1,3]dioxol-5-ylsulfanyl)-purin-9-yl)-ethyl)-amide (WS39)

To a solution of 8-((6-iodobenzo[d][1,3]dioxol-5-yl)thio)-9H-purin-6-amine (100 mg, 0.24 mmol) in 3 mL of dry DMF was added 2-methyl-propane-2-sulfinic acid (2-bromo-ethyl)-amide (90 mg, 0.37 mmol) and $Cs_2CO_3$ (159 mg, 0.49 mmol). The resulting mixture was stirred at a temperature of about 25° C. for 3 hrs, condensed under reduced pressure and purified by flash chromatography to provide compound WS39 as pale yellow solid (70 mg, 51% yield).

$^1$H NMR (500 MHz, MeOH-$d_4$/CDCl$_3$, δ): 8.21 (s, 1H), 7.39 (s, 1H), 7.04 (s, 1H), 6.06 (s, 2H), 4.81 (m, 1H), 4.35-4.44 (m, 2H), 3.63 (m, 1H), 3.46 (m, 1H), 1.11 (s, 9H).

$^{13}$C NMR (125 MHz, MeOH-$d_4$/CDCl$_3$, δ): 154.8, 153.2, 151.9, 149.4, 149.1, 146.1, 128.0, 120.1, 119.2, 112.0, 102.4, 90.6, 56.0, 45.1, 44.4, 22.6.

MS (ESI): m/z=561.0 [M+H]$^+$.

HRMS (ESI) m/z [M+H]$^+$ calc'd. for $C_{18}H_{22}IN_6O_3S_2$=561.0239. found 561.0233.

2-Methyl-propane-2-sulfuric acid {2-[6-amino-8-(6-iodo-indan-5-ylsulfanyl)-purin-9-yl]-ethyl}-amide (WS40)

To a solution of S-6 (50 mg, 0.12 mmol) in 3 mL of dry DMF was added 2-methyl-propane-2-sulfuric acid (2-bromo-ethyl)-amide (40 mg, 0.18 mmol) and $Cs_2CO_3$ (80 mg, 0.25 mmol). The resulting mixture was stirred at a temperature of about 25° C. for 3 hrs, condensed under reduced pressure and purified by flash chromatography to provide compound WS40 as pale yellow solid (35 mg, 51% yield).

$^1$H NMR (500 MHz, MeOH-$d_4$/CDCl$_3$, δ): 8.22 (s, 1H), 7.82 (s, 1H), 7.34 (s, 1H), 4.36-4.44 (m, 2H), 3.60 (m, 1H), 3.44 (m, 1H), 2.92 (t, J=7.4 Hz, 2H), 2.86 (t, J=7.5 Hz, 2H), 2.10 (m, 2H), 1.10 (s, 9H).

MS (ESI): m/z=557.0 [M+H]$^+$.

HRMS (ESI) m/z [M+H]$^+$ calc'd. for $C_{20}H_{26}IN_6OS_2$=557.0654. found 557.0676.

N-(2-(6-amino-8-((5-iodo-2,3-dihydrobenzofuran-6-yl)thio)-9H-purin-9-yl)ethyl)-2-methylpropane-2-sulfinamide (WS41)

To a solution of S2-4 (10 mg, 0.02 mmol) in 1 mL of dry DMF was added 2-methyl-propane-2-sulfinic acid (2-bromo-ethyl)-amide (27 mg, 0.12 mmol) and $Cs_2CO_3$ (16 mg, 0.05 mmol). The resulting mixture was stirred at a temperature of about 25° C. for 3 hrs, condensed under reduced pressure and purified by flash chromatography to provide compound WS41 as pale yellow solid (2.7 mg, 20% yield).

MS (ESI): m/z=559.0 [M+H]$^+$.

HRMS (ESI) m/z [M+H]$^+$ calc'd. for $C_{19}H_{22}IN_6O_2S_2$=559.0447. found 559.0439.

N-(2-(6-amino-8-((6-iodobenzo[d][1,3]dioxol-5-yl)thio)-9H-purin-9-yl)ethyl)-2-methylpropane-2-sulfonamide (WS42)

To a solution of 8-((6-iodobenzo[d][1,3]dioxol-5-yl)thio)-9H-purin-6-amine (30.4 mg, 0.07 mmol) in 3 mL of dry DMF was added 2-methyl-propane-2-sulfonic acid (2-bromo-ethyl)-amide (90 mg, 0.37 mmol) and $Cs_2CO_3$ (80 mg, 0.25 mmol). The resulting mixture was stirred at a temperature of about 25° C. for 3 hrs, condensed under reduced pressure and purified by flash chromatography to provide compound WS42 as pale yellow solid (17 mg, 41% yield).

$^1$H NMR (500 MHz, CDCl$_3$, δ): 8.16 (s, 1H), 7.19 n (s, 2H), 6.83 (br, 1H), 5.90 (br, 2H), 5.88 (s, 2H), 4.32 (t, J=5.6 Hz, 2H), 3.68 (m, 2H), 1.23 (s, 9H).

MS (ESI): m/z=577.1 [M+H]$^+$.

HRMS (ESI) m/z [M+H]$^+$ calc'd. for $C_{18}H_{22}IN_6O_4S_2$=577.0189. found 577.0172.

N-(2-(6-amino-8-((6-iodo-2,3-dihydro-1H-inden-5-yl)thio)-9H-purin-9-yl)ethyl)-2-methylpropane-2-sulfonamide (WS43)

To a solution of S2-4 (25 mg, 0.06 mmol) in 2 mL of dry DMF was added 2-methyl-propane-2-sulfonic acid (2-bromo-ethyl)-amide (90 mg, 0.37 mmol) and $Cs_2CO_3$ (60 mg, 0.18 mmol). The resulting mixture was stirred at a temperature of about 25° C. for 3 hrs, condensed under reduced pressure and purified by flash chromatography to provide compound WS43 as a white powder (3.6 mg, 10% yield).

$^1$H NMR (500 MHz, CDCl$_3$, δ): 8.25 (s, 1H), 7.56 (s, 1H), 6.42 (s, 1H), 5.88 (brs, 1H), 5.58 (brs, 2H), 4.49 (m, 2H), 4.31 (m, 2H), 3.51 (m, 2H), 3.11 (m, 2H), 1.12 (s, 9H).

MS (ESI): m/z=575.0 [M+H]$^+$.

HRMS (ESI) m/z [M+H]$^+$ calc'd. for $C_{19}H_{24}IN_6O_3S_2$=575.0396. found 575.0399.

N-(2-(6-amino-8-((5-iodo-2,3-dihydrobenzofuran-6-yl)thio)-9H-purin-9-yl)ethyl)-2-methylpropane-2-sulfonamide (WS44)

To a solution of S-6 (20 mg, 0.05 mmol) in 2 mL of dry DMF was added 2-methyl-propane-2-sulfonic acid (2-bromo-ethyl)-amide (90 mg, 0.37 mmol) and $Cs_2CO_3$ (60 mg, 0.18 mmol). The resulting mixture was stirred at a temperature of about 25° C. for 3 hrs, condensed under reduced pressure and purified by flash chromatography to provide compound WS44 as a white powder (11 mg, 31% yield).

$^1$H NMR (500 MHz, CDCl$_3$, δ): 8.34 (s, 1H), 7.74 (s, 1H), 6.89 (s, 1H), 6.58 (brs, 1H), 5.78 (brs, 2H), 4.42 (m, 2H), 3.71 (m, 2H), 2.89 (m, 2H), 2.75 (m, 2H), 2.06 (m, 2H), 1.32 (s, 9H).

MS (ESI): m/z=573.1 [M+H]$^+$.

HRMS (ESI) m/z [M+H]$^+$ calc'd. for $C_{20}H_{25}IN_6O_2S_2$=573.0603. found 573.0597.

Scheme 8. Synthesis of S-linked dimethylamino derivatives.

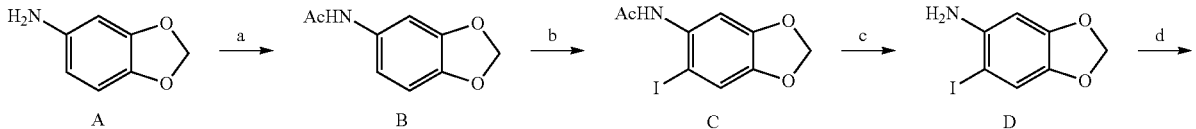

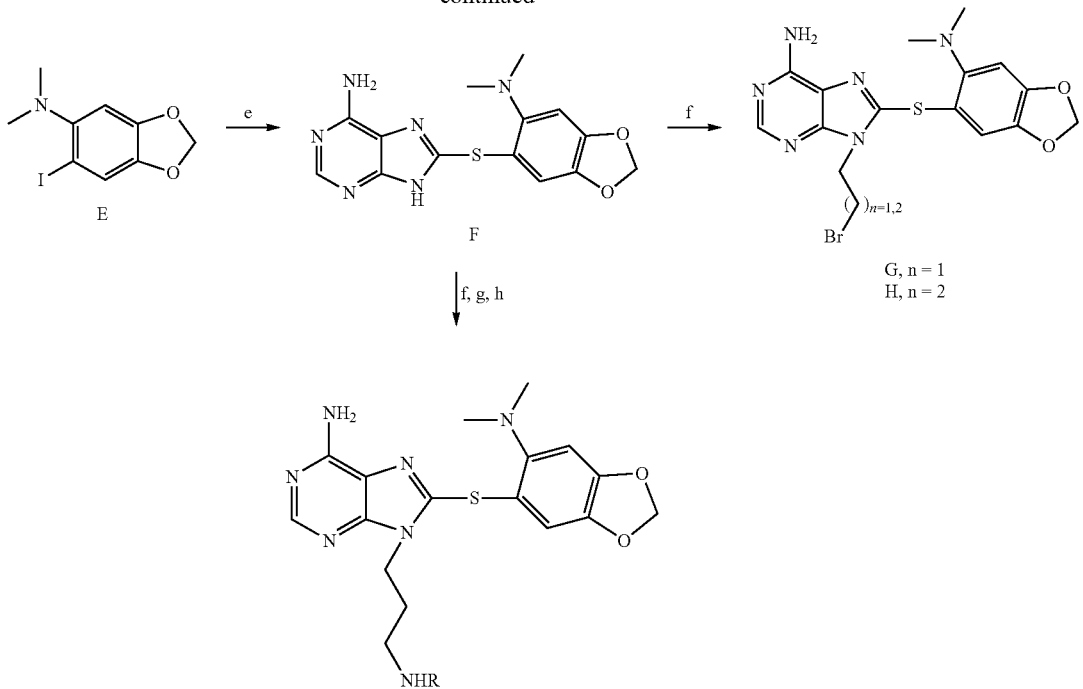

R = cyclopropane carbonyl MRP-I-28
R = t-butylcarbonyl MRP-I-29
R = cyclopropane sulfonyl MRP-I-31

Reagents and conditions: (a) Ac₂O, AcOH, rt; (b) ICl, CH₂Cl₂, AcOH, rt; (c) NaOH, EtOH, H₂O, reflux; (d) paraformaldehyde, NaBH₃CN, MeOH, 50° C.; (e) 8-mercaptoadenine, neocuproine, CuI, NaOtBu, DMF, 115° C.; (f) 2-(3-bromopropyl)isoindoline-1,3-dione, Cs₂CO₃, DMF, rt; (g) hydrazine hydrate, CH₂Cl₂/MeOH, rt; (h) TEA, corresponding acid chlorides or sulfonamide, DMF;

2-(3-(6-Amino-8-(6-(dimethylamino)benzo[d][1,3]dioxol-5-ylthio)-9H-purin-9-yl)propyl)isoindoline-1,3-dione. F (0.720 g, 2.18 mmol), Cs$_2$CO$_3$ (0.851 g, 2.62 mmol), 2-(3-bromopropyl)isoindoline-1,3-dione (2.05 g, 7.64 mmol) in DMF (15 mL) was stirred for 2 h at rt. The mixture was dried under reduced pressure and the residue purified by column chromatography (CH$_2$Cl$_2$:MeOH:AcOH, 15:1:0.5) to give 0.72 g (63%) of the titled compound. $^1$H NMR (500 MHz, CDCl$_3$/MeOH-d$_4$): δ 8.16 (s, 1H), 7.85-7.87 (m, 2H), 7.74-7.75 (m, 2H), 6.87 (s, 1H), 6.71 (s, 1H), 5.88 (s, 2H), 4.37 (t, J=6.4 Hz, 2H), 3.73 (t, J=6.1 Hz, 2H), 2.69 (s, 6H), 2.37-2.42 (m, 2H); HRMS (ESI) m/z [M+H]$^+$ calcd. for C$_{25}$H$_{24}$N$_7$O$_4$S, 518.1610. found 518.1601.

9-(3-Aminopropyl)-8-(6-(dimethylamino)benzo[d][1,3]dioxol-5-ylthio)-9H-purin-6-amine 2-(3-(6-Amino-8-(6-(dimethylamino)benzo[d][1,3]dioxol-5-ylthio)-9H-purin-9-yl)propyl)isoindoline-1,3-dione (0.72 g, 1.38 mmol), hydrazine hydrate (2.86 g, 2.78 mL, 20.75 mmol), in CH$_2$Cl$_2$:MeOH (4 mL:28 mL) was stirred for 2 h at rt. The mixture was dried under reduced pressure and the residue purified by column chromatography (CH$_2$Cl$_2$:MeOH—NH$_3$(7N), 20:1) to give 430 mg (80%) of the titled compound. $^1$H NMR (500 MHz, CDCl$_3$): δ 8.33 (s, 1H), 6.77 (s, 1H), 6.49 (s, 1H), 5.91 (s, 2H), 5.85 (br s, 2H), 4.30 (t, J=6.9 Hz, 2H), 2.69 (s, 6H), 2.65 (t, J=6.5 Hz, 2H), 1.89-1.95 (m, 2H); $^{13}$C NMR (125 MHz, CDCl$_3$): δ 154.5, 153.1, 151.7, 148.1, 147.2, 146.4, 144.8, 120.2, 120.1, 109.3, 109.2, 101.7, 45.3, 45.2, 40.9, 38.6, 333; HRMS (ESI) m/z [M+H]$^+$ calcd. for C$_{17}$H$_{22}$N$_7$O$_2$S, 388.1556. found 388.1544.

N-(3-(6-Amino-8-(6-(dimethylamino)benzo[d][1,3]dioxol-5-ylthio)-9H-purin-9-yl)propyl)cyclopropanecarboxamide (MRP-I-28)

9-(3-Aminopropyl)-8-(6-(dimethylamino)benzo[d][1,3]dioxol-5-ylthio)-9H-purin-6-amine (60 mg, 0.155 mmol), triethylamine (17 mg, 24 μL, 0.170 mmol), cyclopropane carbonyl chloride (16 mg, 14 μL, 0.155 mmol) in CH$_2$Cl$_2$ (3 mL) was stirred for 2 h at rt. The mixture was dried under reduced pressure and the residue purified by preparatory TLC (CH$_2$Cl$_2$:MeOH—NH$_3$(7N), 20:1) to give MRP-I-28 (66 mg, 93%). $^1$H NMR (600 MHz, CDCl$_3$): δ 8.33 (s, 1H), 7.40 (t, J=6.1 Hz, 1H), 6.77 (s, 1H), 6.52 (s, 1H), 6.40 (br s, 2H), 5.90 (s, 2H), 4.29 (t, J=6.2 Hz, 2H), 3.11 (q, J=6.0 Hz, 2H), 2.68 (s, 6H), 1.87-1.91 (m, 2H), 1.45-1.49 (m, 1H), 0.98-0.96 (m, 2H), 0.77-0.74 (m, 2H); $^{13}$C NMR (150 MHz, CDCl$_3$): δ 173.7, 154.9, 153.0, 151.8, 148.3, 147.5, 146.6, 144.7, 119.9, 119.5, 109.6, 102.5, 101.7, 45.3, 40.6, 35.3, 29.1, 14.9, 7.1 HRMS (ESI) m/z [M+H]$^+$ calcd. for C$_{21}$H$_{26}$N$_7$O$_3$S, 456.1818. found 456.1812.

N-(3-(6-Amino-8-(6-(dimethylamino)benzo[d][1,3]dioxol-5-ylthio)-9H-purin-9-yl)propyl)pivalamide (MRP-I-29)

9-(3-Aminopropyl)-8-(6-(dimethylamino)benzo[d][1,3]dioxol-5-ylthio)-9H-purin-6-amine (60 mg, 0.155 mmol), triethylamine (17 mg, 24 μL, 0.170 mmol), pivaloyl chloride (19 mg, 19 μL, 0.155 mmol) in CH$_2$Cl$_2$ (3 mL) was stirred for 2 h at rt. The mixture was dried under reduced pressure and the residue purified by preparatory TLC (CH$_2$Cl$_2$:MeOH—NH$_3$(7N), 20:1) to give MRP-I-29 (65 mg, 89%). $^1$H NMR (600 MHz, CDCl$_3$): δ 8.30 (s, 1H), 7.65 (t, J=6.2 Hz, 1H), 6.77 (s, 1H), 6.50 (s, 1H), 6.39 (br s, 2H), 5.90 (s, 2H), 4.26 (t, J=6.0 Hz, 2H), 3.04 (q, J=6.0 Hz, 2H), 2.68 (s, 6H), 1.83-1.87 (m, 2H), 1.27 (s, 9H); $^{13}$C NMR (150 MHz, CDCl$_3$): δ 178.8, 154.9, 152.9, 151.9, 148.3, 147.5, 146.6, 144.7, 119.8, 119.7, 109.5, 102.5, 101.7, 45.3, 40.3, 38.8, 34.8, 28.9, 27.7; (ESI) m/z [M+H]$^+$ calcd. for C$_{22}$H$_{30}$N$_7$O$_3$S, 472.2131. found 472.2128.

N-(3-(6-Amino-8-(6-(dimethylamino)benzo[d][1,3]dioxol-5-ylthio)-9H-purin-9-yl)propyl)cyclopropanesulfonamide (MRP-I-31)

9-(3-Aminopropyl)-8-(6-(dimethylamino)benzo[d][1,3]dioxol-5-ylthio)-9H-purin-6-amine (61 mg, 0.158 mmol), triethylamine (18 mg, 24 μL, 0.174 mmol), cyclopropane sulfonyl chloride (22 mg, 17 μL, 0.158 mmol) in CH$_2$Cl$_2$ (3 mL) was stirred for 2 h at rt. The mixture was dried under reduced pressure and the residue purified by preparatory TLC (CH$_2$Cl$_2$:MeOH—NH$_3$(7N), 20:1) to give MRP-I-31 (55 mg, 71%). $^1$H NMR (600 MHz, CDCl$_3$): δ 8.30 (s, 1H), 6.78 (s, 1H), 6.66 (t, J=6.8 Hz, 1H), 6.51 (s, 1H), 6.29 (br s, 2H), 5.91 (s, 2H), 4.31 (t, J=6.0 Hz, 2H), 3.02 (q, J=6.1 Hz, 2H), 2.70 (s, 6H), 2.34-2.38 (m, 1H), 1.95-1.99 (m, 2H), 1.15-1.17 (m, 2H), 0.93-0.96 (m, 2H); $^{13}$C NMR (150 MHz, CDCl$_3$): δ 154.9, 153.1, 151.7, 148.4, 147.6, 146.3, 144.8, 119.8, 119.4, 109.6, 102.4, 101.8, 45.4, 40.0, 39.0, 30.4, 30.2, 5.26; HRMS (ESI) m/z [M+H]$^+$ calcd. for C$_{20}$H$_{26}$N$_7$O$_4$S$_2$, 492.1488. found 492.1468.

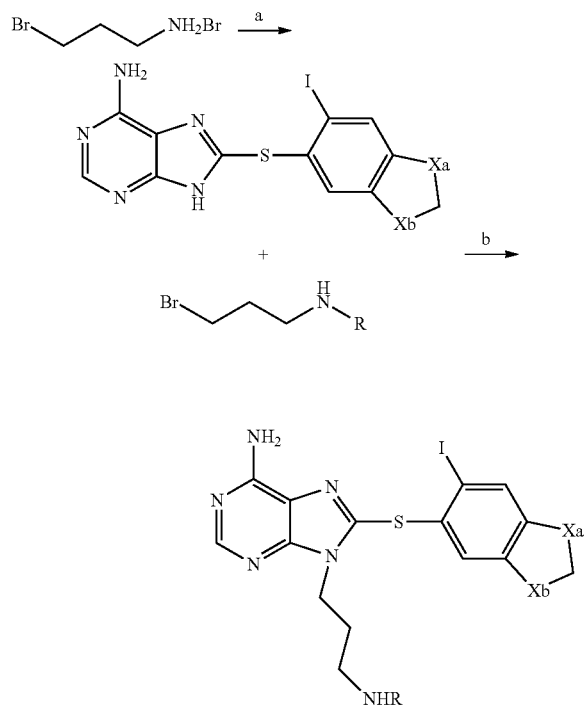

Scheme 9. Synthesis of S-linked amide, sulfonamide or sulfinamide derivatives

-continued
Xa = Xb = O, R = t-butylcarbonyl WS45
Xa = Xb = O, R = i-propylcarbonyl WS46
Xa = Xb = O, R = i-propylsulfonyl WS48
Xa = Xb = O, R = t-butylsulfinyl WS49
Xa = Xb = O, R = isobutylsulfonyl WS50
Xa = Xb = O, R = cyclopropanecarbonyl WS51
Xa = Xb = O, R = t-butylsulfonyl WS52
Xa = Xb = O, R = lactyl WS55
Xa = Xb = O, R = cyclopropanesulfonyl WS56
Xa = Xb = O, R = 2-hydroxy-2-methylpropanyl WS58
Xa = CH$_2$, Xb = O, R = cyclopropanecarbonyl WS61
X = CH2, Xb = O, R = t-butylsulfinyl WS62
Xa = Xb = CH$_2$, R = t-butylsulfinyl WS63
Xa = H, Xb = O, R = t-butylcarbonyl WS64
Reagents and conditions: (a) triethylamine, acid chloride or sulfonyl chloride or sulfinyl chloride; (b) Cs$_2$CO$_3$, DMF.

N-(3-Bromopropyl)pivalamide

To a suspension of 3-bromopropylamine hydrobromide (290 mg, 1.3 mmol) in CH$_2$Cl$_2$ (10 mL) cooled in ice bath was added triethylamine (470 uL). The resulting mixture was stirred for 5 min and trimethylacetyl chloride (163 uL, 1.3 mmol) was added dropwise. The reaction mixture was stirred at 0° C. for 2 hrs, condensed under vacuum, purified by flash chromatography to yield N-(3-bromopropyl)pivalamide as colorless oil (160 mg, 55%). $^1$H NMR (500 MHz, CDCl$_3$): δ (5.97 (br s, 1H), 3.40 (m, 4H), 2.07 (m, 2H), 1.17 (s, 9H); $^{13}$C NMR (125 MHz, CDCl$_3$): δ 178.7, 37.2, 32.1, 31.1, 27.6.

The preparation of other amides, sulfonamides and sulfinamides followed the same procedure as described above using 3-bromopropylamine hydrobromide and corresponding acid chloride, sulfonyl chloride or sulfinyl chloride.

N-(3-(6-amino-8-((6-iodobenzo[d][1,3]dioxol-5-yl)thio)-9H-purin-9-yl)propyl)pivalamide (WS45)

To a solution of 8-((6-iodobenzo[d][1,3]dioxol-5-yl)thio-9H-purin-6-amine (74 mg, 0.18 mmol) in DMF (2 mL) was added N-(3-bromopropyl)pivalamide (80 mg, 0.36 mmol) and Cs$_2$CO$_3$ (117 mg, 0.36 mmol). The resulting mixture was stirred at room temperature overnight. The reaction mixture was condensed under vacuum and the residue was purified by Prep TLC (CH$_2$Cl$_2$:NH$_3$-MeOH (7N), 20:1) to yield WS45 as a white solid (18 mg, 18%). $^1$H NMR (500 MHz, CDCl$_3$): δ 8.23 (s, 1H), 7.45 (br s, 1H), 7.19 (s, 1H), 6.88 (s, 1H), 5.93 (s, 2H), 5.69 (br s, 2H), 4.20 (t, J=6.1 Hz, 2H), 3.00 (m, 2H), 1.80 (m, 2H), 1.21 (s, 9H); HRMS (ESI) m/z [M+H]$^+$ calcd. for C$_{20}$H$_{24}$IN$_6$O$_3$S, 555.0675. found 555.0681.

N-(3-(6-Amino-8-((6-iodobenzo[d][1,3]dioxol-5-yl)thio)-9H-purin-9-yl)propyl)isobutyramide (WS46)

To a solution of 8-((6-iodobenzo[d][1,3]dioxol-5-yl)thio-9H-purin-6-amine (50 mg, 0.12 mmol) in DMF (2 mL) was added N-(3-bromopropyl)isobutyramide (50 mg, 0.24 mmol) and Cs$_2$CO$_3$ (78 mg, 0.24 mmol). The resulting mixture was stirred at room temperature overnight. The reaction mixture was condensed under vacuum and the residue was purified by Prep TLC (CH$_2$Cl$_2$:NH$_3$-MeOH (7N), 20:1) to yield WS46 as a white solid (22 mg, 34%). $^1$H NMR (500 MHz, CDCl$_3$/MeOH-d$_4$): δ 8.22 (s, 1H), 7.61 (br s, 1H), 7.41 (s, 1H), 7.08 (s, 1H), 6.07 (s, 2H), 4.27 (m, 2H), 3.21 (m, 2H), 2.45 (s, 1H), 2.02 (m, 2H), 1.19 (d, J=6.9 Hz, 6H); HRMS (ESI) m/z [M+H]$^+$ calcd. for C$_{19}$H$_{22}$IN$_6$O$_3$S, 541.0519. found 541.0508.

N-(3-(6-Amino-8-((6-iodobenzo[d][1,3]dioxol-5-yl)thio)-9H-purin-9-yl)propyl)propane-2-sulfonamide (WS48)

To a solution of 8-((6-iodobenzo[d][1,3]dioxol-5-yl)thio-9H-purin-6-amine (118 mg, 0.28 mmol) in DMF (2 mL) was added N-(3-bromopropyl)propane-2-sulfonamide (350 mg, 1.4 mmol) and $Cs_2CO_3$ (188 mg, 0.56 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS48 as a white solid (33 mg, 20%). $^1$H NMR (500 MHz, $CDCl_3$/MeOH-$d_4$): δ 8.20 (s, 1H), 7.41 (s, 1H), 7.09 (s, 1H), 6.08 (s, 2H), 4.35 (t, J=7.0 Hz, 2H), 3.10-3.22 (m, 3H), 2.07 (m, 2H), 1.37 (d, J=6.9 Hz, 6H); $^{13}$C NMR (125 MHz, $CDCl_3$/MeOH-$d_4$): δ 158.4, 156.1, 155.1, 153.9, 153.5, 151.8, 129.2, 123.5, 123.3, 117.9, 106.6, 98.3, 57.0, 44.8, 43.9, 34.3, 20.2; HRMS (ESI) m/z calcd. for $C_{18}H_{22}IN_6O_4S_2$, 577.0189. found 577.0193.

N-3-(6-Amino-8-((6-iodobenzo[d][1,3]dioxol-5-yl)thio)-9H-purin-9-yl)propyl)-2-methylpropane-2-sulfinamide (WS49)

To a solution of 8-((6-iodobenzo[d][1,3]dioxol-5-yl)thio-9H-purin-6-amine (118 mg, 0.07 mmol) in DMF (2 mL) was added N-(3-bromopropyl)-2-methlpropane-2-sulfinamide (50 mg, 0.21 mmol) and $Cs_2CO_3$ (23 mg, 0.14 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS49 as a white solid (14 mg, 35%). $^1$H NMR (600 MHz, $CDCl_3$): δ 8.31 (s, 1H), 7.33 (s, 1H), 6.94 (s, 1H), 6.02 (s, 2H), 5.87 (br s, 2H), 4.91 (t, J=6.7 Hz, 1H), 4.40-4.45 (m, 1H), 4.31-4.36 (m, 1H), 3.10-3.17 (m, 1H), 2.97-3.04 (m, 1H), 2.11-2.17 (m, 1H), 1.96-2.08 (m, 1H), 1.26 (s, 9H); $^{13}$C NMR (150 MHz, $CDCl_3$): δ 154.5, 152.9, 151.9, 149.3, 149.2, 146.5, 127.3, 119.9, 119.3, 112.6, 102.4, 91.8, 55.9, 42.1, 40.5, 31.1, 22.8; HRMS (ESI) m/z [M+H]$^+$ calcd. for $C_{19}H_{24}IN_6O_3S_2$, 575.0396. found 575.0379.

N-3-(6-Amino-8-((6-iodobenzo[d][1,3]dioxol-5-yl)thio)-9H-purin-9-yl)propyl)-2-methylpropane-1-sulfonamide (WS50)

To a solution of 8-((6-iodobenzo[d][1,3]dioxol-5-yl)thio-9H-purin-6-amine (24 mg, 0.06 mmol) in DMF (1.5 mL) was added N-(3-bromopropyl)-2-methlpropane-1-sulfonamide (60 mg, 0.24 mmol) and $Cs_2CO_3$ (38 mg, 0.12 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS50 as a white solid (16 mg, 46%). $^1$H NMR (500 MHz, $CDCl_3$/MeOH-$d_4$): δ 8.07 (s, 1H), 7.25 (s, 1H), 6.94 (s, 1H), 5.93 (s, 2H), 4.20 (t, J=6.2 Hz, 2H), 2.97 (t, J=5.6 Hz, 2H), 2.78 (d, J=6.5 Hz, 2H), 2.05-2.16 (m, 1H), 1.87-1.97 (m, 2H), 0.98 (d, J=6.7 Hz, 6H); $^{13}$C NMR (125 MHz, $CDCl_3$/MeOH-$d_4$): δ 158.3, 156.2, 155.1, 153.9, 153.4, 151.6, 129.3, 123.5, 123.2, 117.9, 106.6, 98.3, 64.2, 44.7, 43.4, 34.0, 28.8, 26.3; HRMS (ESI) m/z [M+H]$^+$ calcd. for $C_{19}H_{24}IN_6O_4S_2$, 591.0345. found 591.0333.

N-3-(6-amino-8-((6-iodobenzo[d][1,3]dioxol-5-yl)thio)-9H-purin-9-yl)propyl)cyclopropane carboxamide (WS51)

To a solution of 8-((6-iodobenzo[d][1,3]dioxol-5-yl)thio-9H-purin-6-amine (30 mg, 0.07 mmol) in DMF (1.5 mL) was added N-(3-bromopropyl)cyclopropanecarboxamide (60 mg, 0.28 mmol) and $Cs_2CO_3$ (48 mg, 0.14 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS51 as a white solid (14 mg, 35%). $^1$H NMR (500 MHz, $CDCl_3$/MeOH-$d_4$): δ 8.16 (s, 1H), 7.31 (s, 1H), 6.99 (s, 1H), 5.98 (s, 2H), 4.21 (t, J=7.0 Hz, 2H), 3.16 (t, J=6.6 Hz, 2H), 1.88-1.98 (m, 2H), 1.40-1.44 (m, 1H), 0.83-0.91 (m, 2H), 0.66-0.74 (m, 2H); $^{13}$C NMR (125 MHz, $CDCl_3$/MeOH-$d_4$): δ 179.1, 174.7, 154.3, 152.2, 151.2, 149.9, 149.4, 147.7, 125.4, 119.5, 113.9, 102.6, 94.3, 41.1, 35.9, 28.9, 14.5, 7.0; HRMS (PSI) m/z [M+H]$^+$ calcd. for $C_{19}H_{20}IN_6O_3S$, 539.0362. found 539.0362.

N-3-(6-Amino-8-((6-iodobenzo[d][1,3]dioxol-5-yl)thio)-9H-purin-9-yl)propyl)-2-methylpropane-2-sulfonamide (WS52)

To a solution of 8-((6-iodobenzo[d][1,3]dioxol-5-yl)thio-9H-purin-6-amine (37 mg, 0.09 mmol) in DMF (1.5 mL) was added N-(3-bromopropyl)-2-methylpropane-2-sulfonamide (70 mg, 0.27 mmol) and $Cs_2CO_3$ (59 mg, 0.18 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS52 as a white solid (9 mg, 16%). $^1$H NMR (600 MHz, $CDCl_3$): δ 8.20 (s, 1H), 7.25 (s, 1H), 6.89 (s, 1H), 6.35 (t, J=6.7 Hz, 1H), 5.94 (s, 2H), 5.69 (br s, 2H), 4.32 (t, J=6.0 Hz, 2H), 2.93-2.99 (m, 2H), 1.87-1.99 (m, 2H), 1.28 (s, 9H); $^{13}$C NMR (150 MHz, $CDCl_3$): δ 154.5, 152.8, 152.0, 149.34, 149.32, 146.9, 126.9, 119.8, 119.4, 112.9, 102.4, 92.3, 59.7, 40.3, 40.1, 31.3, 24.4; HRMS (PSI) m/z [M+H]$^+$ calcd. for $C_{19}H_{24}IN_6O_4S_2$, 591.0345. found 591.0353.

(S)—N-3-(6-Amino-8-((6-iodobenzo[d][1,3]dioxol-5-yl)thio)-9H-purin-9-yl)propyl)-2-hydroxypropanamide (WS55)

To a solution of 8-((6-iodobenzo[d][1,3]dioxol-5-yl)thio-9H-purin-6-amine (71 mg, 0.17 mmol) in DMF (2 mL) was added (S)-1-(3-bromopropyl)amino)-1-oxopropa-2-yl acetate (130 mg, 0.51 mmol) and $Cs_2CO_3$ (112 mg, 0.34 mmol). The resulting mixture was stirred at room temperature over night. The reaction mixture was condensed under vacuum and the residue was purified by Prep TLC ($CH_2Cl_2$:$NH_3$-MeOH (7N), 20:1) to yield WS55 as a white solid (13 mg, 14%). $^1$H NMR (600 MHz, $CDCl_3$): δ 8.23 (s, 1H), 7.64 (t, J=6.0 Hz, 1H), 7.26 (s, 1H), 6.90 (s, 1H), 5.94 (s, 2H), 5.73 (br s, 2H), 4.10-4.23 (m, 3H), 3.05-3.25 (m, 2H), 1.85-1.95 (m, 2H), 1.39 (dd, J=15.1, 6.8 Hz, 3H); HRMS (ESI) m/z [M+H]$^+$ calcd. for $C_{18}H_{20}IN_6O_4S$, 543.0312. found 543.0310.

N-3-(6-Amino-8-((6-iodobenzo[d][1,3]-dioxol-5-yl)thio)-9H-purin-9-yl)propyl)cyclopropanesulfonamide (WS56)

To a solution of 8-((6-iodobenzo[d][1,3]dioxol-5-yl)thio-9H-purin-6-amine (45 mg, 0.11 mmol) in DMF (2 mL) was added N-(3-bromopropyl)cyclopropanesulfonamide (120 mg, 0.44 mmol) and $Cs_2CO_3$ (71 mg, 0.22 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS56 as a white solid (12 mg, 19%). $^1$H NMR (600 MHz, $CDCl_3$/MeOH-$d_4$): δ 8.13 (s, 1H), 7.32 (s, 1H), 7.00 (s, 1H), 5.99 (s, 2H), 4.26 (t, J=7.0 Hz, 2H), 3.08 (t, J=6.3 Hz, 2H), 2.32-2.38 (m, 1H), 1.95-2.02 (m, 2H), 1.03-1.09 (m, 2H), 0.89-0.95 (m, 2H); HRMS (ESI) m/z [M+H]+ calcd. for $C_{18}H_{20}IN_6O_4S_2$, 575.0032. found 575.0042.

1-((3-(6-Amino-8-((6-iodobenzo[d][1,3]dioxol-5-yl) thio)-9H-purin-9-yl)propyl)amino)-2-methyl-1-oxopropan-2-yl acetate (WS57)

To a solution of 8-((6-iodobenzo[d][1,3]dioxol-5-yl)thio)-9H-purin-6-amine (59 mg, 0.14 mmol) in DMF (1.5 mL) was added 1-((3-bromopropyl)amino)-2-methyl-1-oxopropan-2-yl acetate (120 mg, 0.48 mmol) and $Cs_2CO_3$ (93 mg, 0.28 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS57 as a white solid (19 mg, 22%). $^1$H NMR (600 MHz, $CDCl_3$): δ 8.23 (s, 1H), 7.90 (t, J=6.0 Hz, 1H), 7.26 (s, 1H), 6.85 (s, 1H), 5.95 (s, 2H), 5.54 (br s, 2H), 4.21 (t, J=5.9 Hz, 2H), 2.93-2.99 (m, 2H), 2.08 (s, 3H), 1.83-1.90 (m, 2H), 1.59 (s, 6H); HRMS (ESI) m/z [M+H]+ calcd. for $C_{21}H_{24}IN_6O_5S$, 599.0574. found 599.0579.

N-(3-(6-Amino-8-((6-iodobenzo[d][1,3]dioxol-5-yl) thio)-9H-purin-9-yl)propyl)-2-hydroxy-2-methylpropanamide (WS58)

To a solution of WS57 in MeOH/THF/$H_2O$ (0.3 mL/0.3 mL/0.3 mL) was added LiOH (5 mg). The reaction mixture was stirred at room temperature for 2 hrs. The resulting mixture was condensed, purified by Prep TLC ($CH_2Cl_2$:$NH_3$-MeOH (7N), 20:1) to yield WS58 as a white solid (10 mg, 83%). $^1$H NMR (600 MHz, $CDCl_3$): δ 8.24 (s, 1H), 7.79 (br s, 1H), 7.25 (s, 1H), 6.88 (s, 1H), 5.94 (s, 2H), 5.67 (br s, 2H), 4.20 (t, J=6.4 Hz, 2H), 3.02-3.20 (m, 2H), 1.83-1.96 (m, 2H), 1.43 (s, 6H); $^{13}$C NMR (150 MHz, $CDCl_3$): δ 176.9, 154.5, 152.9, 151.9, 149.32, 149.31, 146.9, 127.0, 120.0, 119.4, 112.9, 102.4, 92.3, 72.9, 40.6, 35.4, 29.2, 28.0; HRMS (ESI) m/z [M+H]+ calcd. for $C_{19}H_{22}IN_6O_4S$, 557.0468. found 557.0447.

N-(3-(6-Amino-8-((5-iodo-2,3-dihydrobenzofuran-6-yl)thio)-9H-purin-9-yl)propyl)cyclopropanecarboxamide (WS61)

To a solution of 8-((5-iodo-2,3-dihydrobenzofuran-6-yl) thio)-9H-purin-6-amine (26 mg, 0.06 mmol) in DMF (1.5 mL) was added N-(3-bromopropyl)cyclopropanecarboxamide (39 mg, 0.18 mmol) and $Cs_2CO_3$ (41 mg, 0.12 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS61 as a white solid (12 mg, 35%). $^1$H NMR (600 MHz, $CDCl_3$): δ 8.30 (s, 1H), 7.57 (s, 1H), 7.16 (m, 1H), 6.55 (s, 1H), 5.67 (br s, 2H), 4.50 (t, J=8.8 Hz, 2H), 4.22 (t, J=6.3 Hz, 2H), 3.13 (t, J=8.6 Hz, 2H), 3.01-3.07 (m, 2H), 1.80-1.86 (m, 2H), 1.38-1.44 (m, 1H), 0.87-0.93 (m, 2H), 0.67-0.72 (m, 2H); HRMS (ESI) m/z [M+H]+ calcd. for $C_{20}H_{22}IN_6O_2S$, 537.0570. found 537.0567.

N-(3-(6-Amino-8-((5-iodo-2,3-dihydrobenzofuran-6-yl)thio)-9H-purin-9-yl)propyl)-2-methylpropane-2-sulfinamide (WS62)

To a solution of 8-((5-iodo-2,3-dihydrobenzofuran-6-yl) thio)-9H-purin-6-amine (26 mg, 0.06 mmol) in DMF (1.5 mL) was added N-(3-bromopropyl)-2-methlpropane-2-sulfinamide (49 mg, 0.18 mmol) and $Cs_2CO_3$ (41 mg, 0.12 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS62 as a white solid (11 mg, 30%). $^1$H NMR (600 MHz, $CDCl_3$): δ 8.33 (s, 1H), 7.66 (s, 1H), 6.61 (s, 1H), 5.85 (br s, 2H), 4.84 (t, J=6.7 Hz, 1H), 4.59 (t, J=8.7 Hz, 2H), 4.37-4.44 (m, 1H), 4.29-4.35 (m, 1H), 3.22 (t, J=8.5 Hz, 2H), 3.09-3.16 (m, 1H), 2.95-3.02 (m, 1H), 2.06-2.15 (m, 1H), 1.93-2.05 (m, 1H), 1.29 (s, 9H); HRMS (ESI) m/z [M+H]+ calcd. for $C_{20}H_{26}IN_6O_2S_2$, 573.0603. found 573.0620.

N-(3-(6-Amino-8-((6-iodo-2,3-dihydro-1H-inden-5-yl)thio)-9H-purin-9-yl)propyl)-2-methylpropane-2-sulfinamide (WS63)

To a solution of 8-((6-iodo-2,3-dihydro-1H-inden-5-yl) thio)-9H-purin-6-amine (13 mg, 0.03 mmol) in DMF (1.5 mL) was added N-(3-bromopropyl)-2-methlpropane-2-sulfinamide (23 mg, 0.1 mmol) and $Cs_2CO_3$ (21 mg, 0.06 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS63 as a white solid (5 mg, 27%). $^1$H NMR (600 MHz, $CDCl_3$): δ 8.22 (s, 1H), 7.68 (s, 1H), 7.05 (s, 1H), 5.70 (br s, 2H), 4.83 (t, J=6.7 Hz, 1H), 4.28-4.36 (m, 1H), 4.17-4.27 (m, 1H), 2.99-3.07 (m, 1H), 2.85-2.93 (m, 1H), 2.81 (t, J=7.4 Hz, 2H), 2.72 (t, J=7.5 Hz, 2H), 1.83-2.08 (m, 4H), 1.20 (m, 9H); HRMS (ESI) m/z [M+H]+ calcd. for $C_{21}H_{28}IN_6OS_2$, 571.0811. found 571.0809.

N-(3-(6-Amino-8-((2-iodo-5-methoxyphenyl)thio)-9H-purin-9-yl)propyl)pivalamide (WS64)

To a solution of 8-((2-iodo-5-methoxyphenyl)thio)-9H-purin-6-amine (200 mg, 0.5 mmol) in DMF (3 mL) was added N-(3-bromopropyl)pivalamide (445 mg, 2 mmol) and $Cs_2CO_3$ (326 mg, 1 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS64 as a white solid (53 mg, 20%). $^1$H NMR (500 MHz, $CDCl_3$): δ 8.26 (s, 1H), 7.66 (d, J=8.7 Hz, 1H), 7.43 (br s, 1H), 6.66 (s, 1H), 6.50 (d, J=8.7 Hz, 1H), 5.86 (br s, 2H), 4.20 (t, J=6.1 Hz, 2H), 3.61 (s, 3H), 2.78 (m, 2H), 1.82 (m, 2H), 1.21 (s, 9H); $^{13}$C NMR (125 MHz, $CDCl_3$): δ 178.8, 160.5, 155.0, 153.2, 152.0, 145.0, 140.6, 137.7, 120.1, 117.2, 115.4, 88.4, 55.5, 40.7, 38.8, 34.8, 29.1, 27.7; HRMS (ESI) m/z [M+H]+ calcd. for $C_{20}H_{26}IN_6O_2S$, 541.0883. found 541.0898.

Scheme 10. Synthesis of S-linked reversed sulfonamide derivatives

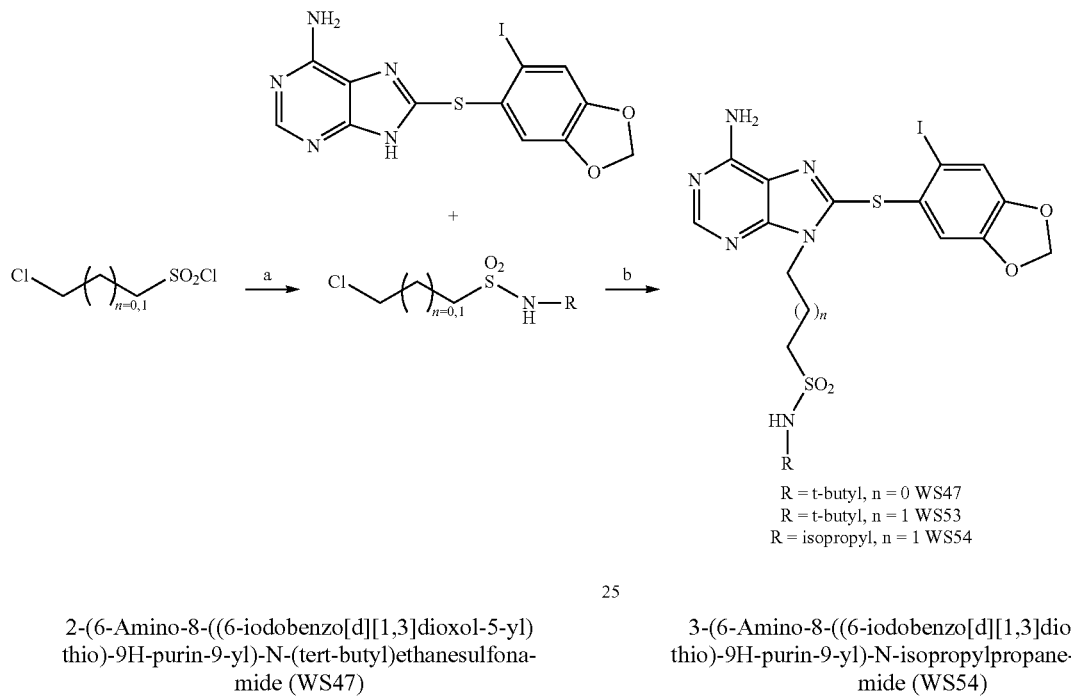

R = t-butyl, n = 0 WS47
R = t-butyl, n = 1 WS53
R = isopropyl, n = 1 WS54

2-(6-Amino-8-((6-iodobenzo[d][1,3]dioxol-5-yl)thio)-9H-purin-9-yl)-N-(tert-butyl)ethanesulfonamide (WS47)

To a solution of 8-((6-iodobenzo[d][1,3]dioxol-5-yl)thio-9H-purin-6-amine (56 mg, 0.13 mmol) in DMF (2 mL) was added N-t-butyl-2-chloroethanesulfonamide (50 mg, 0.25 mmol) and $Cs_2CO_3$ (88 mg, 0.27 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS47 as a white solid (10 mg, 13%). $^1$H NMR (500 MHz, $CDCl_3$/MeOH-$d_4$): δ 8.22 (s, 1H), 7.39 (s, 1H), 7.08 (s, 1H), 6.06 (s, 2H), 4.69 (t, J=7.0 Hz, 2H), 3.57 (t, J=7.1 Hz, 2H), 1.35 (s, 9H); $^{13}$C NMR (125 MHz, $CDCl_3$/MeOH-$d_4$): δ 158.3, 156.4, 155.1, 153.9, 153.4, 151.5, 129.2, 123.5, 123.3, 117.8, 106.6, 98.1, 58.5, 57.3, 42.7, 33.8; HRMS (ESI) m/z [M+H]$^+$ calcd. for $C_{18}H_{22}IN_6O_4S_2$, 577.0189. found 577.0217.

3-(6-Amino-8-((6-iodobenzo[c/][1,3]dioxol-5-yl)thio)-9H-purin-9-yl)-N-(tert-butyl)propane-1-sulfonamide (WS53)

To a solution of 8-((6-iodobenzo[d][1,3]dioxol-5-yl)thio-9H-purin-6-amine (56 mg, 0.13 mmol) in DMF (2 mL) was added N-t-butyl-3-chloro-N-propane-1-sulfonamide (144 mg, 0.65 mmol) and $Cs_2CO_3$ (88 mg, 0.27 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS53 as a white solid (18 mg, 22%). $^1$H NMR (600 MHz, $CDCl_3$/MeOH-$d_4$): δ 8.21 (s, 1H), 7.40 (s, 1H), 7.06 (s, 1H), 6.06 (s, 2H), 4.38 (t, J=7.3 Hz, 2H), 3.12 (t, J=7.4 Hz, 2H), 2.13-2.44 (m, 2H), 1.33 (s, 9H); $^{13}$C NMR (150 MHz, $CDCl_3$/MeOH-$d_4$: δ 155.8, 153.8, 152.4, 151.5, 151.0, 149.0, 126.7, 121.0, 120.8, 115.3, 104.1, 95.7, 55.7, 51.1, 43.6, 31.5, 25.9; HRMS (ESI) m/z [M+H]$^+$ calcd. for $C_{19}H_{24}IN_6O_4S_2$, 591.0345. found 591.0361.

3-(6-Amino-8-((6-iodobenzo[d][1,3]dioxol-5-yl)thio)-9H-purin-9-yl)-N-isopropylpropane-1-sulfonamide (WS54)

To a solution of 8-((6-iodobenzo[d][1,3]dioxol-5-yl)thio-9H-purin-6-amine (39 mg, 0.09 mmol) in DMF (2 mL) was added 3-chloro-N-isopropylpropane-1-sulfonamide (100 mg, 0.45 mmol) and $Cs_2CO_3$ (62 mg, 0.19 mmol). The resulting mixture was stirred at room temperature overnight. The reaction mixture was condensed under vacuum and the residue was purified by Prep TLC ($CH_2Cl_2$:$NH_3$-MeOH (7N), 20:1) to yield WS54 as a white solid (14 mg, 26%). $^1$H NMR (500 MHz, $CDCl_3$/MeOH-$d_4$): δ 8.00 (s, 1H), 7.19 (s, 1H), 6.86 (s, 1H), 5.86 (s, 2H), 4.17 (t, J=7.3 Hz, 2H), 3.34 (septet, J=6.6 Hz, 1H), 2.89 (t, J=7.6 Hz, 2H), 2.05-2.13 (m, 2H), 0.99 (d, J=6.6 Hz, 6H); HRMS (ESI) m/z [M+H]$^+$ calcd. for $C_{15}H_{22}IN_6O_4S_2$, 577.0189. found 577.0194.

Scheme 11. Synthesis of methylene-linked amide, sulfonamide and sulfinamide derivatives

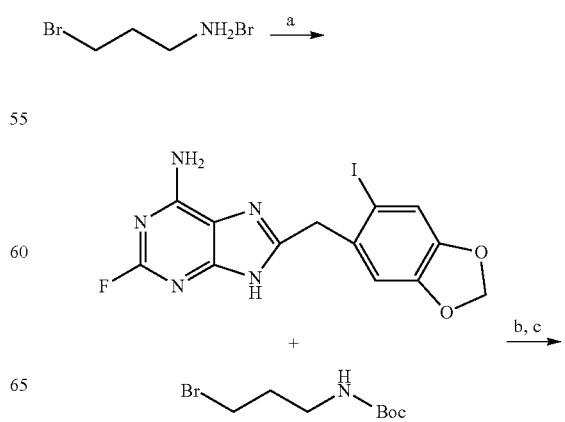

509

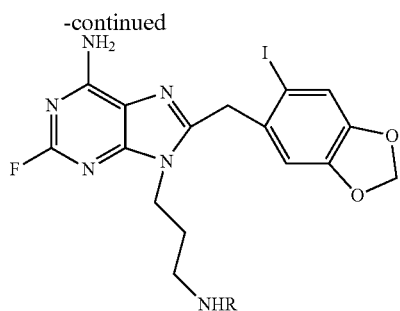

R = t-butylsulfinyl WS60
R = H WS65
R = t-butylcarbonyl WS66
R = cyclopropanecarbonyl WS71
R = cyclopropanesulfonyl WS72

Reagents and conditions: (a) triethylamine, (Boc)₂O; (b) TFA; (c) acid chloride, or sulfonyl chloride or sulfinyl chloride.

t-Butyl (3-bromopropyl)carbamate

To a suspension of 3-bromopropylamine hydrobromide (10 g, 45.7 mmol) in $CH_2Cl_2$ (100 mL) cooled in an ice bath was added triethylamine (15.9 mL, 113 mmol). Di-t-butyl-dicarbonate (10 g, 45.7 mmol) was added slowly in portions and the resulting mixture was stirred at 0° C. for 2 hrs and allowed to warm up to room temperature and stirred overnight. The reaction mixture was filtered, condensed and purified by flash chromatography to yield t-butyl (3-bromopropyl)carbamate (9.8 g, 90%). $^1H$ NMR (500 MHz, $CDCl_3$/MeOH-$d_4$): δ 4.75 (br s, 1H), 3.44 (t, J=6.6 Hz, 2H), 3.27 (m, 2H), 2.05 (m, 2H), 1.45 (s, 9H).

9-(3-Aminopropyl)-2-fluoro-8-((6-iodobenzo[d][1,3]dioxol-5-yl)methyl)-9H-purin-6-amine (WS65)

To a solution of 2-fluoro-8-((6-iodobenzo[d][1,3]dioxol-5-yl)methyl)-9H-purin-6-amine (3.3 g, 8 mmol) in DMF (50 mL) was added t-butyl (3-bromopropyl)carbamate (9.6 g, 40 mmol) and $Cs_2CO_3$ (5.26 g, 16 mmol). The resulting mixture was stirred at room temperature for 1 day. The reaction mixture was condensed and purified by flash chromatography to yield t-butyl (3-(6-amino-2-fluoro-8-((6-iodobenzo[d][1,3]dioxol-5-yl)methyl)-9H-purin-9-yl)propyl)carbamate as white solid (3.1 g, 66%). The solution of t-butyl (3-(6-amino-2-fluoro-8-((6-iodobenzo[d][1,3]dioxol-5-yl)methyl)-9H-purin-9-yl)propyl)carbamate (1.9 g, 3.3 mmol) in the mixture of TFA/$CH_2Cl_2$ (10 mL/2 mL) was stirred at room temperature for 2 hrs. The reaction mixture was condensed, purified by flash chromatography to yield 9-(3-aminopropyl)-2-fluoro-8-((6-iodobenzo[d][1,3]dioxol-5-yl)methyl)-9H-purin-6-amine as yellow solid (1.4 g, 89%). $^1H$ NMR (600 MHz, $CDCl_3$/MeOH-$d_4$): δ 7.28 (s, 1H), 6.70 (s, 1H), 5.98 (s, 2H), 4.21 (s, 2H), 4.13 (t, J=7.1 Hz, 2H), 2.67 (t, J=6.8 Hz, 2H), 1.89 (m, 2H); $^{13}C$ NMR (150 MHz, $CDCl_3$/MeOH-$d_4$): δ 160.8, 159.4, 157.8, 153.7, 152.1, 150.4, 149.4, 132.4, 120.1, 117.2, 111.3, 103.4, 89.8, 41.7, 40.4, 39.3, 33.6; HRMS (ESI) m/z $[M+H]^+$ calcd. for $C_{16}H_{17}IFN_6O_2$, 471.0436. found 471.0442.

N-(3-(6-Amino-2-fluoro-8-((6-iodobenzo[d][1,3]dioxol-5-yl)methyl)-9H-purin-9-yl)propyl)-2-methylpropane-2-sulfinamide (WS60)

To a solution of 9-(3-aminopropyl)-2-fluoro-8-((6-iodobenzo[d][1,3]dioxol-5-yl)methyl)-9H-purin-6-amine (80 mg, 0.17 mmol) in DCM (3 mL) was added t-butylsulfinyl chloride (28 uL, 0.25 mmol) and triethylamine (30 uL, 0.25 mmol). The resulting mixture was stirred at room temperature overnight. The reaction mixture was condensed and purified by flash chromatography to yield WS60 as a white solid (45 mg, 46%). $^1H$ NMR (500 MHz, $CDCl_3$): δ 7.28 (s, 1H), 6.62 (s, 1H), 6.04 (brs, 2H), 5.97 (s, 2H), 4.60 (t, J=6.5 Hz, 1H), 4.24 (s, 2H), 4.20 (m, 1H), 4.09 (m, 1H), 3.13 (m, 1H), 2.97 (m, 1H), 2.00 (m, 1H), 1.85 (m, 1H), 1.27 (s, 9H). HRMS (ESI) m/z $[M+H]^+$ calcd. for $C_{20}H_{25}IFN_6O_3S$, 575.0725. found 575.0738.

N-(3-(6-Amino-2-fluoro-8-((6-iodobenzo[d][1,3]dioxol-5-yl)methyl)-9H-purin-9-yl)propyl)pivalamide (WS66)

To a solution of WS65 (100 mg, 0.21 mmol) in DMF (3 mL) was added trimethylacetyl chloride (40 μL, 0.32 mmol) and triethylamine (90 μL, 0.96 mmol). The resulting mixture was stirred at room temperature overnight. The reaction mixture was condensed and purified by flash chromatography to yield WS66 as white solid (80 mg, 68%). $^1H$ NMR (500 MHz, $CDCl_3$): δ 7.22 (s, 1H), 6.58 (s, 1H), 6.37 (br s, 2H), 5.90 (s, 2H), 4.17 (s, 2H), 4.00 (t, J=6.1 Hz, 2H), 3.10 (m, 2H), 1.66-1.73 (m, 2H), 1.16 (s, 9H); HRMS (ESI) m/z $[M+H]^+$ calcd. for $C_{21}H_{25}IFN_6O_3$, 555.1017. found 555.1015.

N-(3-(6-Amino-2-fluoro-8-((6-iodobenzo[d][1,3]dioxol-5-yl)methyl)-9H-purin-9-yl)propyl)cyclopropanecarboxamide (WS71)

To a solution of 9-(3-aminopropyl)-2-fluoro-8-((6-iodobenzo[d][1,3]dioxol-5-yl)methyl)-9H-purin-6-amine (100 mg, 0.21 mmol) in DMF (3 mL) was added cyclopropanecarbonyl chloride (29 μL, 0.32 mmol) and triethylamine (90 μL, 0.96 mmol). The resulting mixture was stirred at room temperature overnight. The reaction mixture was condensed and purified by flash chromatography to yield WS71 as a white solid (75 mg, 65%). $^1H$ NMR (600 MHz, $CDCl_3$/MeOH-$d_4$): δ 7.32 (s, 1H), 6.77 (s, 1H), 6.02 (s, 2H), 4.24 (s, 2H), 4.16 (t, J=7.3 Hz, 2H), 3.26 (t, J=6.2 Hz, 2H), 1.91-2.01 (m, 2H), 1.50-1.57 (m, 1H), 0.90-0.95 (m, 2H), 0.76-0.82 (m, 2H); HRMS (ESI) m/z $[M+H]^+$ calcd. for $C_{20}H_{21}FIN_6O_3$, 539.0704. found 539.0705.

N-(3-(6-Amino-2-fluoro-8-((6-iodobenzo[d][1,3]dioxol-5-yl)methyl)-9H-purin-9-yl)propyl)cyclopropanesulfonamide (WS72)

To a solution of 9-(3-aminopropyl)-2-fluoro-8-((6-iodobenzo[d][1,3]dioxol-5-yl)methyl)-9H-purin-6-amine (100 mg, 0.21 mmol) in DMF (3 mL) was added cyclopropanesulfonyl chloride (89 mg, 0.32 mmol) and triethylamine (90 uL, 0.96 mmol). The resulting mixture was stirred at room temperature overnight. The reaction mixture was condensed and purified by flash chromatography to yield WS72 as a white solid (82 mg, 67%). $^1H$ NMR (600 MHz, $CDCl_3$/MeOH-$d_4$): δ 7.32 (s, 1H), 6.79 (s, 1H), 6.02 (s, 2H), 4.27 (s, 2H), 4.22 (t, J=7.3 Hz, 2H), 3.18 (t, J=6.4 Hz, 2H), 2.45-2.50 (m, 1H), 2.00-2.06 (m, 2H), 1.12-1.17 (m, 2H), 0.99-1.04 (m, 2H); $^{13}C$ NMR (150 MHz, $CDCl_3$/MeOH-$d_4$): δ 159.0 (d, J=209.8 Hz), 156.9 (d, J=19.7 Hz), 152.4 (d, J=18.5 Hz), 151.2 (d, J=2.3 Hz), 149.3, 148.4, 131.4, 119.0, 116.3 (d, J=3.6 Hz), 110.4, 102.4, 88.7, 40.7, 40.1, 39.3, 30.2, 29.9, 5.3; HRMS (ESI) m/z $[M+H]^+$ calcd. for $C_{19}H_{21}FIN_6O_4S$, 575.0374. found 575.0390.

Scheme 12. Synthesis of S-linked acetylene derivatives.

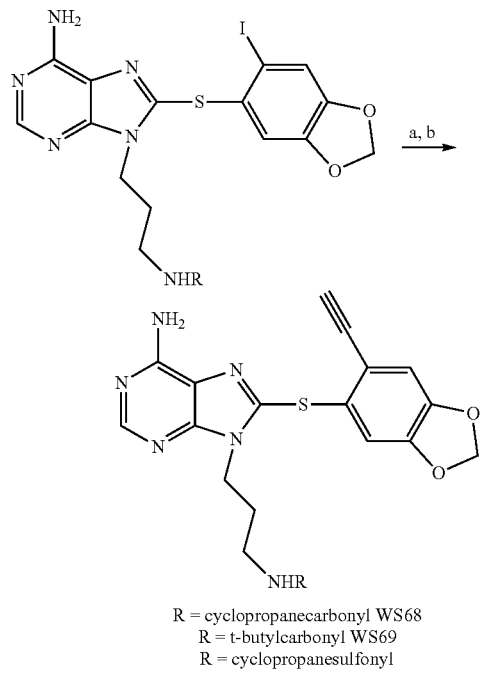

R = cyclopropanecarbonyl WS68
R = t-butylcarbonyl WS69
R = cyclopropanesulfonyl

Reagents and conditions: (a) CuI, PdCl$_2$(PPh$_3$)$_2$, trimethylsilanylacetylene, Et$_3$N, DMF, 60° C.; (b) KOH.

N-(3-(6-Amino-8-((6-ethynylbenzo[d][1,3]dioxol-5-yl)thio)-9H-purin-9-yl)propyl)cyclopropanecarboxamide (WS68)

To a solution of WS51 (150 mg, 0.28 mmol) in DMF (3 mL) was added trimethylsilanylacetylene (116 μL, 0.84 mmol), PdCl$_2$(PPh$_3$)$_2$ (20 mg, 0.03 mmol), CuI (5 mg, 0.03 mmol) and triethylamine (389 uL, 2.8 mmol). The resulting mixture was stirred at 60° C. for 30 min, condensed and filtered through silica gel. The filtrate was condensed under reduced pressure and the resulting residue was dissolved in CH$_2$Cl$_2$/MeOH (1 mL/1 mL). To the resulting mixture was added KOH (20 mg) and stirred for 3 hrs. The reaction mixture was condensed and purified by flash chromatography to yield WS68 as a white solid (42 mg, 35%). $^1$H NMR (600 MHz, CDCl$_3$/MeOH-d$_4$): δ 8.11 (s, 1H), 6.96 (s, 1H), 6.89 (s, 1H), 5.98 (s, 2H), 4.21 (t, J=7.3 Hz, 2H), 3.45 (s, 1H), 3.18 (m, 2H), 1.88-1.96 (m, 2H), 1.43-1.49 (m, 1H), 0.78-0.84 (m, 2H), 0.65-0.71 (m, 2H); HRMS (ESI) m/z [M+H]$^+$ calcd. for C$_{21}$H$_2$IN$_6$O$_3$S, 437.1396. found 437.1393.

N-(3-(6-Amino-8-((6-ethynylbenzo[d][1,3]dioxol-5-yl)thio)-9H-purin-9-yl)propyl)pivalamide (WS69)

To a solution of WS45 (150 mg, 0.27 mmol) in DMF (3 mL) was added trimethylsilanylacetylene (113 μL, 0.81 mmol), PdCl$_2$(PPh$_3$)$_2$ (19 mg, 0.03 mmol), CuI (5 mg, 0.03 mmol) and triethylamine (377 uL, 2.7 mmol). The resulting mixture was stirred at 60° C. for 30 min, condensed and filtered through silica gel. The filtrate was condensed under reduced pressure and the resulting residue was dissolved in CH$_2$Cl$_2$/MeOH (1 mL/1 mL). To the resulting mixture was added KOH (20 mg) and stirred for 3 hrs. The reaction mixture was condensed and purified by flash chromatography to yield WS69 as a white solid (53 mg, 43%). $^1$H NMR (600 MHz, CDCl$_3$): δ 8.31 (s, 1H), 7.56 (t, J=6.1 Hz, 1H), 7.00 (s, 1H), 6.88 (s, 1H), 6.01 (s, 2H), 5.77 (br s, 2H), 4.29 (t, J=5.9 Hz, 2H), 3.30 (s, 1H), 3.02-3.09 (m, 2H), 1.86-1.94 (m, 2H), 1.28 (s, 9H); HRMS (ESI) m/z [M+H]$^+$ calcd. for C$_{22}$H$_{25}$N$_6$O$_3$S, 453.1709. found 453.1721.

N-(3-(6-Amino-8-((6-ethynylbenzo[d][1,3]dioxol-5-yl)thio)-9H-purin-9-yl)propyl)cyclopropanesulfonamide (WS70)

To a solution of WS56 (100 mg, 0.17 mmol) in DMF (3 mL) was added trimethylsilanylacetylene (72 μL, 0.61 mmol), PdCl$_2$(PPh$_3$)$_2$ (12 mg, 0.02 mmol), CuI (3 mg, 0.02 mmol) and triethylamine (243 μL, 1.7 mmol). The resulting mixture was stirred at 60° C. for 30 min, condensed and filtered through silica gel. The filtrate was concentrated under reduced pressure and the resulting residue was dissolved in CH$_2$Cl$_2$/MeOH (1 mL/1 mL). To the resulting mixture was added KOH (20 mg) and stirred for 3 hrs. The reaction mixture was condensed and purified by flash chromatography to yield WS70 as a white solid (43 mg, 52%). $^1$H NMR (600 MHz, CDCl$_3$/MeOH-d$_4$): δ 8.20 (s, 1H), 7.06 (s, 1H), 7.00 (s, 1H), 6.08 (s, 2H), 4.37 (t, J=7.1 Hz, 2H), 3.54 (s, 1H), 3.18 (t, J=6.6 Hz, 2H), 2.43-2.51 (m, 1H), 2.04-2.12 (m, 2H), 1.10-1.14 (m, 2H), 0.99-1.04 (m, 2H); HRMS (ESI) m/z [M+H]$^+$ calcd. for C$_{20}$H$_2$IN$_6$O$_4$S$_2$, 473.1066. found 473.1053.

Scheme 13. Synthesis of DZ5-49-N9.

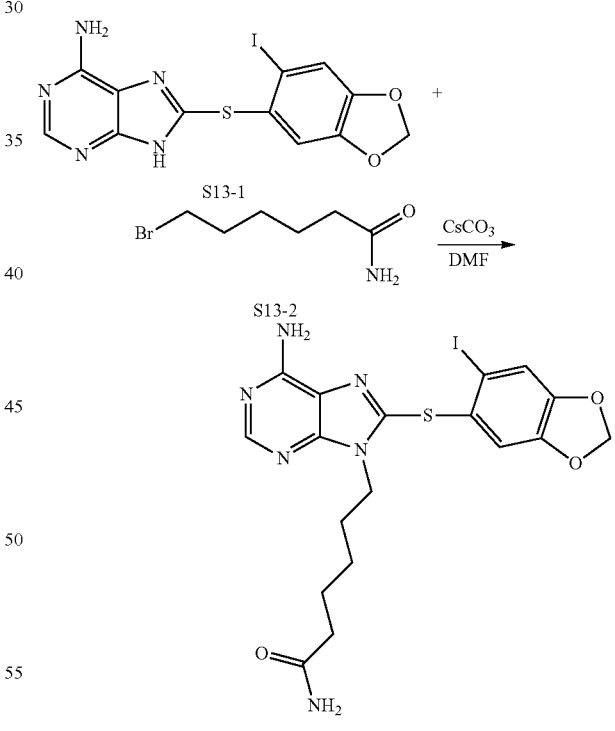

DZ5-49-N9

6-(6-Amino-8-(6-iodobenzo[d][1,3]dioxol-5-ylthio)-9H-purin-9-yl)hexanamide [DZ5-49-N9]

50 mg (0.121 mmol) of 8-(6-iodobenzo[d][1,3]dioxol-5-ylthio)-9H-purin-6-amine (S13-1) was dissolved in DMF (2 mL). 47 mg (0.145 mmol) of Cs$_2$CO$_3$ and 117.4 mg (0.605 mmol) of 6-bromohexanamide (S13-2) were added and the mixture was stirred at rt for 2 h. Solvent was removed under reduced pressure and the resulting residue was purified by preparatory TLC (CH$_2$Cl$_2$:MeOH—NH$_3$ (7N), 10:1) to give 12.7 mg (20%) of DZ5-49-N9. $^1$H NMR (500 MHz, CDCl$_3$/MeOH-d$_4$): δ 8.13 (s, 1H), 7.31 (s, 1H), 6.97 (s, 1H), 5.98 (s, 2H), 4.13 (t, J=7.6 Hz, 2H), 2.14 (t, J=7.6 Hz, 2H), 1.71-1.80 (m, 2H), 1.55-1.65 (m, 2H), 1.28-1.39 (m, 2H); HRMS (ESI) m/z [M+H]$^+$ calcd. for C$_{18}$H$_{20}$IN$_6$O$_3$S, 527.0362. found 527.0364.

Hsp90 Binding Assay:

For the binding studies, fluorescence polarization (FP) assays were performed similarly as was previously reported [Du et al. (2007) "High-throughput screening fluorescence polarization assay for tumor-specific Hsp90" *J. Biomol. Screen* 12:915-924]. Briefly, FP measurements were performed on an Analyst GT instrument (Molecular Devices, Sunnyvale, Calif.). Measurements were taken in black 96-well microtiter plates (Corning #3650) where both the excitation and the emission occurred from the top of the well. A stock of 10 µM cy3B-GM was prepared in DMSO and diluted with HFB buffer (20 mM Hopes (K), pH 7.3, 50 mM KCl, 2 mM DTT, 5 mM MgCl$_2$, 20 mM Na$_2$MoO$_4$, and 0.01% NP40 with 0.1 mg/mL BGG). The test compounds were dissolved in DMSO and added at several concentrations to the HFB assay buffer containing both 6 nM cy3B-GM and transgenic mouse brain lysate (6 µg JNPL3 lysate) or human cancer cell lysate (3 µg SKBr3 lysate) in a final volume of 100 µL. Drugs were added to triplicate wells. Free cy3B-GM (6 nM cy3B-GM), bound cy3B-GM (6 nM cy3B-GM+lysate, as indicated above) and buffer only containing wells (background) were included as controls in each plate. Plates were incubated on a shaker at 4° C., and polarization values measured at 24 h. Percentage inhibition was calculated as follows: (% Control)=100−((mP$_c$−mP$_f$)/(mP$_b$−mP$_f$))×100, where mP$_c$ is the recorded mP$_b$ from compound wells, mP$_f$ is the average recorded mP from cy3B-GM-only wells, and mP$_b$ is the average recorded mP from wells containing both cy3B-GM and lysate, and plotted against values of competitor concentrations. The inhibitor concentration at which 50% of bound cy3B-GM was displaced was obtained by fitting the data using a nonlinear regression analysis as implemented in Prism 4.0 (GraphPad Software).

hERG Fluorescence Polarization Assay:

Following the manufacturer's protocol, the hERG assay was performed using Predictor hERG Fluorescence Polarization Assay kit (catalog no. PV5365) from Invitrogen. Briefly, FP measurements were performed on an Analyst GT instrument (Molecular Devices, Sunnyvale, Calif.). Measurements were taken in black 384-well plates (Corning #3677), where both the excitation and the emission occurred from the top of the well. The test compounds were dissolved in DMSO and added at several concentrations to the Predictor hERG FP assay buffer containing 4 nM Predictor hERG tracer red and 10 uL of Predictor hERG membrane in a final volume of 20 uL. Drugs were added to triplicate wells. E-4031 as positive control was included in each plate. Plates were then kept on a shaker at room temperature and polarization values were measured after 4 hrs. The inhibition concentration at which 50% of tracer red gets displaced was obtained by fitting the data using a nonlinear regression analysis as implemented in Prism 5.0 (GraphPad Software).

Table 12 shows results of testing for various representative compounds for their activity in Hsp90 binding assays and hERG fluorescence polarization assay. In interpreting these test results, it will be appreciated that binding to Hsp90 is desirable for activity in the treatment of cancer or neurodegenerative disorders. In contrast, it is generally undesirable to have binding to hERG since binding to hERG can result in undesirable cardiac side effects. Therefore, having a low value for binding to Hsp90 and a high value for binding to hERG is desirable, bearing in mind that the units for the two measurement are different.

For comparison, it is noted that values for PU-H71, a compound with the structure

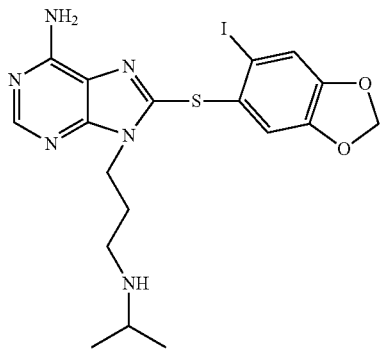 [SMILES: CC(C)NCCCn1c(Sc2cc3c(cc2I)OCO3)nc2c(N)ncnc21]

has a Hsp90 binding value of 20 nM and an hERG assay result of 1. Many of the compounds of the invention tested, have hERG values more than 100 times greater than PU-H71 and are therefore expected to have lower toxicity/side effect issues.

TABLE 12

| Compound Designation No. | Synthetic Designation | Hsp90 Binding Assay (nM) | hERG assay (µM) |
|---|---|---|---|
| 1A-10 | WS35 | 6.3 | NA |
| 1A-11 | WS42 | 71.5 | NA |
| 1A-12 | WS39 | 33 | NA |
| 1A-15 | WS54 | 20.5 | >100 |
| 1A-19 | WS53 | 44 | NA |
| 1A-22 | WS48 | 47 | >100 |
| 1A-24 | WS34 | 11.5 | NA |
| 1A-25 | WS52 | 24 | NA |
| 1A-26 | WS49 | 12 | >100 |
| 1A-27 | WS50 | 64 | NA |
| 1A-28 | WS56 | 19.7 | NA |
| 1A-43 | WS45 | 11 | >100 |
| 1A-44 | WS46 | 68 | NA |
| 1A-45 | WS51 | 9.8 | >100 |
| 1A-46 | WS55 | 24.2 | NA |
| 1A-47 | WS57 | 16.5 | NA |
| 1A-48 | WS58 | 22.1 | 12 |
| 1A-49 | WS64 | 28.3 | NA |
| 1A-5 | WS47 | 78 | NA |
| 1A-50 | DZ5-49-N9 | 76.5 | NA |
| 1B-28 | WS70 | 53 | >100 |
| 1B-43 | WS69 | 28 | >100 |
| 1B-45 | WS68 | 37 | >100 |
| 1G-28 | MRP-I-31 | 22 | NA |
| 1G-43 | MRP-I-29 | 11 | >100 |
| 1G-45 | MRP-I-28 | 15 | 76 |
| 2A-11 | WS43 | 51 | NA |
| 2A-12 | WS41 | 68 | NA |
| 2A-26 | WS62 | 17 | NA |
| 2A-45 | WS61 | 11.8 | NA |
| 3A-10 | WS36 | 3.5 | NA |
| 3A-11 | WS44 | 68 | NA |
| 3A-12 | WS40 | 29.6 | NA |
| 3A-24 | WS37 | 8.1 | NA |
| 3A-26 | WS63 | 20.1 | NA |
| 3A-43 | WS38 | 37.4 | NA |
| 4A-26 | WS60 | 26.2 | >100 |
| 4A-28 | WS72 | 24 | >100 |
| 4A-43 | WS66 | 33.1 | >100 |
| 4A-45 | WS71 | 20 | >100 |

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those in the art and are intended to fall within the scope of the appended claims. A number of references have been cited, the entire disclosures of which are incorporated herein by reference for all purposes.

What is claimed:

1. A Compound of Formula (IA) or (IB):

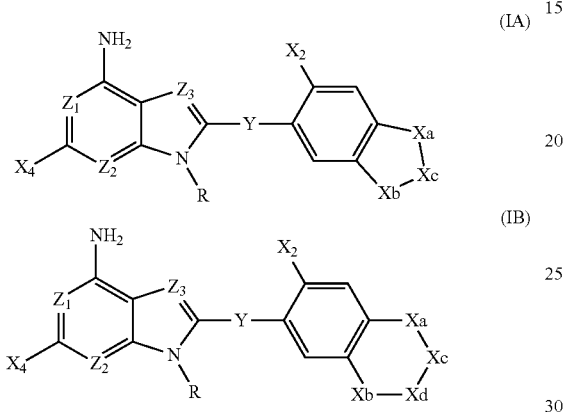

or a pharmaceutically acceptable salt thereof, wherein:
(a) each of $Z_1$, $Z_2$ and $Z_3$ is N;
(b) Y is S;
(c) Xa, Xb, Xc and Xd are O, O, $CH_2$, and $CH_2$, respectively;
(d) $X_4$ is hydrogen or halogen; and
(e) $X_2$ and R are a combination selected from the following:
   (i) in formula (IA):
      (a) $X_2$ is $NR_1R_2$, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A SO_2$—, —C(O)N($R_A$)—, or —$NR_A$C(O)— groups, and/or terminated by an —S(O)$NR_A R_B$, —$NR_A$S(O)$R_B$, —$SO_2 NR_A R_B$, —$NR_A SO_2 R_B$, —C(O)$NR_A R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
      (b) $X_2$ is halogen, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A SO_2$—, or —C(O)N($R_A$)— groups, and/or terminated by an —S(O)$NR_A R_B$, —$NR_A$S(O)$R_B$, —$SO_2 NR_A R_B$, —$NR_A SO_2 R_B$, —C(O)$NR_A R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
      (c) $X_2$ is halogen, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —$NR_A$C(O)— groups, and/or terminated by an —$NR_A$C(O)$R_B$ group, wherein each $R_A$ is independently selected from $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyland, and each $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
      (d) $X_2$ is aryl or alkynyl, R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, or —$NR_A$C(O)— groups, and/or terminated by an —S(O)$NR_A R_B$, —$NR_A$S(O)$R_B$, —$NR_A SO_2 R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
      (e) $X_2$ is aryl or alkynyl, R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —$NR_A SO_2$— or —C(O)N($R_A$)— groups, and/or terminated by an —$SO_2 NR_A R_B$ or —C(O)$NR_A R_B$ group, wherein each $R_A$ is independently selected from $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl;
      (f) $X_2$ is halogen, aryl, alkynyl, or $NR_1R_2$, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl; and R is straight-chain-substituted or unsubstituted alkyl, straight-chain-substituted or unsubstituted alkenyl, straight-chain-substituted or unsubstituted alkynyl, or substituted or unsubstituted cycloalkyl wherein the R group is terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$ group, wherein R$_A$ is independently selected from hydrogen, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and R$_B$ is independently selected from C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and (ii) in formula (IB):

(g) X$_2$ is halogen, aryl, alkynyl, or NR$_1$R$_2$, wherein R$_1$ and R$_2$ are each independently H, C$_1$-C$_6$ alkyl, C$_1$-C$_6$ alkenyl, C$_1$-C$_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N(R$_A$)—, —NR$_A$S(O)—, or —SO$_2$N(R$_A$)— groups, and/or terminated by an —S(O)NR$_A$R$_B$ or —NR$_A$S(O)R$_B$ group, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or (h) X$_2$ is halogen, aryl, alkynyl, or NR$_1$R$_2$, wherein R$_1$ and R$_2$ are each independently H, C$_1$-C$_6$ alkyl, C$_1$-C$_6$ alkenyl, C$_1$-C$_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —NR$_A$SO$_2$—, —C(O)N(R$_A$)—, or —NR$_A$C(O)— groups, and/or terminated by an —SO$_2$NR$_A$R$_B$, —NR$_A$SO$_2$R$_B$, —C(O)NR$_A$R$_B$, or —NR$_A$C(O)R$_B$ group, wherein each R$_A$ is independently selected from C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or (j) X$_2$ is halogen, aryl, alkynyl, or NR$_1$R$_2$, wherein R$_1$ and R$_2$ are each independently H, C$_1$-C$_6$ alkyl, C$_1$-C$_6$ alkenyl, C$_1$-C$_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl; and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$ group, wherein R$_A$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and R$_B$ is independently selected from C$_2$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

2. The compound of claim 1 which is a Compound of Formula (1):

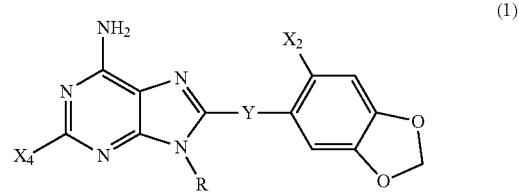

(1)

or a pharmaceutically acceptable salt thereof, wherein Y is S.

3. The compound of claim 1 which is Compound of Formula (6):

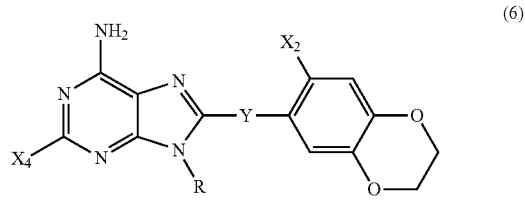

(6)

or a pharmaceutically acceptable salt thereof.

4. The compound of claim 1, wherein in formula (IA):

(i)(b) X$_2$ is halogen, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N(R$_A$)—, —NR$_A$S(O)—, —SO$_2$N(R$_A$)—, —NR$_A$SO$_2$—, or —C(O)N(R$_A$)— groups, and/or terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$ group, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or (i)(c) X$_2$ is halogen, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —NR$_A$C(O)— groups, and/or terminated by an —NR$_A$C(O)R$_B$ group, wherein each R$_A$ is independently selected from C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyland, and each R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

5. The compound of claim 1, wherein in formula (IA):
(i)(d) X$_2$ is aryl or alkynyl, R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N(R$_A$)—, —NR$_A$S(O)—, —SO$_2$N(R$_A$)—, or —NR$_A$C(O)— groups, and/or terminated by an —S(O)NR$_A$R$_B$, —NR$_A$S(O)R$_B$, —NR$_A$SO$_2$R$_B$, or —NR$_A$C(O)R$_B$ group, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(i)(e) X$_2$ is aryl or alkynyl, R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —NR$_A$SO$_2$— or —C(O)N(R$_A$)— groups, and/or terminated by an —SO$_2$NR$_A$R$_B$ or —C(O)NR$_A$R$_B$ group, wherein each R$_A$ is independently selected from C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

6. The compound of claim 1, wherein in formula (IA), (i)(f) X$_2$ is halogen, aryl, alkynyl, or NR$_1$R$_2$, wherein R$_1$ and R$_2$ are each independently H, C$_1$-C$_6$ alkyl, C$_1$-C$_6$ alkenyl, C$_1$-C$_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl; and R is straight-chain-substituted or unsubstituted alkyl, straight-chain-substituted or unsubstituted alkenyl, straight-chain-substituted or unsubstituted alkynyl, or substituted or unsubstituted cycloalkyl wherein the R group is terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$ group, wherein R$_A$ is independently selected from hydrogen, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and R$_B$ is independently selected from C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

7. The compound of claim 1, wherein R is cyclopropane carboxylic acid 3-propyl-amide, N-3-propyl 2,2-dimethyl-propionamide, N-propyl-2-methyl-propane-2-sulfinamide, t-butanesulfonic acid 3-propylamide, or cyclopropanesulfonic acid 3-propylamide.

8. The compound of claim 1, wherein X$_4$ is H or F.

9. The compound of claim 1, wherein X$_2$ is optionally substituted heteroaryl.

10. The compound of claim 9, wherein X$_2$ is furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, or 5-methyloxazol-2-yl.

11. The compound of claim 1, wherein X$_2$ is alkynyl or NR$_1$R$_2$.

12. The compound of claim 11, wherein X$_2$ is ethynyl or dimethylamino.

13. The compound of claim 1, wherein X$_2$ is halo.

14. The compound of claim 13, wherein X$_2$ is I.

15. A pharmaceutical composition comprising the compound of claim 1 and a pharmaceutically acceptable carrier.

16. A method for the inhibition of Hsp90, comprising contacting Hsp90 with an Hsp90 function inhibiting amount of a compound of claim 1.

17. A Compound of Formula (IA) or (IB):

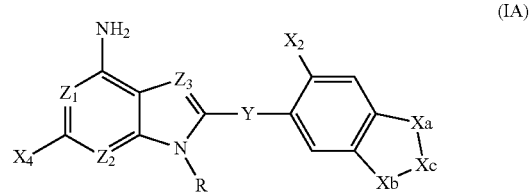

(IA)

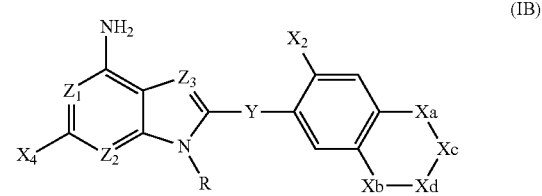

(IB)

or a pharmaceutically acceptable salt thereof, wherein:
(a) each of Z$_1$, Z$_2$ and Z$_3$ is N;
(b) Y is CH$_2$;
(c) Xa, Xb, Xc and Xd are O, O, CH$_2$, and CH$_2$, respectively;
(d) X$_4$ is hydrogen or halogen; and
(i) in formula (IA):
(a) X$_2$ is NR$_1$R$_2$, wherein R$_1$ and R$_2$ are each independently H, C$_1$-C$_6$ alkyl, C$_1$-C$_6$ alkenyl, C$_1$-C$_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N(R$_A$)—, —NR$_A$S(O)—, —SO$_2$N(R$_A$)—, —NR$_A$SO$_2$—, —C(O)N(R$_A$)—, or —NR$_A$C(O)— groups, and/or terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$ group, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(b) $X_2$ is halogen, and R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_A$$R_B$, —$NR_A$S(O)$R_B$, —$NR_A$$SO_2$$R_B$, —C(O)$NR_A$$R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(c) $X_2$ is halogen, and R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl wherein the R group is terminated by a —$SO_2$$NR_A$$R_B$ group, wherein $R_A$ is selected from $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and $R_B$ is selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(d) $X_2$ is aryl or alkynyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_A$$R_B$, —$NR_A$S(O)$R_B$, —$NR_A$$SO_2$$R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(e) $X_2$ is aryl or alkynyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is terminated by an —$SO_2$$NR_A$$R_B$ or —C(O)$NR_A$$R_B$ group, wherein each $R_A$ is independently selected from $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; and (ii) in formula (IB),
(a) $X_2$ is $NR_1$$R_2$, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_A$$R_B$, —$NR_A$S(O)$R_B$, —$SO_2$$NR_A$$R_B$, —$NR_A$$SO_2$$R_B$, —C(O)$NR_A$$R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(b) $X_2$ is halogen, aryl, or alkynyl, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_A$$R_B$, —$NR_A$S(O)$R_B$, —$NR_A$$SO_2$$R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(c) $X_2$ is halogen, aryl, or alkynyl, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is terminated by an —$SO_2$$N_A$$R_B$ or —C(O)$NR_A$$R_B$ group, wherein each $R_A$ is independently selected from $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

18. The compound of claim 17 which is a Compound of the following Formula:

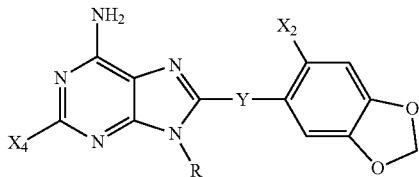

or a pharmaceutically acceptable salt thereof.

19. The compound of claim 17, wherein $X_2$ is optionally substituted heteroaryl, and wherein the optionally substituted heteroaryl comprises furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, or 5-methyloxazol-2-yl.

20. The compound of claim 17, wherein $X_2$ is ethynyl, I, or dimethylamino.

21. The compound of claim 17, wherein in formula (IA), $X_2$ is $NR_1R_2$, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_AR_B$, —$NR_A$S(O)$R_B$, —$SO_2NR_AR_B$, —$NR_ASO_2R_B$, —C(O)$NR_AR_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

22. The compound of claim 17, wherein in formula (IA):
(i)(d) $X_2$ is aryl or alkynyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_AR_B$, —$NR_A$S(O)$R_B$, —$SO_2NR_AR_B$, —$NR_ASO_2R_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
(i)(e) $X_2$ is aryl or alkynyl, and R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is terminated by an —$SO_2NR_AR_B$ or —C(O)$NR_AR_B$ group, wherein each $R_A$ is independently selected from $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and each $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

23. A pharmaceutical composition comprising the compound of claim 17 and a pharmaceutically acceptable carrier.

24. A Compound of Formula (IA) or (IB):

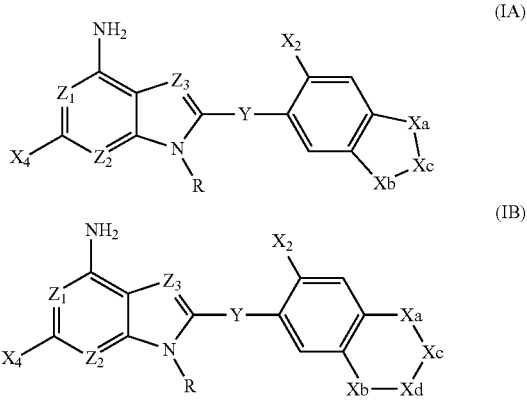

or a pharmaceutically acceptable salt thereof, wherein:
(a) each of $Z_1$, $Z_2$ and $Z_3$ is N;
(b) Y is O;
(c) Xa, Xb, Xc and Xd are independently selected from CH, $CH_2$, O, N, NH, S, carbonyl, fluoromethylene, and difluoromethylene selected so as to satisfy valence, wherein each bond to an X group is either a single bond or a double bond;
(d) $X_2$ is halogen, aryl, alkynyl, or $NR_1R_2$, wherein $R_1$ and $R_2$ are each independently H, $C_1$-$C_6$ alkyl, $C_1$-$C_6$ alkenyl, $C_1$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl;
(e) $X_4$ is hydrogen or halogen; and
(f) R is straight-chain- or branched-substituted or unsubstituted alkyl, straight-chain- or branched-substituted or unsubstituted alkenyl, straight-chain- or branched-substituted or unsubstituted alkynyl, or substituted or unsubstituted cycloalkyl wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups, and/or terminated by an —S(O)$NR_AR_B$, —$NR_A$S(O)$R_B$, —$SO_2NR_AR_B$, —$NR_ASO_2R_B$, —C(O)$NR_AR_B$, or —$NR_A$C(O)$R_B$ group, wherein each $R_A$ and $R_B$ is independently selected from hydrogen, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

25. The compound of claim 24, wherein $X_2$ is optionally substituted heteroaryl, and wherein the optionally substituted heteroaryl comprises furan-2-yl, furan-3-yl, 5-methylfuran-2-yl, 1H-pyrazol-2-yl, 1H-pyrazol-3-yl, thiazol-2-yl, 5-methylthiazol-2-yl, oxazol-2-yl, or 5-methyloxazol-2-yl.

26. The compound of claim 24, wherein $X_2$ is ethynyl, I, or dimethylamino.

27. The compound of claim 24, wherein the R group is interrupted by one or more —S(O)N($R_A$)—, —$NR_A$S(O)—, —$SO_2$N($R_A$)—, —$NR_A$$SO_2$—, —C(O)N($R_A$)—, or —$NR_A$C(O)— groups.

28. The compound of claim 24, wherein the R group is terminated by an —S(O)NR$_A$R$_B$, —NR$_A$S(O)R$_B$, —SO$_2$NR$_A$R$_B$, —NR$_A$SO$_2$R$_B$, —C(O)NR$_A$R$_B$, or —NR$_A$C(O)R$_B$ group.

29. A pharmaceutical composition comprising the compound of claim 24 and a pharmaceutically acceptable carrier.

30. The compound of claim 17, wherein in formula (IA),
   (b) X$_2$ is halogen, and R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl wherein the R group is interrupted by one or more —S(O)N(R$_A$)—, —NR$_A$S(O)—, —SO$_2$N(R$_A$)—, —NR$_A$SO$_2$—, —C(O)N(R$_A$)—, or —NR$_A$C(O)— groups, and/or terminated by an —S(O)NR$_A$R$_B$, —NR$_A$S(O)R$_B$, —NR$_A$SO$_2$R$_B$, —C(O)NR$_A$R$_B$, or —NR$_A$C(O)R$_B$ group, wherein each R$_A$ and R$_B$ is independently selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl; or
   (c) X$_2$ is halogen, and R is straight-chain- or branched- substituted or unsubstituted alkyl, straight-chain- or branched- substituted or unsubstituted alkenyl, straight-chain- or branched- substituted or unsubstituted alkynyl, or substituted or unsubstituted cycloalkyl wherein the R group is terminated by a —SO$_2$NR$_A$R$_B$ group, wherein R$_A$ is selected from C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl, and R$_B$ is selected from hydrogen, C$_1$-C$_6$ alkyl, C$_2$-C$_6$ alkenyl, C$_2$-C$_6$ alkynyl, cycloalkyl, heteroalkyl, heterocycloalkyl, aryl, heteroaryl, alkylaryl, arylalkyl, alkylheteroaryl, heteroarylalkyl, and alkylheteroarylalkyl.

31. The compound of claim 30, wherein R is straight-chain- unsubstituted C$_1$-C$_6$ alkyl, which is terminated by a —NR$_A$S(O)R$_B$, —NR$_A$SO$_2$R$_B$, or —NR$_A$C(O)R$_B$ group, wherein each R$_A$ and R$_B$ is independently selected from hydrogen and C$_1$-C$_6$ alkyl.

32. The compound of claim 31, wherein X$_2$ is Iodo, R is straight-chain- unsubstituted C$_1$-C$_6$ alkyl, which is terminated by a —NR$_A$S(O)R$_B$, —NR$_A$SO$_2$R$_B$, or —NR$_A$C(O)R$_B$ group, wherein R$_A$ is hydrogen, and R$_B$ is tert-butyl or cyclopropyl.

33. The compound of claim 32, which is a compound of the formula:

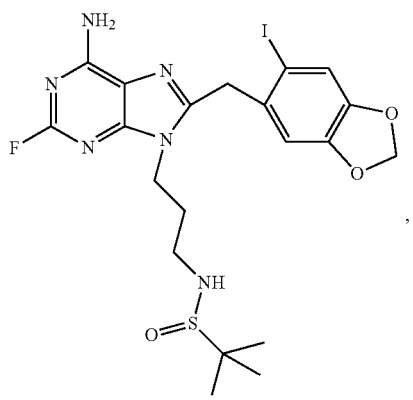

,

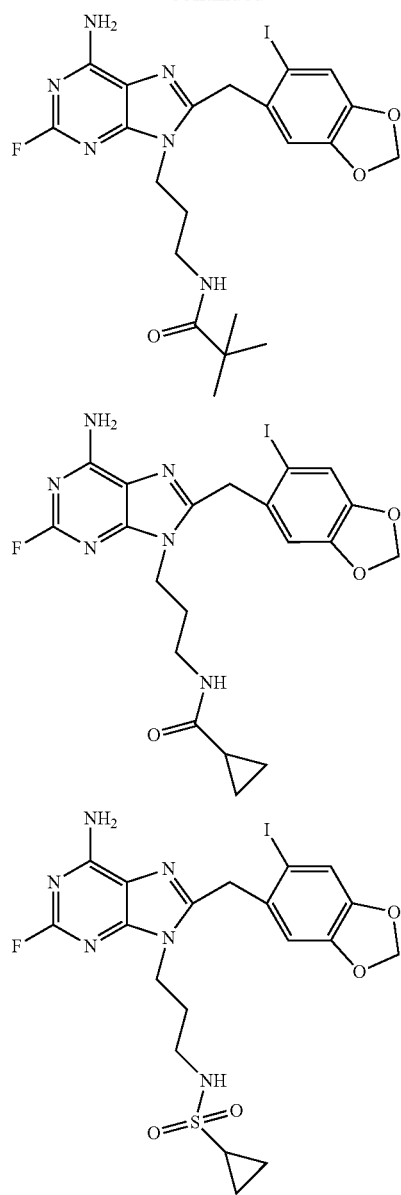

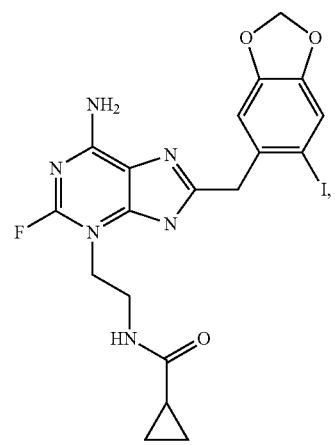

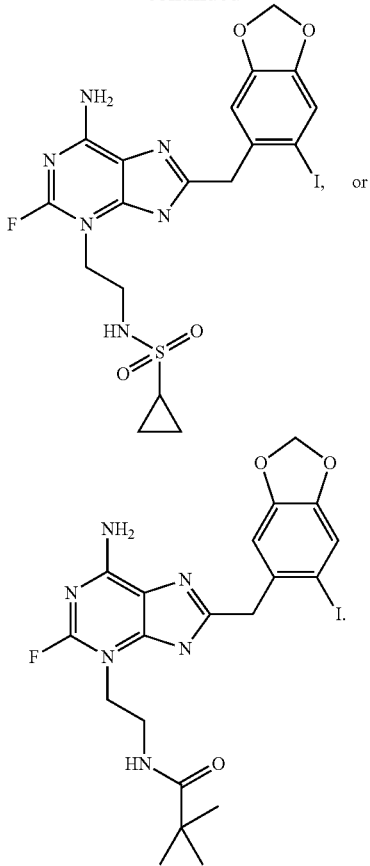

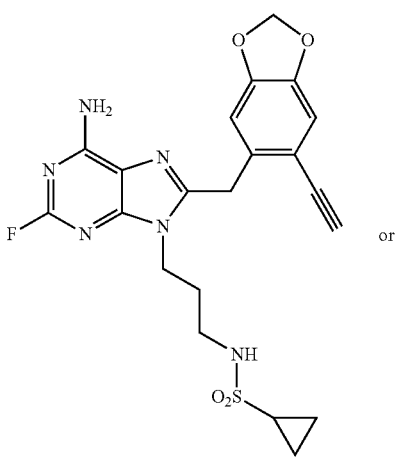

34. The compound of claim 22, wherein X₂ is alkynyl, and R is straight-chain- unsubstituted C₁-C₆ alkyl, which is terminated by a —NR_AS(O)R_B, —NR_ASO₂R_B, or —NR_AC(O)R_B group, wherein each R_A and R_B is independently selected from hydrogen and C₁-C₆ alkyl.

35. The compound of claim 34, wherein X₂ is ethynyl, R is straight-chain- unsubstituted C₁-C₆ alkyl, which is terminated by a —NR_AS(O)R_B, —NR_ASO₂R_B, or —NR_AC(O)R_B group, wherein R_A is hydrogen, and R_B is tert-butyl or cyclopropyl.

36. The compound of claim 35, which is a compound of the formula:

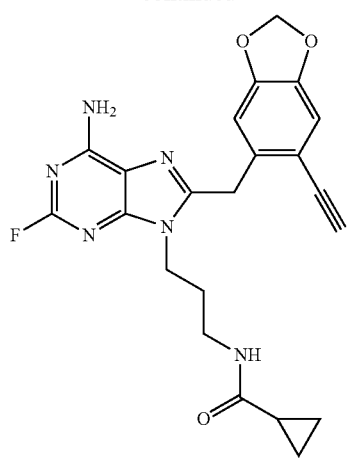

37. A method for the inhibition of Hsp9O, comprising contacting Hsp9O with an Hsp9O function inhibiting amount of a compound of claim 17.

38. A method for the inhibition of Hsp9O, comprising contacting Hsp9O with an Hsp9O function inhibiting amount of a compound of claim 24.

39. The compound of claim 4, wherein R is straight-chain-unsubstituted C₁-C₆ alkyl, which is interrupted by one or more —S(O)N(R_A)—, —NR_AS(O)—, —SO₂N(R_A)—, —NR_ASO₂—, or —C(O)N(R_A)— groups, and/or terminated by an —S(O)NR_AR_B, —NR_AS(O)R_B, —SO₂NR_AR_B, —NR_ASO₂R_B, —C(O)NR_AR_B group, wherein each R_A and R_B is independently selected from hydrogen, C₁-C₆ alkyl, and cycloalkyl.

40. The compound of claim 39, wherein X₂ is Iodo, R is straight-chain- unsubstituted C₁-C₆ alkyl, which is terminated by an —S(O)NR_AR_B, —NR_AS(O)R_B, —SO₂NR_AR_B, —NR_ASO₂R_B, —C(O)NR_AR_B group, wherein R_A is hydrogen, and R_B is tert-butyl or cyclopropyl.

41. The compound of claim 6, wherein X₂ is halogen, R is straight-chain- unsubstituted C₁-C₆ alkyl, which is terminated by a —S(O)NR_AR_B, —NR_AS(O)R_B, —SO₂NR_AR_B, —NR_ASO₂R_B, —C(O)NR_AR_B, or —NR_AC(O)R_B group, wherein R_A is hydrogen, and each R_B is independently selected from C₁-C₆ alkyl and cycloalkyl.

42. The compound of claim 41, wherein X₂ is Iodo, R is straight-chain- unsubstituted C₁-C₆ alkyl, which is terminated by a —S(O)NR_AR_B, —NR_AS(O)R_B, —SO₂NR_AR_B, —NR_ASO₂R_B, —C(O)NR_AR_B, or —NR_AC(O)R_B group, wherein R_A is hydrogen, and RB is tert-butyl or cyclopropyl.

43. The compound of claim 6, wherein X2 is alkynyl, R is straight-chain- unsubstituted C₁-C₆ alkyl, which is terminated by a 13 S(O)NR_AR_B, —NR_AS(O)R_B, —SO₂NR_AR_B, —NR_ASO₂R_B, —C(O)NR_AR_B, or —NR_AC(O)R_B group, wherein R_A is hydrogen, and each R_B is independently selected from C₁-C₆ alkyl and cycloalkyl.

44. The compound of claim 43, wherein X2 is ethynyl, R is straight-chain- unsubstituted C₁-C₆ alkyl, which is terminated by a 13 S(O)NR_AR_B, —NR_AS(O)R_B, —SO₂NR_AR_B, —NR_ASO₂R_B, —C(O)NR_AR_B, or —NR_AC(O)R_B group, wherein R_A is hydrogen, and R_B is tert-butyl or cyclopropyl.

* * * * *